United States Patent
Valamehr et al.

(10) Patent No.: US 12,203,098 B2
(45) Date of Patent: *Jan. 21, 2025

(54) CELLS HAVING SOLID TUMOR TARGETING BACKBONE AND USE THEREOF

(71) Applicant: FATE THERAPEUTICS, INC., San Diego, CA (US)

(72) Inventors: Bahram Valamehr, San Diego, CA (US); Tom Tong Lee, San Diego, CA (US); Martin Hosking, San Diego, CA (US); Eigen Peralta, San Diego, CA (US); Chia-Wei Chang, San Diego, CA (US)

(73) Assignee: FATE THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/345,885

(22) Filed: Jun. 30, 2023

(65) Prior Publication Data

US 2023/0357716 A1 Nov. 9, 2023

Related U.S. Application Data

(63) Continuation of application No. PCT/US2023/065550, filed on Apr. 7, 2023.

(60) Provisional application No. 63/380,378, filed on Oct. 20, 2022, provisional application No. 63/329,364, filed on Apr. 8, 2022.

(51) Int. Cl.
| | |
|---|---|
| *C12N 5/078* | (2010.01) |
| *A61K 39/00* | (2006.01) |
| *A61K 39/395* | (2006.01) |
| *A61P 35/00* | (2006.01) |
| *C07K 14/705* | (2006.01) |
| *C07K 14/715* | (2006.01) |
| *C07K 14/725* | (2006.01) |
| *C07K 16/28* | (2006.01) |
| *C07K 16/30* | (2006.01) |
| *C07K 16/32* | (2006.01) |

(52) U.S. Cl.
CPC ............ *C12N 5/0634* (2013.01); *A61P 35/00* (2018.01); *C07K 14/7051* (2013.01); *C07K 16/3015* (2013.01); *C07K 2317/565* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 6,140,081 A | 10/2000 | Barbas | |
| 6,352,694 B1 | 3/2002 | June et al. | |
| 6,453,242 B1 | 9/2002 | Eisenberg et al. | |
| 6,534,261 B1 | 3/2003 | Cox et al. | |
| 7,888,121 B2 | 2/2011 | Urnov et al. | |
| 7,972,854 B2 | 7/2011 | Miller et al. | |
| 8,409,577 B2 | 4/2013 | Thompson et al. | |
| 9,447,194 B2 | 9/2016 | Jensen | |
| 9,587,020 B2 | 3/2017 | Wu et al. | |
| 10,927,346 B2* | 2/2021 | Valamehr | ............ C07K 14/7155 |
| 11,365,394 B2* | 6/2022 | Valamehr | ............... A61K 35/17 |
| 2004/0101519 A1 | 5/2004 | June et al. | |
| 2006/0034810 A1 | 2/2006 | Riley et al. | |
| 2011/0145940 A1 | 6/2011 | Voytas et al. | |
| 2014/0134142 A1 | 5/2014 | Smith et al. | |
| 2014/0219975 A1 | 8/2014 | June et al. | |
| 2015/0140665 A1 | 5/2015 | Calos et al. | |
| 2016/0046700 A1 | 2/2016 | Foster et al. | |
| 2016/0058857 A1 | 3/2016 | Spencer et al. | |
| 2017/0166877 A1 | 6/2017 | Bayle et al. | |
| 2017/0183407 A1 | 6/2017 | Cooper et al. | |
| 2018/0326032 A1* | 11/2018 | Priceman | ............ C07K 16/2863 |
| 2020/0102366 A1 | 4/2020 | Cooper et al. | |
| 2020/0399397 A1 | 12/2020 | Lee et al. | |
| 2021/0024959 A1* | 1/2021 | Valamehr | ......... C07K 14/70596 |
| 2021/0087537 A1* | 3/2021 | Valamehr | ............ C07K 14/7155 |
| 2021/0139605 A1 | 5/2021 | Wang et al. | |
| 2021/0163622 A1* | 6/2021 | Valamehr | ............ C07K 14/7051 |
| 2021/0163895 A1* | 6/2021 | Valamehr | ............ C07K 14/5443 |

(Continued)

FOREIGN PATENT DOCUMENTS

| | | |
|---|---|---|
| CN | 112391414 A | 2/2021 |
| WO | WO 1998/053058 A1 | 11/1998 |

(Continued)

OTHER PUBLICATIONS

Hudecek et al., "The nonsignaling extracellular spacer domain of chimeric antigen receptors is decisive for in vivo antitumor activity," *Cancer Immunol Res*, 3(2):125-135 (2015).

Itai et al., "H2Mab-77 is a Sensitive and Specific Anti-HER2 Monoclonal Antibody Against Breast Cancer," *Monoclon Antib Immunodiagn Immunother.*, 36(4):143-148 (2017).

Stock et al., "Optimizing Manufacturing Protocols of Chimeric Antigen Receptor T Cells for Improved Anticancer Immunotherapy," *Int J Mol Sci.*, 20(24):6223 (2019).

(Continued)

*Primary Examiner* — Ilia I Ouspenski
(74) *Attorney, Agent, or Firm* — Greenberg Traurig, LLP

(57) ABSTRACT

Provided are methods and compositions for obtaining functionally enhanced derivative effector cells obtained from directed differentiation of genomically engineered iPSCs. Also provided are derivative cells having stable and functional genome editing that delivers improved or enhanced therapeutic effects. Further provided are therapeutic compositions and the use thereof comprising the functionally enhanced derivative effector cells alone, or with antibodies or checkpoint inhibitors in combination therapies.

30 Claims, 53 Drawing Sheets

Specification includes a Sequence Listing.

(56) References Cited

U.S. PATENT DOCUMENTS

| | | | |
|---|---|---|---|
| 2021/0308183 A1* | 10/2021 | Schrepfer | C12N 9/22 |
| 2021/0388389 A1* | 12/2021 | Chen | C07K 16/2803 |
| 2022/0089750 A1 | 3/2022 | June et al. | |
| 2022/0275333 A1* | 9/2022 | Valamehr | A61K 48/005 |
| 2022/0378831 A1* | 12/2022 | Valamehr | C07K 14/70578 |
| 2023/0016034 A1* | 1/2023 | Valamehr | A61K 35/545 |
| 2024/0002531 A1* | 1/2024 | Kato | A61K 39/395 |
| 2024/0002532 A1* | 1/2024 | Valamehr | C07K 14/7051 |

FOREIGN PATENT DOCUMENTS

| | | |
|---|---|---|
| WO | WO 1998/053059 A1 | 11/1998 |
| WO | WO 1998/053060 A1 | 11/1998 |
| WO | WO 2002/016536 A1 | 2/2002 |
| WO | WO 2003/016496 A2 | 2/2003 |
| WO | WO 2011/159726 A2 | 12/2011 |
| WO | WO 2017/078807 A1 | 5/2014 |
| WO | WO 2015/134652 A1 | 9/2015 |
| WO | WO 2016/149665 A1 | 9/2016 |
| WO | WO 2017/066634 A1 | 4/2017 |
| WO | WO 2017/079694 A2 | 5/2017 |
| WO | WO 2017/127755 A1 | 7/2017 |
| WO | WO 2019/075057 A1 | 4/2019 |
| WO | WO 2019/112899 A2 | 6/2019 |
| WO | WO 2019/126748 A1 | 6/2019 |
| WO | WO 2019/191495 A1 | 10/2019 |
| WO | WO 2020/018620 A1 | 1/2020 |
| WO | WO 2020/188573 A1 | 9/2020 |
| WO | WO 2020/191434 A1 | 10/2020 |
| WO | WO 2021/071962 A1 | 4/2021 |
| WO | WO 2021/077117 A1 | 4/2021 |
| WO | WO 2021/151119 A1 | 7/2021 |
| WO | WO 2021/235894 A1 | 11/2021 |
| WO | WO 2022/098914 A1 | 5/2022 |
| WO | WO 2022/098925 A1 | 5/2022 |
| WO | WO 2022/114163 A1 | 6/2022 |
| WO | WO 2023/196982 A1 | 10/2023 |

OTHER PUBLICATIONS

Yamada et al., "Establishment of H2Mab-119, an Anti-Human Epidermal Growth Factor Receptor 2 Monoclonal Antibody, Against Pancreatic Cancer," *Monoclon Antib Immunodiagn Immunother.*, 36(6):287-290 (2017).

Casneuf et al., "Effects of daratumumab on natural killer cells and impact on clinical outcomes in relapsed or refractory multiple myeloma," *Blood Adv.*, 1(23):2105-2114 (2017).

Christodoulou et al., "Engineering CAR-NK cells to secrete IL-15 sustains their anti-AML functionality but is associated with systemic toxicities," *J. ImmunoTher. Cancer*, 9(12):e003894 (2021).

Donnelly et al., "The 'cleavage' activities of foot-and-mouth disease virus 2A site-directed mutants and naturally occurring '2A-like' sequences," *J. Gen. Virol.*, 82:1027-1041 (2001).

Dragomir et al., "Key questions about the checkpoint blockade-are microRNAs an answer?," *Cancer Biol. Med.*, 15(2):103-115 (2018).

Hegde et al., "Tandem Car T cells targeting HER2 and IL13Rα2 mitigate tumor antigen escape," *J. Clin. Invest.*, 126(8):3036-3052 (2016).

Kohli et al., "Key chemokines direct migration of immune cells in solid tumors," *Cancer Gene Ther.*, 29:10-21 (2021).

Mo et al., "Engineered off-the-shelf therapeutic T cells resist host immune rejection," *Nat. Biotechnol.*, 39(1):56-63 (2020).

Ryan et al., "Cleavage of foot-and-mouth disease virus polyprotein is mediated by residues located within a 19 amino acid sequence," *J. Gen. Virol.*, 72:2727-2732 (2001).

* cited by examiner

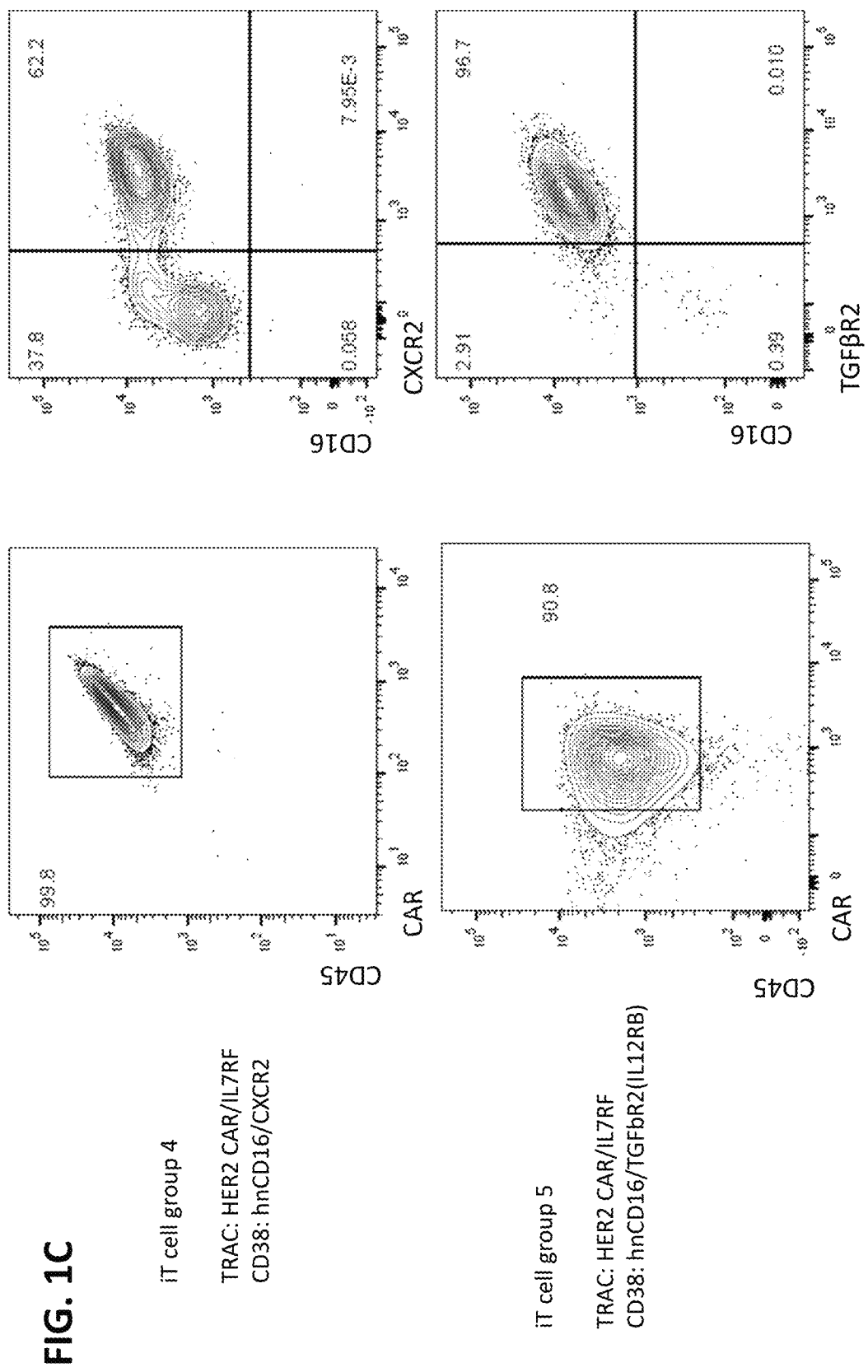

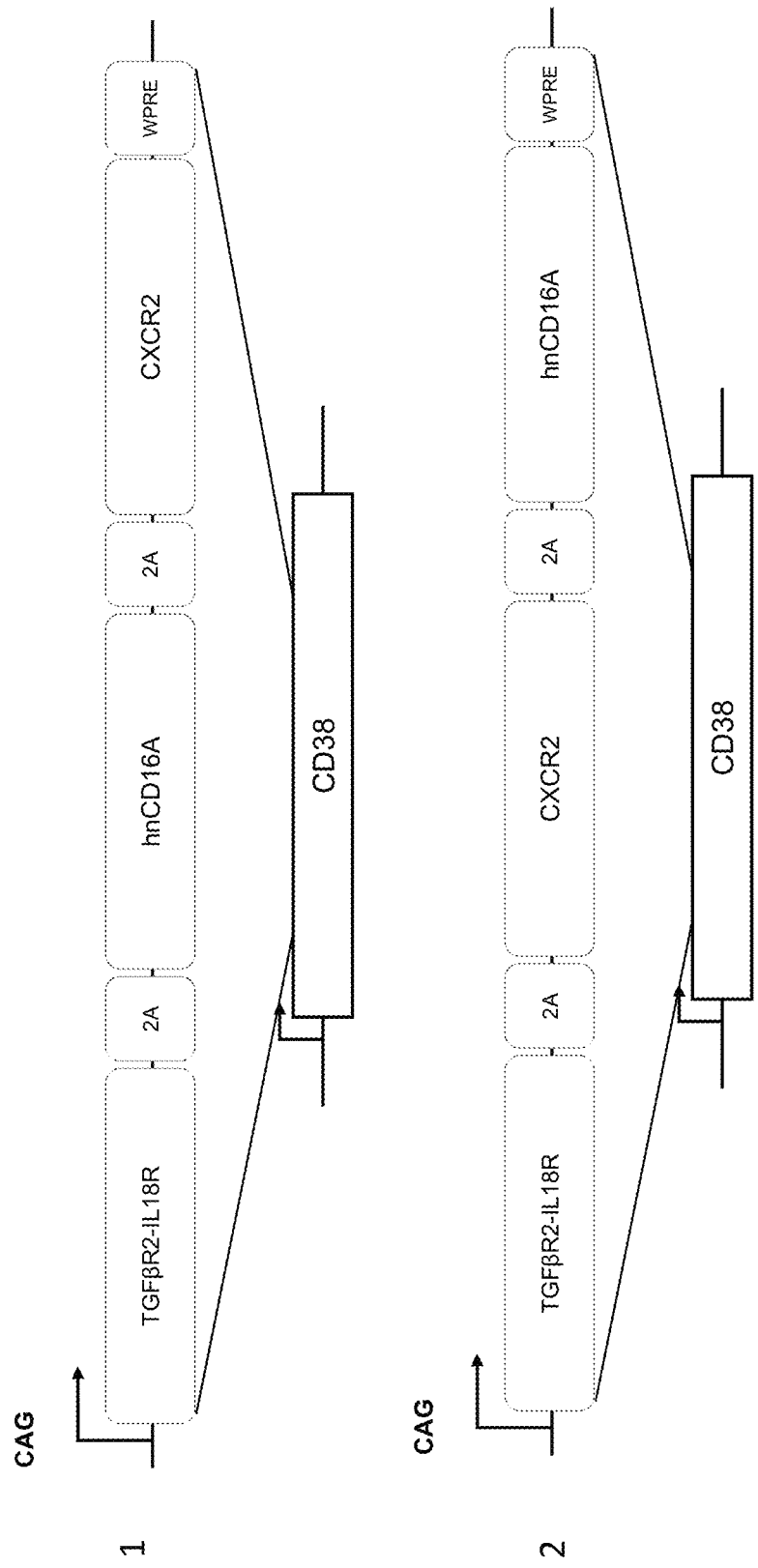

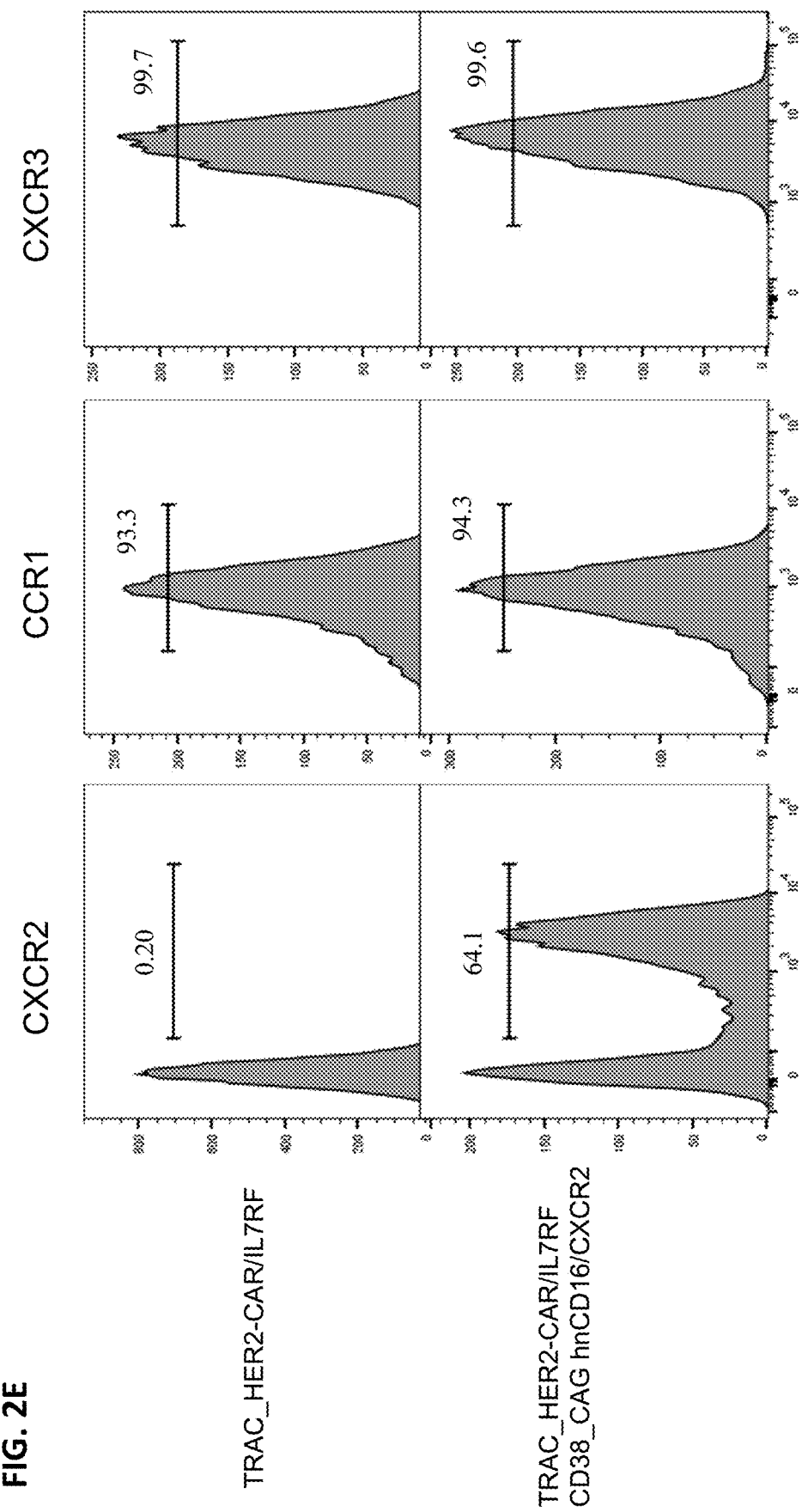

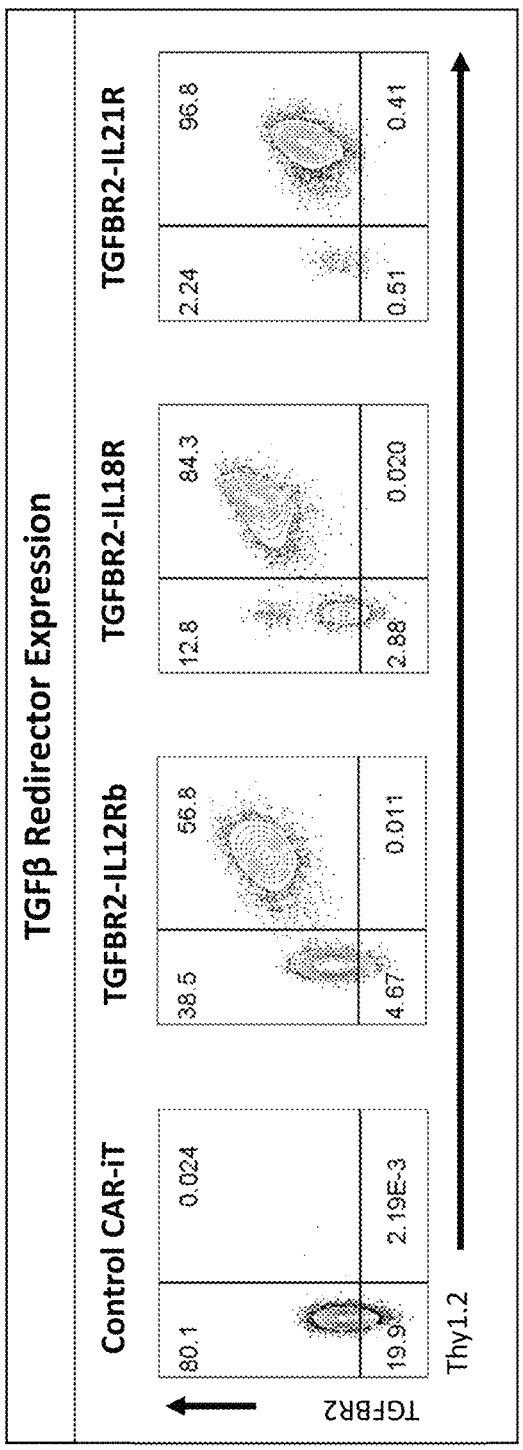
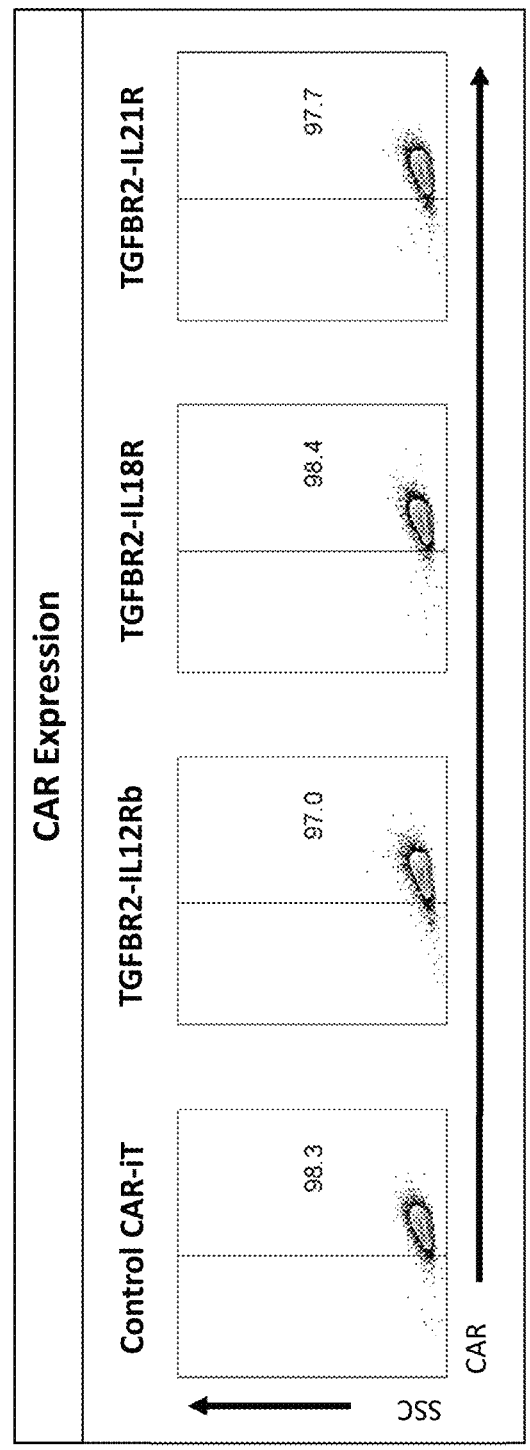
FIG. 4B
FIG. 4C

CELLS HAVING SOLID TUMOR TARGETING BACKBONE AND USE THEREOF

RELATED APPLICATIONS

This application claims priority to U.S. Provisional Application Ser. No. 63/329,364, filed Apr. 8, 2022, and to U.S. Provisional Application Ser. No. 63/380,378, filed Oct. 20, 2022, the disclosures of which are hereby incorporated by reference in their entireties.

PARTIES TO A JOINT RESEARCH AGREEMENT

The presently claimed subject matter was made by, or on behalf of, one or more parties to a joint research agreement. The parties to the joint research agreement are Fate Therapeutics, Inc. and Ono Pharmaceutical Co., Ltd.

INCORPORATION BY REFERENCE OF SEQUENCE LISTING

The Sequence Listing titled 184143-641601_SL.xml, which was created on Mar. 15, 2023 and is 192,945 bytes in size, is hereby incorporated by reference in its entirety.

FIELD OF THE INVENTION

The present disclosure is broadly concerned with the field of off-the-shelf immunocellular products. More particularly, the present disclosure is concerned with strategies for developing multifunctional effector cells capable of delivering therapeutically relevant properties in vivo. Cell products developed under the present disclosure address critical limitations of patient-sourced cell therapies.

BACKGROUND OF THE INVENTION

The field of adoptive cell therapy is currently focused on using patient- and donor-sourced cells, which makes it particularly difficult to achieve consistent manufacturing of cancer immunotherapies and to deliver therapies to all patients who may benefit therefrom. There is also a need to improve the efficacy and persistence of adoptively transferred lymphocytes to promote favorable patient outcomes. Lymphocytes such as T cells and natural killer (NK) cells are potent anti-tumor effectors that play an important role in innate and adaptive immunity. However, the use of these immune cells for adoptive cell therapies remains challenging and has unmet needs for improvement. Therefore, there remain significant opportunities to harness the full potential of T and NK cells, or other immune effector cells in adoptive immunotherapy.

SUMMARY OF THE INVENTION

There is a need for functionally improved effector cells that address issues ranging from response rate, cell exhaustion, loss of transfused cells (survival and/or persistence), tumor escape through target loss or lineage switch, tumor targeting precision, off-target toxicity, off-tumor effect, to efficacy against solid tumors, i.e., tumor microenvironment and related immune suppression, recruiting, trafficking and infiltration.

It is an object of embodiments of the present invention to provide methods and compositions to generate derivative non-pluripotent cells differentiated from a single cell derived iPSC (induced pluripotent stem cell) clonal line, which iPSC line comprises one or several genetic modifications in its genome. In some embodiments, the one or several genetic modifications include one or more of DNA insertion, deletion, and substitution, and which modifications are retained and remain functional in subsequently derived cells after differentiation, expansion, passaging and/or transplantation.

The iPSC derived non-pluripotent cells of the present application include, but are not limited to, $CD34^+$ cells, hemogenic endothelium cells, HSCs (hematopoietic stem and progenitor cells), hematopoietic multipotent progenitor cells, T cell progenitors, NK cell progenitors, T cells, NKT cells, NK cells, and B cells. The iPSC-derived non-pluripotent cells of the present application comprise one or several genetic modifications in their genome through differentiation from an iPSC comprising the same genetic modifications. In some embodiments, the engineered clonal iPSC differentiation strategy for obtaining genetically engineered derivative cells benefits from the developmental potential of the iPSC in a directed differentiation that is not significantly adversely impacted by the engineered modality in the iPSC, and also that the engineered modality functions as intended in the derivative cell. Further, this strategy overcomes the present barrier in engineering primary lymphocytes, such as T cells or NK cells obtained from peripheral blood, as such cells are difficult to engineer, with engineering of such cells often lacking reproducibility and uniformity, resulting in cells exhibiting poor cell persistence with high cell death and low cell expansion. Moreover, this strategy avoids production of a heterogenous effector cell population otherwise obtained using primary cell sources which are heterogenous to start with.

Accordingly, in one aspect, the present invention provides a cell or population thereof, wherein: (i) the cell is (a) an immune cell; (b) an induced pluripotent cell (iPSC); or (c) a derivative effector cell obtained from differentiating the iPSC; (ii) the cell comprises a solid tumor targeting backbone comprising two or more of: (a) a polynucleotide encoding a C—X—C motif chemokine receptor or a variant thereof; (b) a polynucleotide encoding a TGFβ signaling redirector receptor (TGFβ-SRR) comprising a partial or full peptide of the extracellular domain (ECD) of transforming growth factor beta receptor (TGFβR); and (c) a polynucleotide encoding an allo-immune defense receptor (ADR). In some embodiments, the ADR is specific to 4-1BB. In some embodiments, the cell has improved trafficking, tumor microenvironment (TME) resistance, and/or alloreactive resistance in solid tumors in comparison to a counterpart cell without the solid tumor targeting backbone. In various embodiments of the cell or population thereof, the solid tumor targeting backbone further comprises: (i) CD38 knockout; (ii) a polynucleotide encoding an exogenous CD16 or a variant thereof; and (iii) a polynucleotide encoding a cytokine signaling complex comprising a partial or full peptide of a cell surface expressed exogenous cytokine and/or a receptor thereof. In some embodiments of the cell or population thereof, the cell further comprises one or more of: (i) a chimeric antigen receptor (CAR); (ii) HLA-I deficiency and/or HLA-II deficiency; (iii) introduction of HLA-G or non-cleavable HLA-G, or knockout of one or both of CD58 and CD54; (iv) disruption of least one of B2M, CIITA, TAP1, TAP2, Tapasin, NLRC5, RFXANK, RFX5, RFXAP, TCR, NKG2A, NKG2D, CD25, CD44, CD54, CD56, CD58, CD69, CIS, CBL-B, SOCS2, PD1, CTLA4, LAG3, TIM3, and TIGIT; (v) introduction of at least one of HLA-E, 4-1BBL, CD3, CD4, CD8, CD47, CD113, CD131, CD137, CD80, PDL1, A$_{2A}$R, antigen-specific TCR, chimeric fusion receptor (CFR), Fc receptor, an antibody or functional variant or fragment thereof, a checkpoint inhibitor, an engager, and surface triggering receptor for coupling with an agonist; or (vi) at least one of the genotypes listed in Table 4.

In some embodiments of the cell or population thereof, the C—X—C motif chemokine receptor comprises CXCR2 or CXCR3. In some embodiments of the cell or population thereof, the TGFβ-SRR further comprises a partial or full peptide of the intracellular domain (ICD) of a cytokine receptor comprising IL2R, IL12R, IL18R, IL21R, or any combination thereof. In some embodiments of the cell or population thereof, (a) the cytokine receptor is IL2Rβ, thereby forming a TGFβRβ-IL2Rβ redirector receptor, and the intracellular domain (ICD) of IL2Rβ comprises an amino acid sequence represented by SEQ ID NO: 11 (NCRNTGPWLKKVLKCNTPDPSKFF-SQLSSEHGGDVQKWLSSPFPSSSFSPGGLAPEISPL EVLERDKVTQLLLQQDKVPEPASLSSNHSLT-SCFTNQGYFFFHLPDALEIEACQVYFTYDP YSEEDP-DEGVAGAPTGSSPQPLQPLSGEDDAYCTFPSRD-DLLLFSPSLLGGPSPPSTAPGGS GAGEERM-PPSLQERVPRDWDPQPLGPPTPGVPDLVDFQPPPEL-VLREAGEEVPDAGPREG VSFPWSRPPGQGEFRAL-NARLPLNTDAYLSLQELQGQDPTHLV); or (b) the cytokine receptor is IL12Rβ, thereby forming a TGFβR2-IL12Rβ redirector receptor, and the intracellular domain (ICD) of IL12Rβ comprises an amino acid sequence represented by (i) SEQ ID NO: 12 (HYFQQKVFVL-LAALRPQWCSREIPDPANSTCAKKYPIAEEKTQLPL-DRLLIDWPTPEDPE PLVI-SEVLHQVTPVFRHPPCSNWPQREKGIQGHQASEKD-MMHSASSPPPPRALQAESRQL VDLYKVLESRGSDPKPENPACPWTVL-PAGDLPTHDGYLPSNIDDLPSHEAPLADSLEELEP QHISLSVFPSSSLHPLTFSCGDKLTLDQLKMRCD-SLML), or (ii) SEQ ID NO: 13 (SDPKPENPACPWTVL-PAGDLPTHDGYLPSNIDDLPSHEAPLADSLEELEPQ); or (c) the cytokine receptor is IL18Rβ, thereby forming a TGFβR2-IL18Rβ redirector receptor, and the intracellular domain (ICD) of IL18Rβ comprises an amino acid sequence represented by SEQ ID NO: 14 (YRVDLVLFYRHLTRR-DETLTDGKTYDAFVSYLKECRPENGEEHTFAVEIL-PRVLEKHFGY KLCIFERDVVPGGAVV-DEIHSLIEKSRRLIIVLSKSYMSNEVRYELESGLHEAL-VERKIKIIL IEFTPVTDFTFLPQSLKLLLK-SHRVLKWKADKSLSYNSRFWKNLLYLM-PAKTVKPGRDEPE VLPVLSES); or (d) the cytokine receptor is IL21R, thereby forming a TGFβR2-IL21R redirector receptor, and the intracellular domain (ICD) of IL21Rβ comprises an amino acid sequence represented by SEQ ID NO: 15 (SLKTHPLWRLWKKIWAVPSPERFFM-PLYKGCSGDFKKWVGAPFTGSSLELGPWSPEVPS TLEVYSCHPPRSPAKRLQLTELQEPAELVES-DGVPKPSFWPTAQNSGGSAYSEERDRPYGL VSIDTVTVLDAEGPCTWPCSCEDDGYPALDLDAG-LEPSPGLEDPLLDAGTTVLSCGCVSA GSPGLGG-PLGSLLDRLKPPLADGEDWAGGLPWGGR-SPGVSESEAGSPLAGLDMDTFDS GFVGSDCSSPVECDFTSPGDEGPPRSYLRQWVVIPP-PLSSPGPQAS); or (e) the extracellular domain (ECD) of TGFβR comprises an amino acid sequence represented by SEQ ID NO: 10 (TIPPHVQKSVNNDMIVTDNN-GAVKFPQLCKFCDVRFSTCDNQKSCMSNC-SITSICEKPQE VCVAVWRKNDENITLETVCH-DPKLPYHDFILEDAASPKCIMKEKKKPGETFFMCSC-SSDE CNDNIIFSEEYNTSNPDLLLVIFQ). In some embodiments of the cell or population thereof, the cytokine receptor is a fragment of IL2Rβ, forming a TGFβR2-trIL12Rβ redirector receptor which comprises an amino acid sequence having sequence identity of at least 80%, 85%, 90%, 95%, or 97%, 98%, or 99% to a sequence represented by SEQ ID NO: 16 (TIPPHVQKSVNNDMIVTDNN-GAVKFPQLCKFCDVRFSTCDNQKSCMSNC-SITSICEKPQE VCVAVWRKNDENITLETVCH-DPKLPYHDFILEDAASPKCIMKEKKKPGETFFMCSC-SSDE CNDNIIFSEEYNTSNPDLLLVIFQVTGISLLP-PLGVAISVIIIFYCYRVNSDPKPENPACPWTV LPAGDLPTHDGYLPSNIDDLPSHEAPLADSLEELEPQ), wherein an amino acid sequence represented by SEQ ID NO: 17 (VTGISLLPPLGVAISVIIIFYCYRVN) comprised in SEQ ID NO: 16 may vary.

In various embodiments of the cell or population thereof, two or more polynucleotides of the solid tumor targeting backbone are inserted at an endogenous CD38 locus to knock out CD38. In some embodiments of the cell or population thereof, the polynucleotide encoding the exogenous CD16 or variant thereof and two or more polynucleotides of the solid tumor targeting backbone are co-expressed in a tri-cistronic construct. In some embodiments of the cell or population thereof, the exogenous CD16 or variant thereof comprises at least one of: (a) a high affinity non-cleavable CD16 (hnCD16); (b) F176V and S197P in ectodomain domain of CD16; (c) a full or partial ectodomain originated from CD64; (d) a non-native (or non-CD16) transmembrane domain; (e) a non-native (or non-CD16) intracellular domain; (f) a non-native (or non-CD16) signaling domain; (g) a non-native stimulatory domain; and (h) transmembrane, signaling, and stimulatory domains that are not originated from CD16, and are originated from a same or different polypeptide.

In various embodiments of the cell or population thereof, the cell further comprises the cytokine signaling complex comprising: (a) a partial or full peptide of a cell surface expressed exogenous cytokine or a receptor thereof comprising at least one of IL2, IL4, IL6, IL7, IL9, IL10, IL11, IL12, IL15, IL18, IL21, or respective receptor thereof; or (b) at least one of: (i) co-expression of IL15 and IL15Rα with a self-cleaving peptide in-between; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15Rβ; (vi) a fusion protein of IL15 and common receptor γC, wherein the common receptor γC is native or modified; and (vii) a homodimer of IL15Rβ; optionally wherein any one of (b)(i)-(vii) can be co-expressed with a CAR in separate constructs or in a bi-cistronic construct; or (c) at least one of: (i) a fusion protein of IL7 and IL7Rα; (ii) a fusion protein of IL7 and common receptor γC, wherein the common receptor γC is native or modified; and (iii) a homodimer of IL7Rβ, optionally wherein any one of (c)(i)-(iii) is optionally co-expressed with a CAR in separate constructs or in a bi-cistronic expression cassette; and optionally, (d) is transiently expressed.

In various embodiments of the cell or population thereof, the cell further comprises a CAR, wherein the CAR is: (i) T cell specific or NK cell specific; (ii) a bi-specific antigen binding CAR; (iii) a switchable CAR; (iv) a dimerized CAR; (v) a split CAR; (vi) a multi-chain CAR; (vii) an inducible CAR; (viii) co-expressed with another CAR; (ix) co-expressed with the cytokine signaling complex in a bi-cistronic construct; (x) co-expressed with a checkpoint inhibitor, optionally in separate constructs or in a bi-cistronic construct; (xi) specific to at least one tumor associated antigen comprising CD19, B7H3, BCMA, CD20, CD22, CD38, CD123, CD79b, CD52, EGFR, EGP2/EpCAM, GD2, GPRC5D, HER2, KLK2, MICA/B, MSLN, VEGF-R2, PSMA and PDL1; and/or (xii) specific to at least one tumor associated antigen comprising ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein-2 (EGP-2), epithelial glycoprotein-40 (EGP-40), epithelial cell adhesion molecule (Ep-CAM), EGFRvIII, receptor tyrosine-protein kinases □erbDB2,3,4, EGFIR, EGFR-VIII, ERBB folate-binding protein (FBP), fetal acetylcholine receptor (AChR), folate receptor-α, Ganglioside G2 (GD2), Ganglioside G3 (GD3), human Epidermal Growth Factor Receptor 2 (HER2), human telomerase reverse transcriptase (hTERT), ICAM-1, Integrin B7, Interleukin-13 receptor subunit alpha-2 (IL13Rα2), κ-light chain, kinase insert domain receptor (KDR), Lewis A (CA19.9), Lewis Y (LeY), L1 cell adhesion molecule (L1-CAM), LILRB2, melanoma antigen family A1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBCI, TRBC2, vascular endothelial growth factor R2 (VEGF-R2), Wilms tumor protein (WT-1), and a pathogen antigen; and optionally, wherein the CAR of any one of (i) to (xii) is inserted at a TCR locus, and/or is driven by an endogenous promoter of the TCR, and/or the TCR is knocked out by the CAR insertion. In some embodiments of the cell or population thereof, the TCR locus is a constant region of TCR alpha and/or TCR beta, and optionally wherein the CAR is operatively linked to an endogenous promoter of TCR.

In some embodiments of the cell or population thereof, the CAR comprises: (a) an ectodomain comprising an antigen binding domain specific to a tumor associated antigen; (b) a transmembrane domain; and (c) an endodomain comprising at least one signaling domain; wherein the at least one signaling domain responds specifically to binding of the CAR to the tumor associated antigen, thereby generating a cancer antigen specific response. In some embodiments of the cell or population thereof, the at least one signaling domain comprises: (a) any one of: 2B4 (Natural killer Cell Receptor 2B4), 4-1BB (Tumor necrosis factor receptor superfamily member 9), CD28 (T-cell-specific surface glycoprotein CD28), CD3ζ (T-cell surface glycoprotein CD3 zeta chain), DAP10 (Hematopoietic cell signal transducer), DAP12 (TYRO protein tyrosine kinase-binding protein), DNAM1 (CD226 antigen), FcERIγ (High affinity immunoglobulin epsilon receptor subunit gamma), IL21R (Interleukin-21 receptor), IL2Rβ/IL15Rβ (Interleukin-2 receptor subunit beta), IL2Rγ (Cytokine receptor common subunit gamma), IL7R (Interleukin-7 receptor subunit alpha), KIR2DS2 (Killer cell immunoglobulin-like receptor 2DS2), NKG2D (NKG2-D type II integral membrane protein), NKp30 (Natural cytotoxicity triggering receptor 3), NKp44 (Natural cytotoxicity triggering receptor 2), NKp46 (Natural cytotoxicity triggering receptor 1), CS1 (SLAM family member 7), and CD8 (T-cell surface glycoprotein CD8 alpha chain); (b) an amino acid sequence that has at least about 85%, about 90%, about 95%, about 96%, about 97%, about 98%, or about 99% identity to the cytoplasmic domain, or a portion thereof, of 2B4, 41BB, CD16, CD2, CD28, CD28H, CD3ζ, DAP10, DAP12, DNAM1, FcERIγ, IL21R, IL2Rβ (IL15Rβ), IL2Rγ, IL7R, KIR2DS2, NKG2D, NKp30, NKp44, NKp46, CD3ζ1XX, CS1, or CD8, represented by SEQ ID NOs: 54-76, respectively; and/or (c) an amino acid sequence that has at least about 85%, about 90%, about 95%, about 96%, about 97%, about 98%, or about 99% identity to the cytoplasmic domain, or a portion thereof, of 2B4, CD28, CD3ζ, DAP10, NKG2D, CD3ζ, CD3ζ1XX, DNAM1, CS1, or combinations thereof. In some embodiments of the cell or population thereof, the endodomain comprises two different signaling domains, and wherein said endodomain domain comprises fused cytoplasmic domains, or portions thereof, in any one of the forms: CD28-CD3ζ, CD28-CD3ζ1XX, 41BB-CD3ζ, 41BB-CD3ζ1XX, 2B4-CD3ζ and 2B4-CD3ζ1XX. In some embodiments of the cell or population thereof, the transmembrane domain comprises an amino acid sequence that has at least about 85%, about 90%, about 95%, about 96%, about 97%, about 98%, or about 99% identity to a transmembrane region, or a portion thereof, of CD2, CD3δ, CD3ε, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide. In some embodiments of the cell or population thereof, the transmembrane domain comprises an amino acid sequence that has at least about 85%, about 90%, about 95%, about 96%, about 97%, about 98%, or about 99% identity to a transmembrane region, or a portion thereof, of 2B4, CD2, CD16, CD28, CD28H, CD3ζ, DAP10, DAP12, DNAM1, FcERIγ, KIR2DS2, NKG2D, NKp30, NKp44, NKp46, CS1, or CD8, represented by SEQ ID NOs: 32-53, respectively. In some embodiments of the cell or population thereof, the transmembrane domain and its immediately linked signaling domain are from a same protein or from different proteins.

In various embodiments of the cell or population thereof, the tumor associated antigen comprises HER2, and wherein the CAR comprises: (a) an ectodomain comprising an antigen binding domain recognizing a HER2 (human epidermal growth factor receptor 2) antigen, wherein the antigen binding domain comprises: (i) a heavy chain variable (VH) domain comprising a heavy chain complementary determining region 1 (H-CDR1) comprising SEQ ID NO: 103 (NYGMS), a heavy chain complementary determining region 2 (H-CDR2) comprising SEQ ID NO: 104 (TINNNGGGTYYPDSVKG), and a heavy chain complementary determining region 3 (H-CDR3) comprising SEQ ID NO: 105 (PGLLWDA); and optionally (ii) a light chain variable (VL) domain comprising a light chain complementary determining region 1 (L-CDR1) comprising SEQ ID NO: 106 (KSSQSLLDSDGRTYLN), a light chain complementary determining region 2 (L-CDR2) comprising SEQ ID NO: 107 (LVSKLDS), and a light chain complementary determining region 3 (L-CDR3) comprising SEQ ID NO: 108 (WQGTHFPQT); (b) a transmembrane domain; and (c) an endodomain comprising at least one signaling domain; wherein the at least one signaling domain responds specifically to binding of the CAR to a HER2 antigen expressed on a cancer cell, thereby generating a cancer antigen specific response. In some embodiments of the cell or population thereof, the antigen binding domain of the CAR: (a) comprises a VH domain with at least 80% sequence identity to SEQ ID NO: 109; (b) comprises a VL domain with at least 80% sequence identity to SEQ ID NO: 110; (c) comprises a single chain variable fragment (scFV) comprising VH-linker-VL or VL-linker-VH, wherein the linker varies in length and sequence, and optionally wherein the linker has at least 80% sequence identity to SEQ ID NOs: 111-114; (d) comprises an scFV represented by an amino acid sequence that is of at least about 99%, about 98%, about 96%, about 95%, about 90%, about 85%, or about 80% identity to SEQ ID NO: 115 or SEQ ID NO: 116, wherein each of SEQ ID NOs: 115 and 116 comprises a linker that varies in length and sequence; and/or (e) is humanized. In some embodiments of the cell or population thereof, the ectodomain comprises one or more of: (a) a signal peptide; and/or (b) a spacer/hinge. In some embodiments, the spacer/hinge comprises: (a) an IgG4 spacer, a CD28 spacer, a CD8 spacer, a CH3 spacer, a CH2/CH3 spacer, or any combination thereof; (b) a short spacer of about 10 to about 80 amino acids; a medium spacer of more than 80 to about 180 amino acids; or a long spacer of more than 180 amino acids; and/or (c) an amino acid sequence of at least about 80%, about 85%, about 90%, about 95%, about 96%, about 97%, about 98%, or about 99% identity to any of SEQ ID NOs: 96-100. In some embodiments, the spacer/hinge comprises a medium spacer, wherein the spacer comprises an amino acid sequence of at least about 80%, about 85%, about 90%, about 95%, about 96%, about 97%, about 98%, or about 99% identity to SEQ ID NO: 99.

In various embodiments of the cell or population thereof, the CAR comprises an amino acid sequence of at least about 90%, about 95%, about 96%, about 97%, about 98%, or about 99% identity to SEQ ID NO: 117. In some embodiments, wherein the at least one signaling domain of the CAR responds specifically to binding of the CAR to a HER2 antigen expressed on a cancer cell, thereby generating a cancer antigen specific response, the cancer cell is a breast cancer cell, an ovary cancer cell, an endometrium cancer cell, a lung cancer cell, an esophageal cancer cell, a salivary gland cancer cell, a bladder cancer cell, a gastric cancer cell, a colorectal cancer cell, or a head and neck cancer cell.

In various embodiments of the cell or population thereof, (i) the iPSC is a clonal iPSC, a single cell dissociated iPSC, an iPSC cell line cell, or an iPSC master cell bank (MCB) cell; or (ii) the derivative cell comprises a derivative CD34$^+$ cell, a derivative hematopoietic stem and progenitor cell, a derivative hematopoietic multipotent progenitor cell, a derivative T cell progenitor, a derivative NK cell progenitor, a derivative T lineage cell, a derivative NKT lineage cell, a derivative NK lineage cell, or a derivative B lineage cell; or (iii) the derivative cell comprises a derivative effector cell having one or more functional features that are not present in a counterpart primary T, NK, NKT, and/or B cell. In some embodiments, the derivative cell has therapeutic properties comprising one or more of (i) increased cytotoxicity; (ii) improved persistency and/or survival; (iii) enhanced ability in migrating, and/or activating or recruiting bystander immune cells, to tumor sites; (iv) improved tumor infiltration; (v) enhanced ability to reduce tumor immunosuppression; (vi) improved ability in rescuing tumor antigen escape; (vii) controlled apoptosis; (viii) enhanced or acquired ADCC; and (ix) ability to avoid fratricide, in comparison to its counterpart primary cell obtained from peripheral blood, umbilical cord blood, or any other donor tissues without the same genetic edit(s). In some embodiments of the cell or population thereof, the cell is an NK lineage cell or a T lineage cell, wherein: (i) the NK lineage cell or the T lineage cell has improved infiltration and/or retention at tumor sites; (ii) the NK lineage cell is capable of recruiting, and/or migrating T cells to tumor sites; or (iii) the NK lineage cell or the T lineage cell is capable of reducing tumor immunosuppression in the presence of one or more checkpoint inhibitors.

In another aspect, the present invention provides a cell or population thereof, wherein (i) the cell is (a) an immune cell; (b) an induced pluripotent cell (iPSC); or (c) a derivative effector cell obtained from differentiating the iPSC; (ii) the cell comprises a chimeric antigen receptor (CAR) comprising: (a) an ectodomain comprising an antigen binding domain recognizing a HER2 (human epidermal growth factor receptor 2) antigen, wherein the antigen binding domain comprises: (1) a heavy chain variable (VH) domain comprising a heavy chain complementary determining region 1 (H-CDR1) comprising SEQ ID NO: 103 (NYGMS), a heavy chain complementary determining region 2 (H-CDR2) comprising SEQ ID NO: 104 (TINNNGGGTYYPDSVKG), and a heavy chain complementary determining region 3 (H-CDR3) comprising SEQ ID NO: 105 (PGLLWDA); and (2) a light chain variable (VL) domain comprising a light chain complementary determining region 1 (L-CDR1) comprising SEQ ID NO: 106 (KSSQSLLDSDGRTYLN), a light chain complementary determining region 2 (L-CDR2) comprising SEQ ID NO: 107 (LVSKLDS), and a light chain complementary determining region 3 (L-CDR3) comprising SEQ ID NO: 108 (WQGTHFPQT); (b) a transmembrane domain; and (c) an endodomain comprising at least one signaling domain; wherein the at least one signaling domain responds specifically to binding of the CAR to a HER2 antigen expressed on a cancer cell, thereby generating a cancer antigen specific response. In some embodiments of the cell or population thereof, the antigen binding domain: (a) comprises a VH domain with at least 80% sequence identity to SEQ ID NO: 109; (b) comprises a VL domain with at least 80% sequence identity to SEQ ID NO: 110; (c) comprises a single chain variable fragment (scFV) comprising VH-linker-VL or VL-linker-VH, wherein the linker varies in length and sequence, and optionally wherein the linker has at least 80% sequence identity to SEQ ID NOs: 111-114; (d) comprises an scFV represented by an amino acid sequence that is of at least about 99%, about 98%, about 96%, about 95%, about 90%, about 85%, or about 80% identity to SEQ ID NO: 115 or SEQ ID NO: 116, wherein each of SEQ ID NOs: 115 and 116 comprises a linker that varies in length and sequence; and/or (e) is humanized. In some embodiments of the cell or population thereof, the at least one signaling domain comprises: (a) any one of: 2B4 (Natural killer Cell Receptor 2B4), 4-1BB (Tumor necrosis factor receptor superfamily member 9), CD16 (IgG Fc region Receptor III-A), CD2 (T-cell surface antigen CD2), CD28 (T-cell-specific surface glycoprotein CD28), CD28H (Transmembrane and immunoglobulin domain-containing protein 2), CD3ζ (T-cell surface glycoprotein CD3 zeta chain), DAP10 (Hematopoietic cell signal transducer), DAP12 (TYRO protein tyrosine kinase-binding protein), DNAM1 (CD226 antigen), FcERIγ (High affinity immunoglobulin epsilon receptor subunit gamma), IL21R (Interleukin-21 receptor), IL2Rβ/IL15Rβ (Interleukin-2 receptor subunit beta), IL2Rγ (Cytokine receptor common subunit gamma), IL7R (Interleukin-7 receptor subunit alpha), KIR2DS2 (Killer cell immunoglobulin-like receptor 2DS2), NKG2D (NKG2-D type II integral membrane protein), NKp30 (Natural cytotoxicity triggering receptor 3), NKp44 (Natural cytotoxicity triggering receptor 2), NKp46 (Natural cytotoxicity triggering receptor 1), CS1 (SLAM family member 7), and CD8 (T-cell surface glycoprotein CD8 alpha chain); (b) an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ, IL21R, IL2Rβ (IL15Rβ), IL2Rγ, IL7R, KIR2DS2, NKG2D, NKp30, NKp44, NKp46, CS1, or CD8, represented by SEQ ID NOs: 54-76, respectively; and/or (c) an amino acid sequence that has at least about 85%, about 90%, about 95%, about 96%, about 97%, about 98%, or about 99% identity to the cytoplasmic domain, or a portion thereof, of 2B4, CD28, CD3ζ, DAP10, NKG2D, CD3ζ1XX, DNAM1, CS1, or combinations thereof. In some embodiments of the cell or population thereof, the endodomain comprises two different signaling domains, and wherein said endodomain domain comprises fused cytoplasmic domains, or portions thereof, in any one of the forms: 2B4-CD3ζ/1XX, 2B4-DNAM1, 2B4-FcERIγ, 2B4-DAP10, CD16-DNAM1, CD16-DAP10, CD16-DAP12, CD2-CD3ζ/1XX, CD2-DNAM1, CD2-FcERIγ, CD2-DAP10, CD28-DNAM1, CD28-FcERIγ, CD28-DAP10, CD28-DAP12, CD28-CD3ζ/1XX, CD28H-CD3ζ/1XX, DAP10-CD3ζ/1XX, DAP10-DAP12, DAP12-CD3ζ/1XX, DAP12-DAP10, DNAM1-CD3ζ/1XX, KIR2DS2-CD3ζ/1XX, KIR2DS2-DAP10, KIR2DS2-2B4, or NKp46-2B4.

In some embodiments of the cell or population thereof, the transmembrane domain comprises an amino acid sequence that has at least about 85%, about 90%, about 95%, about 96%, about 97%, about 98%, or about 99% identity to a transmembrane region, or a portion thereof, of: (a) CD2, CD3δ, CD3ε, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide; (b) 2B4, CD2, CD16, CD28, CD28H, CD3ζ, DAP10, DAP12, DNAM1, FcERIγ, KIR2DS2, NKG2D, NKp30, NKp44, NKp46, CS1, or CD8; or (c) 2B4, CD28, CD28H, DAP10, DNAM1, KIR2DS2, and NKG2D. In some embodiments of the cell or population thereof, the transmembrane domain and its immediately linked signaling domain are from a same protein or from different proteins. In some embodiments of the cell or population thereof, the ectodomain comprises one or more of: (a) a signal peptide; and/or (b) a spacer/hinge. In some embodiments, the spacer/hinge comprises: (a) an IgG4 spacer, a CD28 spacers, a CD8 spacer, a CH3 spacer, a CH2/CH3 spacer, or any combination thereof; (b) a short spacer of about 10 to about 80 amino acids; a medium spacer of more than 80 to about 180 amino acids; or a long spacer of more than 180 amino acids; and/or (c) an amino acid sequence of at least about 80%, about 85%, about 90%, about 95%, about 96%, about 97%, about 98%, or about 99% identity to any of SEQ ID NOs: 96-100. In one embodiment, the spacer/hinge comprises a medium spacer, wherein the spacer comprises an amino acid sequence of at least about 80%, about 85%, about 90%, about 95%, about 96%, about 97%, about 98%, or about 99% identity to SEQ ID NO: 99.

In some embodiments of the cell or population thereof, the CAR comprises an amino acid sequence of at least about 90%, about 95%, about 96%, about 97%, about 98%, or about 99% identity to SEQ ID NO: 117. In some embodiments of the cell or population thereof, the cell further comprises a solid tumor targeting backbone comprising at least one of: (a) a polynucleotide encoding a C—X—C motif chemokine receptor or a variant thereof; (b) a polynucleotide encoding a TGFβ signaling redirector receptor (TGFβ-SRR) comprising a partial or full peptide of the extracellular domain (ECD) of transforming growth factor beta receptor (TGFβR); and (c) a polynucleotide encoding an allo-immune defense receptor (ADR); optionally wherein the cell has improved trafficking, tumor microenvironment (TME) resistance, and/or alloreactive resistance in solid tumors in comparison to a counterpart cell without the solid tumor targeting backbone. In some embodiments, the ADR is specific to 4-1BB. In some embodiments of the cell or population thereof, the solid tumor targeting backbone further comprises: (i) CD38 knockout; (ii) a polynucleotide encoding an exogenous CD16 or a variant thereof; and (iii) a polynucleotide encoding a cytokine signaling complex comprising a partial or full peptide of a cell surface expressed exogenous cytokine and/or a receptor thereof. In some embodiments of the cell or population thereof, the cell further comprises one or more of: (i) HLA-I deficiency and/or HLA-II deficiency; (ii) introduction of HLA-G or non-cleavable HLA-G, or knockout of one or both of CD58 and CD54; (iii) disruption of least one of B2M, CIITA, TAP1, TAP2, Tapasin, NLRC5, RFXANK, RFX5, RFXAP, TCR, NKG2A, NKG2D, CD25, CD44, CD54, CD56, CD58, CD69, CIS, CBL-B, SOCS2, PD1, CTLA4, LAG3, TIM3, and TIGIT; (iv) introduction of at least one of HLA-E, 4-1BBL, CD3, CD4, CD8, CD47, CD113, CD131, CD137, CD80, PDL1, $A_{2A}R$, antigen-specific TCR, chimeric fusion receptor (CFR), Fc receptor, an antibody or functional variant or fragment thereof, a checkpoint inhibitor, an engager, and surface triggering receptor for coupling with an agonist; or (v) at least one of the genotypes listed in Table 4.

In some embodiments of the cell or population thereof, the C—X—C motif chemokine receptor comprises CXCR2 or CXCR3. In some embodiments of the cell or population thereof, the TGFβ-SRR further comprises a partial or full peptide of the intracellular domain (ICD) of a cytokine receptor comprising IL2R, IL12R, IL18R, IL21R, or any combination thereof. In some embodiments of the cell or population thereof, (a) the cytokine receptor is IL2Rβ, thereby forming a TGFβR2-IL2Rβ redirector receptor, and the intracellular domain (ICD) of IL2Rβ comprises an amino acid sequence represented by SEQ ID NO: 11 (NCRNTGPWLKKVLKCNTPDPSKFF-SQLSSEHGGDVQKWLSSPFPSSSFSPGGLAPEISPL EVLERDKVTQLLLQQDKVPEPASLSSNHSLT-SCFTNQGYFFFHLPDALEIEACQVYFTYDP YSEEDP-DEGVAGAPTGSSPQPLQPLSGEDDAYCTFPSRD-DLLLFSPSLLGGPSPPSTAPGGS GAGEERM-PPSLQERVPRDWDPQPLGPPTPGVPDLVDFQPPPEL-VLREAGEEVPDAGPREG VSFPWSRPPGQGEFRAL-NARLPLNTDAYLSLQELQGQDPTHLV); or (b) the cytokine receptor is IL12Rβ, thereby forming a TGFβR2-IL12Rβ redirector receptor, and the intracellular domain (ICD) of IL12Rβ comprises an amino acid sequence represented by SEQ ID NO: 12 (HYFQQKVFVL-LAALRPQWCSREIPDPANSTCAKKYPIAEEKTQLPL-DRLLIDWPTPEDPE PLVI-SEVLHQVTPVFRHPPCSNWPQREKGIQGHQASEKD-MMHSASSPPPPRALQAESRQL VDLYKVLESRGSDPKPENPACPWTVL-PAGDLPTHDGYLPSNIDDLPSHEAPLADSLEELEP QHISLSVFPSSSLHPLTFSCGDKLTLDQLKMRCD- SLML), or SEQ ID NO: 13 (SDPKPENPACPWTVLPAGDLPTHDGYLPSNIDDLPSHEAPLADSLEELEPQ); or (c) the cytokine receptor is IL18Rβ, thereby forming a TGFβR2-IL18Rβ redirector receptor, and the intracellular domain (ICD) of IL18Rβ comprises an amino acid sequence represented by SEQ ID NO: 14 (YRVDLVLFYRHLTRRDETLTDGKTYDAFVSYLKECRPENGEEHTFAVEILPRVLEKHFGY KLCIFERDVVPGGAVVDEIHSLIEKSRRLIIVLSKSYMSNEVRYELESGLHEALVERKIKIIL IEFTPVTDFTFLPQSLKLLKSHRVLKWKADKSLSYNSRFWKNLLYLMPAKTVKPGRDEPE VLPVLSES); or (d) the cytokine receptor is IL21R, thereby forming a TGFβR2-IL21R redirector receptor, and the intracellular domain (ICD) of IL21Rβ comprises an amino acid sequence represented by SEQ ID NO: 15 (SLKTHPLWRLWKKIWAVPSPERFFMPLYKGCSGDFKKWVGAPFTGSSLELGPWSPEVPS TLEVYSCHPPRSPAKRLQLTELQEPAELVESDGVPKPSFWPTAQNSGGSAYSEERDRPYG LVSIDTVTVLDAEGPCTWPCSCEDDGYPALDLDAGLEPSPGLEDPLLDAGTTVLSCGCVS AGSPGLGGPLGSLLDRLKPPLADGEDWAGGLPWGGRSPGGVSESEAGSPLAGLDMDTF DSGFVGSDCSSPVECDFTSPGDEGPPRSYLRQWVVIPPPLSSPGPQAS); or (e) the extracellular domain (ECD) of TGFβR comprises an amino acid sequence represented by SEQ ID NO: 10 (TIPPHVQKSVNNDMIVTDNNGAVKFPQLCKFCDVRFSTCDNQKSCMSNCSITSICEKPQE VCVAVWRKNDENITLETVCHDPKLPYHDFILEDAASPKCIMKEKKKPGETFFMCSCSSDE CNDNIIFSEEYNTSNPDLLLVIFQ). In some embodiments of the cell or population thereof, the cytokine receptor is a fragment of IL2Rβ, thereby forming a TGFβR2-trIL12Rβ redirector receptor which comprises an amino acid sequence having sequence identity of at least 80%, 85%, 90%, 95%, or 97%, 98%, or 99% to a sequence represented by SEQ ID NO: 16 (TIPPHVQKSVNNDMIVTDNNGAVKFPQLCKFCDVRFSTCDNQKSCMSNCSITSICEKPQE VCVAVWRKNDENITLETVCHDPKLPYHDFILEDAASPKCIMKEKKKPGETFFMCSCSSDE CNDNIIFSEEYNTSNPDLLLVIFQVTGISLLPPLGVAISVIIIFYCYRVNSDPKPENPACPWTV LPAGDLPTHDGYLPSNIDDLPSHEAPLADSLEELEPQ), wherein an amino acid sequence represented by SEQ ID NO: 17 (VTGISLLPPLGVAISVIIIFYCYRVN) comprised in SEQ ID NO: 16 may vary.

In some embodiments of the cell or population thereof, the one or more polynucleotides of the solid tumor targeting backbone are inserted at an endogenous CD38 locus to knock out CD38. In some embodiments, the polynucleotide encoding the exogenous CD16 or variant thereof and two or more polynucleotides of the solid tumor targeting backbone are co-expressed in a tri-cistronic construct. In some embodiments, the exogenous CD16 or variant thereof comprises at least one of: (a) a high affinity non-cleavable CD16 (hnCD16); (b) F176V and S197P in ectodomain domain of CD16; (c) a full or partial ectodomain originated from CD64; (d) a non-native (or non-CD16) transmembrane domain; (e) a non-native (or non-CD16) intracellular domain; (f) a non-native (or non-CD16) signaling domain; (g) a non-native stimulatory domain; and (h) transmembrane, signaling, and stimulatory domains that are not originated from CD16, and are originated from a same or different polypeptide. In some embodiments of the cell or population thereof, the cell further comprises the cytokine signaling complex comprising: (a) a partial or full peptide of a cell surface expressed exogenous cytokine or a receptor thereof comprising at least one of IL2, IL4, IL6, IL7, IL9, IL10, IL11, IL12, IL15, IL18, IL21, or respective receptor thereof; or (b) at least one of: (i) co-expression of IL15 and IL15Rα with a self-cleaving peptide in-between; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15Rβ; (vi) a fusion protein of IL15 and common receptor γC, wherein the common receptor γC is native or modified; and (vii) a homodimer of IL15Rβ; wherein any one of (b)(i)-(vii) can be co-expressed with a CAR in separate constructs or in a bi-cistronic construct; or (c) at least one of: (i) a fusion protein of IL7 and IL7Rα; (ii) a fusion protein of IL7 and common receptor γC, wherein the common receptor γC is native or modified; and (iii) a homodimer of IL7Rβ, wherein any one of (c)(i)-(iii) is optionally co-expressed with a CAR in separate constructs or in a bi-cistronic expression cassette; and optionally, (d) is transiently expressed. In some embodiments, (i) the CAR is co-expressed with a cytokine signaling complex in a bicistronic construct; and/or (ii) wherein the CAR is inserted at a TCR locus, and optionally is operatively linked to an endogenous promoter of the TCR. In some embodiments, (i) the TCR locus is a constant region of TCR alpha and/or TCR beta; and/or (ii) the TCR is knocked out by the CAR insertion.

In some embodiments, wherein the at least one signaling domain of the CAR responds specifically to binding of the CAR to a HER2 antigen expressed on a cancer cell, thereby generating a cancer antigen specific response, the cancer cell is a breast cancer cell, an ovary cancer cell, an endometrium cancer cell, a lung cancer cell, an esophageal cancer cell, a salivary gland cancer cell, a bladder cancer cell, a gastric cancer cell, a colorectal cancer cell, or a head and neck cancer cell.

In various embodiments of the cell or population thereof, (i) the iPSC is a clonal iPSC, a single cell dissociated iPSC, an iPSC cell line cell, or an iPSC master cell bank (MCB) cell; or (ii) the derivative cell comprises a derivative CD34+ cell, a derivative hematopoietic stem and progenitor cell, a derivative hematopoietic multipotent progenitor cell, a derivative T cell progenitor, a derivative NK cell progenitor, a derivative T lineage cell, a derivative NKT lineage cell, a derivative NK lineage cell, or a derivative B lineage cell; or (iii) the derivative cell comprises a derivative effector cell having one or more functional features that are not present in a counterpart primary T, NK, NKT, and/or B cell. In some embodiments, the derivative cell has therapeutic properties comprising one or more of: (i) increased cytotoxicity; (ii) improved persistency and/or survival; (iii) enhanced ability in migrating, and/or activating or recruiting bystander immune cells, to tumor sites; (iv) improved tumor infiltration; (v) enhanced ability to reduce tumor immunosuppression; (vi) improved ability in rescuing tumor antigen escape; (vii) controlled apoptosis; (viii) enhanced or acquired ADCC; and (ix) ability to avoid fratricide, in comparison to its counterpart primary cell obtained from peripheral blood, umbilical cord blood, or any other donor tissues without the same genetic edit(s). In some embodiments of the cell or population thereof, the cell is an NK lineage cell or a T lineage cell, wherein: (i) the NK lineage cell or the T lineage cell has improved infiltration and/or retention at tumor sites; (ii) the NK lineage cell is capable of recruiting, and/or migrating T cells to tumor sites; or (iii) the NK lineage cell or the T lineage cell is capable of reducing tumor immunosuppression in the presence of one or more checkpoint inhibitors.

In another aspect, the present invention provides a composition comprising the cell or population thereof provided herein. In various embodiments of the composition, the composition further comprises one or more therapeutic agents. In some embodiments of the composition, the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). In some embodiments of the composition wherein the therapeutic agent is a checkpoint inhibitor, the checkpoint inhibitor comprises: (a) one or more antagonists to checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpi, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one or more of atezolizumab, avelumab, durvalumab, ipilimumab, IPH4102, IPH43, IPH33, lirimumab, monalizumab, nivolumab, pembrolizumab, and their derivatives or functional equivalents; or (c) at least one of atezolizumab, nivolumab, and pembrolizumab. In some embodiments of the composition wherein the therapeutic agent is an antibody, the antibody comprises (a) an anti-CD20 antibody, an anti-HER2 antibody, an anti-CD52 antibody, an anti-EGFR antibody, an anti-CD123 antibody, an anti-GD2 antibody, an anti-PDL1 antibody, or an anti-CD38 antibody; or (b) one or more of rituximab, veltuzumab, ofatumumab, ublituximab, ocaratuzumab, obinutuzumab, trastuzumab, pertuzumab, alemtuzumab, cetuximab, dinutuximab, avelumab, daclizumab, basiliximab, M-A251, 2A3, BC69, 24204, 22722, 24212, MAB23591, FN50, 298614, AF2359, CY1G4, DF1513, bivatuzumab, RG7356, G44-26, 7G3, CSL362, elotuzumab, daratumumab, isatuximab, MOR202, and their humanized or Fc modified variants or fragments and their functional equivalents and biosimilars thereof. In some embodiments of the composition wherein the therapeutic agent is an engager, the engager comprises: (i) a bispecific T cell engager (BiTE); (ii) a bispecific killer cell engager (BiKE); or (iii) a tri-specific killer cell engager (TriKE); or the engager comprises: (a) a first binding domain recognizing an extracellular portion of CD3, CD28, CD5, CD16, CD64, CD32, CD33, CD89, NKG2C, NKG2D, or any functional variants thereof of the cell or a by-stander immune effector cell; and (b) a second binding domain specific to an antigen comprising any one of: B7H3, CD10, CD19, CD20, CD22, CD24, CD30, CD33, CD34, CD38, CD44, CD52, CD79a, CD79b, CD123, CD138, CD179b, CEA, CLEC12A, CS-1, DLL3, EGFR, EGFRvIII, EpCAM, FLT-3, FOLR1, FOLR3, GD2, gpA33, HER2, HM1.24, LGR5, MSLN, MCSP, MICA/B, Mucd, Muc16, PDL1, PSMA, PAMA, P-cadherin, ROR1, or VEGF-R2.

In another aspect, the present invention provides therapeutic use of the composition provided herein by introducing the composition to a subject in need of an adoptive cell therapy, wherein the subject has an autoimmune disorder, a hematological malignancy, a solid tumor, cancer, or a virus infection. In another aspect, the present invention provides a master cell bank (MCB) comprising the clonal iPSC provided herein.

In another aspect, the present invention provides a method of manufacturing the derivative cell provided herein, wherein the derivative cell is an immune effector cell, and the method comprises: (i) obtaining a genetically engineered iPSC, wherein the iPSC comprises a solid tumor targeting backbone comprising two or more of: (a) a polynucleotide encoding a C—X—C motif chemokine receptor or a variant thereof; (b) a polynucleotide encoding a TGFβ signaling redirector receptor (TGFβ-SRR) comprising a partial or full peptide of the extracellular domain (ECD) of transforming growth factor beta receptor (TGFβR); and (c) a polynucleotide encoding an allo-immune defense receptor (ADR); (ii) differentiating the genetically engineered iPSC to a derivative $CD34^+$ cell; and (iii) differentiating the derivative $CD34^+$ cell to an immune effector cell, wherein the immune effector cell retains the solid tumor targeting backbone. In some embodiments, the ADR is specific to 4-1BB. In some embodiments of the method of manufacturing, obtaining the genetically engineered iPSC comprising the solid tumor targeting backbone comprises: (a) integrating two or more polynucleotides for co-expression at an endogensous CD38 locus and knocking out CD38; wherein the two or more polynucleotides for co-expression are in a cistronic construct; and wherein the polynucleotides encode at least two of: (i) a C—X—C motif chemokine receptor; (ii) a TGFβ-SRR; and (iii) an allo-immune defense receptor (ADR). In some embodiments of the method of manufacturing, (i) the cistronic construct further comprises a polynucleotide encoding an exogenous CD16 or a variant thereof; (ii) the C—X—C motif chemokine receptor comprises CXCR2 or CXCR3; (iii) the TGFβ-SRR comprises a TGFβR2-IL2Rβ, a TGFβR2-IL12Rβ, a TGFβR2-IL18Rβ, or a TGFβR2-trIL12Rβ redirector receptor; or (iv) the ADR is specific to 4-1BB or to CD38.

In various embodiments of the method of manufacturing, the method further comprises genetically engineering the iPSC comprising a solid tumor targeting backbone by integrating a polynucleotide encoding a chimeric antigen receptor (CAR) at a TCR locus, optionally wherein (i) the CAR is operatively linked to an endogenous promoter of the TCR, and/or (ii) the TCR is knocked out by the CAR insertion. In some embodiments, the CAR is co-expressed with a cytokine signaling complex in a bi-cistronic construct; or wherein the TCR locus is a constant region of TCR alpha or TCR beta. In some embodiments, the cytokine signaling complex comprises at least one of: (i) a fusion protein of IL7 and IL7Rα; (ii) a fusion protein of IL15 and IL15Rα; and (iii) an IL15/IL15Rα fusion protein with intracellular domain of IL15Rα truncated.

In some embodiments of the method of manufacturing, the CAR is: (i) specific to a tumor associated antigen; (ii) specific to a solid tumor associated antigen; (iii) specific to a pan-tumor antigen; or (iv) specific to one of B7H3, BCMA, CD19, CD38, CD79b, EGP2/EpCAM, GPRC5D, HER2, KLK2, MICA/B, and MR1. In some embodiments, the CAR specific to the HER2 antigen expressed on a cancer cell comprises an antigen binding domain comprising: (i) a heavy chain variable (VH) domain comprising a heavy chain complementary determining region 1 (H-CDR1) comprising SEQ ID NO: 103 (NYGMS), a heavy chain complementary determining region 2 (H-CDR2) comprising SEQ ID NO: 104 (TINNNGGGTYYPDSVKG), and a heavy chain complementary determining region 3 (H-CDR3) comprising SEQ ID NO: 105 (PGLLWDA); and optionally (ii) a light chain variable (VL) domain comprising a light chain complementary determining region 1 (L-CDR1) comprising SEQ ID NO: 106 (KSSQSLLDSDGRTYLN), a light chain complementary determining region 2 (L-CDR2) comprising SEQ ID NO: 107 (LVSKLDS), and a light chain complementary determining region 3 (L-CDR3) comprising SEQ ID NO: 108 (WQGTHFPQT). In some embodiments of the method of manufacturing, the antigen binding domain: (a) comprises a VH domain with at least 80% sequence identity to SEQ ID NO: 109; (b) comprises a VL domain with at least 80% sequence identity to SEQ ID NO: 110; (c) comprises a single chain variable fragment (scFV) comprising VH-linker-VL or VL-linker-VH, wherein the linker varies in length and sequence, and optionally wherein the linker has at least 80% sequence identity to SEQ ID NOs: 111-114; (d) comprises an scFV represented by an amino acid sequence that is of at least about 99%, about 98%, about 96%, about 95%, about 90%, about 85%, or about 80% identity to SEQ ID NO: 115 or SEQ ID NO: 116, wherein each of SEQ ID NOs: 115 and 116 comprises a linker that varies in length and sequence; and/or (e) is humanized.

In some embodiments of the method of manufacturing, the method further comprises genetically engineering the iPSC comprising a solid tumor targeting backbone by one or more of: (a) introducing HLA-I deficiency, and/or HLA-II deficiency; (b) deleting or disrupting one or more of B2M, CIITA, TAP1, TAP2, Tapasin, NLRC5, RFXANK, RFX5, RFXAP, TCR, NKG2A, NKG2D, CD25, CD44, CD54, CD56, CD58, CD69, CIS, CBL-B, SOCS2, PD1, CTLA4, LAG3, TIM3, and TIGIT; and (c) introducing at least one of HLA-G, HLA-E, 4-1BBL, CD3, CD4, CD8, CD16, CD47, CD113, CD131, CD137, CD80, PDL1, $A_{2A}R$, antigen-specific TCR, chimeric fusion receptor (CFR), Fc receptor, an antibody or functional variant or fragment thereof, a checkpoint inhibitor, an engager, and surface triggering receptor for coupling with an agonist. In some embodiments, the genomic engineering comprises targeted editing. In some embodiments, the targeted editing is carried out by CRISPR, ZFN, TALEN, homing nuclease, homology recombination, or any other functional variation of these methods.

In another aspect, the present invention provides a method of treating a subject in need of an adoptive cell therapy, wherein the method comprises infusing the subject with effector cells, wherein the effector cells comprise the derivative cell or population thereof, as provided herein. In some embodiments of the method of treating, the effector cell comprises a CAR specific to HER2 antigen expressed on a cancer cell, wherein the CAR comprises: (i) a heavy chain variable (VH) domain comprising a heavy chain complementary determining region 1 (H-CDR1) comprising SEQ ID NO: 103 (NYGMS), a heavy chain complementary determining region 2 (H-CDR2) comprising SEQ ID NO: 104 (TINNNGGGTYYPDSVKG), and a heavy chain complementary determining region 3 (H-CDR3) comprising SEQ ID NO: 105 (PGLLWDA); and optionally (ii) a light chain variable (VL) domain comprising a light chain complementary determining region 1 (L-CDR1) comprising SEQ ID NO: 106 (KSSQSLLDSDGRTYLN), a light chain complementary determining region 2 (L-CDR2) comprising SEQ ID NO: 107 (LVSKLDS), and a light chain complementary determining region 3 (L-CDR3) comprising SEQ ID NO: 108 (WQGTHFPQT); wherein the CAR is at TRAC locus, and the CAR expression is driven by an endogenous TCR promoter; and wherein the subject in need of the adoptive cell therapy has breast cancer, ovary cancer, endometrium cancer, lung cancer, esophageal cancer, salivary gland cancer, bladder cancer, gastric cancer, colorectal cancer, or head and neck cancer.

In some embodiments of the method of treating, the effector cell further comprises a solid tumor targeting backbone, and wherein the effector cell comprises: (i) at CD38 locus, two or more of: (a) a polynucleotide encoding a CXCR2; (b) a polynucleotide encoding a TGFβR2-IL18Rβ redirector receptor or a TGFβR2-trIL12Rβ redirector receptor; and (c) a polynucleotide encoding an allo-immune defense receptor (ADR); (ii) at CD38 locus, a polynucleotide encoding an exogenous CD16 or a variant thereof; (iii) at TRAC locus, a polynucleotide encoding a fusion protein of IL7 and IL7Rα; and (iv) CD38 knockout and TCR knockout. In some embodiments, the ADR is specific to 4-1BB. In some embodiments of the method of treating, the method further comprises administering one or more therapeutic agents to the subject, wherein the one or more therapeutic agents comprise: (i) a cytokine, an antibody, an engager, a checkpoint inhibitor, a chemotherapeutic agent or a radioactive moiety, or an immunomodulatory drug (IMiD); (ii) an anti-CD38 antibody comprising daratumumab, isatuximab, or MOR202; (iii) an engager comprising a BiTE (bi-specific T cell engager) or a TriKE (tri-specific Killer cell engager); (iv) a checkpoint inhibitor comprising atezolizumab, avelumab, durvalumab, ipilimumab, IPH4102, IPH43, IPH33, lirimumab, monalizumab, nivolumab, or pembrolizumab; and/or (v) a chemotherapeutic agent comprising cyclophosphamide and fludarabine (Cy/Flu). In some embodiments of the method of treating, the effector cell comprises CD38 knockout and TCR knockout, and optionally an ADR specific to 4-1BB, wherein the method comprises administering to the subject an anti-CD38 antibody, and wherein the method does not require, or require minimal, lymphodepletion comprising administering Cy/Flu to the subject. In some embodiments of the method of treating, the effector cells are allogeneic, and wherein infusing the subject with effector cells is in an out-patient setting.

In another aspect, the present invention provides a method of improving an adoptive cell therapy in treating a subject having a solid tumor, wherein the method comprises administering a population of derivative cells provided herein, and optionally wherein the derivative cells have improved trafficking, tumor microenvironment (TME) resistance, and/or alloreactive resistance in solid tumors in comparison to a counterpart cell without the solid tumor targeting backbone.

In another aspect, the present invention provides a method of improving anti-HER2 monoclonal antibody (mAb) treatment, comprising: introducing to a subject in need of the treatment a composition comprising effector cells comprising a polynucleotide encoding CasMab250-CAR, a polynucleotide encoding a CXCR2, a polynucleotide encoding a TGFβ-SRR, and a polynucleotide encoding an exogenous CD16 or a variant thereof, and introducing to the subject an anti-HER2 mAb. In various embodiments, the anti-HER2 mAb is trastuzumab (Herceptin™).

In one aspect, the present invention provides a method of selecting NK cells comprising a transgene of interest. In some embodiments, the method comprises: (i) obtaining engineered NK cells comprising a construct co-expressing the transgene of interest and a partial or full peptide of a cell surface expressed exogenous cytokine or a receptor thereof comprising at least one of IL15 or respective receptor thereof; or at least one of (1) to (7): (1) co-expression of IL15 and IL15Rα with a self-cleaving peptide in-between; (2) a fusion protein of IL15 and IL15Rα; (3) an IL15/IL15Rα fusion protein with intracellular domain of IL15Rα truncated; (4) a fusion protein of IL15 and membrane bound Sushi domain of IL15Rα; (5) a fusion protein of IL15 and IL15Rβ; (6) a fusion protein of IL15 and common receptor γC, wherein the common receptor γC is native or modified; and (7) a homodimer of IL15Rβ; (ii) culturing the engineered NK cells without supplying exogenous IL15 cytokine to the cells; and (iii) collecting NK cells that expand without the exogenous IL15 cytokine, thereby selecting engineered NK cells comprising the transgene of interest.

Various objects and advantages of the compositions and methods as provided herein will become apparent from the following description taken in conjunction with the accompanying drawings wherein are set forth, by way of illustration and example, certain embodiments of this invention.

BRIEF DESCRIPTION OF THE DRAWINGS

FIGS. 1A-1E show engineering and differentiation of bi-cistronic expression CAR-iT cells. FIG. 1A shows an overview of the genetically-engineered iPSC differentiation process used to prepare effector cells in accordance with some embodiments of the invention. FIG. 1B shows evaluation of lymphoid commitment of CAR-iT cells with one of more components of a solid tumor backbone design by assessing CD45 and CD7 expression via flow cytometry. FIG. 1C shows high transgene expression by exemplary groups of engineered CAR-iT cells. FIG. 1D shows exemplary tri-cistronic constructs for CD38 locus insertion and CD38 knockout. FIG. 1E shows high expression levels of tricistron engineered CAR-iT cells compared to parental unengineered T cells.

FIG. 2E shows chemokine receptor expression of CAR-T cells engineered with TRAC_HER2-CAR/IL7RF, as compared to CAR-T cells engineered with both TRAC_HER2-CAR/IL7RF and CD38_hnCD16/CXCR2.

FIG. 4B shows flow cytometric detection of the TGFβ redirector receptors expressed by engineered CAR-iT cells. FIG. 4C shows that CAR-iT cells expressing a TGFβ redirector receptor can be successfully differentiated from a bulk-engineered iPSC population.

FIG. 21A shows representative FACS plots depicting a gating schematic of CD3+ T and CD56+ NK cells after nine days of co-culture with indicated iNK cells. FIG. 21B shows quantification of T and NK cell counts co-cultured with CAR-iNK±ADR at a 2.1 iNK cell to PBMC ratio.

FIG. 22A shows representative FACS plots of T cells after nine days of co-culture with iNK cells and analyzed for expression of CD38 and 4-1BB among CD3+ T cells as depicted in FIG. 2. FIG. 22B shows the compilation of % CD38 and %4-1BB expression among donor CD4+ and CD8+ T cells in CAR-iNK±ADR co-cultures.

DETAILED DESCRIPTION OF THE INVENTION

Figure 1A:
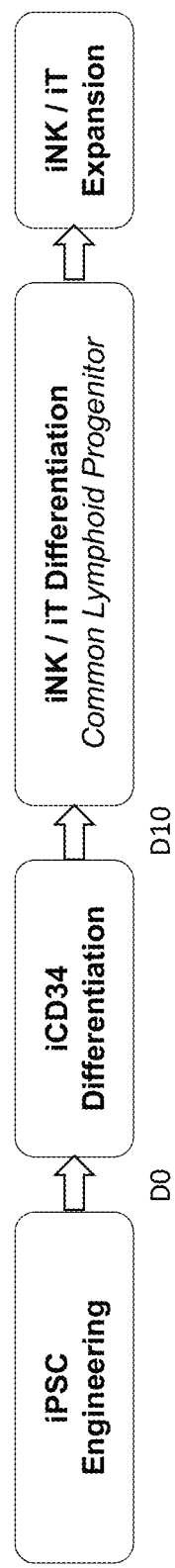

Genomic modification of iPSCs (induced pluripotent stem cells) can include one or more of polynucleotide insertion, deletion, and substitution. Exogenous gene expression in genome-engineered iPSCs often encounters problems such as gene silencing or reduced gene expression after prolonged clonal expansion of the original genome-engineered iPSCs, after cell differentiation, and in dedifferentiated cell types from the cells derived from the genome-engineered iPSCs. On the other hand, direct engineering of primary immune cells such as T or NK cells is challenging and presents a hurdle to the preparation and delivery of engineered immune cells for adoptive cell therapy. In various embodiments, the present invention provides an efficient, reliable, and targeted approach for stably integrating one or more exogenous genes, including suicide genes and other functional modalities, which provide improved therapeutic properties relating to engraftment, trafficking, homing, migration, cytotoxicity, viability, maintenance, expansion, longevity, self-renewal, persistence, and/or survival, into iPSC derivative cells, including but not limited to HSCs (hematopoietic stem and progenitor cells), T cell progenitor cells, NK cell progenitor cells, T lineage cells, NKT lineage cells, and NK lineage cells.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" are used herein to refer to one or to more than one (i.e., to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% of a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition at a functionally inert, low concentration. Similar meaning can be applied to the term "absence of," where referring to the absence of a particular substance or its source thereof of a composition.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the terms "reprogramming" or "dedifferentiation" or "increasing cell potency" or "increasing developmental potency" refer to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or "iPSCs", refers to stem cells that are produced in vitro from differentiated adult, neonatal or fetal cells that have been induced or changed, i.e., reprogrammed into cells capable of differentiating into tissues of all three germ or dermal layers: mesoderm, endoderm, and ectoderm. In some embodiments, the reprogramming process uses reprogramming factors and/or small molecule chemical driven methods. The iPSCs produced do not refer to cells as they are found in nature.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta (i.e., are not totipotent).

As used herein, the term "multipotent stem cell" refers to a cell that has the developmental potential to differentiate into cells of one or more germ layers (i.e., ectoderm, mesoderm and endoderm), but not all three. Thus, a multipotent cell can also be termed a "partially differentiated cell." Multipotent cells are known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to the state of a cell with a degree of developmental potential that is less than totipotent and pluripotent.

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) the ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "naïve" or "ground" state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed state of pluripotency. Under standard pluripotent cell culture conditions such cells remain in the primed state unless the exogenous transgene expression is maintained, wherein characteristics of the ground state are observed.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical inter-cell spacing.

As used herein, the term "subject" refers to any animal, preferably a human patient, livestock, or other domesticated animal.

A "pluripotency factor," or "reprogramming factor," refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate" or "maintain" refers to the sustaining, propagating (growing) and/or differentiating of cells outside of tissue or the body, for example in a sterile plastic (or coated plastic) cell culture dish or flask. "Cultivation" or "maintaining" may utilize a culture medium as a source of nutrients, hormones and/or other factors helpful to propagate and/or sustain the cells.

As used herein, the term "mesoderm" refers to one of the three germinal layers that appears during early embryogenesis and which gives rise to various specialized cell types including blood cells of the circulatory system, muscles, the heart, the dermis, skeleton, and other supportive and connective tissues.

As used herein, the term "definitive hemogenic endothelium" (HE) or "pluripotent stem cell-derived definitive hemogenic endothelium" (iHE) refers to a subset of endothelial cells that give rise to hematopoietic stem and progenitor cells in a process called endothelial-to-hematopoietic transition. The development of hematopoietic cells in the embryo proceeds sequentially from lateral plate mesoderm through the hemangioblast to the definitive hemogenic endothelium and hematopoietic progenitors.

The term "hematopoietic stem and progenitor cells," "hematopoietic stem cells," "hematopoietic progenitor cells," or "hematopoietic precursor cells" refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term "definitive hematopoietic stem cell" as used herein, refers to $CD34^+$ hematopoietic cells capable of giving rise to both mature myeloid and lymphoid cell types including T lineage cells, NK lineage cells and B lineage cells. Hematopoietic cells also include various subsets of primitive hematopoietic cells that give rise to primitive erythrocytes, megakarocytes and macrophages.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells in an MHC class I-restricted manner. AT cell can be any T cell, such as a cultured T cell, e.g., a primary T cell, or a T cell from a cultured T cell line, e.g., Jurkat, SupT1, etc., or a T cell obtained from a mammal. The T cell can be a $CD3^+$ cell. The T cell can be any type of T cell and can be of any developmental stage, including but not limited to, $CD4^+$/$CD8^+$ double positive T cells, $CD4^+$ helper T cells (e.g., Th1 and Th2 cells), $CD8^+$ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3 (Treg), Th17, Th9, or Tfh cells. Additional types of memory T cells include cells such as central memory T cells (Tcm cells), effector memory T cells (Tem cells and TEMRA cells). The term "T cell" can also refer to a genetically engineered T cell, such as a T cell modified to express a T cell receptor (TCR) or a chimeric antigen receptor (CAR). A T cell or T cell like effector cell can also be differentiated from a stem cell or progenitor cell ("a derived T cell" or "a derived T cell like effector cell", or collectively, "a derivative T lineage cell"). A derived T cell like effector cell may have a T cell lineage in some respects, but at the same time has one or more functional features that are not present in a primary T cell. In this application, a T cell, a T cell like effector cell, a derived T cell, a derived T cell like effector cell, or a derivative T lineage cell, are collectively termed as "a T lineage cell".

"$CD4^+$ T cells" refers to a subset of T cells that express CD4 on their surface and are associated with cell-mediated immune response. They are characterized by secretion profiles following stimulation, which may include secretion of cytokines such as IFN-gamma, TNF-alpha, IL2, IL4 and IL10. "CD4" molecules are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"$CD8^+$ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

As used herein, the term "NK cell" or "Natural Killer cell" refer to a subset of peripheral blood lymphocytes defined by the expression of CD56 or CD16 and the absence of the T cell receptor (CD3). An NK cell can be any NK cell, such as a cultured NK cell, e.g., a primary NK cell, or an NK cell from a cultured or expanded NK cell or a cell-line NK cell, e.g., NK-92, or an NK cell obtained from a mammal that is healthy or with a disease condition. As used herein, the terms "adaptive NK cell" and "memory NK cell" are interchangeable and refer to a subset of NK cells that are phenotypically $CD3^-$ and $CD56^+$, expressing at least one of NKG2C and CD57, and optionally, CD16, but lack expression of one or more of the following: PLZF, SYK, FceRγ, and EAT-2. In some embodiments, isolated subpopulations of $CD56^+$ NK cells comprise expression of CD16, NKG2C, CD57, NKG2D, NCR ligands, NKp30, NKp40, NKp46, activating and inhibitory KIRs, NKG2A and/or DNAM-1. $CD56^+$ can be dim or bright expression. An NK cell, or an NK cell like effector cell may be differentiated from a stem cell or progenitor cell ("a derived NK cell" or "a derived NK cell like effector cell", or collectively, "a derivative NK lineage cell"). A derivative NK cell like effector cell may have an NK cell lineage in some respects, but at the same time has one or more functional features that are not present in a primary NK cell. In this application, an NK cell, an NK cell like effector cell, a derived NK cell, a derived NK cell like effector cell, or a derivative NK lineage cell, are collectively termed as "an NK lineage cell".

As used herein, the term "NKT cells" or "natural killer T cells" or "NKT lineage cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are recognized. Invariant or type I NKT cells express a very limited TCR repertoire—a canonical α-chain (Vα24-Jα18 in humans) associated with a limited spectrum of R chains (Vβ11 in humans). The second population of NKT cells, called non-classical or non-invariant type II NKT cells, display a more heterogeneous TCR αβ usage. Type I NKT cells are considered suitable for immunotherapy. Adaptive or invariant (type I) NKT cells can be identified by the expression of one or more of the following markers: TCR Vα24-Jα18, Vb11, CD1d, CD3, CD4, CD8, aGalCer, CD161 and CD56.

The term "effector cell" generally is applied to certain cells in the immune system that carry out a specific activity in response to stimulation and/or activation, or to cells that effect a specific function upon activation. As used herein, the term "effector cell" includes, and in some contexts is interchangeable with, immune cells, "differentiated immune cells," and primary or differentiated cells that are edited and/or modulated to carry out a specific activity in response to stimulation and/or activation. Non-limiting examples of effector cells include primary-sourced or iPSC-derived T cells, NK cells, NKT cells, B cells, macrophages, and neutrophils.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, isolated from a tissue or biopsy sample. The term also includes a cell that is removed from at least one, some or all components as the cell is found in non-naturally occurring environments, for example, isolated form a cell culture or cell suspension. Therefore, an "isolated cell" is partly or completely separated from at least one component, including other substances, cells or cell populations, as it is found in nature or as it is grown, stored or subsisted in non-naturally occurring environments. Specific examples of isolated cells include partially pure cell compositions, substantially pure cell compositions and cells cultured in a medium that is non-naturally occurring. Isolated cells may be obtained by separating the desired cells, or populations thereof, from other substances or cells in the environment, or by removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as "encoding" the protein or other product of that gene or cDNA.

A "construct" refers to a macromolecule or complex of molecules comprising a polynucleotide to be delivered to a host cell, either in vitro or in vivo. A "vector," as used herein refers to any nucleic acid construct capable of directing the delivery or transfer of a foreign genetic material to target cells, where it can be replicated and/or expressed. Thus, the term "vector" comprises the construct to be delivered. A vector can be a linear or a circular molecule. A vector can be integrating or non-integrating. The major types of vectors include, but are not limited to, plasmids, episomal vectors, viral vectors, cosmids, and artificial chromosomes. Viral vectors include, but are not limited to, adenovirus vectors, adeno-associated virus vectors, retrovirus vectors, lentivirus vectors, Sendai virus vectors, and the like.

As used from time to time throughout the application, the expression of "TRAC_[construct]", with "[construct]" being a variable expression construct having components and arrangement thereof specified in a given context, means that the expression construct is inserted at the TRAC locus to knock out TCR and with the component(s) of the expression construct expressed or co-expressed under the control of the endogenous TCR promoter.

As used from time to time throughout the application, the expression of "CD38_[construct]", with "[construct]" being a variable expression construct having components and arrangement thereof specified in a given context, means that the expression construct is inserted at the CD38 locus to knock out CD38 and with the component(s) of the expression construct expressed or co-expressed, whether under control of the endogenous CD38 promoter or under an exogenous promoter in the construct.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site. In the case, where there is a deletion at the insertion site, "integration" may further comprise replacement of the endogenous sequence or a nucleotide that is deleted with the one or more inserted nucleotides.

As used herein, the term "exogenous" is intended to mean that the referenced molecule or the referenced activity is introduced into, or is non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e., a polypeptide found in nature) or fragment thereof; a variant polypeptide (i.e., a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. "Polynucleotide" also refers to both double- and single-stranded molecules.

As used herein, the terms "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

As used herein, the term "subunit" refers to each separate polypeptide chain of a protein complex, where each separate polypeptide chain can form a stable folded structure by itself. Many protein molecules are composed of more than one subunit, where the amino acid sequences can either be identical for each subunit, or similar, or completely different. For example, CD3 complex is composed of CD3α, CD3ε, CD3δ, CD3γ, and CD3ζ subunits, which form the CD3ε/CD3γ, CD3ε/CD3δ, and CD3ζ/CD3ζ dimers. Within a single subunit, contiguous portions of the polypeptide chain frequently fold into compact, local, semi-independent units that are called "domains". Many protein domains may further comprise independent "structural subunits", also called subdomains, contributing to a common function of the domain. As such, the term "subdomain" as used herein refers to a protein domain inside of a larger domain, for example, a binding domain within an ectodomain of a cell surface receptor; or a stimulatory domain or a signaling domain of an endodomain of a cell surface receptor.

"Operably-linked" or "operatively linked," interchangeable with "operably connected" or "operatively connected," refers to the association of nucleic acid sequences on a single nucleic acid fragment (or amino acids in a polypeptide with multiple domains) so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or antisense orientation. As a further example, a receptor-binding domain can be operatively connected to an intracellular signaling domain, such that binding of the receptor to a ligand transduces a signal responsive to said binding.

"Fusion proteins" or "chimeric proteins", as used herein, are proteins created through genetic engineering to join two or more partial or whole polynucleotide coding sequences encoding separate proteins, and the expression of these joined polynucleotides results in a single peptide or multiple polypeptides with functional properties derived from each of the original proteins or fragments thereof. Between two neighboring polypeptides of different sources in the fusion protein, a linker (or spacer) peptide can be added.

As used herein, the term "genetic imprint" refers to genetic or epigenetic information that contributes to preferential therapeutic attributes in a source cell or an iPSC, and is retainable in the source cell derived iPSCs, and/or the iPSC-derived hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom are sometimes collectively called "derived" or "derivative" cells depending on the context. For example, derivative effector cells, or derivative NK cells or derivative T cells, as used throughout this application are cells differentiated from an iPSC, as compared to their primary counterpart obtained from natural/native sources such as peripheral blood, umbilical cord blood, or other donor tissues. As used herein, the genetic imprint(s) conferring a preferential therapeutic attribute is incorporated into the iPSCs either through reprogramming a selected source cell that is donor-, disease-, or treatment response-specific, or through introducing genetically modified modalities to iPSCs using genomic editing. In the aspect of a source cell obtained from a specifically selected donor, disease or treatment context, the genetic imprint contributing to preferential therapeutic attributes may include any context-specific genetic or epigenetic modifications which manifest a retainable phenotype, i.e., a preferential therapeutic attribute, that is passed on to derivative cells of the selected source cell, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof, resistance to tumor microenvironment; induction of bystander immune cells and immune modulations; improved on-target specificity with reduced off-tumor effect; and/or resistance to treatment such as chemotherapy. When derivative cells having one or more therapeutic attributes are obtained from differentiating an iPSC that has genetic imprint(s) conferring a preferential therapeutic attribute incorporated thereto, such derivative cells are also called "synthetic cells". In general, a synthetic cell possesses one or more non-native cell functions when compared to its closest counterpart primary cell, whether the synthetic cell is differentiated from engineered pluripotent cells or obtained by engineering a primary cell from natural/native sources, such as peripheral blood, umbilical cord blood, or other donor tissues. For example, synthetic effector cells, or synthetic NK cells or synthetic T cells, as used throughout this application are cells differentiated from a genomically modified iPSC, as compared to their primary counterpart obtained from natural/native sources such as peripheral blood, umbilical cord blood, or other donor tissues. In some embodiments, the synthetic cell possesses one or more non-native cell functions when compared to its closest counterpart primary cell.

The term "enhanced therapeutic property" as used herein, refers to a therapeutic property of a cell that is enhanced as compared to a typical immune cell of the same general cell type. For example, an NK cell with an "enhanced therapeutic property" will possess an enhanced, improved, and/or augmented therapeutic property as compared to a typical, unmodified, and/or naturally occurring NK cell. Therapeutic properties of an immune cell may include, but are not limited to, cell engraftment, trafficking, homing, viability, self-renewal, persistence, immune response regulation and modulation, survival, and cytotoxicity. Therapeutic properties of an immune cell are also manifested by antigen targeting receptor expression; HLA presentation or lack thereof; resistance to tumor microenvironment; induction of bystander immune cells and immune modulations; improved on-target specificity with reduced off-tumor effect; and/or resistance to treatment such as chemotherapy.

As used herein, the term "engager" refers to a molecule, e.g., a fusion polypeptide, which is capable of forming a link between an immune cell (e.g., a T cell, a NK cell, a NKT cell, a B cell, a macrophage, a neutrophil), and a tumor cell; and activating the immune cell. Examples of engagers include, but are not limited to, bi-specific T cell engagers (BiTEs), bi-specific killer cell engagers (BiKEs), tri-specific killer cell engagers (TriKEs), or multi-specific killer cell engagers, or universal engagers compatible with multiple immune cell types.

As used herein, the term "surface triggering receptor" refers to a receptor capable of triggering or initiating an immune response, e.g., a cytotoxic response. Surface triggering receptors may be engineered, and may be expressed on effector cells, e.g., a T cell, a NK cell, a NKT cell, a B cell, a macrophage, or a neutrophil. In some embodiments, the surface triggering receptor facilitates bi- or multi-specific antibody engagement between the effector cells and a specific target cell (e.g., a tumor cell) independent of the effector cells' natural receptors and cell types. Using this approach, one may generate iPSCs comprising a universal surface triggering receptor, and then differentiate such iPSCs into populations of various effector cell types that express the universal surface triggering receptor. By "universal", it is meant that the surface triggering receptor can be expressed in, and activate, any effector cells irrespective of the cell type, and all effector cells expressing the universal receptor can be coupled or linked to the engagers recognizable by the surface triggering receptor, regardless of the engager's tumor binding specificities. In some embodiments, engagers having the same tumor targeting specificity are used to couple with the universal surface triggering receptor. In some embodiments, engagers having different tumor targeting specificity are used to couple with the universal surface triggering receptor. As such, one or multiple effector cell types can be engaged to kill one specific type of tumor cells in some cases, and to kill two or more types of tumors in other cases. A surface triggering receptor generally comprises a co-stimulatory domain for effector cell activation and an anti-epitope that is specific to the epitope of an engager. A bi-specific engager is specific to the anti-epitope of a surface triggering receptor on one end, and is specific to a tumor antigen on the other end.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch protein could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g., a prodrug, that when activated, triggers apoptosis and/or cell death of a therapeutic cell. Examples of safety switch proteins include, but are not limited to, suicide genes such as caspase 9 (or caspase 3 or 7), thymidine kinase, cytosine deaminase, B cell CD20, modified EGFR, and any combination thereof. In this strategy, a prodrug that is administered in the event of an adverse event is activated by the suicide-gene product and kills the transduced cell.

As used herein, the term "pharmaceutically active proteins or peptides" refers to proteins or peptides that are capable of achieving a biological and/or pharmaceutical effect on an organism. A pharmaceutically active protein has healing, curative or palliative properties against a disease and may be administered to ameliorate, relieve, alleviate, reverse or lessen the severity of a disease. A pharmaceutically active protein also has prophylactic properties and is used to prevent the onset of a disease or to lessen the severity of such disease or pathological condition when it does emerge. "Pharmaceutically active proteins" include an entire protein or peptide or pharmaceutically active fragments thereof. The term also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. Examples of pharmaceutically active proteins or peptides include, but are not limited to, receptors, binding proteins, transcription and translation factors, tumor growth suppressing proteins, antibodies or fragments thereof, growth factors, and/or cytokines.

As used herein, the term "signaling molecule" refers to any molecule that modulates, participates in, inhibits, activates, reduces, or increases, cellular signal transduction. "Signal transduction" refers to the transmission of a molecular signal in the form of chemical modification by recruitment of protein complexes along a pathway that ultimately triggers a biochemical event in the cell. Examples of signal transduction pathways are known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "targeting modality" refers to a molecule, e.g., a polypeptide, that is genetically incorporated into a cell to promote antigen and/or epitope specificity that includes, but is not limited to, i) antigen specificity as it relates to a unique chimeric antigen receptor (CAR) or T cell receptor (TCR), ii) engager specificity as it relates to monoclonal antibodies or bispecific engagers, iii) targeting of transformed cells, iv) targeting of cancer stem cells, and v) other targeting strategies in the absence of a specific antigen or surface molecule.

As used herein, the term "specific" or "specificity" can be used to refer to the ability of a molecule, e.g., a receptor or an engager, to selectively bind to a target molecule, in contrast to non-specific or non-selective binding.

The term "adoptive cell therapy" as used herein refers to a cell-based immunotherapy that relates to the transfusion of autologous or allogeneic lymphocytes, whether the immune cells are isolated from a human donor, or effector cells obtained from in vitro differentiation of a pluripotent cell; whether they are genetically modified or not; or whether they are primary donor cells or cells that have been passaged, expanded, or immortalized, ex vivo, after isolation from a donor.

As used herein, "radiation" refers to the emission or transmission of energy in the form of waves or particles. Exemplary forms of radiation include, but are not limited to, electromagnetic radiation (e.g., radio waves, microwaves, infrared, visible light, ultraviolet, x-rays, and gamma radiation), particle radiation (e.g., alpha radiation, beta radiation, proton radiation and neutron radiation), and acoustic radiation (e.g., ultrasound, sound and seismic waves). In various embodiments, the amount of radiation is measured as a Gray (Gy), which is defined as the absorption of one joule of radiation energy per kilogram of matter. In radiation therapy, the amount of radiation applied varies depending on the type and stage of cancer being treated. For curative cases, the typical dose for a solid epithelial tumor ranges from 60 to 80 Gy, while lymphomas are typically treated with 20 to 40 Gy. Preventive (adjuvant) doses are typically around 45-60 Gy in 1.8-2 Gy fractions (for, e.g., breast, head, and neck cancers). In various embodiments, radiation may be used as a sensitizing agent as disclosed herein.

As used herein, "radiation therapy" or "radiotherapy" are used interchangeably to refer to a type of cancer treatment that involves use of radiation to damage cells by destroying the genetic material that controls how cells grow and divide. While both healthy and cancerous cells are damaged by radiation therapy, the goal of radiation therapy is to destroy as few normal, healthy cells as possible. The term "radiation therapy" often refers to external beam radiation therapy, wherein high-energy beams (e.g., x-rays, gamma rays, photons, protons, neutrons, ions, and any other forms of energy applicable to such treatments) are produced by a machine outside of the subject being treated, and are aimed at a precise point on the subject's body. However, the term "radiation therapy" also includes brachytherapy, wherein seeds, ribbons, or capsules that contain or are otherwise linked to a radiation source are placed inside the subject's body in or near a tumor or cancer cell. Included in brachytherapy are low-dose rate implants, high-dose rate implants, and permanent implants. Also included in the term "radiation therapy" is systemic radiation therapy, wherein radioactive drugs (e.g., radiopharmaceuticals or radionuclides, including radiopeptides) are given to the subject orally or intravenously and collect within the subject's body at the tumor or area where cancers cells are located. Similar to antibody-drug candidates, where an antibody that binds to a tumor antigen is linked to a toxic drug, radiopharmaceuticals incorporate a radioactive compound linked to a targeting molecule (such as an antibody) that specifically binds to a tumor antigen. Examples of radioactive compounds useful in radiopharmaceuticals include, but are not limited to calcium-47, carbon-11, carbon-14, chromium-51, cobalt-57, cobalt-58, erbium-169, fluorine-18, gallium-67, gallium-68, hydrogen-3, indium-111, iodine-123, iodine-125, iodine-131, iorn-59, krypton-81m, lutetium-177, nitrogen-13, oxygen-15, phosphorus-32, radium-223, rubidium-82, samarium-153, selenium-75, sodium-22, sodium-24, strontium-89, technetium-99m, thallium-201, xenon-133, and yttrium-90. In various embodiments, radiation therapy may be used as a sensitizing agent as disclosed herein.

As used herein, "lymphodepletion" and "lympho-conditioning" are used interchangeably to refer to the destruction of lymphocytes and T cells, typically prior to immunotherapy. The purpose of lympho-conditioning prior to the administration of an adoptive cell therapy is to promote homeostatic proliferation of effector cells as well as to eliminate regulatory immune cells and other competing elements of the immune system that compete for homeostatic cytokines. Thus, lympho-conditioning is typically accomplished by administering one or more chemotherapeutic agents to the subject prior to a first dose of the adoptive cell therapy. In various embodiments, lympho-conditioning precedes the first dose of the adoptive cell therapy by a few hours to a few days. Exemplary chemotherapeutic agents useful for lympho-conditioning include, but are not limited to, cyclophosphamide (CY), fludarabine (FLU), and those described below. However, a sufficient lymphodepletion through anti-CD38 mAb could provide an alternative conditioning process for the present iNK cell therapy, without or with minimal need of a CY/FLU-based lympho-conditioning procedure, as further described herein.

As used herein, "homing" or "trafficking" refers to active navigation (migration) of a cell to a target site (e.g., a cell, tissue (e.g., tumor), or organ). A "homing molecule" refers to a molecule that directs cells to a target site. In some embodiments, a homing molecule functions to recognize and/or initiate interaction of a cell to a target site. In some embodiments, a homing molecule is a chemokine receptor.

As used herein, "chemokine receptor" refers to a cell surface molecule that binds to a chemokine. A chemokine receptor can comprise a naturally occurring or recombinant chemokine receptor or a variant thereof. Exemplary chemokine receptors include, but are not limited to, a CXC chemokine receptor (for example, CXCR1, CXCR2, CXCR3, CXCR4, CXCR5, CXCR6, or CXCR7), a CC chemokine receptor (for example, CCR1, CCR2, CCR3, CCR4, CCR5, CCR6, CCR7, CCR8, CCR9, CCR10, or CCR11), a CX3C chemokine receptor (for example, CX3CR1), an XC chemokine receptor (for example, XCR1), or a variant thereof.

A "therapeutically sufficient amount", as used herein, includes within its meaning a non-toxic, but sufficient and/or effective amount of a particular therapeutic agent and/or pharmaceutical composition to which it is referring to provide a desired therapeutic effect. The exact amount required will vary from subject to subject, depending on factors such as the patient's general health, the patient's age and the stage and severity of the condition being treated. In particular embodiments, a "therapeutically sufficient amount" is sufficient and/or effective to ameliorate, reduce, and/or improve at least one symptom associated with a disease or condition of the subject being treated.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate lineage-specific differentiation. "Embryoid bodies" are three-dimensional clusters that have been shown to mimic embryo development as they give rise to numerous lineages within their three-dimensional area. Through the differentiation process, typically a few hours to days, simple EBs (for example, aggregated pluripotent stem cells elicited to differentiate) continue maturation and develop into a cystic EB at which time, typically days to a few weeks, they are further processed to continue differentiation. EB formation is initiated by bringing pluripotent stem cells into close proximity with one another in three-dimensional multilayered clusters of cells. Typically, this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (i.e., ectoderm, mesoderm and endoderm germ layers) with modest proliferation within the EB cell cluster. Although proven to facilitate cell differentiation, EBs, however, give rise to heterogeneous cells in variable differentiation states because of the inconsistent exposure of the cells in the three-dimensional structure to the differentiation cues within the environment. In addition, EBs are laborious to create and maintain. Moreover, cell differentiation through EB formation is accompanied with modest cell expansion, which also contributes to low differentiation efficiency.

In comparison, "aggregate formation," as distinct from "EB formation," can be used to expand the populations of pluripotent stem cell derived cells. For example, during aggregate-based pluripotent stem cell expansion, culture media are selected to maintain proliferation and pluripotency. Cell proliferation generally increases the size of the aggregates, forming larger aggregates, which can be mechanically or enzymatically dissociated into smaller aggregates to maintain cell proliferation within the culture and increase numbers of cells. As distinct from EB culture, cells cultured within aggregates in maintenance culture media maintain markers of pluripotency. The pluripotent stem cell aggregates require further differentiation cues to induce differentiation.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation to initiate differentiation. Because monolayer culturing does not mimic embryo development such as is the case with EB formation, differentiation towards specific lineages is deemed to be minimal as compared to all three germ layer differentiation in EB formation.

As used herein, a "dissociated cell" or "single dissociated cell" refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be enzymatically or mechanically dissociated from each other, such as by dissociation into a suspension of clusters, single cells or a mixture of single cells and clusters. In yet another alternative embodiment, adherent cells can be dissociated from a culture plate or other surface. Dissociation thus can involve breaking cell interactions with extracellular matrix (ECM) and substrates (e.g., culture surfaces), or breaking the ECM between cells.

As used herein, a "master cell bank" or "MCB" refers to a clonal master engineered iPSC line, which is a clonal population of iPSCs that have been engineered to comprise one or more therapeutic attributes, have been characterized, tested, qualified, and expanded, and have been shown to reliably serve as the starting cellular material for the production of cell-based therapeutics through directed differentiation in manufacturing settings. In various embodiments, an MCB is maintained, stored, and/or cryopreserved in multiple vessels to prevent genetic variation and/or potential contamination by reducing and/or eliminating the total number of times the iPS cell line is passaged, thawed or handled during the manufacturing processes.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an antimitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell type, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

"Functional" as used in the context of genomic editing or modification of iPSC, and derived non-pluripotent cells differentiated therefrom, or genomic editing or modification of non-pluripotent cells and derived iPSCs reprogrammed therefrom, refers to (1) at the gene level-successful knocked-in, knocked-out, knocked-down gene expression, transgenic or controlled gene expression such as inducible or temporal expression at a desired cell development stage, which is achieved through direct genomic editing or modification, or through "passing-on" via differentiation from or reprogramming of a starting cell that is initially genomically engineered; or (2) at the cell level-successful removal, addition, or alteration of a cell function/characteristic via (i) gene expression modification obtained in said cell through direct genomic editing, (ii) gene expression modification maintained in said cell through "passing-on" via differentiation from or reprogramming of a starting cell that is initially genomically engineered; (iii) down-stream gene regulation in said cell as a result of gene expression modification that only appears in an earlier development stage of said cell, or only appears in the starting cell that gives rise to said cell via differentiation or reprogramming; or (iv) enhanced or newly attained cellular function or attribute displayed within the mature cellular product, initially derived from the genomic editing or modification conducted at the iPSC, progenitor or dedifferentiated cellular origin.

"HLA deficient", including HLA class I deficient, HLA class II deficient, or both, refers to cells that either lack, or no longer maintain, or have a reduced level of surface expression of a complete MHC complex comprising an HLA class I protein heterodimer and/or an HLA class II heterodimer, such that the diminished or reduced level is less than the level naturally detectable by other cells or by synthetic methods.

"Modified HLA deficient iPSC," as used herein, refers to an HLA deficient iPSC that is further modified by introducing genes expressing proteins related, but not limited to improved differentiation potential, antigen targeting, antigen presentation, antibody recognition, persistence, immune evasion, resistance to suppression, proliferation, costimulation, cytokine stimulation, cytokine production (autocrine or paracrine), chemotaxis, and cellular cytotoxicity, such as non-classical HLA class I proteins (e.g., HLA-E and HLA-G), chimeric antigen receptor (CAR), T cell receptor (TCR), CD16 Fc Receptor, BCL11b, NOTCH, RUNX1, IL15, 4-1BB, DAP10, DAP12, CD24, CD3ζ, 4-1BBL, CD47, CD113, and PDL1. The cells that are "modified HLA deficient" also include cells other than iPSCs.

The term "ligand" refers to a substance that forms a complex with a target molecule to produce a signal by binding to a site on the target. The ligand may be a natural or artificial substance capable of specific binding to the target. The ligand may be in the form of a protein, a peptide, an antibody, an antibody complex, a conjugate, a nucleic acid, a lipid, a polysaccharide, a monosaccharide, a small molecule, a nanoparticle, an ion, a neurotransmitter, or any other molecular entity capable of specific binding to a target. The target to which the ligand binds, may be a protein, a nucleic acid, an antigen, a receptor, a protein complex, or a cell. A ligand that binds to and alters the function of the target and triggers a signaling response is called "agonistic" or "an agonist". A ligand that binds to a target and blocks or reduces a signaling response is "antagonistic" or "an antagonist."

The term "antibody" is used herein in the broadest sense and refers generally to an immune-response generating molecule that contains at least one binding site that specifically binds to a target, wherein the target may be an antigen, or a receptor that is capable of interacting with certain antibodies. For example, an NK cell can be activated by the binding of an antibody or the Fc region of an antibody to its Fc-gamma receptors (FcγR), thereby triggering the ADCC (antibody-dependent cellular cytotoxicity) mediated effector cell activation. A specific piece or portion of an antigen or receptor, or a target in general, to which an antibody binds is known as an epitope or an antigenic determinant. The term "antibody" includes, but is not limited to, native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. An antibody may be a murine antibody, a human antibody, a humanized antibody, a camel IgG, a single variable new antigen receptor (VNAR), a shark heavy-chain antibody (Ig-NAR), a chimeric antibody, a recombinant antibody, a single-domain antibody (dAb), an anti-idiotype antibody, a bi-specific-, multi-specific- or multimeric-antibody, or antibody fragment thereof. Anti-idiotype antibodies are specific for binding to an idiotope of another antibody, wherein the idiotope is an antigenic determinant of an antibody. A bi-specific antibody may be a BiTE (bi-specific T cell engager) or a BiKE (bi-specific killer cell engager), and a multi-specific antibody may be a TriKE (tri-specific Killer cell engager). Non-limiting examples of antibody fragments include Fab, Fab', F(ab')2, F(ab')3, Fv, Fabc, pFc, Fd, single chain fragment variable (scFv), tandem scFv (scFv)2, single chain Fab (scFab), disulfide stabilized Fv (dsFv), minibody, diabody, triabody, tetrabody, single-domain antigen binding fragments (sdAb), camelid heavy-chain IgG and Nanobody® fragments, recombinant heavy-chain-only antibody (VHH), and other antibody fragments that maintain the binding specificity of the antibody.

"Fc receptors," abbreviated FcR, are classified based on the type of antibody that they recognize. For example, those that bind the most common class of antibody, IgG, are called Fc-gamma receptors (FcγR), those that bind IgA are called Fc-alpha receptors (FcαR) and those that bind IgE are called Fc-epsilon receptors (FcεR). The classes of FcRs are also distinguished by the cells that express them (macrophages, granulocytes, natural killer cells, T and B cells) and the signaling properties of each receptor. Fc-gamma receptors (FcγR) include several members, FcγRI (CD64), FcγRIIA (CD32), FcγRIIB (CD32), FcγRIIIA (CD16a), and FcγRIIIB (CD16b), which differ in their antibody affinities due to their different molecular structures.

"Chimeric Receptor" is a general term used to describe an engineered, artificial, or a hybrid receptor protein molecule that is made to comprise two or more portions of amino acid sequences that are originated from at least two different proteins. The chimeric receptor proteins have been engineered to give a cell the ability to initiate signal transduction and carry out downstream function upon binding of an agonistic ligand to the receptor. Exemplary "chimeric receptors" include, but are not limited to, chimeric antigen receptors (CARs), chimeric fusion receptors (CFRs), chimeric Fc receptors (CFcRs), as well as fusions of two or more receptors.

"Chimeric Fc Receptor," abbreviated as CFcR, is a term used to describe engineered Fc receptors having their native transmembrane and/or intracellular signaling domains modified or replaced with non-native transmembrane and/or intracellular signaling domains. In some embodiments of the chimeric Fc receptor, in addition to having one of, or both of, the transmembrane and signaling domains being non-native, one or more stimulatory domains can be introduced to the intracellular portion of the engineered Fc receptor to enhance cell activation, expansion and function upon triggering of the receptor. Unlike a chimeric antigen receptor (CAR), which contains an antigen binding domain to a target antigen, the chimeric Fc receptor binds to an Fc fragment, or the Fc region of an antibody, or the Fc region comprised in an engager or a binding molecule and activates the cell function with or without bringing the targeted cell close in vicinity. For example, a Fcγ receptor can be engineered to comprise selected transmembrane, stimulatory, and/or signaling domains in the intracellular region that respond to the binding of IgG at the extracellular domain, thereby generating a CFcR. In one example, a CFcR is produced by engineering CD16, a Fcγ receptor, by replacing its transmembrane domain and/or intracellular domain. To further improve the binding affinity of the CD16-based CFcR, the extracellular domain of CD64 or the high-affinity variants of CD16 (F176V, for example) can be incorporated. In some embodiments of the CFcR where a high affinity CD16 extracellular domain is involved, the proteolytic cleavage site comprising a serine at position 197 is eliminated or is replaced such at the extracellular domain of the receptor is non-cleavable, i.e., not subject to shedding, thereby obtaining a hnCD16-based CFcR.

CD16, a FcγR receptor, has been identified to have two isoforms, Fc receptors FcγRIIIa (CD16a) and FcγRIIIb (CD16b). CD16a is a transmembrane protein expressed by NK cells, which binds monomeric IgG attached to target cells to activate NK cells and facilitate antibody-dependent cell-mediated cytotoxicity (ADCC). "High affinity CD16," "non-cleavable CD16," or "high affinity non-cleavable CD16" (abbreviated as hnCD16), as used herein, refers to a natural or non-natural variant of CD16. The wildtype CD16 has low affinity and is subject to ectodomain shedding, a proteolytic cleavage process that regulates the cells surface density of various cell surface molecules on leukocytes upon NK cell activation. F176V and F158V are exemplary CD16 polymorphic variants having high affinity. A CD16 variant having the cleavage site (position 195-198) in the membrane-proximal region (position 189-212) altered or eliminated is not subject to shedding. The cleavage site and the membrane-proximal region are described in detail in WO2015/148926, the complete disclosure of which is incorporated herein by reference. The CD16 S197P variant is an engineered non-cleavable version of CD16. A CD16 variant comprising both F158V and S197P has high affinity and is non-cleavable. Another exemplary high affinity and non-cleavable CD16 (hnCD16) variant is an engineered CD16 comprising an ectodomain originated from one or more of the 3 exons of the CD64 ectodomain.

In some embodiments, provided herein are cells comprising a set of engineered components that collectively complement (and in some cases synergize with) one another to enhance the activity of an effector cell, in the context of treating a tumor in general, and for a solid tumor microenvironment in particular. The selected set of engineered components are referred to herein as a "backbone;" for its compatibility with any tumor antigen binding molecule to be expressed in the effector cell, including but not limited to, a CAR, an antibody, a bispecific antibody, and a TCR. However, the term "backbone" does not require any particular physical relationship between the individual components of the set, or their location within the cell; although certain association and/or arrangements (e.g., order in a co-expression construct of two or more of the individual components) may be optimized for higher expression level or ease of processing, among other considerations in a manufacturing setting. For example, a backbone may comprise integration of two expression cassettes, each at a different location in the genome of the cell. In some embodiments, the backbone comprises a plurality of genomic modifications, such as the insertion of one or more polynucleotides and/or modification to knockout one or more genes. Modifications may be made simultaneously or sequentially. Non-limiting examples of effector cell function that may be increased by the modifications of the backbone include one or more of improving cell growth, proliferation, expansion, and/or effector function autonomously without contacting additionally supplied soluble cytokines in vitro or in vivo, as well as enhanced homing, trafficking, depletion or reduction of alloreactive host immune cells, and retention at tumor sites, in which the tumor cells could be sensitized to synergize with the functional features provided to the effector cells. A solid tumor targeting backbone of the present disclosure can be particularly beneficial in the context of an iPSC comprising the backbone, such as by providing a master cell bank providing a source of starting cells that can be modified by the simple addition of a tumor antigen binding molecule for an indication intended to be treated, and then being used as a source for differentiating enhanced effector cells with therapeutic properties for one or more intended tumor indications.

I. Cells and Compositions Useful for Adoptive Cell Therapies with Enhanced Properties Provided herein is a strategy to systematically engineer the regulatory circuitry of a clonal iPSC without impacting the differentiation potency and cell development biology of the iPSC and its derivative cells, while enhancing the therapeutic properties of the derivative cells differentiated from the iPSC. The iPSC-derived cells are functionally improved and suitable for adoptive cell therapies following a combination of selective modalities being introduced to the cells at the level of iPSC through genomic engineering. It was previously unclear whether altered iPSCs comprising one or more provided genetic edits still have the capacity to enter cell development, and/or to mature and generate functional differentiated cells while retaining modified activities and/or properties. Unanticipated failures during directed cell differentiation from iPSCs have been attributed to aspects including, but not limited to, development stage specific gene expression or lack thereof, requirements for HLA complex presentation, protein shedding of introduced surface expressing modalities, and the need for reconfiguration of differentiation protocols enabling phenotypic and/or functional change in the cell. The present application has shown that the one or more selected genomic modifications as provided herein does not negatively impact iPSC differentiation potency, and the functional effector cells derived from the engineered iPSC have enhanced and/or acquired therapeutic properties attributable to the individual or combined genomic modifications retained in the effector cells following the iPSC differentiation. Further, all genomic modifications and combinations thereof as may be described in the context of iPSC and iPSC-derived effector cells are applicable to primary sourced cells, including primary immune cells such as T, NK, or immunregulatory cells, whether cultured or expanded, the modification of which results in engineered immune cells useful for adoptive cell therapy.

Further, while CAR-T cells have been shown to be effective and potent in treating several hematologic malignancies, engineered T cell therapies have had limited success in addressing solid tumors. Unlike liquid tumors where uniformly-expressed antigens are accessible and can be effectively targeted, tumor access, lack of tumor-exclusive antigen targets, and antigen heterogeneity are significant barriers to the successful development of CAR-T cells in solid tumors. In addition, inherent genetic engineering variability seen with patient- and donor-derived immune cells limits the wide application of CAR-T cell therapy. The present application provides genomic engineering aspects in the form of a solid tumor targeting backbone, as well as other genetic modalities, to improve on-target specificity with reduced off-tumor effect in the off-the-shelf adoptive cell therapy setting using effector cells derived from engineered iPSCs, to evade allorejection, as well as to overcome suppressive tumor microenvironment, a heightened challenge especially with solid tumors.

1. C—X—C Motif Chemokine Receptor Overexpression

Chemokines are a family of homogeneous serum proteins of about 7 to about 16 kDa originally characterized by their ability to induce leukocyte migration. Most of chemokines have four characteristic cysteines (Cys) and are classified into C—X—C (or alpha, CXC), C—C (or beta), C (or gamma), and CX3C (or delta) chemokine classes, according to motifs displayed by the first two cysteines. Subfamilies of C—X—C (or alpha, CXC) are further classified, according to the presence of an ELR motif (Glu-Leu-Arg) preceding the first cysteine, into two groups: ELR-CXC chemokines and non-ELR-CXC chemokines.

CXC chemokine receptor 2 (CXCR2), also known as CD128, interleukin 8 receptor beta (IL8Rβ), or L8 receptor type B, is a chemokine receptor mostly expressed by neutrophils, mast cells, monocytes, and macrophages. It is known that CD56 dim NK cells express CXCR2, however its expression can be downregulated upon NK cell activation. T cells typically do not express CXCR2. iPSCs and iPSC-derived T cells do not express CXCR2 without transducing exogenous polynucleotides encoding CXCR2 as disclosed in this application. The chemokine IL8 (also known as CXCL8) is secreted by mononuclear macrophages, neutrophils, eosinophils, T lymphocytes, epithelial cells, and fibroblasts, and functions as a chemotactic factor by guiding the neutrophils to the site of infection. CXCL8 is also secreted by tumor cells and promotes tumor migration, invasion, angiogenesis and metastasis. CXCL8 is one of the ligands to multiple CXC chemokine receptors including CXCR1 and CXCR2. Additional chemokines known to bind to CXCR2 include, but are not limited to, CXCL1, GROβ (CXCL2), CXCL3, CXCL5, CXCL6, and CXCL7.

CXC chemokine receptor 3 (CXCR3), also known as G Protein-coupled Receptor 9 (GPR9) and CD183, is a G Protein-coupled receptor that binds to the chemokines CXCL9, CXCL10, and CXCL11. CXCR3 is expressed primarily in activated T-helper type 1 (Th1) lymphocytes, but is also present in natural killer cells, macrophages, dendritic cells, and B lymphocyte subsets. The interaction of CXCR3 and its ligands is involved in guiding receptor-bearing cells to specific parts of the body, especially sites of inflammation, immune impairment, and immune dysfunction.

In various embodiments, the present application provides effector cells or iPSCs genetically engineered to comprise, among other editing as contemplated and described herein, a solid tumor targeting backbone comprising, among other genetic modalities, a C—X—C motif chemokine receptor. In various embodiments, the C—X—C motif chemokine receptor comprises CXCR2 or CXCR3, or variants thereof. A non-limiting example of the amino acid sequence of human CXCR2 is one registered as UniProtKB No: P25025. In one embodiment, the CXCR2 comprises an amino acid sequence of at least 75%, 80%, 85%, 90%, 95% or 99% identity to SEQ ID NO: 1. In some embodiments, the CXCR2 comprises an amino acid sequence of at least 90% identity to SEQ ID NO: 1. In some embodiments, the CXCR2 comprises an amino acid sequence of at least 95% identity to SEQ ID NO: 1. In some embodiments, the CXCR2 comprises the amino acid sequence of SEQ ID NO: 1. In some embodiments, the variant of CXCR2 comprises a CXCR2 isoform represented by SEQ ID NOs: 2, 3, 4, 5, or 6. In some embodiments, the variant of CXCR2 comprises an amino acid sequence of at least 75%, 80%, 85%, 90%, 95% or 99% identity to any one of SEQ ID NOs: 2, 3, 4, 5, and 6. In some embodiments, the variant of CXCR2 comprises an amino acid sequence of at least 90% identity to any one of SEQ ID NOs: 2, 3, 4, 5, and 6. In some embodiments, the variant of CXCR2 comprises an amino acid sequence of at least 95% identity to any one of SEQ ID NOs: 2, 3, 4, 5, and 6. In some embodiments, the variant of CXCR2 comprises the amino acid sequence of SEQ ID NO: 2. In some embodiments, the variant of CXCR2 comprises the amino acid sequence of SEQ ID NO: 3. In some embodiments, the variant of CXCR2 comprises the amino acid sequence of SEQ ID NO: 4. In some embodiments, the variant of CXCR2 comprises the amino acid sequence of SEQ ID NO: 5. In some embodiments, the variant of CXCR2 comprises the amino acid sequence of SEQ ID NO: 6. As used herein and throughout the application, the percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm recognized in the art.

```
                                                             SEQ ID NO: 1
MEDFNMESDSFEDFWKGEDLSNYSYSSTLPPFLLDAAPCEPESLEINKYFVVIIYALVFLLSLLGNSLVML

VILYSRVGRSVTDVYLLNLALADLLFALTLPIWAASKVNGWIFGTFLCKVVSLLKEVNFYSGILLLACISV

DRYLAIVHATRTLTQKRYLVKFICLSIWGLSLLLALPVLLFRRTVYSSNVSPACYEDMGNNTANWRMLLRI

LPQSFGFIVPLLIMLFCYGFTLRTLFKAHMGQKHRAMRVIFAVVLIFLLCWLPYNLVLLADTLMRTQVIQE

TCERRNHIDRALDATEILGILHSCLNPLIYAFIGQKFRHGLLKILAIHGLISKDSLPKDSRPSFVGSSSGH

TSTTL
(360 a.a. CXCR2; UniProtKB No: P25025)

SEQ ID NO: 2
MEDFNMESDSFEDFW
(15 a.a. CXCR2 Isoform 1 (residues 1-15 of CXCR2); UniProtKB No: Q6LCZ7)

SEQ ID NO: 3
MEDFNMESDSFEDFWKGEDLSNYSYSSTLPPFLLDAAPCEPESLEINKYFVVIIYALVFL

LSLLGNSLVMLVILYSRVGRSVTDVYLLNLALADLLFALTLPIWAASKVNGWIFGTFLCK

VVSLLKEVNFYSGILLLACISVDRYLAIVHATRTLTQKRYLVKFICLSIWGLSLLLALPV

LLFRRTVYSSNVSPACYEDM
(200 a.a. CXCR2 Isoform 2 (residues 1-200 of CXCR2);
UniProtKB No: C9JW47)

SEQ ID NO: 4
MEDFNMESDSFEDFWKGEDLSNYSYSSTLPPFLLDAAPCEPESLEINKYFVVIIYALVFL

LSLLGNSLVMLVILYSRVGRSVTDVYLLNLALADLLFALTLPIWAASKVNGWIFGTFLCK

VVSLLKEVNFYSGIL
(135 a.a. CXCR2 Isoform 3 (residues 1-135 of CXCR2);
UniProtKB No: C9JG19)
```

```
                                                         SEQ ID NO: 5
MEDFNMESDSFEDFWKGEDLSNYSYSSTLPPFLLDAAPCEPESLEINKYFVVIIYALVFL

LSLLGNSLVMLVILYSRVGRSVTDVYLLNLALADLLFALTLPIWAASKVNGWIFGTFLCK

VVSLLKEVNFYSGILLLACISVDRYLAIVHATRTLTQKRYLVKFICLSIWGL
(172 a.a. CXCR2 Isoform 4 (residues 1-172 of CXCR2);
UniProtKB No: C9J1J7)

SEQ ID NO: 6
MEDFNMESDSFEDFWKGEDLSNYSYSSTLPPFLLDAAPCEPESLEINKYFVVIIYALVFL

LSLLGNSLVMLVILYSRVGRSVTDVYLLNLALADLLFALTLPIWAASKVNGWIFGTFLCK

VVSLLKEVNFYSGILLLA
(138 a.a. CXCR2 Isoform 5 (residues 1-138 of CXCR2);
UniProtKB No: C9J2F9)
```

A non-limiting example of the amino acid sequence of human CXCR3 is one registered as UniProtKB No: P49682. In one embodiment, the CXCR3 comprises an amino acid sequence of at least 75%, 80%, 85%, 90%, 95% or 99% identity to SEQ ID NO: 7. In some embodiments, the CXCR3 comprises an amino acid sequence of at least 90% identity to SEQ ID NO: 7. In some embodiments, the CXCR3 comprises an amino acid sequence of at least 95% identity to SEQ ID NO: 7. In some embodiments, the CXCR3 comprises the amino acid sequence of SEQ ID NO: 7. In some embodiments, the variant of CXCR3 comprises a CXCR3 isoform represented by SEQ ID NOs: 8 or 9. In some embodiments, the variant of CXCR3 comprises an amino acid sequence of at least 75%, 80%, 85%, 90%, 95% or 99% identity to SEQ ID NOs: 8 or 9. In some embodiments, the variant of CXCR3 comprises an amino acid sequence of at least 90% identity to SEQ ID NOs: 8 or 9. In some embodiments, the variant of CXCR3 comprises an amino acid sequence of at least 95% identity to SEQ ID NOs: 8 or 9. In some embodiments, the variant of CXCR3 comprises the amino acid sequence of SEQ ID NO: 8. In some embodiments, the variant of CXCR3 comprises the amino acid sequence of SEQ ID NO: 9

```
                                                         SEQ ID NO: 7
MVLEVSDHQVLNDAEVAALLENFSSSYDYGENESDSCCTSPPCPQDFSLN

FDRAFLPALYSLLFLLGLLGNGAVAAVLLSRRTALSSTDTFLLHLAVADT

LLVLTLPLWAVDAAVQWVFGSGLCKVAGALFNINFYAGALLLACISFDRY

LNIVHATQLYRRGPPARVTLTCLAVWGLCLLFALPDFIFLSAHHDERLNA

THCQYNFPQVGRTALRVLQLVAGFLLPLLVMAYCYAHILAVLLVSRGQRR

LRAMRLVVVVVVAFALCWTPYHLVVLVDILMDLGALARNCGRESRVDVAK

SVTSGLGYMHCCLNPLLYAFVGVKFRERMWMLLLRLGCPNQRGLQRQPSS

SRRDSSWSETSEASYSGL
(368 a.a. CXCR3; UniProtKB No: P49682)

SEQ ID NO: 8
MELRKYGPGRLAGTVIGGAAQSKSQTKSDSITKEFLPGLYTAPSSPFPPS

QVSDHQVLNDAEVAALLENFSSSYDYGENESDSCCTSPPCPQDFSLNFDR

AFLPALYSLLFLLGLLGNGAVAAVLLSRRTALSSTDTFLLHLAVADTLLV

LTLPLWAVDAAVQWVFGSGLCKVAGALFNINFYAGALLLACISFDRYLNI

VHATQLYRRGPPARVTLTCLAVWGLCLLFALPDFIFLSAHHDERLNATHC

QYNFPQVGRTALRVLQLVAGFLLPLLVMAYCYAHILAVLLVSRGQRRLRA

MRLVVVVVVAFALCWTPYHLVVLVDILMDLGALARNCGRESRVDVAKSVT

SGLGYMHCCLNPLLYAFVGVKFRERMWMLLLRLGCPNQRGLQRQPSSSRR

DSSWSETSEASYSGL
(415 a.a. CXCR3 Isoform 2; UniProtKB No: P49682-2)

SEQ ID NO: 9
MVLEVSDHQVLNDAEVAALLENFSSSYDYGENESDSCCTSPPCPQDFSLN

FDRAFLPALYSLLFLLGLLGNGAVAAVLLSRRTALSSTDTFLLHLAVADT

LLVLTLPLWAVDAAVQWVFGSGLCKVAGALFNINFYAGALLLACISFDRY

LNIVHATQLYRRGPPARVTLTCLAVWGLCLLFALPDFIFLSAHHDERLNA

THCQYNFPQGSSSGSGCGCCSCAWAAPTREGSRGSHRLPAGIHPGLRPQR

PPTRACEAGIRAPLSPI
(267 a.a. CXCR3 Isoform 3; UniProtKB No: P49682-3)
```

In various embodiments, the polynucleotide encoding the C—X—C motif chemokine receptor or variant thereof is inserted in a selected locus of a primary-sourced effector cell or an iPSC for deriving functional effector cells comprising the same genetic editing through directed differentiation. In some embodiments, the selected locus for insertion of the C—X—C motif chemokine receptor comprises a safe harbor locus, a gene locus intended to be disrupted or knocked out, a gene locus that provides an endogenous promoter that provides spacial and/or temporal control of the exogenous gene expression. In some embodiments, the selected locus for C—X—C motif chemokine receptor insertion comprises AAVS1, CCR5, ROSA26, collagen, HTRP, H11, GAPDH, RUNX1, B2M, TAP1, TAP2, Tapasin, NLRC5, CIITA, RFXANK, RFX5, RFXAP, TCR, NKG2A, NKG2D, CD38, CD25, CD69, CD44, CD58, CD54, CD56, CD71, CIS, CBL-B, SOCS2, PD1, CTLA4, LAG3, TIM3, or TIGIT. In one embodiment, the selected locus for C—X—C motif chemokine receptor insertion is the TCR locus. In one embodiment, the selected locus for C—X—C motif chemokine receptor insertion is the CD38 locus.

In some embodiments, the C—X—C motif chemokine receptor is co-expressed with one or more exogenous polynucleotides encoding a polypeptide of interest through separate expression constructs, or a single bi- or tri-cistronic expression cassette. In some embodiments, the single bi- or tri-cistronic expression cassette comprising the C—X—C motif chemokine receptor and one or more exogenous polynucleotides encoding a polypeptide of interest comprises a 2A sequence, such that the C—X—C motif chemokine receptor and the additional polynucleotide(s) are in a single open reading frame (ORF). The bi-cistronic design allows coordinated expression of multiple polynucleotides both in timing and quantity, and under the same control mechanism that may be chosen to incorporate, for example, an inducible promoter for the expression of the single ORF. Self-cleaving peptides are found in members of the Picornaviridae virus family, including aphthoviruses such as foot-and-mouth disease virus (FMDV), equine rhinitis A virus (ERAV), Thosea asigna virus (TaV) and porcine tescho virus-1 (PTV-I) (Donnelly, M L, et al, J. Gen. Virol, 82, 1027-101 (2001); Ryan, M D, et al., J. Gen. Virol., 72, 2727-2732 (2001)), and cardioviruses such as Theilovirus (e.g., Theiler's murine encephalomyelitis) and encephalomyocarditis viruses. The 2A peptides derived from FMDV, ERAV, PTV-I, and TaV are sometimes also referred to as "F2A", "E2A", "P2A", and "T2A", respectively. In some embodiments, the exogenous polynucleotides that could be co-expressed with the C—X—C motif chemokine receptor encode one or more polypeptides comprising a CAR, a CD16 or a variant thereof, a cytokine, a cytokine receptor, a cytokine signaling complex, a chimeric fusion receptor, a chimeric Fc receptor, an engager, a checkpoint inhibitor, an Fc receptor, or an antibody or functional variant or fragment thereof. In one embodiment, the exogenous polynucleotides that are co-expressed with the C—X—C motif chemokine receptor in a bi-cistronic cassette do not encode a CAR. In one embodiment, at least one exogenous polynucleotide that is co-expressed in a bi-cistronic cassette with the C—X—C motif chemokine receptor encodes an exogenous CD16. In some embodiments, the primary-sourced or derived effector cells comprising the C—X—C motif chemokine receptor or variant thereof are T lineage cells. In some embodiments, the primary-sourced or derived effector cells comprising the C—X—C motif chemokine receptor or a variant thereof are NK lineage cells.

Additionally provided in this application is a master cell bank comprising single cell sorted and expanded clonal engineered iPSCs having at least one modification or phenotype as provided herein, including but not limited to, a C—X—C motif chemokine receptor or a variant thereof, wherein the cell bank provides clonal engineered iPSCs for additional engineering and a renewable source for manufacturing off-the-shelf, engineered, homogeneous cell therapy products, including but not limited to derivative NK and T cells, which are well-defined and uniform in composition, and can be mass produced at significant scale in a cost-effective mainer.

2. Exogenously Introduced TGFβ Redirector Receptor

Transforming growth factor beta (TGFβ) is a multipotent immunosuppressive cytokine with complex roles in tumorigenesis including epithelial to mesenchymal transition, angiogenesis, tumor cell motility and metastasis, cancer associated fibroblast (CAF) proliferation, and immunosuppression. TGFβ exists in its latent form in the tumor microenvironment, and is known to suppress T cell effector function, in part, through Smad-mediated downregulation of the target genes granzyme, perform, and interferon. Furthermore, the detection of a TGFβ gene expression signature correlates with T cell exclusion from tumors and resistance to immunotherapy. One aspect of the present application provides a multi-element solid tumor targeting backbone design that incorporates a synthetic transforming growth factor beta receptor (TGFβR) signaling redirector receptor, among other editing as contemplated and described herein, to equip allogeneic effector cells, including those derived from genetically engineered iPSCs for better efficacy in tumors in general, and in solid tumors in particular. In general, a "signaling (or signal) redirector receptor" or "SRR" redirects the signaling of an extracellular domain from a first receptor (e.g., a TGFβ receptor) through an intracellular domain from a different receptor (e.g., a cytokine receptor) by joining the extracellular domain of the first receptor and intracellular domains of the different receptor. In the context of TGFβR, the signaling redirector receptor may be referred to as a "TGFβR redirector" or "TGFβR redirector receptor" or "TGFβ signal redirector receptor" or "TGFβ-SRR" throughout this application.

In some embodiments, iPSCs and derivative cells therefrom comprise a polynucleotide encoding a TGFβ redirector receptor (TGFβ-SRR), which comprises a partial or full peptide of an extracellular domain (ECD) of TGFβR. In some embodiments, the TGFβ redirector receptor comprises: (i) an extracellular domain, or a fragment thereof, of transforming growth factor beta receptor (TGFβR); and (ii) an intracellular domain (ICD), or a fragment thereof, of a cytokine receptor comprising IL2R, IL12R, IL18R, IL21R, or any combination thereof.

In some embodiments, the TGFβ redirector receptor comprising the ECD and ICD as described above further comprises a transmembrane domain (TM). In various embodiments, the transmembrane (TM) domain of the TGFβ redirector receptor can: (i) originate from the same molecule providing the intracellular domain, (ii) originate from the same molecule providing the extracellular domain, or (iii) may be modified or replaced with a transmembrane domain of any other membrane bound proteins. In some embodiments, the cytokine receptor providing an intracellular domain or a fragment thereof of the TGFβ redirector receptor comprises at least one of IL2R, IL4R, IL6R, IL7R, IL9R, IL10R, IL11R, IL12R, IL15R, IL18R and IL21R.

In some embodiments, the extracellular domain (ECD) of TGFβR comprises an amino acid sequence having at least about 85%, about 90%, about 95%, about 96%, about 97%, about 98%, or about 99% identity to SEQ ID NO: 10. In some embodiments, the extracellular domain (ECD) of TGFβR comprises an amino acid sequence having at least about 90% identity to SEQ ID NO: 10. In some embodiments, the extracellular domain (ECD) of TGFβR comprises an amino acid sequence having at least about 95% identity to SEQ ID NO: 10. In some embodiments, the extracellular domain (ECD) of TGFβR comprises the amino acid sequence of SEQ ID NO: 10. In some embodiments, the intracellular domain (ICD) of IL2Rβ comprises an amino acid sequence having at least about 85%, about 90%, about 95%, about 96%, about 97%, about 98%, or about 99% identity to SEQ ID NO: 11. In some embodiments, the intracellular domain (ICD) of IL2Rβ comprises an amino acid sequence having at least about 90% identity to SEQ ID NO: 11. In some embodiments, the intracellular domain (ICD) of IL2Rβ comprises an amino acid sequence having at least about 95% identity to SEQ ID NO: 11. In some embodiments, the intracellular domain (ICD) of IL2Rβ comprises the amino acid sequence of SEQ ID NO: 11. In some embodiments, the intracellular domain (ICD) of IL12Rβ comprises an amino acid sequence having at least about 85%, about 90%, about 95%, about 96%, about 97%, about 98%, or about 99% identity to SEQ ID NO: 12. In some embodiments, the intracellular domain (ICD) of IL12Rβ comprises an amino acid sequence having at least about 90% identity to SEQ ID NO: 12. In some embodiments, the intracellular domain (ICD) of IL12Rβ comprises an amino acid sequence having at least about 95% identity to SEQ ID NO: 12. In some embodiments, the intracellular domain (ICD) of IL12Rβ comprises the amino acid sequence of SEQ ID NO: 12. In some embodiments, a fragment of the intracellular domain of IL12Rβ comprises an amino acid sequence having at least about 85%, about 90%, about 95%, about 96%, about 97%, about 98%, or about 99% identity to SEQ ID NO: 13. In some embodiments, a fragment of the intracellular domain of IL12Rβ comprises an amino acid sequence having at least about 90% identity to SEQ ID NO: 13. In some embodiments, a fragment of the intracellular domain of IL12Rβ comprises an amino acid sequence having at least about 95% identity to SEQ ID NO: 13. In some embodiments, a fragment of the intracellular domain of IL12Rβ comprises the amino acid sequence of SEQ ID NO: 13. In some embodiments, the intracellular domain (ICD) of IL18Rβ comprises an amino acid sequence having at least about 85%, about 90%, about 95%, about 96%, about 97%, about 98%, or about 99% identity to SEQ ID NO: 14. In some embodiments, the intracellular domain (ICD) of IL18Rβ comprises an amino acid sequence having at least about 90% identity to SEQ ID NO: 14. In some embodiments, the intracellular domain (ICD) of IL18Rβ comprises an amino acid sequence having at least about 95% identity to SEQ ID NO: 14. In some embodiments, the intracellular domain (ICD) of IL18Rβ comprises the amino acid sequence of SEQ ID NO: 14. In some embodiments, the intracellular domain (ICD) of IL21Rβ comprises an amino acid sequence having at least about 85%, about 90%, about 95%, about 96%, about 97%, about 98%, or about 99% identity to SEQ ID NO: 15. In some embodiments, the intracellular domain (ICD) of IL21Rβ comprises an amino acid sequence having at least about 90% identity to SEQ ID NO: 15. In some embodiments, the intracellular domain (ICD) of IL21Rβ comprises an amino acid sequence having at least about 95% identity to SEQ ID NO: 15. In some embodiments, the intracellular domain (ICD) of IL21Rβ comprises the amino acid sequence of SEQ ID NO: 15.

```
                                           SEQ ID NO: 10
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDLLLVIFQ
(ECD of TGFβR)

SEQ ID NO: 11
NCRNTGPWLKKVLKCNTPDPSKFFSQLSSEHGGDVQKWLSSPFPSSSFSP

GGLAPEISPLEVLERDKVTQLLLQQDKVPEPASLSSNHSLTSCFTNQGYF

FFHLPDALEIEACQVYFTYDPYSEEDPDEGVAGAPTGSSPQPLQPLSGED

DAYCTFPSRDDLLLFSPSLLGGPSPPSTAPGGSGAGEERMPPSLQERVPR

DWDPQPLGPPTPGVPDLVDFQPPPELVLREAGEEVPDAGPREGVSFPWSR

PPGQGEFRALNARLPLNTDAYLSLQELQGQDPTHLV
(ICD of IL2Rβ)

SEQ ID NO: 12
HYFQQKVFVLLAALRPQWCSREIPDPANSTCAKKYPIAEEKTQLPLDRLL

IDWPTPEDPEPLVISEVLHQVTPVFRHPPCSNWPQREKGIQGHQASEKDM

MHSASSPPPPRALQAESRQLVDLYKVLESRGSDPKPENPACPWTVLPAGD

LPTHDGYLPSNIDDLPSHEAPLADSLEELEPQHISLSVFPSSSLHPLTFS

CGDKLTLDQLKMRCDSLML
(ICD of IL12Rβ)

SEQ ID NO: 13
SDPKPENPACPWTVLPAGDLPTHDGYLPSNIDDLPSHEAPLADSLEELEP

Q
(an ICD fragment of IL12Rβ)

SEQ ID NO: 14
YRVDLVLFYRHLTRRDETLTDGKTYDAFVSYLKECRPENGEEHTFAVEIL

PRVLEKHFGYKLCIFERDVVPGGAVVDEIHSLIEKSRRLIIVLSKSYMSN

EVRYELESGLHEALVERKIKIILIEFTPVTDFTFLPQSLKLLKSHRVLKW

KADKSLSYNSRFWKNLLYLMPAKTVKPGRDEPEVLPVLSES
(ICD of IL8Rβ)

SEQ ID NO: 15
SLKTHPLWRLWKKIWAVPSPERFFMPLYKGCSGDFKKWVGAPFTGSSLEL

GPWSPEVPSTLEVYSCHPPRSPAKRLQLTELQEPAELVESDGVPKPSFWP

TAQNSGGSAYSEERDRPYGLVSIDTVTVLDAEGPCTWPCSCEDDGYPALD

LDAGLEPSPGLEDPLLDAGTTVLSCGCVSAGSPGLGGPLGSLLDRLKPPL

ADGEDWAGGLPWGGRSPGGVSESEAGSPLAGLDMDTFDSGFVGSDCSSPV

ECDFTSPGDEGPPRSYLRQWVVIPPPLSSPGPQAS
(ICD of IL21Rβ)
```

In some embodiments, the signaling receptor comprises an extracellular domain or a fragment thereof of TGFβR and an intracellular domain or a fragment thereof of the cytokine receptor IL2Rβ, thereby forming a TGFβR2-IL2Rβ signaling redirector receptor. In some embodiments, the signaling receptor comprises an extracellular domain or a fragment thereof of TGFβR and an intracellular domain or a fragment thereof of the cytokine receptor IL12Rβ, thereby forming a TGFβR2-IL12Rβ signaling redirector receptor. In some embodiments, the signaling receptor comprises an extracellular domain or a fragment thereof of TGFβR and an intracellular domain or a fragment thereof of the cytokine receptor IL18Rβ, thereby forming a TGFβR2-IL18Rβ signaling redirector receptor. In some embodiments, the signaling receptor comprises an extracellular domain or a fragment thereof of TGFβR and an intracellular domain or a fragment thereof of the cytokine receptor IL21R, thereby forming a TGFβR2-IL21R signaling redirector receptor.

In some embodiments, TGFβR2-IL12Rβ signaling redirector receptor comprises an amino acid sequence having sequence identity of at least 80%, 85%, 90%, 95%, or 97%, 98%, or 99% to a sequence represented by SEQ ID NO: 16 (termed specifically as TGFβR2-triL12Rβ throughout the application). In some embodiments, TGFβR2-IL12Rβ signaling redirector receptor comprises an amino acid sequence having sequence identity of at least 90% to SEQ ID NO: 16. In some embodiments, TGFβR2-IL12Rβ signaling redirector receptor comprises an amino acid sequence having sequence identity of at least 95% to SEQ ID NO: 16. In some embodiments, TGFβR2-IL12Rβ signaling redirector receptor comprises the amino acid sequence of SEQ ID NO: 16. In some embodiments, the transmembrane domain (TM) sequence represented by SEQ ID NO: 17 that is comprised within SEQ ID NO: 16 may vary in sequence or in length, or may even be replaced with a transmembrane domain of another transmembrane protein.

SEQ ID NO: 16
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDLLLVIFQ

_VTGISLLPPLGVAISVIIIFYCYRVN_

SDPKPENPACPWTVLPAGDLPTHDGYLPSNIDDLPSHEAPLADSLEELEP

Q
(TGFβR2-_TM_-trIL12Rβ)

SEQ ID NO: 17
VTGISLLPPLGVAISVIIIFYCYRVN
(exemplary and variable portion of
TGFβR2-trIL12Rβ)

As such, in various embodiments, any of the TGFβ-SRRs provided herein may be introduced to iPSCs using one or more of the construct designs described above, and to their derivative cells upon iPSC differentiation. In addition to an induced pluripotent cell (iPSC), a clonal iPSC, a clonal iPS cell line, or iPSC-derived cells comprising at least one engineered modality as disclosed herein are provided. Also provided is a master cell bank comprising single cell sorted and expanded clonal engineered iPSCs having at least a TGFβ-SRR as described in this section, wherein the cell bank provides a platform for additional iPSC engineering and a renewable source for manufacturing off-the-shelf, engineered, homogeneous cell therapy products, which are well-defined and uniform in composition, and can be mass produced at a significant scale in a cost-effective manner.

Accordingly, in some embodiments, the present invention provides immune cells, iPSCs, and iPSC derived cells comprising a solid tumor targeting backbone comprising a polynucleotide encoding a TGFβ redirector receptor ("TGFβ-SRR" in Table 4), among other genetic modalities, wherein the cells, such as derivative T and NK cells, are useful for overcoming or reducing tumor microenvironment suppression associated with a tumor, and particularly, a solid tumor. In some embodiments, the iPSC and derivative cells thereof comprise a solid tumor targeting backbone comprising two or more of: a polynucleotide encoding a C—X—C motif chemokine receptor or a variant thereof, a polynucleotide encoding a TGFβ redirector receptor, and and/or one or more additional genomic edits as described herein, without adversely impacting the differentiation potential of the iPSC and function of the derived effector cells, such as derivative T and NK cells.

Also provided is a master cell bank comprising single cell sorted and expanded clonal engineered iPSCs having at least an exogenously introduced polynucleotide encoding a TGFβ redirector receptor, and optionally a polynucleotide encoding a C—X—C motif chemokine receptor or a variant thereof, wherein the cell bank provides a platform for additional iPSC engineering and a renewable source for manufacturing off-the-shelf, engineered, homogeneous cell therapy products, which are well-defined and uniform in composition, and can be mass produced at a significant scale in a cost-effective manner

3. Allo-Immune Defense Receptor (ADR) Expression

Unwanted activation of T- and NK-cells often promotes allo-immune reactions leading to development of graft-versus-host disease (GvHD). Although some steps may be taken to reduce the reactivity of allogeneic cells in the recipient individual, such cells would still be targeted by the immune system of the recipient (primarily T- and NK-cells), which would recognize them as foreign leading to rejection and limiting therapeutic benefit. On the other hand, modulating a host immune system to reduce allo-immune reactions, for example, by lympho-conditioning using chemotherapy such as Cy/Flu (cyclophosphamide/fludarabine) often leads to associated hematologic toxicities, including increased susceptibility to severe infections, due to indiscrimitive lymphodepletion and a severely compromised immune system as a result. To control pathogenic conditions due to unwanted activation of the immune system, in various embodiments, the present application provides a solid tumor targeting backbone comprising an allo-immune defense receptor (ADR), among other components. Another aspect of the application provides immune cells, iPSCs, and iPSC-derived effector cells that are genetically engineered to comprise, among other editing as contemplated and described herein, a 4-1BB or CD38 specific allo-immune defense receptor (ADR) for effector cell potentiation as well as selective depletion of alloreactive host NK cells and T cells with upregulated 4-1BB and/or CD38 expression, the latter of which include pathogenic T cells, and regulatory T cells, while sparing resting cells in the recipient.

In some embodiments of the ADR that is specific to 4-1BB (CD137, also referred to as "41BB"), the ADR comprises an extracellular domain that targets 4-1BB upregulated on host T or NK cells when they are activated, and a signaling domain promoting effector cell activation. For example, the 41BB-ADR extracellular domain may comprise any suitable ligand for 4-1BB, including 4-1BBL, an antibody (or functional fragment thereof) that targets 4-1BB, a fusion of Fc with 4-1BBL, or functional derivatives or fragments thereof. In some embodiments, the 41BB-ADR extracellular domain comprises 4-1BBL, or a fragment thereof effective to bind 4-1BB. In some embodiments, the 41BB-ADR extracellular domain comprises an amino acid sequence with at least about 85%, about 90%, about 95%, about 96%, about 97%, about 98%, or about 99% sequence identity to SEQ ID NO: 145. In some embodiments, the 41BB-ADR extracellular domain comprises an amino acid sequence with at least about 90% sequence identity to SEQ ID NO: 145. In some embodiments, the 41BB-ADR extracellular domain comprises an amino acid sequence with at least about 95% sequence identity to SEQ ID NO: 145. In some embodiments, the 41BB-ADR extracellular domain comprises the amino acid sequence of SEQ ID NO: 145

SEQ ID NO: 145
GLLDLRQGMFAQLVAQNVLLIDGPLSWYSDPGLAGVSLTGGLSYKEDTKE

LVVAKAGVYYVFFQLELRRVVAGEGSGSVSLALHLQPLRSAAGAAALALT

VDLPPASSEARNSAFGFQGRLLHLSAGQRLGVHLHTEARARHAWQLTQGA

TVLGLFRVTPEIPAGLPSPRSE

In one embodiment of the CD38 specific ADR, the CD38-ADR comprises an extracellular domain comprising a CD38 binding domain or fragments thereof. In some embodiments, the CD38 binding domain or fragment thereof is from an anti-CD38 antibody. In some embodiments, the anti-CD38 antibody comprises a murine antibody, a human antibody, a humanized antibody, a camel Ig, a single variable new antigen receptor (VNAR), a shark heavy-chain-only antibody (Ig NAR), a chimeric antibody, a recombinant antibody, or an antibody fragment thereof. Non-limiting examples of antibody binding domain or fragments thereof include Fab, Fab', F(ab')2, F(ab')3, Fv, single chain antigen binding fragment (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody.

In some embodiments, the CD38 binding domain or fragments thereof comprised in the CD38-ADR comprises a variable region of the heavy chain and/or a variable region of the light chain represented by an amino acid sequence that is of at least about 99%, about 98%, about 96%, about 95%, about 90%, about 85%, and/or at least about 80% identity to SEQ ID NOs: 146 and 147 respectively, SEQ ID NOs: 148 and 149 respectively, SEQ ID NOs: 150 and 151 respectively, SEQ ID NOs: 152 and 153 respectively, SEQ ID NOs: 154 and 155 respectively, SEQ ID NOs: 156 and 157 respectively, SEQ ID NOs: 158 and 159 respectively, SEQ ID NOs: 160 and 161 respectively, SEQ ID NOs: 162 and 163 respectively, SEQ ID NOs: 164 and 165 respectively, SEQ ID NOs: 166 and 167 respectively, SEQ ID NOs: 168 and 169 respectively, SEQ ID NOs: 170 and 171 respectively, SEQ ID NOs: 172 and 173 respectively, SEQ ID NOs: 174 and 175 respectively, SEQ ID NOs: 176 and 177 respectively, SEQ ID NOs: 178 and 179 respectively, SEQ ID NOs: 180 and 181 respectively, SEQ ID NOs: 182 and 183 respectively, SEQ ID NOs: 184 and 185 respectively, SEQ ID NOs: 186 and 187 respectively, or SEQ ID NOs: 188 and 189 respectively. Selected VH and VL sequences of exemplary CD38 binding domains are provided in Table 1A as numbered pairs 1-23. In some embodiments, the CD38⁻ADR extracellular domain comprises an amino acid sequence with at least about 90% sequence identity to the VH and/or VL sequence of any of pairs 1-23 in Table 1A. In some embodiments, the CD38-ADR extracellular domain comprises an amino acid sequence with at least about 95% sequence identity to the VH and/or VL sequence of any of pairs 1-23 in Table 1A. In some embodiments, the CD38-ADR extracellular domain comprises the amino acid sequence of the VH and/or VL sequence of any of pairs 1-23 in Table 1A.

TABLE 1A

| | VH | VL |
|---|---|---|
| 1 | QVQLKQSGPSLVQPSQRLSITCTVSGFSLISYGVHWVRQSPGKGLEWLGVIWRGGSTDYNAAFMSRLSITKDNSKSQVFFKMNSLQADDTAIYFCAKTLITTGYAMDYWGQGTSVTVSS (SEQ ID NO: 146) | DIQLTQSSSSFSVSLGDRVTITCKASEDIYNRLAWYQQKPGNAPRLLISGATSLETGVPSRFSGSGSGKDYTLSITSLQTEDVATYYCQQYWSTPTFGGGTKLEIK (SEQ ID NO: 147) |
| 2 | QVELVESGGSLKLSCAASGFDFSRSWMNWVRQAPGKGLEWIGEINPDSSTINYTTSLKDKFIISRDNAKNTLYLQMTKVRSEDTALYYCARYGNWFPYWGQGTLVTVSS (SEQ ID NO: 148) | DILMTQSQKIMPTSVGDRVSVTCKASQNVDTNVAWYQQKPGQSPKALIYSASYRYSGVPDRFTGSGSGTDFTLTITNVQSEDLAEYFCQQYDSYPLTFGAGTKLDLK (SEQ ID NO: 149) |
| 3 | QVQLKQSGPGLVHPSQSLSITCTVSGFSLTSYGVHWVRQSPGKGLEWLGVMWRGGSTDYNAAFMSRLNITKDNSKRQVFFKMNSLQADDTAIYYCAKSMITTGFVMDSWGQGTSVTVSS (SEQ ID NO: 150) | DIQLTQSPSSFSVSLGDRVTITCKASEDIYNRLTWYQQKPGNAPRLLISGATSLETGVPSRFSGSGSGKDYTLSITSLQTEDVATYYCQQYWSNPYTFGGGTKLEIR (SEQ ID NO: 151) |
| 4 | QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVYTGFAYWGQGTLVTVSS (SEQ ID NO: 152) | DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVL (SEQ ID NO: 153) |
| 5 | QVQLVQSGAEVKKPGASVKVSCKASGYTFTSYSINWVRQAPGQGLEWMGYIDPNRGNTNYAQKFQGRVTMTRDTSISTAYMELSSLRSEDTAVYYCAREYIYFIHGMLDFWGQGTLVTVSS (SEQ ID NO: 154) | DIVMTQSPLSLPVTPGEPASISCRSSQSLLFIDGNNYLNWYLQKPGQSPQLLIYLGSNRASGVPDRFSGSGSGTDFTLKISRVEAEDVGVYYCQQYSSKSATFGQGTKVEIK (SEQ ID NO: 155) |
| 6 | QVQLVESGGGLVQPGGSLRLSCAASGFTFSNYGMHWVRQAPGKGLEWVSNIRSDGSWTYYADSVKGRFTISRDNSKNTLYLQMNSLRAEDTAVYYCARRYWSKSHASVTDYWGQGTLVTVSS (SEQ ID NO: 156) | DIQMTQSPSSLSASVGDRVTITCRASQDISAFLNWYQQKPGKAPKLLIYKVSNLQSGVPSRFSGSGSGTDFTLTISSLQPEDFATYYCQQAYSGSITFGQGTKVEIK (SEQ ID NO: 157) |
| 7 | EVQLLESGGGLVQPGGSLRLSCAASGFTFDDYGMSWVRQAPGKGLEWVSDISWNGGKTHYVDSVKGQFTISRDNSKNTLYLQMNSLRAEDTAVYYCARGSLPHDSSGFYFGHWGQGTLVTVSS (SEQ ID NO: 158) | QSVLTQPPSASGTPGQRVTISCSGSSSNIGDNYVSWYQQLPGTAPKLLIYRDSQRPSGVPDRFSGSKSGTSASLAISGLRSEDEADYYCQSYDSSLSGSVFGGGTKLTVL (SEQ ID NO: 159) |
| 8 | EVQLLESGGGLVQPGGSLRLSCAASGFTFNNYDMTWVRQAPGKGLEWVAVISYDGSDKDYADSVKGRFTISRDNSKNTLYLQMNSLRAEDTAVYYCARVYYYGFSGPSMDVWGQGTLVTVSS (SEQ ID NO: 160) | QSVLTQPPSASGTPGQRVTISCSGSNSIGSNTVNWYQQLPGTAPKLLIYSDSNRPSGVPDRFSGSKSGTSASLAISGLRSEDEADYYCQSYDSSLSGSRVFGGGTKLTVL (SEQ ID NO: 161) |
| 10 | EVQLLESGGGLVQPGGSLRLSCAASGFTFSSYGMNWVRQAPGKGLEWVSGISGSGSTYYADSVKGRFTISRDNSKNTLYLQMNSLRAEDTAVYYCAKDSNYDFWSGYYYGMDVWGQGTLVTVSS (SEQ ID NO: 162) | QSVLTQPPSASGTPGQRVTISCSGSSSNIGSKTVSWYQQLPGTAPKLLIYDNNKRPSGVPDRFSGSKSGTSASLAISGLRSEDEADYYCSSYAARSTNIIFGGGTKLTVL (SEQ ID NO: 163) |
| 11 | EVQLLESGGGLVQPGGSLRLSCAASGFTFSSYGMHWVRQAPGKGLEWVSRINSDGSSTSYADSMKGQFTISRDNSKNTLYLQMNSLRAEDTAVYYCARGGYYYYAMDVWGQGTLVTVSS (SEQ ID NO: 164) | QSVLTQPPSASGTPGQRVTISCSGSSSNIGYKTVNWYQQLPGTAPKLLIYDNNKRPSGVPDRFSGSKSGTSASLAISGLRSEDEADYYCAAWDDSLNGLVFGGGTKLTVL (SEQ ID NO: 165) |
| 12 | QIQLVQSGPELKKPGETVKISCKASGYTLTSYGMNWVKQAPGKGLKWMGWINTYTGEPTYADDFKGRFAFSLETSASTAFLQINNLKNEDTATYFCVRRGFAYWGQGTLVTVSA (SEQ ID NO: 166) | NIVLTQSPASLAVSLGQRATISCRASESVEIYGNGFMNWFQQKPGQPPKLLIYRASNLESGIPARFSGSGSRTEFTLTIDPVEADDVATYYCQQINEDPFTFGSGTKLEIK (SEQ ID NO: 167) |
| 13 | QIQLVQSGPELKKPGETVKISCKASGYTFTNSGMNWVKQAPGKGLKWMGWINTYTGEPTYADDFKGRFAFSLETSASSAYLQISNLKNEDTATYFCARRGFVYWGQGTLVTVSA (SEQ ID NO: 168) | DIVLTQSPASLAVSLGQRATISCRASESVAIYGNSFLKWFQQKPGQPPKLLIYRASNLESGIPARFSGSGSGTDFTLTINPVEADDVATYYCQQINEDPYTFGGGTKLEIK (SEQ ID NO: 169) |
| 14 | QVQLQQSGAELARPGTSVKLSCKASGYTFTDYWMQWVKQRPGQGLEWIGTIYPGDGDTGYAQKFKGKATLTADKSSKTVY | DIVMAQSHKFMSTVGDRVSTICKASQDVSTVVAWYQQKPGQSPKRLIYSASYRYIGVPDRFTGSGSGTDFTFTISSVQA |

TABLE 1A-continued

| | VH | VL |
|---|---|---|
| | MHLSSLASEDSAVYYCARGD YYGSNSLDYWGQGTSVTVSS (SEQ ID NO: 170) | EDLAVYYCQQHYSPPYTFGG GTKLEIK (SEQ ID NO: 171) |
| 15 | NVQLVESGGGLVQPGGSRKL SCAASGFTFSNFGMHWVRQA PEKGLEWVAYIRSGSGTIYY SDTVKGRFTISRDNPKNTLF LQMTSLRSEDTAMYYCARSY YDFGAWFAYWGQGTLVTVSA (SEQ ID NO: 172) | DIVMTQSQKFMSTSVGDRVS VTCKASQNVGTNVAWYQHKP GQSPKIMIYSASSRYSGVPD RFTGSGSGTLFTLTINNVQS EDLAEYFCQQYNSYPLTFGS GTKLEIK (SEQ ID NO: 173) |
| 16 | QVQLVQSGAEVAKPGTSVKL SCKASGYTFTDYWMQWVKQR PGQGLEWIGTIYPDGDGTGY AQKFQGKATLTADKSSKTVY MHLSSLASEDSAVYYCARGD YYGSNSLDYWGQGTSVTVSS (SEQ ID NO: 174) | DIVMTQSHLSMSTSLGDPVS ITCKASQDVSTVVAWYQQKP GQSPRRLIYSASYRYIGVPD RFTGSGAGTDFTFTISSVQA EDLAVYYCQQHYSPPYTFGG GTKLEIK (SEQ ID NO: 175) |
| 17 | EVQLLESGGGLVQPGGSLRL SCAVSGFTFNSFAMSWVRQA PGKGLEWVSAISGSGGGTYY ADSVKGRFTISRDNSKNTLY LQMNSLRAEDTAVYFCAKDK ILWFGEPVFDYWGQGTLVTV SS (SEQ ID NO: 176) | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPPTFGQ GTKVEIK (SEQ ID NO: 177) |
| 18 | QVQLVQSGAEVKKPGSSVKV SCKAFGGTFSSYAISWVRQA PGQGLEWMGRIIRFLGIANY AQKFQGRVTLIADKSTNTAY MELSSLRSEDTAVYYCAGEP GERDPDAVDIWGQGTMVTVS S (SEQ ID NO: 178) | DIQMTQSPSSLSASVGDRVT ITCRASQGIRSWLAWYQQKP EKAPKSLIYAASSLQSGVPS RFSGSGSGTDFTLTISSLQP EDFATYYCQQYNSYPLTFGG GTKVEIK (SEQ ID NO: 179) |
| 19 | EVQLVQSGAEVKKPGESLKI SCKGSGYSFSNYWIGWVRQM PGKGLEWMGIIYPHDSDARY SPSFQGQVTFSADKSISTAY LQWSSLKASDTAMYYCARHV GWGSRYWYFDLWGRGTLVTV SS (SEQ ID NO: 180) | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPPTFGQ GTKVEIK (SEQ ID NO: 181) |
| 20 | QVQLVQSGAEVKKPGSSVKV SCKASGGTFSSYAFSWVRQA PGQGLEWMGRVIPFLGIANS AQKFQGRVTITADKSTSTAY MDLSSLRSEDTAVYYCARDD IAALGPFDYWGQGTLVTVSS AS (SEQ ID NO: 182) | DIQMTQSPSSLSASVGDRVT ITCRASQGISSWLAWYQQKP EKAPKSLIYAASSLQSGVPS RFSGSGSGTDFTLTISSLQP EDFATYYCQQYNSYPRTFGQ GTKVEIK (SEQ ID NO: 183) |
| 21 | QVQLVQSGAEVKKPGSSVKV SCKAFGGTFSSYAISWVRQA PGQGLEWMGRIIRFLGKTNH AQKFQGRVTLTADKSTNTAY MELSSLRSEDTAVYYCAGEP GDRDPDAVDIWGQGTMVTVS S (SEQ ID NO: 184) | DIQMTQSPSSLSASVGDRVT ITCRASQGIRSWLAWYQQKP EKAPKSLIYAASSLQSGVPS RFSGSGSGTDFTLTISSLQP EDFATYYCQQYNSYPLTFGG GTKVEIK (SEQ ID NO: 185) |
| 22 | QVQLVQSGAEVKKPGSSVKV SCKPSGGTFRSYAISWVRQA PGQGLEWMGRIIVFLGKVNY AQRFQGRVTLTADKSTTTAY MELSSLRSEDTAVYYCTGEP GARDPDAFDIWGQGTMVTVS S (SEQ ID NO: 186) | DIQMTQSPSSLSASVGDRVT ITCRASQGIRSWLAWYQQKP EKAPKSLIYAASSLQSGVPS RFSGSGSGTDFTLTISSLQP EDFATYYCQQYNNYPLTFGG GTKVEIK (SEQ ID NO: 187) |
| 23 | QVQLVQSGAEVKKPGSSVKV SCKAFGGTFSSYAISWVRQA PGQGLEWMGRIIRFLGIANY AQKFQGRVTLIADKSTNTAY | DIQMTQSPSSLSASVGDRVT ITCRASQGISNYLAWFQQKP GKAPKSLIYAASSLQSGVPS RFSGSGSGTDFTLTISSLQP |
| | MELSSLRSEDTAVYYCAGEP GERDPDAVDIWGQGTMVTVS S (SEQ ID NO: 188) | EDFATYYCQQYNSYPYTFGQ GTKLEIK (SEQ ID NO: 189) |

In some embodiments, the extracellular domain of the 41BB-ADR or CD38-ADR may be operably linked to one or more signaling domains that mediate downstream signaling upon effector cell activation upon the binding to the 4-11BB or CD38, respectively, of alloreactive host immune cells. In particular embodiments, the ADR comprises CD3ζ, represented by an amino acid sequence of at least about 85% u, about 90% u, about 95% u, about 96% u, about 97%, about 98%, or about 99% sequence identity to SEQ ID NO: 60 or a functional fragment thereof, or comprises a CD3ζ derivative (for example, CD3ζ1XX, represented by an amino acid sequence of at least about 85%, about 90%, about 95%, about 96%, about 97%, about 98%, or about 99% sequence identity to SEQ ID NO: 61 or a functional fragment thereof). In some embodiments, the CD3ζ comprises an amino acid sequence of at least about 9000 sequence identity to SEQ ID NO: 60. In some embodiments, the CD3 comprises an amino acid sequence of at least about 95% sequence identity to SEQ ID NO: 60. In some embodiments, the CD3ζ comprises the amino acid sequence of SEQ ID NO: 60. In some embodiments, the CD3ζ derivative comprises an amino acid sequence of at least about 90% sequence identity to SEQ ID NO: 61. In some embodiments, the CD3ζ derivative comprises an amino acid sequence of at least about 95% sequence identity to SEQ ID NO: 61. In some embodiments, the CD3ζ derivative comprises the amino acid sequence of SEQ ID NO: 61. CD3ζ mediates downstream ITAM-derived signaling during effector T or NK cell activation. Other ITAM-containing signaling domains may include those derived from DAP12, Fc receptors, and other CD3 subunits.

SEQ ID NO: 60
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR
(CD3ζ)

SEQ ID NO: 61
RVKFSRSADAPAYQQGQNQLYNELNLGRREEYDVLDKRRGRDPEMGGKPR

RKNPQEGLFNELQKDKMAEAFSEIGMKGERRRGKGHDGLFQGLSTATKDT

FDALHMQALPPR
(CD3ζ1XX - containing 2 mutations in ITAM1)

In some embodiments, the intracellular domain of ADR comprising a signaling domain further comprises one, two, three, or more costimulatory domains that enhance cytokine production from the effector cells that express the ADR. The costimulatory domains may be derived from the intracellular signaling domains of costimulatory proteins including, but not limited to, CD28, CD27, 4-1BB, OX40, ICOS, CD30, HVEM, CD40, and so forth. In some embodiments the ADR comprising CD3 further comprises a costimulatory domain derived from 4-1BB endodomain. In some embodiments, the endodomain is represented by an amino acid sequence of at least about 85%, about 90%, about 95%, about 96%, about 97%, about 98%, or about 99% sequence identity to SEQ ID NO: 190 or a functional fragment thereof. In some embodiments, the endodomain comprises an amino acid sequence of at least about 90% sequence identity to SEQ ID NO: 190. In some embodiments, the endodomain comprises an amino acid sequence of at least about 95% sequence identity to SEQ ID NO: 190. In some embodiments, the endo-domain comprises the amino acid sequence of SEQ ID NO: 190. In one embodiment, when the ADR comprises 4-1BBL in its extracellular domain, the costimulatory domain of the ADR is not derived from 4-1BB.

SEQ ID NO: 190
*KRGRKKLLYIFKQPFMRPVQTTQEEDGCSCRFPEEEEGGCEL*

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
(41BB endo-CD3ζ)

The intracellular domain of an ADR may be non-covalently linked to the extracellular domain of the ADR via a transmembrane domain. In some embodiments, the ADR comprises a transmembrane domain that may be of any kind so long as it allows the CD3ζ component of the ADR to be located intracellularly and the extracellular domain that targets 4-1BB or CD38 to be located extracellularly. In other instances, ADRs are soluble proteins that can bind to the respective ligand on activated T cells and promote cytotoxicity by crosslinking TCR (e.g., ADR-CD3 T-cell engager protein). In a case wherein the extracellular domain is from a surface protein having a transmembrane domain, (CD40, for example), the ADR may comprise the transmembrane domain from that corresponding endogenous molecule. In some embodiments in which the ADR molecule comprises one or more costimulatory domains, the transmembrane domain (TM) may be from the same endogenous molecule that has the costimulatory domain. Non limiting examples of TMs include those from CD3, CD8a, CD27, CD28, 4-1BB, OX40, and CD4.

In some embodiments, the ADR comprises a spacer between the extracellular protein and the transmembrane domain. In some embodiments, the spacer may comprise a sequence that is inert or contributes substantially little or nothing with respect to any function the ADR may have; whereas in other cases the spacer comprises a sequence that enhances a function of the ADR and/or allows it to be detectable and/or able to be targeted for inhibition. In specific embodiments, the spacer comprises an encoded protein sequence that facilitates detection of cells that express the ADR. For example, the spacer may encode an Fc region or fragments thereof that would allow for surface detection of the cells expressing the ADR, such as by using anti-Fc antibodies. In particular embodiments, the spacer provides separation between the ligand binding extracellular domain and the membrane to avoid potential steric hindrances. As understood by one skilled in the art, the spacer can vary in sequence and/or in length, whether a function other than being a physical separation is intended or not. Exemplary spacers that may be included in the ADR are commonly known in the art, including, but not limited to, IgG4 spacers, CD28 spacers, CD8 spacers, or combinations of more than one spacer. The length of the spacers may also vary, from about 15 amino acids (a.a.) to about 300 a.a. or more. Non-limiting exemplary spacer peptides include those represented by an amino acid sequence of at least about 80%, about 85%, about 90%, about 95%, about 96%, about 97%, about 98%, or about 99% identity to SEQ ID NO: 140 or 141. In some embodiments, the spacer peptide comprises an amino acid sequence of at least about 90% identity to SEQ ID NO: 140 or 141. In some embodiments, the spacer peptide comprises an amino acid sequence of at least about 95% identity to SEQ ID NO: 140 or 141. In some embodiments, the spacer peptide comprises the amino acid sequence of SEQ ID NO: 140. In some embodiments, the spacer peptide comprises the amino acid sequence of SEQ ID NO: 141.

SEQ ID NO: 140
ESKYGPPCPPCPGGGSSGGGSGGQPREPQVYTLPPSQEEMTKNQVSLTCL

VKGFYPSDIAVEWESNGQPENNYKTTPPVLDSDGSFFL
(88 a.a.)

SEQ ID NO: 141
*ESKYGPPCPPCP*

GQPREPQVYTLPPSRDELTKNQVSLTCLVKGFYPSDIAVEWESNGQPENNY

KTTPPVLDSDGSFFLYSKLTVDKSRWQQGNVFSCSVMHEALHNAYTQKSL

SLSPGKKDPK
(123 a.a. *IgG4 hinge*-IgG1 CH3)

In one embodiment of the 4-1BB specific ADR, the 41BB-ADR is represented by an amino acid sequence of at least about 85%, about 90%, about 95%, about 96%, about 97%, about 98%, or about 99% sequence identity to SEQ ID NO: 18 or SEQ ID NOs: 142-144. In some embodiments, the the 41BB-ADR comprises an amino acid sequence of at least about 90% identity to SEQ ID NO: 18 or SEQ ID NOs: 142-144. In some embodiments, the the 41BB-ADR comprises an amino acid sequence of at least about 95% identity to SEQ ID NO: 18 or SEQ ID NOs: 142-144. In some embodiments, the the 41BB-ADR comprises the amino acid sequence of SEQ ID NO: 18. In some embodiments, the the 41BB-ADR comprises the amino acid sequence of SEQ ID NO: 142. In some embodiments, the the 41BB-ADR comprises the amino acid sequence of SEQ ID NO: 143. In some embodiments, the the 41BB-ADR comprises the amino acid sequence of SEQ ID NO: 144.

SEQ ID NO: 18
*MEFGLSWLFLVAILKGVQC*

GLLDLRQGMFAQLVAQNVLLIDGPLSWYSDPGLAGVSLTGGLSYKEDTKE

LVVAKAGVYYVFFQLELRRVVAGEGSGSVSLALHLQPLRSAAGAAALALT

VDLPPASSEARNSAFGFQGRLLHLSAGQRLGVHLHTEARARHAWQLTQGA

TVLGLFRVTPEIPAGLPSPRSE

*ESKYGPPCPPCPGQPREPQVYT*

*LPPSRDELTKNQVSLTCLVKGF*

*YPSDIAVEWESNGQPENNYKTT*

*PPVLDSDGSFFLYSKLTVDKSR*

*WQQGNVFSCSVMHEALHNAYTQ*

*KSLSLSPGKKDPK*

FWVLVVVGGVLACYSLLVTVAFIIFWVRS

RVKFSRSADAPAYQQGQNQLYN

ELNLGRREEYDVLDKRRGRDPE

-continued
MGGKPRRKNPQEGLYNELQKDK

MAEAYSEIGMKGERRRGKGHDG

LYQGLSTATKDTYDALHMQALP

PR
*Signal peptide*-41BBL-*spacer*-**CD28
(TM)-CD3z** (the signal peptide, spacer
and TM/transmembrane domain may vary)

SEQ ID NO: 142

*MEFGLSWLFLVAILKGVQC*

GLLDLRQGMFAQLVAQNVLLIDGPLSWYSDPGLAGVSLTGGLSYKEDTKE

LVVAKAGVYYVFFQLELRRVVAGEGSGSVSLALHLQPLRSAAGAAALALT

VDLPPASSEARNSAFGFQGRLLHLSAGQRLGVHLHTEARARHAWQLTQGA

TVLGLFRVTPEIPAGLPSPRSE

*ESKYGPPCPPCPGQPREPQVYT*

*LPPSRDELTKNQVSLTCLVKGF*

*YPSDIAVEWESNGQPENNYKTT*

*PPVLDSDGSFFLYSKLTVDKSR*

*WQQGNVFSCSVMHEALHNAYTQ*

*KSLSLSPGKKDPK*

FWVLVVVGGVLACYSLLVTVAFIIFWVRS

KRSRLLHSDYMNMTPRRPGPTRKHYQPYAPPRDFAAYRS

RVKFSRSADAPAYQQGQNQLYNELNLGRR

EEYDVLDKRRGRDPEMGGKPRRKNPQEGL

YNELQKDKMAEAYSEIGMKGERRRGKGHD

GLYQGLSTATKDTYDALHMQALPPR
*Signal peptide*-41BBL-*spacer*-**CD28
(TM)-CD28 (ICD)-CD3z** (the signal
peptide, spacer and TM/
transmembrane domain may vary)

SEQ ID NO: 143

*MEFGLSWLFLVAILKGVQC*

GLLDLRQGMFAQLVAQNVLLIDGPLSWYSDPGLAGVSLTGGLSYKEDTKE

LVVAKAGVYYVFFQLELRRVVAGEGSGSVSLALHLQPLRSAAGAAALALT

VDLPPASSEARNSAFGFQGRLLHLSAGQRLGVHLHTEARARHAWQLTQGA

TVLGLFRVTPEIPAGLPSPRSE

*ESKYGPPCPPCPGQPREPQVYT*

*LPPSRDELTKNQVSLTCLVKGF*

*YPSDIAVEWESNGQPENNYKTT*

*PPVLDSDGSFFLYSKLTVDKSR*

*WQQGNVFSCSVMHEALHNAYTQ*

*KSLSLSPGKKDPK*

FWVLVVVGGVLACYSLLVTVAFIIFWVRS

RVKFSRSADAPAYQQGQNQLYN

ELNLGRREEYDVLDKRRGRDPE

MGGKPRRKNPQEGLFNELQKDK

MAEAFSEIGMKGERRRGKGHDG

LFQGLSTATKDTFDALHMQALP

PR
*Signal peptide*-41BBL-*spacer*-**CD28
(TM)-CD3z1xx** (the signal peptide,
spacer and TM/transmembrane
domain may vary)

SEQ ID NO: 144

*MEFGLSWLFLVAILKGVQC*

GLLDLRQGMFAQLVAQNVLLIDGPLSWYSDPGLAGVSLTGGLSYKEDTKE

LVVAKAGVYYVFFQLELRRVVAGEGSGSVSLALHLQPLRSAAGAAALALT

VDLPPASSEARNSAFGFQGRLLHLSAGQRLGVHLHTEARARHAWQLTQGA

TVLGLFRVTPEIPAGLPSPRSE

*ESKYGPPCPPCPGQPREPQVYT*

*LPPSRDELTKNQVSLTCLVKGF*

YPSDIAVEWESNGQPENNYKTT

*PPVLDSDGSFFLYSKLTVDKSR*

*WQQGNVFSCSVMHEALHNAYTQ*

*KSLSLSPGKKDPK*

FWVLVVVGGVLACYSLLVTVAFIIFWVRS

KRSRLLHSDYMNMTPRRPGPTRKHYQPYAPPRDFAAYRS

RVKFSRSADAPAYQQGQNQLYNELNLGRR

EEYDVLDKRRGRDPEMGGKPRRKNPQEGL

FNELQKDKMAEAFSEIGMKGERRRGKGHD

GLFQGLSTATKDTFDALHMQALPPR
*Signal peptide*-41BBL-*spacer*-**CD28
(TM)-CD28 (ICD)-CD3z1xx** (the
signal peptide, spacer and TM/
transmembrane domain may vary)

In one embodiment of the CD38 specific ADR, the CD38-ADR is represented by an amino acid sequence of at least about 85%, about 90%, about 95%, about 96%, about 97%, about 98%, or about 99% sequence identity to SEQ ID NO: 191. In some embodiments, the CD38-ADR comprises an amino acid sequence of at least about 90% sequence identity to SEQ ID NO: 191. In some embodiments, the CD38-ADR comprises an amino acid sequence of at least about 95% sequence identity to SEQ ID NO: 191. In some embodiments, the CD38-ADR comprises the amino acid sequence of SEQ ID NO: 191.

SEQ ID NO: 191

*MDFQVQIFSFLLISASVIMSR*

DIQMTQSPSSLSASVGDRVTITCRASQGIRSWLAWYQQKPEKAPKSLIYA

ASSLQSGVPSRFSGSGSGTDFTLTISSLQPEDFATYYCQQYNNYPLTFGG

GTKVEIK

*GGGGSGGGGSGGGGS*QVQLVQSGAEVKK

PGSSVKVSCKPSGGTFRSYAISWVRQAPGQGLEWMGRIIVFLGKVNYAQR

FQGRVTLTADKSTTTAYMELSSLRSEDTAVYYCTGEPGARDPDAFDIWGQ

GTMVTVSS

-continued

TSTPAPRPPTPAPTIASQPLSLRPEACR

PAAGGAVHTRGLDFACDIYIWAPLAGTC

GVLLLSLVITLYC

KRGRKKLLYIFKQPFMRPVQTTQEEDGCSCRFPEEEEGGCEL

RVKFSRSADAPAYQQGQNQLYNELNLGR

REEYDVLDKRRGRDPEMGGKPRRKNPQE

GLYNELQKDKMAEAYSEIGMKGERRRGK

GHDGLYQGLSTATKDTYDALHMQALPPR
Signal peptide-antiCD38VH-linker-
antiCD38VL-CD8 (TM)-41BB (endo)-
CD3z (endo) (the signal peptide,
linker, and TM/transmembrane
domain may vary)

Accordingly, in some embodiments, the present application provides a solid tumor targeting backbone comprising a polynucleotide encoding an ADR specific to 4-1BB or CD38, among other components of the backbone, to equip an allogeneic effector cell with the ability to selectively deplete activated host immune cells while potentiating the effector cell through increased expansion in a tumor environment. Also provided in this application are immune cells, iPSCs, and iPSC-derived effector cells comprising a solid tumor targeting backbone comprising a polynucleotide encoding a 4-1BB specific ADR or a CD38 specific ADR, among other selected components, wherein the effector cells, including the genetically engineered T and NK cells, possess alloreactive resistance to the host immune system associated with the allogeneic use of the effector cells for treatment of tumors and infectious diseases in a patient.

4. CD38 Knockout

The cell surface molecule CD38 is highly upregulated in multiple hematologic malignancies derived from both lymphoid and myeloid lineages, including multiple myeloma and a CD20 negative B-cell malignancy, which makes it an attractive target for antibody therapeutics to deplete cancer cells. Antibody mediated cancer cell depletion is usually attributable to a combination of direct cell apoptosis induction and activation of immune effector mechanisms such as ADCC (antibody-dependent cell-mediated cytotoxicity). In addition to ADCC, the immune effector mechanisms in concert with the therapeutic antibody may also include antibody-dependent cell-mediated phagocytosis (ADCP) and/or complement-dependent cytotoxicity (CDC).

Other than being highly expressed on malignant cells, CD38 is also expressed on plasma cells, as well as on NK cells and activated T and B cells. During hematopoiesis, CD38 is expressed on $CD34^+$ stem cells and lineage-committed progenitors of lymphoid, erythroid, and myeloid, and during the final stages of maturation which continues through the plasma cell stage. As a type II transmembrane glycoprotein, CD38 carries out cell functions as both a receptor and a multifunctional enzyme involved in the production of nucleotide-metabolites. As an enzyme, CD38 catalyzes the synthesis and hydrolysis of the reaction from $NAD^+$ to ADP-ribose, thereby producing secondary messengers CADPR and NAADP which stimulate release of calcium from the endoplasmic reticulum and lysosomes, critical for the calcium dependent process of cell adhesion. As a receptor, CD38 recognizes CD31 and regulates cytokine release and cytotoxicity in activated NK cells. CD38 is also reported to associate with cell surface proteins in lipid rafts, to regulate cytoplasmic $Ca^{2+}$ flux, and to mediate signal transduction in lymphoid and myeloid cells.

In malignancy treatment, systemic use of CD38 antigen binding receptor transduced T cells has been shown to lyse the $CD38^+$ fractions of $CD34^+$ hematopoietic progenitor cells, monocytes, NK cells, T cells and B cells, leading to incomplete treatment responses and reduced or eliminated efficacy because of the impaired recipient immune effector cell function. In addition, in multiple myeloma patients treated with daratumumab, a CD38-specific antibody, NK cell reduction in both bone marrow and peripheral blood was observed, although other immune cell types, such as T cells and B cells, were unaffected despite their CD38 expression (Casneuf et al., Blood Advances. 2017; 1(23):2105-2114).

Without being limited by theories, the present application includes a strategy to leverage the full potential of CD38 targeted cancer treatment by knocking out CD38 in the effector cell, thereby overcoming CD38-specific antibody and/or CD38 antigen binding domain-induced effector cell depletion or reduction through fratricide. In addition, since CD38 is upregulated on activated lymphocytes such as T or B cells, by suppressing activation of these recipient lymphocytes using a CD38-specific antibody, such as daratumumab, in the recipient of allogeneic effector cells, host allorejection against these effector cells would be reduced and/or prevented, thereby increasing effector cell survival and persistency. As such, a CD38-specific antibody, a secreted CD38-specific engager or a CD38-CAR (chimeric antigen receptor) against activation of recipient T, Treg, NK, and/or B cells can be used as a replacement for lymphodepletion using chemotherapy such as Cy/Flu (cyclophosphamide/fludarabine) prior to adoptive cell transferring.

In addition, when targeting $CD38^+$ T and pbNK cells using $CD38^-$ effector cells in the presence of anti-CD38 antibodies or CD38 inhibitors, the depletion of $CD38^+$ alloreactive cells increases the $NAD^+$ (nicotinamide adenine dinucleotide, a substrate of CD38) availability and decreases $NAD^+$ consumption related cell death, which, among other advantages, boosts effector cell responses in an immunosuppressive tumor microenvironment and supports cell rejuvenation in aging, degenerative or inflammatory diseases.

Moreover, the strategy as provided herein, i.e., CD38 knockout, is compatible with other components and processes contemplated for establishing a solid tumor targeting backbone as disclosed in this application, thereby providing an immune cell, an iPSC and differentiated effector cell therefrom comprising a CD38 knockout with additional backbone edits. As disclosed herein, in various embodiments, the solid tumor targeting backbone comprised in the iPSC line or a derivative thereof, comprises at least two of a C—X—C-motif chemokine receptor or a variant thereof, a TGFβ-SRR, and an ADR specific to 4-1BB; and a CD38 knockout. In some embodiments, the provided $CD38^{neg}$ iPSC line optionally comprises one or more additional engineered modalities described herein, and as shown in Table 4. As such, these $CD38^{neg}$ derivative effector cells comprising a solid tumor targeting backbone are protected against fratricide and allorejection when CD38 targeted therapeutic moieties are employed with the effector cells, among other advantages including improved metabolic fitness, increased resistance to oxidative stress and inducing a protein expression program in the effector cell that enhances cell activation and effector function. In addition, anti-CD38 monoclonal antibody therapy significantly depletes a patient's activated immune system without adversely affecting the patient's hematopoietic stem cell compartment. A CD38$^{neg}$ derivative cell has the ability to resist CD38 antibody mediated depletion, and may be effectively administered in combination with an anti-CD38 antibody or CD38-CAR without the use of toxic conditioning agents, thereby reducing and/or replacing chemotherapy-based lymphodepletion.

In one embodiment as provided herein, the CD38 knock-out in an iPSC line is a bi-allelic knockout. In another embodiment, knocking out CD38 at the same time as inserting one or more transgenes, including a C—X—C-motif chemokine receptor or a variant thereof, a TGFβ-SRR, and/or an ADR specific to 4-1BB or CD38 as provided herein, at a selected position in CD38 can be achieved, for example, by a CD38-targeted knock-in/knockout (CD38-KI/KO) construct. In some embodiments of the construct, the construct comprises a pair of CD38 targeting homology arms for position-selective insertion within the CD38 locus. In some embodiments, the preselected targeting site is within an exon of CD38. The CD38-KI/KO constructs provided herein allow the transgene(s) to express either under the CD38 endogenous promoter or under an exogenous promoter comprised in the construct. When two or more transgenes are to be inserted at a selected location in the CD38 locus, a linker sequence, for example, a 2A linker or IRES, is placed between any two transgenes. The 2A linker encodes a self-cleaving peptide derived from FMDV, ERAV, PTV-I, and TaV (referred to as "F2A", "E2A", "P2A", and "T2A", respectively), allowing for separate proteins to be produced from a single translation. In some embodiments, insulators are included in the construct to reduce the risk of transgene and/or exogenous promoter silencing. The exogenous promoter comprised in a CD38-KI/KO construct may be CAG, or other constitutive, inducible, temporal-, tissue-, or cell type-specific promoters including, but not limited to CMV, EF1α, PGK, and UBC.

In various embodiments, said iPSC is capable of directed differentiation to produce functional derivative hematopoietic cells including, but not limited to, mesodermal cells with definitive hemogenic endothelium (HE) potential, definitive HE, CD34$^+$ hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages. In some embodiments, the CD38 negative effector cells are NK lineage cells derived from iPSCs. In some embodiments, the CD38 negative effector cells are T lineage cells derived from iPSCs. In some embodiments, the iPSC and derivative cells thereof comprise a solid tumor targeting backbone comprising CD38$^{neg}$ and at least two of: a polynucleotide encoding a C—X—C motif chemokine receptor or a variant thereof, a polynucleotide encoding a TGFβ-SRR, and a polynucleotide encoding a 41BB-ADR, and optionally include one or more additional genomic edits as described herein.

5. CD16 Knock-In

CD16 has been identified as two isoforms, Fc receptors FcγRIIIa (CD16a; NM_000569.6) and FcγRIIIb (CD16b; NM_000570.4). CD16a is a transmembrane protein expressed by NK cells, which binds monomeric IgG attached to target cells to activate NK cells and facilitate antibody-dependent cell-mediated cytotoxicity (ADCC). CD16b is exclusively expressed by human neutrophils. "High affinity CD16," "non-cleavable CD16," or "high affinity non-cleavable CD16" (abbreviated as hnCD16), as used herein, refers to various CD16 variants. The wildtype CD16 has low affinity and is subject to ectodomain shedding, a proteolytic cleavage process that regulates cell surface density of various cell surface molecules on leukocytes upon NK cell activation. F176V (also called F158V in some publications) is an exemplary CD16 polymorphic variant having high affinity; whereas S197P variant is an example of genetically engineered non-cleavable version of CD16. An engineered CD16 variant comprising both F176V and S197P has high affinity and is non-cleavable, which was described in greater detail in WO2015/148926, the complete disclosure of which is incorporated herein by reference. In addition, a chimeric CD16 receptor with the ectodomain of CD16 essentially replaced with at least a portion of CD64 ectodomain can also achieve the desired high affinity and non-cleavable features of a CD16 receptor capable of carrying out ADCC. In some embodiments, the replacement ectodomain of a chimeric CD16 comprises one or more of EC1, EC2, and EC3 exons of CD64 (UniPRotKB_P12314 or its isoform or polymorphic variant).

As such, various embodiments of an exogenous CD16 introduced to a cell include functional CD16 variants and chimeric receptors thereof. In some embodiments, the functional CD16 variant is a high-affinity non-cleavable CD16 receptor (hnCD16). An hnCD16, in some embodiments, comprises both F176V and S197P; and in some embodiments, comprises F176V and with the cleavage region eliminated. In some embodiments, an hnCD16 comprises a sequence having identity of at least 50%, 55%, 60%, 65%, 70%, 75%, 80%, 85%, 90%, 95%, 99%, 100%, or any percentage in-between, when compared to any of the exemplary sequences, SEQ ID NOs. 19, 20 and 21, and each comprises at least a portion of CD64 ectodomain. In some embodiments, the hnCD16 comprises an amino acid sequence of at least 90% identity to any of SEQ ID NOs. 19-21, and optionally one or more of F176V, S197P, and at least a portion of CD64 ectodomain. In some embodiments, the hnCD16 comprises an amino acid sequence of at least 95% identity to any of SEQ ID NOs. 19-21, and optionally one or more of F176V, S197P, and at least a portion of CD64 ectodomain. In some embodiments, the hnCD16 comprises the amino acid sequence of SEQ ID NO 19. In some embodiments, the hnCD16 comprises the amino acid sequence of SEQ ID NO 20. In some embodiments, the hnCD16 comprises the amino acid sequence of SEQ ID NO 21.

```
                                              SEQ ID NO: 19
MWFLTTLLLWVPVDGQVDTTKAVITLQPPWVSVFQEETVTLHCEVLHLPG

SSSTQWFLNGTATQTSTPSYRITSASVNDSGEYRCQRGLSGRSDPIQLEI

HRGWLLLQVSSRVFTEGEPLALRCHAWKDKLVYNVLYYRNGKAFKFFHWN

SNLTILKTNISHNGTYHCSGMGKHRYTSAGISVTVKELFPAPVLNASVTS

PLLEGNLVTLSCETKLLLQRPGLQLYFSFYMGSKTLRGRNTSSEYQILTA

RREDSGLYWCEAATEDGNVLKRSPELELQVLGLQLPTPVWFH

YQVSFCLVMVLLFAVDTGLYFSV

KTNIRSSTRDWKDHKFKWRKDPQDK
(340 a. a. CD64 domain-based construction;
CD16TM; CD16ICD)
```

-continued

SEQ ID NO: 20
MWFLTTLLLWVPVDGQVDTTKAVITLQPPWVSVFQEETVTLHCEVLHLPG

SSSTQWFLNGTATQTSTPSYRITSASVNDSGEYRCQRGLSGRSDPIQLEI

HRGWLLLQVSSRVFTEGEPLALRCHAWKDKLVYNVLYYRNGKAFKFFHWN

SNLTILKTNISHNGTYHCSGMGKHRYTSAGISVTVKELFPAPVLNASVTS

PLLEGNLVTLSCETKLLLQRPGLQLYFSFYMGSKTLRGRNTSSEYQILTA

RREDSGLYWCEAATEDGNVLKRSPELELQVLGL

FFPPGYQ*VSFCLVMVLLFAVDTGLYFSV*

*KTNIRSSTRDWKDHKFKWRKDPQDK*
(336 a.a. CD64 exon-based construction;
CD16TM; *CD16ICD*)

SEQ ID NO: 21
MWFLTTLLLWVPVDGQVDTTKAVITLQPPWVSVFQEETVTLHCEVLHLPG

SSSTQWFLNGTATQTSTPSYRITSASVNDSGEYRCQRGLSGRSDPIQLEI

HRGWLLLQVSSRVFTEGEPLALRCHAWKDKLVYNVLYYRNGKAFKFFHWN

SNLTILKTNISHNGTYHCSGMGKHRYTSAGISVTVKELFPAPVLNASVTS

PLLEGNLVTLSCETKLLLQRPGLQLYFSFYMGSKTLRGRNTSSEYQILTA

RREDSGLYWCEAATEDGNVLKRSPELELQVLG

FFPPGYQ*VSFCLVMVLLFAVDTGLYFSV*

*KTNIRSSTRDWKDHKFKWRKDPQDK*
(335 a.a. CD64 exon-based construction;
CD16TM; *CD16ICD*)

Accordingly, provided herein are effector cells or iPSCs genetically engineered to comprise a solid tumor targeting backbone that comprises, among other editing as contemplated and described herein, an exogenous CD16 or a variant thereof, wherein the effector cells are cells from primary sources or derived from iPSC differentiation, or wherein the genetically engineered iPSCs are capable of differentiating into derived effector cells comprising the exogenous CD16 or a variant thereof introduced to the iPSCs. In some embodiments, the exogenous CD16 is a high-affinity non-cleavable CD16 receptor (hnCD16). In some embodiments, the exogenous CD16 comprises at least a portion of the CD64 ectodomain. In some embodiments, the exogenous CD16 is in a form of a CD16-based chimeric Fc receptor (CFcR) that comprises a transmembrane domain, a stimulatory domain and/or a signaling domain that is not derived from CD16.

In some embodiments, the primary-sourced or derived effector cells comprising the exogenous CD16 or variant thereof are NK lineage cells. In some embodiments, the primary-sourced or derived effector cells comprising the exogenous CD16 or variant thereof are T lineage cells. In some embodiments, the exogenous CD16 or functional variants thereof comprised in iPSC or effector cells has high affinity in binding to a ligand that triggers downstream signaling upon such binding. Non-limiting examples of ligands binding to the exogenous CD16 or functional variants thereof include not only ADCC antibodies or fragments thereof, but also to bi-tri-, or multi-specific engagers or binders that recognize the CD16 or CD64 extracellular binding domains of the exognous CD16. Examples of bi-, tri-, or multi-specific engagers or binders are further described below in this application. As such, at least one of the aspects of the present application provides a derivative effector cell comprising a solid tumor targeting backbone, or a cell population thereof, preloaded with one or more pre-selected ADCC antibodies through an exogenous CD16 expressed on the derivative effector cell, in an amount sufficient for therapeutic use in a treatment of a condition, a disease, or an infection as further detailed in this application, wherein the exogenous CD16 comprises an extracellular binding domain of CD64, or of a CD16 having F176V and S197P.

In some other embodiments, an exogenous CD16 comprises a CD16-, or variants thereof, based CFcR. A chimeric Fc receptor (CFcR) is produced to comprise a non-native transmembrane domain, a non-native stimulatory domain and/or a non-native signaling domain by modifying or replacing the native CD16 transmembrane- and/or the intracellular-domain. The term "non-native" used herein means that the transmembrane, stimulatory or signaling domain are derived from a different receptor other than the receptor which provides the extracellular domain. In the illustration here, the CFcR based on CD16 or variants thereof does not have a transmembrane, stimulatory or signaling domain that is derived from CD16. In some embodiments, the exogenous CD16-based CFcR comprises a non-native transmembrane domain derived from CD3δ, CD3ε, CD3γ, CD3ζ, CD4, CD8, CD8a, CD8b, CD27, CD28, CD40, CD84, CD166, 4-1BB, OX40, ICOS, ICAM-1, CTLA4, PD1, LAG3, 2B4, BTLA, CD16, IL7, IL12, IL15, KIR2DL4, KIR2DS1, NKp30, NKp44, NKp46, NKG2C, NKG2D, or T cell receptor polypeptide. In some embodiments, the exogenous CD16-based CFcR comprises a non-native stimulatory/inhibitory domain derived from CD27, CD28, 4-1BB, OX40, ICOS, PD1, LAG3, 2B4, BTLA, DAP10, DAP12, CTLA4, or NKG2D polypeptide. In some embodiments, the exogenous CD16-based CFcR comprises a non-native signaling domain derived from CD3ζ, 2B4, DAP10, DAP12, DNAM1, CD137 (4-1BB), IL21, IL7, IL12, IL15, NKp30, NKp44. NKp46, NKG2C, or NKG2D polypeptide. In one embodiment of the CD16-based CFcR, the provided chimeric Fc receptor comprises a transmembrane domain and a signaling domain both derived from one of IL7, IL12, IL15, NKp30, NKp44, NKp46. NKG2C, and NKG2D polypeptide. One embodiment of the CD16-based chimeric Fc receptor comprises a transmembrane domain of NKG2D, a stimulatory domain of 2B4, and a signaling domain of CD3ζ; wherein the extracellular domain of the CFcR is derived from a full length or partial sequence of the extracellular domain of CD64 or CD16, and wherein the extracellular domain of CD16 comprises F176V and S197P. Another exemplary embodiment of the CD16-based chimeric Fc receptor comprises a transmembrane domain and a signaling domain of CD3ζ; wherein the extracellular domain of the CFcR is derived from a full length or partial sequence of the extracellular domain of CD64 or CD16, wherein the extracellular domain of CD16 comprises F176V and S197P.

The various embodiments of the CD16-based chimeric Fc receptor as described above are capable of binding, with high affinity, to the Fc region of an antibody or fragment thereof; or to a bi-, tri-, or multi-specific engager or binder. Upon binding, the stimulatory and/or signaling domains of the chimeric receptor enable the activation and cytokine secretion of the effector cells, and the killing of the tumor cells targeted by the antibody, or the bi-, tri-, or multi-specific engager or binder having a tumor antigen binding component as well as the Fc region. Without being limited by theory, through the non-native transmembrane, stimulatory and/or signaling domains, or through an engager binding to the ectodomain, of the CD16-based chimeric Fc receptor, the CFcR could contribute to effector cells' killing ability while increasing the effector cells' proliferation and/or expansion potential. The antibody and the engager can bring tumor cells expressing the antigen and the effector cells expressing the CFcR into close proximity, which also contributes to the enhanced killing of the tumor cells. Exemplary tumor antigens for bi-, tri-, multi-specific engagers or binders include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, and ROR1. Some non-limiting exemplary bi-, tri-, multi-specific engagers or binders suitable for engaging effector cells expressing the CD16-based CFcR in attacking tumor cells include CD16 (or CD64)-CD30, CD16 (or CD64)-BCMA, CD16 (or CD64)-IL15-EPCAM, and CD16 (or CD64)-IL15-CD33.

Unlike the endogenous CD16 expressed by primary NK cells which gets cleaved from the cellular surface following NK cell activation, the various non-cleavable versions of CD16 in derivative NK cells avoid CD16 shedding and maintain constant expression. In derivative NK cells, non-cleavable CD16 increases expression of TNFα and CD107a, indicative of improved cell functionality. Non-cleavable CD16 also enhances the antibody-dependent cell-mediated cytotoxicity (ADCC), and the engagement of bi-, tri-, or multi-specific engagers. ADCC is a mechanism of NK cell mediated lysis through the binding of CD16 to antibody-coated target cells. The additional high affinity characteristics of the introduced hnCD16 in a derived NK cell also enables in vitro loading of an ADCC antibody to the NK cell through hnCD16 before administering the cell to a subject in need of a cell therapy. As provided herein, the hnCD16 may comprise F176V and S197P in some embodiments, or may comprise a full or partial ectodomain originated from CD64 as exemplified by SEQ ID NO: 19, 20 or 21, or may further comprise at least one of non-native transmembrane domain, stimulatory domain and signaling domain. As disclosed, the present application also provides a derivative NK cell comprising a solid tumor targeting backbone, or a cell population thereof, preloaded with one or more pre-selected ADCC antibodies in an amount sufficient for therapeutic use in a treatment of a condition, a disease, or an infection as further detailed in this application. In some embodiments, the preloaded CD38 antibody is daratumumab. In some embodiments, the derived NK cells comprising a solid tumor targeting backbone which comprises an exogenous CD16 or a variant thereof, further comprises at least two of a C—X—C-motif chemokine receptor or a variant thereof, a TGFβ-SRR, and an ADR specific to 4-1BB, as provided herein. In some embodiments, the derived NK cells comprising a solid tumor targeting backbone comprising at least two of a C—X—C-motif chemokine receptor or a variant thereof, a TGFβ-SRR, and an ADR specific to 4-1BB, and exogenous CD16 or a variant thereof, further comprise a CAR. In some embodiments, said derived NK cells are preloaded with one or more of an anti-HER2 antibody (e.g., trastuzumab, pertuzumab), an anti-EGFR antibody (e.g., cetuximab), or an anti-PDL1 antibody (e.g., avelumab).

Unlike primary NK cells, mature T cells from a primary source (i.e., natural/native sources such as peripheral blood, umbilical cord blood, or other donor tissues) do not express CD16. It was previously unexpected that iPSC comprising an expressed exogenous non-cleavable CD16 did not impair the T cell developmental biology and was able to differentiate into functional derivative T lineage cells that not only express the exogenous CD16, but also are capable of carrying out function through an acquired ADCC mechanism. This acquired ADCC in the derivative T lineage cell can additionally be used as an approach for dual targeting and/or to rescue antigen escape often occurred with CAR-T cell therapy, where the tumor relapses with reduced or lost CAR-T targeted antigen expression or expression of a mutated antigen to avoid recognition by the CAR (chimeric antigen receptor). When the derivative T lineage cell comprises acquired ADCC through exogenous CD16, including functional variants and CD16-based CFcR, expression, and when an antibody targets a different tumor antigen from the one targeted by the CAR, the antibody can be used to rescue CAR-T antigen escape and reduce or prevent relapse or recurrence of the targeted tumor often seen in CAR-T treatment. Such a strategy to reduce and/or prevent antigen escape while achieving dual targeting is equally applicable to NK cells expressing one or more CARs.

As such, the application provides a derivative T lineage cell comprising a solid tumor targeting backbone comprising an exogenous CD16 or a variant thereof. In some embodiments, the solid tumor targeting backbone derivative comprised in the T lineage cell obtained herein comprises an exogenous CD16 and at least two of a C—X—C-motif chemokine receptor or a variant thereof, a TGFβ-SRR, and an ADR specific to 4-1BB. In other embodiments, the derivative T lineage cell obtained herein comprises a CAR in addition to the solid tumor targeting backbone. In some embodiments, the exogenous CD16 comprised in the solid tumor targeting backbone comprised in the derivative T lineage cell is an hnCD16 comprising F176V and S197P. In some other embodiments, the hnCD16 comprised in the solid tumor targeting backbone comprises a full or partial ectodomain originated from CD64 as exemplified by SEQ ID NO: 19, 20 or 21; or may further comprise at least one of non-native transmembrane domain, stimulatory domain and signaling domain. As explained herein, such derivative T lineage cells have an acquired mechanism to target tumors with a monoclonal antibody mediated by ADCC to enhance the therapeutic effect of the antibody. As disclosed, the present application also provides a derivative T lineage cell comprising a solid tumor targeting backbone, or a cell population thereof, preloaded with one or more pre-selected ADCC antibodies in an amount sufficient for therapeutic use in a treatment of a condition, a disease, or an infection as further detailed below.

As provided further, the cell or population thereof, comprising the solid tumor targeting backbone, and optionally a CAR, and an exogenous CD16 or a variant thereof ("CD16$^{exo}$" in Table 4), may further comprise one or more additional engineered modalities described herein, and/or as shown in Table 4. Additionally provided in this application is a master cell bank comprising single cell sorted and expanded clonal engineered iPSCs having at least one phenotype as provided herein, including but not limited to, a solid tumor targeting backbone comprising, among other genetic modalities, an exogenous CD16 or a variant thereof, wherein the cell bank provides a platform for additional iPSC engineering and a renewable source for manufacturing off-the-shelf, engineered, homogeneous cell therapy products, including but not limited to derivative NK and T cells, which are well-defined and uniform in composition, and can be mass produced at significant scale in a cost-effective manner.

6. Exogenously Introduced Cytokine Signaling Complex

By avoiding systemic high-dose administration of clinically relevant cytokines, the risk of dose-limiting toxicities due to such a practice is reduced while cytokine-mediated cell autonomy is being established. To achieve lymphocyte autonomy without the need to additionally administer soluble cytokines, a cytokine signaling complex comprising a partial or full length peptide of one or more of IL2, IL4, IL6, IL7, IL9, IL10, IL11, IL12, IL15, IL18, IL21, and/or their respective receptors may be introduced to the cell as part of the solid tumor targeting backbone to enable cytokine signaling with or without the expression of the cytokine itself, thereby maintaining or improving cell growth, proliferation, expansion, and/or effector function with reduced risk of cytokine toxicities. In some embodiments, the introduced cytokine and/or its respective native or modified receptor for cytokine signaling (signaling complex) are expressed on the cell surface. In some embodiments, the cytokine signaling is constitutively activated. In some embodiments, the activation of the cytokine signaling is inducible. In some embodiments, the activation of the cytokine signaling is transient and/or temporal. In some embodiments, the transient/temporal expression of a cell surface cytokine/cytokine receptor is through an expression construct carried by a retrovirus, Sendai virus, an adenovirus, an episome, mini-circle, or RNAs including mRNA.

Various construct designs for introducing a protein complex for signaling of one, two, or more cytokines including, but not limited to, IL2, IL4, IL6, IL7, IL9, IL10, IL11, IL12, IL15, IL18 and IL21, into the cell are provided herein. For example, in embodiments where the signaling complex is for IL15, the transmembrane (TM) domain can be native to the IL15 receptor or may be modified or replaced with the transmembrane domain of any other membrane bound proteins. In various embodiments, the cytokine signaling complex comprises an IL15 receptor fusion (IL15RF) comprising a full or partial length of IL15 and a full or partial length of IL15 receptor (IL15R). In some embodiments, IL15 and IL15Rα are co-expressed by using a self-cleaving peptide, mimicking trans-presentation of IL15, without eliminating cis-presentation of IL15. In other embodiments, IL15Rα is fused to IL15 at the C-terminus through a linker, mimicking trans-presentation without eliminating cis-presentation of IL15 as well as ensuring that IL15 is membrane-bound. In other embodiments, IL15Rα with truncated intracellular domain is fused to IL15 at the C-terminus through a linker, mimicking trans-presentation of IL15, maintaining IL15 membrane-bound, and additionally eliminating cis-presentation and/or any other potential signal transduction pathways mediated by a normal IL15R through its intracellular domain. In other embodiments, IL15Rα is fused to IL15 without an intracellular domain (IL15A), as described in International Pub. Nos. WO 2019/191495 and WO 2019/126748, the entire disclosure of each of which is incorporated herein by reference.

In various embodiments, such a truncated construct comprises an amino acid sequence of at least 75%, 80%, 85%, 90%, 95% or 99% identity to SEQ ID NO: 22. In some embodiments, the IL15/IL15Rα comprises an amino acid sequence of at least 90% sequence identity to SEQ ID NO: 22. In some embodiments, the IL15/IL15Rα comprises an amino acid sequence of at least 95% sequence identity to SEQ ID NO: 22. In some embodiments, the IL15/IL15Rα comprises the amino acid sequence of SEQ ID NO: 22. In one embodiment of the truncated IL15/IL15Rα, the construct does not comprise the last 4 amino acid residues (KSRQ) of SEQ ID NO: 22, and comprises an amino acid sequence of at least 75%, 80%, 85%, 90%, 95% or 99% identity to SEQ ID NO: 23. In some embodiments, the IL15/IL15Rα comprises an amino acid sequence of at least 90% sequence identity to SEQ ID NO: 23. In some embodiments, the IL15/IL15Rα comprises an amino acid sequence of at least 95% sequence identity to SEQ ID NO: 23. In some embodiments, the IL15/IL15Rα comprises the amino acid sequence of SEQ ID NO: 23.

```
                                          SEQ ID NO: 22
MDWTWILFLVAAATRVHSGIHVFILGCFSAGLPKTEANWVNVISDLKKIE

DLIQSMHIDATLYTESDVHPSCKVTAMKCFLLELQVISLESGDASIHDTV

ENLIILANNSLSSNGNVTESGCKECEELEEKNIKEFLQSFVHIVQMFINT

SSGGGSGGGGSGGGGSGGGGSGGGSLQITCPPPMSVEHADIWVKSYSLYS

RERYICNSGFKRKAGTSSLTECVLNKATNVAHWTTPSLKCIRDPALVHQR

PAPPSTVTTAGVTPQPESLSPSGKEPAASSPSSNNTAATTAAIVPGSQLM

PSKSPSTGTTEISSHESSHGTPSQTTAKNWELTASASHQPPGVYPQGHSD

TTVAISTSTVLLCGLSAVSLLACYLKSRQ
(379 a.a.; signal and linker peptides are
underlined)
```

```
                                          SEQ ID NO: 23
MDWTWILFLVAAATRVHSGIHVFILGCFSAGLPKTEANWVNVISDLKKIE

DLIQSMHIDATLYTESDVHPSCKVTAMKCFLLELQVISLESGDASIHDTV

ENLIILANNSLSSNGNVTESGCKECEELEEKNIKEFLQSFVHIVQMFINT

SSGGGSGGGGSGGGGSGGGGSGGGSLQITCPPPMSVEHADIWVKSYSLYS

RERYICNSGFKRKAGTSSLTECVLNKATNVAHWTTPSLKCIRDPALVHQR

PAPPSTVTTAGVTPQPESLSPSGKEPAASSPSSNNTAATTAAIVPGSQLM

PSKSPSTGTTEISSHESSHGTPSQTTAKNWELTASASHQPPGVYPQGHSD

TTVAISTSTVLLCGLSAVSLLACYL
(375 a.a.; signal and linker peptides are
underlined)
```

In yet other embodiments, the cytoplasmic domain of IL15Rα can be omitted without negatively impacting the autonomous feature of the effector cell equipped with IL15. In other embodiments, essentially the entire IL15Rα is removed except for the Sushi domain fused with IL15 at one end and a transmembrane domain on the other (mb-Sushi), optionally with a linker between the Sushi domain and the trans-membrane domain. The fused IL15/mb-Sushi is expressed at the cell surface through the transmembrane domain of any membrane bound protein. Thus, unnecessary signaling through IL15Rα, including cis-presentation, is eliminated when only the desirable trans-presentation of IL15 is retained. In some embodiments, the component comprising IL15 fused with Sushi domain comprises an amino acid sequence of at least 75%, 80%, 85%, 90%, 95% or 99% identity to SEQ ID NO: 24. In some embodiments, the component comprising IL15 fused with Sushi domain comprises an amino acid sequence of at least 90% identity to SEQ ID NO: 24. In some embodiments, the component comprising IL15 fused with Sushi domain comprises an amino acid sequence of at least 95% identity to SEQ ID NO: 24. In some embodiments, the component comprising IL15 fused with Sushi domain comprises the amino acid sequence of SEQ ID NO: 24.

```
                                          SEQ ID NO: 24
MDWTWILFLVAAATRVHSGIHVFILGCFSAGLPKTEANWVNVISDLKKIE

DLIQSMHIDATLYTESDVHPSCKVTAMKCFLLELQVISLESGDASIHDTV
```

-continued

ENLIILANNSLSSNGNVTESGCKECEELEEKNIKEFLQSFVHIVQMFINT

SSGGGSGGGGSGGGGSGGGGSGGGSLQITCPPPMSVEHADIWVKSYSLYS

RERYICNSGFKRKAGTSSLTECVLNKATNVAHWTTPSLKCIR
(242 a.a.; signal and linker peptides are
underlined)

In other embodiments, a native or modified IL15Rβ is fused to IL15 at the C-terminus through a linker, enabling constitutive signaling and maintaining IL15 membrane-bound and trans-representation. In other embodiments, a native or modified common receptor γC is fused to IL15 at the C-terminus through a linker for constitutive signaling and membrane bound trans-presentation of the cytokine. The common receptor γC is also called the common gamma chain or CD132, which is also known as IL2 receptor subunit gamma or IL2RG. γC is a cytokine receptor subunit that is common to the receptor complexes for many interleukin receptors, including, but not limited to, IL2, IL4, IL7, IL9, IL15 and IL21 receptors. In other embodiments, engineered IL15Rβ that forms a homodimer in the absence of IL15 is useful for producing constitutive signaling of the cytokine.

In other various embodiments, the cytokine signaling complex comprises an IL7 receptor fusion (IL7RF) comprising a full or partial length of IL7 and a full or partial length of IL7 receptor. The transmembrane (TM) domain can be native to the IL7 receptor or may be modified or replaced with a transmembrane domain of any other membrane bound proteins. In one embodiment, a native (or wildtype) or modified IL7R may be fused to IL7 at the C-terminus through a linker, enabling constitutive signaling and maintaining membrane-bound IL7. In some embodiments, such a construct comprises an amino acid sequence of at least 75%, 80%, 85%, 90%, 95% or 99% identity to SEQ ID NO: 25, with transmembrane domain, signal peptide and linker being flexible and varying in length and/or sequences. In some embodiments, the IL7 construct comprises an amino acid sequence of at least 90% identity to SEQ ID NO: 25, with transmembrane domain, signal peptide and linker being flexible and varying in length and/or sequences. In some embodiments, the IL7 construct comprises an amino acid sequence of at least 95% identity to SEQ ID NO: 25, with transmembrane domain, signal peptide and linker being flexible and varying in length and/or sequences. In some embodiments, the IL7 construct comprises the amino acid sequence of SEQ ID NO: 25.

SEQ ID NO: 25
MDWTWILFLVAAATRVHS

DCDIEGKDGKQYESVLMVSIDQLLDSMKEIG

SNCLNNEFNFFKRHICDANKEGMFLFRAARK

LRQFLKMNSTGDFDLHLLKVSEGTTILLNCT

GQVKGRKPAALGEAQPTKSLEENKSLKEQKK

LNDLCFLKRLLQEIKTCWNKILMGTKEHS

GGGSGGGGSGGGGSGGGGSGGGS

LQESGYAQNGDLEDAELDDYSFSCYSQLEVNGSQHSLTCAFEDPDVNITN

LEFEICGALVEVKCLNFRKLQEIYFIETKKFLLIGKSNICVKVGEKSLTC

KKIDLTTIVKPEAPFDLSVVYREGANDEVVTFNTSHLQKKYVKVLMHDVA

YRQEKDENKWTHVNLSSTKLTLLQRKLQPAAMYEIKVRSIPDHYFKGFWS

EWSPSYYFRTPEINNSSGEMDPILLTISILSFFSVALLVILACVLWKKRI

KPIVWPSLPDHKKTLEHLCKKPRKNLNVSFNPESFLDCQIHRVDDIQARD

EVEGFLQDTFPQQLEESEKQRLGGDVQSPNCPSEDVVITPESFGRDSSLT

CLAGNVSACDAPILSSSRSLDCRESGKNGPHVYQDLLLSLGTTNSTLPPP

FSLQSGILTLNPVAQGQPILTSLGSNQEEAYVTMSSFYQNQ
(Signal peptide-IL7-linker-IL7R;
transmembrane domain (TM), signal
peptide and linker can vary in
length and sequences)

In another embodiment, a native or modified common receptor γC is fused to IL7 at the C-terminus through a linker for constitutive and membrane-bound cytokine signaling complex. In addition, engineered IL7R that forms a homodimer in the absence of IL7 is useful for producing constitutive signaling of the cytokine as well.

One having ordinary skill in the art would appreciate that the signal peptide and the linker sequences above are illustrative and in no way limit their variations suitable for use as a signal peptide or linker. There are many suitable signal peptide or linker sequences known and available to those in the art. The ordinary skilled in the art understands that the signal peptide and/or linker sequences may be substituted for another sequence without altering the activity of the functional peptide led by the signal peptide or linked by the linker.

In iPSCs and derivative cells therefrom comprising both CAR and exogenous cytokine and/or cytokine receptor signaling (cytokine signaling complex or "IL"), the CAR and IL may be expressed in separate constructs, or may be co-expressed in a bi-cistronic construct comprising both CAR and IL. In some further embodiments, the signaling complex can be linked to either the 5' or the 3' end of a CAR expression construct through a self-cleaving 2A coding sequence. As such, an IL signaling complex (e.g., IL7 signaling complex) and CAR may be in a single open reading frame (ORF). In one embodiment, the signaling complex is comprised in CAR-2A-IL or IL-2A-CAR construct. When CAR-2A-IL or IL-2A-CAR is expressed, the self-cleaving 2A peptide allows the expressed CAR and IL to dissociate, and the dissociated IL can then be presented at the cell surface, with the transmembrane domain anchored in the cell membrane. The CAR-2A-IL or IL-2A-CAR bi-cistronic design allows for coordinated CAR and IL signaling complex expression both in timing and quantity, and under the same control mechanism that may be chosen to incorporate, for example, an inducible promoter or promoter with temporal or spatial specificity for the expression of the single ORF. Self-cleaving peptides are found in members of the Picornaviridae virus family, including aphthoviruses such as foot-and-mouth disease virus (FMDV), equine rhinitis A virus (ERAV), Thosea asigna virus (TaV) and porcine tescho virus-1 (PTV-I) (Donnelly, M L, et al, J. Gen. Virol, 82, 1027-101 (2001); Ryan, M D, et al., J. Gen. Virol., 72, 2727-2732 (2001)), and cardioviruses such as Theilovirus (e.g., Theiler's murine encephalomyelitis) and encephalo-myocarditis viruses. The 2A peptides derived from FMDV, ERAV, PTV-I, and TaV are sometimes also referred to as "F2A", "E2A", "P2A", and "T2A", respectively.

The bi-cistronic CAR-2A-IL or IL-2A-CAR embodiment as disclosed herein is also contemplated for expression of any other cytokine or cytokine signaling complex provided herein, for example, IL2, IL4, IL6, IL9, IL10, IL11, IL12, IL18, and IL21. In some embodiments, the bi-cistronic CAR-2A-IL or IL-2A-CAR is for expression of one or more of IL2, IL4, IL7, IL9, IL15 and IL21.

In some embodiments, the iPSC and its derivative effector cells comprising any one of the genotypes in Table 4 may additionally comprise disruption of at least one of TAP1, TAP2, Tapasin, NLRC5, PD1, LAG3, TIM3, RFXANK, RFX5, RFXAP, RAG1, and any gene in the chromosome 6p21 region; or introduction of at least one of HLA-E, 4-1BBL, CD4, CD8, CD47, CD113, CD131, CD137, CD80, PDL1, $A_{2A}R$, TCR, Fc receptor, an antibody, and surface triggering receptor for coupling with bi-, multi-specific or universal engagers.

As such, in various embodiments, the cytokines IL15 or IL7 and/or receptors thereof, may be introduced to iPSCs using one or more of the construct designs described above, and to their derivative cells upon iPSC differentiation. In addition, provided herein is an induced pluripotent cell (iPSC), a clonal iPSC, a clonal iPS cell line, or iPSC-derived cells comprising a solid tumor targeting backbone comprising two or more of a polynucleotide encoding C—X—C motif chemokine receptor or variant thereof, a polynucleotide enconding a TGFβ-SRR, and a 41BB-ADR and optionally a polynucleotide encoding a cytokine signaling complex and/or one or more engineered modalities as disclosed herein. Also provided is a master cell bank comprising single cell sorted and expanded clonal engineered iPSCs having a solid tumor targeting backbone comprising two or more of a polynucleotide encoding C—X—C motif chemokine receptor or variant thereof, a polynucleotide enconding a TGFβ-SRR, and a 41BB-ADR and optionally a polynucleotide encoding a cytokine signaling complex and/or one or more engineered modalities, wherein the cytokine signaling complex comprises a partial or full peptide of a cell surface expressed exogenous cytokine and/or a receptor thereof, as described in this section, wherein the cell bank provides a platform for additional iPSC engineering and a renewable source for manufacturing off-the-shelf, engineered, homogeneous cell therapy products, which are well-defined and uniform in composition, and can be mass produced at a significant scale in a cost-effective manner.

7. HLA-I- and HLA-II-Deficiency

Multiple HLA class I and class II proteins must be matched for histocompatibility in allogeneic recipients to avoid allogeneic rejection problems. Provided herein is an iPSC cell line and its derivative cells differentiated therefrom with eliminated or substantially reduced expression of HLA class I and/or HLA class II proteins. HLA class I deficiency can be achieved by functional deletion of any region of the HLA class I locus (chromosome 6p21), or deletion or disruption of HLA class-I associated genes including, but not limited to, beta-2 microglobulin (B2M) gene, TAP1 gene, TAP2 gene and Tapasin. For example, the B2M gene encodes a common subunit essential for cell surface expression of all HLA class I heterodimers. B2M negative cells are HLA-I deficient. HLA class II deficiency can be achieved by functional deletion or disruption of HLA class II associated genes including, but not limited to, RFXANK, CIITA, RFX5 and RFXAP. CIITA is a transcriptional coactivator, functioning through activation of the transcription factor RFX5 required for class II protein expression. CIITA negative cells are HLA-II deficient. As such, this application provides an iPSC and derivative cells therefrom comprising HLA-I and/or HLA-II deficiency, for example by lacking B2M and/or CIITA expression, wherein the obtained derivative effector cells enable allogeneic cell therapies by eliminating the need for MHC (major histocompatibility complex) matching, and avoiding recognition and killing by host (allogeneic) T cells.

Furthermore, a lack of HLA class I expression leads to lysis by host NK cells. Therefore, in addition to the above-discussed approach of CD38 conditioning to remove activated CD38-expressing host NK cells, to overcome this "missing self" response, HLA-E, HLA-G or other non-classical HLA-I proteins may be optionally knocked in to avoid NK cell recognition and killing of the HLA-I deficient effector cells derived from an engineered iPSC. In one embodiment, the provided HLA-I deficient iPSC and its derivative cells further comprise HLA-G knock-in.

Alternatively, in one embodiment, the provided HLA-I deficient iPSC and its derivative cells further comprise one or both of CD58 knockout and CD54 knockout. CD58 (or LFA-3) and CD54 (or ICAM-1) are adhesion proteins initiating signal-dependent cell interactions, and facilitating cell, including immune cell, migration. It was previously shown that CD58 and/or CD54 disruption effectively reduces the susceptibility of HLA-I deficient iPSC-derived effector cells to allogeneic NK cell killing. While it was shown that CD58 knockout has a higher efficiency in reducing allogeneic NK cell activation than CD54 knockout, double knockout of both CD58 and CD54 was shown to provide the most enhanced reduction of NK cell activation. In some observations, the CD58 and CD54 double knockout is even more effective than HLA-G overexpression for HLA-I deficient cells in overcoming "missing-self" effect.

As provided herein, in some embodiments, the iPSC and its derivative cells comprising a solid tumor targeting backbone comprising two or more of: a C—X—C-motif chemokine receptor or a variant thereof, a TGFβ-SRR, and a 41BB-ADR, said cells are HLA-I and/or HLA-II deficient. In some embodiments, said HLA-I and/or HLA-II deficient iPSC and its derivative cells are CD58 negative. In some other embodiments, said HLA-I and/or HLA-II deficient iPSC and its derivative cells are CD54 negative. In yet some other embodiments, said HLA-I and/or HLA-II deficient iPSC and its derivative cells are CD54 negative and CD58 negative. Further, in some embodiments of the iPSC and its derivative cells comprising a solid tumor targeting backbone as described herein, said cells are HLA-I and/or HLA-II deficient and have an exogenous polynucleotide encoding HLA-G. In some embodiments of the iPSC and its derivative cells comprising a solid tumor targeting backbone as described herein, the cells are HLA-I and/or HLA-II deficient and are CD54 negative. In yet some other embodiments of the iPSC and its derivative cells comprising a solid tumor targeting backbone as described herein, and optionally CD38 knockout, exogenous CD16 or a variant thereof, and a CAR, the cells are HLA-I and/or HLA-II deficient, and are both CD58 negative and CD54 negative.

In some embodiments, the engineering for HLA-I and/or HLA-II deficiency may be bypassed, or kept intact, by expressing an inactivation CAR targeting an upregulated surface protein in activated recipient immune cells to avoid allorejection. In some embodiments, the upregulated surface protein in the activated recipient immune cells includes, but is not limited to, CD38, CD25, CD69, CD44, 4-1BB, OX40, or CD40L. When the cell expresses such an inactivation CAR, it is preferable that the cell does not express, or has knockout of, the same surface protein targeted by CAR. In some embodiments, the inactivation CAR comprises at least one of a CD38-CAR, a CD25-CAR, a CD69-CAR, a CD44-CAR, a 4-1BB-CAR, an OX40-CAR, and a CD40L-CAR.

Additionally provided in this application is a master cell bank comprising single cell sorted and expanded clonal engineered iPSCs having at least one phenotype as provided herein, including but not limited to, a solid tumor targeting backbone as described herein and HLA modification ("HLA" in Table 4: HLA-I and/or HLA-II deficiency with or without HLA-E or HLA-G knock in, or with knockout of one or both of CD58 and CD54), wherein the cell bank provides a platform for additional iPSC engineering and a renewable source for manufacturing off-the-shelf, engineered, homogeneous cell therapy products, including but not limited to derivative NK and T cells, which are well-defined and uniform in composition, and can be mass produced at significant scale in a cost-effective manner.

8. Cell Surface Chimeric Fusion Receptor (CFR)

Effector cells engineered to express a CFR enable the effector cell to initiate an appropriate signal transduction cascade through CFR binding with a selected agonist for enhanced therapeutic properties. Such enhanced effector cell therapeutic properties include, but are not limited to, increased activation and cytotoxicity, acquired dual targeting capability, prolonged persistency, improved trafficking and tumor infiltration, enhanced ability in priming, activating or recruiting bystander immune cells to tumor sites, enhanced ability to resist immunosuppression, improved ability in rescuing tumor antigen escape, and/or controlled cell signaling feedback, metabolism and apoptosis.

As such, this application provides, in some embodiments, an iPSC and derivative cells therefrom comprising, among other edits, a CFR that comprises an ectodomain, a transmembrane domain, and an endodomain, wherein the ectodomain, the transmembrane domain and the endodomain do not comprise any endoplasmic reticulum (ER) retention signals or endocytosis signals. The ectodomain of the CFR is for initiating signal transduction upon binding to an engager; the transmembrane domain is for membrane anchoring of the CFR; and the endodomain comprises at least one signaling domain that regulates (i.e., activates or deactivates) a signaling pathway of choice for enhancing cell therapeutic properties including, but not limited to, tumor killing, persistence, mobility, differentiation, TME counteracting, and/or controlled apoptosis. The elimination of ER retention signals from the CFR permits CFR cell surface presentation by itself when expressed, and the elimination of endocytosis signals from the CFR reduces CFR internalization and surface downregulation. It is important to either select domain components that have neither ER retention nor endocytosis signals, or remove ER retention or endocytosis signals from selected components of the CFR using molecular engineering tools. In addition, the domains of the CFRs as provided by some embodiments herein are modular, meaning for a given endodomain of a CFR, the ectodomain of the CFR is switchable depending on the binding specificity of a selected agonist, such as an antibody, a BiTE, a TriKE, or any other type of engager, to be used with said CFR; and for a given ectodomain and a specificity matching agonist, the endodomain is switchable depending on the desired signaling pathway to be activated. Additionally, the transmembrane domain in accordance with some embodiments is switchable for a given ectodomain and/or a given endodomain, so long as the transmembrane domain does not comprise any endoplasmic reticulum (ER) retention signals or endocytosis signals.

In some embodiments, the ectodomain of a CFR applicable to the cells described herein comprises a full or partial length of the extracellular portion of a protein that is involved in cell-cell signaling or interactions. In some embodiments, the ectododomain of the CFR comprises a full or partial length of the extracellular portion of CD3ε, CD3γ, CD3δ, CD28, CD5, CD16, CD64, CD32, CD33, CD89, NKG2C, NKG2D, or any functional variants, or combinations and chimerics thereof. In some embodiments, the ectodomain of the CFR is recognized by at least an agonist, for example, an antibody or an engager (e.g., BiTE, BiKE or TriKE), that comprises a binding domain specific to an epitope comprised in the ectodomain of said CFR. In some embodiments, the antibody or engager to be used with a CFR expressing cell binds to at least one extracellular epitope of said CFR, wherein the CFR comprises a full or partial length of the extracellular portion of CD3ε, CD3γ, CD3δ, CD28, CD5, CD16, CD64, CD32, CD33, CD89, NKG2C, NKG2D, or any functional variants or combined/chimeric forms thereof. In some embodiments, the engager recognizes at least one tumor antigen comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1. In some embodiments of the CFR ectodomain, both ER retention and endocytosis signals are absent, or are removed or eliminated, from the CFR ectodomain using genetic engineering methods.

In some embodiments, the ectodomain of the CFR comprises a full or partial length of the extracellular portion of CD3Rε, CD3γ, CD3δ or any functional variants or combined/chimeric forms thereof, to utilize a CD3-based agonist. Non-limiting exemplary CD3⁻ based agonists, including but not limited to antibodies or engagers, comprise CD3×CD19, CD3×CD20, CD3×CD33, blinatumomab, catumaxomab, ertumaxomab, R06958688, AFM11, MT110/AMG 110, MT111/AMG211/MEDI-565, AMG330, MT112/BAY2010112, MOR209/ES414, MGD006/S80880, MGD007, and/or FBTA05. In some embodiments, the ectodomain of the CFR comprises a full or partial length of the extracellular portion of NKG2C, or any functional variants thereof, to utilize an NKG2C-based agonist. Non-limiting exemplary NKG2C-based agonists, including but not limited to antibodies or engagers, comprise NKG2C-IL15-CD33, NKG2C-IL15-CD19, and/or NKG2C-IL15-CD20 tri-specific engagers. In some other embodiments, the ectodomain of the CFR comprises a full or partial length of the extracellular portion of CD28 or any functional variants thereof, to utilize a CD28-based agonist. Non-limiting exemplary CD28-based agonists, including but not limited to antibodies or engagers, comprise at least one of 15E8, CD28.2, CD28.6, YTH913.12, 37.51, 9D7 (TGN1412), 5.11A1, ANC28.1/5D10, and/or 37407.

In some embodiments, the ectodomain of the CFR comprises a full or partial length of the extracellular portion of CD16, CD64, or any functional variants or combined/chimeric forms thereof, to utilize a CD16- or CD64-based agonist. Non-limiting exemplary CD16- or CD64-based agonists, including but not limited to antibodies or engagers, comprise IgG antibodies, or CD16- or CD64-based engagers. When the Fc portion of an IgG antibody binds the CD16- or CD64-based CFRs, it activates antibody dependent cell mediated cytotoxicity (ADCC) in the CFR-expressing cells along with other enhanced therapeutic properties that are imparted by the signaling domains comprised in the endodomains of the CFR. Non-limiting exemplary CD16- or CD64-based agonists, including but not limited to antibodies or engagers, comprise at least one of CD16×CD30, CD64× CD30, CD16×BCMA, CD64×BCMA, CD16-IL-EPCAM or CD64-IL-EPCAM, CD16-IL-CD33 or CD64-IL-CD33, wherein "IL" in a TriKE comprises all or a portion of at least one cytokine comprising IL2, IL4, IL6, IL7, IL9, IL10, IL11, IL12, IL15, IL18, IL21, or any functional variants or combined/chimeric forms thereof.

In general, a transmembrane domain is a three-dimensional protein structure which is thermodynamically stable in a membrane such as the phospholipid bilayer of a biological membrane (e.g., a membrane of a cell or cell vesicle). Thus, in some embodiments, the transmembrane domain of a CFR of the present invention comprises a single alpha helix, a stable complex of several transmembrane alpha helices, a transmembrane beta barrel, a beta-helix of gramicidin A, or any combination thereof. In various embodiments, the transmembrane domain of the CFR comprises all or a portion of a "transmembrane protein" or "membrane protein" that is within the membrane. As used herein, a "transmembrane protein" or "membrane protein" is a protein located at and/or within a membrane. Examples of transmembrane proteins that are suitable for providing a transmembrane domain comprised in a CFR according to some embodiments of the invention include, but are not limited to, a receptor, a ligand, an immunoglobulin, a glycophorin, or a combination thereof. In some embodiments, the transmembrane domain comprised in the CFR comprises all or a portion of a transmembrane domain of CD3ε, CD3γ, CD3δ, CD3ζ, CD4, CD8, CD8a, CD8b, CD27, CD28, CD40, CD84, CD137, CD166, FcERIγ, 4-1BB, OX40, ICOS, ICAM-1, CTLA-4, PD-1, LAG-3, 2B4, BTLA, CD16, IL7, I112, L15, KIR2DL4, KIR2DS1, NKp30, NKp44, NKp46, NKG2C, NKG2D, a T cell receptor (such as TCRα and/or TCRβ), a nicotinic acetylcholine receptor, a GABA receptor, or a combination thereof. In some embodiments, the transmembrane domain comprises all or a portion of a transmembrane domain of IgG, IgA, IgM, IgE, IgD, or a combination thereof. In some embodiments, the transmembrane domain comprises all or a portion of a transmembrane domain of glycophorin A, glycophorin D or a combination thereof. In some embodiments of the CFR transmembrane domain, both ER retention and endocytosis signals are absent or are removed using genetic engineering. In various embodiments, both ER retention and endocytosis signals are absent or are removed or eliminated from the CFR transmembrane domain using genetic engineering methods. In some embodiments, the transmembrane domain comprises all or a portion of a transmembrane domain of CD3ε, CD28, CD27, CD8, ICOS, or CD4.

In some embodiments, the endodomain of a CFR described herein comprises at least one signaling domain that activates an intracellular signaling pathway of choice. In various embodiments of the CFR endodomain, both ER retention and endocytosis signals are absent or are removed or eliminated therefrom using genetic engineering methods. In some embodiments, the endodomain comprises at least a cytoxicity domain. In some other embodiments, the endodomain may optionally comprise, in addition to a cytoxicity domain, one or more of a co-stimulatory domain, a persistency signaling domain, a death-inducing signaling domain, a tumor cell control signaling domain, or any combinations thereof. In some embodiments, the cytoxicity domain of the CFR comprises at least a full length or a portion of a polypeptide of CD3ζ, 2B4, DAP10, DAP12, DNAM1, CD137 (4-1BB), IL21, IL7, IL12, IL15, NKp30, NKp44, NKp46, NKG2C, or NKG2D. In one embodiment, the cytoxicity domain of a CFR comprises an amino acid sequence that has at least about 85%, about 90%, about 95%, about 96%, about 97%, about 98%, or about 99% identity to at least one ITAM (immunoreceptor tyrosine-based activation motif) of CD3ζ. In one embodiment, the cytoxicity domain of the CFR comprises a modified CD3ζ, represented by an amino acid sequence having at least about 85%, about 90%, about 95%, about 96%, about 97%, about 98%, or about 99% identity to SEQ ID NO: 26. In some embodiments, the cytoxicity domain of the CFR comprises an amino acid sequence having at least about 90% identity to SEQ ID NO: 26. In some embodiments, the cytoxicity domain of the CFR comprises an amino acid sequence having at least about 95% identity to SEQ ID NO: 26. In some embodiments, the cytoxicity domain of the CFR comprises the amino acid sequence of SEQ ID NO: 26.

```
                                              SEQ ID NO: 26
MKWKALFTAAILQAQLPITEAQSFGLLDPKLCYLLDGILFIYGVILTALF

LRVKFSRSADAPAYQQGQNQL

YNELNLGRREEYDVLDKRRGRDPEMGGK

PRRKNPQEGLYNELQKDKMAE

*AYSEIGM*KG*ERRRGKGHDGLYQ*

*GLSTATKDTYDALHMQ*ALPPR
(...ITAM1..*ITAM2*...ITAM3...)
```

In some embodiments, the CFR comprises an endodomain further comprising a co-stimulatory domain in addition to a cytoxicity signaling domain. Co-stimulatory domains suitable for use in the CFR include, but are not limited to, a full length or at least a portion of a polypeptide of CD2, CD27, CD28, CD40L, 4-1BB, OX40, ICOS, PD-1, LAG-3, 2B4, BTLA, DAP10, DAP12, CTLA-4, or NKG2D, or any combination thereof. In some embodiments of the CFR, the co-stimulatory domain thereof comprises a full length or at least a portion of a polypeptide of CD28, 4-1BB, CD27, CD40L, ICOS, CD2, or combinations thereof. In some embodiments, the CFR comprises an endodomain comprising a co-stimulatory domain of CD28 and a cytoxicity domain of CD3ζ (also referred to as "28ζ"). In some embodiments, the -CD28-CD3ζ portion of an endodomain of the CFR is represented by an amino acid sequence having at least about 85%, about 90%, about 95%, about 96%, about 97%, about 98%, or about 99% identity to SEQ ID NO: 27. In some embodiments, the -CD28-CD3ζ portion of an endodomain of the CFR comprises an amino acid sequence having at least about 90% identity to SEQ ID NO: 27. In some embodiments, the -CD28-CD3ζ portion of an endodomain of the CFR comprises an amino acid sequence having at least about 95% identity to SEQ ID NO: 27. In some embodiments, the -CD28-CD3ζ portion of an endodomain of the CFR comprises the amino acid sequence of SEQ ID NO: 27.

```
                                              SEQ ID NO: 27
RSKRSRLLHSDYMNMTPRRPGPTRKHYQPYAPPRDFAAYR

SRVKFSRSADAPAYQQGQNQLYNELNLGRREEYDVLDKRR
```

```
-continued
GRDPEMGGKPRRKNPQEGLFNELQKDKMAEAFSEIGMKGE

RRRGKGHDGLFQGLSTATKDTFDALHMQALPPR
(153 a.a. CD28 co-stim + CD3ζITAM)
```

In some embodiments, the CFR comprises an endodomain further comprising a persistency signaling domain in addition to a cytotoxicity signaling domain and/or a co-stimulatory domain. Persistency signaling domains suitable for use in the CFR include, but are not limited to, all or a part of an endodomain of a cytokine receptor such as, IL2R, IL7R, IL15R, IL18R, IL12R, IL23R, or combinations thereof. In addition, an endodomain of a receptor tyrosine kinase (RTK) such as EGFR provides tumor cell control, or a tumor necrosis factor receptor (TNFR) such as FAS provides controlled cell death.

In some exemplary designs, the CFR comprises an ectodomain of one CD3 subunit, in some other designs the CFR comprises a single chain heterodimeric ectodomain that comprises the ectodomain of CD3ε linked with that of CD3δ or CD3γ (SEQ ID NO: 28 or SEQ ID NO: 29, respectively). The linker type and length in the single chain heterodimeric ectodomain may vary. In some embodiments, the ectodomain comprises an amino acid sequence of at least about 85%, about 90%, about 95%, about 96%, about 97%, about 98%, or about 99% identity to SEQ ID NO: 28 or 29. In some embodiments, the ectodomain comprises an amino acid sequence of at least about 90% identity to SEQ ID NO: 28 or 29. In some embodiments, the ectodomain comprises an amino acid sequence of at least about 95% identity to SEQ ID NO: 28 or 29. In some embodiments, the ectodomain comprises the amino acid sequence of SEQ ID NO: 28. In some embodiments, the ectodomain comprises the amino acid sequence of SEQ ID NO: 29.

```
                                   SEQ ID NO: 28
GYYVCYPRGSKPEDANFYLYLRARVCENCMEMDGSADDAK

KDAAKKDDAKKDDAKKDGSFKIPIEELEDRVFVNCNTSIT

WVEGTVGTLLSDITRLDLGKRILDPRGIYRCNGTDIYKDK

ESTVQVHYRMCQSCVELDPATVA (3ε-linker-3δ; linker sequence and
length may vary)
                                   SEQ ID NO: 29
DGNEEMGGITQTPYKVSISGTTVILTCPQYPGSEILWQHN

DKNIGGDEDDKNIGSDEDHLSLKEFSELEQSGYYVCYPRG

SKPEDANFYLYLRARVCENCMEMDGSADDAKKDAAKKDDA

KKDDAKKDGSQSIKGNHLVKVYDYQEDGSVLLTCDAEAKN

ITWFKDGKMIGFLTEDKKKWNLGSNAKDPRGMYQCKGSQN

KSKPLQVYYRMCQNCIELNAATIS
(3ε-linker-3γ; linker sequence and
length may vary)
```

The cell surface expressed CFR (including CD3-based CFR, also called a cs-CD3) in various constructions as described herein can function as a cell surface triggering receptor for binding with molecules having selected binding specificity, which molecules include antibodies, engagers, and/or CARs (chimerical antigen receptors). As described herein, in some embodiments, the cells comprising a solid tumor targeting backbone comprising polynucleotides encoding encoding two or more of a C—X—C-motif chemokine receptor or a variant thereof, a TGFβ-SRR, and an ADR specific to 4-1BB, optionally comprise polynucleotides encoding one or more CFRs. Said cells may be any type of cells, including human cells and non-human cells, pluripotent cells or non-pluripotent cells, immune cells or immune regulatory cells, APC (antigen presenting cells) or feeder cells, cells from primary sources (e.g., PMBC), or from cultured or engineered cells (e.g., cell lines, cells, and/or derivative cells differentiated from iPSCs). In some embodiments, the cells comprising a solid tumor targeting backbone as described herein, and optionally CD38 knock-out, exogenous CD16 or a variant thereof, HLA-I and/or HLA-II deficiency and one or more CFRs comprise primary or derivative CD34 cells, hematopoietic stem and progenitor cells, hematopoietic multipotent progenitor cells, T cell progenitors, NK cell progenitors, T lineage cells, NKT lineage cells, NK lineage cells, or B lineage cells. In some embodiments, the derivative cells comprising polynucleotides encoding the one or more genetic modalities described herein are effector cells obtained from differentiating an iPSC comprising polynucleotides encoding the one or more genetic modalities described herein.

Additionally provided in this application is a master cell bank comprising single cell sorted and expanded clonal engineered iPSCs having at least one phenotype as provided herein, including but not limited to, a solid tumor targeting backbone as described herein and a CFR, wherein the cell bank provides a platform for additional iPSC engineering and a renewable source for manufacturing off-the-shelf, engineered, homogeneous cell therapy products, including but not limited to derivative NK and T cells, which are well-defined and uniform in composition, and can be mass produced at significant scale in a cost-effective manner.

9. Chimeric Antigen Receptor (CAR) Expression

Applicable to the genetically engineered immune cells, iPSCs and derivative effector cells thereof may be any CAR design known in the art. CAR is a fusion protein generally including an ectodomain that comprises a target binding region (for example, an antigen recognition domain), a transmembrane domain, and an endodomain. In some embodiments, the ectodomain can further include a signal peptide or leader sequence and/or a spacer. In some embodiments, the endodomain can further comprise a signaling peptide that activates the effector cell expressing the CAR. In some embodiments, the signaling peptide of the endodomain (or intracellular domain) comprises a full length or at least a portion of a polypeptide of 2B4, CD2, CD3ζ, CD3ζ1XX, CD8, CD28, CD28H, CD137 (4-1BB), CS1, DAP10, DAP12, DNAM1, FcERIγ, IL2Rγ, IL7R, IL21R, IL2Rβ (IL15Rβ), IL21, IL7, IL12, IL15, IL21, KIR2DS2, NKp30, NKp44, NKp46, NKG2C, or NKG2D. In one embodiment, the signaling peptide of a CAR comprises an amino acid sequence that has at least about 85%, about 90%, about 95%, about 96%, about 97%, about 98%, or about 99% identity to at least one ITAM (immunoreceptor tyrosine-based activation motif) of CD3ζ. Exemplary N-terminal signal peptides include MALPVTALLLPLALLLHA (SEQ ID NO: 30; CD8asp) or MDFQVQIFSFLLISASVI-MSR (SEQ ID NO: 31; IgKsp), or any signal peptide sequence or functional variants thereof known in the art.

In some embodiments, the antigen recognition domain can specifically bind an antigen. In some embodiments, the CAR is suitable to activate T, NK or NKT cells expressing said CAR. In some embodiments, the CAR is NK cell specific for comprising NK-specific signaling components. In some embodiments, the CAR is NKT cell specific for comprising NKT-specific signaling components. In certain embodiments, said T cells are derived from a CAR expressing iPSCs comprising a solid tumor targeting backbone as described herein, and the derivative T cells may comprise T helper cells, cytotoxic T cells, memory T cells, regulatory T cells, natural killer T cells, αβ T cells, γδ T cells, or a combination thereof. In certain embodiments, said NK cells are derived from a CAR expressing iPSCs comprising a solid tumor targeting backbone as described herein. In certain embodiments, said NKT cells are derived from a CAR expressing iPSCs comprising a solid tumor targeting backbone as described herein.

In various embodiments, the antigen recognition region comprises a murine antibody, a human antibody, a humanized antibody, a camel Ig, a single variable new antigen receptor (VNAR), a shark heavy-chain antibody (Ig-NAR), a chimeric antibody, a recombinant antibody, a single-domain antibody (dAb), an anti-idiotype antibody, a bi-specific-, multi-specific- or multimeric-antibody, or antibody fragment thereof. Anti-idiotype antibodies are specific for binding to an idiotope of another antibody, wherein the idiotope is an antigenic determinant of an antibody. A bi-specific antibody may be a BiTE (bi-specific T cell engager) or a BiKE (bi-specific killer cell engager), and a multi-specific antibody may be a TriKE (tri-specific Killer cell engager). Non-limiting examples of antibody fragments include Fab, Fab', F(ab')2, F(ab')3, Fv, Fabc, pFc, Fd, single chain fragment variable (scFv), tandem scFv (scFv)2, single chain Fab (scFab), disulfide stabilized Fv (dsFv), minibody, diabody, triabody, tetrabody, single-domain antigen binding fragments (sdAb), camelid heavy-chain IgG and Nanobody® fragments, recombinant heavy-chain-only antibody (VHH), and other antibody fragments that maintain the binding specificity of the antibody. In some embodiments an antigen binding domain of a CAR comprises CDR1, CDR2, and CDR3 of a heavy chain (H-CDRs) of an antibody or fragments thereof. In some embodiments, the antigen binding domain of a CAR comprising the H-CDRs of an antibody further comprises the CDRs of a light chain (L-CDRs) of the antibody.

In some embodiments, the antigen recognition domain of a CAR specifically binds an antigen associated with a disease or pathogen. In some embodiments, the disease-associated antigen is a tumor antigen, wherein the tumor may be a liquid or a solid tumor. In some embodiments of a CAR, the CAR targets antigens of hematological malignancies, which include, but are not limited to, acute and chronic leukemias (acute myelogenous leukemia (AML), acute lymphoblastic leukemia (ALL), chronic myelogenous leukemia (CML), lymphomas, non-Hodgkin lymphoma (NHL), Hodgkin's disease, multiple myeloma, and myelodysplastic syndromes.

In some embodiments of CARs targeting solid cancer antigens, the antigens are associated with sarcomas and carcinomas. In some embodiments, the solid cancers suitable for CAR targeting include, but are not limited to, bladder cancer, bone cancer, brain/CNS cancer, breast cancer, breast lung cancer, cervical cancer, colorectal cancer, esophageal cancer, gastric/stomach cancer, head and neck cancer, kidney cancer, larynx cancer, liver cancer, lung cancer, metastatic cancer, ovarian cancer, pancreatic cancer, prostate cancer, rectal cancer, renal cancer, salivary gland cancer, skin cancer, testicular tumor, thyroid tumor, urothelial cancer, and uterine/endometrial cancer. More specifically, in some embodiments the CAR targets an antigen associated to adenocarcinoma, basal cell carcinoma, bile duct carcinoma, bladder carcinoma, bronchogenic carcinoma, cholangiocarcinoma, chondrosarcoma, choriocarcinoma, colon carcinoma, Ewing's tumor, fibrosarcoma, gallbladder carcinoma, hepatocellular carcinoma, hepatoma, leiomyosarcoma, liposarcoma, lymphoid malignancy, medullary carcinoma, medullary thyroid carcinoma, melanoma, mesothelioma, myxosarcoma, non-small cell lung cancer, osteosarcoma, papillary adenocarcinoma, papillary carcinoma, papillary thyroid carcinoma, pheochromocytomas sebaceous gland carcinoma, peritoneal carcinoma, renal cell carcinoma, rhabdomyosarcoma, sarcoma, seminoma, squamous cell carcinoma, sweat gland carcinoma, synovial sarcoma, synovioma, and Wilms' tumor. In some embodiments, the CAR targets antigens of CNS tumors including, but not limited to, acoustic neuroma, astrocytoma, CNS lymphoma, ependymoma, hemangioblastoma, germinoma, glioma (including brainstem glioma and mixed gliomas), glioblastoma (also known as glioblastoma multiforme), medulloblastoma, menangioma, neuroblastoma, oligodendroglioma, pinealoma, retinoblastoma, Schwannoma craniopharyogioma, and brain metastases.

Non-limiting examples of antigens that may be targeted by a CAR include oncofetal antigen (h5T4), 8H9, 9D7, ACPP, α actinin-4 (ACTN4), ADAM12, ADRB3, ADGRE2/EMR2, AFP, AKAP-4, ALK, ALPP, ALPPL2, Androgen receptor, ASGR1 (asialoglycoprotein receptor 1), ASGR2 (asialoglycoprotein receptor 2), AXL, B7H3, B7H6, BAGE, β-catenin, BCR, BCR-ABL, Bigh3, BING-4, BORIS, BRCA1/2, BST2, carbonic anhydrase IX (CAIX/CA9), CA125, C—C motif chemokine receptor 1 (CCR1), CCR4, carcinoembryonic antigen (CEA/CECAM5), Calcium-activated chloride channel 2 (CLCA4), Carbohydrates (Le), CD3, CD4, CD5, CD7, CD8, CD10, CD19, CD20, CD22, CD24, CD30, CD33, CD34, CD37, CD38, CD41, CD44, CD44V6, CD44v7/8, CD47, CD49f, CD52, CD56, CD70, CD72, CD74, CD79a, CD79b, CD97, CD99, CD123, CD133, CD138, CD171, CD179a, CD207, CD269 (BCMA), CD300LF, CDCl 27, CDH3 (p-cadherin), CDH6, cadherin 19 (CDH19), CDK4, CFC1, CLCA1, CLDN6, CLDN18.2, CLEC12A, CLL-1, c-MET, CML66, an antigen of a cytomegalovirus (CMV) infected cell (e.g., a cell surface antigen), CR1L, CS-1, CSPG4, CXCR2, CXCR5, CXORF61, Cyclin B1 (CCNB1), CYP1B1, DLL3, EFNA4, EGFR (or erbB-1), EGFRvIII, EGF1R, epithelial cell adhesion molecule/epithelial glycoprotein-2 (EpCAM/EGP2), epithelial glycoprotein-40 (EGP40), ELF2M, ENPP3, EphA2, EphA3, EphB2, ERBB2 (or HER2/neu), ERBB3, ERBB4, ERG (TMPRSS2 ETS fusion gene), ETA, ETV6-AML, FAP, folate-binding protein (FBP), FCAR, FCRL5, fetal acetylcholine receptor (AChR), Fibronectin, FLT3, folate receptor-α, (FR-α/FOLR1), Folate receptor beta (FR-β/FOLR2), FOLR3, Fos-related antigen 1 (FOSL1), FRcc, FZD10, GAGE, gangliosides (GM1, FucGM1, GM2, GM3, GD2, o-acetyl-GD2, GD3), GloboH, GpA33, Gp75, Gp100, Glypican-1 (GPC1), Glypican-2 (GPC2), Glypican-3 (GPC3), GPNMB, GPR20, GPR27, GPR35, GPR119, GPRC5D, guanylate cyclase C (GC-C), GUCY2C, HAVCR1, HERV-envelope protein, HLA-A1, HM1.24, HMWMAA, HPV E6, HPV E7, human telomerase reverse transcriptase (hTERT), IGFr/IGF1R, IGLL1 (CD179b), IL11Rα, Interleukin-13 receptor subunit alpha-2 (IL13Rα2), IL13Rcc2, Immature laminin receptor (iLRP), Integrin uV03, Integrin alpha5β, Integrin B7, intercellular adhesion molecule 1 (ICAM1), intestinal carboxyl esterase (iCE), κ-light chain, kinase insert domain receptor (KDR), KIT, KISS1R, LAIR1, LAGE-1a, LAMP-1, LCK, legumain, Lewis A (CA19.9), Lewis Y (LeY), L1 cell adhesion molecule (L1-CAM), LILRA2, LILRB2, LIV-1, LMP2, LRRC15, LY6K, LY75, LYPD3, MAD-CT-1, MAD-CT-2, melanoma antigen family A1 (MAGE-A1), MC1R, MelanA/MART1, MART2, melanoma-associated chondroitin sulfate proteoglycan (MCSP), c-Met, MICA/B, Mesothelin (MSLN), ML-IAP, MR1, multidrug resistance-associated protein 3 (MRP3), MS4A12, Mucin 1 (MUC1, tMUC1), MUC2, MUC5A, MUC12, MUC16, MUC17, MUC21, Mud, MUM1, MUM2, MUM3, mut hsp70-2, MYCN, NA17, NA88-1, NCAM, Nectin4, NKCSI, NKG2D ligands, NPM, NY-BR-1, cancer-testis antigen NY-ESO-1, OA1, OGT, OR51E2, OY-TES1, p53, p53 mutant, PANX3, PAP, PAX3, PAX5, PCTA-1/Galectin 8, PDGFR-beta, PDL1, periostin, PLAC1, PRAME, PRLR, Prostase (KLK2, KLK4), prostein (P501S), PRSS21, Polysialic acid (PSA), prostate stem cell antigen (PSCA), PSC1, PRAME prostate-specific membrane antigen (PSMA/FOLH1), PTK7, QRFPR, RAGE-1, RANKL, Ras, Ras mutant, RCC, RhoC, Ron Kinase, ROR1, RU1, RU2, SAGE, SAP1, sarcoma translocation breakpoints, SART3, SIGLEC-15, Sialo-epitope CA6, SLC6A3, SLC12A3, SLC13A5, SLC22A1, SLC22A7, SLC30A4, SLC30A8, SLC34A2, SLC45A3, sLe, SLITRK6, SPARC, Sperm protein 17 (SP17), SSEA-4, SSTR1, SSX2, STEAP, sTN, Survivin, tumor-associated glycoprotein 72 (TAG72), TARP, TEM1/CD248, TEM7R, TEMs, Telomerase, TGF-B receptor, TGS5, Tie 2, Tissue Factor (TF), TIM-3, TMEFF2 (TENB2), TMEM238, TMPRSS11B, TMPRSS11E, TnAg, TNC, TP-3, TRAILR1, TRAILR2, TRBC1, TRBC2, TRF2, TRG, TROP2, TRP1, TRP2, TSHR, TSTA, Tyrosinase, UGT1A1, UPK1B, UPK2, VEGF, VEGFR, vascular endothelial growth factor R2 (VEGF-R2), VTCN1 (B7H4), Wilms tumor protein (WTi), XAGEi, and various pathogen antigen known in the art. Non-limiting examples of pathogens include viruses, bacteria, fungi, parasites and protozoa capable of causing diseases.

Non-limiting examples of solid tumor antigens that may be targeted by a CAR include h5T4, 8H9, 9D7, ACPP, ACTN4, ADAM12, ADRB3, AFP, AKAP-4, ALK, ALPP, ALPPL2, Androgen receptor, ASGR1, ASGR2, AXL, B7H3, B7H6, BAGE, β-catenin, BCMA (CD269), BCR, BCR-ABL, Bigh3, BING-4, BORIS, BRCA1/2, BST2, CAIX/CA9, CA19.9, CA125, CCR1, CCR4, Carbohydrates (Le), CCNB1, CD3, CD4, CD10, CD19, CD20, CD22, CD24, CD30, CD33, CD37, CD38, CD44, CD44v6, CD44v7/8, CD47, CD49f, CD56, CD70, CD72, CD74, CD79a, CD79b, CD97, CD99, CD123, CD133, CD138, CD171, CD179a, CD207, CD300LF, CDCl 27, CDH3, CDH6, CDH19, CDK4, CEA/CECAM5, CFC1, CLCA1, CLCA4, CLDN6, CLDN18.2, CLEC12A, CLL-1, c-MET, CML66, CR1L, CS-1, CSPG4, CXCR2, CXCR5, CXORF61, CYP1B1, DLL3, EFNA4, EGFR, EGFRvIII, EGP2/EpCAM, EGP40, ELF2M, EMR2, ENPP3, EphA2, EphA3, EphB2, ERBB2 (HER2/neu), ERBB3, ERBB4, periostin, ERG (TMPRSS2 ETS fusion gene), ETA, ETV6-AML, FAP, FBP, FCAR, FCRL5, fetal AchR, Fibronectin, FLT3, FR-α/FOLR1, FR-β/FOLR2, FOLR3, FOSL1, FRec, FZD10, GAGE, gangliosides (GM1, FucGM1, GM2, GM3, GD2, o-acetyl-GD2, GD3), GloboH, GpA33, Gp75, Gp100, GPC1, GPC2, GPC3, GPNMB, GPR20, GPR27, GPR35, GPR119, GPRC5D, GC-C, GUCY2C, HAVCR1, HER2, HERV-envelope protein, HLA-A1, HM1.24, HMWMAA, HPV E6, HPV E7, hTERT, iCE, ICAM1, IGFr/IGF1R, IGLL1 (CD179b), IL-11Rα, IL13-Rα2, IL-13Rcc2, iLRP, Integrin αVβ3, Integrin alpha5β, KDR, KIT, KISS1R, KLK2, KLK4, LAIR1, LAGE-1a, LAMP-1, LCK, legumain, LeY, L1-CAM, LILRA2, LIV-1, LILRB2, LMP2, LRRC15, LY6K, LY75, LYPD3, MAD-CT-1, MAD-CT-2, MAGE-A1, MC1R, MelanA/MART1, MART2, MCSP, MICA/B, ML-IAP, MR1, MRP3, MS4A12, MSLN, MUC1, tMUC1, MUC2, MUC5A, MUC12, MUC16, MUC17, MUC21, Mud, MUM1, MUM2, MUM3, mut hsp70-2, MYCN, NA17, NA88-1, NCAM, Nectin4, NKG2D ligands, NPM, NY-BR-1, NY-ESO-1, OA1, OGT, OR51E2, OY-TES1, p53, p53 mutant, PANX3, PAP, PAX3, PAX5, PCTA-1/Galectin 8, PDGFR-beta, PDL1, PLAC1, PRAME, PRLR, P501S, PRSS21, PSA, PSCA, PSC1, PSMA/FOLH1, PTK7, QRFPR, RAGE-1, RANKL, Ras, Ras mutant, RCC, RhoC, Ron Kinase, ROR1, RU1, RU2, SAGE, SAP1, sarcoma translocation breakpoints, SART3, SIGLEC-15, Sialo-epitope CA6, SLC6A3, SLC12A3, SLC13A5, SLC22A1, SLC22A7, SLC30A4, SLC30A8, SLC34A2, SLC45A3, sLe, SLITRK6, SPARC, SP17, SSEA-4, SSTR1, SSX2, STEAP, sTN, Survivin, TAG72, TARP, TEM1/CD248, TEM7R, TEMs, Telomerase, TGF-B receptor, TGS5, Tie 2, Tissue Factor (TF), TIM-3, TMEFF2 (TENB2), TMEM238, TMPRSS11B, TMPRSS11E, Tn Ag, TNC, TP-3, TRAILR1, TRAILR2, TRF2, TRG, TROP2, TRP1, TRP2, TSHR, TSTA, Tyrosinase, UGT1A1, UPK1B, UPK2, VEGF, VEGFR, VEGFR-II, VTCN1 (B7H4), WTi, and XAGEi.

Non-limiting examples of solid cancers with corresponding tumor antigens are provided in Table 1B.

TABLE 1B

Exemplary Solid Tumors and Solid Tumor Associated Antigens

| Cancer Type | Antigen | Antibody |
| --- | --- | --- |
| Bladder Cancer | HER2, MICA/B, CD207, EFNA4, LY6K, LYPD3, Nectin4, PTK7, SLITRK6, TIM-3, TNC, UPK1B, UPK2 | enfortumab, trastuzumab, pertuzumab, SLITRK6 |
| Bone Cancer | MICA/B, ADAM12, CCR1, CD99, CD248, EPHA2, GPNMB, LRRC15, TP-3 | huM25, DS-8895a variant 1, DS-8895a variant 2, glembatumab |
| Brain Cancer | MICA/B, CD133, DLL3, EGFRvIII, TNC | AMG595, ABT806, rovalpituzumab, depatuxizumab |
| Breast Cancer | HER2, MICA/B, ADAM12, ADGRE2/EMR2, CCR4, CD49f, CD133, CDH3 (p-cadherin), CLDN6, c-MET, CXCR2, EFNA4, EGFR, EPCAM/EGP2, EPHA2, GPNMB, ICAM1, LAMP-1, LIV-1, LILRB2, LRRC15, LYPD3, MUC1, tMUC1, PRLR, PTK7, Sialo-epitope CA6, TNC, TROP2 | trastuzumab, pertuzumab, sacituzumab, ladiratuzumab, huLiv1-14, Liv1-1.7A4, huLiv1-22, huDS6, glembatumumab, PF-0664720, MEDI-547, DS-8895a variant 1, DS-08895a variant 2 |
| Breast Lung Cancer | HER2, MICA/B, ADGRE2/EMR2, EPCAM/EGP2, ROR1 | |

TABLE 1B-continued

Exemplary Solid Tumors and Solid Tumor Associated Antigens

| Cancer Type | Antigen | Antibody |
| --- | --- | --- |
| Cervical Cancer | MICA/B, EFNA4, LY6K, MUC1, MUC16, LYPD3, PTK7, SLC12A3, SSTR1 | PF-0664720, anetumumab, 4H11, 4H5, huDS6, sofituzumab |
| Cholangiocarcinoma | MICA/B, tMUC1 | |
| Colorectal Cancer | HER2, MICA/B, ADAM12, CA19.9, CD3, CD49f, CD133, CEA/CECAM5, CLCA1, c-MET, EFNA4, EPHB2, GPA33, GPR35, GUCY2C, ICAM1, LGR5/GPR49, LRRC15, MS4A12, MUC12, MUC17, TIM-3, TMEM238 | huM25, PR1A3, humanized PR1A3, pantumumab, cetuximab, nimotuzumab, zalutumumab |
| Esophageal Cancer | HER2, MICA/B, CA19.9, CD10, CEA/CECAM5, EFNA4, EPHB2, MUC21, TMEM238, TMPRSS11B, TMPRSS11E | |
| Gallbladder Carcinoma | EPCAM/EGP2 | |
| Gastric (Stomach) Cancer | HER2, MICA/B, CEA/CECAM5, CLDN18.2, c-MET, CRIL, EFNA4, EPHB2, LGR5/GPR49, MUC17, PSCA, TIM-3, TMEM238 | sofituzumab, anetumab, pertuzumab, trastuzumab, humanized PR1A3 |
| Glioma | MICA/B, ADGRE2/EMR2, CD49f, CD133, EGFR, EGFRVIII, EPHA2, HM1.24, IL13-Ra2 | |
| Head and Neck Cancer | HER2, MICA/B, ADAM12, CD3, c-MET, EFNA4, LRRC15, LY6K, LYPD3, PTK7, TNC | cetuximab, panitumumab, nimtuzumab, PF-0664720, pantumumab, cetuximab, nimotuzumab, zalutumumab |
| Kidney Cancer | MICA/B, CD70, CDH6, c-MET, ENPP3, HAVCR1 | AGS-16M8F, AGS-16C3, the antibody of CDX-014, onartuzumab |
| Liver Cancer | MICA/B, ASGR1, ASGR2, C9 (CAIX), CA19.9, CEA/CECAM5, CCR1, CD3, CD133, EPCAM/EGP2, GPC3, ICAM1, LGR5/GPR49, SLC13A5, SLC22A1, SLC22A7, TIM-3, TRF2, UGT1A1 | codrituzumab, oportuzumab, humanized PR1A3 |
| Lung Cancer | HER2, MICA/B, ADAM12, ADGRE2/EMR2, CCR1, CCR4, CD56, CD133, CEA/CECAM5, CXCR2, DLL3, EFNA4, EGFR, EGFRvIII, FOLR1, GPC3, HM1.24, ICAM1, LILRB2, LRRC15, LY6K, LYPD3, MSLN, MUC1, MUC16, PDL1, PTK7, SLC34A2, TIM-3 | panitumumab, cetuximab, pembrolizumab, nivolumab, atezolizumab, and nimotuzumab, lifastuzumab, anetumab, PF-0664720, farletuzumab, rovalpituzumab, lifastuzumab, sofituzumab, huDS6, ABT806, AMG595, huM25 |
| Mesothelioma | MICA/B, FAP, MSLN | |
| Metastatic Cancer | MICA/B, MSLN, VEGFR-II | |
| Neuroblastoma | MICA/B, GD2 | |
| Non-Small Cell Lung Cancer (NSCLC) | MICA/B, c-MET, EGFR | |
| Ovarian Cancer | HER2, MICA/B, CCR1, CD3, CD133, CLDN6, c-MET, EFNA4, EPCAM/EGP2, FAP, FOLR1, FOLR3, FR-α, FZD10, GPR27, GPR119, LRRC15, MSLN, MUC1, MUC16, PTK7, SLC34A2, sTN, TMEM238, VTCN1 | sofituzumab, 4H11, 4H5, huDS6, farletuzumab, anetumab, trastuzumab, pertuzumab, PF-0664720, sibrotuzumab, huM25, lifastuzumab |
| Pancreatic Cancer | MICA/B, ADAM12, CA19.9, CFC1, EFNA4, EPCAM/EGP2, ICAM1, LILRB2, LRRC15, MSLN, MUC1, tMUC1, MUC5A, MUC16, MUC17, PSCA, PTK7, SLC30A8 | PF-0664720, clivatuzumab, 4H11, 4H5, anetumumab, huDS6, sofituzumab, huM25, RG7841 |
| Peritoneal Carcinoma | FOLR3 | |
| Prostate Cancer | MICA/B, ACPP, CD10, CD49f, CD133, EFNA4, OR51E2, PSCA, PSMA/FOLH1, PTK7, SLC30A4, SLC45A3, STEAP, TIM-3, TMEFF2 (TENB2) | mirvetuximab, J591 variant 1, J591 variant 2 |
| Renal Cancer | MICA/B, CD3, CD70, ICAM1, KISS1R, LILRB2, QRFPR, SLC6A3, TIM-3 | |
| Sarcoma | MICA/B, LRRC15 | |
| Salivary Gland Cancer | HER2, MICA/B | |
| Skin Cancer | CCR4, CD3, CD10, ICAM1 | |
| Synovial Sarcoma (Soft Tissue Cancer) | CD99 | |

TABLE 1B-continued

Exemplary Solid Tumors and Solid Tumor Associated Antigens

| Cancer Type | Antigen | Antibody |
| --- | --- | --- |
| Thyroid Tumor | MICA/B, CD10, c-MET, PTK7, TSHR | |
| Urothelial Cancer | MICA/B, CLDN6, EPCAM/EGP2, SIGLEC-15, TIM-3, UPK2 | |
| Uterine/Endometrial Cancer | HER2, MICA/B, ALPP, ALPPL2, CCR1, CLDN6, EFNA4, EPHB2, FOLR1, LILRB2, LY6K, LYPD3, MUC1, MUC16, PTK7 | PF-0664720, anetumumab, 4H11, 4H5, huDS6, sofituzumab, farletuzumab |

In some embodiments, the antigen recognition domain of a CAP comprises CDRs of the heavy chain (H-DRs), CDRs of both the heavy and the light chains (H- and L-CDRs), the variable region of the heavy chain (VH), or a single chain of the variable regions of both the heavy and light chains (VH and VL) of the binding domains of an antibody that is specific to a tumor antigen, including those exemplified in this application. In some embodiments, the CAR is designed based on the binding domains of an antibody comprising trastuzumab, cetuximab, panitumumab, ofatumumab, belimumab, ipilimumab, pertuzumab, tremelimumab, nivolumab, pembrolizumab, atezolizumab, MDX-1105, dacetuzumab, urelumab, MPDL3280A, lambrolizumab, blinatumomab, nimotuzumab, zalutumumab, onartuzumab, patritumab, clivatuzumab, sofituzumab, edrecolomab, adecatumumab, anetumab, huDS6, lifastuzumab, sacituzumab, PR1A3, humanized PR1A3, humanized Ab2-3, claudiximab, AMG595, ABT806, sibrotuzumab, DS-8895a variant 1, DS-8895a variant 2, MEDI-547, narnatumab, RG7841, farletuzumab, mirvetuximab, J591 variant 1, J591 variant 2, rovalpituzumab, PF-06647020, ladiratuzumab, cirmtuzumab, ladiratuzumab, huLiv1-14, Liv1-1.7A4, huLiv1-22, 4H11, 4H5, glembatumumab, oportuzumab, enfortumab, depatuxizumab, or codrituzumab.

Accordingly, in some embodiments, the antigen recognition domain of the CAR specifically binds to an antigen present on bladder cancer. In some embodiments, the CAR targeting a bladder cancer associated antigen specifically binds to HER2, MICA/B, CD207, EFNA4, LY6K, LYPD3, Nectin4, PTK7, SLITRK6, TIM-3, TNC, UPK1B, or UPK2. In some embodiments, the antigen recognition domain of said CAR comprises the H-CDRs, H- and L-CDRs, the VH, or a single chain of VH and VL of an antibody comprising enfortumab, trastuzumab, pertuzumab or SLITRK6.

In some embodiments, the antigen recognition domain of the CAR specifically binds to an antigen present on bone cancer. In some embodiments, the CAR targeting a bone cancer associated antigen specifically binds to MICA/B, ADAM12, CCR1, CD99, CD248, EPHA2, GPNMB, LRRC15, or TP-3. In some embodiments, the antigen recognition domain of said CAR comprises the H-CDRs, H- and L-CDRs, the VH, or a single chain of VH and VL of an antibody comprising huM25, DS-8895a variant 1, DS-8895a variant 2, or glembatumab.

In some embodiments, the antigen recognition domain of the CAR specifically binds to an antigen present on brain cancer. In some embodiments, the CAR targeting a brain cancer associated antigen specifically binds to MICA/B, CD133, DLL3, EGFRvIII, or TNC. In some embodiments, the antigen recognition domain of said CAR comprises the H-CDRs, H- and L-CDRs, the VH, or a single chain of VH and VL of an antibody comprising AMG595, ABT806, rovalpituzumab or depatuxizumab.

In some embodiments, the antigen recognition domain of the CAR specifically binds to an antigen present on a breast cancer cell. In some embodiments, the CAR targeting a breast cancer associated antigen specifically binds to HER2, MICA/B, ADAM12, ADGRE2/EMR2, CCR4, CD49f, CD133, CDH3 (p-cadherin), CLDN6, c-MET, CXCR2, EFNA4, EGFR, EPCAM/EGP2, EPHA2, GPNMB, ICAM1, LAMP-1, LIV-1, LILRB2, LRRC15, LYPD3, MUC1, tMUC1, PRLR, PTK7, Sialo-epitope CA6, TNC, or TROP2. In some embodiments, the antigen recognition domain of said CAR comprises the H-CDRs, H- and L-CDRs, the VH, or a single chain of VH and VL of an antibody comprising trastuzumab, pertuzumab, sacituzumab, ladiratuzumab, huLiv1-14, Liv1-1.7A4, huLiv1-22, huDS6, glembatumumab, PF-0664720, MEDI-547, DS-8895a variant 1, or DS-08895a variant 2.

In some embodiments, the antigen recognition domain of the CAR specifically binds to an antigen present on a breast lung cancer cell. In some embodiments, the CAR targeting a breast lung cancer associated antigen specifically binds to HER2, MICA/B, ADGRE2/EMR2, EPCAM/EGP2, or ROR1.

In some embodiments, the antigen recognition domain of the CAR specifically binds to an antigen present on cervical/uterine/endometrial cancer. In some embodiments, the CAR targeting a cervical/uterine/endometrial cancer associated antigen specifically binds to MICA/B, EFNA4, LY6K, MUC1, MUC16, LYPD3, PTK7, SLC12A3, or SSTR1. In some embodiments, the antigen recognition domain of said CAR comprises the H-CDRs, H- and L-CDRs, the VH, or a single chain of VH and VL of an antibody comprising PF-0664720, anetumumab, 4H11, 4H5, huDS6, or sofituzumab.

In some embodiments, the antigen recognition domain of the CAR specifically binds to an antigen present on a cholangiocarcinoma cell. In some embodiments, the CAR targeting a cholangiocarcinoma associated antigen specifically binds to MICA/B or tMUC1.

In some embodiments, the antigen recognition domain of the CAR specifically binds to an antigen present on colorectal cancer. In some embodiments, the CAR targeting a colorectal cancer associated antigen specifically binds to HER2, MICA/B, ADAM12, CA19.9, CD3, CD49f, CD133, CEA/CECAM5, CLCA1, c-MET, EFNA4, EPHB2, GPA33, GPR35, GUCY2C, ICAM1, LGR5/GPR49, LRRC15, MS4A12, MUC12, MUC17, TIM-3, or TMEM238. In some embodiments, the antigen recognition domain of said CAR comprises the H-CDRs, H- and L-CDRs, the VH, or a single chain of VH and VL of an antibody comprising huM25, PR1A3, humanized PR1A3, pantumumab, cetuximab, nimotuzumab, or zalutumumab.

In some embodiments, the antigen recognition domain of the CAR specifically binds to an antigen present on an esophageal cancer cell. In some embodiments, the CAR targeting an esophageal cancer associated antigen specifically binds to HER2, MICA/B, CA19.9, CD10, CEA/CECAM5, EFNA4, EPHB2, MUC21, TMEM238, TMPRSS11B, or TMPRSS11E.

In some embodiments, the antigen recognition domain of the CAR specifically binds to an antigen present on a gall bladder carcinoma cell. In some embodiments, the CAR targeting a gall bladder carcinoma associated antigen specifically binds to EPCAM/EGP2.

In some embodiments, the antigen recognition domain of the CAR specifically binds to an antigen present on gastric/stomach cancer. In some embodiments, the CAR targeting a gastric/stomach cancer associated antigen specifically binds to HER2, MICA/B, CEA/CECAM5, CLDN18.2, c-MET, CR1L, EFNA4, EPHB2, LGR5/GPR49, MUC17, PSCA, TIM-3, or TMEM238. In some embodiments, the antigen recognition domain of said CAR comprises the H-CDRs, H- and L-CDRs, the VH, or a single chain of VH and VL of an antibody comprising sofituzumab, anetumab, pertuzumab, trastuzumab, or humanized PR1A3.

In some embodiments, the antigen recognition domain of the CAR specifically binds to an antigen present on a glioma cancer cell. In some embodiments, the CAR targeting a glioma cancer associated antigen specifically binds to MICA/B, ADGRE2/EMR2, CD49f, CD133, EGFR, EGFRvIII, EPHA2, HM1.24, or IL13-Rα2.

In some embodiments, the antigen recognition domain of the CAR specifically binds to an antigen present on head and neck cancer. In some embodiments, the CAR targeting a head and neck cancer associated antigen specifically binds to HER2, MICA/B, ADAM12, CD3, c-MET, EFNA4, LRRC15, LY6K, LYPD3, PTK7, or TNC. In some embodiments, the antigen recognition domain of said CAR comprises the H-CDRs, H- and L-CDRs, the VH, or a single chain of VH and VL of an antibody comprising cetuximab, panitumumab, nimtuzumab, PF-0664720, pantumumab, cetuximab, nimotuzumab, or zalutumumab.

In some embodiments, the antigen recognition domain of the CAR specifically binds to an antigen present on kidney cancer. In some embodiments, the CAR targeting a kidney cancer associated antigen specifically binds to MICA/B, CD70, CDH6, c-MET, ENPP3, or HAVCR1. In some embodiments, the antigen recognition domain of said CAR comprises the H-CDRs, H- and L-CDRs, the VH, or a single chain of VH and VL of an antibody comprising AGS-16M8F, AGS-16C3, the antibody of CDX-014, or onartuzumab.

In some embodiments, the antigen recognition domain of the CAR specifically binds to an antigen present on liver cancer. In some embodiments, the CAR targeting a liver cancer associated antigen specifically binds to MICA/B, ASGR1, ASGR2, C9 (CAIX), CA19.9, CEA/CECAM5, CCR1, CD3, CD133, EPCAM/EGP2, GPC3, ICAM1, LGR5/GPR49, SLC13A5, SLC22A1, SLC22A7, TIM-3, TRF2, or UGT1A1. In some embodiments, the antigen recognition domain of said CAR comprises the H-CDRs, H- and L-CDRs, the VH, or a single chain of VH and VL of an antibody comprising codrituzumab, oportuzumab, or humanized PR1A3.

In some embodiments, the antigen recognition domain of the CAR specifically binds to an antigen present on lung cancer. In some embodiments, the CAR targeting a lung cancer associated antigen specifically binds to HER2, MICA/B, ADAM12, ADGRE2/EMR2, CCR1, CCR4, CD56, CD133, CEA/CECAM5, CXCR2, DLL3, EFNA4, EGFR, EGFRvIII, FOLR1, GPC3, HM1.24, ICAM1, LILRB2, LRRC15, LY6K, LYPD3, MSLN, MUC1, MUC16, PDL1, PTK7, SLC34A2, or TIM-3. In some such embodiments, the antigen recognition domain of said CAR comprises the H-CDRs, H- and L-CDRs, the VH, or a single chain of VH and VL of an antibody comprising panitumumab, cetuximab, pembrolizumab, nivolumab, atezolizumab, and nimotuzumab, lifastuzumab, anetumab, PF-0664720, farletuzumab, rovalpituzumab, lifastuzumab, sofituzumab, huDS6, ABT806, AMG595, or huM25.

In some embodiments, the antigen recognition domain of the CAR specifically binds to an antigen present on a mesothelioma cell. In some embodiments, the CAR targeting a mesothelioma associated antigen specifically binds to MICA/B, FAP, or MSLN.

In some embodiments, the antigen recognition domain of the CAR specifically binds to an antigen present on a metastatic cancer cell. In some embodiments, the CAR targeting a metastatic cancer cell associated antigen specifically binds to MICA/B, MSLN, or VEGFR-II.

In some embodiments, the antigen recognition domain of the CAR specifically binds to an antigen present on a neuroblastoma cell. In some embodiments, the CAR targeting a neuroblastoma associated antigen specifically binds to MICA/B or GD2.

In some embodiments, the antigen recognition domain of the CAR specifically binds to an antigen present on a non-small cell lung cancer (NSCLC) cell. In some embodiments, the CAR targeting a non-small cell lung cancer associated antigen specifically binds to MICA/B, c-MET, or EGFR.

In some embodiments, the antigen recognition domain of the CAR specifically binds to an antigen present on ovarian cancer. In some embodiments, the CAR targeting an ovarian cancer associated antigen specifically binds to HER2, MICA/B, CCR1, CD3, CD133, CLDN6, c-MET, EFNA4, EPCAM/EGP2, FAP, FOLR1, FOLR3, FR-α, FZD10, GPR27, GPR119, LRRC15, MSLN, MUC1, MUC16, PTK7, SLC34A2, sTN, TMEM238, or VTCN1. In some embodiments, the antigen recognition domain of said CAR comprises the H-CDRs, H- and L-CDRs, the VH, or a single chain of VH and VL of an antibody comprising sofituzumab, 4H11, 4H5, huDS6, farletuzumab, anetumab, trastuzumab, pertuzumab, PF-0664720, sibrotuzumab, huM25, or lifastuzumab.

In some embodiments, the antigen recognition domain of the CAR specifically binds to an antigen present on pancreatic cancer. In some embodiments, the CAR targeting a pancreatic cancer associated antigen specifically binds to MICA/B, ADAM12, CA19.9, CFC1, EFNA4, EPCAM/EGP2, ICAM1, LILRB2, LRRC15, MSLN, MUC1, tMUC1, MUC5A, MUC16, MUC17, PSCA, PTK7, or SLC30A8. In some embodiments, the antigen recognition domain of said CAR comprises the H-CDRs, H- and L-CDRs, the VH, or a single chain of VH and VL of an antibody comprising PF-0664720, clivatuzumab, 4H11, 4H5, anetumumab, huDS6, sofituzumab, huM25, or RG7841.

In some embodiments, the antigen recognition domain of the CAR specifically binds to an antigen present on a peritoneal carconima cell. In some embodiments, the CAR targeting a peritoneal carconima associated antigen specifically binds to FOLR3.

In some embodiments, the antigen recognition domain of the CAR specifically binds to an antigen present on prostate cancer. In some embodiments, the CAR targeting a prostate cancer associated antigen specifically binds to MICA/B, ACPP, CD10, CD49f, CD133, EFNA4, OR51E2, PSCA, PSMA/FOLH1, PTK7, SLC30A4, SLC45A3, STEAP, TIM- 3, or TMEFF2/TENB2. In some embodiments, the antigen recognition domain of said CAR comprises the H-CDRs, H- and L-CDRs, the VH, or a single chain of VH and VL of an antibody comprising mirvetuximab, or J591 variant 1 or 2.

In some embodiments, the antigen recognition domain of the CAR specifically binds to an antigen present on a renal cancer cell. In some embodiments, the CAR targeting a renal cancer associated antigen specifically binds to MICA/B, CD3, CD70, ICAM1, KISS1R, LILRB2, QRFPR, SLC6A3, or TIM-3.

In some embodiments, the antigen recognition domain of the CAR specifically binds to an antigen present on a sarcoma. In some embodiments, the CAR targeting a sarcoma associated antigen specifically binds to MICA/B or LRRC15.

In some embodiments, the antigen recognition domain of the CAR specifically binds to an antigen present on a salivary gland cancer cell. In some embodiments, the CAR targeting a salivary gland cancer associated antigen specifically binds to HER2 or MICA/B.

In some embodiments, the antigen recognition domain of the CAR specifically binds to an antigen present on skin cancer. In some embodiments, the CAR targeting a skin cancer associated antigen specifically binds to CCR4, CD3, CD10, or ICAM1.

In some embodiments, the antigen recognition domain of the CAR specifically binds to an antigen present on a synovial sarcoma. In some embodiments, the CAR targeting a synovial sarcoma associated antigen specifically binds to CD99.

In some embodiments, an antibody specifically binds to an antigen present on a thyroid cancer/tumor cell. In some embodiments, the CAR targeting a thyroid cancer/tumor associated antigen specifically binds to MICA/B, CD10, c-MET, PTK7, or TSHR.

In some embodiments, an antibody specifically binds to an antigen present on a urothelial cancer cell. In some embodiments, the CAR targeting a urothelial cancer associated antigen specifically binds to MICA/B, CLDN6, EPCAM/EGP2, SIGLEC-15, TIM-3, or UPK2.

In some embodiments, the antigen recognition domain of the CAR specifically binds to an antigen present on uterine/endometrial cancer cell. In some embodiments, the CAR targeting a uterine/endometrial cancer associated antigen specifically binds to HER2, MICA/B, ALPP, ALPPL2, CCR1, CLDN6, EFNA4, EPHB2, FOLR1, LILRB2, LY6K, LYPD3, MUC1, MUC16, or PTK7. In some embodiments, the antigen recognition domain of said CAR comprises the H-CDRs, H- and L-CDRs, the VH, or a single chain of VH and VL of an antibody comprising PF-0664720, farletuzumab, sofituzumab, 4H11, or 4H5.

In various embodiments, the antigen recognition domain of the CAR specifically binds to a tumor antigen known to be associated with three or more cancer types (sometimes referred to as "pan-tumor antigen"). A non-limiting set of such pan-tumor antigens comprises at least ADAM12, ADGRE2/EMR2, CA19.9, CCR1, CCR4, CD3, CD10, CD49f, CD133, CEA/CECAM5, CLDN6, c-MET, EFNA4, EGFR, EGFRvIII, EPHA2, EPHB2, FOLR1, HER2, ICAM1, LILRB2, LRRC15, LY6K, LYPD3, MICA/B, MSLN, MUC1, tMUC1, MUC16, MUC17, PSCA, PTK7, TIM-3, TMEM238, and TNC as exemplified in Table 2.

TABLE 2

Exemplary Pan-Tumor Antigens and Associated Cancers

| Antigen | Associated Cancers |
| --- | --- |
| ADAM12 | Bone cancer, Breast cancer, Colorectal cancer, Head and Neck cancer, Lung cancer, Pancreatic cancer |
| ADGRE2/EMR2 | Breast cancer, Breast Lung cancer, Glioma, Lung cancer |
| CA19.9 | Colorectal cancer, Esophageal cancer, Liver cancer, Pancreatic cancer |
| CCR1 | Bone cancer, Liver cancer, Lung cancer, Ovarian cancer, Uterine/Endometrial cancer |
| CCR4 | Breast cancer, Lung cancer, Skin cancer |
| CD3 | Colorectal cancer, Head and Neck cancer, Liver cancer, Ovarian cancer, Renal cancer, Skin cancer |
| CD10 | Esophageal cancer, Prostate cancer, Skin cancer, Thyroid tumor |
| CD49f | Breast cancer, Colorectal cancer, Glioma, Prostate cancer |
| CD133 | Brain cancer, Breast cancer, Colorectal cancer, Glioma, Liver cancer, Lung cancer, Ovarian cancer, Prostate cancer |
| CEA/CECAM5 | Colorectal cancer, Esophageal cancer, Gastric/Stomach cancer, Liver cancer, Lung cancer |
| CLDN6 | Breast cancer, Ovarian cancer, Urothelial cancer, Uterine/Endometrial cancer |
| c-MET | Breast cancer, Colorectal cancer, Gastric/Stomach cancer, Head and Neck cancer, Kidney cancer, Non-Small Cell Lung cancer, Ovarian cancer, Thyroid tumor |
| EFNA4 | Bladder cancer, Breast cancer, Cervical cancer, Colorectal cancer, Esophageal cancer, Gastric/Stomach cancer, Head and Neck cancer, Lung cancer, Ovarian cancer, Pancreatic cancer, Prostate cancer, Uterine/Endometrial cancer |
| EGFR | Breast cancer, Glioma, Lung cancer, Non-Small Cell Lung cancer, Neuroblastoma |
| EGFRvIII | Brain cancer, Glioma, Lung cancer |
| EPCAM/EGP2 | Breast cancer, Breast Lung cancer, Gallbladder carcinoma, Liver cancer, Ovarian cancer, Urothelial cancer |
| EPHA2 | Bone cancer, Breast cancer, Glioma |
| EPHB2 | Colorectal cancer, Esophageal cancer, Gastric/Stomach cancer, Uterine/Endometrial cancer |
| FOLR1 | Lung cancer, Ovarian cancer, Uterine/Endometrial cancer |
| HER2 | Bladder cancer, Breast cancer, Breast Lung cancer, Colorectal cancer, Esophageal cancer, Gastric/Stomach cancer, Head and Neck cancer, Lung cancer, Ovarian cancer, Salivary Gland cancer |

TABLE 2-continued

Exemplary Pan-Tumor Antigens and Associated Cancers

| Antigen | Associated Cancers |
|---|---|
| ICAM1 | Breast cancer, Colorectal cancer, Liver cancer, Lung cancer, Pancreatic cancer, Renal cancer, Skin cancer |
| LILRB2 | Breast cancer, Lung cancer, Pancreatic cancer, Renal cancer, Uterine/Endometrial cancer |
| LRRC15 | Bone cancer, Breast cancer, Colorectal cancer, Head and Neck cancer, Lung cancer, Ovarian cancer, Pancreatic cancer, Renal cancer |
| LY6K | Bladder cancer, Cervical cancer, Head and Neck cancer, Lung cancer, Uterine/Endometrial cancer |
| LYPD3 | Bladder cancer, Breast cancer, Cervical cancer, Head and Neck cancer, Lung cancer, Uterine/Endometrial cancer |
| MICA/B | Bladder cancer, Bone cancer, Brain cancer, Breast cancer, Breast Lung cancer, Cervical cancer, Cholangiocarcinoma, Colorectal cancer, Esophageal cancer, Gastric (Stomach) cancer, Glioma, Head and Neck cancer, Kidney cancer, Liver cancer, Lung cancer, Mesothelioma, Metastatic cancer, Neuroblastoma, Non-Small Cell Lung cancer, Ovarian cancer, Pancreatic cancer, Prostate cancer, Renal cancer, Sarcoma, Salivary Gland cancer, Thyroid cancer, Urothelial cancer, Uterine/Endometrial cancer |
| MSLN | Lung cancer, Metastatic cancer, Mesothelioma, Ovarian cancer, Pancreatic cancer |
| MUC1 | Breast cancer, Cervical cancer, Lung cancer, Ovarian cancer, Pancreatic cancer, Uterine/Endometrial cancer |
| tMUC1 | Breast cancer, Cholangiocarcinoma, Pancreatic cancer |
| MUC16 | Cervical cancer, Lung cancer, Ovarian cancer, Pancreatic cancer, Uterine/Endometrial cancer |
| MUC17 | Colorectal cancer, Gastric (Stomach) cancer, Pancreatic cancer |
| PSCA | Gastric (Stomach) cancer, Pancreatic cancer, Prostate cancer |
| PTK7 | Bladder cancer, Breast cancer, Cervical cancer, Head and Neck cancer, Lung cancer, Ovarian cancer, Pancreatic cancer, Prostate cancer, Thyroid tumor, Uterine/Endometrial cancer |
| TIM-3 | Bladder cancer, Colorectal cancer, Gastric (Stomach) cancer, Liver cancer, Lung cancer, Prostate cancer, Renal cancer, Urothelial cancer |
| TMEM238 | Colorectal cancer, Esophageal cancer, Gastric (Stomach) cancer, Ovarian cancer |
| TNC | Bladder cancer, Brain cancer, Breast cancer, Head and Neck cancer |

Accordingly, in some embodiments, the antigen recognition domain of the CAR specifically binds to tumor associated ADAM12, wherein an effector cell comprising said CAR and a solid tumor targeting backbone as disclosed is useful for treating one or more cancers comprising at least bone cancer, breast cancer, colorectal cancer, head and neck cancer, lung cancer, or pancreatic cancer.

In some embodiments, the antigen recognition domain of the CAR specifically binds to tumor associated ADGRE2/EMR2, wherein an effector cell comprising said CAR and a solid tumor targeting backbone as disclosed is useful for treating one or more cancers comprising at least breast cancer, breast lung cancer, glioma, or lung cancer.

In some embodiments, the antigen recognition domain of the CAR specifically binds to tumor associated CA19.9, wherein an effector cell comprising said CAR and a solid tumor targeting backbone as disclosed is useful for treating one or more cancers comprising at least colorectal cancer, esophageal cancer, liver cancer, or pancreatic cancer.

In some embodiments, the antigen recognition domain of the CAR specifically binds to tumor associated CCR1, wherein an effector cell comprising said CAR and a solid tumor targeting backbone as disclosed is useful for treating one or more cancers comprising at least bone cancer, liver cancer, lung cancer, ovarian cancer, or uterine/endometrial cancer.

In some embodiments, the antigen recognition domain of the CAR specifically binds to tumor associated CCR4, wherein an effector cell comprising said CAR and a solid tumor targeting backbone as disclosed is useful for treating one or more cancers comprising at least breast cancer, lung cancer, or skin cancer.

In some embodiments, the antigen recognition domain of the CAR specifically binds to tumor associated CD3, wherein an effector cell comprising said CAR and a solid tumor targeting backbone as disclosed is useful for treating one or more cancers comprising at least colorectal cancer, head and neck cancer, liver cancer, ovarian cancer, renal cancer, or skin cancer.

In some embodiments, the antigen recognition domain of the CAR specifically binds to tumor associated CD10, wherein an effector cell comprising said CAR and a solid tumor targeting backbone as disclosed is useful for treating one or more cancers comprising at least esophageal cancer, prostate cancer, skin cancer, or thyroid tumor.

In some embodiments, the antigen recognition domain of the CAR specifically binds to tumor associated CD49f, wherein an effector cell comprising said CAR and a solid tumor targeting backbone as disclosed is useful for treating one or more cancers comprising at least breast cancer, colorectal cancer, glioma, or prostate cancer.

In some embodiments, the antigen recognition domain of the CAR specifically binds to tumor associated CD133, wherein an effector cell comprising said CAR and a solid tumor targeting backbone as disclosed is useful for treating one or more cancers comprising at least brain cancer, breast cancer, colorectal cancer, glioma, liver cancer, lung cancer, ovarian cancer, or prostate cancer.

In some embodiments, the antigen recognition domain of the CAR specifically binds to tumor associated CEA/CECAM5, wherein an effector cell comprising said CAR and a solid tumor targeting backbone as disclosed is useful for treating one or more cancers comprising at least colorectal cancer, esophageal cancer, gastric/stomach cancer, liver cancer, or lung cancer.

In some embodiments, the antigen recognition domain of the CAR specifically binds to tumor associated CLDN6, wherein an effector cell comprising said CAR and a solid tumor targeting backbone as disclosed is useful for treating one or more cancers comprising at least breast cancer, ovarian cancer, urothelial cancer, or uterine/endometrial cancer.

In some embodiments, the antigen recognition domain of the CAR specifically binds to tumor associated c-MET, wherein an effector cell comprising said CAR and a solid tumor targeting backbone as disclosed is useful for treating one or more cancers comprising at least breast cancer, colorectal cancer, gastric/stomach cancer, head and neck cancer, kidney cancer, non-small cell lung cancer, ovarian cancer, or thyroid tumor.

In some embodiments, the antigen recognition domain of the CAR specifically binds to tumor associated EFNA4, wherein an effector cell comprising said CAR and a solid tumor targeting backbone as disclosed is useful for treating one or more cancers comprising at least bladder cancer, breast cancer, cervical cancer, colorectal cancer, esophageal cancer, gastric/stomach cancer, head and neck cancer, lung cancer, ovarian cancer, pancreatic cancer, prostate cancer, or uterine/endometrial cancer.

In some embodiments, the antigen recognition domain of the CAR specifically binds to tumor associated EGFR, wherein an effector cell comprising said CAR and a solid tumor targeting backbone as disclosed is useful for treating one or more cancers comprising at least breast cancer, glioma, lung cancer, non-small cell lung cancer, or neuroblastoma.

In some embodiments, the antigen recognition domain of the CAR specifically binds to tumor associated EGFRvIII, wherein an effector cell comprising said CAR and a solid tumor targeting backbone as disclosed is useful for treating one or more cancers comprising at least brain cancer, glioma, or lung cancer.

In some embodiments, the antigen recognition domain of the CAR specifically binds to tumor associated EPCAM/EGP2, wherein an effector cell comprising said CAR and a solid tumor targeting backbone as disclosed is useful for treating one or more cancers comprising at least breast cancer, breast lung cancer, gallbladder carcinoma, liver cancer, ovarian cancer, or urothelial cancer.

In some embodiments, the antigen recognition domain of the CAR specifically binds to tumor associated EPHA2, wherein an effector cell comprising said CAR and a solid tumor targeting backbone as disclosed is useful for treating one or more cancers comprising at least bone cancer, breast cancer, or glioma.

In some embodiments, the antigen recognition domain of the CAR specifically binds to tumor associated EPHB2, wherein an effector cell comprising said CAR and a solid tumor targeting backbone as disclosed is useful for treating one or more cancers comprising at least colorectal cancer, esophageal cancer, gastric/stomach cancer, or uterine/endometrial cancer.

In some embodiments, the antigen recognition domain of the CAR specifically binds to tumor associated FOLR1, wherein an effector cell comprising said CAR and a solid tumor targeting backbone as disclosed is useful for treating one or more cancers comprising at least lung cancer, ovarian cancer, or uterine/endometrial cancer.

In some embodiments, the antigen recognition domain of the CAR specifically binds to tumor associated HER2, wherein an effector cell comprising said CAR and a solid tumor targeting backbone as disclosed is useful for treating one or more cancers comprising at least bladder cancer, breast cancer, breast lung cancer, colorectal cancer, esophageal cancer, gastric/stomach cancer, head and neck cancer, lung cancer, ovarian cancer, or salivary gland cancer.

In some embodiments, the antigen recognition domain of the CAR specifically binds to tumor associated ICAM1, wherein an effector cell comprising said CAR and a solid tumor targeting backbone as disclosed is useful for treating one or more cancers comprising at least breast cancer, colorectal cancer, liver cancer, lung cancer, pancreatic cancer, renal cancer, or skin cancer.

In some embodiments, the antigen recognition domain of the CAR specifically binds to tumor associated LILRB2, wherein an effector cell comprising said CAR and a solid tumor targeting backbone as disclosed is useful for treating one or more cancers comprising at least breast cancer, lung cancer, pancreatic cancer, renal cancer, or uterine/endometrial cancer.

In some embodiments, the antigen recognition domain of the CAR specifically binds to tumor associated LRRC15, wherein an effector cell comprising said CAR and a solid tumor targeting backbone as disclosed is useful for treating one or more cancers comprising at least bone cancer, breast cancer, colorectal cancer, head and neck cancer, lung cancer, ovarian cancer, pancreatic cancer, or renal cancer.

In some embodiments, the antigen recognition domain of the CAR specifically binds to tumor associated LY6K, wherein an effector cell comprising said CAR and a solid tumor targeting backbone as disclosed is useful for treating one or more cancers comprising at least bladder cancer, cervical cancer, head and neck cancer, lung cancer, or uterine/endometrial cancer.

In some embodiments, the antigen recognition domain of the CAR specifically binds to tumor associated LYPD3, wherein an effector cell comprising said CAR and a solid tumor targeting backbone as disclosed is useful for treating one or more cancers comprising at least bladder cancer, breast cancer, cervical cancer, head and neck cancer, lung cancer, or uterine/endometrial cancer.

In some embodiments, the antigen recognition domain of the CAR specifically binds to tumor associated MICA/B, wherein an effector cell comprising said CAR and a solid tumor targeting backbone as disclosed is useful for treating one or more cancers comprising at least bladder cancer, bone cancer, brain cancer, breast cancer, breast lung cancer, cervical cancer, cholangiocarcinoma, colorectal cancer, esophageal cancer, gastric/stomach cancer, glioma, head and neck cancer, kidney cancer, liver cancer, lung cancer, mesothelioma, metastatic cancer, neuroblastoma, non-small cell lung cancer, ovarian cancer, pancreatic cancer, prostate cancer, renal cancer, sarcoma, salivary gland cancer, thyroid cancer, urothelial cancer, or uterine/endometrial cancer.

In some embodiments, the antigen recognition domain of the CAR specifically binds to tumor associated MSLN, wherein an effector cell comprising said CAR and a solid tumor targeting backbone as disclosed is useful for treating one or more cancers comprising at least lung cancer, metastatic cancer, mesothelioma, ovarian cancer, or pancreatic cancer.

In some embodiments, the antigen recognition domain of the CAR specifically binds to tumor associated MUC1, wherein an effector cell comprising said CAR and a solid tumor targeting backbone as disclosed is useful for treating one or more cancers comprising at least breast cancer, cervical cancer, lung cancer, ovarian cancer, pancreatic cancer, or uterine/endometrial cancer.

In some embodiments, the antigen recognition domain of the CAR specifically binds to tumor associated tMUC1, wherein an effector cell comprising said CAR and a solid tumor targeting backbone as disclosed is useful for treating one or more cancers comprising at least breast cancer, cholangiocarcinoma, or pancreatic cancer.

In some embodiments, the antigen recognition domain of the CAR specifically binds to tumor associated MUC16, wherein an effector cell comprising said CAR and a solid tumor targeting backbone as disclosed is useful for treating one or more cancers comprising at least cervical cancer, lung cancer, ovarian cancer, pancreatic cancer, or uterine/endometrial cancer.

In some embodiments, the antigen recognition domain of the CAR specifically binds to tumor associated MUC17, wherein an effector cell comprising said CAR and a solid tumor targeting backbone as disclosed is useful for treating one or more cancers comprising at least colorectal cancer, gastric/stomach cancer, or pancreatic cancer.

In some embodiments, the antigen recognition domain of the CAR specifically binds to tumor associated PSCA, wherein an effector cell comprising said CAR and a solid tumor targeting backbone as disclosed is useful for treating one or more cancers comprising at least gastric/stomach cancer, pancreatic cancer, or prostate cancer.

In some embodiments, the antigen recognition domain of the CAR specifically binds to tumor associated PTK7, wherein an effector cell comprising said CAR and a solid tumor targeting backbone as disclosed is useful for treating one or more cancers comprising at least bladder cancer, breast cancer, cervical cancer, head and neck cancer, lung cancer, ovarian cancer, pancreatic cancer, prostate cancer, thyroid tumor, or uterine/endometrial cancer.

In some embodiments, the antigen recognition domain of the CAR specifically binds to tumor associated TIM-3, wherein an effector cell comprising said CAR and a solid tumor targeting backbone as disclosed is useful for treating one or more cancers comprising at least bladder cancer, colorectal cancer, gastric/stomach cancer, liver cancer, lung cancer, prostate cancer, renal cancer, or urothelial cancer.

In some embodiments, the antigen recognition domain of the CAR specifically binds to tumor associated TMEM238, wherein an effector cell comprising said CAR and a solid tumor targeting backbone as disclosed is useful for treating one or more cancers comprising at least colorectal cancer, esophageal cancer, gastric/stomach cancer, or ovarian cancer.

In some embodiments, the antigen recognition domain of the CAR specifically binds to tumor associated TNC, wherein an effector cell comprising said CAR and a solid tumor targeting backbone as disclosed is useful for treating one or more cancers comprising at least bladder cancer, brain cancer, breast cancer, or head and neck cancer.

In various embodiments, the CARs applicable to the cells described herein include at least an ectodomain, a transmembrane domain, and an endodomain. In some embodiments, the endodomain of the CAR comprises at least one signaling domain that is activated upon antigen binding. In some embodiments of the CAR endodomain, one or more co-stimulation domains (oftentimes referred to as "additional signaling domain(s)") is further included for optimized functionality. Exemplary signal transducing proteins suitable for a CAR design include, but are not limited to, 2B4, 4-1BB, CD16, CD2, CD28, CD28H, CD3ζ/1XX (i.e., CD3ζ or CD3ζ/1XX), DAP10, DAP12, DNAM1, FcERIγ, IL21R, IL-2Rβ (IL-15Rβ), IL-2Rγ, IL-7R, KIR2DS2, NKG2D), NKp30, NKp44, NKp46, CS1 and CD8. The description of the exemplary signal transducing proteins, including transmembrane and cytoplasmic sequences of the proteins are provided below, and further in Table 3A.

TABLE 3A

| | Protein name | UniProtKB Accession No. | Transmembrane Sequence | Cytoplasmic Sequence |
|---|---|---|---|---|
| 2B4 | Natural killer cell receptor 2B4 | Q9BZW8 | FL VIIVIL SALFLGTL ACFCV (SEQ ID NO: 32) | WRRKRKEKQSETSPKEFLTIYEDVK DLKTRRNHEQEQTFPGGGSTIYSMI QSQSSAPTSQEPAYTLYSLIQPSRKS GSRKRNHSPSFNSTIYEVIGKSQPKA QNPARLSRKELENFDVYS (SEQ ID NO: 54) |
| 4-1BB | Tumor necrosis factor receptor superfamily member 9 | Q07011 | IISFFLALTSTALLFL LFFLTLRFSVV (SEQ ID NO: 33) | KRGRKKLLYIFKQPFMRPVQTTQEE DGCSCRFPEEEEGGCEL (SEQ ID NO: 55) |
| CD16 | IgG Fc region Receptor III-A | P08637 | VSFCLVMVLLFAVD TGLYFSVKTNIRSST RD (SEQ ID NO: 34) | WKDHKFKWRKDPQDK (SEQ ID NO: 56) |
| CD2 | T-cell surface antigen CD2 | P06729 | IYLIIGICGGGSLLM VFVALLVFYITKRK KQRSRRNDEELETR AHRVATEERGRKPH QIPASTPQNPATSQH PPPPPGHRSQAPSHR PPPPGHRVQ (SEQ ID NO: 35) | HQPQKRPPAPSGTQVHQQKGPPLPR PRVQPKPPHGAAENSLSPSSN (SEQ ID NO: 57) |
| CD28 | T-cell-specific surface | P10747 | FWVLVVVGGVLAC YSLLVTVAFIIFWV (SEQ ID NO: 36) | RSKRSRLLHSDYMNMTPRRPGPTR KHYQPY APPRDFAAYRS (SEQ ID NO: 58) |

TABLE 3A-continued

| | Protein name | UniProtKB Accession No. | Transmembrane Sequence | Cytoplasmic Sequence |
|---|---|---|---|---|
| | glycoprotein CD28 | | | |
| CD28H | Transmembrane and immunoglobulin domain-containing protein 2 | Q96BF3 | FLFVLLGVGSMGVA AIVWGAW (SEQ ID NO: 37) | FWGRRSCQQRDSGNSPGNAFYSNV LYRPRGAPKKSEDCSGEGKDQRGQS IYSTSFPQPAPRQPHLASRPCPSPRP CPSPRPGHPVSMRVSPRPSPTQQP RPKGFPKVGEE (SEQ ID NO: 59) |
| CD3ζ/1 XX | T-cell surface glycoprotein CD3 zeta chain | P20963 | LCYLLDGILFIYGVI LTALFL (SEQ ID NO: 38) | RVKFSRSADAPAYQQGQNQLYNEL NLGRREEYDVLDKRRGRDPEMGG KPQRRKNPQEGLYNELQKDKMAE AYSEIGMKGERRRGKGHDGLYQGL STATKDTYDALHMQALPPR (SEQ ID NO: 60; CD3ζ) Or RVKFSRSADAPAYQQGQNQLYNEL NLGRREEYDVLDKRRGRDPEMGG KPRRKNPQEGLFNELQKDKMAEAF SEIGMKGERRRGKGHDGLFQGLST ATKDTFDALHMQALPPR (SEQ ID NO: 61; containing 2 mutations in ITAM1; CD3ζ1XX) |
| DAP10 | Hematopoietic cell signal transducer | Q9UBK5 | LLAGLVAADAVASL LIVGAVF (SEQ ID NO: 39) | LCARPRRSPAQEDGKVYINMPGRG (SEQ ID NO: 62) |
| DAP12 | TYRO protein tyrosine kinase-binding protein | O43914 | GVLAGIVMGDLVLT VLIALAV (SEQ ID NO: 40) | YFLGRLVPRGRGAAEAATRKQRITE TESPYQELQGQRSDVYSDLNTQRPY YK (SEQ ID NO: 63) |
| DNAM1 | CD226 antigen | Q15762 | GGTVLLLLFVISITTI IVIFL (SEQ ID NO: 41) | NRRRRRERRDLFTESWDTQKAPNN YRSPISTSQPTNQSMDDTREDIYVN YPTFSRRPKTRV (SEQ ID NO: 64) |
| FCERIγ | High affinity immunoglobulin epsilon receptor subunit gamma | P30273 | CYILDAILFLYGIVL TLLYC (SEQ ID NO: 42) | RLKIQVRKAAITSYEKSDGVYTGLS TRNQETYETLKHEKPPQ (SEQ ID NO: 65) |
| IL-21R | Interleukin-21 receptor | Q9HBE5 | GWNPHLLLLLLLVI VFIPAFW (SEQ ID NO: 43) | SLKTHPLWRLWKKIWAVPSPERFF MPLYKGCSGDFKKWVGAPFTGSSL ELGPWSPEVPSTLEVYSCHPPRSPA KRLQLTELQEPAELVESDGVPKPSF WPTAQNSGGSAYSEERDRPYGLVSI DTVTVLDAEGPCTWPCSCEDDGYP ALDLDAGLEPSPGLEDPLLDAGTTV LSCGCVSAGSPGLGGPLGSLLDRLK PPLADGEDWAGGLPWGGRSPGGVS ESEAGSPLAGLDMDTFDSGFVGSDC SSPVECDFTSPGDEGPPRSYLRQWV VIPPPLSSPGPQAS (SEQ ID NO: 66) |
| IL-2Rβ (IL-15Rβ) | Interleukin-2 receptor subunit beta | P14784 | IPWLGHLLVGLSGA FGFIIL VYLLI (SEQ ID NO: 44) | NCRNTGPWLKKVLKCNTPDPSKFF SQLSSEHGGDVQKWLSSPFPSSSFSP GGLAPEISPLEVLERDKVTQLLLQQ DKVPEPASLSSNHSLTSCFTNQGYF FFHLPDALEIEACQVYFTYDPYSEE DPDEGVAGAPTGSSPQPLQPLSGED DAYCTFPSRDDLLLFSPSLLGGPSPP STAPGGSGAGEERMPPSLQERVPRD WDPQPLGPPPTPGVPDLVDFQPPPEL VLREAGEEVPDAGPREGVSFPWSRP PGQGEFRALNARLPLNTDAYLSLQE LQGQDPTHLV (SEQ ID NO: 67) |

TABLE 3A-continued

| Protein name | | UniProtKB Accession No. | Transmembrane Sequence | Cytoplasmic Sequence |
|---|---|---|---|---|
| IL-2Rγ | Cytokine receptor common subunit gamma | P31785 | VVISVGSMGLIISLL CVYFWL (SEQ ID NO: 45) | ERTMPRIPTLKNLEDLVTEYHGNFS AWSGVSKGLAESLQPDYSERLCLV SEIPPKGGALGEGPGASPCNQHSPY WAPPCYTLKPET (SEQ ID NO: 68) |
| IL-7R | Interleukin-7 receptor subunit alpha | P16871 | PILLTISILSFFSVALL VILACVLW (SEQ ID NO: 46) | KKRIKPIVWPSLPDHKKTLEHLCKK PRKNLNVSFNPESFLDCQIHRVDDI QARDEVEGFLQDTFPQQLEESEKQR LGGDVQSPNCPSEDVVITPESFGRD SSLTCLAGNVSACDAPILSSSRSLDC RESGKNGPHVYQDLLLSLGTTNSTL PPPPFSLQSGILTLNPVAQGQPILTSLG SNQEEAYVTMSSFYQNQ (SEQ ID NO: 69) |
| KIR2DS2 | Killer cell immunoglobulin-like receptor 2DS2 | P43631 | VLIGTSVVKIPFTILL FFLL (SEQ ID NO: 47) | HRWCSNKKNAAVMDQEPAGNRTV NSEDSDEQDHQEVSYA (SEQ ID NO: 70) |
| NKG2D | NKG-D type II integral membrane protein | P26718 | PFFFCCFIAVAMGIR FIIMVA (SEQ ID NO: 48) | IWSAVFLNSLFNQEVQIPLTESYCGP CPKNWICYKNNCYQFFDESKNWYE SQASCMSQNASLLKVYSKEDQDLL KLVKSYHWMGLVHIPTNGSWQWE DGSILSPNLLTIIEMQKGDCALYASS FKGYIENCSTPNTYICMQRTV (SEQ ID NO: 71) |
| NKp30 | Natural cytotoxicity triggering receptor 3 | O14931 | AGTVLLLRAGFYAV SFLSVAV (SEQ ID NO: 49) | GSTVYYQGKCLTWKGPRRQLPAVV PAPLPPPCGSSAHLLPPVPGG (SEQ ID NO: 72) |
| NKp44 | Natural cytotoxicity triggering receptor 2 | O95944 | LVPVFCGLLVAKSL VLSALLV (SEQ ID NO: 50) | WWGDIWWKTMMELRSLDTQKAT CHLQQVTDLPWTSVSSPVEREILYH TVARTKISDDDDEHTL (SEQ ID NO: 73) |
| NKp46 | Natural cytotoxicity triggering receptor 1 | O76036 | GLAFLVLVALVWFL VEDWLS (SEQ ID NO: 51) | RKRTRERASRASTWEGRRRLNTQT L (SEQ ID NO: 74) |
| CS1 | SLAM family member 7 | Q9NQ25 | VLLCLLLVPLLLSLF VLGLFL (SEQ ID NO: 52) | WFLKRERQEEYIEEKKRVDICRETP NICPHSGENTEYDTIPHTNRTILKED PANTVYSTVEIPKKMENPHSLLTMP DTPRLFAYENVI (SEQ ID NO: 75) |
| CD8 | T-cell surface glycoprotein CD8 alpha chain | P01732 | IYIWAPLAGTC (SEQ ID NO: 53) | GVLLLSLVITLYCNHRNRRRVCKCP RPVVKSGDKPSLSARYV (SEQ ID NO: 76) |

In some embodiments of the CAR applicable to the cells provided herein, the endodomain of the CAR comprises at least a first signaling domain having an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ IL21R, IL-2Rβ (IL-15Rβ), IL-2Rγ, IL-7R, KIR2DS2, NKG2D, NKp30, NKp44, NKp46, CS1, or CD8, represented by SEQ ID NOs: 54-76, respectively. In some embodiments, the first signaling domain comprises an amino acid sequence of at least 90% identity to any of SEQ ID NOs: 54-76. In some embodiments, the first signaling domain comprises an amino acid sequence of at least 95% identity to any of SEQ ID NOs: 54-76. In some embodiments, the first signaling domain comprises the amino acid sequence of any of SEQ ID NOs: 54-76. In some embodiments, the signaling domain of the CAR comprises only a portion of the cytoplasmic domain of 2B4, 4-1BB, CD16, CD2, CD28, CD28H, CD3ζ, CD3ζ1XX, DAP10, DAP12, DNAM1, FcERIγ IL21R, IL-2Rβ (IL-15Rβ), IL-2Rγ, IL-7R, KIR2DS2, NKG2D, NKp30, NKp44, NKp46, CS1, or CD8. In some embodiments, the portion of the cytoplasmic domain selected for the CAR signaling domain comprises an amino acid sequence that has at least about 85%, about 90%, about 95%, about 96%, about 97%, about 98%, or about 99% identity to an ITAM (immunoreceptor tyrosine-based activation motif), a YxxM motif, a TxYxxV/I motif, FcRγ, hemi-ITAM, and/or an ITT-like motif.

In some embodiments of the CAR as provided, the endodomain of the CAR comprising a first signaling domain further comprises a second signaling domain comprising an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ IL21R, IL-2Rβ (IL-15Rβ), IL-2Rγ, IL-7R, KIR2DS2, NKG2D, NKp30, NKp44, NKp46, CS1 or CD8, represented by SEQ ID NOs: 54-76, respectively, wherein the second signaling domain is different from the first signaling domain. In some embodiments, the second signaling domain comprises an amino acid sequence of at least 90% identity to any of SEQ ID NOs: 54-76. In some embodiments, the second signaling domain comprises an amino acid sequence of at least 95% identity to any of SEQ ID NOs: 54-76. In some embodiments, the second signaling domain comprises the amino acid sequence of any of SEQ ID NOs: 54-76.

In some embodiments of the CAR as provided, the endodomain of the CAR comprising a first and a second signaling domain further comprises a third signaling domain comprising an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ, IL21R, IL-2Rβ (IL-15Rβ), IL-2Rγ, IL-7R, KIR2DS2, NKG2D, NKp30, NKp44, NKp46, CS1, or CD8, represented by SEQ ID NOs: 54-76, respectively, wherein the third signaling domain is different from the first and the second signaling domains. In some embodiments, the third signaling domain comprises an amino acid sequence of at least 90% identity to any of SEQ ID NOs: 54-76. In some embodiments, the third signaling domain comprises an amino acid sequence of at least 95% identity to any of SEQ ID NOs: 54-76. In some embodiments, the third signaling domain comprises the amino acid sequence of any of SEQ ID NOs: 54-76. In some embodiments, signal transducing proteins suitable for designing a signaling domain of a CAR endodomain further comprise CD27, OX40, ICOS, PD-1, LAG-3, BTLA, or CTLA-4.

In some exemplary embodiments of a CAR having an endodomain comprised of only one signaling domain, said endodomain comprises an amino acid sequence that has at least about 85%, about 90%, about 95%, about 96%, about 97%, about 98%, or about 99% identity to the cytoplasmic domain or a portion thereof, of a protein including, but not limited to, DNAM1, CD28H, KIR2DS2, DAP12 or DAP10.

In some exemplary embodiments of a CAR having an endodomain comprised of two different signaling domains, said endodomain comprises fused cytoplasmic domains, or portions thereof, in a form including, but not limited to, 2B4-CD3ζ/1XX (i.e., 2B4-CD3ζ or 2B4-CD3ζ1XX; same below), 2B4-DNAM1, 2B4-FcERIγ, 2B4-DAP10, CD16-DNAM1, CD16-DAP10, CD16-DAP12, CD2-CD3ζ1XX, CD2-DNAM1, CD2-FcERIγ, CD2-DAP10, CD28-DNAM1, CD28-FcERIγ, CD28-DAP10, CD28-DAP12, CD28-CD3ζ/1XX, CD28H-CD3/1XX, DAP10-CD3ζ/1XX, DAP10-DAP12, DAP12-CD3ζ/1XX, DAP12-DAP10, DNAM1-CD3/1XX, KIR2DS2-CD3ζ/1XX, KIR2DS2-DAP10, KIR2DS2-2B4, or NKp46-2B4.

In some exemplary embodiments of a CAR having an endodomain comprised of three different signaling domains, said endodomain comprises fused cytoplasmic domains, or portions thereof, in a form including, but not limited to, 2B4-DAP10-CD3ζ/1XX, 2B4-IL21R-DAP10, 2B4-IL2RB-DAP10, 2B4-IL2RB-CD3ζ/1XX, 2B4-41BB-DAP10, CD16-2B4-DAP10, or KIR2DS2-2B4-CD3ζ/1XX.

In some embodiments, the transmembrane domain of the CAR comprises an amino acid sequence that has at least about 85%, about 90%, about 95%, about 96%, about 97%, about 98%, or about 99% identity to a full length or a portion of the transmembrane region of CD2, CD3δ, CD38, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide. In some other embodiments, the transmembrane domain of a CAR comprises an amino acid sequence that has at least about 85%, about 90%, about 95%, about 96%, about 97%, about 98%, or about 99% identity to a full length or a portion of the transmembrane region of (a) 2B4, CD16, CD2, CD28, CD28H, CD3ζ, DAP10, DAP12, DNAM1, FcERIγ, KIR2DS2, NKG2D, NKp30, NKp44, NKp46, CS1, or CD8, represented by SEQ ID NOs: 32, 34-42, 47-53, respectively; or of (b) 2B4, CD28, CD28H, DAP10, DNAM1, KIR2DS2, and NKG2D. In some embodiments, the transmembrane domain comprises an amino acid sequence of at least about 90% identity to any of SEQ ID NOs: 32, 34-42, 47-53. In some embodiments, the transmembrane domain comprises an amino acid sequence of at least about 95% identity to any of SEQ ID NOs: 32, 34-42, 47-53. In some embodiments, the transmembrane domain comprises the amino acid sequence of any of SEQ ID NOs: 32, 34-42, 47-53. In some embodiments of the CAR, the transmembrane domain and its immediately linked signaling domain are from the same protein. In some other embodiments of the CAR, the transmembrane domain and the signaling domain that is immediately linked are from different proteins.

Non-limiting examples of CAR constructs comprising a transmembrane domain (TM) and an endodomain (labelled as: TM-(endodomain)) are shown in Table 3B. In general, the illustrated CAR constructs each comprise a transmembrane domain, and an endodomain comprising one or more signaling domains derived from the cytoplasmic region of one or more signal transducing proteins. In general, a transmembrane domain is a three-dimensional protein structure which is thermodynamically stable in a membrane such as the phospholipid bilayer of a biological membrane (e.g., a membrane of a cell or cell vesicle). Thus, in some embodiments, the transmembrane domain of the CAR applicable to the cells provided herein comprises a single alpha helix, a stable complex of several transmembrane alpha helices, a transmembrane beta barrel, a beta-helix of gramicidin A, or any combination thereof. In various embodiments, the transmembrane domain of the CAR comprises all or a portion of a "transmembrane protein" or "membrane protein" that is within the membrane. As used herein, a "transmembrane protein" or "membrane protein" is a protein located at and/or within a membrane. Examples of transmembrane proteins that are suitable for providing a transmembrane domain comprised in a CAR according to some embodiments of the invention include, but are not limited to, a receptor, a ligand, an immunoglobulin, a glycophorin, or any combination thereof. In some embodiments, the transmembrane domain comprised in the CAR comprises all or a portion of a transmembrane domain of 2B4, 4-1BB, BTLA, CD2, CD3δ, CD3ε, CD3γ, CD3ζ, CD4, CD8, CD8a, CD8b, CD16, CD27, CD28, CD28H, CD40, CD84, CD166, CS1, CTLA-4, DNAM1, DAP10, DAP12, FcERIγ, ICOS, ICAM-1, IL7, IL12, IL15, KIR2DL4, KIR2DS1, KIR2DS2, LAG3, PD1, NKp30, NKp44, NKp46, NKG2C, NKG2D, OX40, T cell receptor polypeptide (such as TCRα and/or TCRβ), a nicotinic acetylcholine receptor, a GABA receptor, or any combination thereof.

In some embodiments, one or more signaling domains comprised in the CAR endodomain are derived from the same or a different protein from which the TM is derived. As shown in Table 3B, the portion representing the transmembrane domain of the CAR is underlined, the domains comprised in the endodomain appear in parenthesis, "( )", with each of the TM and signaling domains designated by the name of the signal transducing protein from which the domain sequence is derived. In embodiments, the amino acid sequence of each TM or signaling domains may be of about 85%, about 90%, about 95%, about 96%, about 97%, about 98%, or about 99% identity to a full length or a portion of the corresponding transmembrane or cytoplasmic regions of the designated signal transducing protein. Exemplary CAR constructs comprising a transmembrane domain and an endodomain as provided herein include, but are not limited to: NKG2D-(2B4-IL2RB-CD3ζ), CD8-(41BB-CD3ζ1XX), CD28-(CD28-2B4-CD3ζ), CD28-(CD28-CD3ζ1XX), CD28H-(CD28H-CD3ζ), DNAM1-(DNAM1-CD3ζ), DAP10-(DAP10-CD3ζ), KIR2DS2-(KIR2DS2-CD3ζ), KIR2DS2-(KIR2DS2-DAP10), KIR2DS2-(KIR2DS2-2B4), CD16-(CD16-2B4-DAP10), CD16-(CD16-DNAM1), NKp46-(NKp46-2B4), NKp46-(NKp46-2B4-CD3ζ), NKp46-(NKp46-CD2-DAP10), CD2-(CD2-CD3ζ), 2B4-(2B4-CD3ζ), 2B4-(2B4-FcERIγ), and CS1-(CS1-CD3ζ). In some embodiments, each of the above exemplary CAR constructs comprising a transmembrane domain and an endodomain comprises an amino acid sequence of at least about 85%, about 90%, about 95%, about 96%, about 97%, about 98%, about 99%, or 100% identity to a sequence represented by each of SEQ ID NOs: 77-95 in Table 3B. In some embodiments, the CAR comprises an amino acid sequence of at least about 90% identity to any of SEQ ID NOs: 77-95. In some embodiments, the CAR comprises an amino acid sequence of at least about 95% identity to any of SEQ ID NOs: 77-95. In some embodiments, the CAR comprises the amino acid sequence of any of SEQ ID NOs: 77-95. The illustrative sequence for each construct provided in Table 3B has text formatted to match the formatting of the corresponding region in the illustration at left of the sequence (i.e., underlined, normal, or bolded text). For most of the illustrative constructs of Table 3B3, the TM is the first sequence region; however, constructs may include an extracellular domain preceeding the TM (see, e.g., Construct 7 in Table 3B3), and may be from the same or a different protein as the TM. In some embodiments, two or more signaling domains comprised in the CAR endodomain may be separated by one or more additional sequences, such as a spacer or a linker.

TABLE 3B

| Construct | Sequence Domains TM-(endodomain) | Illustrative Sequence | SEQ ID NO: |
|---|---|---|---|
| 1 | NKG2D-(2B4-IL2Rβ-CD3ζ) | SNLFVASWIAVMIIFRIGMAVAIFCCFFFPSWRRKRKEK QSETSPKEFLTIYEDVKDLKTRRNHEQEQTFPGGGSTI YSMIQSQSSAPTSQEPAYTLYSLIQPSRKSGSRKRNHSP SFNSTIYEVIGKSQPKAQNPARLSRKELENFDVYSNCR NTGPWLKKVLKCNTPDPSKFFSQLSSEHGGDVQKWLSSPF PSSSFSPGGLAPEISPLEVLERDKVTQLLLQQDKVPEPAS LSSNHSLTSCFTNQGYFFFHLPDALEIEACQVYFTYDPYS EEDPDEGVAGAPTGSSPQPLQPLSGEDDAYCTFPSRDDLL LFSPSLLGGPSPPSTAPGGSGAGEERMPPSLQERVPRDWD PQPLGPPTPGVPDLVDFQPPPELVLREAGEEVPDAGPREG VSFPWSRPPGQGEFRALNARLPLNTDAYLSLQELQGQDP THLVRVKFSRSADAPAYQQGQNQLYNELNLGRRREEY DVLDKRRGRDPEMGGKPRRKNPQEGLYNELQKDKM AEAYSEIGMKGERRRGKGHDGLYQGLSTATKDTYDA LHMQALPPR | 77 |
| 2 | CD8-(41BB-CD3ζ1XX) | IYIWAPLAGTCGVLLLSLVITLYCKRGRKKLLYIFKQP FMRPVQTTQEEDGCSCRFPEEEEGGCELRVKFSRSADA PAYQQGQNQLYNELNLGRREEYDVLDKRRGRDPEMGG KPRRKNPQEGLFNELQKDKMAEAFSEIGMKGERRRGKG HDGLFQGLSTATKDTFDALHMQALPPR | 78 |
| 3 | CD28-(CD28-2B4-CD3ζ) | FWVLVVVGGVLACYSLLVTVAFIIFWVRSKRSRLLHSD YMNMTPRRPGPTRKHYQPYAPPRDFAAYRSWRRKRKEK QSETSPKEFLTIYEDVKDLKTRRNHEQEQTFPGGGSTI YSMIQSQSSAPTSQEPAYTLYSLIQPSRKSGSRKRNHSP SFNSTIYEVIGKSQPKAQNPARLSRKELENFDVYSRVK FSRSADAPAYQQGQNQLYNELNLGRREEYDVLDKRRGR DPEMGGKPRRKNPQEGLYNELQKDKMAEAYSEIGMKGE RRRGKGHDGLYQGLSTATKDTYDALHMQALPPR | 79 |
| 4 | CD28-(CD28-CD3ζ1XX) | FWVLVVVGGVLACYSLLVTVAFIIFWVRSKRSRLLHSDY MNMTPRRPGPTRKHYQPYAPPRDFAAYRSRVKFSRSAD APAYQQGQNQLYNELNLGRREEYDVLDKRRGRDPE MGGKPRRKNPQEGLFNELQKDKMAEAFSEIGMKGE RRRGKGHDGLFQGLSTATKDTFDALHMQALPPR | 80 |
| 5 | CD28H-(CD28H-CD3ζ) | FLFVLLGVGSMGVAAIVWGAWFWGRRSCQQRDSGNSP GNAFYSNVLYRPRGAPKKSEDCSGEGKDQRGQSIYSTSF PQPAPRQPHLASRPCPSPRPCPSPRPGHPVSMVRVSPRP | 81 |

TABLE 3B-continued

| Construct | Sequence Domains TM-(endodomain) | Illustrative Sequence | SEQ ID NO: |
|---|---|---|---|
| | | SPTQQPRPKGFPKVGEERVKFSRSADAPAYQQGQNQLYN ELNLGRREEYDVLDKRRGRDPEMGGKPRRKNPQEGL YNELQKDKMAEAYSEIGMKGERRRGKGHDGLYQGL STATKDTYDALHMQALPPR | |
| 6 | DNAM1-(DNAM1-CD3ζ) | GGTVLLLLFVISITTIIVIFLNRRRRERRDLFTESWD TQKAPNNYRSPISTSQPTNQSMDDTREDIYVNYPTFSR RPKTRVRVKFSRSADAPAYQQGQNQLYNELNLGRREEY DVLDKRRGRDPEMGGKPRRKNPQEGLYNELQKDKMAEA YSEIGMKGERRRGKGHDGLYQGLSTATKDTYDALH MQALPPR | 82 |
| 7 | DAP10-(DAP10-CD3ζ) | TTPGERSSLPAFYPGTSGSCSGCGSLSLPLLAGLVAADAV ASLLIVGAVFLCARPRRSPAQEDGKVYINMPGRGRVKFS RSADAPAYQQGQNQLYNELNLGRREEYDVLDKRRGR DPEMGGKPRRKNPQEGLYNELQKDKMAEAYSEIGM KGERRRGKGHDGLYQGLSTATKDTYDALHMQALPP R | 83 |
| 8 | KIR2DS-(KIR2DS2-CD3ζ) | VLIGTSVVKIPFTILLFFLLHRWCSNKKNAAVMDQEPAG NRTVNSEDSDEQDHQEVSYARVKFSRSADAPAYQQGQ NQLYNELNLGRREEYDVLDKRRGRDPEMGGKPRRK NPQEGLYNELQKDKMAEAYSEIGMKGERRRGKGHD GLYQGLSTATKDTYDALHMQALPPR | 84 |
| 9 | KIR2DS-(KIR2DS2-DAP10) | VLIGTSVVKIPFTILLFFLLHRWCSNKKNAAVMDQEPAG NRTVNSEDSDEQDHQEVSYALCARPRRSPAQEDGKVYI NMPGRG | 85 |
| 10 | KIR2DS-(KIR2DS2-2B4) | VLIGTSVVKIPFTILLFFLLHRWCSNKKNAAVMDQEPAG NRTVNSEDSDEQDHQEVSYAWRRKRKEKQSETSPKEF LTIYEDVKDLKTRRNHEQEQTFPGGGSTIYSMIQSQSS APTSQEPAYTLYSLIQPSRKSGSRKRNHSPSFNSTIYEV IGKSQPKAQNPARLSRKELENFDVYS | 86 |
| 11 | CD16-(CD16-2B4-DAP10) | VSFCLVMVLLFAVDTGLYFSVKTNIRSSTRDWKDHKFK WRKDPQDKWRRKRKEKQSETSPKEFLTIYEDVKDLK TRRNHEQEQTFPGGGSTIYSMIQSQSSAPTSQEPAYTL YSLIQPSRKSGSRKRNHSPSFNSTIYEVIGKSQPKAQNP ARLSRKELENFDVYSLCARPRRSPAQEDGKVYINMPGR G | 87 |
| 12 | CD16-(CD16-DNAM1) | VSFCLVMVLLFAVDTGLYFSVKTNIRSSTRDWKDHKFK WRKDPQDKNRRRRRERRDLFTESWDTQKAPNNYRSPI STSQPTNQSMDDTREDIYVNYPTFSRRPKTRV | 88 |
| 13 | NKp46-(NKp46-2B4) | MGLAFLVLVALVWFLVEDWLSRKRTRERASRASTWEGR RRLNTQTLWRRKRKEKQSETSPKEFLTIYEDVKDLKT RRNHEQEQTFPGGGSTIYSMIQSQSSAPTSQEPAYTL YSLIQPSRKSGSRKRNHSPSFNSTIYEVIGKSQPKAQ NPARLSRKELENFDVYS | 89 |
| 14 | NKp46-(NKp46-2B4-CD3ζ) | MGLAFLVLVALVWFLVEDWLSRKRTRERASRASTWEGR RRLNTQTLWRRKRKEKQSETSPKEFLTIYEDVKDLKT RRNHEQEQTFPGGGSTIYSMIQSQSSAPTSQEPAYTLY SLIQPSRKSGSRKRNHSPSFNSTIYEVIGKSQPKAQNP ARLSRKELENFDVYSRVKFSRSADAPAYQQGQNQLYNE LNLGRREEYDVLDKRRGRDPEMGGKPRRKNPQEGLYNE LQKDKMAEAYSEIGMKGERRRGKGHDGLYQGLSTATKD TYDALHMQALPPR | 90 |
| 15 | NKp46-(NKp46-CD2-DAP10) | MGLAFLVLVALVWFLVEDWLSRKRTRERASRASTWEGR RRLNTQTLKRKKQRSRRNDEELETRAHRVATEERGRKP HQIPASTPQNPATSQHPPPPPGHRSQAPSHRPPPPG HRVQHPQKRPPAPSGTQVHQQKGPPLPRPRVQPKP PHGAAENSLSPSSNLCARPRRSPAQEDGKVYINMPGRG | 91 |
| 16 | CD2-(CD2-CD3ζ) | IYLIIGICGGGSLLMVFVALLVFYITKRKKQRSRRNDEE LETRAHRVATEERGRKPHQIPASTPQNPATSQHPPPPPG HRSQAPSHRPPPPGHRVQHPQKRPPAPSGTQVHQQKGP PLPRPRVQPKPPHGAAENSLSPSSNRVKFSRSADAPAYQ QGQNQLYNELNLGRREEYDVLDKRRGRDPEMGGKPRR KNPQEGLYNELQKDKMAEAYSEIGMKGERRRGKGH DGLYQGLSTATKDTYDALHMQALPPR | 92 |

TABLE 3B-continued

| Construct | Sequence Domains TM-(endodomain) | Illustrative Sequence | SEQ ID NO: |
|---|---|---|---|
| 17 | 2B4-(2B4-CD3ζ) | FLVIIVILSALFLGTLACFCVWRRKRKEKQSETSPKEFLT IYEDVKDLKTRRNHEQEQTFPGGGSTIYSMIQSQSSAPTS QEPAYTLYSLIQPSRKSGSRKRNHSPSFNSTIYEVIGKSQ PKAQNPARLSRKELENFDVYSRVKFSRSADAPAYQQGQN QLYNELNLGRREEYDVLDKRRGRDPEMGGKPRRKNP QEGLYNELQKDKMAEAYSEIGMKGERRRGKGHDGL YQGLSTATKDTYDALHMQALPPR | 93 |
| 18 | 2B4-(2B4-FCERIγ) | FLVIIVILSALFLGTLACFCVWRRKRKEKQSETSPKEFLT IYEDVKDLKTRRNHEQEQTFPGGGSTIYSMIQSQSSAPTS QEPAYTLYSLIQPSRKSGSRKRNHSPSFNSTIYEVIGKSQ PKAQNPARLSRKELENFDVYSRLKIQVRKAAITSYEKSDG VYTGLSTRNQETYETLKHEKPPQ | 94 |
| 19 | CS1-(CS1-CD3ζ) | VLLCLLLVPLLLSLFVLGLFLWFLKRERQEEYIEEKKRVD ICRETPNICPHSGENTEYDTIPHTNRTILKEDPANTVYST VEIPKKMENPHSLLTMPDTPRLFAYENVIRVKFSRSADAP AYQQGQNQLYNELNLGRREEYDVLDKRRGRDPEMG GKPRRKNPQEGLYNELQKDKMAEAYSEIGMKGERR RGKGHDGLYQGLSTATKDTYDALHMQALPPR | 95 |

In some embodiments, the ectodomain can further include a signal peptide or leader sequence and/or a spacer/hinge. In some embodiments, there is a spacer/hinge between the antigen recognition region/domain and the transmembrane domain of the CAR, although in some other embodiments such spacer/hinge is not required. Exemplary spacers that may be included in a CAR or an ADR are commonly known in the art, including, but not limited to, IgG4 spacers, CD28 spacers, CD8 spacers, or combinations of more than one spacer. The length of the spacers may also vary, from about 15 amino acids (a.a.) to about 300 a.a. or more. In this application, for ease of description, a spacer of less than around 80 a.a., for example 10-80 a.a., is considered short; a spacer of about 80-180 a.a. is considered medium; and a spacer of more than 180 a.a. is considered long. Non-limiting exemplary spacer peptides include those represented by an amino acid sequence of at least about 80%, about 85%, about 90%, about 95%, about 96%, about 97%, about 98%, or about 99% identity to any of SEQ ID NOs: 96-100. In some embodiments, the spacer peptide comprises an amino acid sequence of at least about 90% identity to any of SEQ ID NOs: 96-100. In some embodiments, the spacer peptide comprises an amino acid sequence of at least about 95% identity to any of SEQ ID NOs: 96-100. In some embodiments, the spacer peptide comprises the amino acid sequence of any of SEQ ID NOs: 96-100.

SEQ ID NO: 96
IEVMYPPPYLDNEKSNGTIIHVKGKHLCPSPLFPGPSKP
(39 a.a.)

SEQ ID NO: 97
ESKYGPPCPPCPGGGSSGGGSGGQPREPQVYTLPPSQEEM

TKNQVSLTCLVKGFYPSDIAVEWESNGQPENNYKTTPPVL

DSDGSFFL
(88 a.a.)

SEQ ID NO: 98
ESKYGPPCPPCPAPEFEGGPSVFLFPPKPKDTLMISRTPE

VTCVVVDVSQEDPEVQFNWYVDGVEVHNAKTKPREEQFQS

TYRVVSVLT
(89 a.a.)

SEQ ID NO: 99
ESKYGPPCPPCPGGGSSGGGSGGQPREPQVYTLPPSQEEM

TKNQVSLTCLVKGFYPSDIAVEWESNGQPENNYKTTPPVL

DSDGSFFLYSRLTVDKSRWQEGNVFSCSVMHEALHNHYTQ

KSLSLSLGK
(129 a.a.)

SEQ ID NO: 100
ESKYGPPCPPCPAPEFEGGPSVFLFPPKPKDTLMISRTPE

VTCVVVDVSQEDPEVQFNWYVDGVEVHNAKTKPREEQFQS

TYRVVSVLTVLHQDWLNGKEYKCKVSNKGLPSSIEKTISK

AKGQPREPQVYTLPPSQEEMTKNQVSLTCLVKGFYPSDIA

VEWESNGQPENNYKTTPPVLDSDGSFFLYSRLTVDKSRWQ

EGNVFSCSVMHEALHNHYTQKSLSLSLGK
(229 a.a.)

In one embodiment, the CAR provided herein comprises a co-stimulatory domain derived from CD28, and a signaling domain comprising the native or modified ITAM1 of CD3ζ, represented by an amino acid sequence having at least about 85%, about 90%, about 95%, about 96%, about 97%, about 98%, or about 99% identity to SEQ ID NO: 80. In some embodiments, the signaling domain comprises an amino acid sequence with at least about 90% identity to SEQ ID NO: 80. In some embodiments, the signaling domain comprises an amino acid sequence with at least about 95% identity to SEQ ID NO: 80. In some embodiments, the signaling domain comprises the amino acid sequence of SEQ ID NO: 80. In a further embodiment, the CAR comprising a co-stimulatory domain derived from CD28, and a native or modified ITAM1 of CD3ζ also comprises a hinge domain (or "spacer") and trans-membrane domain derived from CD28, wherein an scFv may be connected to the transmembrane domain through the hinge, and the CAR comprises an amino acid sequence of at least about 85%, about 90%, about 95%, about 96%, about 97%, about 98%, or about 99% identity to SEQ ID NO: 101, wherein the spacer may vary in length and sequence. In some embodiments, the CAR comprises an amino acid sequence of at least 80% to SEQ ID NO: 101, wherein the spacer may vary in length and sequence. In some embodiments, the CAR comprises an amino acid sequence of at least 90% to SEQ ID NO: 101, wherein the spacer may vary in length and sequence. In some embodiments, the CAR comprises an amino acid sequence of at least 95% to SEQ ID NO: 101, wherein the spacer may vary in length and sequence. In some embodiments, the CAR comprises the amino acid sequence of SEQ ID NO: 101.

SEQ ID NO: 101
ESKYGPPCPPCPGGGSSGGGSGGQPREPQVYTLPPSQEEM

TKNQVSLTCLVKGFYPSDIAVEWESNGQPENNYKTTPPVL

DSDGSFFLYSRLTVDKSRWQEGNVFSCSVMHEALHNHYTQ

KSLSLSLGKMFWVLVVVGGVLACYSLLVTVAFIIFWVRSK

RSRLLHSDYMNMTPRRPGPTRKHYQPYAPPRDFAAYRS*RV*

*KFSRSADAPAYQQGQNQLYNELNLGRREEYDVLDKRRGRD*

*PEMGGKPRRKNPQEGLFNELQKDKMAEAFSEIGMKGERRR*

*GKGHDGLFQGLSTATKDTFDALHMQALPPR*
(spacer-CD28 TM-CD28 Costim-
CD3ζ1XX activation)

In another embodiment, the CAR applicable to the cells provided herein comprises a transmembrane domain derived from NKG2D, a co-stimulatory domain derived from 2B4, and a signaling domain comprising the native or modified CD3ζ, represented by an amino acid sequence of at least about 85%, about 90%, about 95%, about 96%, about 97%, about 98%, or about 99% identity to SEQ ID NO: 102. In some embodiments, the CAR comprises an amino acid sequence of at least about 90% identity to SEQ ID NO: 102. In some embodiments, the CAR comprises an amino acid sequence of at least about 95% identity to SEQ ID NO: 102. In some embodiments, the CAR comprises the amino acid sequence of SEQ ID NO: 102. Said CAR comprising a transmembrane domain derived from NKG2D, a co-stimulatory domain derived from 2B4, and a signaling domain comprising the native or modified CD3ζ may further comprise a hinge.

SEQ ID NO: 102
SNLFVASWIAVMIIFRIGMAVAIFCCFFFPSWRRKRKEKQ

SETSPKEFLTIYEDVKDLKTRRNHEQEQTFPGGGSTIYSM

IQSQSSAPTSQEPAYTLYSLIQPSRKSGSRKRNHSPSFNS

TIYEVIGKSQPKAQNPARLSRKELENFDVYS*RVKFSRSAD*

*APAYKQGQNQLYNELNLGRREEYDVLDKRRGRDPEMGGKP*

*RRKNPQEGLYNELQKDKMAEAYSEIGMKGERRRGKGHDGL*

*YQGLSTATKDTYDALHMQALPPR*
(263 a.a NKG2D TM-2B4-CD3ζ)

In one example, the genetically engineered immune cells, iPSCs and derivative effector cells comprise a solid tumor targeting backbone as disclosed herein and a CAR comprising an antigen recognition region specific to a tumor cell surface HER2 antigen. Unless otherwise specified, the antigen binding domain of the HER2-CAR in this application is based on the CDRs of CasMab250, a HER2 cancer-specific monoclonal antibody (CasMab), and this CasMab250 based HER2-CAR is also referred to "CasMab250-CAR" from time to time in this application. In some embodiments, the antigen recognition domain of the ectodomain of the HER2-CAR comprises a heavy chain variable (VH) domain comprising a heavy chain complementary determining region 1 (H-CDR1) comprising SEQ ID NO: 103 (NYGMS), a heavy chain complementary determining region 2 (H-CDR2) comprising SEQ ID NO: 104 (TINNNGGGTYYPDSVKG), and a heavy chain complementary determining region 3 (H-CDR3) comprising SEQ ID NO: 105 (PGLLWDA); and a light chain variable (VL) domain comprising a light chain complementary determining region 1 (L-CDR1) comprising SEQ ID NO: 106 (KSSQSLLDSDGRTYLN), a light chain complementary determining region 2 (L-CDR2) comprising SEQ ID NO: 107 (LVSKLDS), and a light chain complementary determining region 3 (L-CDR3) comprising SEQ ID NO: 108 (WQGTHFPQT).

In some embodiments, the antigen binding domain of the CAR comprises a VH domain having a sequence identity of at least 50%, 55%, 60%, 65%, 70%, 75%, 80%, 85%, 90%, 95%, 99%, 100%, or any percentage in-between, when compared to the exemplary sequence represented by SEQ ID NO: 109. In some embodiments, the VH domain comprises an amino acid sequence of at least about 90% identity to SEQ ID NO: 109. In some embodiments, the VH domain comprises an amino acid sequence of at least about 95% identity to SEQ ID NO: 109. In some embodiments, the VH domain comprises the amino acid sequence of SEQ ID NO: 109. In some embodiments, the antigen binding domain of the CAR comprises a VL domain having a sequence identity of at least 50%, 55%, 60%, 65%, 70%, 75%, 80%, 85%, 90%, 95%, 99%, 100%, or any percentage in-between, when compared to the exemplary sequence represented by SEQ ID NO: 110. In some embodiments, the VL domain comprises an amino acid sequence of at least about 90% identity to SEQ ID NO: 110. In some embodiments, the VL domain comprises an amino acid sequence of at least about 95% identity to SEQ ID NO: 110. In some embodiments, the VL domain comprises the amino acid sequence of SEQ ID NO: 110.

SEQ ID NO: 109
RDNAKNTLYLQMSSLKSEDTAMYYCTSPGLLWDAWGAGTTVTVSS

SEQ ID NO: 110
DVVMTQTPLTLSVSIGQPASISCKSSQSLLDSDGRTYLNWLLQRP

GQSPKRLIYLVSKLDSGAPDRFTGSGSGTDFTLKISRVEAEDLGV

YYCWQGTHFPQTFGGGTKLEIK

In some embodiments the antigen binding domain of the CAR comprises a single chain variable fragment (scFV) having a N to C terminus orientation comprising VH-linker-VL or VL-linker-VH, wherein the linker varies in length and sequence. In some embodiments, the linker has a sequence identity of at least 50%, 55%, 60%, 65%, 70%, 75%, 80%, 85%, 90%, 95%, 99%, 100%, or any percentage in-between, when compared to the exemplary sequences represented by SEQ ID NOs: 111-114. In some embodiments, the linker comprises an amino acid sequence of at least about 90% identity to any of SEQ ID NOs: 111-114. In some embodiments, the linker comprises an amino acid sequence of at least about 95% identity to any of SEQ ID NOs: 111-114. In some embodiments, the linker comprises the amino acid sequence of any of SEQ ID NOs: 111-114.

```
                                          SEQ ID NO: 111
        GSTSGGGSGGGSGGGGSS

SEQ ID NO: 112
        GSTSGSGKPGSGEGSTKG

SEQ ID NO: 113
        SSGGGGSGGGGSGGGGS

SEQ ID NO: 114
        GGGGSGGGGSGGGGS
```

In some embodiments the antigen binding domain of the CAR comprises a single chain variable fragment (scFV) having a sequence identity of at least 50%, 55%, 60%, 65%, 70%, 75%, 80%, 85%, 90%, 95%, 99%, 100%, or any percentage in-between, when compared to the exemplary sequences represented by SEQ ID NO: 115 or SEQ ID NO: 116, wherein each of SEQ ID NOs: 115 and 116 comprise a linker that can vary in length and/or sequence. In some embodiments, the scFV comprises an amino acid sequence of at least 90% identity to SEQ ID NO: 115 or 116. In some embodiments, the scFV comprises an amino acid sequence of at least 95% identity to SEQ ID NO: 115 or 116. In some embodiments, the scFV comprises the amino acid sequence of SEQ ID NO: 115. In some embodiments, the scFV comprises the amino acid sequence of SEQ ID NO: 116.

```
                                          SEQ ID NO: 115
        RDNAKNTLYLQMSSLKSEDTAMYYCTSPGLLWDAWGAGTTVTVSS

GSTSGGGSGGGSGGGGSSDVVMTQTPLTLSVSIGQPASISCKSSQ

SLLDSDGRTYLNWLLQRPGQSPKRLIYLVSKLDSGAPDRFTGSGS

GTDFTLKISRVEAEDLGVYYCWQGTHFPQTFGGGTKLEIK

SEQ ID NO: 116
        DVVMTQTPLTLSVSIGQPASISCKSSQSLLDSDGRTYLNWLLQRP

GQSPKRLIYLVSKLDSGAPDRFTGSGSGTDFTLKISRVEAEDLGV

YYCWQGTHFPQTFGGGTKLEIKGSTSGGGSGGGSGGGGSSEVQLV

ESGGGLVQPGGSLKLSCAASGFTFSNYGMSWVRQTPDRRLELVAT

INNNGGGTYYPDSVKGRFTISRDNAKNTLYLQMSSLKSEDTAMYY

CTSPGLLWDAWGAGTTVTVSS
```

In one embodiment, the CAR provided herein comprises an amino acid sequence of at least about 85%, about 90%, about 95%, about 96%, about 97%, about 98%, or about 99% identity to SEQ ID NO: 117, wherein the linker in the ectodomain and the spacer between the ectodomain and transmembrane domain may vary in length and sequence. In some embodiments, the CAR comprises an amino acid sequence of at least about 90% identity to SEQ ID NO: 117, wherein the linker in the ectodomain and the spacer between the ectodomain and transmembrane domain may vary in length and sequence. In some embodiments, the CAR comprises an amino acid sequence of at least about 95% identity to SEQ ID NO: 117, wherein the linker in the ectodomain and the spacer between the ectodomain and transmembrane domain may vary in length and sequence. In some embodiments, the CAR comprises the amino acid sequence of SEQ ID NO: 117. In some embodiments, the CAR provided herein recognizes a HER2 antigen specific to cells of solid tumors. In some embodiments, the CAR provided herein recognizes a HER2 antigen of a tumor comprising breast cancer, ovary cancer, endometrium cancer, lung cancer, esophageal cancer, salivary gland cancer, bladder cancer, gastric cancer, colorectal cancer, or head and neck cancer. In yet some other embodiments, the CAR provided herein recognizes a HER2 antigen of a tumor and does not respond, or has a low level of response, to HER2 expressed on non-cancer or normal cells.

```
                                          SEQ ID NO: 117
        EVQLVESGGGLVQPGGSLKLSCAASGFTFSNYGMSWVRQT

PDRRLELVATINNNGGGTYYPDSVKGRFTISRDNAKNTLY

LQMSSLKSEDTAMYYCTSPGLLWDAWGAGTTVTVSSGSTS

GGGSGGGSGGGGSSDVVMTQTPLTLSVSIGQPASISCKSS

QSLLDSDGRTYLNWLLQRPGQSPKRLIYLVSKLDSGAPDR

FTGSGSGTDFTLKISRVEAEDLGVYYCWQGTHFPQTFGGG

TKLEIKESKYGPPCPPCPGGGSSGGGSGGQPREPQVYTLP

PSQEEMTKNQVSLTCLVKGFYPSDIAVEWESNGQPENNYK

TTPPVLDSDGSFFLYSRLTVDKSRWQEGNVFSCSVMHEAL

HNHYTQKSLSLSLGKMFWVLVVVGGVLACYSLLVTVAFII

FWVRSKRSRLLHSDYMNMTPRRPGPTRKHYQPYAPPRDFA

AYRSRVKFSRSADAPAYQQGQNQLYNELNLGRREEYDVLD

KRRGRDPEMGGKPRRKNPQEGLFNELQKDKMAEAFSEIGM

KGERRRGKGHDGLFQGLSTATKDTFDALHMQALPPR
        (anti-HER2 scFV[linker]-spacer-CD28 TM-
        CD28 Costim-CD3ζ1XX activation)
```

In another example, the genetically engineered immune cells, iPSCs and derivative effector cells comprise a solid tumor targeting backbone as disclosed herein and a CAR comprising an antigen recognition region that targets tumor antigen MICA and MICB (MICA/B). In some embodiments of the MICA/B targeting CAR, the antigen recognition region is a scFV that specifically binds to the conserved α3 domain of MICA and MICB. In one embodiment, the scFV comprises a variable region of the heavy chain represented by an amino acid sequence that is of at least about 99%, about 98%, about 96%, about 95%, about 90%, about 85%, or at least about 80% identity to SEQ ID NO: 118, and a variable region of the light chain represented by an amino acid sequence that is of at least about 99%, about 98%, about 96%, about 95%, about 90%, about 85%, or at least about 80% identity to SEQ ID NO: 119. In some embodiments, the heavy chain variable region comprises an amino acid sequence of at least about 90% identity to SEQ ID NO: 118. In some embodiments, the heavy chain variable region comprises an amino acid sequence of at least about 95% identity to SEQ ID NO: 118. In some embodiments, the heavy chain variable region comprises the amino acid sequence of SEQ ID NO: 118. In some embodiments, the light chain variable region comprises an amino acid sequence of at least about 90% identity to SEQ ID NO: 119. In some embodiments, the light chain variable region comprises an amino acid sequence of at least about 95% identity to SEQ ID NO: 119. In some embodiments, the light chain variable region comprises the amino acid sequence of SEQ ID NO: 119. In one embodiment of the MICA/B scFV, the scFV is represented by an amino acid sequence that is of at least about 99%, about 98%, about 96%, about 95%, about 90%, about 85%, or at least about 80% identity to SEQ ID NO: 120. In some embodiments, the scFV comprises an amino acid sequence of at least 90% identity to SEQ ID NO:

120. In some embodiments, the scFV comprises an amino acid sequence of at least 95% identity to SEQ ID NO: 120. In some embodiments, the scFV comprises the amino acid sequence of SEQ ID NO: 120. In another embodiment of the MICA/B scFV, the scFV is represented by an amino acid sequence that is of at least about 99%, about 98%, about 96%, about 95%, about 90%, about 85%, or at least about 80% identity to SEQ ID NO: 121. In some embodiments, the scFV comprises an amino acid sequence of at least 90% identity to SEQ ID NO: 121. In some embodiments, the scFV comprises an amino acid sequence of at least 95% identity to SEQ ID NO: 121. In some embodiments, the scFV comprises the amino acid sequence of SEQ ID NO: 121.

```
                                              SEQ ID NO: 118
QIQLVQSGPELKKPGETVKVSCKASGYMFTNYAMNWVKQA

PEKGLKWMGWINTHTGDPTYADDFKGRIAFSLETSASTAY

LQINNLKNEDTATYFCVRTYGNYAMDYWGQGTSVTVSS
(118 AA. MICA/B scFV heavy chain (HC))

SEQ ID NO: 119
SLTISNLEPEDIATYYCQQYSKFPRTFGGGTTLEIK
(107 AA. MICA/B scFV light chain (LC))

SEQ ID NO: 120
MDFQVQIFSFLLISASVIMSRQIQLVQSGPELKKPGETVK

VSCKASGYMFTNYAMNWVKQAPEKGLKWMGWINTHTGDPT

YADDFKGRIAFSLETSASTAYLQINNLKNEDTATYFCVRT

YGNYAMDYWGQGTSVTVSSGGGGSGGGGSGGGGSDIQMTQ

TTSSLSASLGDRVTISCSASQDISNYLNWYQQKPDGTVKL

LIYDTSILHLGVPSRFSGSGSGTDYSLTISNLEPEDIATY

YCQQYSKFPRTFGGGTTLEIK
(MICA/B scFV; HC-Linker-LC;

Signal peptide/Leader-other signal peptides
are also possible;
Linker-other linkers are also possible)

SEQ ID NO: 121
MDFQVQIFSFLLISASVIMSRDIQMTQTTSSLSASLGDRV

TISCSASQDISNYLNWYQQKPDGTVKLLIYDTSILHLGVP

SRFSGSGSGTDYSLTISNLEPEDIATYYCQQYSKFPRTFG

GGTTLEIKGGGGSGGGGSGGGGSQIQLVQSGPELKKPGET

VKVSCKASGYMFTNYAMNWVKQAPEKGLKWMGWINTHTGD

PTYADDFKGRIAFSLETSASTAYLQINNLKNEDTATYFCV

RTYGNYAMDYWGQGTSVTVSS
(MICA/B scFV; LC-Linker-HC;
Signal peptide/Leader-other signal peptides
are also possible;
Linker-other linkers are also possible)
```

In another example, the genetically engineered iPSC and its derivative cell comprise a solid tumor targeting backbone as disclosed herein and a CAR that targets tumor antigen BCMA (B cell maturation antigen). In some embodiments of the BCMA targeting CAR, the antigen recognition region is a scFV that specifically binds to the extracellular domain of CD269. In one embodiment, the scFV comprises a variable region of the heavy chain (VH) represented by an amino acid sequence that is of at least about 99%, about 98%, about 96%, about 95%, about 90%, about 85%, or at least about 80% identity to any one of SEQ ID NOs: 122, 124, and 126, and a variable region of the light chain (VL) represented by an amino acid sequence that is of at least about 99%, about 98%, about 96%, about 95%, about 90%, about 85%, or at least about 80% identity to any one of SEQ ID NOs: 123, 125 and 127. In one embodiment of the BCMA scFV for CAR construction, the scFV comprises a VH and a VL, represented by an amino acid sequence that is of at least about 99%, about 98%, about 96%, about 95%, about 90%, about 85%, or at least about 80% identity to SEQ ID NO: 122 and SEQ ID NO: 123, respectively; or SEQ ID NO: 124 and SEQ ID NO: 125, or SEQ ID NO: 126 and SEQ ID NO: 127, respectively.

In some embodiments, the heavy chain variable region comprises an amino acid sequence of at least about 90% identity to any of SEQ ID NOs: 122, 124, or 126. In some embodiments, the heavy chain variable region comprises an amino acid sequence of at least about 95% identity to any of SEQ ID NOs: 122, 124, or 126. In some embodiments, the heavy chain variable region comprises the amino acid sequence of any of SEQ ID NOs: 122, 124, or 126. In some embodiments, the light chain variable region comprises an amino acid sequence of at least about 90% identity to any of SEQ ID NOs: 123, 125, or 127. In some embodiments, the light chain variable region comprises an amino acid sequence of at least about 95% identity to any of SEQ ID NOs: 123, 125, or 127. In some embodiments, the light chain variable region comprises the amino acid sequence of any of SEQ ID NOs: 123, 125, or 127. In one embodiment of the BCMA scFV, the scFV is represented by an amino acid sequence that is of at least about 99%, about 98%, about 96%, about 95%, about 90%, about 85%, or at least about 80% identity to any one of SEQ ID NOs: 128, 129, 130, 131, 132 or 133. In some embodiments, the scFV comprises an amino acid sequence of at least 90% identity to any of SEQ ID NOs: 128-133. In some embodiments, the scFV comprises an amino acid sequence of at least 95% identity to any of SEQ ID NOs: 128-133. In some embodiments, the scFV comprises the amino acid sequence of SEQ ID NO: 128. In some embodiments, the scFV comprises the amino acid sequence of SEQ ID NO: 129. In some embodiments, the scFV comprises the amino acid sequence of SEQ ID NO: 130. In some embodiments, the scFV comprises the amino acid sequence of SEQ ID NO: 131. In some embodiments, the scFV comprises the amino acid sequence of SEQ ID NO: 132. In some embodiments, the scFV comprises the amino acid sequence of SEQ ID NO: 133. One aspect of the present specification provides genetically engineered iPSC and its derivative cell, wherein the cell comprises an exogenous polynucleotide encoding at least a BCMA-CAR. In some embodiments, the iPSC derived effector cell comprising an exogenous polynucleotide encoding at least a BCMA-CAR are T cells. In some embodiments, the iPSC derived effector cell comprising an exogenous polynucleotide encoding at least a BCMA-CAR are NK cells. In some other embodiments, the iPSC derived effector cell comprising an exogenous polynucleotide encoding at least a BCMA-CAR are NKT cells. In some other embodiments, the iPSC derived effector cell comprising an exogenous polynucleotide encoding at least a BCMA-CAR have functional or structural features that are not present or typical in T, NK, or NKT cells or any other immune cells of a natural source. In one example, the present specification provides a CAR comprising an antigen recognition region that targets tumor antigen BCMA.

```
                                                            SEQ ID NO: 122
RDNAKNTLYLQMNSLRAEDTAVYYCASLYYDYGDAYDYWGQGTLVTVSS
(BCMA scFV heavy chain-1 (VH))

SEQ ID NO: 123
EIVMTQSPATLSVSPGERATLSCKASQSVESNVAWYQQKPGQAPRALIYSASLRFSGIPARFSGSGSGTEF

TLTISSLQSEDFAVYYCQQYNNYPLTFGAGTKLELK
(BCMA scFV light chain-1 (VL))

SEQ ID NO: 124
RDTSINTAYMELSSLTSEDTAVYFCASLYDYDWYFDVWGQGTMVTVSS
(BCMA scFV heavy chain-2 (VH))

SEQ ID NO: 125
DIVMTQTPLSLSVTPGQPASISCKSSQSLVHSNGNTYLHWYLQKPGQSPQLLIYKVSNRFSGVPDRFSGSG

SGTDFTLKISRVEAEDVGIYYCSQSSIYPWTFGQGTKLEIK
(BCMA scFV light chain-2 (VL))

SEQ ID NO: 126
QVQLVQSGAEVKKPGASVKVSCKASGYSFPDYYINWVRQAPGQGLEWMGWIYFASGNSEYNQKFTGRVTMT

RDTSSSTAYMELSSLRSEDTAVYFCASLYDYDWYFDVWGQGTMVTVSS
(BCMA scFV heavy chain-3 (VH))

SEQ ID NO: 127
DIVMTQTPLSLSVTPGEPASISCKSSQSLVHSNGNTYLHWYLQKPGQSPQLLIYKVSNRFSGVPDRFSGSG

SGADFTLKISRVEAEDVGVYYCAETSHVPWTFGQGTKLEIK
(BCMA scFV light chain-3 (VL))

SEQ ID NO: 128
MDFQVQIFSFLLISASVIMSREVQLVESGGGLVQPGGSLRLSCAASGFTFSRYWFSWVRQAPGKGLVWVGE

INPSSSTINYAPSLKDKFTISRDNAKNTLYLQMNSLRAEDTAVYYCASLYYDYGDAYDYWGQGTLVTVSSG

STSGSGKPGSGEGSTKGEIVMTQSPATLSVSPGERATLSCKASQSVESNVAWYQQKPGQAPRALIYSASLR

FSGIPARFSGSGSGTEFTLTISSLQSEDFAVYYCQQYNNYPLTFGAGTKLELK
(BCMA scFV-1; VH-Linker-VL;
Signal peptide/Leader-other signal peptides
are also possible;
Linker-other linkers are also possible)

SEQ ID NO: 129
MDFQVQIFSFLLISASVIMSREIVMTQSPATLSVSPGERATLSCKASQSVESNVAWYQQKPGQAPRALIYS

ASLRFSGIPARFSGSGSGTEFTLTISSLQSEDFAVYYCQQYNNYPLTFGAGTKLELKGGGGSGGGGSGGGG

SRDNAKNTLYLQMNSLRAEDTAVYYCASLYYDYGDAYDYWGQGTLVTVSS
(BCMA scFV-2; VL-Linker-VH;
Signal peptide/Leader-other signal peptides
are also possible;
Linker-other linkers are also possible)

SEQ ID NO: 130
MDFQVQIFSFLLISASVIMSRQVQLVQSGAEVKKPGASVKVSCKASGYSFPDYYINWVRQAPGQGLEWMGW

IYFASGNSEYNQKFTGRVTMTRDTSINTAYMELSSLTSEDTAVYFCASLYDYDWYFDVWGQGTMVTVSSGS

TSGSGKPGSGEGSTKGDIVMTQTPLSLSVTPGQPASISCKSSQSLVHSNGNTYLHWYLQKPGQSPQLLIYK

VSNRFSGVPDRFSGSGSGTDFTLKISRVEAEDVGIYYCSQSSIYPWTFGQGTKLEIK
(BCMA scFV-3; VH-Linker-VL; Signal peptide/Leader-other signal
peptides are also possible;
Linker-other linkers are also possible)

SEQ ID NO: 131
MDFQVQIFSFLLISASVIMSRDIVMTQTPLSLSVTPGQPASISCKSSQSLVHSNGNTYLHWYLQKPGQSPQ

LLIYKVSNRFSGVPDRFSGSGSGTDFTLKISRVEAEDVGIYYCSQSSIYPWTFGQGTKLEIKGSTSGSGKP

GSGEGSTKGQVQLVQSGAEVKKPGASVKVSCKASGYSFPDYYINWVRQAPGQGLEWMGWIYFASGNSEYNQ

KFTGRVTMTRDTSINTAYMELSSLTSEDTAVYFCASLYDYDWYFDVWGQGTMVTVSS
(BCMA scFV-4; VL-Linker-VH; Signal peptide/Leader-other signal
peptides are also possible;
Linker-other linkers are also possible)
```

-continued

SEQ ID NO: 132
MDFQVQIFSFLLISASVIMSR<u>QVQLVQSGAEVKKPGASVKVSCKASGYSFPDYYINWVRQAPGQGLEWMGW</u>

<u>IYFASGNSEYNQKFTGRVTMTRDTSSSTAYMELSSLRSEDTAVYFCASLYDYDWYFDVWGQGTMVTVSS</u><u>*GS*</u>

<u>*TSGSGKPGSGEGSTKG*</u><u>DIVMTQTPLSLSVTPGEPASISCKSSQSLVHSNGNTYLHWYLQKPGQSPQLLIYK</u>

<u>VSNRFSGVPDRFSGSGSGADFTLKISRVEAEDVGVYYCAETSHVPWTFGQGTKLEIK</u>
(BCMA scFV-5; VH-Linker-VL; <u>Signal peptide/Leader</u>-other signal
peptides are also possible;
<u>*Linker*</u>-other linkers are also possible)

SEQ ID NO: 133
MDFQVQIFSFLLISASVIMSR<u>DIVMTQTPLSLSVTPGEPASISCKSSQSLVHSNGNTYLHWYLQKPGQSPQ</u>

<u>LLIYKVSNRFSGVPDRFSGSGSGADFTLKISRVEAEDVGVYYCAETSHVPWTFGQGTKLEIK</u><u>*GSTSGSGKP*</u>

<u>*GSGEGSTKG*</u><u>QVQLVQSGAEVKKPGASVKVSCKASGYSFPDYYINWVRQAPGQGLEWMGWIYFASGNSEYNQ</u>

<u>KFTGRVTMTRDTSSSTAYMELSSLRSEDTAVYFCASLYDYDWYFDVWGQGTMVTVSS</u>
(BCMA scFV-6; VL-<u>*Linker*</u>-VH; <u>Signal peptide/Leader</u>-other signal
peptides are also possible;
<u>*Linker*</u>-other linkers are also possible)

In yet another example, the genetically engineered iPSC and its derivative cell comprise a solid tumor targeting backbone as disclosed herein and a CAR that targets tumor antigen B7H3 (CD276). In various embodiments of the CAR targeting a B7H3 tumor antigen, the CAR comprises a recombinant heavy-chain-only antibody (VHH) that specifically binds to B7H3. In one embodiment, the CAR comprises a binding domain comprising an amino acid sequence that is of at least about 99%, about 98%, about 96%, about 95%, about 90%, about 85%, or at least about 80% identity to SEQ ID NO: 134. In another embodiment, the CAR comprises a binding domain comprising an amino acid sequence that is of at least about 99%, about 98%, about 96%, about 95%, about 90%, about 85%, or at least about 80% identity to SEQ ID NO: 135. In another embodiment, the CAR comprises a binding domain comprising an amino acid sequence that is of at least about 99%, about 98%, about 96%, about 95%, about 90%, about 85%, or at least about 80% identity to SEQ ID NO: 136. In another embodiment, the CAR comprises a binding domain comprising an amino acid sequence that is of at least about 99%, about 98%, about 96%, about 95%, about 90%, about 85%, or at least about 80% identity to SEQ ID NO: 137. In another embodiment, the CAR comprises a binding domain comprising an amino acid sequence that is of at least about 99%, about 98%, about 96%, about 95%, about 90%, about 85%, or at least about 80% identity to SEQ ID NO: 138. In another embodiment, the CAR comprises a binding domain comprising an amino acid sequence that is of at least about 99%, about 98%, about 96%, about 95%, about 90%, about 85%, or at least about 80% identity to SEQ ID NO: 139. In some embodiments, the binding domain comprises an amino acid sequence of at least about 90% identity to any of SEQ ID NOs: 134-139. In some embodiments, the binding domain comprises an amino acid sequence of at least about 95% identity to any of SEQ ID NOs: 134-139. In some embodiments, the binding domain comprises the sequence of SEQ ID NO: 134. In some embodiments, the binding domain comprises the sequence of SEQ ID NO: 135. In some embodiments, the binding domain comprises the sequence of SEQ ID NO: 136. In some embodiments, the binding domain comprises the sequence of SEQ ID NO: 137. In some embodiments, the binding domain comprises the sequence of SEQ ID NO: 138. In some embodiments, the binding domain comprises the sequence of SEQ ID NO: 139.

In certain embodiments, the CAR comprises a binding domain comprising a variant of SEQ ID NO: 134, and wherein the variant has one or more mutations at positions comprising 1, 40, 46, 79, 87, 88, 89, 97, 98, and 117 of SEQ ID NO: 134. In other embodiments, the CAR comprises an amino acid sequence represented by a variant of SEQ ID NO: 134, wherein the variant has one or more substitutions comprising Q1E, T40A, E46V, G79L, K87R, P88A, D89E, V97A, S98R, and Q117L according to SEQ ID NO: 134. In other embodiments, the CAR comprises an amino acid sequence represented by any of SEQ ID NOs: 134, 135, 136, 137, 138, and 139.

SEQ ID NO: 134
QVQLVESGGGLVQPGGSLRLSCAASGFTFSSYWMYWVRQT

PGKGLEWVSTINRDGSATWYADSVKGRFTISRDNAKNTGY

LQMNSLKPDDTAVYYCVSDPDNYSSDEMVPYWGQGTQVTV

SS
(122 a. a. VHH camelid B7H3)

SEQ ID NO: 135
EVQLVESGGGLVQPGGSLRLSCAASGFTFSSYWMYWVRQA

PGKGLVWVSTINRDGSATWYADSVKGRFTISRDNAKNTLY

LQMNSLRAEDTAVYYCARDPDNYSSDEMVPYWGQGTLVTV

SS
(122 a.a. VHH1)

SEQ ID NO: 136
RDNAKNTLYLQMNSLRAEDTAVYYCVSDPDNYSSDEMVPY

WGQGTLVTVSS
(122 a.a. VHH2)

SEQ ID NO: 137
RDNAKNTLYLQMNSLRAEDTAVYYCVSDPDNYSSDEMVPY

WGQGTLVTVSS
(122 a.a. VHH3)

SEQ ID NO: 138
EVQLVESGGGLVQPGGSLRLSCAASGFTFSSYWMYWVRQA

PGKGLEWVSTINRDGSATWYADSVKGRFTISRDNAKNTLY

LQMNSLRAEDTAVYYCVSDPDNYSSDEMVPYWGQGTLVTV

SS
(122 a. a. VHH4)

-continued

SEQ ID NO: 139
RDNAKNTGYLQMNSLRPEDTAVYYCVSDPDNYSSDEMVPY

WGQGTLVTVSS
(122 AA. VHH5)

Non-limiting CAR strategies further include heterodimeric, conditionally activated CAR through dimerization of a pair of intracellular domains (see for example, U.S. Pat. No. 9,587,020); a split CAR, where homologous recombination of antigen binding, hinge, and endo-domains to generate a CAR (see for example, U.S. Pub. No. 2017/0183407); a multi-chain CAR that allows non-covalent link between two transmembrane domains connected to an antigen binding domain and a signaling domain, respectively (see for example, U.S. Pub. No. 2014/0134142); CARs having bispecific antigen binding domain (see for example, U.S. Pat. No. 9,447,194), or having a pair of antigen binding domains recognizing same or different antigens or epitopes (see for example, U.S. Pat. No. 8,409,577), or a tandem CAR (see for example, Hegde et al., J Clin Invest. 2016; 126(8):3036-3052); an inducible CAR (see for example, U.S. Pub. Nos. 2016/0046700, 2016/0058857, and 2017/0166877); a switchable CAR (see for example, U.S. Pub. No. 2014/0219975); and any other designs known in the art.

In some embodiments, the polynucleotide encoding a CAR as disclosed is operatively linked to an exogenous promoter. The promoters may be inducible, or constitutive, and may be temporal-, tissue- or cell type-specific. Suitable constitutive promoters for methods disclosed herein include, but are not limited to, cytomegalovirus (CMV), elongation factor 1α (EF1α), phosphoglycerate kinase (PGK), hybrid CMV enhancer/chicken β-actin (CAG) and ubiquitin C (UBC) promoters. In one embodiment, the exogenous promoter is CAG.

As described herein, in some embodiments, the cells comprising a solid tumor targeting backbone comprising polynucleotides encoding encoding two or more of a C—X—C-motif chemokine receptor or a variant thereof, a TGFβ-SRR, and an ADR specific to 4-1BB, optionally comprise a polynucleotide encoding a CAR and/or one or more additional modified modalities provided herein. In iPSCs and derivative cells therefrom comprising both an exogenous cytokine signaling complex ("IL" in Table 4) and a CAR, the IL and CAR may be expressed in separate constructs, or may be co-expressed in a bi-cistronic construct comprising both IL and CAR. Additionally provided in this application is a master cell bank comprising single cell sorted and expanded clonal engineered iPSCs having at least one phenotype as provided herein, including but not limited to, a solid tumor targeting backbone as described herein and a CAR, wherein the cell bank provides a platform for additional iPSC engineering and a renewable source for manufacturing off-the-shelf, engineered, homogeneous cell therapy products, including but not limited to derivative NK and T cells, which are well-defined and uniform in composition, and can be mass produced at significant scale in a cost-effective manner.

9. Genetically Engineered iPSC Line and Derivative Cells Provided Herein

In light of the above, the present application provides an immune cell, an iPSC, an iPS cell line cell, or a population thereof, and a derivative functional cell obtained from differentiating the iPSC, wherein each cell comprises a solid tumor targeting backbone comprising polynucleotides encoding two or more of a C—X—C-motif chemokine receptor or a variant thereof, a TGFβ-SRR, and an ADR specific to 4-1BB, and optionally a CAR and/or one or more additional genetic modifications as described in the application, wherein the cell is an eukaryotic cell, an animal cell, a human cell, an induced pluripotent cell (iPSC), an iPSC-derived effector cell, an immune cell, or a feeder cell. Said cells are suitable for homing or migration of the effectors to tumor sites for CAR targeted tumor killing. In some embodiments, the tumor cells at the tumor sites secrete or overexpress a chemokine that binds to a C—X—C-motif chemokine receptor or a variant thereof. In some embodiments, the C—X—C motif chemokine receptor comprises CXCR2 or CXCR3. In some embodiments, the secreted or overexpressed chemokine by the tumor cells at the tumor sites comprises IL8 (CXCL8). In some embodiments, the functional derivative cells are hematopoietic cells including, but not limited to, mesodermal cells with definitive hemogenic endothelium (HE) potential, definitive HE, $CD34^+$ hematopoietic cells, hematopoietic stem and progenitor cells, hematopoietic multipotent progenitors (MPP), T cell progenitors, NK cell progenitors, myeloid cells, neutrophil progenitors, T lineage cells, NKT lineage cells, NK lineage cells, B lineage cells, neutrophils, dendritic cells, and macrophages. In some embodiments, the functional derivative hematopoietic cells comprise effector cells having one or more functional features that are not present in a counterpart primary T, NK, NKT, and/or B cell.

Further provided herein is an iPSC, an iPS cell line cell, or a clonal population thereof, and a derivative functional cell obtained from differentiating the iPSC, wherein each cell comprises a solid tumor targeting backbone as described herein, and a CAR, and a polynucleotide encoding an exogenous CD16 or a variant thereof, wherein the iPSC is capable of directed differentiation to produce functional derivative hematopoietic cells. Said effector cells have improved ability to home or migrate to, and remain in, tumor sites which include solid tumors, and provide a tumor antigen dual targeting mechanism to tackle tumor antigen heterogeneity and tumor antigen escape. The dual targeting through CAR binding and CD16-mediated ADCC further increases tumor targeting precision, enhancing tumor killing and minimizing the impact of tumor antigen escape.

In some further embodiments, the iPSC, iPS cell line cell, or clonal population thereof, and/or derivative effector cells therefrom comprising a solid tumor targeting backbone as described herein, a CAR and exogenous CD16 or a variant thereof, wherein the solid tumor targeting backbone further comprises CD38 knockout, and said cells are suitable for a subject undergoing an adoptive cell therapy. In certain embodiments, the subject may additionally receive a tumor sensitizing procedure (e.g., administration of a sensitizing agent, such as a chemotherapeutic agent, radiation, or radiotherapeutic) to upregulate tumor cell chemokine expression including, but not limited to, CXCL8 overexpression, to further enhance C—X—C motif chemokine receptor overexpressing effector cell homing, trafficking and retention, and cytotoxicity at the tumor sites. In some embodiments, said effector cells comprise T lineage cells. In some other embodiments, said effector cells comprise NK lineage cells.

In some embodiments of the derivative effector cells, the iPSCs and their derivative cells that comprise a solid tumor targeting backbone comprising polynucleotides encoding at least two of a C—X—C-motif chemokine receptor or a variant thereof, a TGFβ-SRR, and an ADR specific to 4-1BB, and optionally one or more of a CAR, CD38 knockout, exogenous CD16 or a variant thereof, HLA-I and/or HLA-II deficiency, and one or more CFRs, said cells have the CAR inserted in a TCR constant region (TRAC or TRBC), leading to TCR knockout, and optionally placing CAR expression under the control of the endogenous TCR promoter. The disruption of the constant region of TCRα or TCRβ (TRAC or TRBC) produces a TCR$^{neg}$ cell. In addition, the expression of TCR is also negative in a NK lineage effector cell that is differentiated from an iPSC. TCR$^{neg}$ cells do not require HLA matching, have reduced alloreactivity, and are able to prevent GvHD (Graft versus Host Disease) when used in allogeneic adoptive cell therapies. Additional insertion sites of a CAR include, but are not limited to, AAVS1, CCR5, ROSA26, collagen, HTRP, H11, GAPDH, RUNX1, B2M, TAP1, TAP2, tapasin, NLRC5, CIITA, RFXANK, RFX5, RFXAP, NKG2A, NKG2D, CD25, CD38, CD44, CD58, CD54, CD56, CD69, CD71, CIS, CBL-B, SOCS2, PD1, CTLA4, LAG3, TIM3, and TIGIT. In another embodiment, the effector cell, the iPSC and its derivative NK cell described herein comprises a CAR, where the CAR is inserted in the NKG2A locus or NKG2D locus, leading to NKG2A or NKG2D knockout, thereby placing CAR expression under the control of the endogenous NKG2A or NKG2D promoter.

Additionally provided is an iPSC comprising a solid tumor targeting backbone comprising polynucleotides encoding at least two of a C—X—C-motif chemokine receptor or a variant thereof, a TGFβ-SRR, and an ADR specific to 4-1BB, and further comprising a CAR, exogenous CD16 or a variant thereof, CD38 knockout, and a polynucleotide encoding an interleukin (IL) cytokine signaling complex comprising a full or partial length of cytokine and/or a full or partial length of a cytokine receptor to enable cytokine signaling contributing to cell survival, persistence and/or expansion, wherein the iPSC line is capable of directed differentiation to produce functional derivative hematopoietic cells having improved survival, persistency, expansion, and effector cell function, as well as homing, trafficking, tumor site retention and cytotoxicity. In various embodiments, the exogenously introduced IL cytokine signaling(s) comprise the signaling of any one, two, or more of IL2, IL4, IL6, IL7, IL9, IL10, IL11, IL12, IL15, IL18, and IL21. In some embodiments, the introduced IL cytokine signaling complex is for IL15 signaling in the cell, and the cell is optionally an NK lineage cell. In some other specific embodiments, the introduced IL cytokine signaling complex is for IL7 signaling in the cell, and the cell is optionally a T lineage cell. In some embodiments, the introduced IL cytokine signaling complex is expressed on the cell surface. In some embodiments, the IL cytokine signaling is constitutively activated. In some embodiments, activation of the IL cytokine signaling is inducible. In some embodiments, activation of the IL cytokine signaling is transient and/or temporal. In some embodiments, the transient/temporal expression of a cell surface cytokine/cytokine receptor is through a retrovirus, Sendai virus, an adenovirus, an episome, mini-circle, or RNAs including mRNA. Effector cells comprising a solid tumor targeting backbone comprising polynucleotides encoding two or more of a C—X—C-motif chemokine receptor or a variant thereof, a TGFβ-SRR, and an ADR specific to 4-1BB, and a CAR, exogenous CD16 or a variant thereof, IL cytokine signaling complex, and optionally one or more additional genetic modifications as provided in Table 4 and throughout the application are capable of maintaining or improving cell growth, proliferation, expansion, and/or effector function autonomously without contacting additionally supplied soluble cytokines in vitro or in vivo, as well as enhanced homing, trafficking, and retention at tumor sites, in which the tumor cells could be sensitized to synergize with the functional features provided to the effector cells through rational design and precision engineering of a primary-sourced immune cell or a clonal iPSC.

Also provided is an iPSC comprising a solid tumor targeting backbone as provided herein, a CAR and exogenous CD16 or a variant thereof, and a CAR, a B2M knockout and/or a CIITA knockout, and optionally, one of HLA-G overexpression, CD58 knockout and CD54 knockout, wherein the iPSC is capable of directed differentiation to produce functional derivative hematopoietic cells. In various embodiments, said iPSC and its derivative effector cells comprising a solid tumor targeting backbone are HLA-I and/or HLA-II deficient. In a further embodiment, the HLA-I and/or HLA-II deficient iPSC and its derivative effector cells comprising a solid tumor targeting backbone, are also CD38 negative, and can be used with an anti-CD38 antibody to induce ADCC without causing effector cell elimination, thereby increasing the persistence and/or survival of the iPSC and its effector cell. In some embodiments, the effector cell has increased persistence and/or survival in vivo.

As such, the present application provides iPSCs and their functional derivative hematopoietic cells, which comprise any one of the following genotypes in Table 4. "IL", as provided in Table 4, stands for an IL cytokine signaling complex for one of IL2, IL4, IL6, IL7, IL9, IL10, IL11, IL12, IL15, IL18, and IL21, depending on which specific cytokine/receptor expression is selected. Further, "IL" also encompasses the IL15A embodiment, which is detailed above as a truncated fusion protein of IL15 and IL15Rα, but without an intracellular domain. Further, when iPSCs and their functional derivative hematopoietic cells have a genotype comprising both CAR and IL, the CAR and IL may be comprised in a bi- or tri-cistronic expression cassette comprising a 2A sequence. As comparison, in some other embodiments, CAR and IL are in separate expression cassettes comprised in iPSCs and their functional derivative hematopoietic cells. In one embodiment, the iPSCs and their functional derivative effector cells comprising both CAR and IL, IL is IL15, wherein the IL15 construct is comprised in an expression cassette with, or separate from, the CAR.

TABLE 4

Applicable Exemplary Genotypes of the Cells Provided:

| C-X-C-motif | TGFβ-SRR (TGFβR) | ADR | CD38$^{-/-}$ | CD16$^{exo}$ | IL | HLA-I/II Deficiency | CFR | CAR and TCR$^{-/-}$ | Genotype |
|---|---|---|---|---|---|---|---|---|---|
| ✓ | ✓ |  |  |  |  |  |  |  | 1. C-X-C TGFβR |
| ✓ |  | ✓ |  |  |  |  |  |  | 2. C-X-C ADR |
|  | ✓ | ✓ |  |  |  |  |  |  | 3. TGFβR ADR |

TABLE 4-continued

Applicable Exemplary Genotypes of the Cells Provided:

| C-X-C-motif | TGFβ-SRR (TGFβR) | ADR | CD38$^{-/-}$ | CD16$^{exo}$ | IL | HLA-I/II Deficiency | CFR | CAR and TCR$^{-/-}$ | | Genotype |
|---|---|---|---|---|---|---|---|---|---|---|
| ✓ | ✓ | ✓ | | | | | | | 4. | C-X-CTGFβR ADR |
| ✓ | ✓ | | ✓ | | | | | | 5. | C-X-C TGFβR CD38$^{-/-}$ |
| ✓ | ✓ | | | ✓ | | | | | 6. | C-X-C TGFβR CD16$^{exo}$ |
| ✓ | ✓ | | | | ✓ | | | | 7. | C-X-C TGFβR IL |
| ✓ | ✓ | | | | | ✓ | | | 8. | C-X-C TGFβR HLA-I/II |
| ✓ | ✓ | | | | | | ✓ | | 9. | C-X-C TGFβR CFR |
| ✓ | ✓ | | | | | | | ✓ | 10. | C-X-C TGFβR CAR |
| ✓ | | ✓ | ✓ | | | | | | 11. | C-X-C ADR CD38$^{-/-}$ |
| ✓ | | ✓ | | ✓ | | | | | 12. | C-X-C ADR CD16$^{exo}$ |
| ✓ | | ✓ | | | ✓ | | | | 13. | C-X-C ADR IL |
| ✓ | | ✓ | | | | ✓ | | | 14. | C-X-C ADR HLA-I/II |
| ✓ | | ✓ | | | | | ✓ | | 15. | C-X-C ADR CFR |
| ✓ | | ✓ | | | | | | ✓ | 16. | C-X-C ADR CAR |
| | ✓ | ✓ | ✓ | | | | | | 17. | TGFβR ADR CD38$^{-/-}$ |
| | ✓ | ✓ | | ✓ | | | | | 18. | TGFβR ADR CD16$^{exo}$ |
| | ✓ | ✓ | | | ✓ | | | | 19. | TGFβR ADR IL |
| | ✓ | ✓ | | | | ✓ | | | 20. | TGFβR ADR HLA-I/II |
| | ✓ | ✓ | | | | | ✓ | | 21. | TGFβR ADR CFR |
| | ✓ | ✓ | | | | | | ✓ | 22. | TGFβR ADR CAR |
| ✓ | ✓ | ✓ | ✓ | | | | | | 23. | C-X-C TGFβR ADR CD38$^{-/-}$ |
| ✓ | ✓ | ✓ | | ✓ | | | | | 24. | C-X-C TGFβR ADR CD16$^{exo}$ |
| ✓ | ✓ | ✓ | | | ✓ | | | | 25. | C-X-C TGFβR ADR IL |
| ✓ | ✓ | ✓ | | | | ✓ | | | 26. | C-X-C TGFβR ADR HLA-I/II |
| ✓ | ✓ | ✓ | | | | | ✓ | | 27. | C-X-C TGFβR ADR CFR |
| ✓ | ✓ | ✓ | | | | | | ✓ | 28. | C-X-C TGFβR ADR CAR |
| ✓ | ✓ | | ✓ | ✓ | | | | | 29. | C-X-C TGFβR CD38$^{-/-}$ CD16$^{exo}$ |
| ✓ | ✓ | | ✓ | | ✓ | | | | 30. | C-X-C TGFβR CD38$^{-/-}$ IL |
| ✓ | ✓ | | ✓ | | | ✓ | | | 31. | C-X-C TGFβR CD38$^{-/-}$ HLA-I/II |
| ✓ | ✓ | | ✓ | | | | ✓ | | 32. | C-X-C TGFβR CD38$^{-/-}$ CFR |
| ✓ | ✓ | | ✓ | | | | | ✓ | 33. | C-X-C TGFβR CD38$^{-/-}$ CAR |
| ✓ | ✓ | | | ✓ | ✓ | | | | 34. | C-X-C TGFβR CD16$^{exo}$ IL |
| ✓ | ✓ | | | ✓ | | ✓ | | | 35. | C-X-C TGFβR CD16$^{exo}$ HLA-I/II |
| ✓ | ✓ | | | ✓ | | | ✓ | | 36. | C-X-C TGFβR CD16$^{exo}$ CFR |
| ✓ | ✓ | | | ✓ | | | | ✓ | 37. | C-X-C TGFβR CD16$^{exo}$ CAR |
| ✓ | ✓ | | | | ✓ | ✓ | | | 38. | C-X-C TGFβR IL HLA-I/II |
| ✓ | ✓ | | | | ✓ | | ✓ | | 39. | C-X-C TGFβR IL CFR |
| ✓ | ✓ | | | | ✓ | | | ✓ | 40. | C-X-C TGFβR IL CAR |
| ✓ | ✓ | | | | | ✓ | ✓ | | 41. | C-X-C TGFβR HLA-I/II CFR |
| ✓ | ✓ | | | | | ✓ | | ✓ | 42. | C-X-C TGFβR HLA-I/II CAR |
| ✓ | ✓ | | | | | | ✓ | ✓ | 43. | C-X-C TGFβR CFR CAR |
| ✓ | | ✓ | ✓ | ✓ | | | | | 44. | C-X-C ADR CD38$^{-/-}$ CD16$^{exo}$ |
| ✓ | | ✓ | ✓ | | ✓ | | | | 45. | C-X-C ADR CD38$^{-/-}$ IL |
| ✓ | | ✓ | ✓ | | | ✓ | | | 46. | C-X-C ADR CD38$^{-/-}$ HLA-I/II |
| ✓ | | ✓ | ✓ | | | | ✓ | | 47. | C-X-C ADR CD38$^{-/-}$ CFR |
| ✓ | | ✓ | ✓ | | | | | ✓ | 48. | C-X-C ADR CD38$^{-/-}$ CAR |
| ✓ | | ✓ | | ✓ | ✓ | | | | 49. | C-X-C ADR CD16$^{exo}$ IL |
| ✓ | | ✓ | | ✓ | | ✓ | | | 50. | C-X-C ADR CD16$^{exo}$ HLA-I/II |
| ✓ | | ✓ | | ✓ | | | ✓ | | 51. | C-X-C ADR CD16$^{exo}$ CFR |
| ✓ | | ✓ | | ✓ | | | | ✓ | 52. | C-X-C ADR CD16$^{exo}$ CAR |
| ✓ | | ✓ | | | ✓ | ✓ | | | 53. | C-X-C ADR IL HLA-I/II |
| ✓ | | ✓ | | | ✓ | | ✓ | | 54. | C-X-C ADR IL CFR |
| ✓ | | ✓ | | | ✓ | | | ✓ | 55. | C-X-C ADR IL CAR |
| ✓ | | ✓ | | | | ✓ | ✓ | | 56. | C-X-C ADR HLA-I/II CFR |
| ✓ | | ✓ | | | | ✓ | | ✓ | 57. | C-X-C ADR HLA-I/II CAR |
| ✓ | | ✓ | | | | | ✓ | ✓ | 58. | C-X-C ADR CFR CAR |
| | ✓ | ✓ | ✓ | ✓ | | | | | 59. | TGFβR ADR CD38$^{-/-}$ CD16$^{exo}$ |
| | ✓ | ✓ | ✓ | | ✓ | | | | 60. | TGFβR ADR CD38$^{-/-}$ IL |
| | ✓ | ✓ | ✓ | | | ✓ | | | 61. | TGFβR ADR CD38$^{-/-}$ HLA-I/II |
| | ✓ | ✓ | ✓ | | | | ✓ | | 62. | TGFβR ADR CD38$^{-/-}$ CFR |
| | ✓ | ✓ | ✓ | | | | | ✓ | 63. | TGFβR ADR CD38$^{-/-}$ CAR |
| | ✓ | ✓ | | ✓ | ✓ | | | | 64. | TGFβR ADR CD16$^{exo}$ IL |
| | ✓ | ✓ | | ✓ | | ✓ | | | 65. | TGFβR ADR CD16$^{exo}$ HLA-I/II |
| | ✓ | ✓ | | ✓ | | | ✓ | | 66. | TGFβR ADR CD16$^{exo}$ CFR |
| | ✓ | ✓ | | ✓ | | | | ✓ | 67. | TGFβR ADR CD16$^{exo}$ CAR |
| | ✓ | ✓ | | | ✓ | ✓ | | | 68. | TGFβR ADR IL HLA-I/II |
| | ✓ | ✓ | | | ✓ | | ✓ | | 69. | TGFβR ADR IL CFR |
| | ✓ | ✓ | | | ✓ | | | ✓ | 70. | TGFβR ADR IL CAR |
| | ✓ | ✓ | | | | ✓ | ✓ | | 71. | TGFβR ADR HLA-I/II CFR |
| | ✓ | ✓ | | | | ✓ | | ✓ | 72. | TGFβR ADR HLA-I/II CAR |
| | ✓ | ✓ | | | | | ✓ | ✓ | 73. | TGFβR ADR CFR CAR |
| ✓ | ✓ | ✓ | ✓ | ✓ | | | | | 74. | C-X-C TGFβR ADR CD38$^{-/-}$ CD16$^{exo}$ |
| ✓ | ✓ | ✓ | ✓ | | ✓ | | | | 75. | C-X-C TGFβR ADR CD38$^{-/-}$ IL |
| ✓ | ✓ | ✓ | ✓ | | | ✓ | | | 76. | C-X-C TGFβR ADR CD38$^{-/-}$ HLA-I/II |

TABLE 4-continued

Applicable Exemplary Genotypes of the Cells Provided:

| C-X-C-motif | TGFβ-SRR (TGFβR) | ADR | CD38$^{-/-}$ | CD16$^{exo}$ | IL | HLA-I/II Deficiency | CFR | CAR and TCR$^{-/-}$ | Genotype |
|---|---|---|---|---|---|---|---|---|---|
| ✓ | ✓ | ✓ | ✓ | | | | ✓ | | 77. C-X-C TGFβR ADR CD38$^{-/-}$ CFR |
| ✓ | ✓ | ✓ | ✓ | | | | | ✓ | 78. C-X-C TGFβR ADR CD38$^{-/-}$ CAR |
| ✓ | ✓ | ✓ | | ✓ | ✓ | | | | 79. C-X-C TGFβR ADR CD16$^{exo}$ IL |
| ✓ | ✓ | ✓ | | ✓ | | ✓ | | | 80. C-X-C TGFβR ADR CD16$^{exo}$ HLA-I/II |
| ✓ | ✓ | ✓ | | ✓ | | | ✓ | | 81. C-X-C TGFβR ADR CD16$^{exo}$ CFR |
| ✓ | ✓ | ✓ | | ✓ | | | | ✓ | 82. C-X-C TGFβR ADR CD16$^{exo}$ CAR |
| ✓ | ✓ | ✓ | | | ✓ | ✓ | | | 83. C-X-C TGFβR ADR IL HLA-I/II |
| ✓ | ✓ | ✓ | | | ✓ | | ✓ | | 84. C-X-C TGFβR ADR IL CFR |
| ✓ | ✓ | ✓ | | | ✓ | | | ✓ | 85. C-X-C TGFβR ADR IL CAR |
| ✓ | ✓ | ✓ | | | | ✓ | ✓ | | 86. C-X-C TGFβR ADR HLA-I/II CFR |
| ✓ | ✓ | ✓ | | | | ✓ | | ✓ | 87. C-X-C TGFβR ADR HLA-I/II CAR |
| ✓ | ✓ | ✓ | | | | | ✓ | ✓ | 88. C-X-C TGFβR ADR CFR CAR |
| ✓ | ✓ | | ✓ | ✓ | ✓ | | | | 89. C-X-C TGFβR CD38$^{-/-}$ CD16$^{exo}$ IL |
| ✓ | ✓ | | ✓ | ✓ | | ✓ | | | 90. C-X-C TGFβR CD38$^{-/-}$ CD16$^{exo}$ HLA-I/II |
| ✓ | ✓ | | ✓ | ✓ | | | ✓ | | 91. C-X-C TGFβR CD38$^{-/-}$ CD16$^{exo}$ CFR |
| ✓ | ✓ | | ✓ | ✓ | | | | ✓ | 92. C-X-C TGFβR CD38$^{-/-}$ CD16$^{exo}$ CAR |
| ✓ | ✓ | | | ✓ | ✓ | ✓ | | | 93. C-X-C TGFβR CD16$^{exo}$ IL HLA-I/II |
| ✓ | ✓ | | | ✓ | ✓ | | ✓ | | 94. C-X-C TGFβR CD16$^{exo}$ IL CFR |
| ✓ | ✓ | | | ✓ | ✓ | | | ✓ | 95. C-X-C TGFβR CD16$^{exo}$ IL CAR |
| ✓ | ✓ | | | | ✓ | ✓ | ✓ | | 96. C-X-C TGFβR IL HLA-I/II CFR |
| ✓ | ✓ | | | | ✓ | ✓ | | ✓ | 97. C-X-C TGFβR IL HLA-I/II CAR |
| ✓ | ✓ | | | | | ✓ | ✓ | ✓ | 98. C-X-C TGFβR HLA-I/II CFR CAR |
| ✓ | ✓ | | ✓ | | ✓ | ✓ | | | 99. C-X-C TGFβR CD38$^{-/-}$ IL HLA-I/II |
| ✓ | ✓ | | ✓ | | ✓ | | ✓ | | 100. C-X-C TGFβR CD38$^{-/-}$ IL CFR |
| ✓ | ✓ | | ✓ | | ✓ | | | ✓ | 101. C-X-C TGFβR CD38$^{-/-}$ IL CAR |
| ✓ | ✓ | | ✓ | | | ✓ | ✓ | | 102. C-X-C TGFβR CD38$^{-/-}$ HLA-I/II CFR |
| ✓ | ✓ | | ✓ | | | ✓ | | ✓ | 103. C-X-C TGFβR CD38$^{-/-}$ HLA-I/II CAR |
| ✓ | ✓ | | ✓ | | | | ✓ | ✓ | 104. C-X-C TGFβR CD38$^{-/-}$ CFR CAR |
| ✓ | | ✓ | ✓ | ✓ | ✓ | | | | 105. C-X-C ADR CD38$^{-/-}$ CD16$^{exo}$ IL |
| ✓ | | ✓ | ✓ | ✓ | | ✓ | | | 106. C-X-C ADR CD38$^{-/-}$ CD16$^{exo}$ HLA-I/II |
| ✓ | | ✓ | ✓ | ✓ | | | ✓ | | 107. C-X-C ADR CD38$^{-/-}$ CD16$^{exo}$ CFR |
| ✓ | | ✓ | ✓ | ✓ | | | | ✓ | 108. C-X-C ADR CD38$^{-/-}$ CD16$^{exo}$ CAR |
| ✓ | | ✓ | | ✓ | ✓ | ✓ | | | 109. C-X-C ADR CD16$^{exo}$ IL HLA-I/II |
| ✓ | | ✓ | | ✓ | ✓ | | ✓ | | 110. C-X-C ADR CD16$^{exo}$ IL CFR |
| ✓ | | ✓ | | ✓ | ✓ | | | ✓ | 111. C-X-C ADR CD16$^{exo}$ IL CAR |
| ✓ | | ✓ | | | ✓ | ✓ | ✓ | | 112. C-X-C ADR IL HLA-I/II CFR |
| ✓ | | ✓ | | | ✓ | ✓ | | ✓ | 113. C-X-C ADR IL HLA-I/II CAR |
| ✓ | | ✓ | | | | ✓ | ✓ | ✓ | 114. C-X-C ADR HLA-I/II CFR CAR |
| ✓ | | ✓ | ✓ | | ✓ | ✓ | | | 115. C-X-C ADR CD38$^{-/-}$ IL HLA-I/II |
| ✓ | | ✓ | ✓ | | ✓ | | ✓ | | 116. C-X-C ADR CD38$^{-/-}$ IL CFR |
| ✓ | | ✓ | ✓ | | ✓ | | | ✓ | 117. C-X-C ADR CD38$^{-/-}$ IL CAR |
| ✓ | | ✓ | ✓ | | | ✓ | ✓ | | 118. C-X-C ADR CD38$^{-/-}$ HLA-I/II CFR |
| ✓ | | ✓ | ✓ | | | ✓ | | ✓ | 119. C-X-C ADR CD38$^{-/-}$ HLA-I/II CAR |
| ✓ | | ✓ | ✓ | | | | ✓ | ✓ | 120. C-X-C ADR CD38$^{-/-}$ CFR CAR |
| | ✓ | ✓ | ✓ | ✓ | ✓ | | | | 121. TGFβR ADR CD38$^{-/-}$ CD16$^{exo}$ IL |
| | ✓ | ✓ | ✓ | ✓ | | ✓ | | | 122. TGFβR ADR CD38$^{-/-}$ CD16$^{exo}$ HLA-I/II |
| | ✓ | ✓ | ✓ | ✓ | | | ✓ | | 123. TGFβR ADR CD38$^{-/-}$ CD16$^{exo}$ CFR |
| | ✓ | ✓ | ✓ | ✓ | | | | ✓ | 124. TGFβR ADR CD38$^{-/-}$ CD16$^{exo}$ CAR |
| | ✓ | ✓ | | ✓ | ✓ | ✓ | | | 125. TGFβR ADR CD16$^{exo}$ IL HLA-I/II |
| | ✓ | ✓ | | ✓ | ✓ | | ✓ | | 126. TGFβR ADR CD16$^{exo}$ IL CFR |
| | ✓ | ✓ | | ✓ | ✓ | | | ✓ | 127. TGFβR ADR CD16$^{exo}$ IL CAR |
| | ✓ | ✓ | | | ✓ | ✓ | ✓ | | 128. TGFβR ADR IL HLA-I/II CFR |
| | ✓ | ✓ | | | ✓ | ✓ | | ✓ | 129. TGFβR ADR IL HLA-I/II CAR |
| | ✓ | ✓ | | | | ✓ | ✓ | ✓ | 130. TGFβR ADR HLA-I/II CFR CAR |
| | ✓ | ✓ | ✓ | | ✓ | ✓ | | | 131. TGFβR ADR CD38$^{-/-}$ IL HLA-I/II |
| | ✓ | ✓ | ✓ | | ✓ | | ✓ | | 132. TGFβR ADR CD38$^{-/-}$ IL CFR |
| | ✓ | ✓ | ✓ | | ✓ | | | ✓ | 133. TGFβR ADR CD38$^{-/-}$ IL CAR |
| | ✓ | ✓ | ✓ | | | ✓ | ✓ | | 134. TGFβR ADR CD38$^{-/-}$ HLA-I/II CFR |
| | ✓ | ✓ | ✓ | | | ✓ | | ✓ | 135. TGFβR ADR CD38$^{-/-}$ HLA-I/II CAR |
| | ✓ | ✓ | ✓ | | | | ✓ | ✓ | 136. TGFβR ADR CD38$^{-/-}$ CFR CAR |
| ✓ | ✓ | ✓ | ✓ | ✓ | ✓ | | | | 137. C-X-C TGFβR ADR CD38$^{-/-}$ CD16$^{exo}$ IL |
| ✓ | ✓ | ✓ | ✓ | ✓ | | ✓ | | | 138. C-X-C TGFβR ADR CD38$^{-/-}$ CD16$^{exo}$ HLA-I/II |
| ✓ | ✓ | ✓ | ✓ | ✓ | | | ✓ | | 139. C-X-C TGFβR ADR CD38$^{-/-}$ CD16$^{exo}$ CFR |
| ✓ | ✓ | ✓ | ✓ | ✓ | | | | ✓ | 140. C-X-C TGFβR ADR CD38$^{-/-}$ CD16$^{exo}$ CAR |
| ✓ | ✓ | ✓ | | ✓ | ✓ | ✓ | | | 141. C-X-C TGFβR ADR CD16$^{exo}$ IL HLA-I/II |
| ✓ | ✓ | ✓ | | ✓ | ✓ | | ✓ | | 142. C-X-C TGFβR ADR CD16$^{exo}$ IL CFR |
| ✓ | ✓ | ✓ | | ✓ | ✓ | | | ✓ | 143. C-X-C TGFβR ADR CD16$^{exo}$ IL CAR |
| ✓ | ✓ | ✓ | | | ✓ | ✓ | ✓ | | 144. C-X-C TGFβR ADR IL HLA-I/II CFR |
| ✓ | ✓ | ✓ | | | ✓ | ✓ | | ✓ | 145. C-X-C TGFβR ADR IL HLA-I/II CAR |
| ✓ | ✓ | ✓ | | | | ✓ | ✓ | ✓ | 146. C-X-C TGFβR ADR HLA-I/II CFR CAR |
| ✓ | ✓ | ✓ | ✓ | | ✓ | ✓ | | | 147. C-X-C TGFβR ADR CD38$^{-/-}$ IL HLA-I/II |
| ✓ | ✓ | ✓ | ✓ | | ✓ | | ✓ | | 148. C-X-C TGFβR ADR CD38$^{-/-}$ IL CFR |
| ✓ | ✓ | ✓ | ✓ | | ✓ | | | ✓ | 149. C-X-C TGFβR ADR CD38$^{-/-}$ IL CAR |

TABLE 4-continued

Applicable Exemplary Genotypes of the Cells Provided:

| C-X-C motif | TGFβ-SRR (TGFβR) | ADR | CD38−/− | CD16exo | IL | HLA-I/II Deficiency | CFR | CAR and TCR−/− | Genotype |
|---|---|---|---|---|---|---|---|---|---|
| ✓ | ✓ | ✓ | ✓ |  |  | ✓ | ✓ |  | 150. C-X-C TGFβR ADR CD38−/− HLA-I/II CFR |
| ✓ | ✓ | ✓ | ✓ |  |  | ✓ |  | ✓ | 151. C-X-C TGFβR ADR CD38−/− HLA-I/II CAR |
| ✓ | ✓ | ✓ | ✓ |  |  |  | ✓ | ✓ | 152. C-X-C TGFβR ADR CD38−/− CFR CAR |
| ✓ | ✓ |  | ✓ | ✓ | ✓ | ✓ |  |  | 153. C-X-C TGFβR CD38−/− CD16exo IL HLA-I/II |
| ✓ | ✓ |  | ✓ | ✓ | ✓ |  | ✓ |  | 154. C-X-C TGFβR CD38−/− CD16exo IL CFR |
| ✓ | ✓ |  | ✓ | ✓ | ✓ |  |  | ✓ | 155. C-X-C TGFβR CD38−/− CD16exo IL CAR |
| ✓ | ✓ |  | ✓ |  |  |  | ✓ | ✓ | 156. C-X-C TGFβR CD38−/− CFR CAR |
| ✓ | ✓ |  |  | ✓ | ✓ | ✓ | ✓ |  | 157. C-X-C TGFβR CD16exo IL HLA-I/II CFR |
| ✓ | ✓ |  |  | ✓ | ✓ | ✓ |  | ✓ | 158. C-X-C TGFβR CD16exo IL HLA-I/II CAR |
| ✓ | ✓ |  |  | ✓ |  | ✓ | ✓ | ✓ | 159. C-X-C TGFβR CD16exo HLA-I/II CFR CAR |
| ✓ | ✓ |  |  | ✓ | ✓ |  | ✓ | ✓ | 160. C-X-C TGFβR CD16exo IL CFR CAR |
| ✓ | ✓ |  |  |  | ✓ | ✓ | ✓ | ✓ | 161. C-X-C TGFβR IL HLA-I/II CFR CAR |
| ✓ | ✓ |  | ✓ |  | ✓ | ✓ | ✓ |  | 162. C-X-C TGFβR CD38−/− IL HLA-I/II CFR |
| ✓ | ✓ |  | ✓ |  | ✓ | ✓ |  | ✓ | 163. C-X-C TGFβR CD38−/− IL HLA-I/II CAR |
| ✓ | ✓ |  | ✓ |  |  | ✓ | ✓ | ✓ | 164. C-X-C TGFβR CD38−/− HLA-I/II CFR CAR |
| ✓ |  | ✓ | ✓ | ✓ | ✓ | ✓ |  |  | 165. C-X-C ADR CD38−/− CD16exo IL HLA-I/II |
| ✓ |  | ✓ | ✓ | ✓ | ✓ |  | ✓ |  | 166. C-X-C ADR CD38−/− CD16exo IL CFR |
| ✓ |  | ✓ | ✓ | ✓ | ✓ |  |  | ✓ | 167. C-X-C ADR CD38−/− CD16exo IL CAR |
| ✓ |  | ✓ | ✓ |  |  |  | ✓ | ✓ | 168. C-X-C ADR CD38−/− CFR CAR |
| ✓ |  | ✓ |  | ✓ | ✓ | ✓ | ✓ |  | 169. C-X-C ADR CD16exo IL HLA-I/II CFR |
| ✓ |  | ✓ |  | ✓ | ✓ | ✓ |  | ✓ | 170. C-X-C ADR CD16exo IL HLA-I/II CAR |
| ✓ |  | ✓ |  | ✓ |  | ✓ | ✓ | ✓ | 171. C-X-C ADR CD16exo HLA-I/II CFR CAR |
| ✓ |  | ✓ |  | ✓ | ✓ |  | ✓ | ✓ | 172. C-X-C ADR CD16exo IL CFR CAR |
| ✓ |  | ✓ |  |  | ✓ | ✓ | ✓ | ✓ | 173. C-X-C ADR IL HLA-I/II CFR CAR |
| ✓ |  | ✓ | ✓ |  | ✓ | ✓ | ✓ |  | 174. C-X-C ADR CD38−/− IL HLA-I/II CFR |
| ✓ |  | ✓ | ✓ |  | ✓ | ✓ |  | ✓ | 175. C-X-C ADR CD38−/− IL HLA-I/II CAR |
| ✓ |  | ✓ | ✓ |  |  | ✓ | ✓ | ✓ | 176. C-X-C ADR CD38−/− HLA-I/II CFR CAR |
|  | ✓ | ✓ | ✓ | ✓ | ✓ | ✓ |  |  | 177. TGFβR ADR CD38−/− CD16exo IL HLA-I/II |
|  | ✓ | ✓ | ✓ | ✓ | ✓ |  | ✓ |  | 178. TGFβR ADR CD38−/− CD16exo IL CFR |
|  | ✓ | ✓ | ✓ | ✓ | ✓ |  |  | ✓ | 179. TGFβR ADR CD38−/− CD16exo IL CAR |
|  | ✓ | ✓ | ✓ |  |  |  | ✓ | ✓ | 180. TGFβR ADR CD38−/− CFR CAR |
|  | ✓ | ✓ |  | ✓ | ✓ | ✓ | ✓ |  | 181. TGFβR ADR CD16exo IL HLA-I/II CFR |
|  | ✓ | ✓ |  | ✓ | ✓ | ✓ |  | ✓ | 182. TGFβR ADR CD16exo IL HLA-I/II CAR |
|  | ✓ | ✓ |  | ✓ |  | ✓ | ✓ | ✓ | 183. TGFβR ADR CD16exo HLA-I/II CFR CAR |
|  | ✓ | ✓ |  | ✓ | ✓ |  | ✓ | ✓ | 184. TGFβR ADR CD16exo IL CFR CAR |
|  | ✓ | ✓ |  |  | ✓ | ✓ | ✓ | ✓ | 185. TGFβR ADR IL HLA-I/II CFR CAR |
|  | ✓ | ✓ | ✓ |  | ✓ | ✓ | ✓ |  | 186. TGFβR ADR CD38−/− IL HLA-I/II CFR |
|  | ✓ | ✓ | ✓ |  | ✓ | ✓ |  | ✓ | 187. TGFβR ADR CD38−/− IL HLA-I/II CAR |
|  | ✓ | ✓ | ✓ |  |  | ✓ | ✓ | ✓ | 188. TGFβR ADR CD38−/− HLA-I/II CFR CAR |
| ✓ | ✓ | ✓ | ✓ | ✓ | ✓ | ✓ |  |  | 189. C-X-C TGFβR ADR CD38−/− CD16exo IL HLA-I/II |
| ✓ | ✓ | ✓ | ✓ | ✓ | ✓ |  | ✓ |  | 190. C-X-C TGFβR ADR CD38−/− CD16exo IL CFR |
| ✓ | ✓ | ✓ | ✓ | ✓ | ✓ |  |  | ✓ | 191. C-X-C TGFβR ADR CD38−/− CD16exo IL CAR |
| ✓ | ✓ | ✓ | ✓ |  |  |  | ✓ | ✓ | 192. C-X-C TGFβR ADR CD38−/− CFR CAR |
| ✓ | ✓ | ✓ |  | ✓ | ✓ | ✓ | ✓ |  | 193. C-X-C TGFβR ADR CD16exo IL HLA-I/II CFR |
| ✓ | ✓ | ✓ |  | ✓ | ✓ | ✓ |  | ✓ | 194. C-X-C TGFβR ADR CD16exo IL HLA-I/II CAR |
| ✓ | ✓ | ✓ |  | ✓ |  | ✓ | ✓ | ✓ | 195. C-X-C TGFβR ADR CD16exo HLA-I/II CFR CAR |
| ✓ | ✓ | ✓ |  | ✓ | ✓ |  | ✓ | ✓ | 196. C-X-C TGFβR ADR CD16exo IL CFR CAR |
| ✓ | ✓ | ✓ |  |  | ✓ | ✓ | ✓ | ✓ | 197. C-X-C TGFβR ADR IL HLA-I/II CFR CAR |
| ✓ | ✓ | ✓ | ✓ |  | ✓ | ✓ | ✓ |  | 198. C-X-C TGFβR ADR CD38−/− IL HLA-I/II CFR |
| ✓ | ✓ | ✓ | ✓ |  | ✓ | ✓ |  | ✓ | 199. C-X-C TGFβR ADR CD38−/− IL HLA-I/II CAR |
| ✓ | ✓ | ✓ | ✓ |  |  | ✓ | ✓ | ✓ | 200. C-X-C TGFβR ADR CD38−/− HLA-I/II CFR CAR |
| ✓ | ✓ |  | ✓ | ✓ | ✓ | ✓ | ✓ |  | 201. C-X-C TGFβR CD38−/− CD16exo IL HLA-I/II CFR |
| ✓ | ✓ |  | ✓ | ✓ | ✓ | ✓ |  | ✓ | 202. C-X-C TGFβR CD38−/− CD16exo IL HLA-I/II CAR |
| ✓ | ✓ |  | ✓ | ✓ | ✓ |  | ✓ | ✓ | 203. C-X-C TGFβR CD38−/− CD16exo IL CFR CAR |
| ✓ | ✓ |  | ✓ | ✓ |  | ✓ | ✓ | ✓ | 204. C-X-C TGFβR CD38−/− CD16exo HLA-I/II CFR CAR |
| ✓ | ✓ |  | ✓ |  | ✓ | ✓ | ✓ | ✓ | 205. C-X-C TGFβR CD38−/− IL HLA-I/II CFR CAR |
| ✓ | ✓ |  |  | ✓ | ✓ | ✓ | ✓ | ✓ | 206. C-X-C TGFβR CD16exo IL HLA-I/II CFR CAR |
| ✓ |  | ✓ | ✓ | ✓ | ✓ | ✓ | ✓ |  | 207. C-X-C ADR CD38−/− CD16exo IL HLA-I/II CFR |
| ✓ |  | ✓ | ✓ | ✓ | ✓ | ✓ |  | ✓ | 208. C-X-C ADR CD38−/− CD16exo IL HLA-I/II CAR |
| ✓ |  | ✓ | ✓ | ✓ | ✓ |  | ✓ | ✓ | 209. C-X-C ADR CD38−/− CD16exo IL CFR CAR |
| ✓ |  | ✓ | ✓ | ✓ |  | ✓ | ✓ | ✓ | 210. C-X-C ADR CD38−/− CD16exo HLA-I/II CFR CAR |
| ✓ |  | ✓ | ✓ |  | ✓ | ✓ | ✓ | ✓ | 211. C-X-C ADR CD38−/− IL HLA-I/II CFR CAR |
| ✓ |  | ✓ |  | ✓ | ✓ | ✓ | ✓ | ✓ | 212. C-X-C ADR CD16exo IL HLA-I/II CFR CAR |
|  | ✓ | ✓ | ✓ | ✓ | ✓ | ✓ | ✓ |  | 213. TGFβR ADR CD38−/− CD16exo IL HLA-I/II CFR |
|  | ✓ | ✓ | ✓ | ✓ | ✓ | ✓ |  | ✓ | 214. TGFβR ADR CD38−/− CD16exo IL HLA-I/II CAR |
|  | ✓ | ✓ | ✓ | ✓ | ✓ |  | ✓ | ✓ | 215. TGFβR ADR CD38−/− CD16exo IL CFR CAR |
|  | ✓ | ✓ | ✓ | ✓ |  | ✓ | ✓ | ✓ | 216. TGFβR ADR CD38−/− CD16exo HLA-I/II CFR CAR |
|  | ✓ | ✓ | ✓ |  | ✓ | ✓ | ✓ | ✓ | 217. TGFβR ADR CD38−/− IL HLA-I/II CFR CAR |
|  | ✓ | ✓ |  | ✓ | ✓ | ✓ | ✓ | ✓ | 218. TGFβR ADR CD16exo IL HLA-I/II CFR CAR |
| ✓ | ✓ | ✓ | ✓ | ✓ | ✓ | ✓ | ✓ |  | 219. C-X-C TGFβR ADR CD38−/− CD16exo IL HLA-I/II CFR |
| ✓ | ✓ | ✓ | ✓ | ✓ | ✓ | ✓ |  | ✓ | 220. C-X-C TGFβR ADR CD38−/− CD16exo IL HLA-I/II CAR |

TABLE 4-continued

Applicable Exemplary Genotypes of the Cells Provided:

| C-X-C motif | TGFβ-SRR (TGFβR) | ADR | CD38−/− | CD16exo | IL | HLA-I/II Deficiency | CFR | CAR and TCR−/− | Genotype |
|---|---|---|---|---|---|---|---|---|---|
| ✓ | ✓ | ✓ | ✓ | ✓ | ✓ |   | ✓ | ✓ | 221. C-X-C TGFβR ADR CD38−/− CD16exo IL CFR CAR |
| ✓ | ✓ | ✓ | ✓ | ✓ |   | ✓ | ✓ | ✓ | 222. C-X-C TGFβR ADR CD38−/− CD16exo HLA-I/II CFR CAR |
| ✓ | ✓ | ✓ | ✓ |   | ✓ | ✓ | ✓ | ✓ | 223. C-X-C TGFβR ADR CD38−/− IL HLA-I/II CFR CAR |
| ✓ | ✓ | ✓ |   | ✓ | ✓ | ✓ | ✓ | ✓ | 224. C-X-C TGFβR ADR CD16exo IL HLA-I/II CFR CAR |
| ✓ | ✓ |   | ✓ | ✓ | ✓ | ✓ | ✓ | ✓ | 225. C-X-C TGFβR CD38−/− CD16exo IL HLA-I/II CFR CAR |
| ✓ |   | ✓ | ✓ | ✓ | ✓ | ✓ | ✓ | ✓ | 226. C-X-C ADR CD38−/− CD16exo IL HLA-I/II CFR CAR |
| ✓ | ✓ | ✓ | ✓ | ✓ | ✓ | ✓ | ✓ | ✓ | 227. C-X-C TGFβR ADR CD38−/− CD16exo IL HLA-I/II CFR CAR |

10. Additional Modifications

In some embodiments, the genetically modified modalities further comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In some embodiments, the genetically modified iPSC and the derivative cells thereof comprise a genotype listed in Table 4. In some embodiments, the iPSC and its derivative effector cells comprising any one of the genotypes in Table 4 may additionally comprise disruption of at least one of TAP1, TAP2, Tapasin, NLRC5, PD1, LAG3, TIM3, RFXANK, RFX5, RFXAP, and any gene in the chromosome 6p21 region; or introduction of at least one of HLA-E, 4-1BBL, CD3, CD4, CD8, CD47, CD113, CD131, CD137, CD80, PDL1, $A_{2A}R$, antigen-specific TCR, an Fc receptor, an engager, and a surface triggering receptor for coupling with bi-, multi-specific or universal engagers.

Engagers are fusion proteins consisting of two or more single-chain variable fragments (scFvs) of different antibodies, with at least one scFv that binds to an effector cell surface molecule or surface triggering receptor, and at least another to a target cell via a target cell specific surface molecule. Examples of engagers include, but are not limited to, bi-specific T cell engagers (BiTEs), bi-specific killer cell engagers (BiKEs), tri-specific killer cell engagers (TriKEs), multi-specific killer cell engagers, or universal engagers compatible with multiple immune cell types. Thus, engagers can be bi-specific or multi-specific. Such bi-specific or multi-specific engagers are capable of directing an effector cell (e.g., a T cell, a NK cell, an NKT cell, a B cell, a macrophage, and/or a neutrophil) to a tumor cell and activating the immune effector cell, and have shown great potential to maximize the benefits of CAR-T cell therapy.

In some embodiments, the engager is used in combination with a population of the effector cells comprising a solid tumor targeting backbone as described herein by concurrent or consecutive administration, wherein the effector cells comprise a surface molecule, or surface triggering receptor, that is recognized by the engager. In some other embodiments, the engager is a bi-specific antibody expressed by a derivative effector cell through genetically engineering an iPSC comprising a solid tumor targeting backbone as described herein, and directed differentiation of the engineered iPSC. Exemplary effector cell surface molecules, or surface triggering receptors, that can be used for bi- or multi-specific engager recognition, or coupling, include, but are not limited to, CD3, CD28, CD5, CD16, NKG2D, CD64, CD32, CD89, NKG2C, and a chimeric Fc receptor as disclosed herein. As described herein, in some embodiments, the exogenous CD16 expressed on the surface of the derivative effector cells for engager recognition is a hnCD16, comprising a CD16 (containing F176V and optionally S197P) or CD64 extracellular domain, and native or non-native transmembrane, stimulatory and/or signaling domains as described herein. In some embodiments, the exogenous CD16 expressed on the surface of effector cells for engager recognition is a CD16-based chimeric Fc receptor (CFcR). In some embodiments, the CD16-based CFcR comprises a transmembrane domain of NKG2D, a stimulatory domain of 2B4, and a signaling domain of CD3ζ; wherein the extracellular domain of the exogenous CD16 is derived from a full length or partial sequence of the extracellular domain of CD64 or CD16; and wherein the extracellular domain of CD16 comprises F176V and optionally S197P.

In some embodiments, the target cell for an engager is a tumor cell. Exemplary tumor cell surface molecules for bi- or multi-specific engager recognition include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, and ROR1. In one embodiment, the bi-specific engager is a bi-specific antibody specific to CD3 and CD19 (CD3-CD19). In another embodiment, the bi-specific antibody is CD16-CD30 or CD64-CD30. In another embodiment, the bi-specific antibody is CD16-BCMA or CD64-BCMA. In still another embodiment, the bi-specific antibody is CD3-CD33.

In yet another embodiment, the bi-specific antibody further comprises a linker between the effector cell and tumor cell antigen binding domains. For example, a modified IL15 may be used as a linker for effector NK cells to facilitate effector cell expansion (called TriKE, or Tri-specific Killer Engager, in some publications). In one embodiment, the TriKE is CD16-IL15-EPCAM or CD64-IL15-EPCAM. In another embodiment, the TriKE is CD16-IL15-CD33 or CD64-IL15-CD33. In yet another embodiment, the TriKE is NKG2C-IL15-CD33 ("2C1533"). In addition to IL15, cytokines suitable for inclusion in the TriKE include, but are not limited to, IL2, IL4, IL6, IL7, IL9, IL10, IL11, IL12, IL18, and IL21.

In some embodiments, the surface triggering receptor for bi- or multi-specific engagers could be endogenous to the effector cells, sometimes depending on the cell types. In some other embodiments, one or more exogenous surface triggering receptors could be introduced to the effector cells using the methods and compositions provided herein, i.e., through additional engineering of an iPSC comprising a genotype listed in Table 4, then directing the differentiation of the iPSC to T, NK or any other effector cells comprising the same genotype and the surface triggering receptor as the source iPSC.

11. Antibodies for Immunotherapy

In some embodiments, in addition to the genomically engineered effector cells comprising a solid tumor targeting backbone as provided herein, additional therapeutic agents comprising an antibody, or an antibody fragment that targets an antigen associated with a condition, a disease, or an indication may be used with these effector cells in a combinational therapy. In some embodiments, the antibody is used in combination with a population of the effector cells comprising a solid tumor targeting backbone as described herein by concurrent or consecutive administration to a subject. In other embodiments, such antibody or a fragment thereof may be expressed by the effector cells by genetically engineering an iPSC using an exogenous polynucleotide sequence encoding said antibody or fragment thereof, and directing differentiation of the engineered iPSC. In some embodiments, the effector cell expresses an exogenous CD16 variant, wherein the cytotoxicity of the effector cell is enhanced by the antibody via ADCC.

In some embodiments, the therapeutic antibody is a monoclonal antibody. In some embodiments, the therapeutic antibody is a humanized antibody, a humanized monoclonal antibody, or a chimeric antibody. In some embodiments, the therapeutic antibody, or antibody fragment, specifically binds to a viral antigen. In other embodiments, the antibody, or antibody fragment, specifically binds to a tumor antigen. In some embodiments, the tumor- or viral-specific antigen activates the administered iPSC-derived effector cells to enhance their killing ability. In some embodiments, the therapeutic antibodies suitable for combinational treatment as an additional therapeutic agent to the administered iPSC-derived effector cells include, but are not limited to, anti-CD20 antibodies (rituximab, veltuzumab, ofatumumab, ublituximab, ocaratuzumab, obinutuzumab), anti-HER2 antibodies (trastuzumab, pertuzumab), anti-CD52 antibodies (alemtuzumab), anti-EGFR antibodies (cetuximab), anti-GD2 antibodies (dinutuximab), anti-PDL1 antibodies (avelumab), anti-CD38 antibodies (daratumumab, isatuximab, MOR202), anti-CD123 antibodies (7G3, CSL362), anti-SLAMF7 antibodies (elotuzumab), anti-MICA/B antibodies (7C6, 6F11, 1C2) and their humanized or Fc modified variants or fragments or their functional equivalents and biosimilars. In some embodiments, the antibodies suitable for combinational treatment as an additional therapeutic agent to the administered iPSC-derived effector cells further include bi-specific or multi-specific antibodies that target more than one antigen or epitope on a target cell or recruit effector cells (e.g., T cells, NK cells, or macrophage cells) toward target cells while targeting the target cells. Such bi-specific or multi-specific antibodies function as engagers capable of directing an effector cell (e.g., a T cell, a NK cell, an NKT cell, a B cell, a macrophage, and/or a neutrophil) to a tumor cell and activating the immune effector cell, and have shown great potential to maximize the benefits of antibody therapy.

In some embodiments, the iPSC-derived effector cells comprise hematopoietic lineage cells comprising a genotype listed in Table 4. In some embodiments, the iPSC-derived effector cells comprise NK cells comprising a genotype listed in Table 4. In some embodiments, the iPSC-derived effector cells comprise T cells comprising a genotype listed in Table 4.

In some embodiments of a combination useful for treating liquid or solid tumors, the combination comprises iPSC-derived NK or T cells comprising a solid tumor targeting backbone comprising polynucleotides encoding two or more of a C—X—C-motif chemokine receptor or a variant thereof, a TGFβ-SRR, and an ADR specific to 4-1BB, and optionally one or more additional genetic modifications as provided in Table 4; and a therapeutic antibody as described above. In some embodiments of a combination useful for treating liquid or solid tumors, the combination comprises iPSC-derived NK or T cells comprising a solid tumor targeting backbone as described herein, and optionally TCR knockout, a CAR, a cytokine signaling complex, exogenous CD16 or a variant thereof, and CD38 knockout; and a therapeutic antibody as described above. In some embodiments of a combination useful for treating liquid or solid tumors, the combination comprises iPSC-derived NK or T cells comprising a solid tumor targeting backbone as described herein, and optionally TCR knockout, a CAR, IL cytokine signaling complex, exogenous CD16 or a variant thereof, CD38 knockout, and HLA-I and/or HLA-II deficiency; and a therapeutic antibody as described above. In various embodiments of said combination, the CAR targets a solid tumor antigen as set forth herein. In various embodiments of said combination, the exogenous CD16 is hnCD16. Without being limited by the theory, hnCD16 provides enhanced ADCC of the monoclonal antibody, whereas the CAR not only targets a specific tumor antigen but also prevents tumor antigen escape using a dual targeting strategy in combination with a monoclonal antibody targeting a different tumor antigen.

12. Checkpoint Inhibitors

Checkpoints are cell molecules, often cell surface molecules, capable of suppressing or downregulating immune responses when not inhibited. It is now clear that tumors co-opt certain immune-checkpoint pathways as a major mechanism of immune resistance, particularly against T cells that are specific for tumor antigens. Checkpoint inhibitors (CIs) are antagonists capable of reducing checkpoint gene expression or gene products, or deceasing activity of checkpoint molecules, thereby blocking inhibitory checkpoints, and restoring immune system function. The development of checkpoint inhibitors targeting PD1/PDL1 or CTLA4 has transformed the oncology landscape, with these agents providing long term remissions in multiple indications. However, many tumor subtypes are resistant to checkpoint blockade therapy, and relapse remains a significant concern. Thus, one aspect of the present application provides a therapeutic approach to overcome CI resistance by including genomically-engineered functional iPSC-derived cells as provided herein in a combination therapy with CI. In one embodiment of the combination therapy described herein, the iPSC-derived cells are NK cells. In another embodiment of the combination therapy described herein, the iPSC-derived cells are T cells. In addition to exhibiting direct antitumor capacity, the derivative NK cells provided herein have been shown to resist PDL1-PD1 mediated inhibition, and to have the ability to enhance T cell migration, to recruit T cells to the tumor microenvironment, and to augment T cell activation at the tumor site. Therefore, the tumor infiltration of T cells facilitated by the functionally potent genomically engineered derivative NK cells indicate that said NK cells are capable of synergizing with T cell targeted immunotherapies, including the checkpoint inhibitors, to relieve local immunosuppression and to reduce tumor burden.

In some embodiments of the combination therapy, the checkpoint inhibitor is used in combination with a population of the effector cells comprising a solid tumor targeting backbone as described herein by concurrent or consecutive administration thereof to a subject. In some other embodiments, the checkpoint inhibitor is expressed by the effector cells by genetically engineering an iPSC using an exogenous polynucleotide sequence encoding said checkpoint inhibitor, or a fragment or variant thereof, and directing differentiation of the engineered iPSC. Some embodiments of the combination therapy with the effector cells comprising a solid tumor targeting backbone as described herein, comprise at least one checkpoint inhibitor to target at least one checkpoint molecule; wherein the effector cells have a genotype listed in Table 4.

In one embodiment, the iPSC-derived effector cell for checkpoint inhibitor combination therapy comprises a solid tumor targeting backbone comprising polynucleotides encoding two or more of a C—X—C-motif chemokine receptor or a variant thereof, a TGFβ-SRR, and an ADR specific to 4-1BB, and optionally one or more additional genetic modifications as provided in Table 4. In some embodiments, the iPSC-derived effector cell for checkpoint inhibitor combination therapy comprises a solid tumor targeting backbone as provided herein, and optionally one, two, three, four, five or more of: a CAR, exogenous CD16 expression, CFR expression, HLA-I and/or HLA-II deficiency, CD38 knockout, and cytokine signaling complex expression; wherein when B2M is knocked out, a polynucleotide encoding HLA-G or knockout of one or both of CD58 and CD54 is optionally included. In some embodiments, the derivative NK cell comprises any one of the genotypes listed in Table 4. In some embodiments, the above derivative effector cell comprising a solid tumor targeting backbone as provided herein additionally comprises deletion, disruption, or reduced expression of at least one of TAP1, TAP2, Tapasin, NLRC5, PD1, LAG3, TIM3, RFXANK, RFX5, RFXAP, RAG1, and any gene in the chromosome 6p21 region; or introduction of at least one of HLA-E, 4-1BBL, CD3, CD4, CD8, CD47, CD113, CD131, CD137, CD80, PDL1, $A_{2A}R$, CAR, Fc receptor, and surface triggering receptor for coupling with bi-, multi-specific or universal engagers.

In various embodiments, the derivative effector cell is obtained from differentiating an iPSC clonal line comprising a solid tumor targeting backbone comprising polynucleotides encoding two or more of a C—X—C-motif chemokine receptor or a variant thereof, a TGFβ-SRR, and an ADR specific to 4-1BB, and optionally one, two, three, four, five or more of: CAR expression, CFR expression, exogenous CD16 expression, HLA-I and/or HLA-II deficiency, CD38 knockout, and cytokine signaling complex expression; wherein when B2M is knocked out, a polynucleotide encoding HLA-G or knockout of one or both of CD58 and CD54 is optionally introduced. In some embodiments, the above-described iPSC clonal line comprising a solid tumor targeting backbone provided herein further comprises deletion, disruption, or reduced expression of at least one of TAP1, TAP2, Tapasin, NLRC5, PD1, LAG3, TIM3, RFXANK, RFX5, RFXAP, RAG1, and any gene in the chromosome 6p21 region; or introduction of at least one of HLA-E, 4-1BBL, CD3, CD4, CD8, CD47, CD113, CD131, CD137, CD80, PDL1, $A_{2A}R$, CAR, Fc receptor, and surface triggering receptor for coupling with bi-, multi-specific or universal engagers.

Suitable checkpoint inhibitors for combination therapy with the derivative NK or T cells as provided herein include, but are not limited to, antagonists of PD1 (Pdcd1, CD279), PDL-1 (CD274), TIM3 (Havcr2), TIGIT (WUCAM and Vstm3), LAG3 (CD223), CTLA4 (CD152), 2B4 (CD244), 4-1BB (CD137), 4-1BBL (CD137L), $A_{2A}R$, BATE, BTLA, CD39 (Entpd1), CD47, CD73 (NT5E), CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

In some embodiments, the antagonist inhibiting any of the above checkpoint molecules is an antibody. In some embodiments, the checkpoint inhibitory antibodies may be murine antibodies, human antibodies, humanized antibodies, a camel Ig, a single variable new antigen receptor (VNAR), a shark heavy-chain-only antibody (Ig NAR), chimeric antibodies, recombinant antibodies, or antibody fragments thereof. Non-limiting examples of antibody fragments include Fab, Fab', F(ab')2, F(ab')3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the one, or two, or three, or more checkpoint inhibitors comprise at least one of atezolizumab (anti-PDL1 mAb), avelumab (anti-PDL1 mAb), durvalumab (anti-PDL1 mAb), tremelimumab (anti-CTLA4 mAb), ipilimumab (anti-CTLA4 mAb), IPH4102 (anti-KIR antibody), IPH43 (anti-MICA antibody), IPH33 (anti-TLR3 antibody), lirimumab (anti-KIR antibody), monalizumab (anti-NKG2A antibody), nivolumab (anti-PD1 mAb), pembrolizumab (anti-PD1 mAb), and any derivatives, functional equivalents, or biosimilars thereof.

In some embodiments, the antagonist inhibiting any of the above checkpoint molecules is microRNA-based, as many miRNAs are found as regulators that control the expression of immune checkpoints (Dragomir et al., Cancer Biol Med. 2018, 15(2):103-115). In some embodiments, the checkpoint antagonistic miRNAs include, but are not limited to, miR-28, miR-15/16, miR-138, miR-342, miR-20b, miR-21, miR-130b, miR-34a, miR-197, miR-200c, miR-200, miR-17-5p, miR-570, miR-424, miR-155, miR-574-3p, miR-513, and miR-29c.

Some embodiments of the combination therapy with the provided iPSC-derived effector cells comprise at least one checkpoint inhibitor to target at least one checkpoint molecule; wherein the iPSC-derived cells have a genotype listed in Table 4. Some other embodiments of the combination therapy with the provided derivative effector cells comprise two, three or more checkpoint inhibitors such that two, three, or more checkpoint molecules are targeted. In some embodiments of the combination therapy comprising at least one checkpoint inhibitor and the iPSC-derived cells having a genotype listed in Table 4, said checkpoint inhibitor is an antibody, or a humanized or Fc modified variant or fragment, or a functional equivalent or biosimilar thereof, and said checkpoint inhibitor is produced by the iPSC-derived cells by expressing an exogenous polynucleotide sequence encoding said antibody, or a fragment or variant thereof. In some embodiments, the exogenous polynucleotide sequence encoding the antibody, or a fragment or a variant thereof that inhibits a checkpoint is co-expressed with a CAR, either in separate constructs or in a bi- or tri-cistronic construct comprising both the CAR and the sequence encoding the antibody, or the fragment thereof. In some further embodiments, the sequence encoding the antibody or the fragment thereof can be linked to either the 5' or the 3' end of a CAR expression construct through a self-cleaving 2A coding sequence, illustrated as, for example, CAR-2A-CI or CI-2A-CAR. As such, the coding sequences of the checkpoint inhibitor and the CAR may be in a single open reading frame (ORF). When the checkpoint inhibitor is delivered, expressed and secreted as a payload by the derivative effector cells capable of infiltrating the tumor microenvironment (TME), it counteracts the inhibitory checkpoint molecule upon engaging the TME, allowing activation of the effector cells by activating modalities such as CAR or activating receptors. In some embodiments, the checkpoint inhibitor co-expressed with CAR inhibits at least one of the checkpoint molecules: PD-1, PDL-1, TIM-3, TIGIT, LAG-3, CTLA-4, 2B4, 4-1BB, 4-1BBL, $A_{2A}R$, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR. In some embodiments, the checkpoint inhibitor co-expressed with CAR in a derivative cell having a genotype listed in Table 4 comprises atezolizumab, avelumab, durvalumab, tremelimumab, ipilimumab, IPH4102, IPH43, IPH33, lirimumab, monalizunab, nivolumab, pembrolizumab, or their humanized, or Fc modified variants, fragments and their functional equivalents or biosimilars. In some embodiments, the checkpoint inhibitor co-expressed with CAR is atezolizumab, or its humanized, or Fc modified variants, fragments or their functional equivalents or biosimilars. In some other embodiments, the checkpoint inhibitor co-expressed with CAR is nivolumab, or its humanized, or Fc modified variants, fragments or their functional equivalents or biosimilars. In some other embodiments, the checkpoint inhibitor co-expressed with CAR is pembrolizumab, or its humanized, or Fc modified variants, fragments or their functional equivalents or biosimilars.

In some other embodiments of the combination therapy comprising the iPSC-derived cells comprising a solid tumor targeting backbone as provided herein and at least one antibody inhibiting a checkpoint molecule, said antibody is not produced by, or in, the iPSC-derived cells and is additionally administered before, with, or after the administering of the derivative cells having a genotype listed in Table 4. In some embodiments, the administering of one, two, three or more checkpoint inhibitors in a combination therapy with the provided derivative effector cells are simultaneous or sequential. In one embodiment of the combination treatment comprising derived NK cells or T cells having a genotype listed in Table 4, the checkpoint inhibitor included in the treatment is one or more of atezolizumab, avelumab, durvalumab, tremelimumab, ipilimumab, IPH4102, IPH43, IPH33, lirimumab, monalizunab, nivolumab, pembrolizunab, and their humanized or Fc modified variants, fragments and their functional equivalents or biosimilars. In some embodiments of the combination treatment comprising derived NK cells or T cells having a genotype listed in Table 4, the checkpoint inhibitor included in the treatment is atezolizumab, or its humanized or Fc modified variant, fragment and its functional equivalent or biosimilar. In some embodiments of the combination treatment comprising derived NK cells or T cells having a genotype listed in Table 4, the checkpoint inhibitor included in the treatment is nivolumab, or its humanized or Fc modified variant, fragment or its functional equivalent or biosimilar. In some embodiments of the combination treatment comprising derived NK cells or T cells having a genotype listed in Table 4, the checkpoint inhibitor included in the treatment is pembrolizumab, or its humanized or Fc modified variant, fragment or its functional equivalent or biosimilar.

II. Methods for Targeted Genome Editing at Selected Locus in iPSCs

Genome editing, or genomic editing, or genetic editing, as used interchangeably herein, is a type of genetic engineering in which DNA is inserted, deleted, and/or replaced in the genome of a targeted cell. Targeted genome editing (interchangeable with "targeted genomic editing" or "targeted genetic editing") enables insertion, deletion, and/or substitution at pre-selected sites in the genome. When an endogenous sequence is deleted at the insertion site during targeted editing, an endogenous gene comprising the affected sequence may be knocked-out or knocked-down due to the sequence deletion. Therefore, targeted editing may also be used to disrupt endogenous gene expression with precision. Similarly used herein is the term "targeted integration," referring to a process involving insertion of one or more exogenous sequences, with or without deletion of an endogenous sequence at the insertion site. In comparison, randomly integrated genes are subject to position effects and silencing, making their expression unreliable and unpredictable. For example, centromeres and sub-telomeric regions are particularly prone to transgene silencing. Reciprocally, newly integrated genes may affect the surrounding endogenous genes and chromatin, potentially altering cell behavior or favoring cellular transformation. Therefore, inserting exogenous DNA in a pre-selected locus such as a safe harbor locus, or genomic safe harbor (GSH) is important for safety, efficiency, copy number control, and for reliable gene response control.

Targeted editing can be achieved either through a nuclease-independent approach, or through a nuclease-dependent approach. In the nuclease-independent targeted editing approach, homologous recombination is guided by homologous sequences flanking an exogenous polynucleotide to be inserted, through the enzymatic machinery of the host cell.

Alternatively, targeted editing could be achieved with higher frequency through specific introduction of double strand breaks (DSBs) by specific rare-cutting endonucleases. Such nuclease-dependent targeted editing utilizes DNA repair mechanisms including non-homologous end joining (NHEJ), which occurs in response to DSBs. Without a donor vector containing exogenous genetic material, the NHEJ often leads to random insertions or deletions (in/dels) of a small number of endogenous nucleotides. In comparison, when a donor vector containing exogenous genetic material flanked by a pair of homology arms is present, the exogenous genetic material can be introduced into the genome during homology directed repair (HDR) by homologous recombination, resulting in a "targeted integration." In some situations, the targeted integration site is intended to be within a coding region of a selected gene, and thus the targeted integration could disrupt the gene expression, resulting in simultaneous knock-in and knock-out (KI/KO) in one single editing step.

Inserting one or more transgenes at a selected position in a gene locus of interest (GOI) to knock-out the gene at the same time can be achieved. Gene loci suitable for simultaneous knock-in and knockout (KI/KO) include, but are not limited to, B2M, TAP1, TAP2, tapasin, NLRC5, CIITA, RFXANK, RFX5, RFXAP, TCR α or β constant region, NKG2A, NKG2D, CD38, CD25, CD69, CD71, CD44, CD58, CD54, CD56, CIS, CBL-B, SOCS2, PD1, CTLA4, LAG3, TIM3, and TIGIT. With respective site-specific targeting homology arms for position-selective insertion, it allows the transgene(s) to express either under an endogenous promoter at the site or under an exogenous promoter comprised in the construct. When two or more transgenes are to be inserted at a selected location in CD38 locus, a linker sequence, for example, a 2A linker or IRES, is placed between any two transgenes. The 2A linker encodes a self-cleaving peptide derived from, e.g., FMDV, ERAV, PTV-I, or TaV (referred to as "F2A", "E2A", "P2A", and "T2A", respectively), allowing for separate proteins to be produced from a single translation. In some embodiments, insulators are included in the construct to reduce the risk of transgene and/or exogenous promoter silencing. In various embodiments, the exogenous promoter may be CAG, or other constitutive, inducible, temporal-, tissue-, or cell type-specific promoters including, but not limited to CMV, EF1α, PGK, and UBC.

Available endonucleases capable of introducing specific and targeted DSBs include, but are not limited to, zinc-finger nucleases (ZFN), transcription activator-like effector nucleases (TALEN), RNA-guided CRISPR (Clustered Regular Interspaced Short Palindromic Repeats) systems. Additionally, the DICE (dual integrase cassette exchange) system utilizing phiC31 and Bxb1 integrases is also a promising tool for targeted integration.

ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but are not limited to, $C_2H_2$ zinc fingers, $C_3H$ zinc fingers, and $C_4$ zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A "selected" zinc finger domain is a domain not found in nature whose production results primarily from an empirical process such as phage display, interaction trap or hybrid selection. ZFNs are described in greater detail in U.S. Pat. Nos. 7,888,121 and 7,972,854, the complete disclosures of which are incorporated herein by reference. The most recognized example of a ZFN in the art is a fusion of the FokI nuclease with a zinc finger DNA binding domain.

A TALEN is a targeted nuclease comprising a nuclease fused to a TAL effector DNA binding domain. By "transcription activator-like effector DNA binding domain", "TAL effector DNA binding domain", or "TALE DNA binding domain", it is meant the polypeptide domain of TAL effector proteins that is responsible for binding of the TAL effector protein to DNA. TAL effector proteins are secreted by plant pathogens of the genus Xanthomonas during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Pub. No. 2011/0145940, which is herein incorporated by reference. The most recognized example of a TALEN in the art is a fusion polypeptide of the FokI nuclease to a TAL effector DNA binding domain.

Another example of a targeted nuclease that finds use in the subject methods is a targeted Spo11 nuclease, a polypeptide comprising a Spo11 polypeptide having nuclease activity fused to a DNA binding domain, e.g., a zinc finger DNA binding domain, a TAL effector DNA binding domain, etc. that has specificity for a DNA sequence of interest.

Additional examples of targeted nucleases suitable for embodiments of the present invention include, but not limited to Bxb1, phiC31, R4, PhiBT1, and Wβ/SPBc/TP901-1, whether used individually or in combination.

Other non-limiting examples of targeted nucleases include naturally occurring and recombinant nucleases; CRISPR related nucleases from families including cas, cpf, cse, csy, csn, csd, cst, csh, csa, csm, and cmr; restriction endonucleases; meganucleases; homing endonucleases, and the like.

Using Cas9 as an example, CRISPR/Cas9 requires two major components: (1) a Cas9 endonuclease and (2) the crRNA-tracrRNA complex. When co-expressed, the two components form a complex that is recruited to a target DNA sequence comprising PAM and a seeding region near PAM. The crRNA and tracrRNA can be combined to form a chimeric guide RNA (gRNA) to guide Cas9 to target selected sequences. These two components can then be delivered to mammalian cells via transfection or transduction.

DICE-mediated insertion uses a pair of recombinases, for example, phiC31 and Bxb1, to provide unidirectional integration of an exogenous DNA that is tightly restricted to each enzymes' own small attB and attP recognition sites. Because these target att sites that are not naturally present in mammalian genomes, they must be first introduced into the genome, at the desired integration site. See, for example, U.S. Pub. No. 2015/0140665, the disclosure of which is incorporated herein by reference.

One aspect of the present invention provides a construct comprising one or more exogenous polynucleotides for targeted genome integration. In one embodiment, the construct further comprises a pair of homologous arms specific to a desired integration site, and the method of targeted integration comprises introducing the construct to cells to enable site specific homologous recombination by the cell host enzymatic machinery. In another embodiment, the method of targeted integration in a cell comprises introducing a construct comprising one or more exogenous polynucleotides to the cell and introducing a ZFN expression cassette comprising a DNA-binding domain specific to a desired integration site to the cell to enable a ZFN-mediated insertion. In yet another embodiment, the method of targeted integration in a cell comprises introducing a construct comprising one or more exogenous polynucleotides to the cell and introducing a TALEN expression cassette comprising a DNA-binding domain specific to a desired integration site to the cell to enable a TALEN-mediated insertion. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration.

Promising sites for targeted integration include, but are not limited to, safe harbor loci, or genomic safe harbor (GSH), which are intragenic or extragenic regions of the human genome that, theoretically, are able to accommodate predictable expression of newly integrated DNA without adverse effects on the host cell or organism. A useful safe harbor must permit sufficient transgene expression to yield desired levels of the vector-encoded protein or non-coding RNA. A safe harbor also must not predispose cells to malignant transformation nor alter cellular functions. For an integration site to be a potential safe harbor locus, it ideally needs to meet criteria including, but not limited to: absence of disruption of regulatory elements or genes, as judged by sequence annotation; is an intergenic region in a gene dense area, or a location at the convergence between two genes transcribed in opposite directions; keep distance to minimize the possibility of long-range interactions between vector-encoded transcriptional activators and the promoters of adjacent genes, particularly cancer-related and microRNA genes; and has apparently ubiquitous transcriptional activity, as reflected by broad spatial and temporal expressed sequence tag (EST) expression patterns, indicating ubiquitous transcriptional activity. This latter feature is especially important in stem cells, where during differentiation, chromatin remodeling typically leads to silencing of some loci and potential activation of others. Within the region suitable for exogenous insertion, a precise locus chosen for insertion should be devoid of repetitive elements and conserved sequences and to which primers for amplification of homology arms could easily be designed.

Suitable sites for human genome editing, or specifically, targeted integration, include, but are not limited to, the adeno-associated virus site 1 (AAVS1), the chemokine (CC motif) receptor 5 (CCR5) gene locus and the human orthologue of the mouse ROSA26 locus. Additionally, the human orthologue of the mouse H11 locus may also be a suitable site for insertion using the composition and method of targeted integration disclosed herein. Further, collagen and HTRP gene loci may also be used as safe harbor for targeted integration. However, validation of each selected site has been shown to be necessary especially in stem cells for specific integration events, and optimization of insertion strategy including promoter election, exogenous gene sequence and arrangement, and construct design is often needed.

For targeted in/dels, the editing site is often comprised in an endogenous gene whose expression and/or function is intended to be disrupted. In some embodiments, the endogenous gene comprising a targeted in/del is associated with immune response regulation and modulation. In some other embodiments, the endogenous gene comprising a targeted in/del is associated with targeting modality, receptors, signaling molecules, transcription factors, drug target candidates, immune response regulation and modulation, or proteins suppressing engraftment, trafficking, homing, viability, self-renewal, persistence, and/or survival of stem cells and/or progenitor cells, and the derived cells therefrom.

As such, another aspect of the present invention provides a method of targeted integration in a selected locus including genome safe harbor or a preselected locus known or proven to be safe and well-regulated for continuous or temporal gene expression such as the B2M, TAP1, TAP2, Tapasin, TRAC, or CD38 locus as provided herein. In one embodiment, the genome safe harbor for the method of targeted integration comprises one or more desired integration site comprising AAVS1, CCR5, ROSA26, collagen, HTRP, H11, beta-2 microglobulin, CD38, GAPDH, TCR or RUNX1, or other loci meeting the criteria of a genome safe harbor. In one embodiment, the method of targeted integration in a cell comprises introducing a construct comprising one or more exogenous polynucleotides to the cell, and introducing a construct comprising a pair of homologous arms specific to a desired integration site and one or more exogenous sequence, to enable site specific homologous recombination by the cell host enzymatic machinery, wherein the desired integration site comprises AAVS1, CCR5, ROSA26, collagen, HTRP, H11, GAPDH, TCR or RUNX1, or other loci meeting the criteria of a genome safe harbor. Additional integration sites include an endogenous gene locus intended for disruption, such as reduction or knockout, which comprises B2M, TAP1, TAP2, tapasin, NLRC5, CIITA, RFXANK, RFX5, RFXAP, TCR α or β constant region, NKG2A, NKG2D, CD38, CD25, CD69, CD71, CD44, CD54, CD56, CD58, CIS, CBL-B, SOCS2, PD1, CTLA4, LAG3, TIM3, or TIGIT.

In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT.

Further, as provided herein, the above method for targeted integration in a safe harbor is used to insert any polynucleotide of interest, for example, polynucleotides encoding safety switch proteins, targeting modality, receptors, signaling molecules, transcription factors, pharmaceutically active proteins and peptides, drug target candidates, and proteins promoting engraftment, trafficking, homing, viability, self-renewal, persistence, and/or survival of stem cells and/or progenitor cells. In some other embodiments, the construct comprising one or more exogenous polynucleotides further comprises one or more marker genes. In one embodiment, the exogenous polynucleotide in a construct of the invention is a suicide gene encoding a safety switch protein. Suitable suicide gene systems for induced cell death include, but not limited to Caspase 9 (or caspase 3 or 7) and AP1903; thymidine kinase (TK) and ganciclovir (GCV); cytosine deaminase (CD) and 5-fluorocytosine (5-FC). Additionally, some suicide gene systems are cell type specific, for example, the genetic modification of T lymphocytes with the B-cell molecule CD20 allows their elimination upon administration of mAb Rituximab. Further, modified EGFR containing epitope recognized by cetuximab can be used to deplete genetically engineered cells when the cells are exposed to cetuximab. As such, one aspect of the invention provides a method of targeted integration of one or more suicide genes encoding safety switch proteins selected from caspase 9 (caspase 3 or 7), thymidine kinase, cytosine deaminase, modified EGFR, and B cell CD20.

In some embodiments, one or more exogenous polynucleotides integrated by the method described herein are driven by operatively-linked exogenous promoters comprised in the construct for targeted integration. The promoters may be inducible, or constructive, and may be temporal-, tissue- or cell type-specific. Suitable constructive promoters for methods of the invention include, but not limited to, cytomegalovirus (CMV), elongation factor 1α (EF1α), phosphoglycerate kinase (PGK), hybrid CMV enhancer/chicken β-actin (CAG) and ubiquitin C (UBC) promoters. In one embodiment, the exogenous promoter is CAG.

The exogenous polynucleotides integrated by the method described herein may be driven by endogenous promoters in the host genome, at the integration site. In one embodiment, the method described herein is used for targeted integration of one or more exogenous polynucleotides at AAVS1 locus in the genome of a cell. In one embodiment, at least one integrated polynucleotide is driven by the endogenous AAVS1 promoter. In another embodiment, the method described herein is used for targeted integration at ROSA26 locus in the genome of a cell. In one embodiment, at least one integrated polynucleotide is driven by the endogenous ROSA26 promoter. In still another embodiment, the method described herein is used for targeted integration at H11 locus in the genome of a cell. In one embodiment, at least one integrated polynucleotide is driven by the endogenous H11 promoter. In another embodiment, the method described herein is used for targeted integration at collagen locus in the genome of a cell. In one embodiment, at least one integrated polynucleotide is driven by the endogenous collagen promoter. In still another embodiment, the method described herein is used for targeted integration at HTRP locus in the genome of a cell. In one embodiment, at least one integrated polynucleotide is driven by the endogenous HTRP promoter. Theoretically, only correct insertions at the desired location would enable gene expression of an exogenous gene driven by an endogenous promoter.

In some embodiments, the one or more exogenous polynucleotides comprised in the construct for the methods of targeted integration are driven by one promoter. In some embodiments, the construct comprises one or more linker sequences between two adjacent polynucleotides driven by the same promoter to provide greater physical separation between the moieties and maximize the accessibility to enzymatic machinery. The linker peptide of the linker sequences may consist of amino acids selected to make the physical separation between the moieties (exogenous polynucleotides, and/or the protein or peptide encoded therefrom) more flexible or more rigid depending on the relevant function. The linker sequence may be cleavable by a protease or cleavable chemically to yield separate moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the moiety with respect to another adjacent moiety for the moieties to function properly. The linker may also be a simple amino acid sequence of a sufficient length to prevent any steric hindrance between the moieties. In addition, the linker sequence may provide for post-translational modification including, but not limited to, e.g., phosphorylation sites, biotinylation sites, sulfation sites, γ-carboxylation sites, and the like. In some embodiments, the linker sequence is flexible so as not to hold the biologically active peptide in a single undesired conformation. The linker may be predominantly comprised of amino acids with small side chains, such as glycine, alanine, and serine, to provide for flexibility. In some embodiments about 80 to 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a 2A linker sequence allows for two separate proteins to be produced from a single translation. Suitable linker sequences can be readily identified empirically. Additionally, suitable size and sequences of linker sequences also can be determined by conventional computer modeling techniques. In one embodiment, the linker sequence encodes a self-cleaving peptide. In one embodiment, the self-cleaving peptide is 2A. In some other embodiments, the linker sequence provides an Internal Ribosome Entry Sequence (IRES). In some embodiments, any two consecutive linker sequences are different.

The method of introducing into cells a construct comprising exogenous polynucleotides for targeted integration can be achieved using a method of gene transfer to cells known per se. In one embodiment, the construct comprises backbones of viral vectors such as adenovirus vectors, adeno-associated virus vectors, retrovirus vectors, lentivirus vectors, or Sendai virus vectors. In some embodiments, the plasmid vectors are used for delivering and/or expressing the exogenous polynucleotides to target cells (e.g., pAl-11, pXT1, pRc/CMV, pRc/RSV, pcDNAI/Neo) and the like. In some other embodiments, the episomal vector is used to deliver the exogenous polynucleotide to target cells. In some embodiments, recombinant adeno-associated viruses (rAAV) can be used for genetic engineering to introduce insertions, deletions or substitutions through homologous recombination. Unlike lentiviruses, rAAVs do not integrate into the host genome. In addition, episomal rAAV vectors mediate homology-directed gene targeting at much higher rates compared to transfection of conventional targeting plasmids. In some embodiments, an AAV6 or AAV2 vector is used to introduce insertions, deletions or substitutions in a target site in the genome of iPSCs. In some embodiments, the genomically modified iPSCs and their derivative cells obtained using the methods and compositions described herein comprise at least one genotype listed in Table 4.

III. Method of Obtaining and Maintaining Genome-Engineered iPSCs

In various embodiments, the present invention also provides a method of obtaining and maintaining genome-engineered iPSCs comprising one or more targeted edits (e.g., multiplex engineering) at one or more desired sites, wherein the one or more targeted edits remain intact and functional in expanded genome-engineered iPSCs or the iPSC-derived non-pluripotent cells at the respective selected editing sites. The targeted editing introduces into the genome of the iPSC, and derivative cells thereof, insertions, deletions, and/or substitutions (i.e., targeted integration and/ or in/dels at selected sites). In comparison to direct engineering of patient-sourced, peripheral blood originated primary effector cells, the many benefits of obtaining genomically-engineered derivative cells through editing and differentiating iPSC as provided herein include, but are not limited to: unlimited source for engineered effector cells; no need for repeated manipulation of the effector cells, especially when multiple engineered modalities are involved; the obtained effector cells are rejuvenated for having elongated telomere and experiencing less exhaustion; the effector cell population is homogeneous in terms of editing site, copy number, and void of allelic variation, random mutations and expression variegation, largely due to the enabled clonal selection in engineered iPSCs as provided herein.

In some embodiments, the genome-engineered iPSCs comprising one or more targeted edits at one or more selected sites are maintained, passaged and expanded as single cells for an extended period in cell maintenance culture medium (FMM), wherein the iPSCs retain the targeted editing and functional modification at the selected site(s). The iPSCs cultured in FMM have been shown to continue to maintain their undifferentiated, and ground or naïve, profile; provide genomic stability without the need for culture cleaning or selection; and readily to give rise to all three somatic lineages, in vitro differentiation via embryoid bodies or monolayer (without formation of embryoid bodies); and by in vivo differentiation via teratoma formation. See, for example, International Pub. No. WO2015/134652, the disclosure of which is incorporated herein by reference.

In some embodiments, the genome-engineered iPSCs comprising one or more targeted integrations and/or in/dels are maintained, passaged and expanded in a medium (FMM) comprising a MEK inhibitor, a GSK3 inhibitor, and a ROCK inhibitor, and free of, or essentially free of, TGFβ receptor/ALK5 inhibitors, wherein the iPSCs retain the intact and functional targeted edits at the selected sites.

Another aspect of the invention provides a method of generating genome-engineered iPSCs through targeted editing of iPSCs; or through first generating genome-engineered non-pluripotent cells by targeted editing, and then reprogramming the selected/isolated genome-engineered non-pluripotent cells to obtain iPSCs comprising the same targeted editing as the non-pluripotent cells. A further aspect of the invention provides genome-engineering non-pluripotent cells which are concurrently undergoing reprogramming by introducing targeted integration and/or targeted in/dels to the cells, wherein the contacted non-pluripotent cells are under sufficient conditions for reprogramming, and wherein the conditions for reprogramming comprise contacting non-pluripotent cells with one or more reprogramming factors and small molecules. In various embodiments of the method for concurrent genome-engineering and reprogramming, the targeted integrations and/or targeted in/dels may be introduced to the non-pluripotent cells prior to, or essentially concomitantly with, initiating reprogramming by contacting the non-pluripotent cells with one or more reprogramming factors and optionally one or more small molecules.

In some embodiments, to concurrently genome-engineer and reprogram non-pluripotent cells, the targeted integrations and/or in/dels may also be introduced to the non-pluripotent cells after the multi-day process of reprogramming is initiated by contacting the non-pluripotent cells with one or more reprogramming factors and small molecules, and wherein the vectors carrying the constructs are introduced before the reprogramming cells present stable expression of one or more endogenous pluripotent genes including but not limited to, SSEA4, Tra181 and CD30.

In some embodiments, the reprogramming is initiated by contacting the non-pluripotent cells with at least one reprogramming factor, and optionally a combination of a TGFβ receptor/ALK inhibitor, a MEK inhibitor, a GSK3 inhibitor and a ROCK inhibitor. In some embodiments, the genome-engineered iPSCs produced through any methods above are further maintained and expanded using a mixture comprising a combination of a MEK inhibitor, a GSK3 inhibitor and a ROCK inhibitor.

In some embodiments of the method of generating genome-engineered iPSCs, the method comprises: genomically engineering an iPSC by introducing one or more targeted integrations and/or in/dels into iPSCs to obtain genome-engineered iPSCs having a genotype provided herein. Alternatively, the method of generating genome-engineered iPSCs comprises: (a) introducing one or more targeted edits into non-pluripotent cells to obtain genome-engineered non-pluripotent cells comprising targeted integrations and/or in/dels at selected sites, and (b) contacting the genome-engineered non-pluripotent cells with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted integrations and/or in/dels at selected sites. Alternatively, the method of generating genome-engineered iPSCs comprises: (a) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate the reprogramming of the non-pluripotent cells; (b) introducing one or more targeted integrations and/or in/dels into the reprogramming non-pluripotent cells for genome-engineering; and (c) obtaining clonal genome-engineered iPSCs comprising the targeted integrations and/or in/dels at selected sites. Any of the above methods may further comprise single cell sorting of the genome-engineered iPSCs to obtain a clonal iPSC, and/or screening for off-target editing and abnormal karyotypes in the genome-engineered iPSCs. Through clonal expansion of the genome-engineered iPSCs, a master cell bank is generated to comprise single cell sorted and expanded clonal engineered iPSCs having at least one phenotype as provided herein. The master cell bank is subsequently cryopreserved, providing a platform for additional iPSC engineering and a renewable source for manufacturing off-the-shelf, engineered, homogeneous cell therapy products, which are well-defined and uniform in composition, and can be mass produced at significant scale in a cost-effective manner.

The reprogramming factors are selected from the group consisting of OCT4, SOX2, NANOG, KLF4, LIN28, C-MYC, ECAT1, UTF1, ESRRB, SV40LT, HESRG, CDH1, TDGF1, DPPA4, DNMT3B, ZIC3, L1TD1, and any combinations thereof as disclosed in International Pub. Nos. WO2015/134652 and WO 2017/066634, the disclosures of which are incorporated herein by reference. The one or more reprogramming factors may be in the form of polypeptides. The reprogramming factors may also be in the form of polynucleotides encoding the reprogramming factors, and thus may be introduced to the non-pluripotent cells by vectors such as, a retrovirus, a Sendai virus, an adenovirus, an episome, a plasmid, and a mini-circle. In some embodiments, the one or more polynucleotides encoding at least one reprogramming factor are introduced by a lentiviral vector. In some embodiments, the one or more polynucleotides are introduced by an episomal vector. In various other embodiments, the one or more polynucleotides are introduced by a Sendai viral vector. In some embodiments, the one or more polynucleotides introduced by a combination of plasmids. See, for example, International Pub. No. WO2019/075057A1, the disclosure of which is incorporated herein by reference.

In some embodiments, the non-pluripotent cells are transfected with multiple constructs comprising different exogenous polynucleotides and/or different promoters by multiple vectors for targeted integration at the same or different selected sites. These exogenous polynucleotides may comprise a suicide gene, or a gene encoding targeting modalities, receptors, signaling molecules, transcription factors, pharmaceutically active proteins and peptides, drug target candidates, or a gene encoding a protein promoting engraftment, trafficking, homing, viability, self-renewal, persistence, and/or survival of the iPSCs or derivative cells thereof. In some embodiments, the exogenous polynucleotides encode RNA, including but not limited to siRNA, shRNA, miRNA and antisense nucleic acids. These exogenous polynucleotides may be driven by one or more promoters selected from the group consisting of constitutive promoters, inducible promoters, temporal-specific promoters, and tissue or cell type specific promoters. Accordingly, the polynucleotides are expressible when under conditions that activate the promoter, for example, in the presence of an inducing agent or in a particular differentiated cell type. In some embodiments, the polynucleotides are expressed in iPSCs and/or in cells differentiated from the iPSCs. In one embodiment, one or more suicide gene is driven by a constitutive promoter, for example Capase-9 driven by CAG. These constructs comprising different exogenous polynucleotides and/or different promoters can be transfected to non-pluripotent cells either simultaneously or consecutively. The non-pluripotent cells subjected to targeted integration of multiple constructs can simultaneously contact the one or more reprogramming factors to initiate the reprogramming concurrently with the genomic engineering, thereby obtaining genome-engineered iPSCs comprising multiple targeted integrations in the same pool of cells. As such, this robust method enables a concurrent reprogramming and engineering strategy to derive a clonal genomically-engineered iPSC with multiple modalities integrated into one or more selected target sites.

IV. A Method of Obtaining Genetically-Engineered Effector Cells by Differentiating Genome-Engineered iPSC A further aspect of the present invention provides a method of in vivo differentiation of genome-engineered iPSCs by teratoma formation, wherein the differentiated cells derived in vivo from the genome-engineered iPSCs retain the intact and functional targeted edits including targeted integration(s) and/or in/dels at the desired site(s). In some embodiments, the differentiated cells derived in vivo from the genome-engineered iPSCs via teratoma formation comprise one or more inducible suicide genes integrated at one or more desired sites comprising AAVS1, CCR5, ROSA26, collagen, HTRP H11, beta-2 microglobulin, CD38, GAPDH, TCR or RUNX1, or other loci meeting the criteria of a genome safe harbor. In some other embodiments, the differentiated cells derived in vivo from the genome-engineered iPSCs via teratoma formation comprise polynucleotides encoding targeting modalities, or encoding proteins promoting trafficking, homing, viability, self-renewal, persistence, and/or survival of stem cells and/or progenitor cells. In some embodiments, the differentiated cells derived in vivo from the genome-engineered iPSCs via teratoma formation comprising one or more inducible suicide genes further comprise one or more in/dels in endogenous genes associated with immune response regulation and mediation. In some embodiments, the in/del is comprised in one or more endogenous checkpoint genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, and TIGIT.

In some embodiments, the genome-engineered iPSCs comprising one or more genetic modifications as provided herein are used to derive hematopoietic cell lineages or any other specific cell types in vitro, wherein the derived non-pluripotent cells retain the functional genetic modifications including targeted editing at the selected site(s). In some embodiments, the genome-engineered iPSCs used to derive hematopoietic cell lineages or any other specific cell types in vitro are master cell bank cells that are cryopreserved and thawed right before their usage. In one embodiment, the genome-engineered iPSC-derived cells include, but are not limited to, mesodermal cells with definitive hemogenic endothelium (HE) potential, definitive HE, CD34+ hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages, wherein the cells derived from the genome-engineered iPSCs retain the functional genetic modifications including targeted editing at the desired site(s).

Applicable differentiation methods and compositions for obtaining iPSC-derived hematopoietic cell lineages include those depicted in, for example, International Pub. No. WO2017/078807, the disclosure of which is incorporated herein by reference. As provided, the methods and compositions for generating hematopoietic cell lineages are through definitive hemogenic endothelium (HE) derived from pluripotent stem cells, including iPSCs under serum-free, feeder-free, and/or stromal-free conditions and in a scalable and monolayer culturing platform without the need of EB formation. Cells that may be differentiated according to the provided methods range from pluripotent stem cells, to progenitor cells that are committed to particular terminally differentiated cells and transdifferentiated cells, and to cells of various lineages directly transitioned to hematopoietic fate without going through a pluripotent intermediate. Similarly, the cells that are produced by differentiating stem cells range from multipotent stem or progenitor cells, to terminally differentiated cells, and to all intervening hematopoietic cell lineages.

The methods for differentiating and expanding cells of the hematopoietic lineage from pluripotent stem cells in monolayer culturing comprise contacting the pluripotent stem cells with a BMP pathway activator, and optionally, bFGF. As provided, the pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (HE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion and homogeneous differentiation of the cells in a population, and is laborious and of low efficiency.

The provided monolayer differentiation platform facilitates differentiation towards definitive hemogenic endothelium resulting in the derivation of hematopoietic stem cells and differentiated progeny such as T, B, NKT and NK cells. The monolayer differentiation strategy combines enhanced differentiation efficiency with large-scale expansion, and enables the delivery of a therapeutically relevant number of pluripotent stem cell-derived hematopoietic cells for various therapeutic applications. Further, monolayer culturing using the methods provided herein leads to functional hematopoietic lineage cells that enable a full range of in vitro differentiation, ex vivo modulation, and in vivo long term hematopoietic self-renewal, reconstitution and engraftment. As provided, the iPSC-derived hematopoietic lineage cells include, but are not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, and neutrophils.

Thus, in various embodiments, the method for directing differentiation of pluripotent stem cells into cells of a definitive hematopoietic lineage, comprises: (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator, wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential.

In some embodiments, the method further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs, or naïve iPSCs, or iPSCs comprising one or more genetic imprints; and the one or more genetic imprints comprised in the iPSCs are retained in the hematopoietic cells differentiated therefrom. In some embodiments of the method for directing differentiation of pluripotent stem cells into cells of a hematopoietic lineage, the differentiation of the pluripotent stem cells into cells of hematopoietic lineage is void of generation of embryoid bodies and is in a monolayer culturing form.

In some embodiments of the above method, the obtained pluripotent stem cell-derived definitive hemogenic endothelium cells are CD34+. In some embodiments, the obtained definitive hemogenic endothelium cells are CD34+CD43−. In some embodiments, the definitive hemogenic endothelium cells are CD34+CD43−CXCR4−CD73−. In some embodiments, the definitive hemogenic endothelium cells are CD34+CXCR4−CD73−. In some embodiments, the definitive hemogenic endothelium cells are CD34+CD43−CD93−. In some embodiments, the definitive hemogenic endothelium cells are CD34+CD93−.

In some embodiments of the above method, the method further comprises (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, and IL7; and optionally a BMP activator; to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, TPO, BMP activators and ROCK inhibitors, to initiate the differentiation of the pre-T cell progenitors to T cell progenitors or T cells. In some embodiments of the method, the pluripotent stem cell-derived T cell progenitors are $CD34^+CD45^+CD7^+$. In some embodiments of the method, the pluripotent stem cell-derived T cell progenitors are $CD45^+CD7^+$.

In yet some embodiments of the above method for directing differentiation of pluripotent stem cells into cells of a hematopoietic lineage, the method further comprises: (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15; and optionally, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, TPO, BMP activators and ROCK inhibitors, to initiate differentiation of the pre-NK cell progenitors to NK cell progenitors or NK cells. In some embodiments, the pluripotent stem cell-derived NK progenitors are $CD3^-CD45^+CD56^+CD7^+$. In some embodiments, the pluripotent stem cell-derived NK cells are $CD3^-CD45^+CD56^+$, and optionally further defined by being $NKp46^+$, $CD57^+$ and $CD16^+$.

In some embodiments, the genome-engineered iPSC-derived cells obtained from the above methods comprise one or more inducible suicide genes integrated at one or more desired integration sites comprising AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, and TIGIT, or other loci meeting the criteria of a genome safe harbor. In some other embodiments, the genome-engineered iPSC-derived cells comprise polynucleotides encoding safety switch proteins, targeting modality, receptors, signaling molecules, transcription factors, pharmaceutically active proteins and peptides, drug target candidates, or proteins promoting trafficking, homing, viability, self-renewal, persistence, and/or survival of stem cells and/ or progenitor cells. In some embodiments, the genome-engineered iPSC-derived cells comprising one or more suicide genes further comprise one or more in/dels comprised in one or more endogenous genes associated with immune response regulation and mediation, including, but not limited to, checkpoint genes, endogenous T cell receptor genes, and MHC class I suppressor genes. In one embodiment, the genome-engineered iPSC-derived cells comprising one or more suicide genes further comprise an in/del in B2M gene, wherein the B2M is knocked-out.

Additionally, applicable dedifferentiation methods and compositions for obtaining genomic-engineered hematopoietic cells of a first fate to genomic-engineered hematopoietic cells of a second fate include those depicted in, for example, International Pub. No. WO2011/159726, the disclosure of which is incorporated herein by reference. The method and composition provided therein allows partially reprogramming a starting non-pluripotent cell to a non-pluripotent intermediate cell by limiting the expression of endogenous Nanog gene during reprogramming; and subjecting the non-pluripotent intermediate cell to conditions for differentiating the intermediate cell into a desired cell type.

V. Therapeutic Use of Derivative Immune Cells with Functional Modalities Differentiated from Genetically Engineered iPSCs The present invention provides, in some embodiments, a composition comprising an isolated population or subpopulation of functionally enhanced derivative immune cells that have been differentiated from genomically engineered iPSCs using the methods and compositions as disclosed. In some embodiments, the iPSCs of the composition comprise one or more targeted genetic edits as disclosed herein, which are retainable in the iPSC-derived effector cells, wherein the genetically engineered iPSCs and derivative cells thereof are suitable for cell-based adoptive therapies. In one embodiment, the isolated population or subpopulation of genetically engineered effector cells of the composition comprises iPSC-derived $CD34^+$ cells. In one embodiment, the isolated population or subpopulation of genetically engineered effector cells of the composition comprises iPSC-derived HSC cells. In one embodiment, the isolated population or subpopulation of genetically engineered effector cells of the composition comprises iPSC-derived proT or T cells. In one embodiment, the isolated population or subpopulation of genetically engineered effector cells of the composition comprises iPSC-derived proNK or NK cells. In one embodiment, the isolated population or subpopulation of genetically engineered effector cells of the composition comprises iPSC-derived immune regulatory cells or myeloid derived suppressor cells (MDSCs).

In some embodiments of the composition, the iPSC-derived genetically engineered effector cells are further modulated ex vivo for improved therapeutic potential. In one embodiment of the composition, an isolated population or subpopulation of genetically engineered effector cells that have been derived from iPSCs comprises an increased number or ratio of naïve T cells, stem cell memory T cells, and/or central memory T cells. In one embodiment of the composition, the isolated population or subpopulation of genetically engineered effector cells that have been derived from iPSCs comprises an increased number or ratio of type I NKT cells. In another embodiment of the composition, the isolated population or subpopulation of genetically engineered effector cells that have been derived from iPSCs comprises an increased number or ratio of adaptive NK cells. In some embodiments of the composition, the isolated population or subpopulation of genetically engineered $CD34^+$ cells, HSC cells, T cells, NK cells, or myeloid derived suppressor cells derived from iPSCs are allogeneic. In some other embodiments of the composition, the isolated population or subpopulation of genetically engineered $CD34^+$ cells, HSC cells, T cells, NK cells, or MDSCs derived from iPSC are autologous.

In some embodiments of the composition, the iPSC for differentiation comprises genetic imprints selected to convey desirable therapeutic attributes in derived effector cells, provided that cell development biology during differentiation is not disrupted, and provided that the genetic imprints are retained and functional in the differentiated hematopoietic cells derived from said iPSC.

In some embodiments of the composition, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC-derived hematopoietic lineage cells.

In some embodiments of the composition, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In some embodiments of the composition, the genetically modified iPSC and the derivative cells thereof comprise a genotype listed in Table 4. In some other embodiments of the composition, the genetically modified iPSC and the derivative cells thereof comprising a genotype listed in Table 4 further comprise additional genetically modified modalities comprising (1) deletion or disruption of B2M, TAP1, TAP2, tapasin, NLRC5, CIITA, RFXANK, RFX5, RFXAP, TCRα or TCRβ constant region (TRAC or TRBC), NKG2A, NKG2D, CD38, CD25, CD69, CD71, CD44, CD54, CD56, CD58, OX40, 4-1BB, CIS, CBL-B, SOCS2, PD1, CTLA4, LAG3, TIM3, or TIGIT; and/or (2) introduction of HLA-E, HLA-G, 4-1BBL, CD3, CD4, CD8, CD47, CD113, CD131, CD137, CD80, PDL1, $A_{2,4}R$, CAR, TCR, Fc receptor, or surface triggering receptors for coupling with bi- or multi-specific or universal engagers.

In still some other embodiments of the composition, the iPSC-derived hematopoietic lineage cells comprise the therapeutic attributes of the source specific immune cell relating to one or more of: (i) increased cytotoxicity; (ii) improved persistency and/or survival; (iii) enhanced ability in migrating, and/or activating or recruiting bystander immune cells, to tumor sites; (iv) improved tumor infiltration; (v) enhanced ability to reduce tumor immunosuppression; (vi) improved ability in rescuing tumor antigen escape; (vii) controlled apoptosis; (viii) enhanced or acquired ADCC; and (ix) ability to avoid fratricide, in comparison to its counterpart primary cell obtained from peripheral blood, umbilical cord blood, or any other donor tissues without the same genetic edit(s). In some embodiments of the composition, the iPSC-derived hematopoietic lineage cells additionally comprise the therapeutic attributes of promoting homing or trafficking and retension of the effector cells at a tumor site.

In some embodiments of the composition, the iPSC-derived hematopoietic cells comprising a genotype listed in Table 4 express at least one cytokine signaling complex comprising all or a portion of IL2, IL4, IL6, IL7, IL9, IL10, IL11, IL12, IL15, IL18, or IL21, or any modified protein thereof, and express at least a CAR, as described herein. In some embodiments of the composition, the cells comprise a solid tumor targeting backbone as provided herein and express at least one cytokine signaling complex comprising IL2, IL4, IL7, IL9, IL15, and IL21. In some embodiments of the composition, the cells comprise a solid tumor targeting backbone as provided herein and express at least one cytokine signaling complex comprising IL7 or IL15. In some embodiments of the composition, the engineered expression of the cytokine(s) and the CAR(s) is NK cell specific. In some other embodiments of the composition, the engineered expression of the cytokine(s) and the CAR(s) is T cell specific. In some embodiments of the composition, the iPSC-derived hematopoietic effector cells are antigen specific. In some embodiments of the composition, the antigen specific derivative effector cells target a liquid tumor. In some embodiments of the composition, the antigen specific derivative effector cells target a solid tumor. In some embodiments of the composition, the antigen specific iPSC-derived hematopoietic effector cells are capable of rescuing tumor antigen escape. Additionally, the present application makes possible a combined therapeutic approach by providing rationally designed effector cells capable of synergize with a tumor sensitizing procedure that upregulates tumor cell expression of a matching chemokine to augment effector cell tumor site homing, trafficking and retention, which contributes to increased effector cell cytotoxicity and persistency.

As provided herein, exposing a tumor cell to a sensitizing agent (e.g., radiation) elevates secretion and/or surface expression of stress ligands including, but limited to, the chemokine IL8, by the tumor cells. Tumor preconditioning by sensitization, as described herein therefore provides an additional strategy to further enhance the therapeutic efficacy of the effector cells overexpressing a C—X—C motif chemokine receptor or a variant thereof. Without being limited by theory, tumor sensitization may be utilized to overcome tumor resistance by modulating potential tumorigenic mechanisms (including, but not limited to cell cycle progression, inflammation, proliferation, apoptosis, invasion, perfusion, metastasis, and angiogenesis) to make the tumor cells more susceptible to activities of another selective drugs, such as the allogeneic effector cells with desired engineered therapeutic attributes as described herein, thereby enhancing the efficacy of the therapeutic effector cells targeting the tumor.

Without being bound by theory, exemplary sensitizing agents useful in compositions and methods disclosed herein include, but are not limited to, radiation therapy, radiopharmaceuticals, or chemotherapeutic agents. Thus, the above-discussed compositions may further comprise a sensitizing agent, as described above. In various embodiments, the sensitizing agent increases secretion and/or surface expression of a chemokine, including CXCL8, by a tumor cell upon contact therewith.

Embodiments of radiation therapy include, but are not limited to, external beam radiation therapy, wherein high-energy beams (e.g., x-rays, gamma rays, photons, protons, neutrons, ions, and any other forms of energy applicable to such treatments) are produced by a machine and aimed at the tumor; brachytherapy, wherein seeds, ribbons, or capsules that contain or are otherwise linked to a radiation source/particle are placed in or near a tumor or cancer cell. Embodiments of radioactive drugs (e.g., radiopharmaceuticals or radionuclides, including radiopeptides) comprise a radioactive compound linked to a targeting molecule (e.g., an antibody conjugate).

In various embodiments, the amount of radiation agent being exposed to, or contacted with, a cancer or tumor cell ranges from about 0.0001 Gy to about 80 Gy. Thus, in some embodiments, the amount of sensitizing agent provided to a subject and/or included in the compositions provided herein is at least about 0.0001 Gy, at least about 0.0005 Gy, at least about 0.001 Gy, at least about 0.0015 Gy, at least about 0.01 Gy, at least about 0.015 Gy, at least about 0.1 Gy, at least about 0.15 Gy, at least about 1.0 Gy, at least about 1.5 Gy, at least about 10.0 Gy, at least about 15 Gy, at least about 20.0 Gy, at least about 25.0 Gy, at least about 30.0 Gy, at least about 35.0 Gy, at least about 40.0 Gy, at least about 45.0 Gy, at least about 50.0 Gy, at least about 55.0 Gy, at least about 60.0 Gy, at least about 65.0 Gy, at least about 70.0 Gy, at least about 75.0 Gy, at least about 80.0 Gy or any range in-between. In some embodiments, the amount of sensitizing agent is about 25.0 Gy.

Examples of radioactive compounds useful as radiopharmaceuticals include, but are not limited to calcium-47, carbon-11, carbon-14, chromium-51, cobalt-57, cobalt-58, erbium-169, fluorine-18, gallium-67, gallium-68, hydrogen-3, indium-111, iodine-123, iodine-125, iodine-131, iorn-59, krypton-81m, lutetium-177, nitrogen-13, oxygen-15, phosphorus-32, radium-223, rubidium-82, samarium-153, selenium-75, sodium-22, sodium-24, strontium-89, technetium-99m, thallium-201, xenon-133, and yttrium-90.

Exemplary chemotherapeutic agents that can be potentially used for tumor cell sensitization include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable chemotherapeutic agents are those that are approved for human use, including those that will be approved, as chemotherapeutics or radiotherapeutics, and known in the art. Such agents can be referenced through any of a number of standard physicians' and oncologists' references (e.g., Goodman & Gilman's The Pharmacological Basis of Therapeutics, Ninth Edition, McGraw-Hill, N.Y., 1995) or through the National Cancer Institute website (fda.gov/cder/cancer/druglistframe.htm), both as updated from time to time.

A variety of diseases may be ameliorated by introducing the derivative effector cells and/or the compositions disclosed herein to a subject suitable for adoptive cell therapy. In some embodiments, the iPSC-derived hematopoietic cells or the compositions as provided herein are for allogeneic adoptive cell therapies. Additionally, the present invention provides, in some embodiments, therapeutic use of the above immune cells and/or therapeutic compositions and/or combination therapies by introducing the cells or composition to a subject suitable for adoptive cell therapy, wherein the subject has an autoimmune disorder; a hematological malignancy; a solid tumor; or an infection associated with HIV, RSV, EBV, CMV, adenovirus, or BK polyomavirus.

Examples of hematological malignancies include, but are not limited to, acute and chronic leukemias (acute myelogenous leukemia (AML), acute lymphoblastic leukemia (ALL), chronic myelogenous leukemia (CML), lymphomas, non-Hodgkin lymphoma (NHL), Hodgkin's disease, multiple myeloma, and myelodysplastic syndromes. Examples of solid cancers include, but are not limited to, bladder cancer, bone cancer, brain/CNS cancer, breast cancer, breast lung cancer, cervical cancer, colorectal cancer, esophageal cancer, gastric/stomach cancer, head and neck cancer, kidney cancer, larynx cancer, liver cancer, lung cancer, metastatic cancer, ovarian cancer, pancreatic cancer, prostate cancer, rectal cancer, renal cancer, salivary gland cancer, skin cancer, testicular tumor, thyroid tumor, urothelial cancer, and uterine/endometrial cancer. Examples of various autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barre syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's). Examples of viral infections include, but are not limited to, HIV—(human immunodeficiency virus), HSV—(herpes simplex virus), KSHV—(Kaposi's sarcoma-associated herpesvirus), RSV—(Respiratory Syncytial Virus), EBV—(Epstein-Barr virus), CMV—(cytomegalovirus), VZV (Varicella zoster virus), adenovirus-, a lentivirus-, a BK polyomavirus-associated disorders.

The treatment using the derived hematopoietic lineage cells of embodiments disclosed herein, or the compositions provided herein, could be carried out upon symptom presentation, or for relapse prevention. The terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any intervention of a disease in a subject and includes: preventing the disease from occurring in a subject which may be predisposed to the disease but has not yet been diagnosed as having it; and inhibiting the disease, i.e., arresting its development; or relieving the disease, i.e., causing regression of the disease. The therapeutic agent(s) and/or compositions may be administered before, during or after the onset of a disease or an injury. Treatment of ongoing disease, where the treatment stabilizes or reduces the undesirable clinical symptoms of the patient, is also of particular interest. In some embodiments, the subject in need of a treatment has a disease, a condition, and/or an injury that can be contained, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g., a hyperproliferative disorder or a cancer of hematopoietic system, a subject having or at risk of developing a tumor, e.g., a solid tumor, a subject who has or is at risk of having a viral infection or a disease associated with a viral infection.

When evaluating responsiveness to the treatment comprising the derived hematopoietic lineage cells of embodiments disclosed herein, the response can be measured by criteria comprising at least one of: clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST (Response Evalluation Criteria In Solid Tumors) criteria.

The therapeutic composition comprising iPSC-derived effector cells as disclosed herein can be administered to a subject before, during, and/or after other treatments, including sensitization of cancer or tumor cells, as described above. As such a method of combinational therapy can involve the administration or preparation of iPSC-derived effector cells before, during, and/or after the use of one or more additional therapeutic agents. As provided above, the one or more additional therapeutic agents comprise a peptide, a cytokine, a checkpoint inhibitor, an engager, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). The administration of the iPSC-derived immune cells can be separated in time from the administration of an additional therapeutic agent by hours, days, or even weeks. Additionally, or alternatively, the administration can be combined with other biologically active agents or modalities such as, but not limited to, an antineoplastic agent, a non-drug therapy, such as, surgery.

In some embodiments of a combinational cell therapy, the therapeutic combination comprises the iPSC-derived effector cells provided herein and an additional therapeutic agent that is an antibody, or an antibody fragment. In some embodiments, the antibody is a monoclonal antibody. In some embodiments, the antibody may be a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC-derived hematopoietic lineage cells to enhance their killing ability. In some embodiments, the antibodies suitable for combinational treatment as an additional therapeutic agent to the administered iPSC-derived hematopoietic lineage cells include, but are not limited to, anti-CD20 antibodies (e.g., rituximab, veltuzumab, ofatumumab, ublituximab, ocaratuzumab, obinutuzumab), anti-HER2 antibodies (e.g., trastuzumab, pertuzumab), anti-CD52 antibodies (e.g., alemtuzumab), anti-EGFR antibodies (e.g., cetuximab), anti-GD2 antibodies (e.g., dinutuximab), anti-PDL1 antibodies (e.g., avelumab), anti-CD38 antibodies (e.g., daratumumab, isatuximab, MOR202), anti-CD123 antibodies (e.g., 7G3, CSL362), anti-SLAMF7 antibodies (elotuzumab), MICA/B antibodies (7C6, 6F11, 1C2), and their humanized or Fc modified variants or fragments or their functional equivalents or biosimilars. In some embodiments, the present invention provides therapeutic compositions comprising effector cells, including the iPSC-derived hematopoietic lineage cells, having a genotype listed in Table 4 and an additional therapeutic agent that is an antibody, or an antibody fragment, as described above.

In some embodiments, the additional therapeutic agent comprises one or more checkpoint inhibitors. Checkpoints are referred to cell molecules, often cell surface molecules, capable of suppressing or downregulating immune responses when not inhibited. Checkpoint inhibitors are antagonists capable of reducing checkpoint gene expression or gene products, or deceasing activity of checkpoint molecules. Suitable checkpoint inhibitors for combination therapy with the derivative effector cells include, but are not limited to, antagonists of PD1 (Pdcd1, CD279), PDL-1 (CD274), TIM3 (Havcr2), TIGIT (WUCAM and Vstm3), LAG3 (CD223), CTLA4 (CD152), 2B4 (CD244), 4-1BB (CD137), 4-1BBL (CD137L), $A_{2A}R$, BATE, BTLA, CD39 (Entpd1), CD47, CD73 (NT5E), CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

Some embodiments of the combination therapy comprising the provided derivative effector cells further comprise at least one inhibitor targeting a checkpoint molecule. Some other embodiments of the combination therapy with the provided derivative effector cells comprise two, three or more inhibitors such that two, three, or more checkpoint molecules are targeted. In some embodiments, the effector cells for combination therapy as described herein are derivative NK cells as provided. In some embodiments, the effector cells for combination therapy as described herein are derivative T cells. In some embodiments, the derivative NK or T cells for combination therapies are functionally enhanced as provided herein. In some embodiments, the two, three or more checkpoint inhibitors may be administered in a combination therapy with, before, or after the administering of the derivative effector cells. In some embodiments, the two or more checkpoint inhibitors are administered at the same time, or one at a time (sequential). In some embodiments, the present invention provides therapeutic compositions comprising effector cells, including the iPSC-derived effector cells, having a genotype listed in Table 4 and one or more checkpoint inhibitors, as described above.

In some embodiments, the antagonist inhibiting any of the above checkpoint molecules is an antibody. In some embodiments, the checkpoint inhibitory antibodies may be murine antibodies, human antibodies, humanized antibodies, a camel Ig, a single variable new antigen receptor (VNAR), a shark heavy-chain-only antibody (Ig NAR), chimeric antibodies, recombinant antibodies, or antibody fragments thereof. Non-limiting examples of antibody fragments include Fab, Fab', F(ab')2, F(ab')3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the one, or two, or three, or more checkpoint inhibitors comprise at least one of atezolizumab, avelumab, durvalumab, ipilimumab, IPH4102, IPH43, IPH33, lirimumab, monalizumab, nivolumab, pembrolizumab, and their derivatives or functional equivalents.

The combination therapies comprising the derivative effector cells described herein, and one or more check inhibitors are applicable to treatment of liquid and solid cancers, including but not limited to cutaneous T-cell lymphoma, non-Hodgkin lymphoma (NHL), Mycosis fungoides, Pagetoid reticulosis, Sezary syndrome, Granulomatous slack skin, Lymphomatoid papulosis, Pityriasis lichenoides chronica, Pityriasis lichenoides et varioliformis acuta, CD30$^+$ cutaneous T-cell lymphoma, Secondary cutaneous CD30$^+$ large cell lymphoma, non-mycosis fungoides CD30 cutaneous large T-cell lymphoma, Pleomorphic T-cell lymphoma, Lennert lymphoma, subcutaneous T-cell lymphoma, angiocentric lymphoma, blastic NK-cell lymphoma, B-cell Lymphomas, hodgkins lymphoma (HL), Head and neck tumor; Squamous cell carcinoma, rhabdomyocarcoma, Lewis lung carcinoma (LLC), non-small cell lung cancer, esophageal squamous cell carcinoma, esophageal adenocarcinoma, renal cell carcinoma (RCC), colorectal cancer (CRC), acute myeloid leukemia (AML), breast cancer, gastric cancer, prostatic small cell neuroendocrine carcinoma (SCNC), liver cancer, glioblastoma, liver cancer, oral squamous cell carcinoma, pancreatic cancer, thyroid papillary cancer, intrahepatic cholangiocellular carcinoma, hepatocellular carcinoma, bone cancer, metastasis, and nasopharyngeal carcinoma.

In some embodiments, other than the derivative effector cells as provided herein, a combination for therapeutic use comprises one or more additional therapeutic agents comprising a chemotherapeutic agent or a radioactive moiety. "Chemotherapeutic agent" refers to cytotoxic antineoplastic agents, that is, chemical agents which preferentially kill neoplastic cells or disrupt the cell cycle of rapidly proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, examples of which are known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g., Goodman & Gilman's The Pharmacological Basis of Therapeutics, Ninth Edition, McGraw-Hill, N.Y., 1995) or through the National Cancer Institute website (fda.gov/cder/cancer/druglistframe.htm), both as updated from time to time.

Immunomodulatory drugs (IMiDs) such as thalidomide, lenalidomide, and pomalidomide stimulate both NK cells and T cells. As provided herein, IMiDs may be used with the iPSC-derived therapeutic immune cells for cancer treatments.

Other than an isolated population of iPSC-derived hematopoietic lineage cells included in the therapeutic compositions, the compositions suitable for administration to a subject/patient can further include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of embodiments of the present invention (see, e.g., Remington's Pharmaceutical Sciences, 17$^{th}$ ed. 1985, the disclosure of which is hereby incorporated by reference in its entirety).

In one embodiment, the therapeutic composition comprises the iPSC-derived T cells made by the methods and composition disclosed herein. In one embodiment, the therapeutic composition comprises the pluripotent cell derived NK cells made by the methods and composition disclosed herein. In one embodiment, the therapeutic composition comprises the iPSC-derived CD34$^+$ HE cells made by the methods and composition disclosed herein. In one embodiment, the therapeutic composition comprises the pluripotent cell derived HSCs made by the methods and composition disclosed herein. In one embodiment, the therapeutic composition comprises the pluripotent cell derived MDSC made by the methods and composition disclosed herein. A therapeutic composition comprising a population of iPSC-derived hematopoietic lineage cells as disclosed herein can be administered separately by intravenous, intraperitoneal, enteral, or tracheal administration methods or in combination with other suitable compounds to affect the desired treatment goals.

These pharmaceutically acceptable carriers and/or diluents can be present in amounts sufficient to maintain a pH of the therapeutic composition of between about 3 and about 10. As such, a buffering agent can be as much as about 5% on a weight to weight basis of the total composition. Electrolytes such as, but not limited to, sodium chloride and potassium chloride can also be included in the therapeutic composition. In one aspect, the pH of the therapeutic composition is in the range from about 4 to about 10. Alternatively, the pH of the therapeutic composition is in the range from about 5 to about 9, from about 6 to about 9, or from about 6.5 to about 8. In another embodiment, the therapeutic composition includes a buffer having a pH in one of said pH ranges. In another embodiment, the therapeutic composition has a pH of about 7. Alternatively, the therapeutic composition has a pH in a range from about 6.8 to about 7.4. In still another embodiment, the therapeutic composition has a pH of about 7.4.

The invention also provides, in some embodiments, the use of a pharmaceutically acceptable cell culture medium in particular compositions and/or cultures disclosed herein. Such compositions are suitable for administration to human subjects. Generally speaking, any medium that supports the maintenance, growth, and/or health of the iPSC-derived effector cells in accordance with embodiments of the invention are suitable for use as a pharmaceutical cell culture medium. In some embodiments, the pharmaceutically acceptable cell culture medium is a serum free, and/or feeder-free medium. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention and that there are many suitable media known and available to those in the art.

In various embodiments, the iPSC-derived hematopoietic lineage cells can have at least 50%, 60%, 70%, 80%, 90%, 95%, 98%, or 99% T cells, NK cells, NKT cells, proT cells, proNK cells, CD34$^+$ HE cells, HSCs, B cells, myeloid-derived suppressor cells (MDSCs), regulatory macrophages, regulatory dendritic cells, or mesenchymal stromal cells. In some embodiments, the iPSC-derived hematopoietic lineage cells have about 95% to about 100% T cells, NK cells, proT cells, proNK cells, CD34$^+$ HE cells, or myeloid-derived suppressor cells (MDSCs). In some embodiments, the present invention provides therapeutic compositions having purified T cells or NK cells, such as a composition having an isolated population of about 95% T cells, NK cells, proT cells, proNK cells, CD34$^+$ HE cells, or myeloid-derived suppressor cells (MDSCs) to treat a subject in need of the cell therapy.

One aspect of the present application provides a method of treating a subject in need by administering one or more therapeutic doses of effector cells comprising a solid tumor targeting backbone comprising polynucleotides encoding two or more of a C—X—C-motif chemokine receptor or a variant thereof, a TGFβ-SRR, and an ADR specific to 4-1BB, and optionally one, two, three, four, five or more of: CAR expression, CFR expression, exogenous CD16 expression, HLA-I and/or HLA-II modification, CD38 knockout, TCR$^{neg}$ and an exogenous cytokine signaling complex. In some embodiments, the present application provides a method of treating a subject having cancer or a tumor by first sensitizing the cancer or tumor cell in the subject to increase or enhance secretion and/or surface expression of one or more chemokines that are ligands to a C—X—C-motif chemokine receptor, as compared to chemokine secretion and/or surface expression prior to such contacting/exposure. Following sensitization of the cancer or tumor cell, an effector cell or population thereof, as described above, is given/administered to the subject, wherein the effector cell comprises a solid tumor targeting backbone as provided herein, and optionally one or more additional edits described herein, or the effector cell comprises a genotype listed in Table 4. In various embodiments, the effector cell or population thereof may be provided prior to or concurrently with one or more additional therapeutic agents, as described above.

Another aspect of the present application provides a method of treating a subject in need using a combinational cell therapy. In some embodiments of the combinational cell therapy, the method of treating a subject in need comprises administering one or more therapeutic doses of effector cells comprising a solid tumor targeting backbone as provided herein, and optionally one or more other edits described herein, or a genotype listed in Table 4; and one or more therapeutic agents comprising a peptide, a cytokine, a checkpoint inhibitor, an engager, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD), and optionally preconditioning tumor cells in the subject by administering a sensitizing agent. In some embodiments, the combinational cell therapy, or composition used therefor, comprises a population of effector cells derived from genomically engineered iPSCs and one or more therapeutic agents, wherein the engineered iPSCs and the derived effector cells comprise comprise a solid tumor targeting backbone as provided herein, and optionally one or more other edits described herein, or a genotype listed in Table 4. In some embodiments of the method of combinational cell therapy, the method comprises preconditioning tumor cells in the subject by administering a sensitizing agent, wherein the sensitizing agent comprises radiation therapy, radiopharmaceuticals, or chemotherapeutic agents as provided herein. In various embodiments, preconditioning of the tumor cells in the subject occurs prior to, or concurrently with administering the one or more therapeutic doses of effector cells described herein.

As a person of ordinary skill in the art would understand, both autologous and allogeneic hematopoietic lineage cells derived from iPSC based on the methods and compositions provided herein can be used in cell therapies as described above. For autologous transplantation, the isolated population of derived hematopoietic lineage cells are either complete or partial HLA-match with the patient. In another embodiment, the derived hematopoietic lineage cells are not HLA-matched to the subject, wherein the derived hematopoietic lineage cells are NK cells or T cell with HLA-I and/or HLA-II deficiency.

In some embodiments, the number of derived hematopoietic lineage cells in the therapeutic composition is at least $0.1 \times 10^5$ cells, at least $1 \times 10^5$ cells, at least $5 \times 10^5$ cells, at least $1 \times 10^6$ cells, at least $5 \times 10^6$ cells, at least $1 \times 10^7$ cells, at least $5 \times 10^7$ cells, at least $1 \times 10^8$ cells, at least $5 \times 10^8$ cells, at least $1 \times 10^9$ cells, or at least $5 \times 10^9$ cells, per dose. In some embodiments, the number of derived hematopoietic lineage cells in the therapeutic composition is about $0.1 \times 10^5$ cells to about $1 \times 10^6$ cells, per dose; about $0.5 \times 10^6$ cells to about $1 \times 10^7$ cells, per dose; about $0.5 \times 10^7$ cells to about $1 \times 10^8$ cells, per dose; about $0.5 \times 10^8$ cells to about $1 \times 10^9$ cells, per dose; about $1 \times 10^9$ cells to about $5 \times 10^9$ cells, per dose; about $0.5 \times 10^9$ cells to about $8 \times 10^9$ cells, per dose; about $3 \times 10^9$ cells to about $3 \times 10^{10}$ cells, per dose, or any range in-between. Generally, $1 \times 10^8$ cells/dose translates to $1.67 \times 10^6$ cells/kg for a 60 kg patient/subject.

In one embodiment, the number of derived hematopoietic lineage cells in the therapeutic composition is the number of immune cells in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.75 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, at least $30 \times 10^6$ cells/kg of bodyweight, $1 \times 10^8$ cells/kg of bodyweight, $5 \times 10^8$ cells/kg of bodyweight, or $1 \times 10^9$ cells/kg of bodyweight.

In one embodiment, a dose of derived hematopoietic lineage cells is delivered to a subject. In one illustrative embodiment, the effective amount of cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about $8 \times 10^6$ cells/kg, $5 \times 10^6$ cells/kg to about $6 \times 10^6$ cells/kg, $5 \times 10^6$ cells/kg to about $7 \times 10^6$ cells/kg, $5 \times 10^6$ cells/kg to about $8 \times 10^6$ cells/kg, or $6 \times 10^6$ cells/kg to about $8 \times 10^6$ cells/kg, including all intervening doses of cells.

In some embodiments, the therapeutic use of derived hematopoietic lineage cells is a single-dose treatment. In some embodiments, the therapeutic use of derived hematopoietic lineage cells is a multi-dose treatment. In some embodiments, the multi-dose treatment is one dose every day, every 3 days, every 7 days, every 10 days, every 15 days, every 20 days, every 25 days, every 30 days, every 35 days, every 40 days, every 45 days, or every 50 days, or any number of days in-between. In some embodiments, the multi-dose treatment comprises three, four, or five, once-weekly doses. In some embodiments of the multi-dose treatment comprising three, four, or five, once-weekly doses further comprise an observation period for determining whether additional single or multi doses are needed.

The compositions comprising a population of derived hematopoietic lineage cells of embodiments of the invention can be sterile, and can be suitable and ready for administration (i.e., can be administered without any further processing) to human patients/subjects. A cell-based composition that is ready for administration means that the composition does not require any further processing or manipulation prior to transplant or administration to a subject. In other embodiments, the invention provides an isolated population of derived hematopoietic lineage cells that are expanded and/or modulated prior to administration with one or more agents including small chemical molecules. The compositions and methods for modulating immune cells including iPSC-derived effector cells are described in greater detail, for example, in International Pub. No. WO2017/127755, the relevant disclosure of which is incorporated herein by reference. For derived hematopoietic lineage cells that are genetically engineered to express recombinant TCR or CAR, the cells can be activated and expanded using methods as described, for example, in U.S. Pat. No. 6,352,694.

In certain embodiments, the primary stimulatory signal and the co-stimulatory signal for the derived hematopoietic lineage cells can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents such as disclosed in U.S. Pub. Nos. 2004/0101519 and 2006/0034810, the disclosures of which are incorporated by reference, for artificial antigen presenting cells (aAPCs) that are contemplated for use in activating and expanding T lymphocytes in embodiments of the present invention.

Some variation in dosage, frequency, and protocol will necessarily occur depending on the condition of the subject being treated. The person responsible for administration will, in any event, determine the appropriate dose, frequency and protocol for the individual subject.

ILLUSTRATIVE EMBODIMENTS

The present disclosure provides the following illustrative embodiments:

Embodiment 1: A cell or a population thereof, wherein
  (i) the cell is (a) an immune cell; (b) an induced pluripotent cell (iPSC); or (c) a derivative effector cell obtained from differentiating the iPSC; and
  (ii) the cell comprises a solid tumor targeting backbone comprising two or more of:
    (a) a polynucleotide encoding a C—X—C motif chemokine receptor or a variant thereof,
    (b) a polynucleotide encoding a TGFβ signaling redirector receptor (TGFβ-SRR) comprising a partial or full peptide of the extracellular domain (ECD) of transforming growth factor beta receptor (TGFβR); and (c) a polynucleotide encoding an allo-immune defense receptor (ADR).

Embodiment 2: The cell or population thereof of Embodiment 1, wherein the cell has improved trafficking, tumor microenvironment (TME) resistance, and/or alloreactive resistance in solid tumors in comparison to a counterpart cell without the solid tumor targeting backbone.

Embodiment 3: The cell or population thereof of Embodiment 1 or 2, wherein the solid tumor targeting backbone further comprises:
(i) CD38 knockout;
(ii) a polynucleotide encoding an exogenous CD16 or a variant thereof, and
(iii) a polynucleotide encoding a cytokine signaling complex comprising a partial or full peptide of a cell surface expressed exogenous cytokine and/or a receptor thereof.

Embodiment 4: The cell or population thereof of any one of Embodiments 1-3, wherein the cell further comprises one or more of:
(i) a chimeric antigen receptor (CAR);
(ii) HLA-I deficiency and/or HLA-II deficiency;
(iii) introduction of HLA-G or non-cleavable HLA-G;
(iv) disruption of least one of B2M, CIITA, TAP1, TAP2, Tapasin, NLRC5, RFXANK, RFX5, RFXAP, TCR, NKG2A, NKG2D, CD25, CD44, CD54, CD56, CD58, CD69, CIS, CBL-B, SOCS2, PD1, CTLA4, LAG3, TIM3, and TIGIT;
(v) introduction of at least one of HLA-E, 4-1BBL, CD3, CD4, CD8, CD47, CD113, CD131, CD137, CD80, PDL1, $A_{2A}R$, antigen-specific TCR, chimeric fusion receptor (CFR), Fc receptor, an antibody or functional variant or fragment thereof, a checkpoint inhibitor, an engager, and surface triggering receptor for coupling with an agonist; or
(vi) at least one of the genotypes listed in Table 4.

Embodiment 5: The cell or population thereof of any one of Embodiments 1-4, wherein the C—X—C motif chemokine receptor comprises CXCR2 or CXCR3.

Embodiment 6: The cell or population thereof of any one of Embodiments 1-5, wherein the TGFβ-SRR further comprises a partial or full peptide of the intracellular domain (ICD) of a cytokine receptor comprising IL2R, IL12R, IL18R, IL21R, or any combination thereof.

Embodiment 7: The cell or population thereof of Embodiment 6, wherein:
(a) the cytokine receptor is IL2Rβ, thereby forming a TGFβR2-IL2Rβ redirector receptor, and the intracellular domain (ICD) of IL2Rβ comprises an amino acid sequence represented by SEQ ID NO: 11; or
(b) the cytokine receptor is IL12Rβ, thereby forming a TGFβR2-IL12Rβ redirector receptor, and the intracellular domain (ICD) of IL12Rβ comprises an amino acid sequence represented by SEQ ID NO: 12 or SEQ ID NO: 13; or
(c) the cytokine receptor is IL18Rβ, thereby forming a TGFβR2-IL18Rβ redirector receptor, and the intracellular domain (ICD) of IL18Rβ comprises an amino acid sequence represented by SEQ ID NO: 14; or
(d) the cytokine receptor is IL21R, thereby forming a TGFβR2-IL21R redirector receptor, and the intracellular domain (ICD) of IL21Rβ comprises an amino acid sequence represented by SEQ ID NO: 15; or
(e) the extracellular domain (ECD) of TGFβR comprises an amino acid sequence represented by SEQ ID NO: 10.

Embodiment 8: The cell or population thereof of Embodiment 6, wherein the cytokine receptor is a fragment of IL2Rβ, forming a TGFβR2-trIL12Rβ redirector receptor which comprises an amino acid sequence having sequence identity of at least 80%, 85%, 90%, 95%, or 97%, 98%, or 99% to a sequence represented by SEQ ID NO: 16, wherein an amino acid sequence represented by SEQ ID NO: 17 comprised in SEQ ID NO: 16 is variable.

Embodiment 9: The cell or population thereof of any one of Embodiments 1-8, wherein the ADR is specific to 4-1BB or to CD38.

Embodiment 10: The cell or population thereof of any one of Embodiments 1-9, wherein two or more polynucleotides of the solid tumor targeting backbone are inserted at an endogenous CD38 locus to knock out CD38.

Embodiment 11: The cell or population thereof of Embodiment 3, wherein the polynucleotide encoding the exogenous CD16 or variant thereof and two or more polynucleotides of the solid tumor targeting backbone are co-expressed in a tri-cistronic construct.

Embodiment 12: The cell or population thereof of Embodiment 3 or 11, wherein the exogenous CD16 or variant thereof comprises at least one of:
(a) a high affinity non-cleavable CD16 (hnCD16);
(b) F176V and S197P in ectodomain domain of CD16;
(c) a full or partial ectodomain originated from CD64;
(d) a non-native (or non-CD16) transmembrane domain;
(e) a non-native (or non-CD16) intracellular domain;
(f) a non-native (or non-CD16) signaling domain;
(g) a non-native stimulatory domain; and
(h) transmembrane, signaling, and stimulatory domains that are not originated from CD16, and are originated from a same or different polypeptide.

Embodiment 13: The cell or population thereof of any one of Embodiments 3, 11, or 12, wherein the cell further comprises the cytokine signaling complex comprising:
(a) a partial or full peptide of a cell surface expressed exogenous cytokine or a receptor thereof comprising at least one of IL2, IL4, IL6, IL7, IL9, IL10, IL11, IL12, IL15, IL18, IL21, or respective receptor thereof; or
(b) at least one of:
(i) co-expression of IL15 and IL15Rα with a self-cleaving peptide in-between;
(ii) a fusion protein of IL15 and IL15Rα;
(iii) an IL15/IL15Rα fusion protein with intracellular domain of IL15Rα truncated;
(iv) a fusion protein of IL15 and membrane bound Sushi domain of IL15Rα;
(v) a fusion protein of IL15 and IL15Rβ;
(vi) a fusion protein of IL15 and common receptor γC, wherein the common receptor γC is native or modified; and
(vii) a homodimer of IL15Rβ;
wherein any one of (b)(i)-(vii) can be co-expressed with a CAR in separate constructs or in a bi-cistronic construct; or
(c) at least one of:
(i) a fusion protein of IL7 and IL7Rα;
(ii) a fusion protein of IL7 and common receptor γC, wherein the common receptor γC is native or modified; and
(iii) a homodimer of IL7Rβ, wherein any one of (c)(i)-(iii) is optionally co-expressed with a CAR in separate constructs or in a bi-cistronic expression cassette;
and optionally,
(d) is transiently expressed.

Embodiment 14: The cell or a population thereof of Embodiment 4, wherein the cell further comprises a CAR, wherein the CAR is:
  (i) T cell specific or NK cell specific;
  (ii) a bi-specific antigen binding CAR;
  (iii) a switchable CAR;
  (iv) a dimerized CAR;
  (v) a split CAR;
  (vi) a multi-chain CAR;
  (vii) an inducible CAR;
  (viii) co-expressed with another CAR;
  (ix) co-expressed with the cytokine signaling complex in a bi-cistronic construct;
  (x) co-expressed with a checkpoint inhibitor, optionally in separate constructs or in a bi-cistronic construct;
  (xi) specific to at least one tumor associated antigen comprising CD19, B7H3, BCMA, CD20, CD22, CD38, CD123, CD79b, CD52, EGFR, EGP2/EpCAM, GD2, GPRC5D, HER2, KLK2, MICA/B, MSLN, VEGF-R2, PSMA and PDL1; and/or
  (xii) specific to at least one tumor associated antigen comprising ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein-2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-α, Ganglioside G2 (GD2), Ganglioside G3 (GD3), human Epidermal Growth Factor Receptor 2 (HER2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBCI, TRBC2, vascular endothelial growth factor R2 (VEGF-R2), Wilms tumor protein (WT-1), and a pathogen antigen; and optionally,
  wherein the CAR of any one of (i) to (xii) is inserted at a TCR locus, and/or is driven by an endogenous promoter of the TCR, and/or the TCR is knocked out by the CAR insertion.

Embodiment 15: The cell or population thereof of Embodiment 14, wherein the TCR locus is a constant region of TCR alpha and/or TCR beta, and optionally wherein the CAR is operatively linked to an endogenous promoter of TCR.

Embodiment 16: The cell or a population thereof of Embodiment 14 or 15, wherein the CAR comprises:
  (a) an ectodomain comprising an antigen binding domain specific to a tumor associated antigen;
  (b) a transmembrane domain; and
  (c) an endodomain comprising at least one signaling domain;
  wherein the at least one signaling domain responds specifically to binding of the CAR to the tumor associated antigen, thereby generating a cancer antigen specific response.

Embodiment 17: The cell or population thereof of Embodiment 16, wherein the at least one signaling domain comprises:
  (a) any one of: 2B4 (Natural killer Cell Receptor 2B4), 4-1BB (Tumor necrosis factor receptor superfamily member 9), CD28 (T-cell-specific surface glycoprotein CD28), CD3ζ (T-cell surface glycoprotein CD3 zeta chain), DAP10 (Hematopoietic cell signal transducer), DAP12 (TYRO protein tyrosine kinase-binding protein), DNAM1 (CD226 antigen), FcERIγ (High affinity immunoglobulin epsilon receptor subunit gamma), IL21R (Interleukin-21 receptor), IL2Rβ/IL15Rβ (Interleukin-2 receptor subunit beta), IL2Rγ (Cytokine receptor common subunit gamma), IL-7R (Interleukin-7 receptor subunit alpha), KIR2DS2 (Killer cell immunoglobulin-like receptor 2DS2), NKG2D (NKG2-D type II integral membrane protein), NKp30 (Natural cytotoxicity triggering receptor 3), NKp44 (Natural cytotoxicity triggering receptor 2), NKp46 (Natural cytotoxicity triggering receptor 1), CS1 (SLAM family member 7), and CD8 (T-cell surface glycoprotein CD8 alpha chain);
  (b) an amino acid sequence that has at least about 85%, about 90%, about 95%, about 96%, about 97%, about 98%, or about 99% identity to the cytoplasmic domain, or a portion thereof, of 2B4, 41BB, CD16, CD2, CD28, CD28H, CD3ζ, DAP10, DAP12, DNAM1, FcERIγ, IL21R, IL2Rβ (IL15Rβ), IL2Rγ, IL7R, KIR2DS2, NKG2D, NKp30, NKp44, NKp46, CD3ζ1XX, CS1, or CD8, represented by SEQ ID NOs: 54-76, respectively; and/or
  (c) an amino acid sequence that has at least about 85%, about 90%, about 95%, about 96%, about 97%, about 98%, or about 99% identity to the cytoplasmic domain, or a portion thereof, of 2B4, CD28, CD3ζ, DAP10, NKG2D, CD3ζ, CD3ζ1XX, DNAM1, CS1, or combinations thereof.

Embodiment 18: The cell or population thereof of Embodiment 16 or 17, wherein the endodomain comprises two different signaling domains, and wherein said endodomain domain comprises fused cytoplasmic domains, or portions thereof, in any one of the forms: CD28-CD3ζ, CD28-CD3ζ1XX, 41BB-CD3ζ, 41BB-CD3ζ1XX, 2B4-CD3ζ and 2B4-CD3ζ1XX.

Embodiment 19: The cell or population thereof of any one of Embodiments 16-18, wherein the transmembrane domain comprises an amino acid sequence that has at least about 85%, about 90%, about 95%, about 96%, about 97%, about 98%, or about 99% identity to a transmembrane region, or a portion thereof, of CD2, CD3δ, CD38, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide.

Embodiment 20: The cell or population thereof of any one of Embodiments 16-18, wherein the transmembrane domain comprises an amino acid sequence that has at least about 85%, about 90%, about 95%, about 96%, about 97%, about 98%, or about 99% identity to a transmembrane region, or a portion thereof, of 2B4, CD2, CD16, CD28, CD28H, CD3ζ, DAP10, DAP12, DNAM1, FcERIγ, KIR2DS2, NKG2D, NKp30, NKp44, NKp46, CS1, or CD8, represented by SEQ ID NOs: 32-53, respectively.

Embodiment 21: The cell or population thereof of any one of Embodiments 16-20, wherein the transmembrane domain and its immediately linked signaling domain are from a same protein or from different proteins.

Embodiment 22: The cell or population thereof of any one of Embodiments 16-21, wherein the tumor associated antigen comprises HER2, and wherein the CAR comprises:
- (a) an ectodomain comprising an antigen binding domain recognizing a HER2 (human epidermal growth factor receptor 2) antigen, wherein the antigen binding domain comprises:
  - (i) a heavy chain variable (VH) domain comprising a heavy chain complementary determining region 1 (H-CDR1) comprising SEQ ID NO: 103, a heavy chain complementary determining region 2 (H-CDR2) comprising SEQ ID NO: 104, and a heavy chain complementary determining region 3 (H-CDR3) comprising SEQ ID NO: 105; and optionally,
  - (ii) a light chain variable (VL) domain comprising a light chain complementary determining region 1 (L-CDR1) comprising SEQ ID NO: 106, a light chain complementary determining region 2 (L-CDR2) comprising SEQ ID NO: 107, and a light chain complementary determining region 3 (L-CDR3) comprising SEQ ID NO: 108;
- (b) a transmembrane domain; and
- (c) an endodomain comprising at least one signaling domain;
- wherein the at least one signaling domain responds specifically to binding of the CAR to a HER2 antigen expressed on a cancer cell, thereby generating a cancer antigen specific response.

Embodiment 23: The cell or population thereof of Embodiment 22, wherein the antigen binding domain of the CAR:
- (a) comprises a VH domain with at least 80% sequence identity to SEQ ID NO: 109;
- (b) comprises a VL domain with at least 80% sequence identity to SEQ ID NO: 110;
- (c) comprises a single chain variable fragment (scFV) comprising VH-linker-VL or VL-linker-VH, wherein the linker varies in length and sequence, and optionally wherein the linker has at least 80% sequence identity to SEQ ID NOs: 111-114;
- (d) comprises an scFV represented by an amino acid sequence that is of at least about 99%, about 98%, about 96%, about 95%, about 90%, about 85%, or about 80% identity to SEQ ID NO: 115 or SEQ ID NO: 116, wherein each of SEQ ID NOs: 115 and 116 comprises a linker that varies in length and sequence; and/or
- (e) is humanized.

Embodiment 24: The cell or population thereof of Embodiment 22 or 23, wherein the ectodomain comprises one or more of:
- (a) a signal peptide; and/or
- (b) a spacer/hinge.

Embodiment 25: The cell or population thereof of Embodiment 24, wherein the spacer/hinge comprises:
- (a) an IgG4 spacer, a CD28 spacer, a CD8 spacer, a CH3 spacer, a CH2/CH3 spacer, or any combination thereof,
- (b) a short spacer of about 10 to about 80 amino acids; a medium spacer of more than 80 to about 180 amino acids; or a long spacer of more than 180 amino acids; and/or
- (c) an amino acid sequence of at least about 80%, about 85%, about 90%, about 95%, about 96%, about 97%, about 98%, or about 99% identity to any of SEQ ID NOs: 96-100.

Embodiment 26: The cell or population thereof of Embodiment 25, wherein the spacer/hinge comprises a medium spacer, wherein the spacer comprises an amino acid sequence of at least about 80%, about 85%, about 90%, about 95%, about 96%, about 97%, about 98%, or about 99% identity to SEQ ID NO: 99.

Embodiment 27: The cell or population thereof of Embodiment 25, wherein the CAR comprises an amino acid sequence of at least about 90%, about 95%, about 96%, about 97%, about 98%, or about 99% identity to SEQ ID NO: 117.

Embodiment 28: The cell or population thereof of any one of Embodiments 22-27, wherein the cancer cell is a breast cancer cell, an ovary cancer cell, an endometrium cancer cell, a lung cancer cell, an esophageal cancer cell, a salivary gland cancer cell, a bladder cancer cell, a gastric cancer cell, a colorectal cancer cell, or a head and neck cancer cell.

Embodiment 29: The cell or population thereof of any one of Embodiments 1-28, wherein (i) the iPSC is a clonal iPSC, a single cell dissociated iPSC, an iPSC cell line cell, or an iPSC master cell bank (MCB) cell; or (ii) the derivative cell comprises a derivative $CD34^+$ cell, a derivative hematopoietic stem and progenitor cell, a derivative hematopoietic multipotent progenitor cell, a derivative T cell progenitor, a derivative NK cell progenitor, a derivative T lineage cell, a derivative NKT lineage cell, a derivative NK lineage cell, or a derivative B lineage cell; or (iii) the derivative cell comprises a derivative effector cell having one or more functional features that are not present in a counterpart primary T, NK, NKT, and/or B cell.

Embodiment 30: The cell or population thereof of Embodiment 29, wherein the derivative cell has therapeutic properties comprising one or more of:
- (i) increased cytotoxicity;
- (ii) improved persistency and/or survival;
- (iii) enhanced ability in migrating, and/or activating or recruiting bystander immune cells, to tumor sites;
- (iv) improved tumor infiltration;
- (v) enhanced ability to reduce tumor immunosuppression;
- (vi) improved ability in rescuing tumor antigen escape;
- (vii) controlled apoptosis;
- (viii) enhanced or acquired ADCC; and
- (ix) ability to avoid fratricide,
- in comparison to its counterpart primary cell obtained from peripheral blood, umbilical cord blood, or any other donor tissues without the same genetic edit(s).

Embodiment 31: The cell or population thereof of Embodiment 29 or 30, wherein the cell is an NK lineage cell or a T lineage cell, wherein:
- (i) the NK lineage cell or the T lineage cell has improved infiltration and/or retention at tumor sites;
- (ii) the NK lineage cell is capable of recruiting, and/or migrating T cells to tumor sites; or
- (iii) the NK lineage cell or the T lineage cell is capable of reducing tumor immunosuppression in the presence of one or more checkpoint inhibitors.

Embodiment 32: A cell or a population thereof, wherein
- (i) the cell is (a) an immune cell; (b) an induced pluripotent cell (iPSC); or (c) a derivative effector cell obtained from differentiating the iPSC;

(ii) the cell comprises a chimeric antigen receptor (CAR) comprising:
(a) an ectodomain comprising an antigen binding domain recognizing a HER2 (human epidermal growth factor receptor 2) antigen, wherein the antigen binding domain comprises:
(1) a heavy chain variable (VH) domain comprising a heavy chain complementary determining region 1 (H-CDR1) comprising SEQ ID NO: 103, a heavy chain complementary determining region 2 (H-CDR2) comprising SEQ ID NO: 104, and a heavy chain complementary determining region 3 (H-CDR3) comprising SEQ ID NO: 105; and
(2) a light chain variable (VL) domain comprising a light chain complementary determining region 1 (L-CDR1) comprising SEQ ID NO: 106, a light chain complementary determining region 2 (L-CDR2) comprising SEQ ID NO: 107, and a light chain complementary determining region 3 (L-CDR3) comprising SEQ ID NO: 108;
(b) a transmembrane domain; and
(c) an endodomain comprising at least one signaling domain;
wherein the at least one signaling domain responds specifically to binding of the CAR to a HER2 antigen expressed on a cancer cell, thereby generating a cancer antigen specific response.

Embodiment 33: The cell or population thereof of Embodiment 32, wherein the antigen binding domain:
(a) comprises a VH domain with at least 80% sequence identity to SEQ ID NO: 109;
(b) comprises a VL domain with at least 80% sequence identity to SEQ ID NO: 110;
(c) comprises a single chain variable fragment (scFV) comprising VH-linker-VL or VL-linker-VH, wherein the linker varies in length and sequence, and optionally wherein the linker has at least 80% sequence identity to SEQ ID NOs: 111-114;
(d) comprises an scFV represented by an amino acid sequence that is of at least about 99%, about 98%, about 96%, about 95%, about 90%, about 85%, or about 80% identity to SEQ ID NO: 115 or SEQ ID NO: 116, wherein each of SEQ ID NOs: 115 and 116 comprises a linker that varies in length and sequence; and/or
(e) is humanized.

Embodiment 34: The cell or population thereof of Embodiment 32 or 33, wherein the at least one signaling domain comprises:
(a) any one of: 2B4 (Natural killer Cell Receptor 2B4), 4-1BB (Tumor necrosis factor receptor superfamily member 9), CD16 (IgG Fc region Receptor III-A), CD2 (T-cell surface antigen CD2), CD28 (T-cell-specific surface glycoprotein CD28), CD28H (Transmembrane and immunoglobulin domain-containing protein 2), CD3ζ (T-cell surface glycoprotein CD3 zeta chain), DAP10 (Hematopoietic cell signal transducer), DAP12 (TYRO protein tyrosine kinase-binding protein), DNAM1 (CD226 antigen), FcERIγ (High affinity immunoglobulin epsilon receptor subunit gamma), IL21R (Interleukin-21 receptor), IL-2Rβ/IL15Rβ (Interleukin-2 receptor subunit beta), IL-2Rγ (Cytokine receptor common subunit gamma), IL-7R (Interleukin-7 receptor subunit alpha), KIR2DS2 (Killer cell immunoglobulin-like receptor 2DS2), NKG2D (NKG2-D type II integral membrane protein), NKp30 (Natural cytotoxicity triggering receptor 3), NKp44 (Natural cytotoxicity triggering receptor 2), NKp46 (Natural cytotoxicity triggering receptor 1), CS1 (SLAM family member 7), and CD8 (T-cell surface glycoprotein CD8 alpha chain);
(b) an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ, IL21R, IL2Rβ (IL15Rβ), IL2Rγ, IL7R, KIR2DS2, NKG2D, NKp30, NKp44, NKp46, CS1, or CD8, represented by SEQ ID NOs: 54-76, respectively; and/or
(c) an amino acid sequence that has at least about 85%, about 90%, about 95%, about 96%, about 97%, about 98%, or about 99% identity to the cytoplasmic domain, or a portion thereof, of 2B4, CD28, CD3ζ, DAP10, NKG2D, CD3ζ1XX, DNAM1, CS1, or combinations thereof.

Embodiment 35: The cell or population thereof of Embodiment 34, wherein the endodomain comprises two different signaling domains, and wherein said endodomain domain comprises fused cytoplasmic domains, or portions thereof, in any one of the forms: 2B4-CD3ζ/1XX, 2B4-DNAM1, 2B4-FcERIγ, 2B4-DAP10, CD16-DNAM1, CD16-DAP10, CD16-DAP12, CD2-CD3ζ/1XX, CD2-DNAM1, CD2-FcERIγ, CD2-DAP10, CD28-DNAM1, CD28-FcERIγ, CD28-DAP10, CD28-DAP12, CD28-CD3ζ/1XX, CD28H-CD3ζ/1XX, DAP10-CD3ζ/1XX, DAP10-DAP12, DAP12-CD3ζ/1XX, DAP12-DAP10, DNAM1-CD3ζ/1XX, KIR2DS2-CD3ζ/1XX, KIR2DS2-DAP10, KIR2DS2-2B4, or NKp46-2B4.

Embodiment 36: The cell or population thereof of any one of Embodiments 32-35, wherein the transmembrane domain comprises an amino acid sequence that has at least about 85%, about 90%, about 95%, about 96%, about 97%, about 98%, or about 99% identity to a transmembrane region, or a portion thereof, of:
(a) CD2, CD3δ, CD38, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide;
(b) 2B4, CD2, CD16, CD28, CD28H, CD3ζ, DAP10, DAP12, DNAM1, FcERIγ, KIR2DS2, NKG2D, NKp30, NKp44, NKp46, CS1, or CD8; or
(c) 2B4, CD28, CD28H, DAP10, DNAM1, KIR2DS2, and NKG2D.

Embodiment 37: The cell or population thereof of any one of Embodiments 32-36, wherein the transmembrane domain and its immediately linked signaling domain are from a same protein or from different proteins.

Embodiment 38: The cell or population thereof of any one of Embodiments 32-37, wherein the ectodomain comprises one or more of:
(a) a signal peptide; and/or
(b) a spacer/hinge.

Embodiment 39: The cell or population thereof of Embodiment 38, wherein the spacer/hinge comprises:
(a) an IgG4 spacer, a CD28 spacers, a CD8 spacer, a CH3 spacer, a CH2/CH3 spacer, or any combination thereof;
(b) a short spacer of about 10 to about 80 amino acids; a medium spacer of more than 80 to about 180 amino acids; or a long spacer of more than 180 amino acids; and/or (c) an amino acid sequence of at least about 80%, about 85%, about 90%, about 95%, about 96%, about 97%, about 98%, or about 99% identity to any of SEQ ID NOs: 96-100.

Embodiment 40: The cell or population thereof of Embodiment 39, wherein the spacer/hinge comprises a medium spacer, wherein the spacer comprises an amino acid sequence of at least about 80%, about 85%, about 90%, about 95%, about 96%, about 97%, about 98%, or about 99% identity to SEQ ID NO: 99.

Embodiment 41: The cell or population thereof of Embodiment 32, wherein the CAR comprises an amino acid sequence of at least about 90%, about 95%, about 96%, about 97%, about 98%, or about 99% identity to SEQ ID NO: 117.

Embodiment 42: The cell or population thereof of any one of Embodiments 32-41, further comprising a solid tumor targeting backbone comprising at least one of:
 (a) a polynucleotide encoding a C—X—C motif chemokine receptor or a variant thereof;
 (b) a polynucleotide encoding a TGFβ signaling redirector receptor (TGFβ-SRR) comprising a partial or full peptide of the extracellular domain (ECD) of transforming growth factor beta receptor (TGFβR); and
 (c) a polynucleotide encoding an allo-immune defense receptor (ADR).

Embodiment 43: The cell or population thereof of Embodiment 42, wherein the solid tumor targeting backbone further comprises:
 (i) CD38 knockout;
 (ii) a polynucleotide encoding an exogenous CD16 or a variant thereof, and
 (iii) a polynucleotide encoding a cytokine signaling complex comprising a partial or full peptide of a cell surface expressed exogenous cytokine and/or a receptor thereof, Embodiment 44: The cell or population thereof of any one of Embodiments 32-43, wherein the cell further comprises one or more of:
 (i) HLA-I deficiency and/or HLA-II deficiency;
 (ii) introduction of HLA-G or non-cleavable HLA-G;
 (iii) disruption of least one of B2M, CIITA, TAP1, TAP2, Tapasin, NLRC5, RFXANK, RFX5, RFXAP, TCR, NKG2A, NKG2D, CD25, CD44, CD54, CD56, CD58, CD69, CIS, CBL-B, SOCS2, PD1, CTLA4, LAG3, TIM3, and TIGIT;
 (iv) introduction of at least one of HLA-E, 4-1BBL, CD3, CD4, CD8, CD47, CD113, CD131, CD137, CD80, PDL1, $A_{2A}R$, antigen-specific TCR, chimeric fusion receptor (CFR), Fc receptor, an antibody or functional variant or fragment thereof, a checkpoint inhibitor, an engager, and surface triggering receptor for coupling with an agonist; or
 (v) at least one of the genotypes listed in Table 4.

Embodiment 45: The cell or population thereof of any one of Embodiments 42-44, wherein the C—X—C motif chemokine receptor comprises CXCR2 or CXCR3.

Embodiment 46: The cell or population thereof of any one of Embodiments 42-45, wherein the TGFβ-SRR further comprises a partial or full peptide of the intracellular domain (ICD) of a cytokine receptor comprising IL2R, IL12R, IL18R, IL21R, or any combination thereof.

Embodiment 47: The cell or population thereof of Embodiment 46, wherein:
 (a) the cytokine receptor is IL2Rβ, thereby forming a TGFβR2-IL2Rβ redirector receptor, and the intracellular domain (ICD) of IL2Rβ comprises an amino acid sequence represented by SEQ ID NO: 11; or
 (b) the cytokine receptor is IL12Rβ, thereby forming a TGFβR2-IL12Rβ redirector receptor, and the intracellular domain (ICD) of IL12Rβ comprises an amino acid sequence represented by SEQ ID NO: 12 or SEQ ID NO: 13; or
 (c) the cytokine receptor is IL18Rβ, thereby forming a TGFβR2-IL18Rβ redirector receptor, and the intracellular domain (ICD) of IL18Rβ comprises an amino acid sequence represented by SEQ ID NO: 14; or
 (d) the cytokine receptor is IL21R, thereby forming a TGFβR2-IL21R redirector receptor, and the intracellular domain (ICD) of IL21Rβ comprises an amino acid sequence represented by SEQ ID NO: 15; or
 (e) the extracellular domain (ECD) of TGFβR comprises an amino acid sequence represented by SEQ ID NO: 10.

Embodiment 48: The cell or population thereof of Embodiment 46, wherein the cytokine receptor is a fragment of IL2Rβ, forming a TGFβR2-trIL12Rβ redirector receptor which comprises an amino acid sequence having sequence identity of at least 80%, 85%, 90%, 95%, or 97%, 98%, or 99% to a sequence represented by SEQ ID NO: 16, wherein an amino acid sequence represented by SEQ ID NO: 17 comprised in SEQ ID NO: 16 is variable.

Embodiment 49: The cell or population thereof of any one of Embodiments 42-48, wherein the ADR is specific to 4-1BB or to CD38.

Embodiment 50: The cell or population thereof of any one of Embodiments 42-49, wherein one or more polynucleotides of the solid tumor targeting backbone are inserted at an endogenous CD38 locus to knock out CD38.

Embodiment 51: The cell or population thereof of Embodiment 43, wherein the polynucleotide encoding the exogenous CD16 or variant thereof and two or more polynucleotides of the solid tumor targeting backbone are co-expressed in a tri-cistronic construct.

Embodiment 52: The cell or population thereof of Embodiment 43 or 51, wherein the exogenous CD16 or variant thereof comprises at least one of:
 (a) a high affinity non-cleavable CD16 (hnCD16);
 (b) F176V and S197P in ectodomain domain of CD16;
 (c) a full or partial ectodomain originated from CD64;
 (d) a non-native (or non-CD16) transmembrane domain;
 (e) a non-native (or non-CD16) intracellular domain;
 (f) a non-native (or non-CD16) signaling domain;
 (g) a non-native stimulatory domain; and
 (h) transmembrane, signaling, and stimulatory domains that are not originated from CD16, and are originated from a same or different polypeptide.

Embodiment 53: The cell or population thereof of Embodiment 43, 51, or 52, wherein the cell further comprises the cytokine signaling complex comprising:
 (a) a partial or full peptide of a cell surface expressed exogenous cytokine or a receptor thereof comprising at least one of IL2, IL4, IL6, IL7, IL9, IL10, IL11, IL12, IL15, IL18, IL21, or respective receptor thereof; or
 (b) at least one of:
  (i) co-expression of IL15 and IL15Rα with a self-cleaving peptide in-between;
  (ii) a fusion protein of IL15 and IL15Rα;
  (iii) an IL15/IL15Rα fusion protein with intracellular domain of IL15Rα truncated;
  (iv) a fusion protein of IL15 and membrane bound Sushi domain of IL15Rα;
  (v) a fusion protein of IL15 and IL15Rβ;

(vi) a fusion protein of IL15 and common receptor γC, wherein the common receptor γC is native or modified; and
(vii) a homodimer of IL15Rβ;
or
(c) at least one of:
(i) a fusion protein of IL7 and IL7Rα;
(ii) a fusion protein of IL7 and common receptor γC, wherein the common receptor γC is native or modified; and
(iii) a homodimer of IL7Rβ;
and optionally,
(d) is transiently expressed.

Embodiment 54: The cell or population thereof of any one of Embodiments 32-53, wherein
(i) the CAR is co-expressed with a cytokine signaling complex in a bicistronic construct; and/or
(ii) wherein the CAR is inserted at a TCR locus, and optionally is operatively linked to an endogenous promoter of the TCR.

Embodiment 55: The cell or population thereof of Embodiment 54, wherein
(i) the TCR locus is a constant region of TCR alpha and/or TCR beta; and/or
(ii) the TCR is knocked out by the CAR insertion.

Embodiment 56: The cell or population thereof of any one of Embodiments 32-55, wherein the cancer cell is a breast cancer cell, an ovary cancer cell, an endometrium cancer cell, a lung cancer cell, an esophageal cancer cell, a salivary gland cancer cell, a bladder cancer cell, a gastric cancer cell, a colorectal cancer cell, or a head and neck cancer cell.

Embodiment 57: The cell or population thereof of any one of Embodiments 32-56, wherein (i) the iPSC is a clonal iPSC, a single cell dissociated iPSC, an iPSC cell line cell, or an iPSC master cell bank (MCB) cell; or (ii) the derivative cell comprises a derivative $CD34^+$ cell, a derivative hematopoietic stem and progenitor cell, a derivative hematopoietic multipotent progenitor cell, a derivative T cell progenitor, a derivative NK cell progenitor, a derivative T lineage cell, a derivative NKT lineage cell, a derivative NK lineage cell, or a derivative B lineage cell; or (iii) the derivative cell comprises a derivative effector cell having one or more functional features that are not present in a counterpart primary T, NK, NKT, and/or B cell.

Embodiment 58: The cell or population thereof of any one of Embodiments 42-58, wherein the cell has therapeutic properties comprising one or more of:
(i) increased cytotoxicity;
(ii) improved persistency and/or survival;
(iii) enhanced ability in migrating, and/or activating or recruiting bystander immune cells, to tumor sites;
(iv) improved tumor infiltration;
(v) enhanced ability to reduce tumor immunosuppression;
(vi) improved ability in rescuing tumor antigen escape;
(vii) controlled apoptosis;
(viii) enhanced or acquired ADCC; and
(ix) ability to avoid fratricide,
in comparison to its counterpart primary cell obtained from peripheral blood, umbilical cord blood, or any other donor tissues without the same genetic edit(s).

Embodiment 59: The cell or population thereof of Embodiment 58, wherein the cell is an NK lineage cell or a T lineage cell, wherein:
(i) the NK lineage cell or the T lineage cell has improved infiltration and/or retention at tumor sites;
(ii) the NK lineage cell is capable of recruiting, and/or migrating T cells to tumor sites; or
(iii) the NK lineage cell or the T lineage cell is capable of reducing tumor immunosuppression in the presence of one or more checkpoint inhibitors.

Embodiment 60: A composition comprising the cell or population thereof of any one of the Embodiments 1-59.

Embodiment 61: The composition of Embodiment 60, further comprising one or more therapeutic agents.

Embodiment 62: The composition of Embodiment 61, wherein the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD).

Embodiment 63: The composition of Embodiment 62, wherein the checkpoint inhibitor comprises:
(a) one or more antagonists to checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpi, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR;
(b) one or more of atezolizumab, avelumab, durvalumab, ipilimumab, IPH4102, IPH43, IPH33, lirimumab, monalizumab, nivolumab, pembrolizumab, and their derivatives or functional equivalents; or
(c) at least one of atezolizumab, nivolumab, and pembrolizumab.

Embodiment 64: The composition of Embodiment 62, wherein the antibody comprises:
(a) an anti-CD20 antibody, an anti-HER2 antibody, an anti-CD52 antibody, an anti-EGFR antibody, an anti-CD123 antibody, an anti-GD2 antibody, an anti-PDL1 antibody, or an anti-CD38 antibody; or
(b) one or more of rituximab, veltuzumab, ofatumumab, ublituximab, ocaratuzumab, obinutuzumab, trastuzumab, pertuzumab, alemtuzumab, cetuximab, dinutuximab, avelumab, daclizumab, basiliximab, M-A251, 2A3, BC69, 24204, 22722, 24212, MAB23591, FN50, 298614, AF2359, CY1G4, DF1513, bivatuzumab, RG7356, G44-26, 7G3, CSL362, elotuzumab, daratumumab, isatuximab, MOR202, and their humanized or Fc modified variants or fragments and their functional equivalents and biosimilars thereof.

Embodiment 65: The composition of Embodiment 62, wherein the engager comprises:
(i) a bispecific T cell engager (BiTE);
(ii) a bispecific killer cell engager (BiKE); or
(iii) a tri-specific killer cell engager (TriKE); or
wherein the engager comprises:
(a) a first binding domain recognizing an extracellular portion of CD3, CD28, CD5, CD16, CD64, CD32, CD33, CD89, NKG2C, NKG2D, or any functional variants thereof of the cell or a by-stander immune effector cell; and
(b) a second binding domain specific to an antigen comprising any one of: B7H3, CD10, CD19, CD20, CD22, CD24, CD30, CD33, CD34, CD38, CD44, CD52, CD79a, CD79b, CD123, CD138, CD179b, CEA, CLEC12A, CS-1, DLL3, EGFR, EGFRvIII, EpCAM, FLT-3, FOLR1, FOLR3, GD2, gpA33, HER2, HM1.24, LGR5, MSLN, MCSP, MICA/B, Mucd, Muc16, PDL1, PSMA, PAMA, P-cadherin, ROR1, or VEGF-R2.

Embodiment 66: Therapeutic use of the composition of any one of the Embodiments 60-65 by introducing the composition to a subject in need of an adoptive cell therapy, wherein the subject has an autoimmune disorder, a hematological malignancy, a solid tumor, cancer, or a virus infection.

Embodiment 67: A master cell bank (MCB) comprising the iPSC of any one of the Embodiments 1-59.

Embodiment 68: A method of manufacturing the derivative cell of any one of the Embodiments 1-31, wherein the derivative cell is an immune effector cell, and the method comprises:
  (i) obtaining a genetically engineered iPSC, wherein the iPSC comprises a solid tumor targeting backbone comprising two or more of:
    (a) a polynucleotide encoding a C—X—C motif chemokine receptor or a variant thereof,
    (b) a polynucleotide encoding a TGFβ signaling redirector receptor (TGFβ-SRR) comprising a partial or full peptide of the extracellular domain (ECD) of transforming growth factor beta receptor (TGFβR); and
    (c) a polynucleotide encoding an allo-immune defense receptor (ADR);
  (ii) differentiating the genetically engineered iPSC to a derivative CD34+ cell; and
  (iii) differentiating the derivative CD34+ cell to an immune effector cell, wherein the immune effector cell retains the solid tumor targeting backbone.

Embodiment 69: The method of Embodiment 68, wherein obtaining the genetically engineered iPSC comprising the solid tumor targeting backbone comprises integrating two or more polynucleotides for co-expression at an endogensous CD38 locus and knocking out CD38; wherein the two or more polynucleotides for co-expression are in a cistronic construct; and wherein the polynucleotides encode at least two of:
  (i) a C—X—C motif chemokine receptor;
  (ii) a TGFβ-SRR; and
  (iii) an allo-immune defense receptor (ADR).

Embodiment 70: The method of Embodiment 69, wherein
  (i) the cistronic construct further comprises a polynucleotide encoding an exogenous CD16 or a variant thereof;
  (ii) the C—X—C motif chemokine receptor comprises CXCR2 or CXCR3;
  (iii) the TGFβ-SRR comprises a TGFβR2-IL2Rβ, a TGFβR2-IL12Rβ, a TGFβR2-IL18Rβ, or a TGFβR2-trIL12Rβ redirector receptor; or
  (iv) the ADR is specific to 4-1BB or to CD38.

Embodiment 71: The method of Embodiment 68, further comprising genetically engineering the iPSC comprising a solid tumor targeting backbone by integrating a polynucleotide encoding a chimeric antigen receptor (CAR) at a TCR locus, optionally wherein (i) the CAR is operatively linked to an endogenous promoter of the TCR, and/or (ii) the TCR is knocked out by the CAR insertion.

Embodiment 72: The method of Embodiment 71, wherein the CAR is co-expressed with a cytokine signaling complex in a bi-cistronic construct; or wherein the TCR locus is a constant region of TCR alpha or TCR beta.

Embodiment 73: The method of Embodiment 72, wherein the cytokine signaling complex comprises at least one of:

(i) a fusion protein of IL7 and IL7Rα;
  (ii) a fusion protein of IL15 and IL15Rα; and
  (iii) an IL15/IL15Rα fusion protein with intracellular domain of IL15Rα truncated.

Embodiment 74: The method of Embodiment 71, wherein the CAR is:
  (i) specific to a tumor associated antigen;
  (ii) specific to a solid tumor associated antigen;
  (iii) specific to a pan-tumor antigen; or
  (iv) specific to one of B7H3, BCMA, CD19, CD38, CD79b, EGP2/EpCAM, GPRC5D, HER2, KLK2, MICA/B, and MR1.

Embodiment 75: The method of Embodiment 71, wherein the CAR specific to the HER2 antigen expressed on a cancer cell comprises an antigen binding domain comprising:
  (i) a heavy chain variable (VH) domain comprising a heavy chain complementary determining region 1 (H-CDR1) comprising SEQ ID NO: 103, a heavy chain complementary determining region 2 (H-CDR2) comprising SEQ ID NO: 104, and a heavy chain complementary determining region 3 (H-CDR3) comprising SEQ ID NO: 105; and optionally
  (ii) a light chain variable (VL) domain comprising a light chain complementary determining region 1 (L-CDR1) comprising SEQ ID NO: 106, a light chain complementary determining region 2 (L-CDR2) comprising SEQ ID NO: 107, and a light chain complementary determining region 3 (L-CDR3) comprising SEQ ID NO: 108.

Embodiment 76: The method of Embodiment 75, wherein the antigen binding domain of the CAR:
  (a) comprises a VH domain with at least 80% sequence identity to SEQ ID NO: 109;
  (b) comprises a VL domain with at least 80% sequence identity to SEQ ID NO: 110;
  (c) comprises a single chain variable fragment (scFV) comprising VH-linker-VL or VL-linker-VH, wherein the linker varies in length and sequence, and optionally wherein the linker has at least 80% sequence identity to SEQ ID NOs: 111-114;
  (d) comprises an scFV represented by an amino acid sequence that is of at least about 99%, about 98%, about 96%, about 95%, about 90%, about 85%, or about 80% identity to SEQ ID NO: 115 or SEQ ID NO: 116, wherein each of SEQ ID NOs: 115 and 116 comprises a linker that varies in length and sequence; and/or
  (e) is humanized.

Embodiment 77: The method of Embodiment 69, further comprising genetically engineering the iPSC comprising a solid tumor targeting backbone by one or more of:
  (a) introducing HLA-I deficiency, and/or HLA-II deficiency;
  (b) deleting or disrupting one or more of B2M, CIITA, TAP1, TAP2, Tapasin, NLRC5, RFXANK, RFX5, RFXAP, TCR, NKG2A, NKG2D, CD25, CD44, CD54, CD56, CD58, CD69, CIS, CBL-B, SOCS2, PD1, CTLA4, LAG3, TIM3, and TIGIT; and
  (c) introducing at least one of HLA-G, HLA-E, 4-1BBL, CD3, CD4, CD8, CD16, CD47, CD113, CD131, CD137, CD80, PDL1, $A_{2A}R$, antigen-specific TCR, chimeric fusion receptor (CFR), Fc receptor, an antibody or functional variant or fragment thereof, a checkpoint inhibitor, an engager, and surface triggering receptor for coupling with an agonist.

Embodiment 78: The method of any one of Embodiments 68-77, wherein the genomic engineering comprises targeted editing.

Embodiment 79: The method of Embodiment 78, wherein the targeted editing is carried out by CRISPR, ZFN, TALEN, homing nuclease, homology recombination, or any other functional variation of these methods.

Embodiment 80: A method of treating a subject in need of an adoptive cell therapy, wherein the method comprises infusing the subject with effector cells, wherein the effector cells comprise the derivative cell or population thereof according to any one of Embodiments 1-59.

Embodiment 81: The method of Embodiment 80, wherein the effector cells comprise a CAR specific to HER2 antigen expressed on a cancer cell, wherein the CAR comprises:
- (i) a heavy chain variable (VH) domain comprising a heavy chain complementary determining region 1 (H-CDR1) comprising SEQ ID NO: 103, a heavy chain complementary determining region 2 (H-CDR2) comprising SEQ ID NO: 104, and a heavy chain complementary determining region 3 (H-CDR3) comprising SEQ ID NO: 105; and optionally
- (ii) a light chain variable (VL) domain comprising a light chain complementary determining region 1 (L-CDR1) comprising SEQ ID NO: 106, a light chain complementary determining region 2 (L-CDR2) comprising SEQ ID NO: 107, and a light chain complementary determining region 3 (L-CDR3) comprising SEQ ID NO: 108;

wherein the CAR is at TRAC locus, and the CAR expression is driven by an endogenous TCR promoter; and wherein the subject in need of the adoptive cell therapy has breast cancer, ovary cancer, endometrium cancer, lung cancer, esophageal cancer, salivary gland cancer, bladder cancer, gastric cancer, colorectal cancer, or head and neck cancer.

Embodiment 82: The method of Embodiment 81, wherein the effector cells further comprise a solid tumor targeting backbone, and wherein the effector cells comprise:
- (i) at CD38 locus, two or more of:
  - (a) a polynucleotide encoding a CXCR2;
  - (b) a polynucleotide encoding a TGFβR2-IL18Rβ redirector receptor or a TGFβR2-trIL12Rβ redirector receptor; and
  - (c) a polynucleotide encoding an allo-immune defense receptor (ADR);
- (ii) at CD38 locus, a polynucleotide encoding an exogenous CD16 or a variant thereof;
- (iii) at TRAC locus, a polynucleotide encoding a fusion protein of IL7 and IL7Rα; and
- (iv) CD38 knockout and TCR knockout.

Embodiment 83: The method of Embodiment 80, further comprising administering one or more therapeutic agents to the subject, wherein the one or more therapeutic agents comprise:
- (i) a cytokine, an antibody, an engager, a checkpoint inhibitor, a chemotherapeutic agent or a radioactive moiety, or an immunomodulatory drug (IMiD);
- (ii) an anti-CD38 antibody comprising daratumumab, isatuximab, or MOR202;
- (iii) an engager comprising a BiTE (bi-specific T cell engager) or a TriKE (tri-specific Killer cell engager);
- (iv) a checkpoint inhibitor comprising atezolizumab, avelunab, durvalunab, ipilimumab, IPH4102, IPH43, IPH33, lirimumab, monalizumab, nivolumab, or pembrolizumab; and/or
- (v) a chemotherapeutic agent comprising cyclophosphamide and fludarabine (Cy/Flu).

Embodiment 84: The method of Embodiment 80, wherein the effector cells comprise CD38 knockout and TCR knockout, and optionally an ADR, wherein the method comprises administering to the subject an anti-CD38 antibody, and wherein the method does not require, or requires minimal, lymphodepletion comprising administering Cy/Flu to the subject.

Embodiment 85: The method of Embodiment 80, wherein the effector cells are allogeneic, and wherein infusing the subject with effector cells is in an out-patient setting.

Embodiment 86: A method of improving an adoptive cell therapy in treating a subject having a solid tumor, the method comprises administering a population of derivative cells of any one of Embodiments 1-31.

Embodiment 87: A method of improving anti-HER2 monoclonal antibody (mAb) treatment, comprising:
- introducing to a subject in need of the treatment a composition comprising effector cells comprising a polynucleotide encoding CasMab250-CAR, a polynucleotide encoding a CXCR2, a polynucleotide encoding a TGFβ-SRR, and a polynucleotide encoding an exogenous CD16 or a variant thereof, and
- introducing to the subject an anti-HER2 mAb.

Embodiment 88: The method of Embodiment 87, wherein the anti-HER2 mAb is trastuzumab.

Embodiment 89: A method of selecting engineered NK cells comprising a transgene of interest, wherein the method comprises:
- (i) obtaining engineered NK cells comprising a construct co-expressing the transgene of interest and a partial or full peptide of a cell surface expressed exogenous cytokine or a receptor thereof comprising at least one of IL15 or respective receptor thereof; or at least one of (1) to (7):
  - (1) co-expression of IL15 and IL15Rα with a self-cleaving peptide in-between;
  - (2) a fusion protein of IL15 and IL15Rα;
  - (3) an IL15/IL15Rα fusion protein with intracellular domain of IL15Rα truncated; (4) a fusion protein of IL15 and membrane bound Sushi domain of IL15Rα;
  - (5) a fusion protein of IL15 and IL15Rβ;
  - (6) a fusion protein of IL15 and common receptor γC, wherein the common receptor γC is native or modified; and
  - (7) a homodimer of IL15Rβ;
- (ii) culturing the engineered NK cells without supplying exogenous IL15 cytokine to the cells; and
- (iii) collecting NK cells that expand without the exogenous IL15 cytokine, thereby selecting engineered NK cells comprising the transgene of interest.

EXAMPLES

The following examples are offered by way of illustration and not by way of limitation.

Example 1—Materials and Methods

To effectively select and test exogenous gene control and regulation systems under the control of various promoters in combination with different safe harbor loci integration strategies in the context of pluripotent stem cells, a hiPSC platform was used for single cell passaging and high-throughput, 96-well plate-based flow cytometry sorting, to allow for the engineering and derivation of clonal hiPSCs with single or multiple genetic modulations.

hiPSC Maintenance in Small Molecule Culture: hiPSCs were routinely passaged as single cells once confluency of the culture reached 75%-90%. For single-cell dissociation, hiPSCs were washed with PBS (Mediatech) and treated with Accutase (Millipore). The single-cell suspension was then mixed with conventional medium, centrifuged, resuspended in FMM, and plated on Matrigel-coated surface. Passages were typically 1:6-1:8, and fed every 2-3 days with FMM. Cell cultures were maintained in a humidified incubator set at 37° C. and 5-10% $CO_2$.

Human iPSC engineering with ZFN, CRISPR for targeted editing of modalities of interest: Using ROSA26 targeted insertion as an example, for ZFN mediated genome editing, 2 million iPSCs were transfected with a mixture of 2.5 µg ZFN-L, 2.5 µg ZFN-R and 5 µg donor construct, for AAVS1 targeted insertion. For CRISPR mediated genome editing, 2 million iPSCs were transfected with a mixture of 5 µg ROSA26-gRNA/Cas9 and 5 µg donor construct, for ROSA26 targeted insertion. Transfection was done using a Neon transfection system (Life Technologies). On day 2 or 3 after transfection, transfection efficiency was measured using flow cytometry if the plasmids contain artificial promoter-driven GFP and/or RFP expression cassette.

Bulk sort and clonal sort of genome-edited iPSCs: iPSCs with genomic targeted editing using ZFN or CRISPR-Cas9 were bulk sorted and clonal sorted of $GFP^+SSEA4^+TRA181^+$ iPSCs. Single cell dissociated targeted iPSC pools were resuspended in staining buffer made fresh for optimal performance. Conjugated primary antibodies, including SSEA4-PE, TRA181-Alexa Fluor-647 (BD Biosciences), were added to the cell solution. The solution was washed in staining buffer, spun and resuspended in staining buffer containing 10 µM Thiazovivn for flow cytometry sorting. Upon completion of the sort, the 96-well plates were incubated. Colony formation was detected as early as day 2 and most colonies were expanded between days 7-10 post sort. In the first passage, wells were washed with PBS and dissociated with 30 µL Accutase. The dissociated colony is transferred to another well of a 96-well plate previously coated with Matrigel. Subsequent passages were done routinely. Each clonal cell line was analyzed for GFP fluorescence level and TRA1-81 expression level. Clonal lines with near 100% $GFP^+$ and $TRA1-81^+$ were selected for further screening and analysis including but not limited to off-target editing, and/or karyotype of the engineered iPSCs, before the clonal population is cryopreserved to serve as a master cell bank.

Example 2—Multiplex Genomic Engineering to Establish Clonal iPSCs and iPSC-Derived Effector Cells Having a Backbone Structure for Optimized Solid Tumor Targeting Capability A series of bi-cistronic and tri-cistronic constructs were designed and prepared as shown in Table 5 for engineering cells at multiple loci for endogenous gene knockout and at the same time to insert (KO/KI) multiple functional modalities in desired combinations and desired placement in order to explore a functional backbone arrangement that better equips effector cells for solid tumor immuno-therapies.

As a part of the solid tumor targeting backbone construction, the TRAC locus is utilized to insert a solid tumor antigen recognition receptor, for example a CAR, or an exogenous TCR, while knocking out the endogenous TCR to passively avoid host immune detection of the cell. A vector containing a CAR only or a bi-cistronic vector containing a CAR and a cytokine signaling complex was used to compare whether the cytokine signaling complex is suitable to be incorporated as a part of the backbone that, among other advantages, also supports effector cell fitness and/or persistency. For example, to generate effector T cells from the engineered iPSC, an IL7 signaling complex was tested; and to generate effector NK cells from the engineered iPSC, an IL15 signaling complex was tested instead.

A second locus, CD38, was selected for another part of the solid tumor targeting backbone. While inserting at CD38 two or more of CD16, CXCR2 and a TGFβR2 redirector (TGFβ-SRR) using a bi- or tri-cistronic construct to address challenges of the solid tumor environment, the endogenous CD38 gene is knocked out as a result such that an anti-CD38 monoclonal antibody can be applied to selectively deplete CD38-expressing activated host immune cells.

Respective groups of iPSCs were first transduced with the vector for TRAC locus KO/KI as indicated in Table 5. In this example, the exemplary CAR used was one that targets HER2 tumor antigen and comprises an scFV sequence represented by SEQ ID NO: 115 or SEQ ID NO: 116 in this application. After verification of successful TRAC targeting, the CD38 locus was then targeted to introduce hnCD16/CXCR2, hnCD16/TGFβR2 redirectors, or hnCD16/CXCR2/TGFβR2 redirectors. TRAC and CD38 engineered iPSCs were differentiated into CAR iT or CAR iNK cells to verify the pluripotency of the iPSCs with multiplexed genomic editing to hematopoietic cells, a process as illustrated in FIG. 1A. For purposes of this experiment, the TGFβR2 redirector is a fusion protein of TGFβR2 with one of IL12Rb, IL18R, IL21R, or fragments thereof, referred to as TGFβR2-IL12Rb, TGFβR2-IL18R, TGFβR2-IL21R specifically or as TGFβ-SRR in general throughout this application.

TABLE 5

Cell Groups Containing Desired Bi- and Tri-Cistronic Constructs at Specified Loci

| | Insertion Locus in Cell | |
|---|---|---|
| Cell Group | TRAC_ | CD38_ |
| 1 | CAR | |
| 2 | CAR/IL7RF | |
| 3 | CAR | hnCD16/CXCR2 |
| 4 | CAR/IL7RF | hnCD16/CXCR2 |
| 5 | CAR/IL7RF | hnCD16/TGFβR |
| 6 | CAR/IL7RF | TGFβ-SRR/hnCD16/CXCR2 |
| 7 | CAR/IL7RF | TGFβ-SRR/CXCR2/hnCD16 |

Figure 1B:
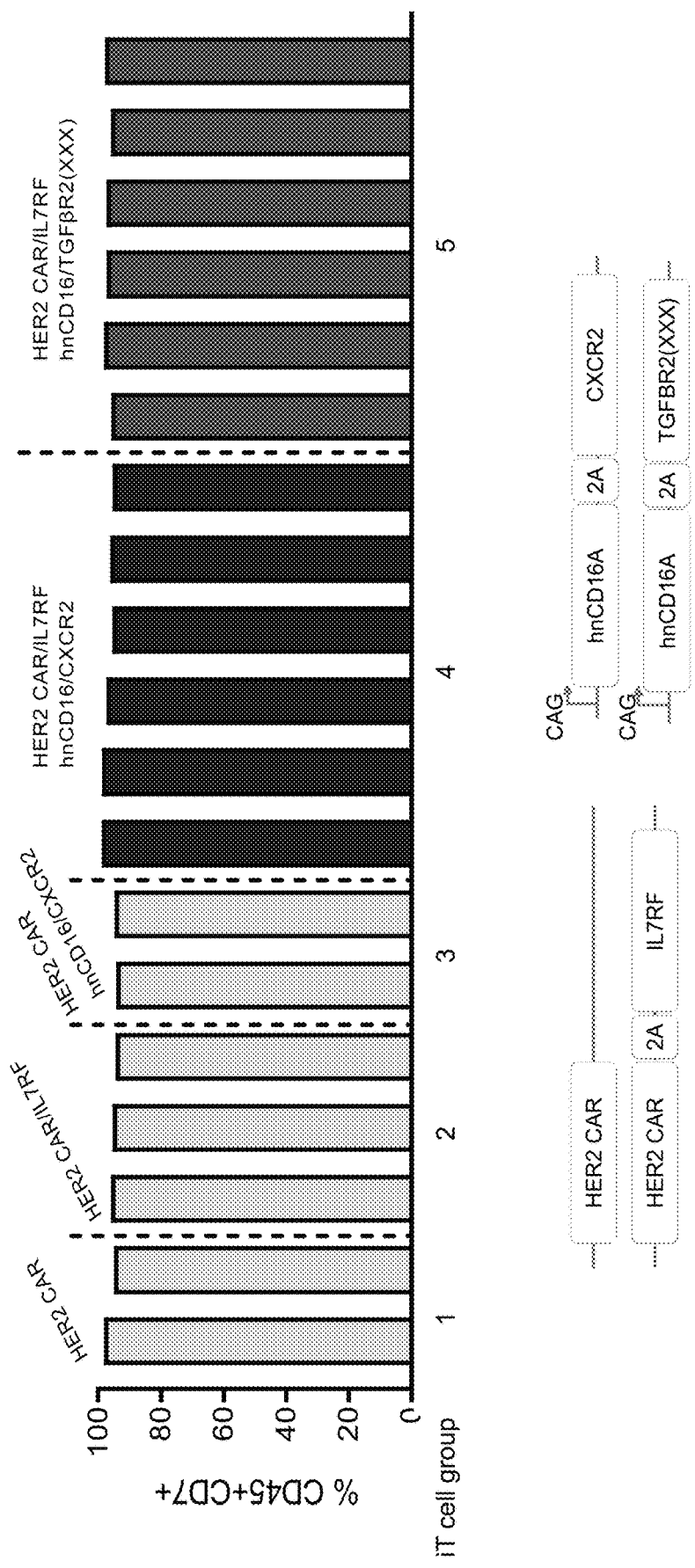

Following differentiation, TCR and CD38 knockout CAR iT cells expressing TRAC_CAR, TRAC_CAR/IL7RF, CD38_hnCD16/CXCR2, and/or CD38_hnCD16/TGFβ-SRR were evaluated for their lymphoid commitment by assessing their CD45 and CD7 expression via flow cytometry on individual clones from each cell group having indicated backbone configurations (FIG. 1B). As shown in FIG. 1B, all evaluated clones co-expressed CD45 and CD7 (95%), demonstrating (i) successful differentiation into immune effector cells and (ii) compatibility of the iPSC engineering strategy with regard to the individual edits of the solid tumor targeting backbone with the effector cell differentiation capacity of the iPSC having the modifications.

Differentiated CAR iT cell groups were further evaluated for CAR, hnCD16, and TGFβ-SRR transgene expression via flow cytometry. As shown in FIG. 1C, fully differentiated CAR-iTs engineered with TRAC_CAR/IL7RF and CD38_hnCD16/CXCR2 expressed high levels of CAR (99.8%), hnCD16 (99.9%), and CXCR2 (62.2%). Additionally, fully differentiated CAR iTs engineered with HER2-CAR/IL7RF and hnCD16/TGFβ-SRR (with IL12Rβ fusion in the data shown) also expressed high levels of CAR (90.8%), hnCD16 (99.6%), and TGFβR2-IL12Rβ (96.7%).

Figure 1E:
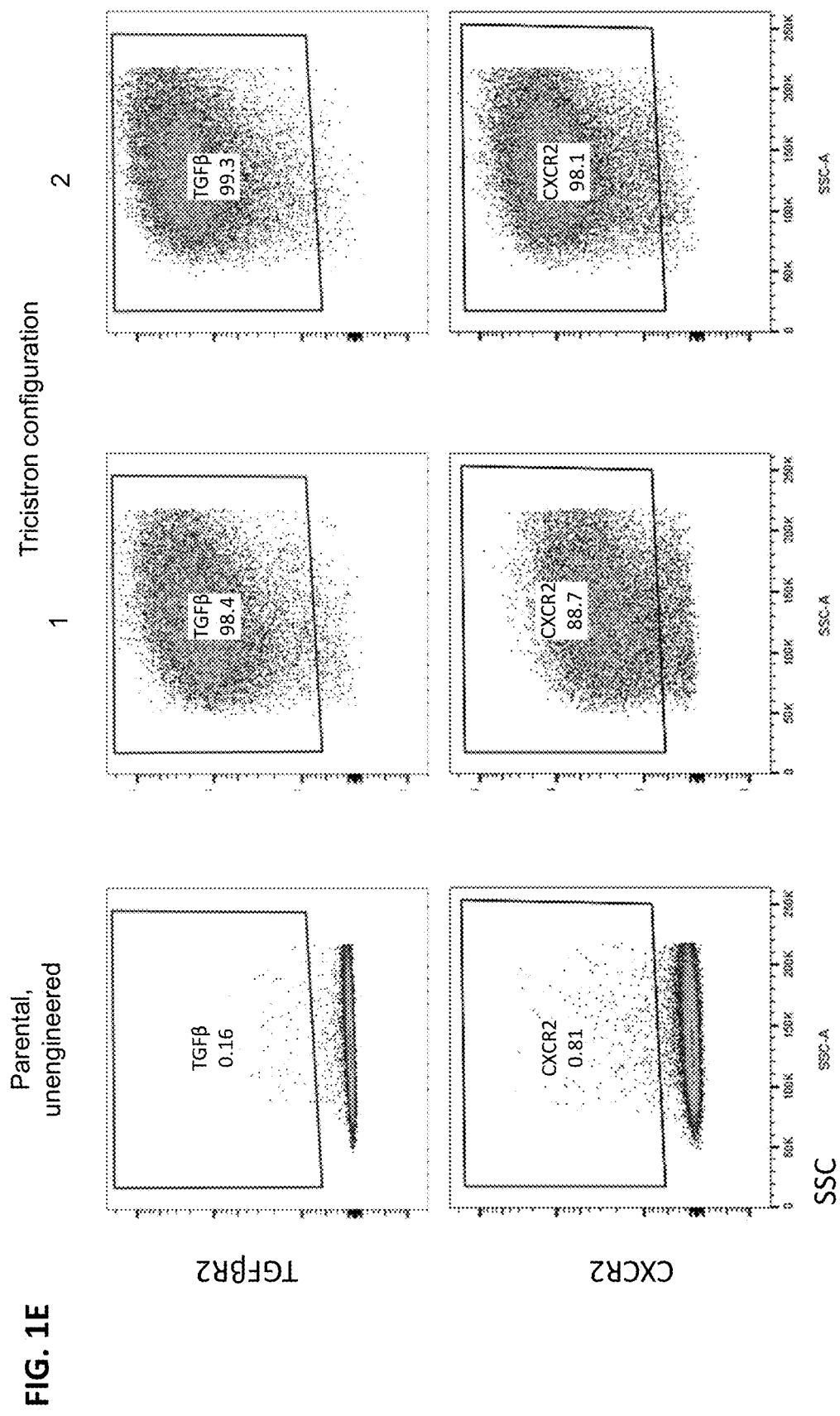

Tri-cistronic constructs specific for CD38 KO/KI, expressing CAG-driven TGFβR2-IL18R, hnCD16, and CXCR2 in the particular configurations as shown in FIG. 1D were further evaluated. Following CD38 engineering and selection of transgene-expressing iPSCs, CXCR2 and TGFβ-SRR expression was determined via flow cytometry and compared to CD38 unengineered parental iPSCs. As shown in FIG. 1E, a tri-cistron engineered iPSCs with either configuration expressed high levels of TGFβ-SRR (98.4% & 99.3%) and CXCR2 (88.7% & 98.1%), demonstrating successful engineering and robust transgene expression from these tricistron-integrated iPSCs.

Example 3—CXCR2 for Effector Cell Solid Tumor Targeting Backbone Incorporation Enhances Cell Migration and Solid Tumor Infiltration Conventional CAR-T therapies have shown modest efficacy in solid tumor settings. In addition to tumor antigen heterogeneity, immunosuppressive tumor microenvironment, and limited effector persistence, appropriate effector trafficking to the tumor itself can be a major barrier for efficacious solid tumor CAR-T therapies. CXCR2 is expressed by myeloid cells such as neutrophils and dendritic cells, rather than T cells. CXCR2, as a part of the solid tumor targeting backbone of the primary or iPSC-derived CAR-T cells, was evaluated for its expression and functional aspects.

Figures 2A, 2B:
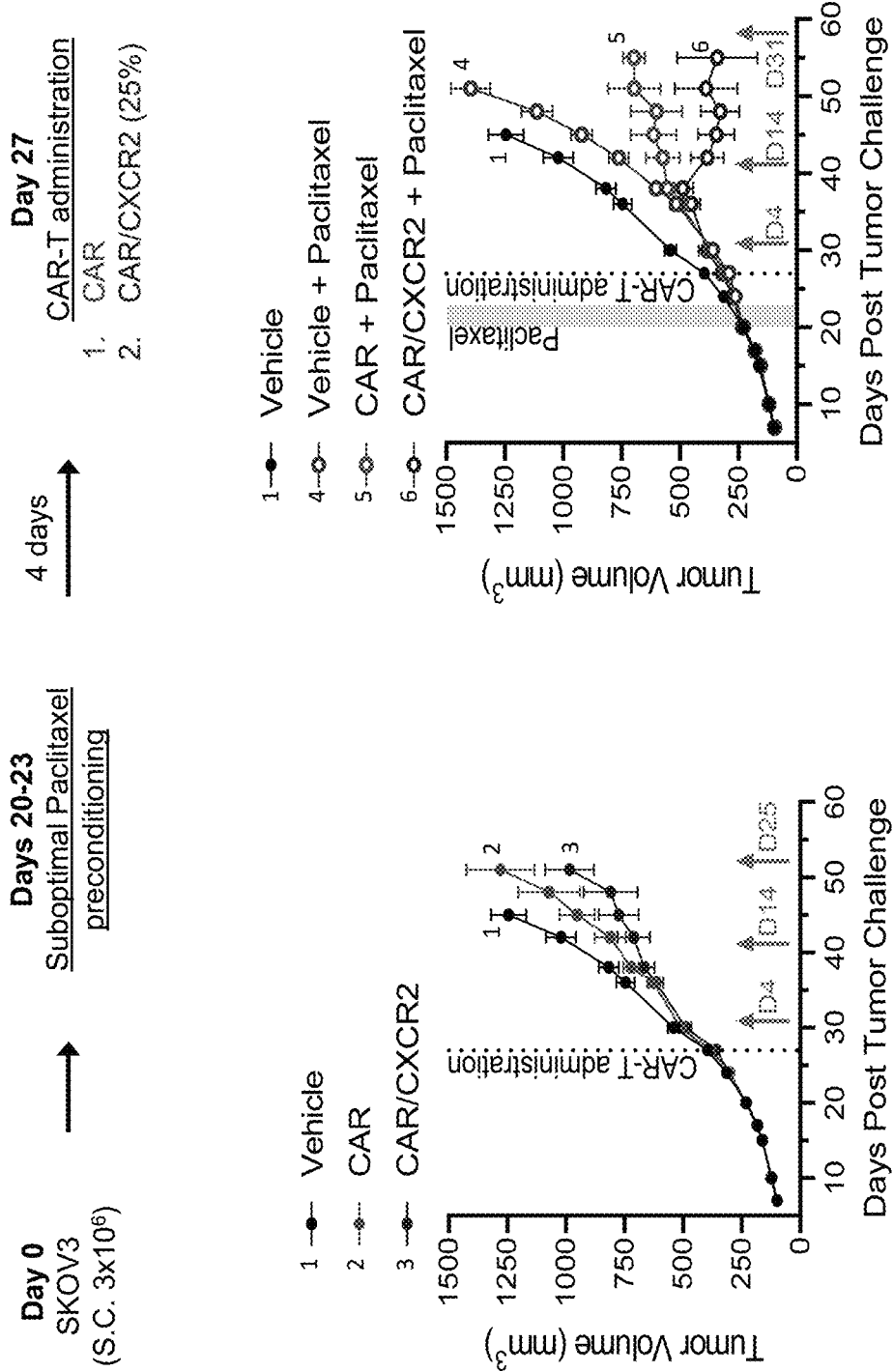
FIG. 2A shows an exemplary experimental design for the in vivo evaluation of CAR-T cells engineered to express CXCR2.
FIGS. 2B and 2C show Day 45 tumor growth (FIG. 2B) and tumor growth inhibition (FIG. 2C) in tumor bearing mice subject to CAR-T cell therapy with and without paclitaxel preconditioning in the context of CXCR2 signaling.
Figure 2C:
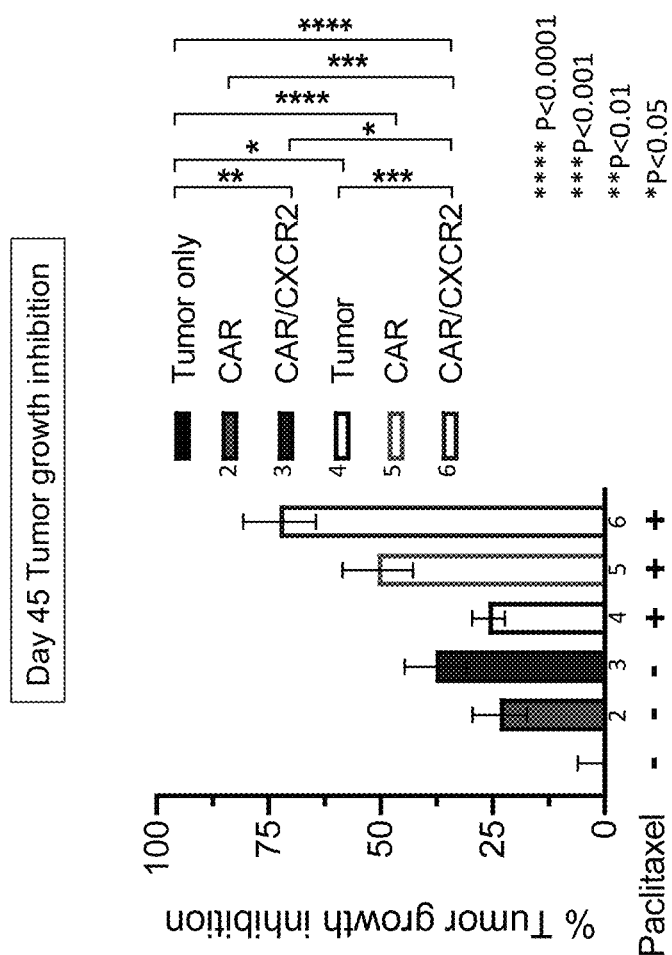
Figure 2D:
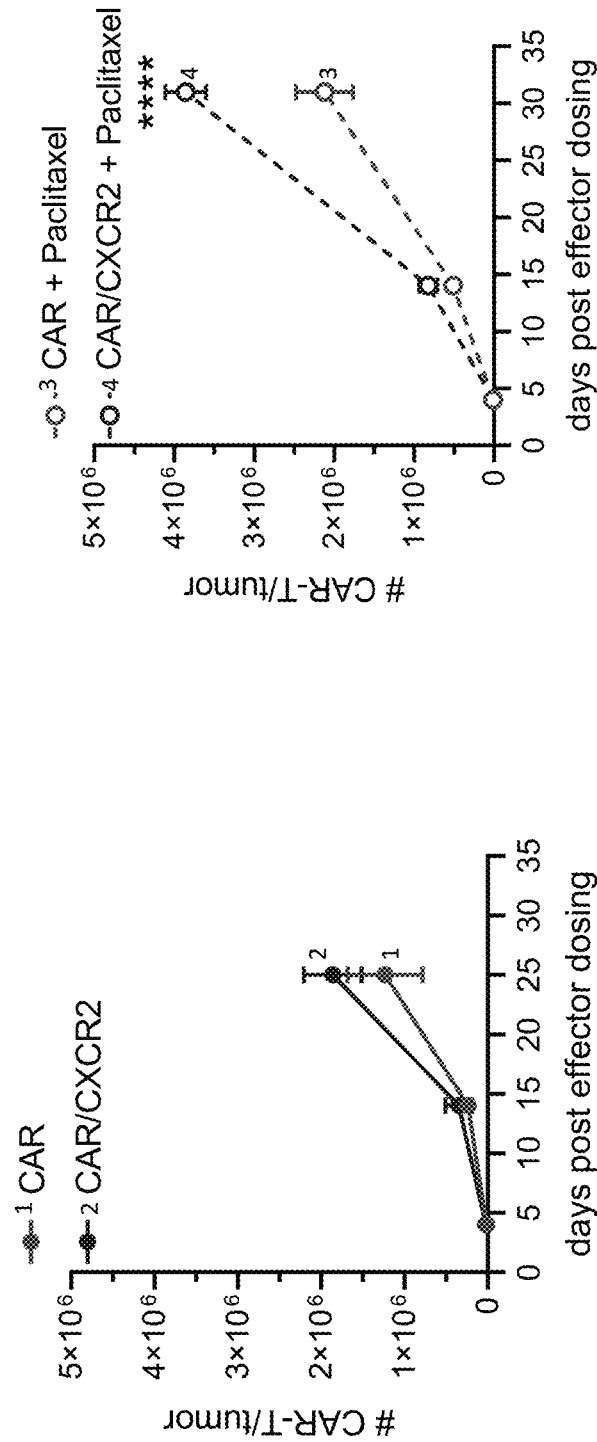
FIG. 2D shows Day 45 infiltration and retention of each indicated CAR-T cell group within tumors with and without paclitaxel preconditioning.

An exemplary experimental design for the in vivo evaluation of primary CAR-T cells engineered to express CXCR2 is shown in FIG. 2A. Briefly, SKOV3 tumor cells were subcutaneously injected into NSG mice and 20 days later, half of the tumor bearing mice were administered Paclitaxel daily until Day 23. The CXCR2 ligand, CXCL8 (IL8), is enriched in multiple tumor types, including breast cancer, and its expression in tumor cells increases following exposure to chemo- or radiotherapy. Paclitaxel was used for preconditioning to increase CXCR2 ligand level in tumor cells. On Day 27, preconditioned and control mice were administered CXCR2$^+$ (~25%+) or CXCR2$^-$ primary HER2 CAR-T cells. Treated mice were monitored for tumor growth (FIG. 2B) and tumor growth inhibition (TGI) was calculated at Day 45 (FIG. 2C). In the absence of preconditioning, CXCR2$^+$ primary HER2 CAR-T cells demonstrated significant tumor growth inhibition of ~40% ($p<0.01$) of SKOV3 tumors. Preconditioning alone did induce ~30% tumor growth inhibition ($p<0.05$) compared to untreated tumor bearing mice. The combination of CXCR2$^+$ CAR-T and chemotherapy preconditioning induced the greatest control of tumor compared to mice receiving tumor alone (>70% $p<0.0001$). The infiltration and retention of CXCR2$^+$ or CXCR2$^-$ CAR-T cells into tumors, with and without preconditioning, was also assessed on Days 4, 14, and 25 (no preconditioning) or 31 (with preconditioning) by flow cytometry. As shown in FIG. 2D, the infiltration and retention of CAR-T cells within tumors was significantly enhanced when CXCR2$^+$ CAR-T cells were combined with chemotherapy preconditioning ($p<0.0001$).

Next, iPSC-derived CAR-T cells were engineered to express TRAC_HER2-CAR/IL7RF, and TRAC_HER2-CAR/IL7RF and CD38_hnCD16/CXCR2, wherein the HER2 binding domain of the CAR was based on the CasMab250 as described herein. Chemokine receptor expression demonstrated high levels of CXCR2 expression in the CD38 null engineered CAR iT cells with 64% of cells expressing high levels of CXCR2, compared to 0.20% in parental CAR iT cells (FIG. 2E, left panels). It was also noted that CCR1 and CXCR3, chemokine signaling receptors that are often important for T cell infiltration into solid tumors, remained unaffected in CXCR2-engineered CAR iT cells compared to their parental CAR iT cells (FIG. 2E, middle and right panels; CCR1: 94.3% vs 93.3%; and CXCR3: 99.6% vs 99.7%, respectively).

Figure 2F:
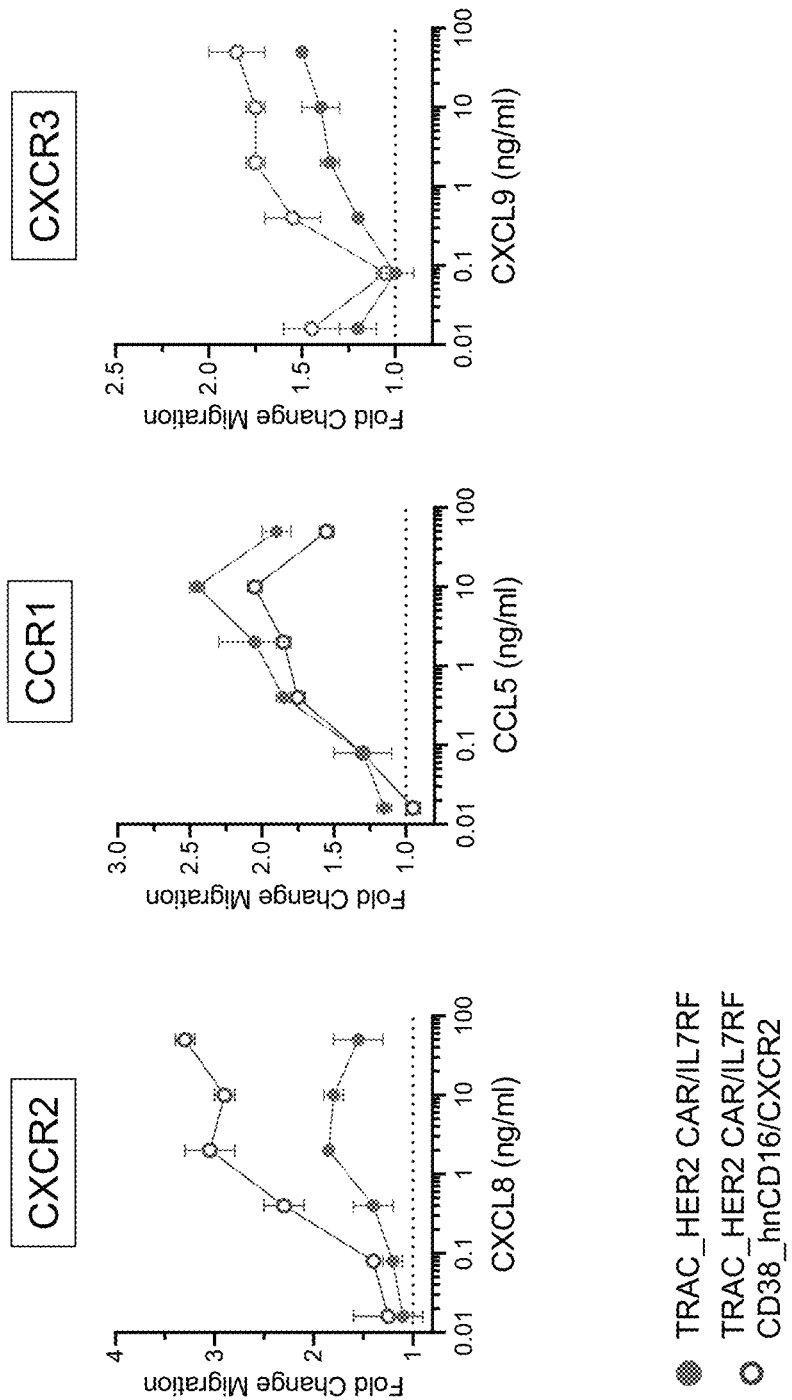
FIG. 2F shows improved CXCR2-engineered CAR-iT cell migration in a dose-responsive manner to varying dilutions of a CXCR2 ligand, whereas sensitivity of CXCR2+ CAR-iT cells to a CCR1 ligand and a CXCR3 ligand were unaffected.

Functional expression of engineered CXCR2 was determined via transwell migration assays. Engineered CXCR2$^+$ and parental CXCR2$^-$ CAR iT cells were plated into a 5 μm transwell insert and chemokines (CXCL8, CCL5, or CXCL9) of varying dilutions (16 μg/ml-50 ng/ml) were added to the bottom chamber. After 3 hours of culture, specific migration of the T cells was calculated. As shown in FIG. 2F, left panel, CXCR2-engineered CAR iT cells functionally migrated in a dose-responsive manner to varying dilutions of CXCL8, a CXCR2 ligand, whereas sensitivity of CXCR2$^+$ CAR iT cells to CCL5 (a CCR1 ligand) and CXCL9 (a CXCR3 ligand) were unaffected (FIG. 2F, middle and right panels). These data demonstrate that engineering of CXCR2 into primary or iPSC-derived CAR T cells enables the cells' functional migration towards CXCR2 ligands, facilitating improved infiltration and retention into solid tumors and enhanced tumor clearance.

Figures 3A, 3B:
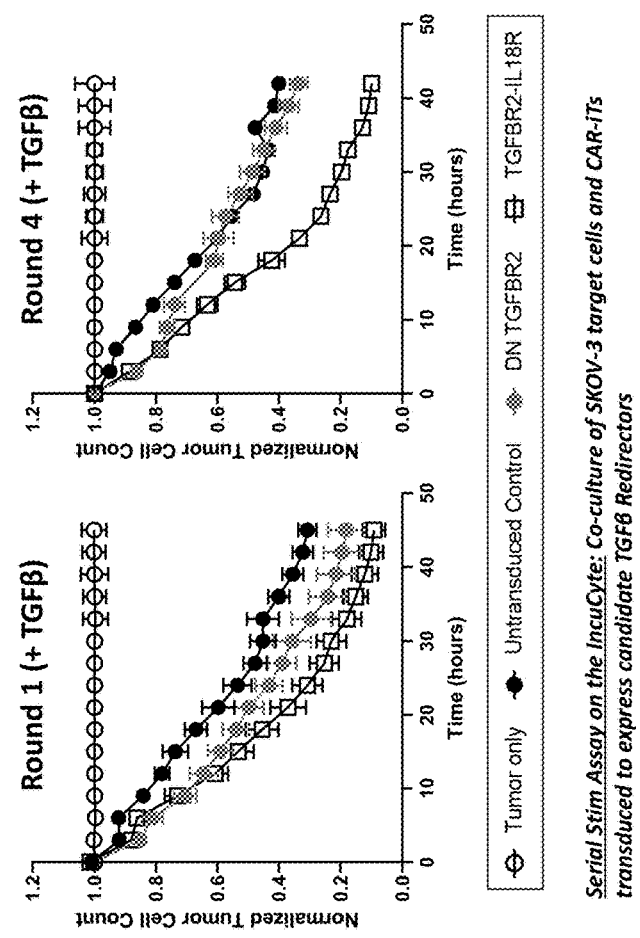
FIG. 3A shows functionality of the cytokine receptor endodomain in the TGFβ redirector constructs.
FIG. 3B shows improved functionality of signal redirector receptors over blockade of TGFβ signaling alone by using dominant negative TGFβ.

Example 4—TGFβ Signal Redirector Receptors Incorporated in Effector Cell Backbone Improve Effector Cell Functionality In this experiment, groups of activated primary CD8 T cells were each lentivirally transduced with a different TGFβ-SRR construct, comprising an extracellular domain from TGFβR and an intracellular domain, or a fragment thereof, of IL2R, IL12R, IL18R, or IL21R. Following a 24-hour rest in T cell media without IL2, the T cells were exposed to the indicated concentrations of TGFβ. After 2 hours, the cells were harvested and analyzed by flow cytometry for the presence of phosphorylated STAT5 (pSTAT5). IL2 spike-in was used as a positive control. As shown in FIG. 3A, the flow data demonstrate functionality of the cytokine receptor endodomains of IL12R, IL21R and IL2R in the TGFβ-SRR constructs in the presence of TGFβ, showing that the percent of pSTAT5 positive CD8 T cells increased to a level similar to what was observed when IL2 was spiked-in.

In a separate experiment, iPSC-derived CAR-T cells (CAR-iTs) were lentivirally transduced to express either dominant negative TGFβR2 (DN TGFβR2 or dnTGFβR2) or a TGFβ-SRR construct. The CAR-iTs were then tested in a serial stimulation assay, where the ability of effector cells in killing tumor cells was measured on an IncuCyte instrument over multiple rounds of co-culture and in the presence of 20 ng/mL TGFβ. For the TGFβ-SRR, the data related to the TGFβR2-IL18R is shown. As shown in FIG. 3B, CAR-iTs expressing TGFβR2-IL18R demonstrated enhanced tumor killing in the presence of TGFβ in the first round of co-culture (FIG. 3B, left plot) compared to TGFβ-SRR CAR-iTs or dnTGFβR2$^+$ CAR-iTs. After four rounds of co-culture and exposure to TGFβ (FIG. 3B, right plot), the dnTGFβR2$^+$ CAR-iTs showed very similar tumor killing kinetics as in the co-culture with untransduced effectors. Importantly, TGFβR2-IL18R CAR-iTs continued to show enhanced tumor killing ability because of the additional cytokine signaling provided by the TGFβ redirector, in this case, through an intracellular domain of IL18R.

Figure 4A:
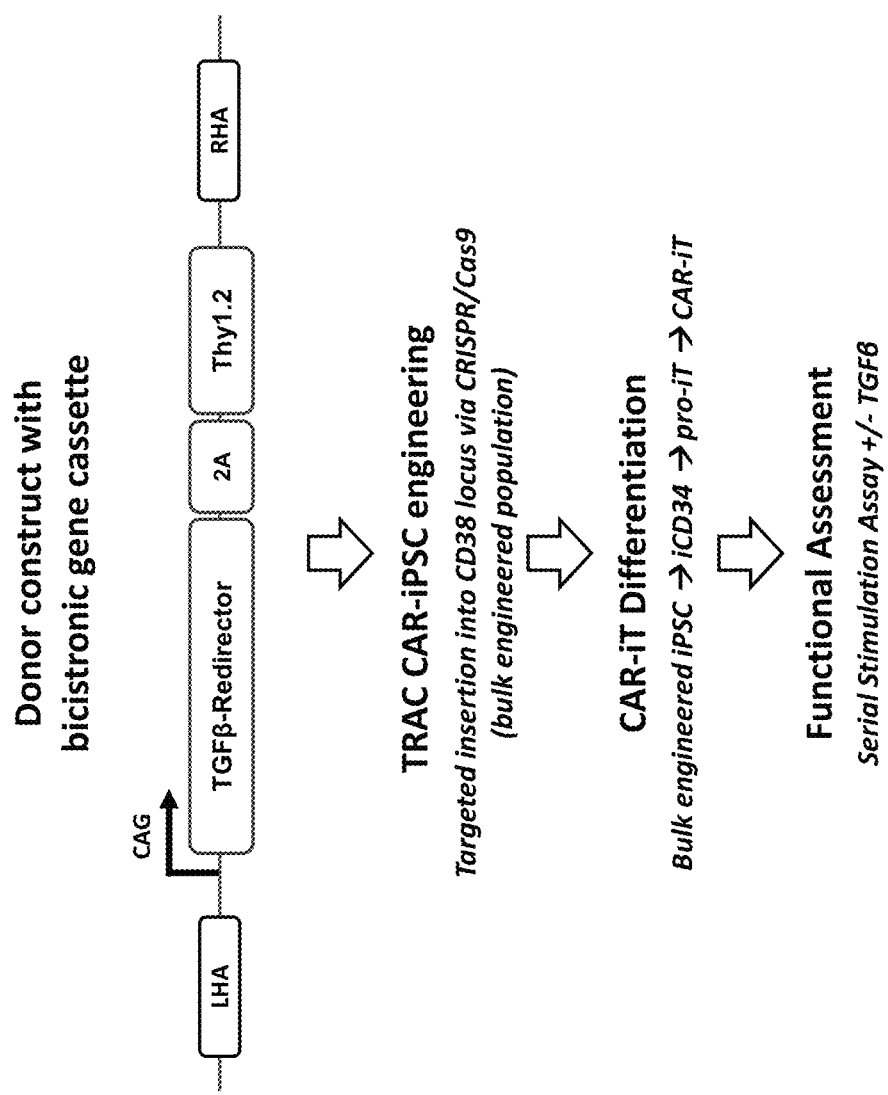
FIG. 4A shows a schematic of an exemplary strategy for generating and testing a population of CAR-iT cells expressing a TGFβ redirector receptor.

In a further experiment, a population of genetically engineered CAR-iTs that express TGFβ-SRRs was prepared using the strategy shown in FIG. 4A. In particular, a bi-cistronic donor cassette was inserted in the CD38 locus of an iPSC population via a CRISPR enzyme, where the iPSC has a CAR inserted at the TRAC locus. The bulk-engineered iPSCs were differentiated into CAR-iT cells and tested in a serial stimulation assay in the presence or absence of TGFβ. Co-expression of the Thy1.2 marker and the TGFβ-SRR indicates the percentage of cells in the CAR-iT population that were successfully engineered. As shown in FIG. 4B, three examples of TGFβ-SRRs that were expressed in CAR-iTs were generated—TGFβR2-IL12Rβ, TGFβR2-IL18R, and TGFβR2-IL21R. Towards the end of the iT differentiation process, when the cells have committed to the T cell lineage, the TRAC promoter becomes active. As shown in FIG. 4C, surface expression of the CAR in the TGFβ-SRR engineered cells indicate successful differentiation into T cells.

Figure 5:
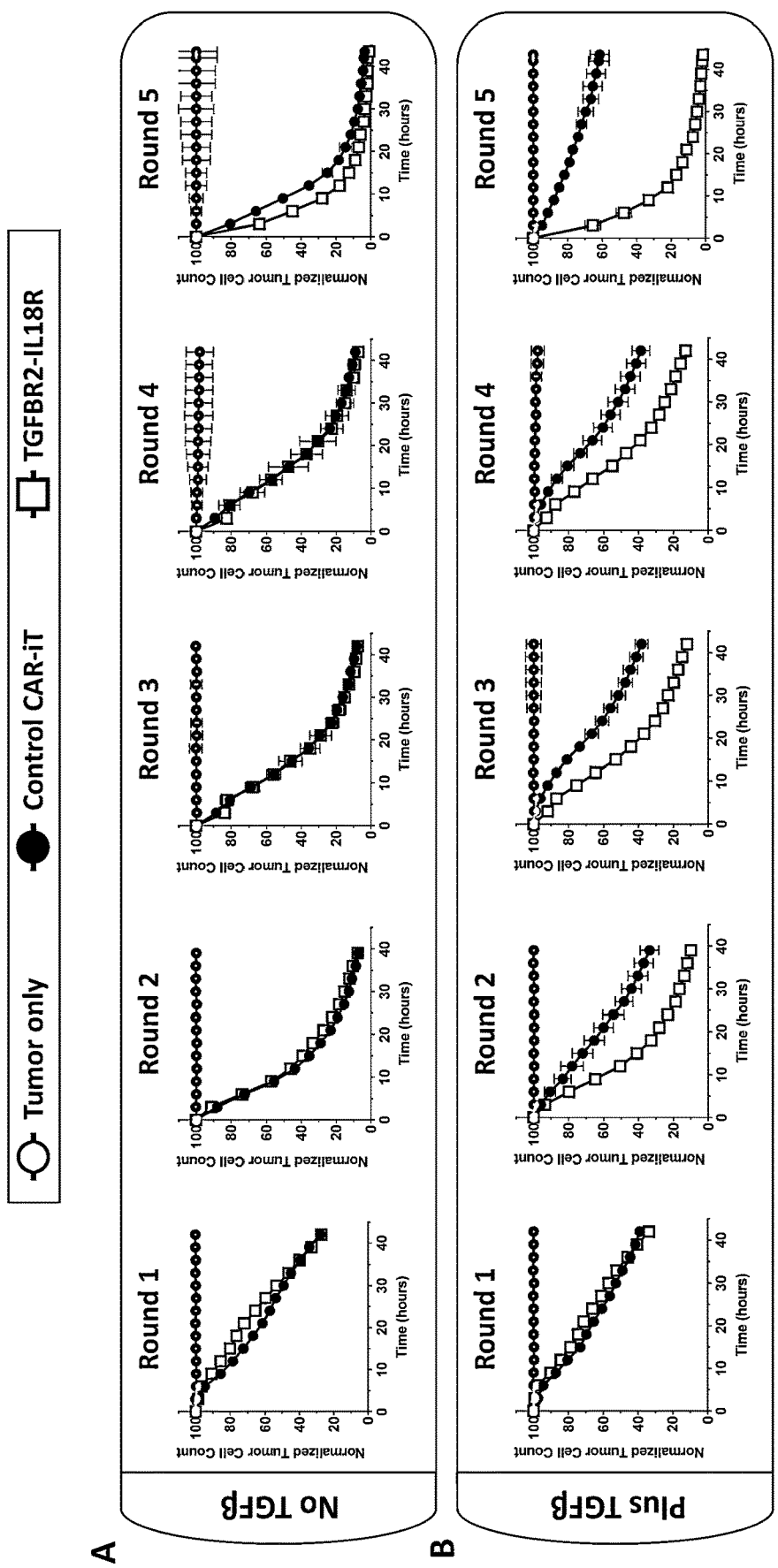
FIG. 5 (parts A and B) shows that CAR-iT cells expressing a TGFβ redirector receptor are capable of resisting TGFβ-mediated suppression of effector function and maintain effector function in the presence of TGFβ.

Using a serial stimulation assay, the CRISPR-engineered CAR-iT cells expressing the TGFβR2-IL18R construct were tested for their ability to resist TGFβ-mediated suppression of effector function. In the absence of TGFβ, the control CAR-iTs showed very similar tumor killing kinetics as the TGFβR2-IL18R CAR-iTs over five rounds of co-culture (FIG. 5, part A, No TGFβ), which demonstrates that TGFβR2-IL18R CAR-iTs would not exhibit unnecessarily high levels of effector function in the absence of TGFβ. With the addition of 20 ng/mL TGFβ to the serial stimulation assay, the control CAR-iT cells exhibited similar cytolytic capacity as the TGFβR2-IL18R CAR-iTs in the first round, demonstrating that acute exposure of TGFβ-SRR CAR-iTs with the TGFβ is not likely to dramatically change the effector function of these cells (FIG. 5, part B, Plus TGFβ). However, an increase in tumor killing activity in the TGFβR2-IL18R CAR-iTs was observed starting in the second round of serial stimulation. As shown in part B of FIG. 5, this increase in effector function persisted for up to five rounds of co-culture. In comparison, the control CAR-iTs progressively lost their ability to kill target cells in the serial stimulation assay with TGFβ spike-in.

Figure 6B:
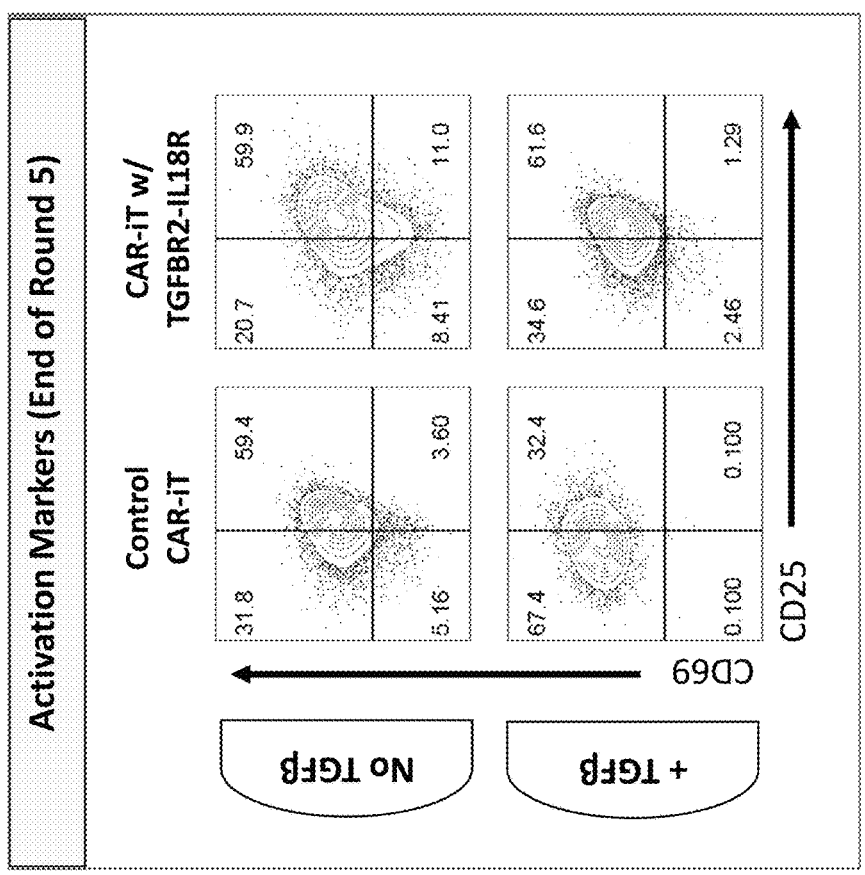
FIG. 6B shows that CAR-iT cells engineered with the TGFβ redirector receptor transgene exhibited enhanced activation profiles in the presence of TGFβ as compared to control CAR-iT cells.
Figure 6A:
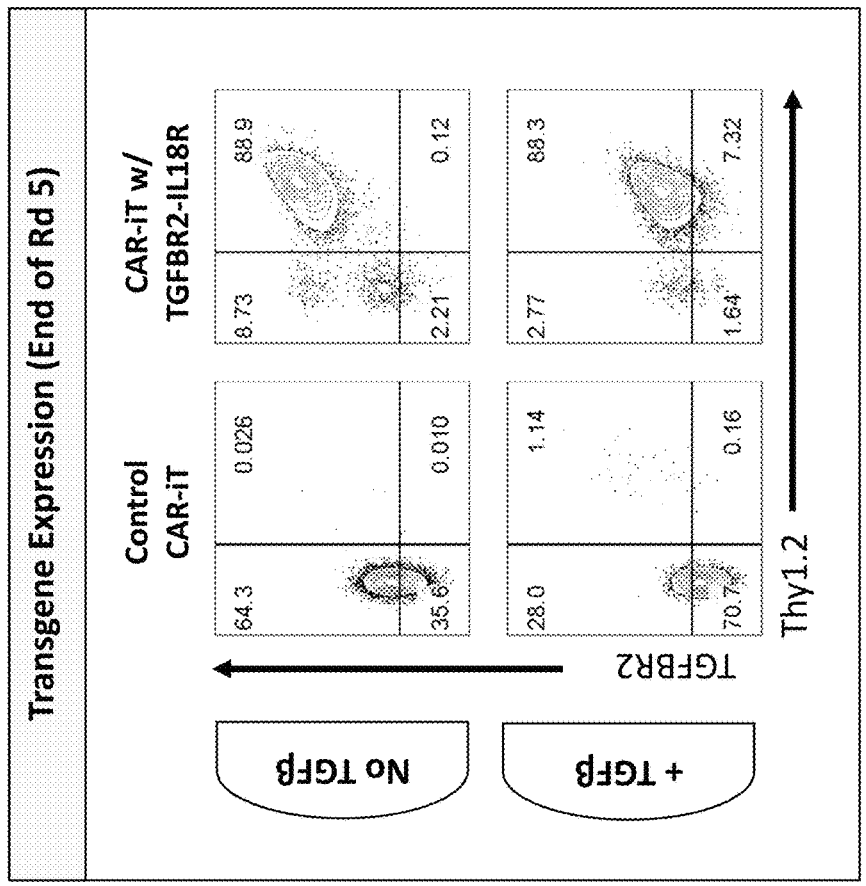
FIG. 6A shows that expression of the TGFβ redirector receptor transgene is maintained in CAR-iT cells after multiple rounds of stimulation with target cells in the presence of TGFβ.

Effector function and antitumor activity of T cells are linked to T cell activation state. To characterize the activation profile of CAR-iT cells expressing the TGFβ-SRR after multiple rounds of stimulation with target cells, control CAR-iTs or TGFβ-SRR CAR-iTs were subjected to five rounds of co-culture with target cells in the presence or absence of TGFβ, and at the end of round 5, the cells were stained for TGFβR2 and Thy1.2 (FIG. 6A). Co-expression of the Thy1.2 marker and TGFβR2 indicates the percent of effector cells that maintained expression of the TGFβ-SRR. The effector cells at the end of five rounds of co-culture with and without TGFβ were also analyzed by flow cytometry for co-expression of the activation markers CD69 and CD25 (FIG. 6B). As shown in FIG. 6B, in the absence of TGFβ, both control and TGFβR2-IL18R CAR-iTs were ~60% positive for both CD69 and CD25. In comparison, in the presence of TGFβ, the control CAR-iTs showed a reduction in the CD69$^+$CD25$^+$ cells (32.4%), while 61.6% of the TGFβR2-IL18R CAR-iTs were double positive for CD69 and CD25 (FIG. 6B). Therefore, CAR-iT cells with the TGFβ-SRR possess an enhanced activation profile even after multiple rounds of stimulation with target cells.

Figure 7:
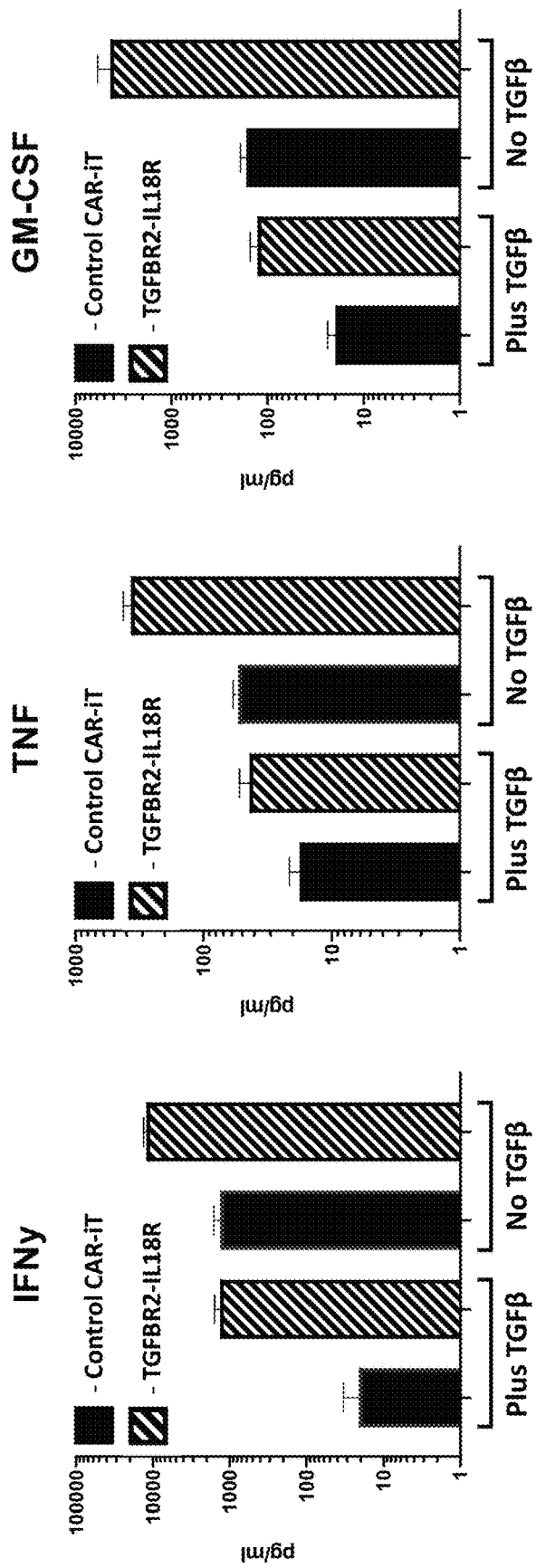
FIG. 7 shows enhanced cytokine secretion production by CAR-iT cells engineered with a TGFβ redirector receptor in the presence of TGFβ in a serial stimulation assay.

Furthermore, supernatants from round 5 of the serial stimulation assay were collected and tested via MSD assay for cytokines, such as IFNγ, TNFα, and GM-CSF. As shown in FIG. 7, in the presence of TGFβ, control CAR-iTs showed a dramatic reduction of cytokines in the co-culture media. In contrast, much higher concentrations of the tested cytokines were found in the co-cultures with the TGFβ-SRR CAR-iTs. Even in the presence of TGFβ, the cytokines measured in the co-cultures of the TGFβR2-IL18R CAR-iTs were similar in amount to that found in the co-cultures of the control CAR-iTs without TGFβ spiked-in. The enhanced cytokine production in the serial stiulation by the target cell in the presence of TGFβ demonstrates the ability of TGFβR2-IL18R CAR-iTs to maintain effector function even in the presence of TGFβ, a representative immunosuppressive feature of a solid tumor environment.

Figure 8:
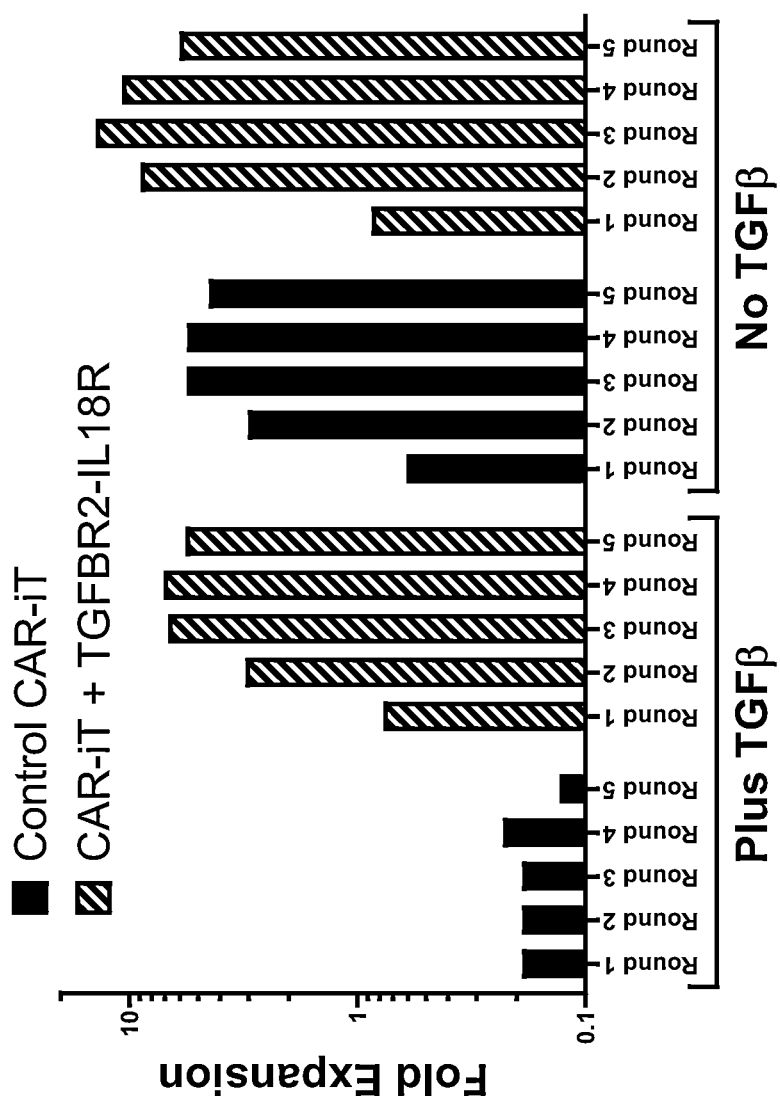
FIG. 8 shows improved expansion of CAR-iT cells engineered with a TGFβR-IL18R redirector receptor in the presence of TGFβ in a serial stimulation assay.

To test if CAR-iT cells with the TGFβ-SRR are capable of expanding after target cell stimulation in a solid tumor environment, control or TGFβR2-IL18R CAR-iTs were subjected to 5 rounds of co-culture with target cells in the presence or absence of TGFβ. Cells were harvested at the end of each round during this serial stimulation assay, and the number of effector cells was determined using counting beads and flow cytometry. As shown in FIG. 8, control CAR-iT cells showed a lack of expansion in the presence of TGFβ, while the TGFβR2-IL18R CAR-iTs exhibited a normal expansion profile similar to the control CAR-iTs serially stimulated in the absence of TGFβ. The TGFβR2-IL18R CAR-iTs also exhibited robust expansion in the absence of TGFβ with a higher fold expansion observed in rounds 2, 3, and 4 compared to the control CAR-iTs. Therefore, the TGFβ-SRR comprised in a solid tumor targeting backbone as disclosed herein provides CAR-iT cells with improved expansion even with multiple rounds of target cell stimulation and in the presence of TGFβ, typical of a solid tumor environment.

A further designed and tested TGFβ-SRR is one comprising a fragment of the cytoplasmic domain of IL12Rb2 in addition to the ectodomain of TGFβR2. The fragment comprising a truncated cytoplasmic domain of IL12Rb2 is represented by SEQ ID NO: 13. The TGFβR2-trIL12Rb2 comprises an exemplary amino acid sequence represented by SEQ ID NO: 16, with understanding by one skilled in the art that the transmembrane domain sequence of which could vary or be replaced with a transmembrane domain of another transmembrane protein.

SEQ ID NO: 13
SDPKPENPACPWTVLPAGDLPTHDGYLPSNIDDLPSH

EAPLADSLEELEPQ

SEQ ID NO: 16
TIPPHVQKSVNNDMIVTDNNGAVKFPQLCKFCDVRFS

TCDNQKSCMSNCSITSICEKPQEVCVAVWRKNDENIT

LETVCHDPKLPYHDFILEDAASPKCIMKEKKKPGETF

FMCSCSSDECNDNIIFSEEYNTSNPDLLLVIFQVTGI

SLLPPLGVAISVIIIFYCYRVN*SDPKPENPACPWTVL*

*PAGDLPTHDGYLPSNIDDLPSHEAPLADSLEELEPQ*
(TGFβR2 ectodomain-transmembrane domain sequence-IL12Rb2 endodomain fragment)

Figure 9:
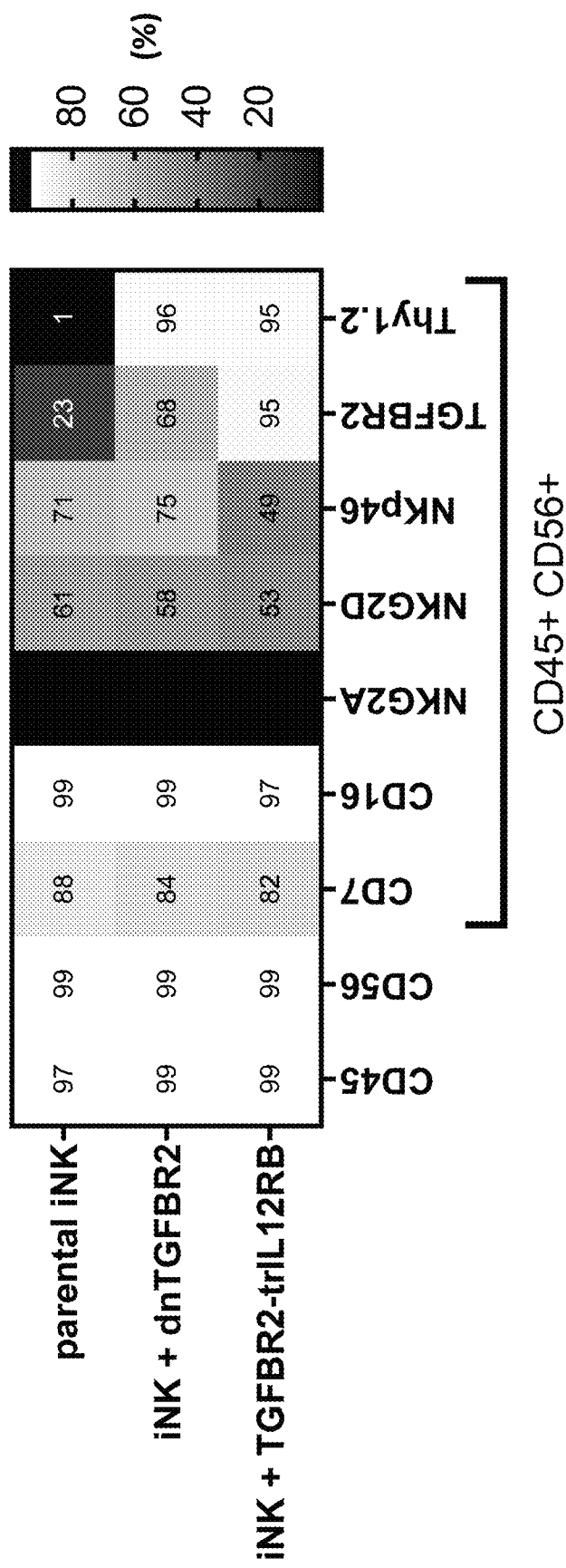
FIG. 9 shows a phentypic profile of iNK cells engineered with a TGFβR-trIL12Rβ redirector receptor.

A bi-cistronic donor cassette comprising the polynucleotides encoding the TGFβR2-trIL12Rβ redirector receptor and hnCD16 was inserted in the CD38 locus of iPSCs using a CRISPR enzyme. The bulk-engineered iPSCs were sorted and differentiated into iNK cells in this experiment using the methods described in this application. Flow cytometry was used to detect surface expression of the indicated NK markers on iNK cells that were differentiated from iPSCs (FIG. 9). The iNK cells expressing dominant negative TGFβR2 (dnTGFβR2) or the TGFβR2-trIL12Rβ redirector receptor exhibited a phenotypic profile similar to that of the parental iNK. This indicates compatibility of the TGFβR2-trIL12Rβ transgene with the iPSC development and iNK differentiation processes. Only the markers associated with the donor cassette, TGFβR2 and Thy1.2, are different in the TGFβR2-trIL12Rβ- and the dnTGFβR2-expressing iNKs, as expected.

Figure 10B:
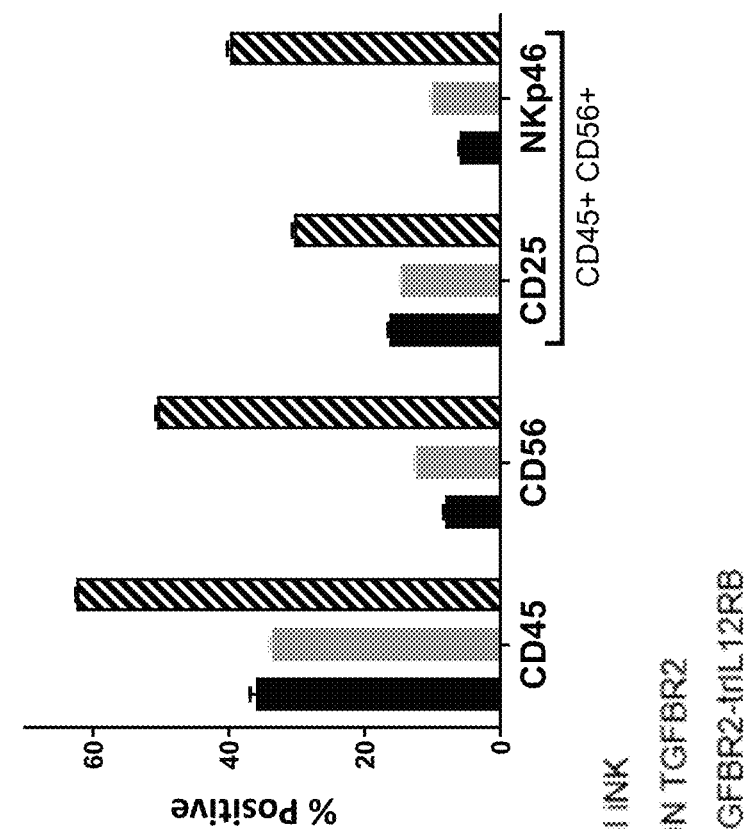
FIG. 10B shows an increased proportion of iNK cells engineered with a TGFβR-trIL12Rβ redirector receptor with desired phenotypic profile and a more activated profile in the presence of TGFβ.
Figure 10A:
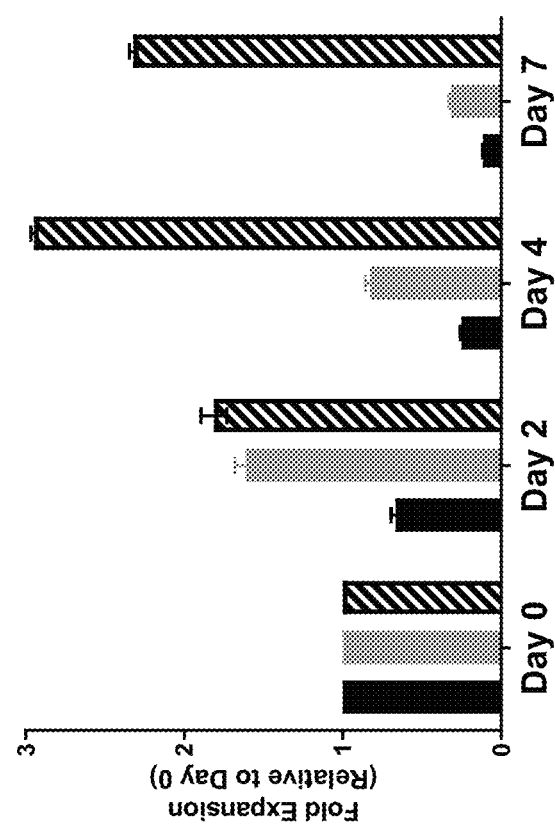
FIG. 10A shows that iNK cells engineered with a TGFβR-trIL12Rβ redirector receptor exhibit robust persistence and expansion in the presence of TGFβ over dnTGFβR transduced iNK cells.

The parental iNKs, the dnTGFβR2 expressing iNKs, and the TGFβR2-trIL12Rβ expressing iNKs were then each co-cultured with K562 target cells at an effector to target (E:T) ratio of 1:1. 20 ng/mL of TGFβ was added to the co-cultures on days 0, 2, and 4. Flow cytometry was used to assess effector cell numbers on days 2, 4, and 7 of the co-culture. As shown in FIG. 10A, both the parental iNKs and the dnTGFβR2 iNKs showed progressive loss in effector cell numbers over the 7 days of co-culture. However, the iNK cells expressing the TGFβR2-trIL12Rβ redirector receptor showed robust expansion and persistence even until day 7 of the assay (FIG. 10A). Without being limited by theory, this increased performance over the dnTGFβR2 iNKs could be due to the redirection of TGFβ signals toward the IL12 signaling pathway through the cytoplasmic domain fragment of the IL12Rb. Cells from day 7 were further analyzed by flow cytometry for the NK phenotypic markers (CD45 and CD56) or activation markers (CD25 and NKp46). As shown in FIG. 10B, the parental iNK and the dnTGFβR2 iNKs showed similar proportions of cells expressing the selected surface markers, whereas the TGFβR2-trIL12Rβ cells showed significantly increased proportions of cells that retained CD45 and CD56 expression. It is also noted that the TGFβR2-trIL12Rβ iNKs showed a more activated profile based on the percentage of effectors expressing CD25 and NKp46 (FIG. 10B).

Figure 11A:
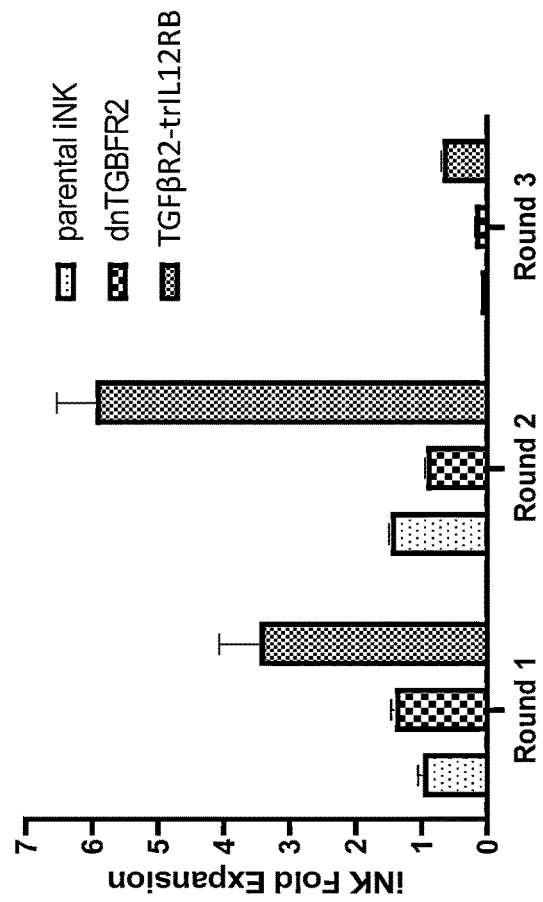
FIG. 11A shows that the TGFβR2-trIL12Rβ iNK cells exhibit robust innate killing capacity toward target cells compared to iNK cells expressing dnTGFβR2 and parental iNK cells.
Figure 11B:
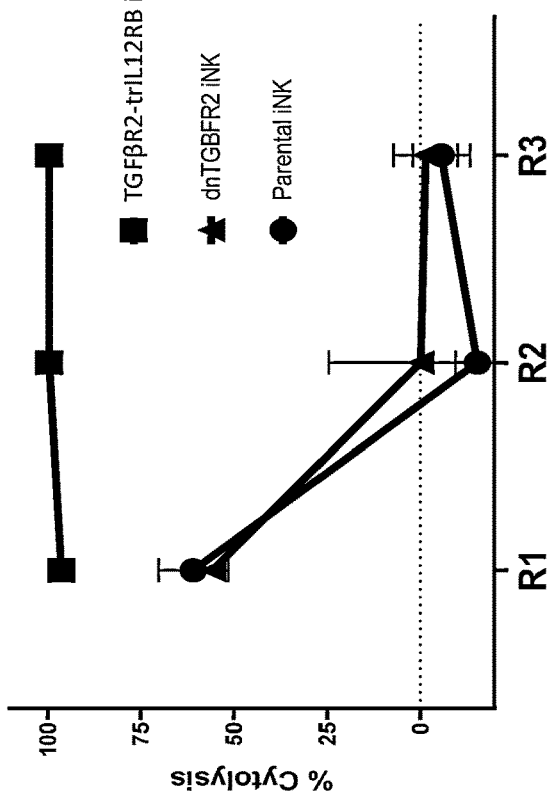
FIG. 11B shows that the TGFβR2-trIL12Rβ iNK cells exhibit increased expansion compared to iNK cells expressing dnTGFβR2 and parental iNK cells over three rounds of restimulation with target cells.

Further, the parental iNKs, the dnTGFβR2 expressing iNKs, and the TGFβR2-trIL12Rβ expressing iNKs were each co-cultured with Raji tumor target cells at an E:T ratio of 1:1. 20 ng/mL of TGFβ was added to the co-cultures on days 0, 2, and 4, and innate killing capacity toward the target cells was measured by flow cytometry over three rounds. As shown in FIG. 11A, both the parental iNKs and the dnTGFβR2 iNKs showed a significant loss in innate killing capacity after the first round of stimulation, while the TGFβR2-trIL12Rβ iNK cells maintained the ability to kill targets over all three rounds of co-culture. At the end of each round of co-culture, flow cytometry was also used to determine the expansion of the effector cells. As shown in FIG. 11B, iNK cells expressing the TGFβR2-trIL12Rβ redirector receptor showed robust expansion compared to the parental iNKs and the dnTGFβR2 iNKs, suggesting that the TGFβR2-trIL12Rβ redirector receptor improves effector cell expansion in the presence of the tumor target cells.

Figure 11C:
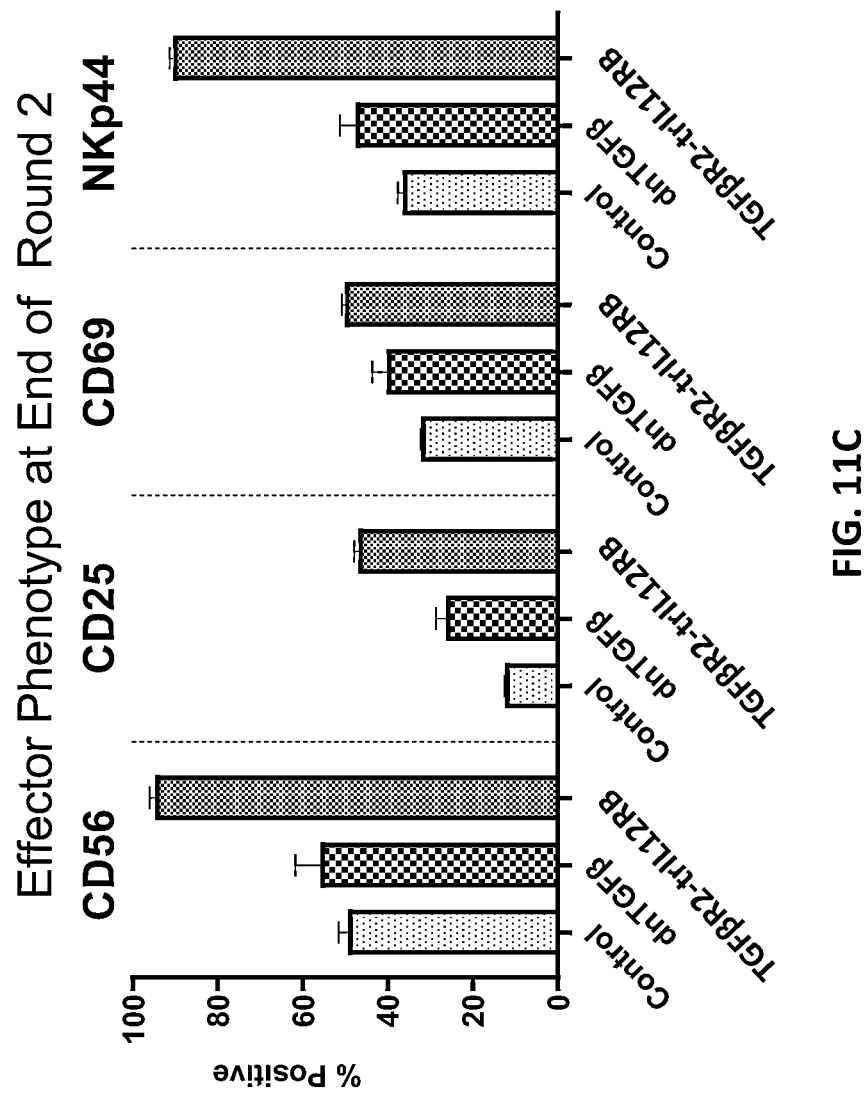
FIG. 11C shows an increased proportion of TGFβR2-trIL12Rβ expressing iNK cells with phenotypic and activation markers as compared with iNK cells expressing dnTGFβR2 and parental iNK cells (control).

Cells from the end of round 2 of restimulation were further analyzed by flow cytometry for the NK phenotypic marker (CD56) and activation markers (CD25, CD69 and NKp44). As shown in FIG. 11C, the TGFβR2-trIL12Rβ iNK cells showed significantly increased proportions of cells expressing the selected surface activation markers compared to the parental iNKs (control) and the dnTGFβR2 iNKs. As in the previous experiment, the TGFβR2-trIL12Rβ iNKs showed a more activated profile based on the percentage of effectors expressing activation markers (FIG. 11C).

Figure 12:
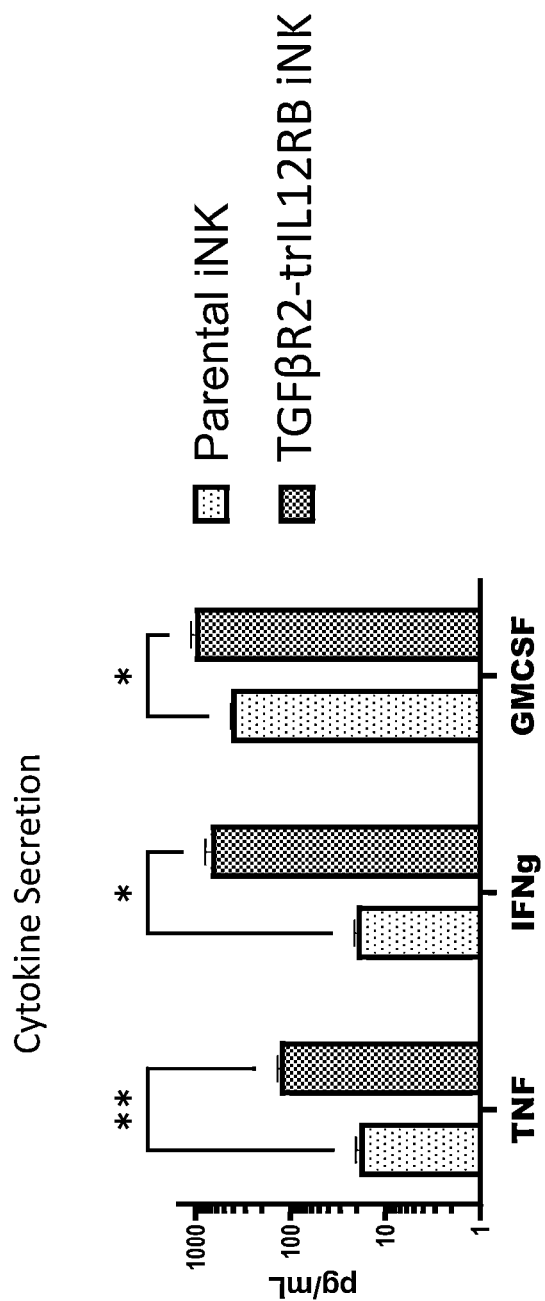
FIG. 12 shows quantification of cytokines TNF, IFNγ, and GMCSF secreted by TGFβR2-trIL12Rβ expressing iNKs cocultured with MDA-MB-231 cells compared to cytokine secretion of parental iNKs against the same targets.

The TGFβR2-trIL12Rβ iNK cells and Parental iNK were co-cultured overnight with MDA-MB-231 cancer cells at an E:T ratio of 5:1 in the presence of 20 ng/ml TGFβ and an anti-PDL1 monoclonal antibody (mAb). The MDA-MB-231 breast cancer cell line overexpresses PDL1. Avelumab is an ADCC-competent monoclonal antibody (mAb) capable of binding to the exogenous CD16 variant comprised in the parental iNK cells for the iNK cells to carry out ADCC mediated cytotoxicity against the target cancer cell. After overnight co-culture, supernatants were harvested, centrifuged, and loaded onto a multianalyte cartridge to quantify secretion of the cytokines TNF, IFNγ, and GMCSF (FIG. 12).

Figure 13A:
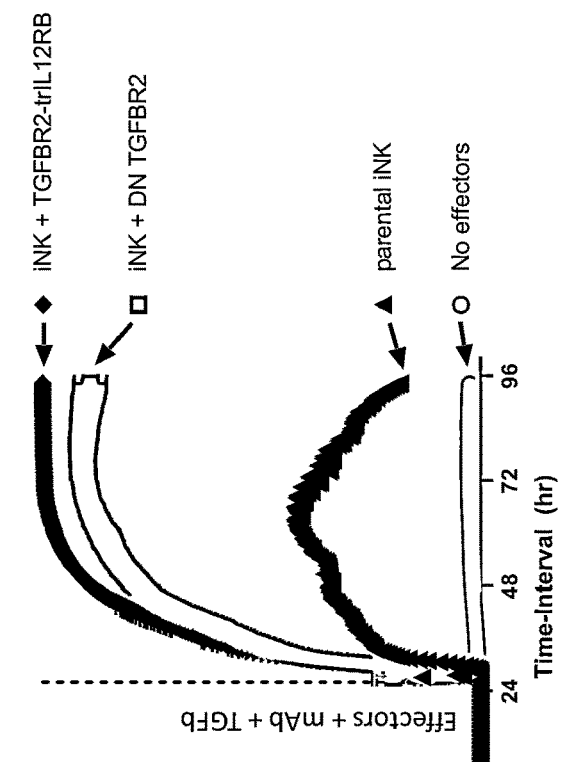
FIGS. 13A and 13B show that iNK cells engineered with a TGFβR-trIL12Rβ redirector receptor exhibit enhanced ADCC and resistance to TGFβ-mediated suppression in an initial round of co-culture with a breast cancer cell line as compared to cells expressing dnTGFβR.
Figure 13B:
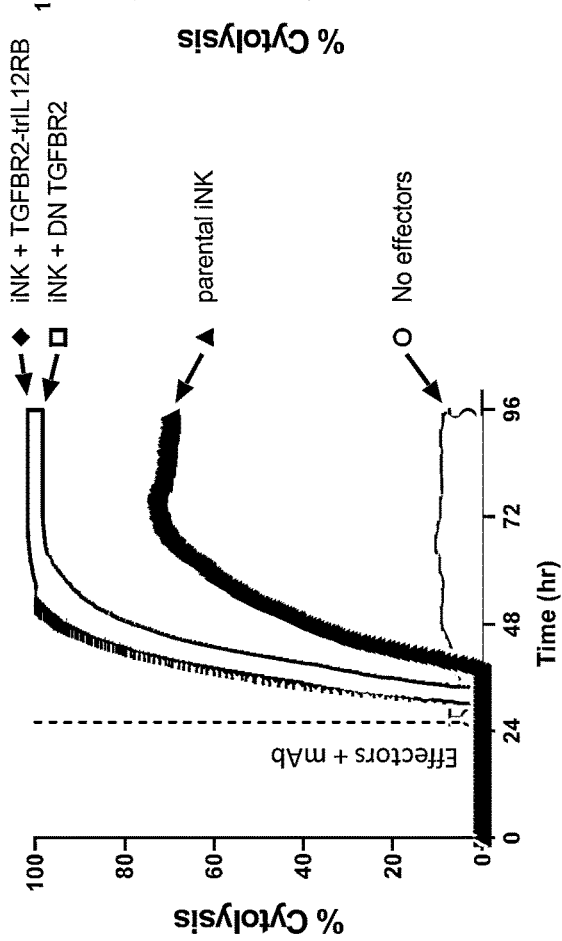

An xCelligence™-based ADCC assay was used to determine the ADCC capacity of the different iNK effectors. As shown in FIG. 13A, in the absence of effectors, addition of the mAb alone (10 μg/mL Avelumab) was not sufficient to induce cytolysis of target cells. Addition of effectors (E:T ratio of 5:1) to the culture resulted in cytolysis of the target cells by each tested iNK cell line. Parental iNK effectors exhibited ADCC toward the MDA-MB-231 target cells, but the iNKs expressing either dnTGFβR2 or the TGFβR2-trIL12Rβ showed much better cytolytic activity. Without being limited by theory, it is possible that blocking TGFβ signaling during the iNK differentiation process can result in iNKs that have improved effector function, such that both dnTGFβR2 and TGFβR2-trIL12Rβ iNKs show better ADCC even in the absence of TGFβ. As demonstrated, when 20 ng/mL TGFβ was added in the culture medium, the parental iNKs had a dramatic loss in ADCC capacity, and the dnTGFβR2 iNKs decreased in overall ADCC activity. However, the TGFβR2-trIL12Rβ iNKs still exhibited complete cytolysis of target cells with TGFβ spike-in by the end of the assay (FIG. 13B).

Figure 14A:
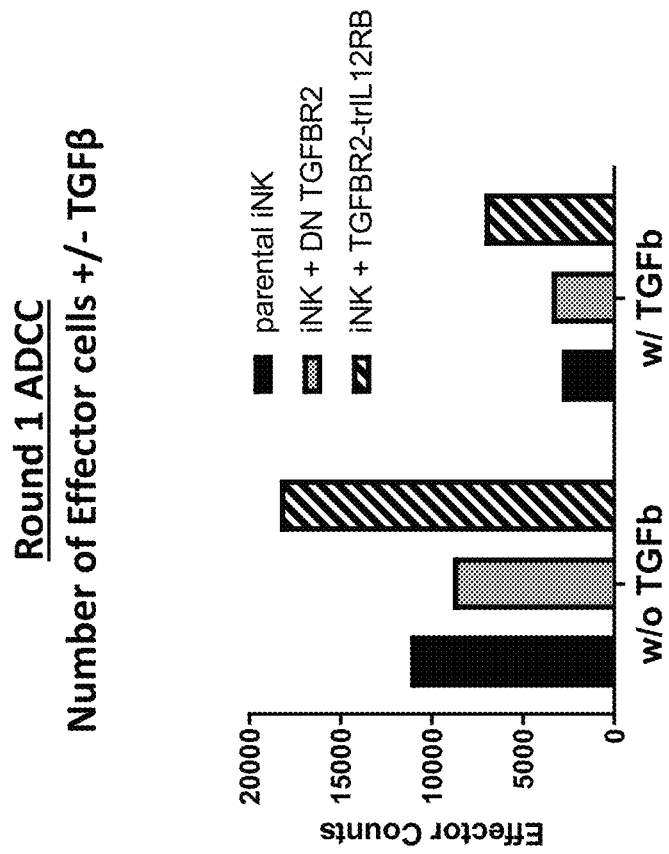
FIGS. 14A and 14B show that iNK cells engineered with a TGFβR-trIL12Rβ redirector receptor are more persistent than dnTGFβR2 iNK cells after a first round of co-culture with MDA-MB-231 target cells by demonstrating the number of effector cells remaining (FIG. 14A) and transgene expression (FIG. 14B) at the end of Round 1 of stimulation.
Figure 14B:
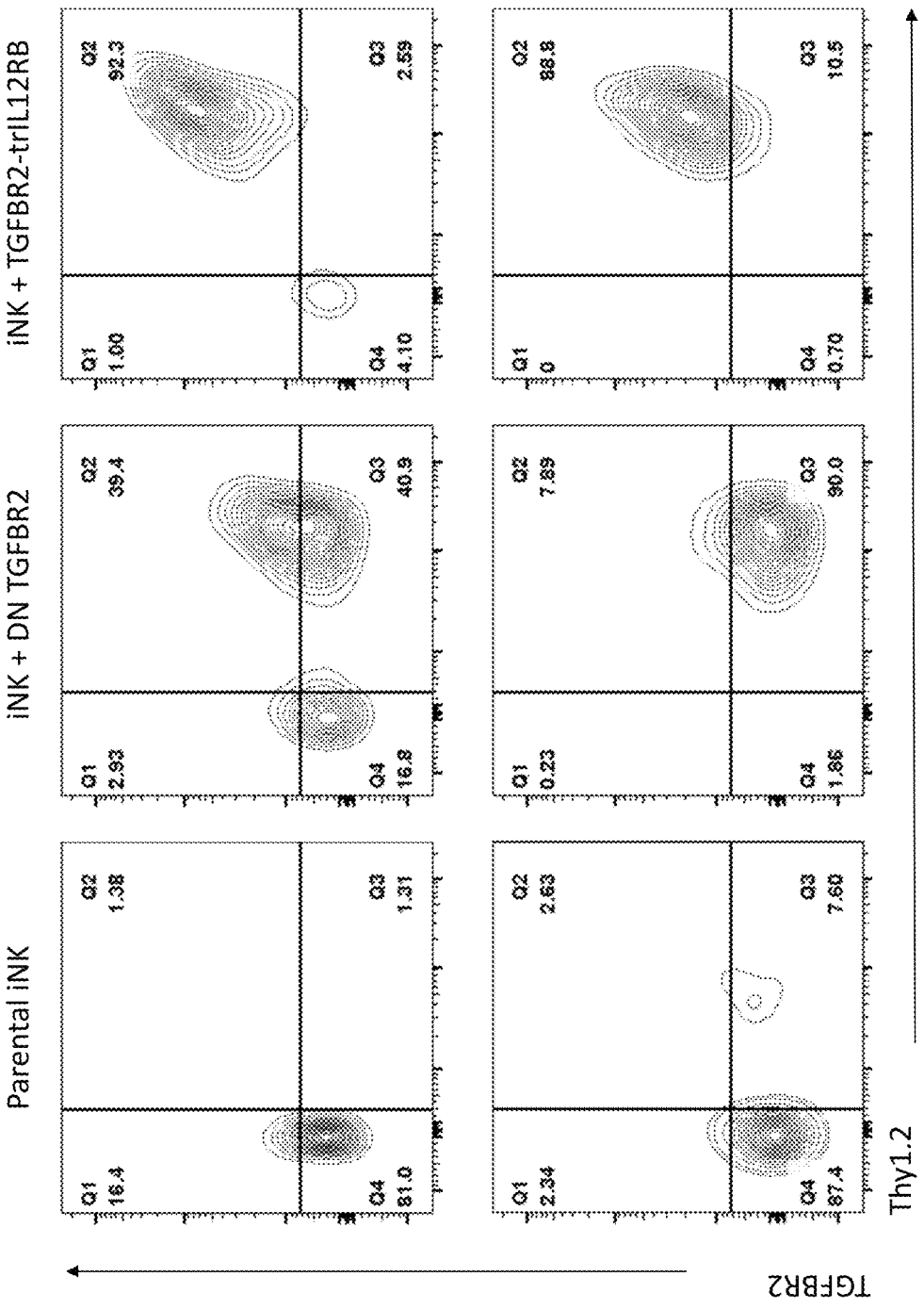

In addition, cells were harvested at the end of the first round of co-culture with the MDA-MB-231 target cells and analyzed by flow cytometry to determine the number of effector cells remaining, and transgene expression at the given time point. Without being limited by theory, the enhanced persistence of TGFβR2-trIL12Rβ expressing iNKs compared to iNKs expressing dnTGFβR2 could be attributed to that the TGFβR2-trIL12Rβ redirector receptor not only blocking TGFβ signaling but also initiating the IL12 signaling cascade (FIG. 14A). Additionally, as shown in FIG. 14B, the TGFβR2-trIL12Rβ construct seems to be more stable and highly expressed on the surface of iNK cells in the presence of TGFβ, a hallmark of suppressive solid tumor environment.

Figure 15A:
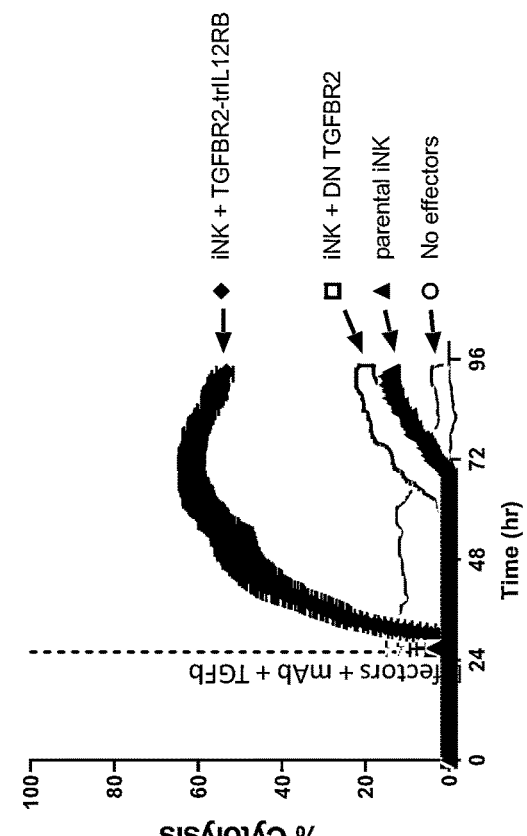
FIGS. 15A and 15B show that iNK cells engineered with a TGFβR-trIL12Rβ redirector receptor exhibit superior antitumor ADCC activity in a second round of co-culture with target cells as compared to multiple control cell groups.
Figure 15B:
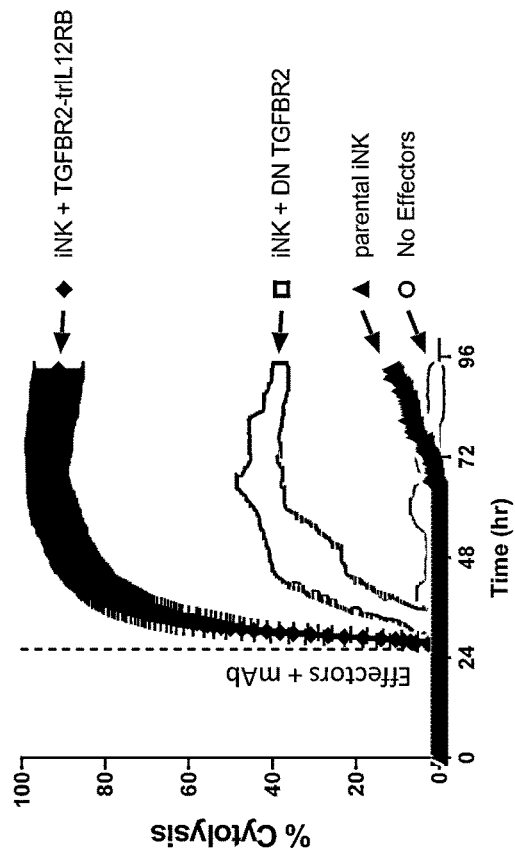

With the same set-up as FIG. 13A, at the end of the Round 1 co-culture, the effector cells were transferred to a second xCelligence™ plate with MDA-MB-231 tumor targets. Following addition of effectors and Avelumab, % cytolysis of Round 2 was measured accordingly. FIG. 15A shows that even in the absence of TGFβ the parental iNKs lost effector function, as almost no ADCC activity was observed toward the target cells. The dnTGFβR2 iNKs retained some amount of ADCC activity, albeit greatly reduced when compared to the TGFβR2-trIL12Rβ iNKs, which were able to lyse the target cells almost completely. Without being limited by theory, a certain level of tonic signaling from the TGFβR2-trIL12Rβ construct could result in iNKs expressing this transgene to have robust effector function even after multiple rounds of target stimulation. In the presence of TGFβ, however, even the dnTGFβR2 iNKs lost almost all their ability to lyse target cells just like the parental iNKs (FIG. 15B). And while the TGFβR2-trIL12Rβ iNKs also show reduced ADCC capacity in the presence of TGFβ, there was a clear benefit in having the TGFβR2-trIL12Rβ transgene over the dnTGFβR2 transgene in overcoming the suppression effect of TGFβ. Such observations in NK cells where expression of TGFβR2-trIL12Rβ resulted in enhanced effector cell expansion, persistence, and effector function could be expected in T cells, as the IL12 signaling pathway is considered as important in T cells as in NK cells.

Figure 16:
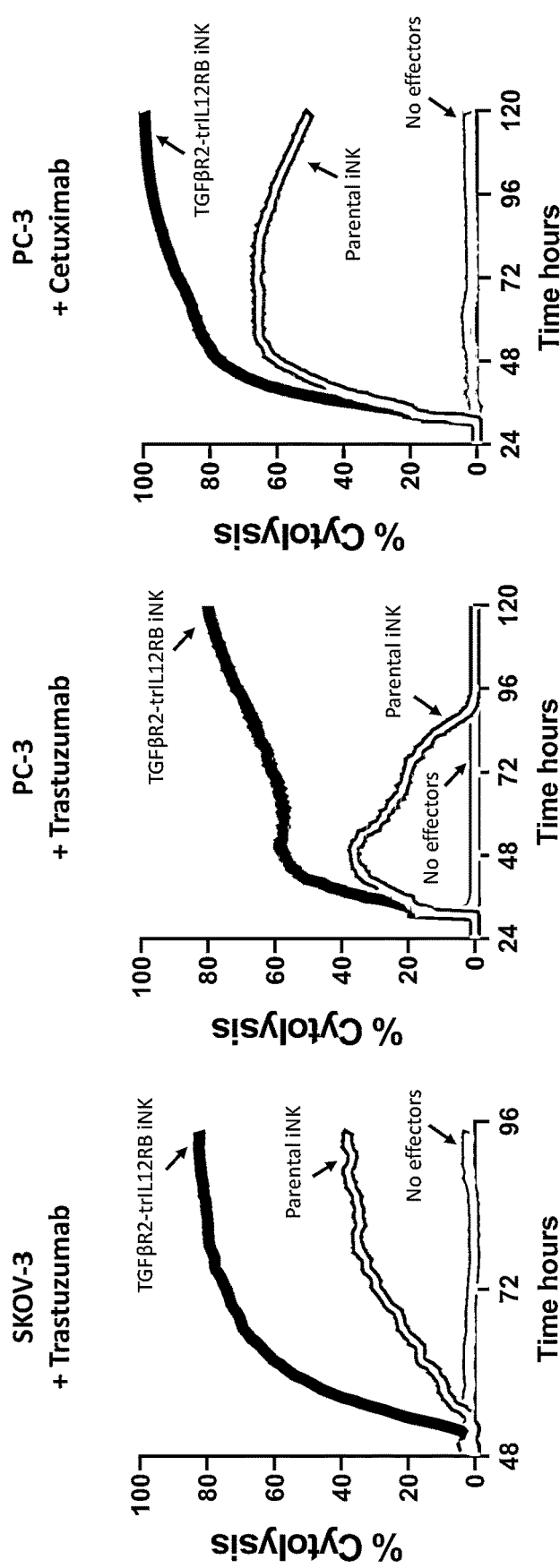
FIG. 16 shows that iNK cells engineered with a TGFβR-SSR exhibit enhanced ADCC cytolysis across various solid cancer cell lines in the presence of suppressive signaling of TGFβ.

To further assess ADCC capacity of the different iNK effectors, the assay was expanded to additional solid cancer cell models including the SKOV3 ovarian cell tumor line and the PC-3 prostate cancer cell line. Since SKOV3 cancer cells overexpress HER2, trastuzumab (an anti-HER2 antibody commercially known as Herceptin™) was selected as an exemplary ADCC-competent mAb against SKOV3 targets, while trastuzumab and cetuximab (an anti-EGFR antibody) were selected as the exemplary mAbs for the PC-3 targets in view of their expression of both HER2 and EGFR. As shown in FIG. 16, the iNKs expressing the TGFβR2-trIL12Rβ showed much better cytolytic activity toward all targets, compared to parental iNK effectors.

Example 5—Selective Depletion of Alloreactive Immune Cells Enabled by CD38 Negative CAR-iT Cells Having the Solid Tumor Targeting Backbone Both autologous and allogeneic cell therapies currently rely on lympho-conditioning of the patient, which induces a cytokine-rich environment for potentiation of adoptively-transferred cells and modulates the host immune system. Lympho-conditioning, however, has been associated with hematologic toxicities, including increased susceptibility to severe infections. The immuno-therapeutic effector cells disclosed herein comprise the solid tumor targeting backbone which strategically incorporates selectively introduced exogenous modelities at selected endogenous loci, knocking out the endogenous gene(s) at the same time as a part of the backbone design. CD38, as one of the two selected endogenous loci, is one of the gene knockout strategies encompassed by the solid tumor targeting backbone design provided herein in seeking to significantly reduce the requirement for chemotherapy-based lympho-conditioning while maintaining the anti-tumor activity of adoptively-transferred cells.

Figure 17:
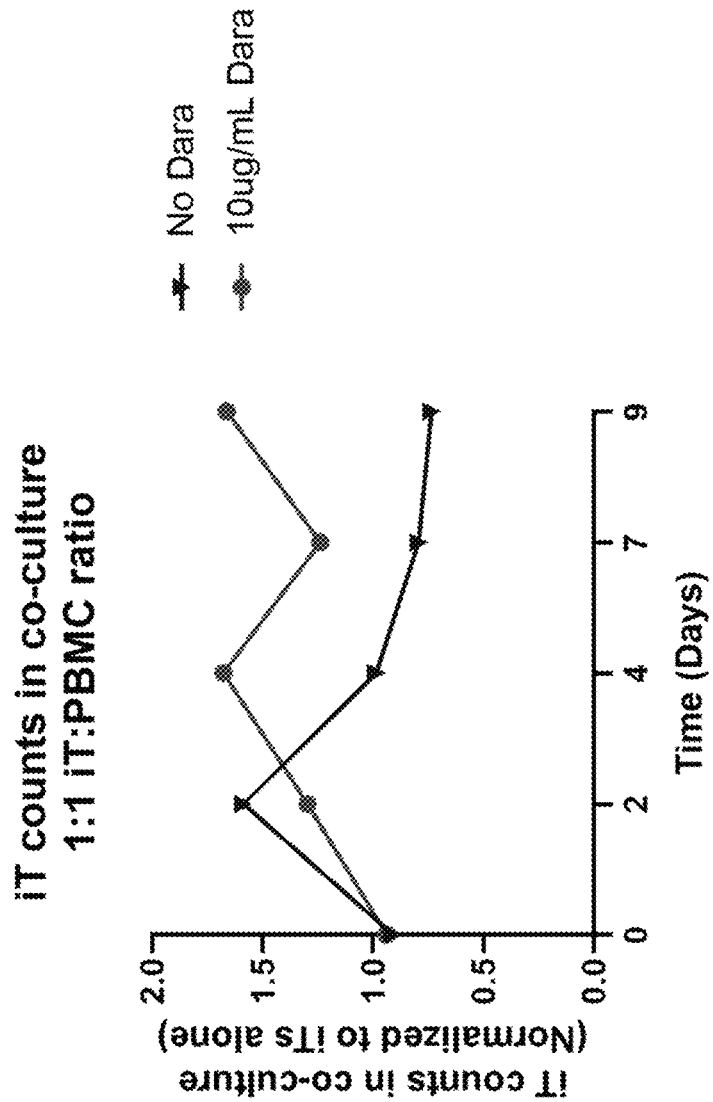
FIG. 17 shows that hnCD16a$^+$/CD38$^-$ CAR-iT cells are not susceptible to depletion in the precense of daratumumab.

A mixed lymphocyte reaction (MLR) was performed to evaluate the ability of anti-CD38 mAb (daratumumab) treated CAR-iT cells to resist rejection by allogeneic lymphocytes. hnCD16a$^+$/CD38$^-$ CAR-iT cells were co-cultured with allogeneic peripheral blood mononuclear cells (PBMCs) from a healthy donor at a 1:1 ratio with and without the anti-CD38 antibody, daratumumab, for 9 days in media supplemented with IL2. Over the duration of co-culture, flow cytometry analysis was performed where CAR-iT cell numbers were counted and plotted at the indicated timepoints (FIG. 17). CAR-iT cell counts were normalized to CAR-iT cell control cultures maintained in the absence of PBMCs. The data show that in the absence of daratumumab, co-cultures of CAR-iT cells were susceptible to PBMC-mediated depletion over time. However, in daratumumab treated co-cultures, CAR-iT cells maintained persistence levels similar to control cultures without PBMCs, and even expanded over time. These data demonstrate that CAR-iT cells having a solid tumor targeting backbone comprising a CD38 knockout as disclosed herein are not susceptible to depletion by the presence of daratumumab. In addition, the daratumumab treatment protects CD38$^-$ CAR-iT cells from depletion by allogeneic lymphocytes in allogeneic solid tumor targeting.

Figure 18:
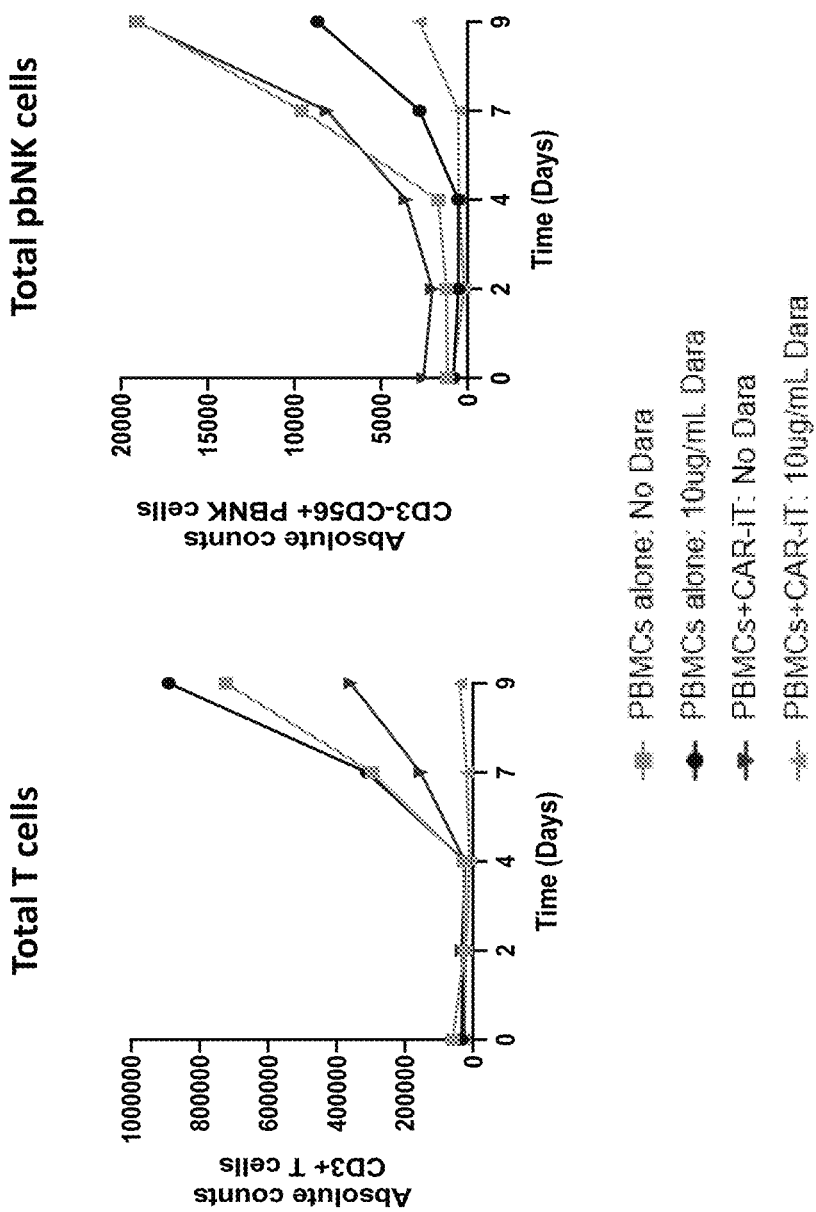
FIG. 18 shows that the combination of daratumumab and CAR-iT cells potently suppresses alloreactive T and pbNK cell expansion in that the allogeneic T and NK cells are depleted in both a daratumumab- and a CAR-iT-dependent manner.

In these co-cultures, T and pbNK cell expansion among the PBMCs was measured over time. As shown in FIG. 18, absolute T (left panel) and pbNK cell (right panel) counts were plotted at the indicated time points. The data indicate that both T and pbNK cells were able to robustly expand when PBMCs were cultured alone. In PBMC cultures where either daratumumab or CAR-iT cells were provided respectively, only partial suppression of T and pbNK cell expansion was observed. However, in the condition where PBMCs were co-cultured with both CAR-iT cells and daratumumab, maximum suppression of T and pbNK cells was observed. These data demonstrate that CAR-iT cells having a solid tumor targeting backbone comprising a CD38 knockout as disclosed herein can utilize daratumumab to suppress allogeneic T and pbNK cell expansion; thereby, providing a mechanism by which CAR-iT cells can evade T and pbNK alloreactivity.

Figures 19A, 19B:
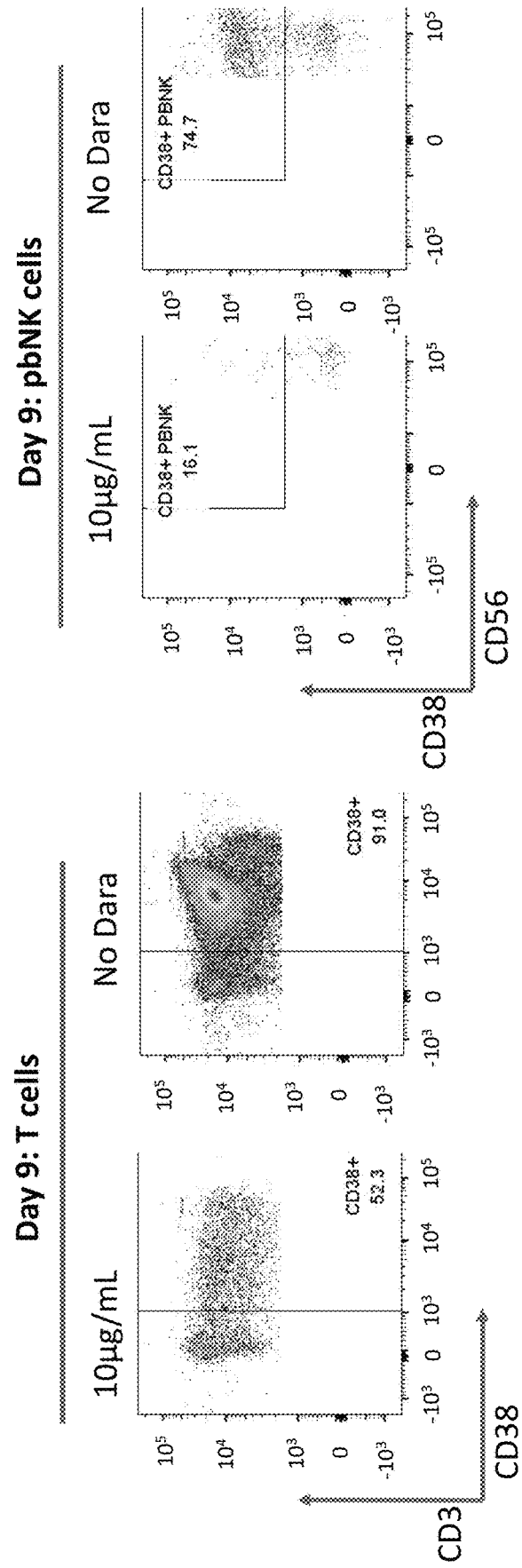
FIGS. 19A and 19B show that CD38$^+$ T and pbNK cell compartments of PBMC are electively depleted in the presence of daratumumab.
Figures 19C, 19D:
FIGS. 19C and 19D show that CD38$^+$ T and pbNK cells of PBMC are depleted in a daratumumab-dependent manner.

In these co-cultures, the ability of daratumumab to selectively deplete CD38$^+$ T and pbNK lymphocytes was also assessed. Representative flow plots demonstrate that in CAR-iT cell co-cultures with PBMCs, 91% of the T (FIG. 19A) and 74% of the pbNK cells (FIG. 19B) expressed CD38. However, in these same co-cultures treated with daratumumab, substantial decreases in the percentages of CD38$^+$ T and pbNK cells was observed (down to 52% in FIG. 19A, and 16% in FIG. 19B, respectively. The absolute counts of CD38$^+$ T and pbNK cells as shown in the representative flow plots were quantitated and plotted as bar graphs. CD38$^+$ T cell counts from co-cultures maintained in the presence of daratumumab showed an approximately 15-fold reduction in detectable CD38$^+$ T cells compared to the control condition (FIG. 19C). Similarly, CD38$^+$ pbNK cell counts from daratumumab treated co-cultures demonstrated an approximate 21-fold reduction in detectable CD38$^+$ pbNK cells compared to the control condition (FIG. 19D). When taken together, these data demonstrate that incorporation of the CD38 knockout into the solid tumor targeting backbone enables anti-CD38 mAb CAR-iT or iNK cells to selectively deplete CD38$^+$ T and pbNK cells while sparing non-alloreactive, CD38 negative lymphocytes, including CD38 null CAR-iT or iNK cells, when the cells are treated with daratumumab.

In addition, it was observed that when targeting CD38$^+$ T and pbNK cells using hnCD16a$^+$/CD38$^-$ iNK and iT cells in the presence of daratumumab, the depletion of CD38$^+$ cells increased NAD$^+$ (nicotinamide adenine dinucleotide, a substrate of CD38) availability and decreased NAD$^+$ consumption-related cell death, which, among other advantages, boosts effector T and NK cell responses and reduces effector cell senescence in a immunosuppressive tumor microenvironment.

It is also noted that treatment with an anti-CD38 antibody to take advantage of CD38 knockout may be utilized only when necessary, providing flexibility in patient settings.

Example 6—Effector Cells Armed with Alloimmune Defense Receptor (ADR) Targeting 4-1BB As an alternative or additional approach to address lympho-conditioning associated challenges, an alloimmune defense receptor (ADR) that selectively targets host immune cells and significantly boosts the functional activity of adoptively-transferred cells was developed. As disclosed herein, an ADR targeting 4-1BB, which is upregulated on activated effector cells, including alloreactive NK and T cells, was adopted to be a part of the solid tumor targeting backbone as configured herein to afford allogeneic effector cells functional persistence and anti-tumor activity in an immuno-competent host system while depleting host immune cell subsets without requiring chemotherapy conditioning.

In an in vitro mixed lymphocyte reaction (MLR) assay, CAR-iNK cells (with or without ADR) and PBMC were co-cultured in a 8:1 ratio. The Day 10 co-culture was analyzed for expression of CD38 and 4-1BB among $CD3^+$ T cells, and it was demonstrated that all detectable 4-1BB expression is restricted to the $CD38^+$ alloreactive populations, indicating that a potential simultaneous use of ADR and CD38 conditioning (i.e., $CD38^-$ effector cell in the presence of anti-CD38 antibody) provides an enhanced alloreactivity defense strategy that can be further incorporated into a solid tumor targeting backbone as disclosed in this application. Initial studies suggested that ADR-modified CAR-iNK cells resist allogeneic rejection while eliciting a durable anti-tumor response which is further enhanced with the combination of anti-CD38 mAb.

Induced pluripotent stem cells were serially or simultaneously engineered to obtain CD38 KO, CD19-CAR, 41BB-ADR, high affinity non-cleavable CD16 (hnCD16), and overexpression of IL15RF using CRISPR nucleases and constructs comprising one or more intended transgenes and a pair of homology arms for position-selective insertion. When the insertion takes place at endogenous CD38 locus, the constructs provided herein allow the transgene(s) to express either under the CD38 endogenous promoter or under an exogenous promoter comprised in the construct. The genomically edited clonal iPSCs were then differentiated according to the methods provided herein to effector cells comprising CD19-CAR, CD38-/-, hnCD16 and IL15RF, with or without 41BB-ADR expression.

Figure 20A:
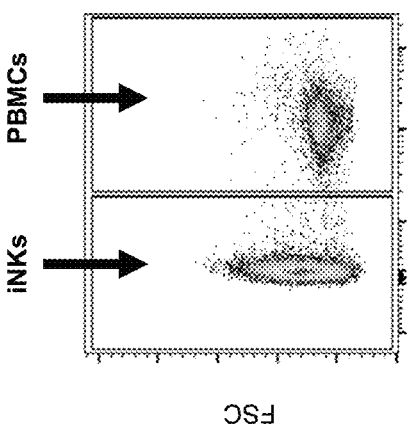
FIG. 20A shows a representative FACS plot depicting a gating schematic to quantify iNK cells against HLA-A2$^+$ PBMCs.
Figure 20B:
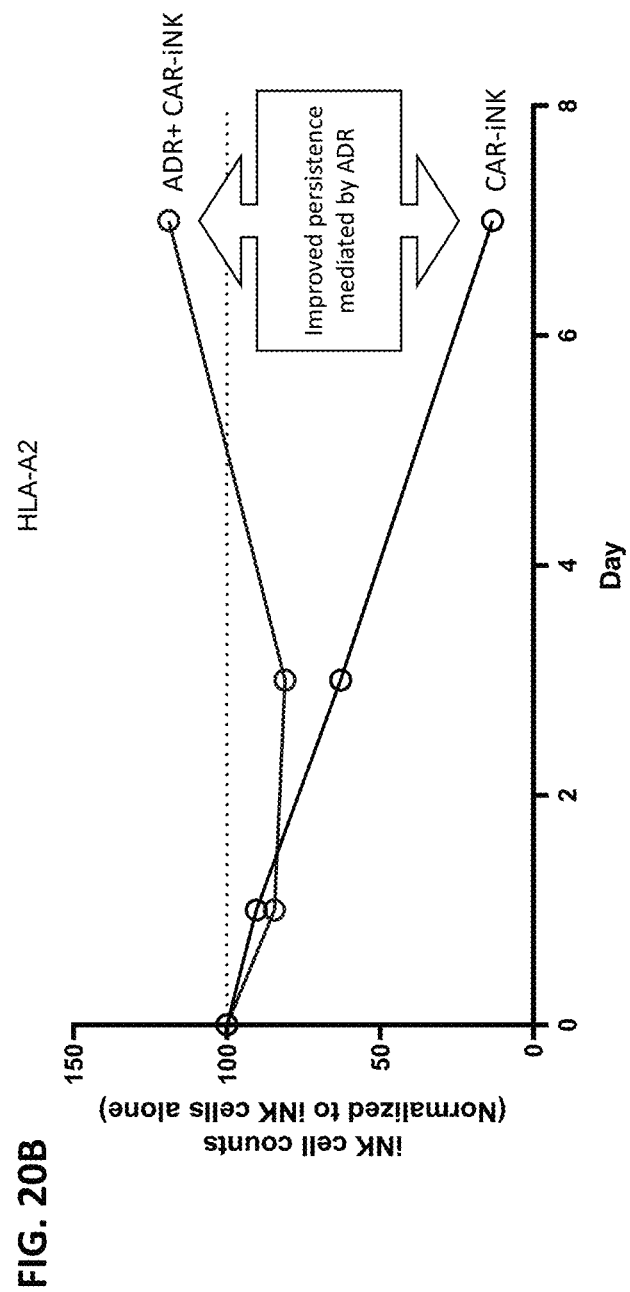
FIG. 20B shows that ADR+ CAR-iNK cells demonstrate enhanced functional persistence against activated allogeneic PBMC attack in mixed lymphocyte reactions (MLR).

A mixed lymphocyte reaction (MLR) was performed to test the longevity of the prepared derivative effector cells in an allogeneic setting. The iNK cell populations (with and without 41BB-ADR) were labelled with an intracellular dye (Celltrace Violet™ or similar Incucytem compatible reagent) immediately prior to assay. The CAR-iNK±ADR cells were co-cultured at a 4:1 iNK cell to PBMC ratio, with the $ADR^+$ CAR-iNK cells demonstrating enhanced functional persistence, as shown in a representative FACS plot depicting a gating schematic against $HLA-A2^+$ PBMCs (FIG. 20A). iNK cell counts from the co-cultures were plotted at the indicated timepoints shown in FIG. 20B, with data normalized to iNK cells cultured without PBMCs.

Figure 21B:
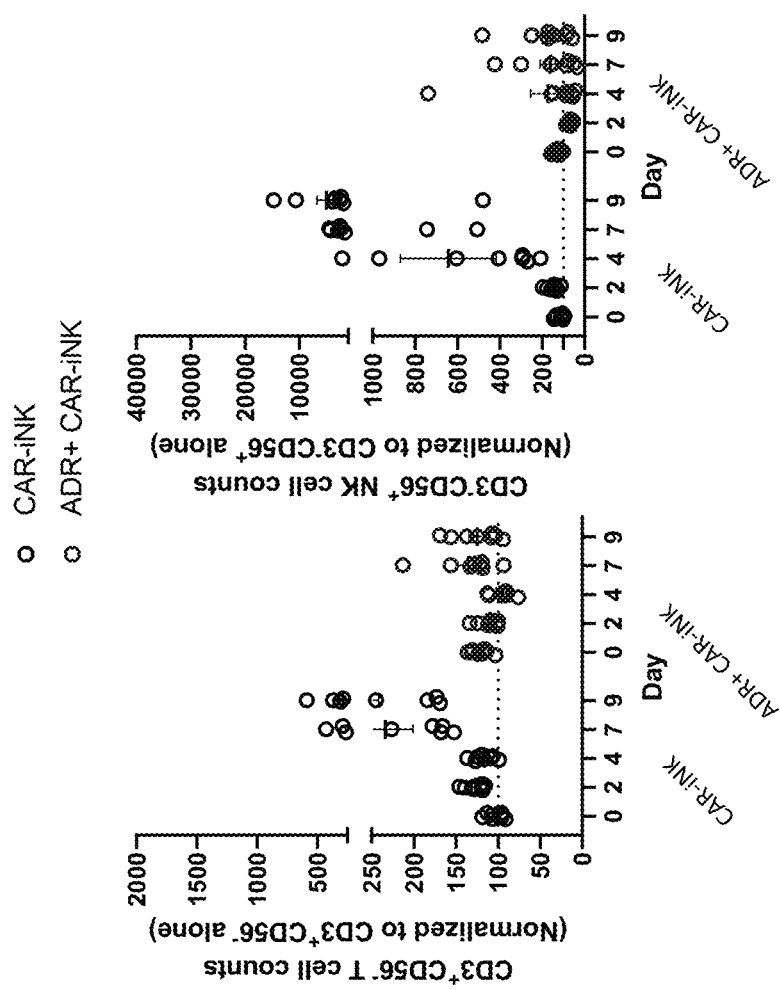
FIGS. 21A and 21B show that ADR+ CAR-iNK cells stifle expansion of allo-reactive T and NK cells.
Figure 21A:
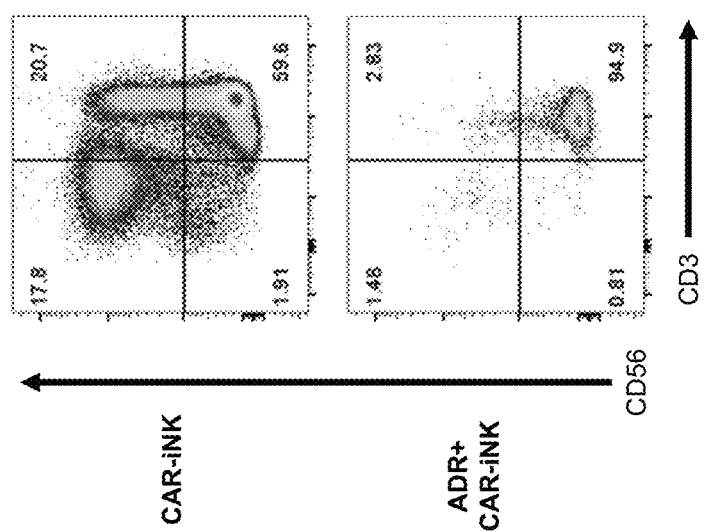
Figures 22A, 22B:
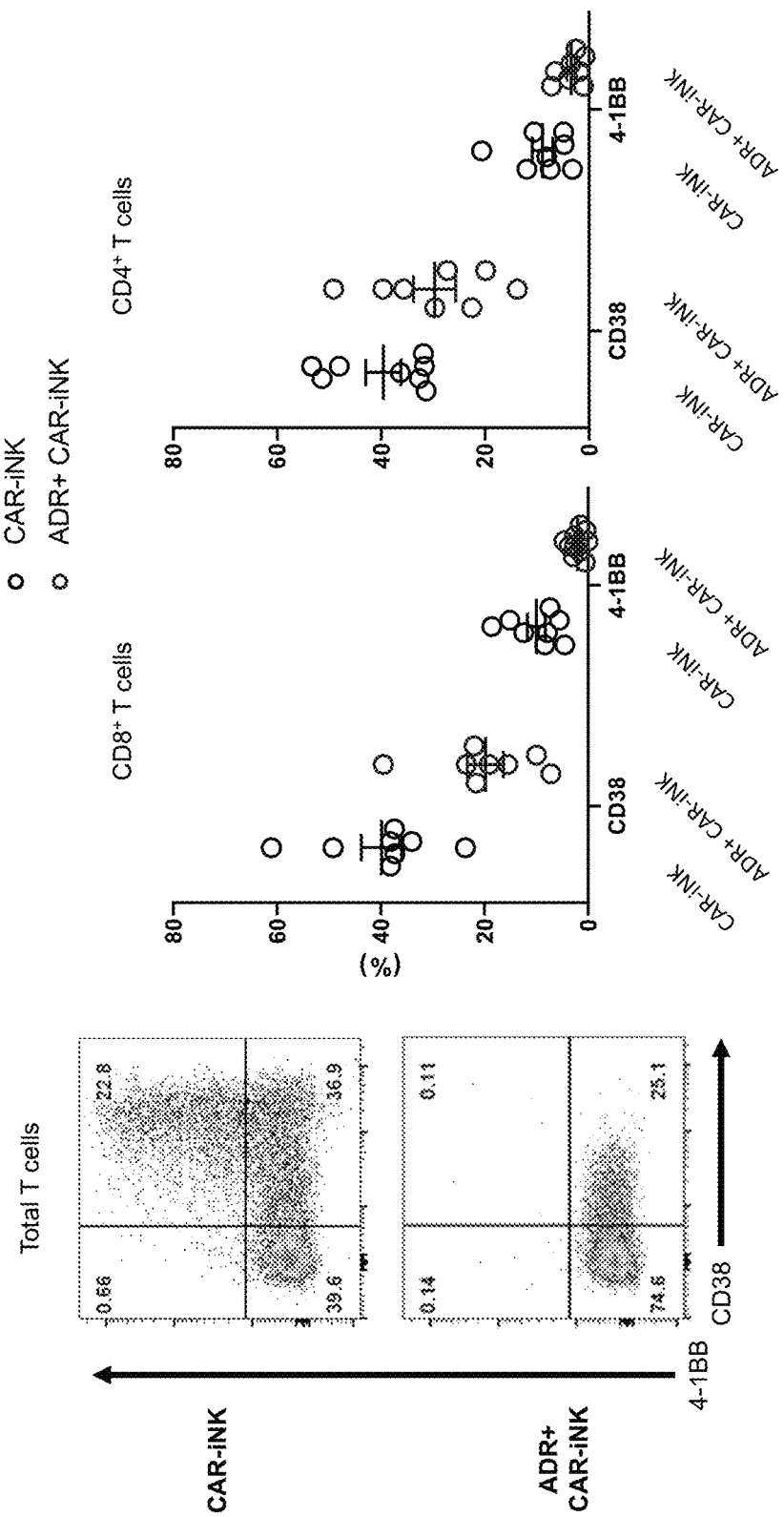
FIGS. 22A and 22B show that ADR+ CAR-iNK cells selectively target both CD4+ and CD8+ alloreactive T cell subsets.

In a separate experiment, the CAR-iNK±ADR cells were co-cultured with PBMCs from eight donors at a 2:1 iNK cell to PBMC ratio for nine days. As shown in FIG. 21A, $ADR^+$ CAR-iNK cells inhibited expansion of alloreactive $CD3^+$ T and $CD56^+$ NK cells, as compared to CD19-CAR iNK cells unarmed with ADR. Quantification of T- and NK cell counts (normalized to T- and NK cell counts from cultures of the donor PBMCs maintained in the absence of iNK cells) shows that expression of ADR prevented expansion of $CD3^+CD56^-$ T cells and $CD3^-CD56^+$ NK cells (FIG. 21B). When analyzed for expression of CD38 and 4-1BB among $CD3^+$ T cells, a significant depletion of $4-1BB^+$ T cells was observed in the presence of $ADR^+$ CAR-iNK cells (FIG. 22A). As shown in FIG. 22B, compilation of % CD38 and %4-1BB expression among $CD4^+$ and $CD8^+$ T cells from the eight donors in CAR-iNK±ADR co-cultures further demonstrates that ADR-armed effector cells selectively target and deplete both $CD4^+$ and $CD8^+$ allo-reactive T-cell subsets.

Figure 23:
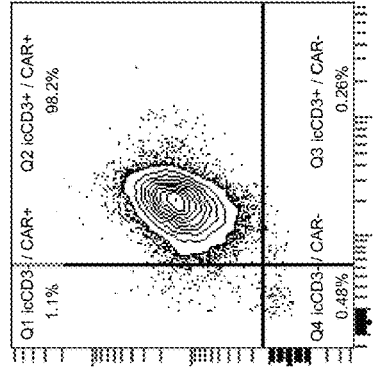
FIG. 23 shows that the iPSCs engineered to carry TRAC-driven CAR and ADR transgenes can be successfully differentiated into T cells with intracellular CD3 expression, and with robust co-expression of the CAR and ADR.
Figure 23:
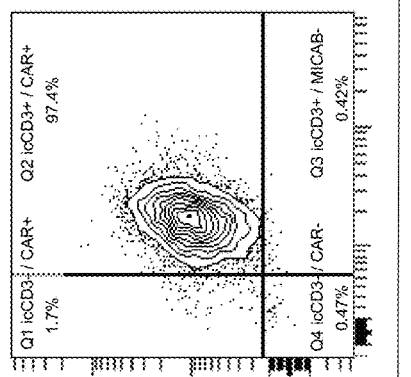
Figure 23:
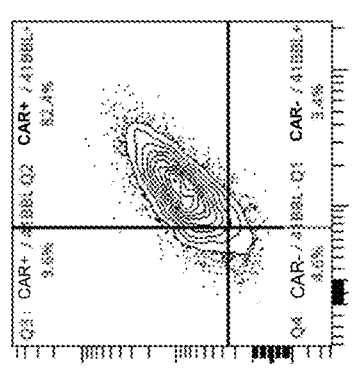
Figure 23:
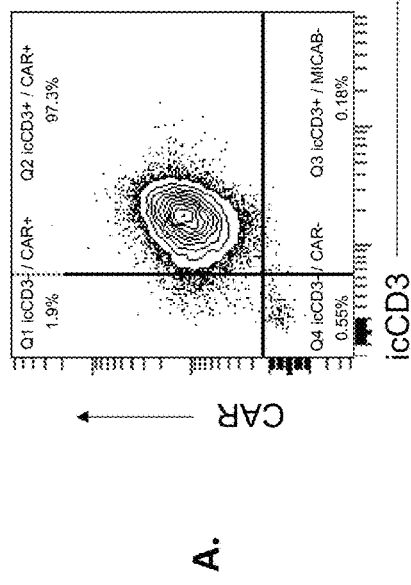
Figure 23:
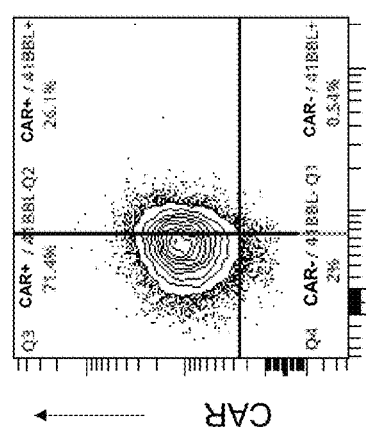
Figure 24:
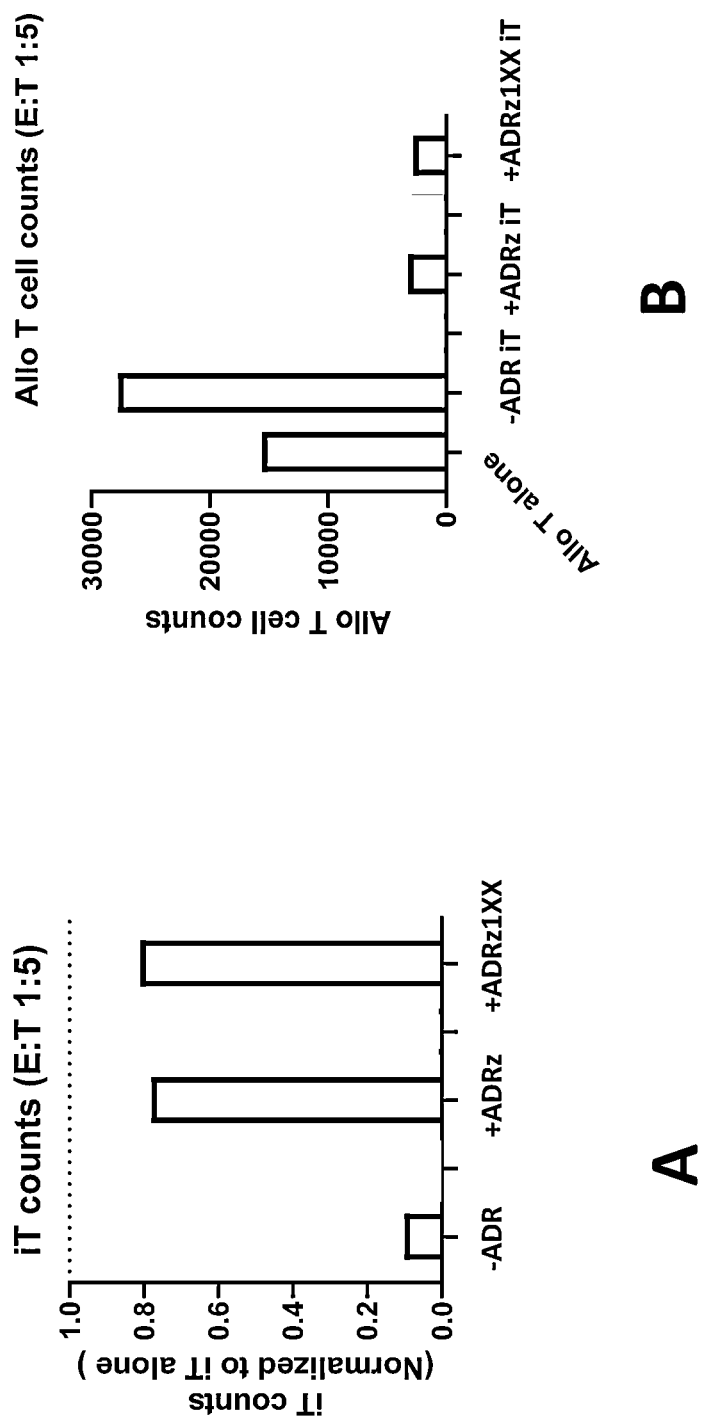
FIG. 24 shows that ADR expression of the iPSC-derived iT cells provides protection from primed allogeneic T cell rejection and depletes the allogeneic T cells.

Further, iPSCs engineered to knock in a bicistroic construct comprising a CAR (in this experiment, MICA/B-CAR is the exemplary CAR modality) and an ADR (41BB-ADR modality comprising either a $CD3\zeta$ or a $CD3\zeta1XX$ signaling domain as described in this application) at the TRAC locus were differentiated into T cells. The derived T cells were subsequently analyzed by flow cytometry for CAR and intracellular CD3 expression. As shown, iPSC engineered to express TRAC-driven CAR and ADR transgenes can be differentiated into committed T cells (FIG. 23 (A)), and the co-expression of the CAR and ADR modalities in the TRAC-engineered iPSC-derived iT cells is robust (FIG. 23 (B)). iT cells that either express or lack the ADR modality were cocultured for 72 h with allogeneic T cells. The iT cells not armed with ADR did not persist and were depleted in the presence of the allogeneic T cells, whereas ADR expressing iT cells persisted (FIG. 24 (A)). In addition, the allogeneic T cells expanded when co-cultured with the ADR deficient iT cells but were depleted in the presence of ADR expressing iT cells (FIG. 24 (B)). Taken together, these data show that ADR can protect iT cells in an allogeneic setting as well.

Collectively, the above in vitro data demonstrate the capability of 41BB-ADR expression by allogeneic effector cells in suppressing activated peripheral T or NK cells by targeting their upregulated 4-1BB, thereby reducing allorejection against the allogeneic effecter cells by these activated peripheral T or NK cells in the recipient of the effector cells.

Figure 25A:
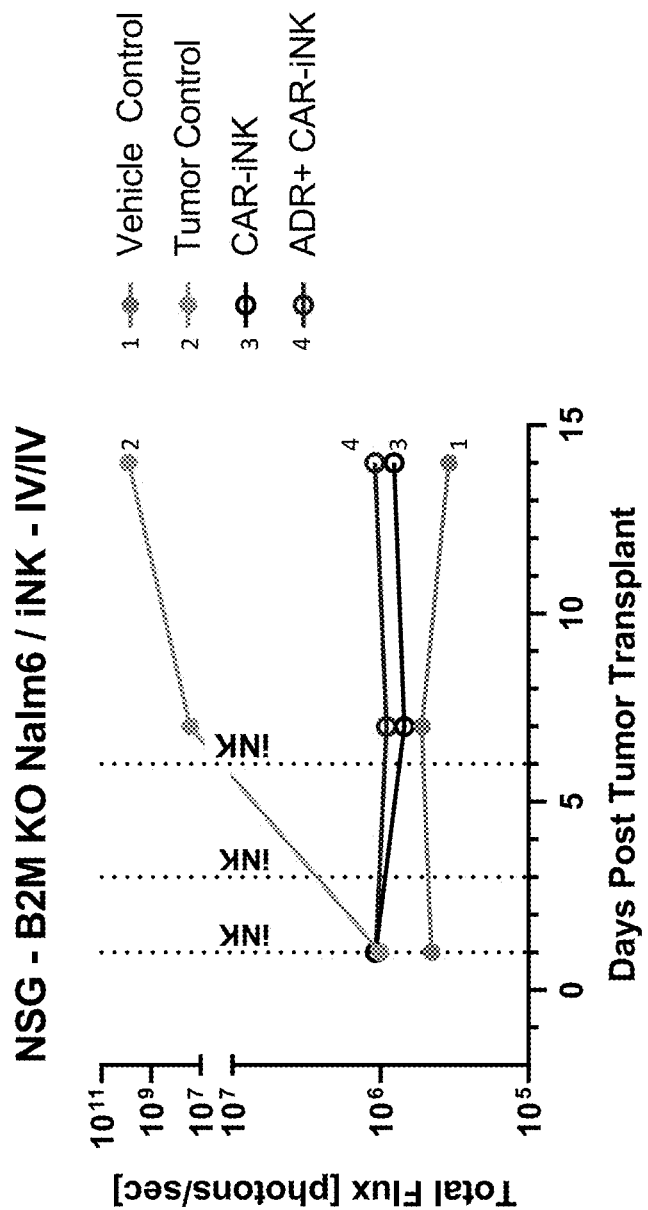
FIGS. 25A and 25B show that ADR+ effector cells exhibit uncompromised tumor control in vivo in the presence of host alloreactive T cells as compared to the effect of alloractive T cells towards the ADR− control cells.
Figure 25B:
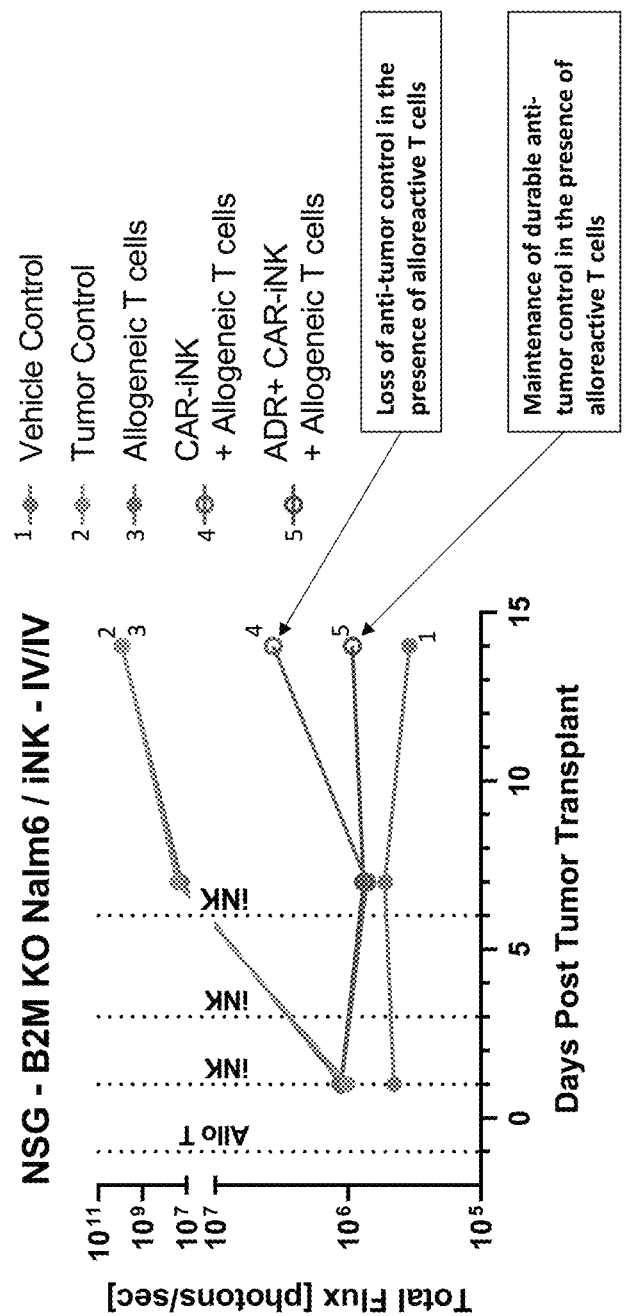

To evaluate the effectiveness of ADR-armed effector cells in vivo, NSG mice were intravenously (IV) injected with about $20 \times 10^6$ alloreactive T cells, followed 24 hours later (Day 0) with IV injection of $1 \times 10^5$ luciferized B2M KO Nalm6 cells. After another 24 hours (Day 1), the mice were IV injected with about $3 \times 10^6$ CAR-iNK cells with or without ADR expression, and then again on Day 3 and Day 6. NSG mice receiving only luciferized B2M KO Nalm6 cells or only vehicle were used as positive and negative controls, respectively. The alloreactive T cells were previously expanded in vitro for 10 days with 100 IU/ml IL2 and Dynabeadsrm Human T-Activator CD3/CD28 as indicated by manufacturer protocol. Bioluminescence-based tumor quantification by total flux was measured to monitor tumor growth in mice receiving alloreactive T cells in comparison to mice that did not receive alloreactive T cell injections in the presence of CAR-iNK±ADR. As shown, in the absence of allogeneic T cells, $ADR^-$ CAR-iNK and $ADR^+$ CAR-iNK cells have similar anti-tumor activities against Nalm6 targets (FIG. 25A). In comparison, with the presence of allogeneic T cells, the rejection of $ADR^-$ CAR-iNK cells leads to the loss of anti-tumor control of the unarmed effector cells (FIG. 25B). In contrast, $ADR^+$ CAR-iNK cells maintained durable anti-tumor control in the presence of allogeneic T cells as seen in the mice without allogeneic T cell challenge. Therefore, ADR-armed effector cells exhibit uncompromised tumor control in vivo in the presence of a host alloreactive T-cell system.

Example 7—IL7 Receptor Fusion (IL7RF) Incorporated in Solid Tumor Targeting Backbone Reduces CAR iT Cell Attrition An IL7 receptor fusion protein (IL7RF), comprising the IL-7 cytokine covalently linked to IL7Rα with a flexible linker, was incorporated into the solid tumor targeting backbone to enhance CAR-iT survival and persistence. HER2-CAR iTs either expressing TRAC_HER2-CAR or expressing TRAC_HER2-CAR/IL7RF and CD38_CAG hnCD16/CXCR2 were co-cultured with $HER2^{High}$ SKOV3 tumor cells at a 1:1 E:T ratio. The cytolytic efficacy of the effector cells and remaining CAR-iT cells after 48 hours of co-culture were then analyzed for each CAR-iT configuration to accertain the contribution of IL7RF to the HER2-CAR effector cell.

Figure 26A:
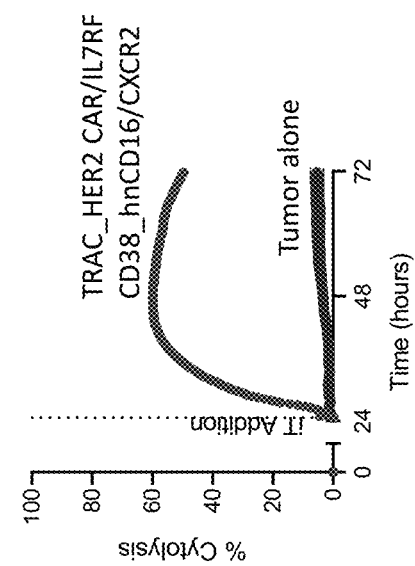
FIG. 26A shows the similar cytolytic efficacy of effector cells with indicated genomically engineered components.
Figure 26A:
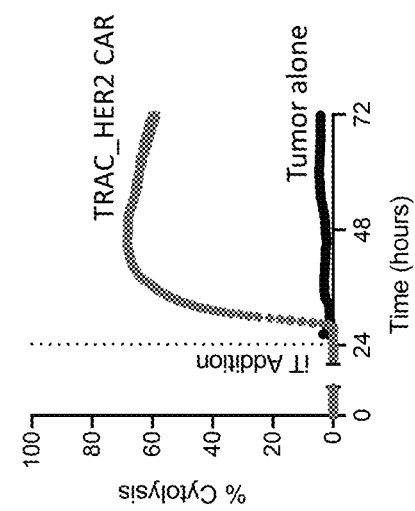
Figure 26B:
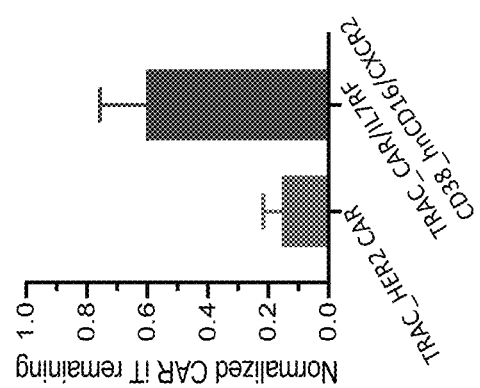
FIG. 26B shows that IL7RF substantially limits CAR-iT attrition and enhances effector cell persistence following activation.

As shown in FIG. 26A, CAR-iT cells with both configurations (TRAC_HER2-CAR; or TRAC_CAR/IL7RF and CD38_hnCD16/CXCR2) demonstrated similar anti-tumor efficacy against the HER2$^{High}$ tumor cells, reaching similar peak cytolytic efficacies of 60-70%. Around 48 hours after co-culture, CAR-iT cells were collected, and remaining CAR-iTs were measured. As shown in FIG. 26B, substantially more IL7RF-expressing CAR-iTs remained in the assay compared to CAR iT cells without IL7RF in the solid tumor targeting backbone (60% vs 15% of input). These data demonstrate that IL7RF expression limits CAR-iT cell attrition and enhances effector cell persistence following activation by target solid tumor cells. For iPSC-derived NK cells, CAR-IL15RF was used for co-expression with a CAR.

Example 8—hnCD16 Incorporated in Solid Tumor Targeting Backbone Complements and Supports CAR Targeting of Solid Tumor Associated Antigens The heterogeneity of even highly expressed solid tumor associated antigens (TAA) is a major barrier for the effective application of cellular immunotherapies in solid tumors. To enable multi-antigen targeting of solid tumor antigens, CAR-iT cells were engineered to express a high affinity, non-cleavable version of CD16a (hnCD16), and the compatibility and supplementation of hnCD16-mediated ADCC with CAR, as a part of the solid tumor targeting backbone as disclosed herein, was evaluated for solid tumor targeting. CAR-iT cells comprising TRAC_HER2-CAR/IL7RF and CAR iT cells comprising TRAC_HER2-CAR/IL7RF in addition to CD38_hnCD16/CXCR2 were each co-cultured with SKOV3 tumor cells for 48 hours along with therapeutic antibodies targeting PDL1 or HER2, and cytolytic efficacy of the effector cells was evaluated via xCELLigence™ assay at a 1:2 E:T ratio.

Figure 27A:
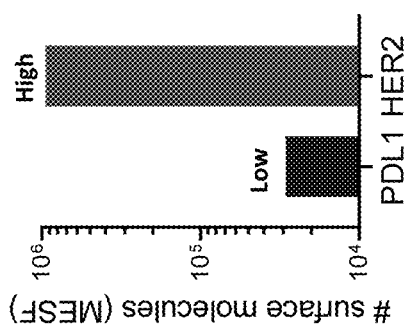
FIG. 27A shows surface expression of PDL1 and HER2 on SKOV3 tumor cells.
Figure 27B:
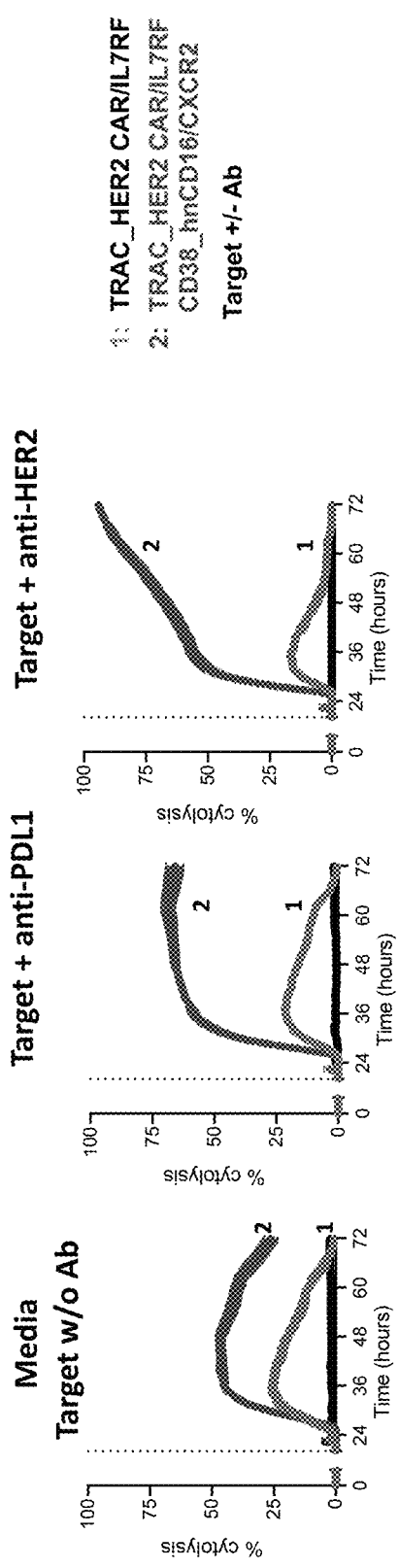
FIG. 27B shows that hnCD16 activation with either anti-PDL1 or anti-HER2 specifically enhanced the efficacy of hnCD16+ CAR-iT cells.
Figure 27C:
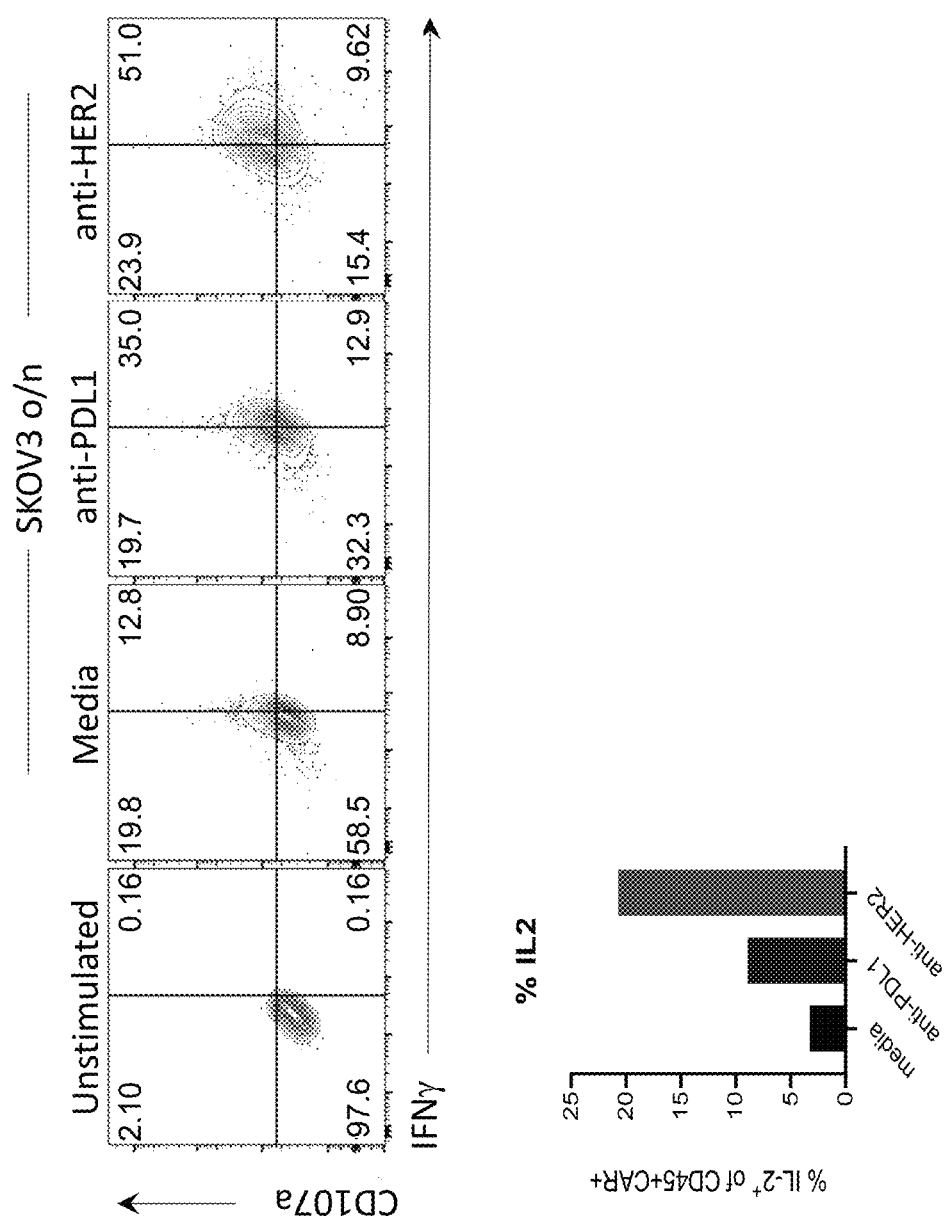
FIG. 27C shows expression of IFNγ, IL2, and CD107a expression (degranulation markers), demonstrating that hnCD16 complements and enhances CAR-based efficacy of CAR iT cells.
Figure 28:
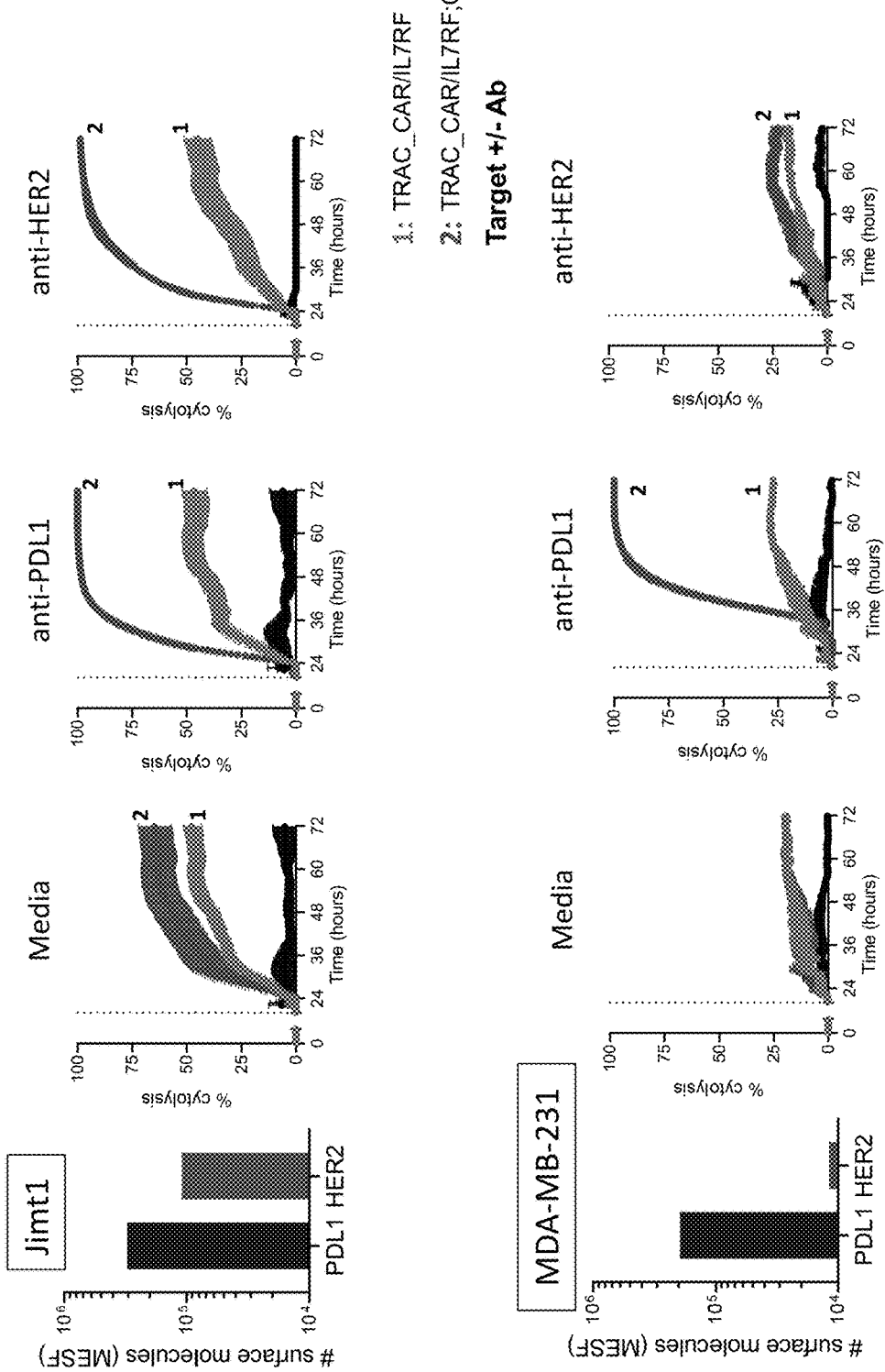
FIG. 28 shows that hnCD16 complements effector cell cytolysis and cytokine production.

Surface expression of PDL1 and HER2 on SKOV3 tumor cells was determined via quantitative flow cytometry, and the assayed SKOV3 tumor cells were PDL1$^{Low}$ and HER2$^{High}$ (FIG. 27A). As shown in FIG. 27B, hnCD16 activation with either anti-PDL1 (middle panel, 69% maximal cytolysis) or anti-HER2 (right panel, 95% maximal cytolysis) specifically enhanced the efficacy of hnCD16$^+$ CAR-iT cells, compared to media alone (left panel, 46% maximal cytolysis) or hnCD16 negative CAR-iT cells (16-25% maximal cytolysis). Importantly, the magnitude of hnCD16 supplementation to cytolysis is directly correlated with the expression levels of either PDL1 or HER2. Additionally, as shown in FIG. 27C, IFNγ, IL2, and CD107a expression (degranulation marker) by hnCD16$^+$ CAR-iTs activated overnight on SKOV3 tumor cells with and without anti-PDL1 or anti-HER2 antibodies further demonstrated that hnCD16 co-activation enhances the effector function of CAR-iT cells in an antigen expression dependent manner (SKOV3+hnCD16 CAR-iT: 12.8% IFNγ$^+$CD107a$^+$; SKOV3$^+$ hnCD16 CAR-iT+anti-PDL1: 35.0% IFNγ$^+$ CD107a$^+$; SKOV3$^+$ hnCD16 CAR-iT+anti-HER2: 51.0% IFNγ$^+$CD107a$^+$).

hnCD16-mediated ADCC further enhanced the cytolytic efficacy of HER2-CAR iT on Herceptin resistant JIMT1 (HER2$^+$ PDL1$^{High}$) and HER2$^{Low}$ MDA-MB-231 (HER2$^{Low}$ PDL1$^{High}$) tumor lines (FIG. 28). As was observed with SKOV3 tumor cells, the relative enhancement of CAR efficacy with hnCD16 activation was proportional to the secondary TAA targeted. For example, on JIMT1 and MDA-MB-231 tumor cells, maximum cytolytic efficacy (100% for both) was observed with anti-PDL1 & CAR iT compared to CAR iT alone (47% & 19%, respectively).

Figure 29:
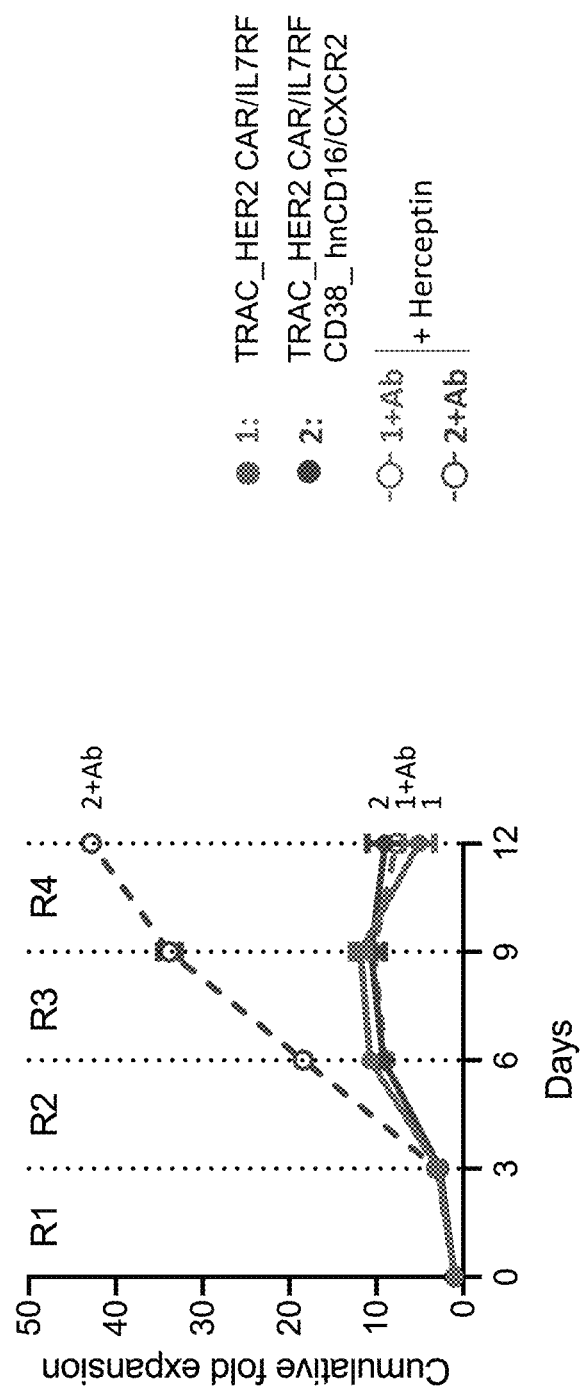
FIG. 29 shows that hnCD16 and CAR co-activation of CAR-iT cells leads to substantially greater expansion of hnCD16+ CAR-iT cells over multiple rounds of tumor challenge.

Next, hnCD16/CAR complementation was evaluated in a repeat antigen stimulation assay. Briefly, HER2-CAR iT expressing TRAC_HER2-CAR/IL7RF or TRAC_HER2-CAR/IL7RF and CD38_hnCD16/CXCR2 were co-cultured with HER2$^{High}$ SKOV3 tumor cells at a 1:1 E:T ratio, in the presence of IL2 with or without anti-HER2 antibodies. After three days of co-culture CAR-iTs were collected and counted before being reseeded with fresh tumor targets at a 1:1 E:T ratio. CAR-iT expansion and cytolytic efficacy was determined via incucyte assay. As shown in FIG. 29, hnCD16 and CAR co-activation of CAR-iT cells lead to substantially greater expansion of hnCD16$^+$ CAR-iT cells over multiple rounds of tumor challenge, reaching >40 fold expansion after four rounds of tumor challenge, compared to 9-fold expansion for hnCD16$^+$ CAR-iTs in the absence of hnCD16 coactivation with anti-HER2 antibodies, and 5-7 fold for hnCD16$^-$ CAR-iT cells with and without anti-HER2 antibodies. Notably, the cytolytic efficacy of hnCD16 and CAR co-activated CAR-iT cells was greatest over all four rounds of tumor challenge. In summary, these data demonstrate that, as components of the solid tumor targeting backbone as disclosed herein, the CAR and the hnCD16 activation are compatible and complementary, with the synergistic benefit in driving effector cell expansion and cytotoxicity, and in tackling solid tumor heterogeneity—supporting multi-antigen targeting across multiple antigen densities and tumor types.

Figure 30:
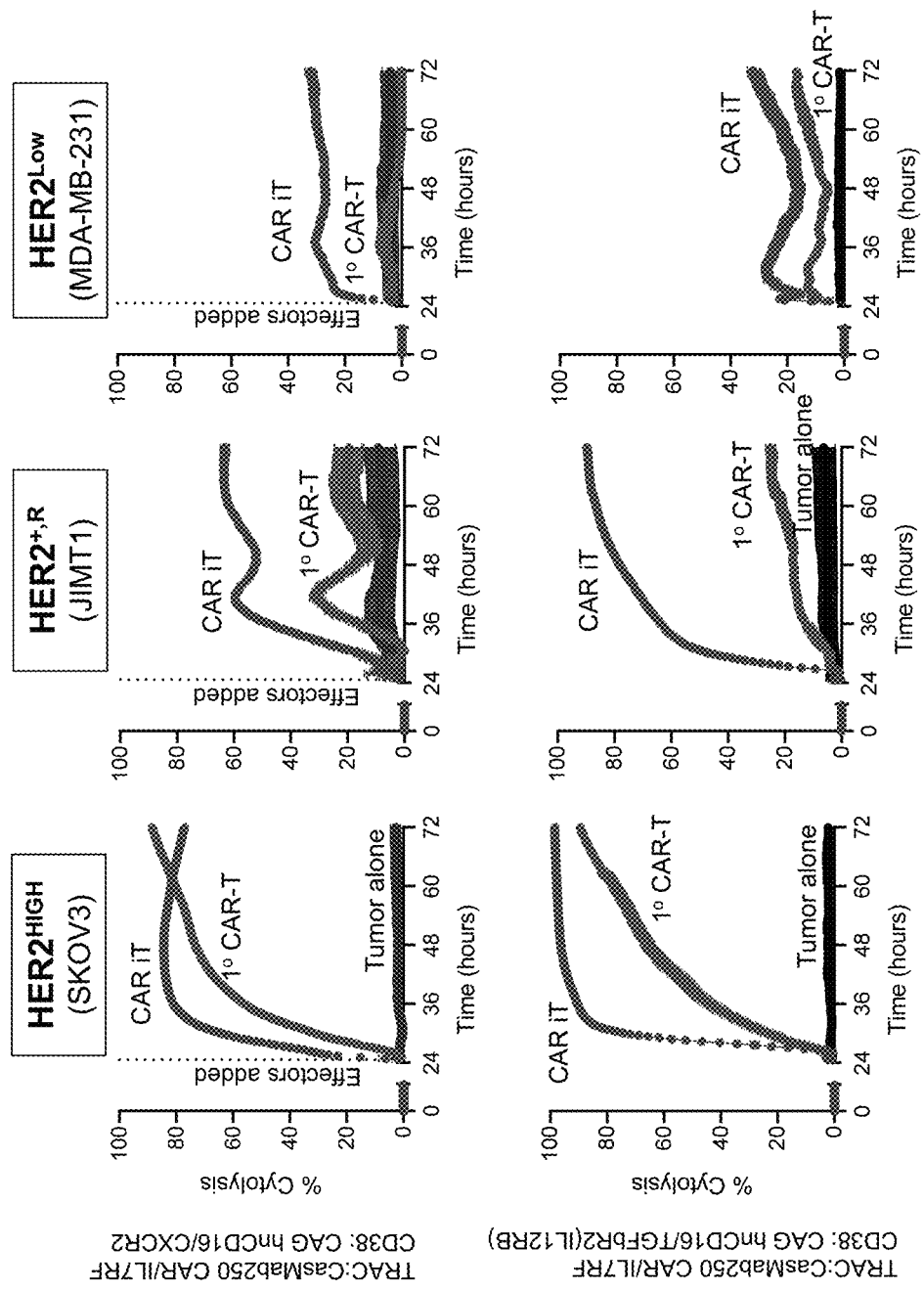
FIG. 30 shows robust and enhanced anti-HER2 efficacy of effector cells comprising indicated solid tumor targeting backbone configurations as compared to primary CAR-T cells having the same HER2-CAR but without a solid tumor targeting backbone.

Example 9—CasMab Based HER2-CAR are Efficacious and Selective for Tumor in Effector Cells Having The Solid Tumor Targeting Backbone Although chimeric antigen receptor (CAR) T-cell therapy has shown remarkable efficacy in liquid tumors, its wider application to solid tumors has been hampered by tumor-associated antigen (TAA) heterogeneity, inefficient CAR-T cell trafficking to the tumor, and immunosuppression inherent to the tumor microenvironment. Moreover, the often-dysfunctional and heterogenous yield of highly-edited (e.g., >2 transgenes) primary, donor-derived CAR-T cells necessary to address these obstacles has limited their efficacy and wider clinical investigation. Therefore, the demonstration of a multiplex-engineered CAR-iT cell product comprising an optimized backbone that is compatible with any solid tumor targeting modality (such as an antigen-specific CAR, ADCC compatible mAbs, BiTEs, TRikEs), is of particular importance for its wide range of application in solid tumor indications. The multiplex-engineered CAR-iT cell product comprising an optimized backbone provided herein is designed and tailored specifically to overcome common barriers observed in solid tumors, including the ability to preferentially traffic to the tumor, to promote tumor microenvironment resistance, and to elicit potent and enhanced anti-tumor activity in both in vitro and in vivo settings. In addition, it is also demonstrated that such product can be manufactured to be available off-the-shelf.

iT cells expressing CasMab250 based HER2-CAR were generated from TiPSCs that had been engineered to express either TRAC_HER2-CAR/IL7RF and CD38_hnCD16/CXCR2 or TRAC_HER2-CAR/IL7RF and CD38_hnCD16/TGFβR2-IL12Rβ, and the efficacy and specificity of CAR targeting was evaluated for each configuration. Briefly, CAR-iTs were co-cultured with HER2$^{High}$ (SKOV3), HER2$^+$ (JIMT1), or HER2$^{Low}$ (MDA-MB-231) tumor cells at 2:1 E:T ratios and the cytolytic efficacy was determined via xCELLigence™ assay as described above. As shown in FIG. 30, both CXCR2 (top row) and TGFβR2 (IL12RB) (bottom row) CAR-iT configurations demonstrated robust anti-HER2 efficacy that (i) correlated closely with HER2 antigen levels of each particular tumor target line and (ii) was enhanced relative to primary CAR-T cells that expressed the same CAR, highlighting the contribution of the solid tumor targeting backbone to effector cell efficacy.

Figure 31:
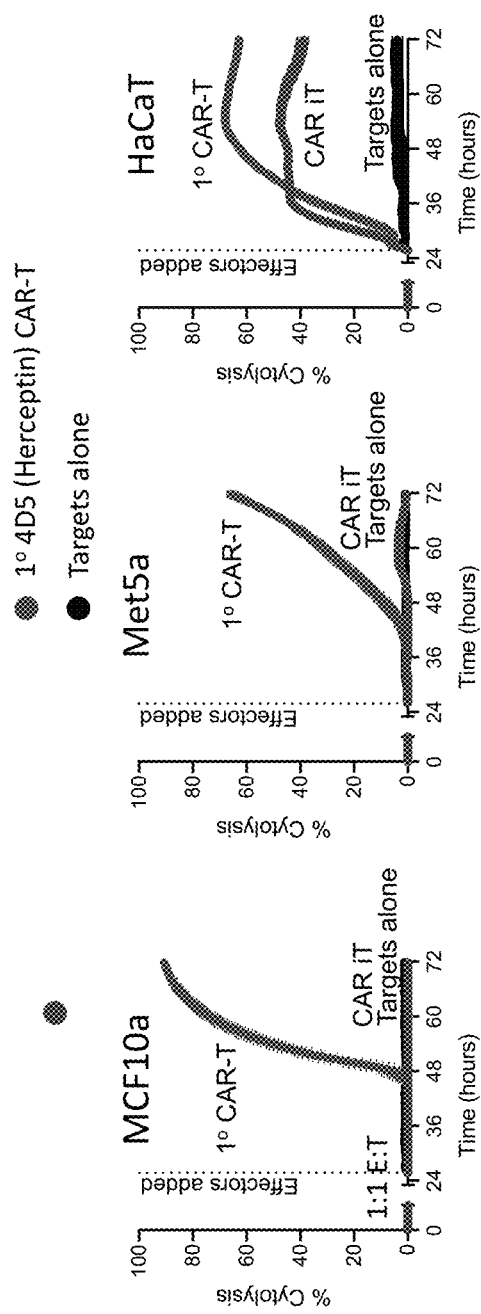
FIG. 31 shows that CasMab250-based CAR efficacy and selectivity towards tumor-associated HER2 antigen as compared to 4D5-based HER2-CAR is maintained in CAR-iT cells engineered with a solid tumor targeting backbone configuration as described.

Next, the anti-tumor specificity versus normal HER2 specificity of the CasMab250-CAR in each of the cell configurations was evaluated. HER2-CAR iTs expressing TRAC_CasMab250-CAR/IL7RF and CD38_hnCD16/CXCR2 and primary CAR-T cells expressing a HER2-CAR derived from Herceptin (4D5) were cultured with the HER2$^+$ normal, non-tumorigenic cell lines MCF10a (Breast), Met5a (Mesothelin), and HaCaT (Keratinocyte) at 1:1 E:T ratios, and cytolytic efficacy was monitored via xCELLigence™ assay. As shown in FIG. 31, 4D5-based primary CAR-Ts readily targeted all assayed HER2$^+$ normal cell lines. CasMab250-based CAR iTs on the other hand demonstrated no reactivity to the MCF10a and Met5a cell lines and limited reactivity to HaCaT targets. It was therefore confirmed that the primary CAR-Ts and TRAC_HER2-CAR iTs carrying CasMab250-based HER2-CARs are specific for HER2$^+$ tumor cells rather than normal HER2$^+$ cells. These data also demonstrate that the CasMab250-based CAR efficacy and selectivity towards tumor-associated HER2 antigen, while largely against non-tumor cell HER2 antigen, as compared to a 4D5-based HER2-CAR, is maintained in CAR-iT cells that are highly engineered with the solid tumor targeting backbone as disclosed herein, which backbone further contributes to the overall effector cell efficacy against tumor cells in general, and with added advantages against solid tumors in particular.

Figure 32:
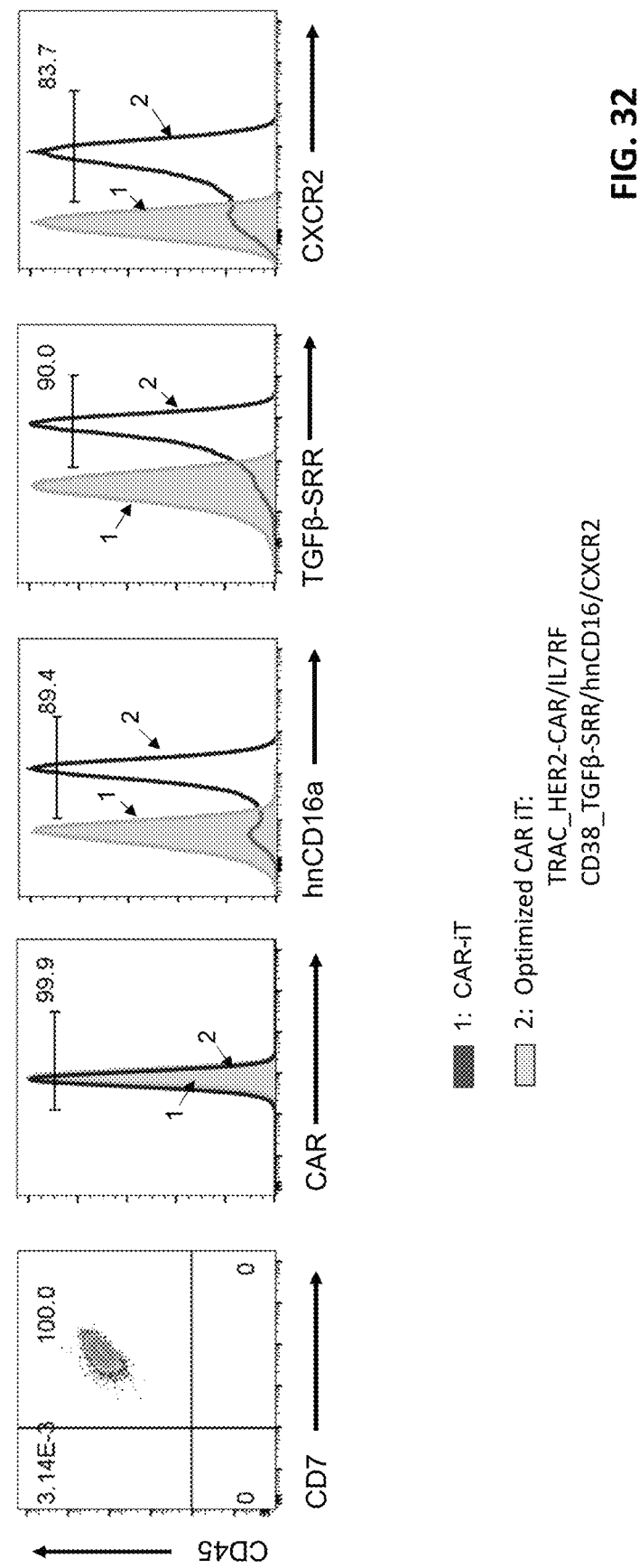
FIG. 32 shows representative flow cytometry plots demonstrating lymphoid commitment ($CD45^{High}CD7^{High}$), along with high and homogenous CAR, hnCD16, TGFβ-SRR, and CXCR2 expression.

As described in Example 2, fully equipped differentiated CAR-iT cells were generated from iPSCs sequentially engineered to express TRAC_CasMab250-CAR-2A-IL7RF (CAR-iT) and CD38_TGFβR2 (IL18R)-2A-hnCD16-2A-CXCR2, which has four solid tumor targeting backbone functional modalities (i.e., TGFβ redirector, CXCR2, hnCD16, and IL7RF) in addition to the CAR (using the exemplary CasMab-based HER2-targeting CAR), TRAC knockout and CD38 knockout (hereinafter referred to as "optimized CAR-iT cells"). Flow cytometry demonstrating lymphoid commitment (CD45$^{High}$ CD7$^{High}$) and high and homogenous CAR, hnCD16, TGFβ-SRR (TGFβR2-IL18R redirector receptor was used in this assay), and CXCR2 expression of the optimized CAR-iT was shown in FIG. 32.

Figure 33:
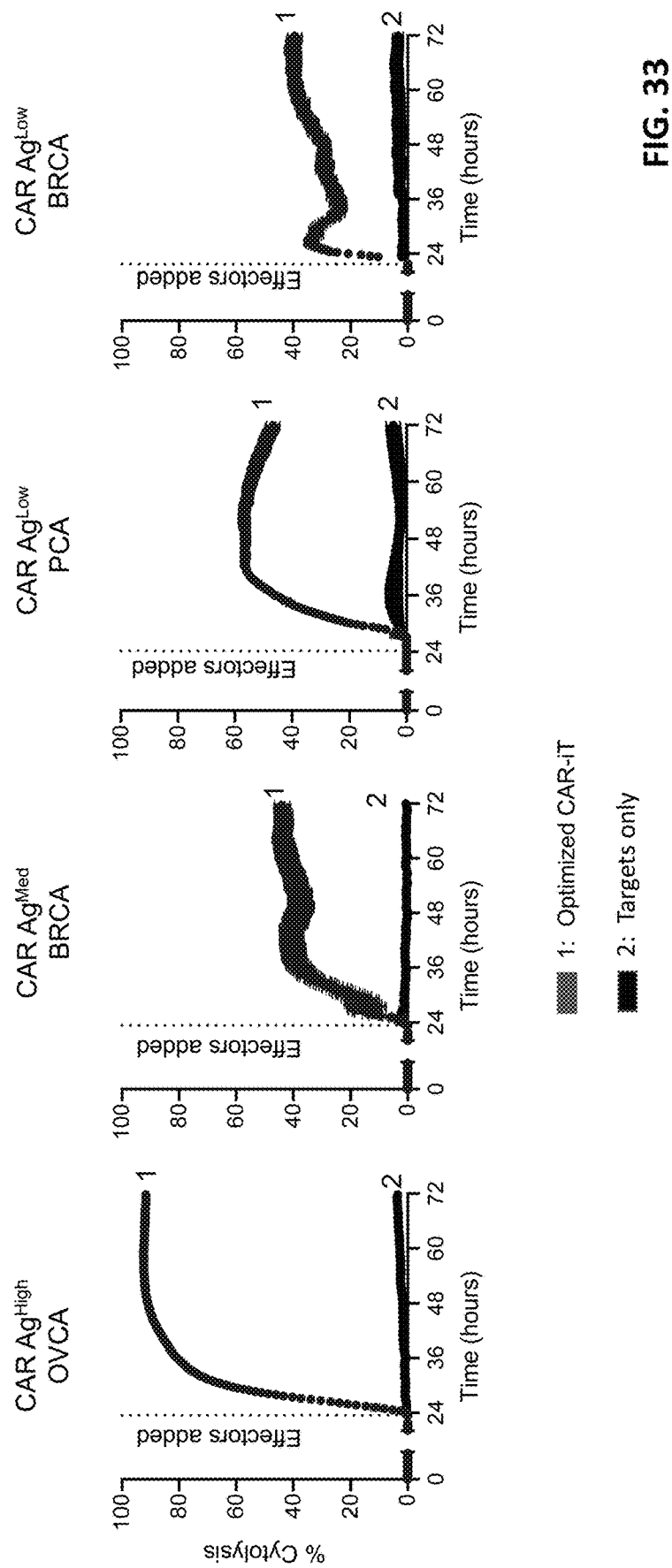
FIG. 33 shows that optimized CAR-iT cells demonstrate robust CAR-dependent anti-tumor efficacy across multiple indications and antigen levels.

To demonstrate transgene function, compatibility, complementation and enhancement, the following assays were conducted with optimized CAR-iTs as compared to CAR-iTs with only TRAC engineering of CAR/IL7RF as control. The CAR in the CAR-iT is CasMab-based HER2-CAR. CasMab250-based CAR anti-tumor cytolytic efficacy was evaluated on HER2$^{High}$ (OVCA, a high-expressing epithelial ovarian cancer cell line), HER2$^{Med}$ (BRCA; a medium-expressing breast cancer cell line), HER2$^{Low}$ (PCA; a low-expressing prostate cancer cell line), and HER2$^{Low}$ (BRCA; a low-expressing breast cancer cell line) tumor cells at a 2:1 Effector:Target ratio via xCELLigence™ assay to demonstrate HER2 dependent tumor clearance. As shown in FIG. 33, the optimized CAR-iTs demonstrated robust CAR-dependent anti-tumor efficacy across multiple solid tumor indications and tumor cells of diverse antigen levels.

Figure 34:
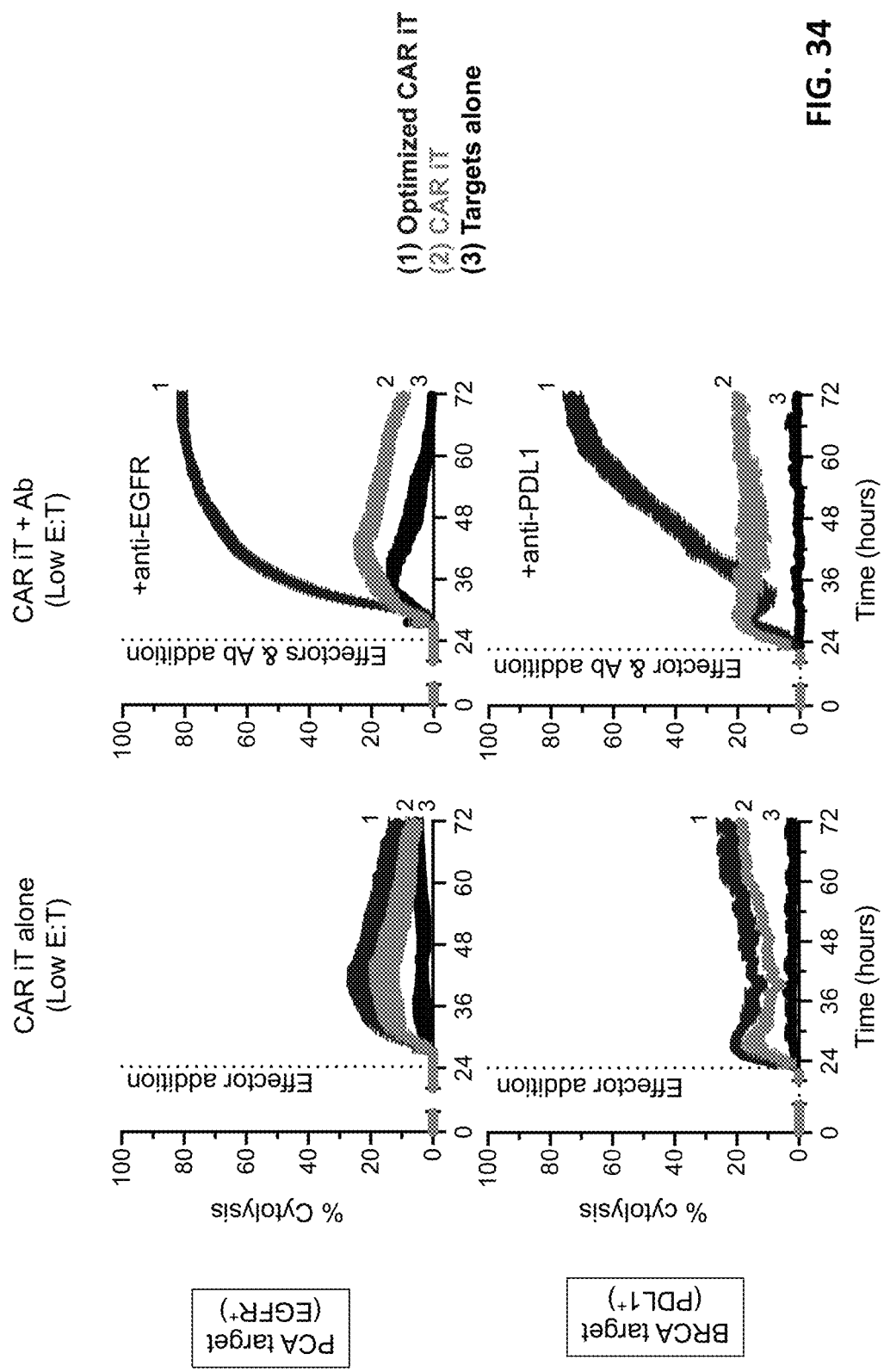
FIG. 34 shows that optimized CAR-iT cells demonstrate hnCD16 complementation of CAR functionality at low E:T ratios of low antigen expressing tumor targets.
Figure 35:
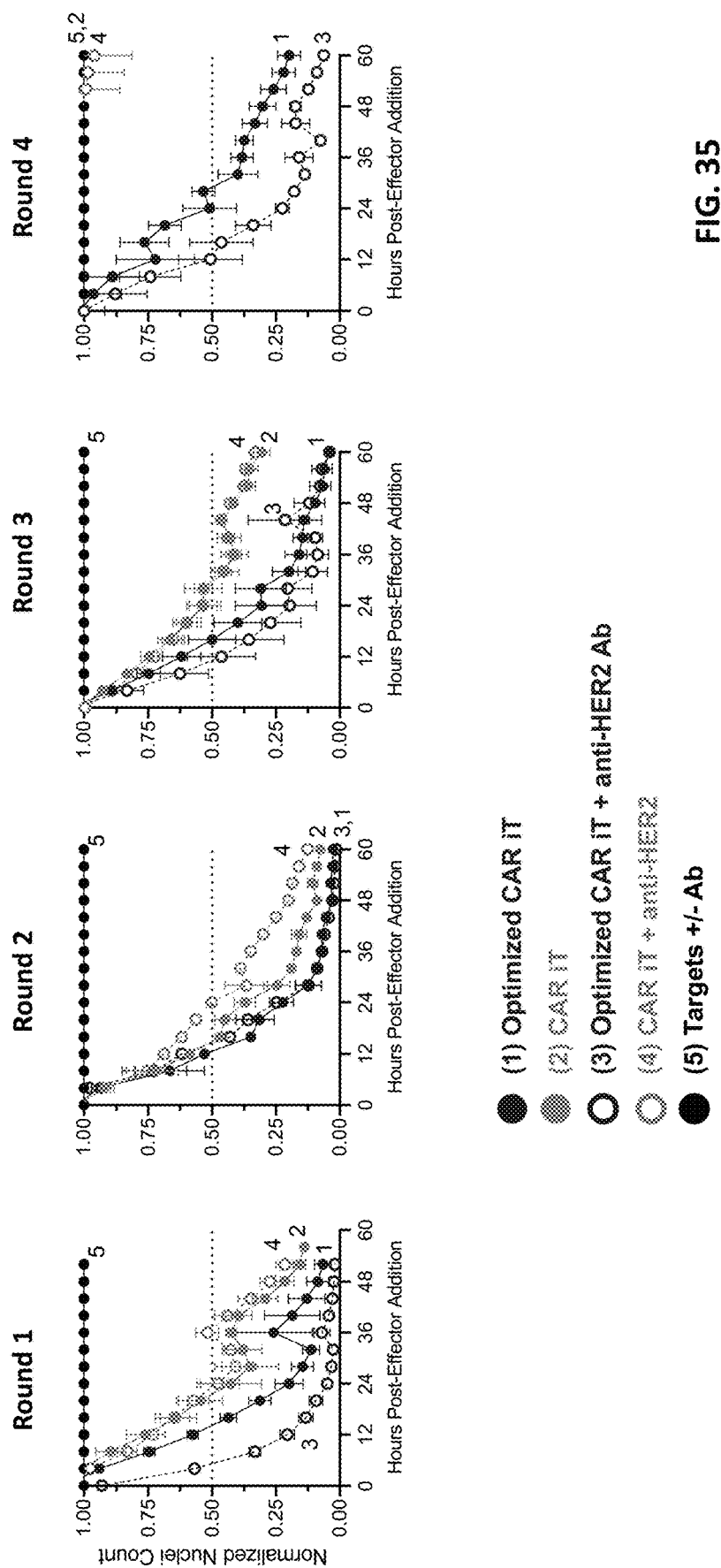
FIG. 35 shows that CAR mediated anti-tumor efficacy of optimized CAR-iT cells is enhanced with hnCD16 activation and therapeutic antibodies over multiple rounds of tumor challenge.

As shown in FIG. 34, hnCD16 complementation of CAR functionality in the optimized CAR-iT was evaluated with HER2$^{Low}$ (PCA) and HER2$^{Low}$ (BRCA) tumor targets and HER2-CAR iTs at low E:T ratios (1:1, top row; 1:2, bottom row) with and without anti-EGFR (top row) or anti-PDL1 antibodies (bottom row) via xCELLigence™ assay. The optimized CAR-iT demonstrated enhanced cytolytic efficacy when co-activated with CAR targeting and hnCD16 mediated secondary TAA-dependent cytolysis. In a serial restimulation Incucyte assay using OVCA tumor targets (HER2$^{High}$) at a 1:1 E:T ratio, the cytolytic efficacy of CAR-iTs and the optimized CAR-iTs was assessed in the presence and absence of anti-HER2 antibodies. At every round of restimulation, the effector:target ratio was reset using fresh tumor targets. As shown in FIG. 35, CAR mediated anti-tumor efficacy is enhanced with hnCD16 activation and the therapeutic antibody at each round in the CAR-iT cells optimized for solid tumors. By round 4, only the optimized CAR-iT cells maintained cytolytic efficacy, which was further enhanced with the presence of the anti-HER2 antibody.

Figure 36:
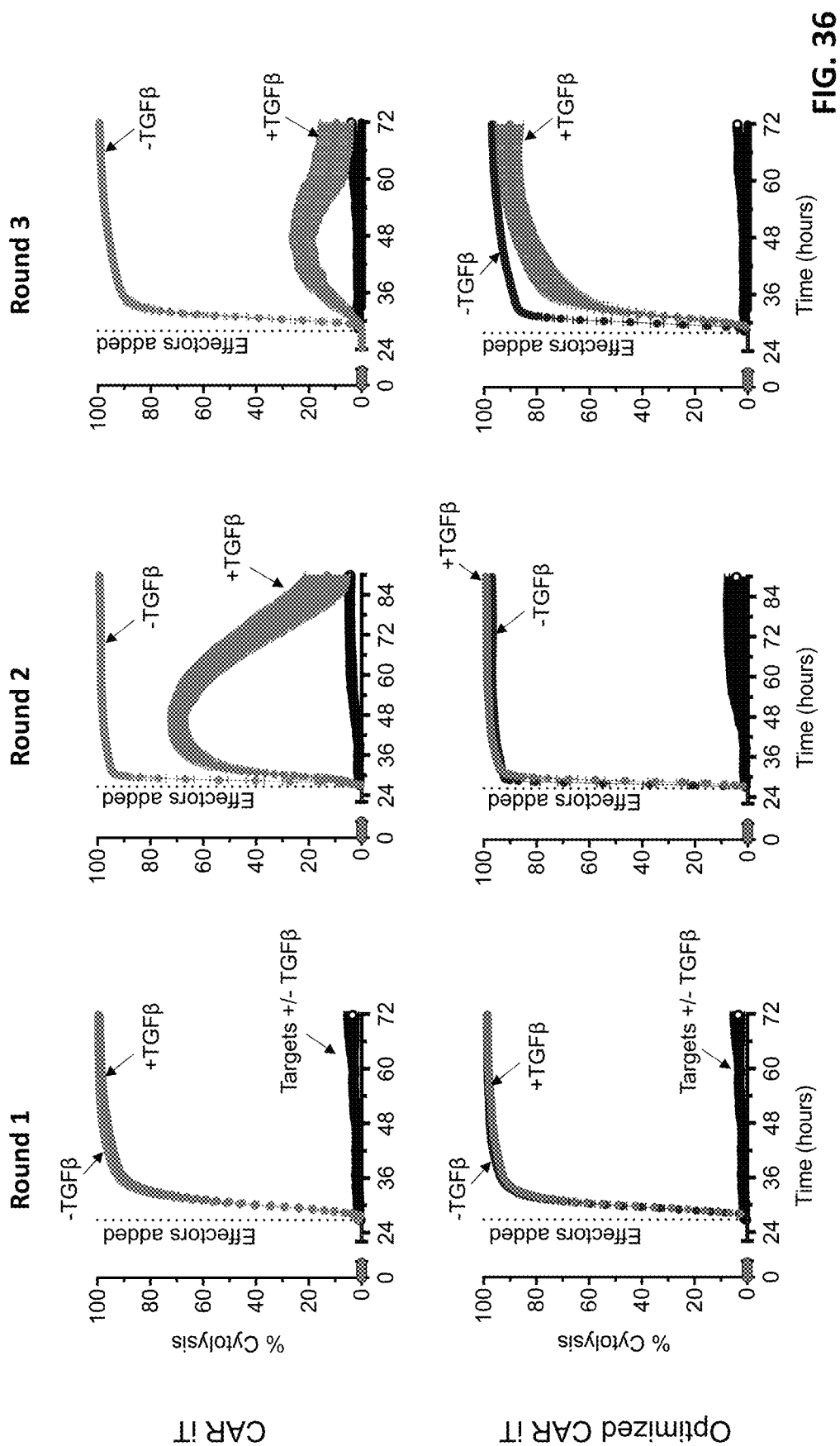
FIG. 36 shows that optimized CAR-iT cells demonstrate resistance to TGFβ-mediated effector suppression via TGFβ-SRR over multiple rounds of tumor challenge.

TGFβ signaling redirection through TGFβ-SRR in the optimized CAR-iT cells was evaluated with repeated HER2$^{High}$ tumor target challenge in the presence or absence of TGFβ. Cytolytic efficacy of CAR-iT (top row) and optimized CAR-iT (bottom row) cells was analyzed by co-culturing with OVCA tumor target cells at a 2.5:1 E:T ratio for multiple rounds of tumor challenge via xCELLigence™ assay. As shown in FIG. 36, the optimized CAR-iTs demonstrate resistance to TGFβ-mediated suppression of effector function with sustained cytolytic efficacy compared to the CAR-iTs with only TRAC engineering of CAR/IL7RF.

Figure 37:
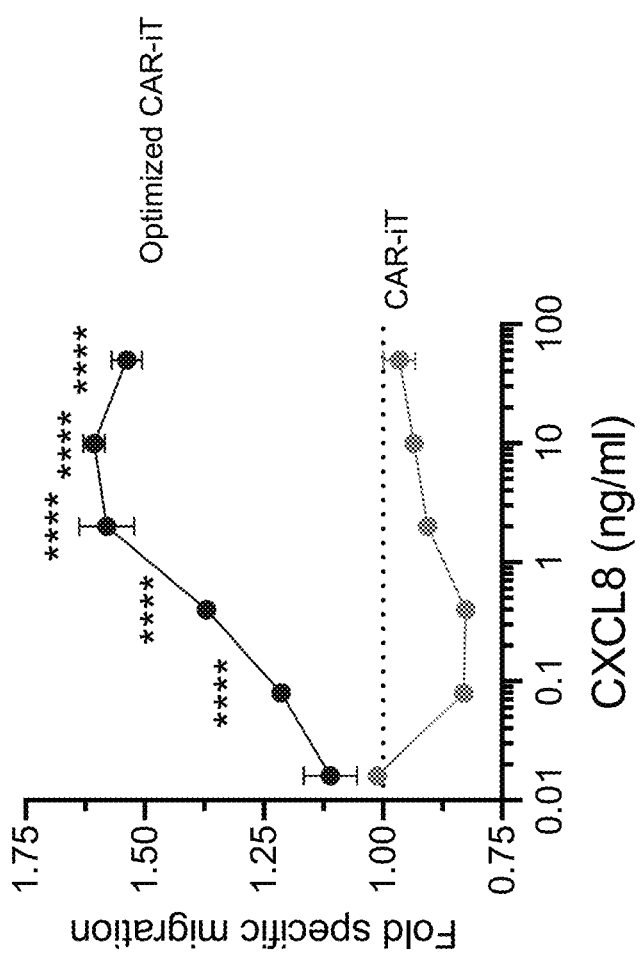
FIG. 37 shows that CXCR2 expression by optimized CAR-iT cells enables CXCL8-specific migration towards tumor.

Further, CXCR2 functionality of the optimized CAR-iT was evaluated in vitro in a transwell assay with serial dilutions of recombinant human CXCL8. As shown in FIG. 37, the optimized CAR-iT cells demonstrated functional and specific migration to CXCL8 in a dose-dependent manner over the entire duration of the assay.

Figure 38A:
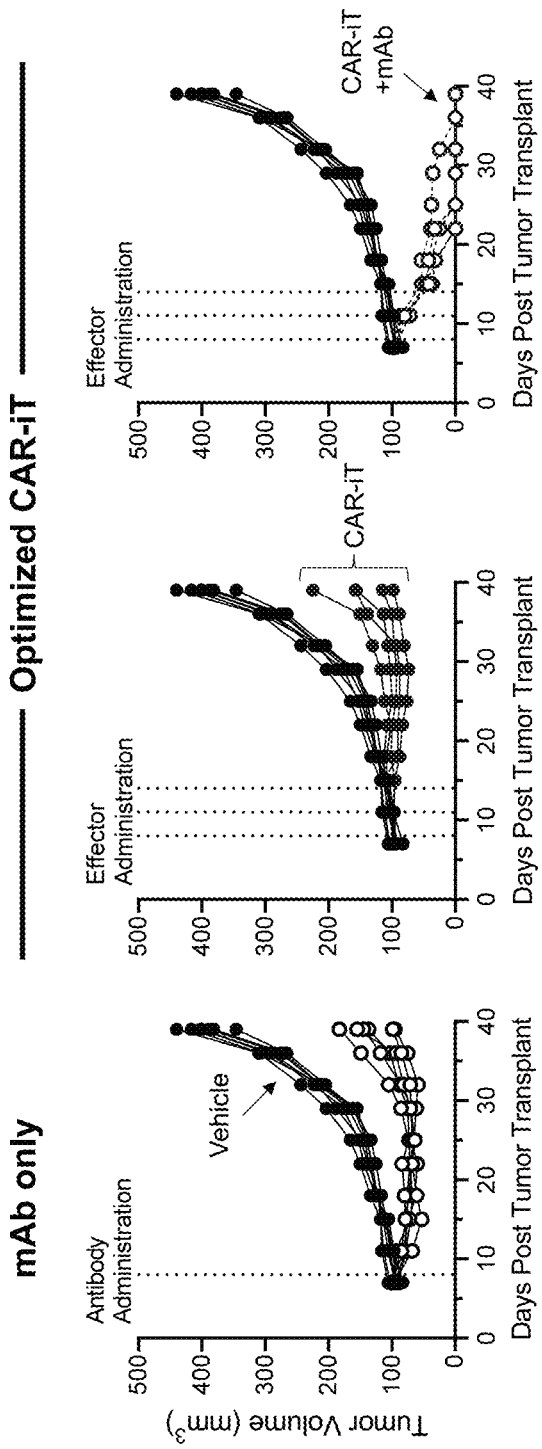
FIGS. 38A and 38B show that optimized CAR-iT cells demonstrate enhanced anti-tumor efficacy in vivo by CAR and CAR/hnCD16 complementation in an aggressive ovarian xenograft model.
Figure 38B:
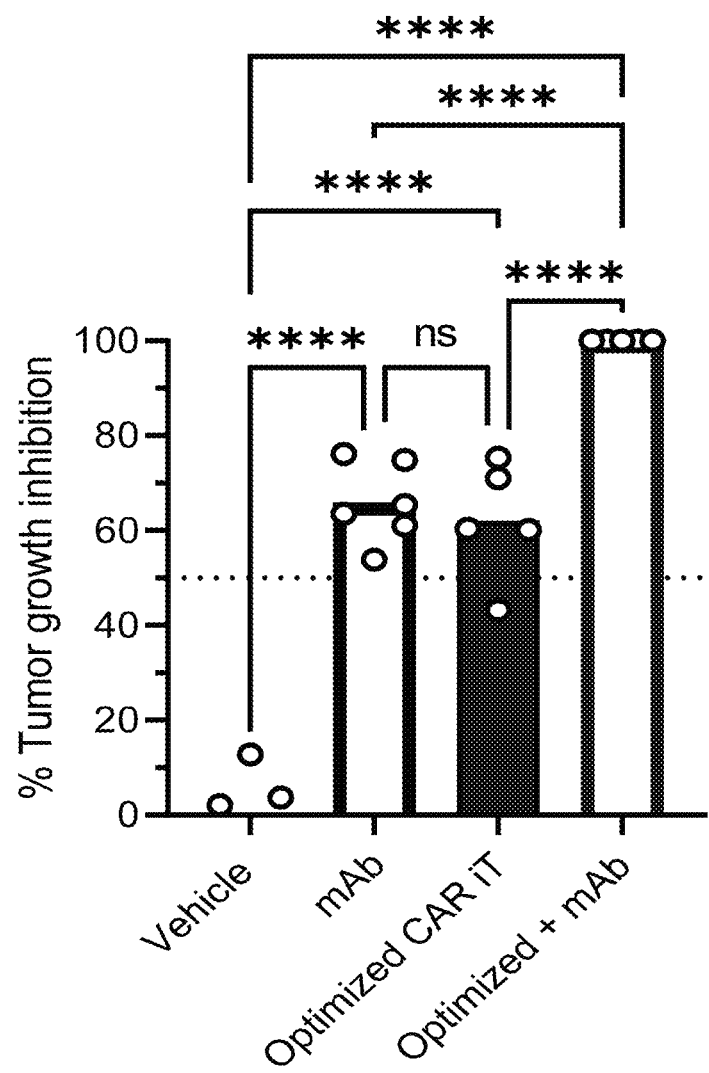

Finally, the anti-tumor efficacy of the optimized CAR-iT cells was evaluated in vivo in an aggressive ovarian xenograft model with or without the anti-HER2 monoclonal antibody (mAb) trastuzumab (Herceptin™). NSG mice bearing established ovarian xenografts were treated with a single dose (8 mg/kg) of mAb on Day 8 post tumor transplant and/or three doses (1e7 each) of optimized CAR-iT cells on Days 8, 11 and 14, as indicated (FIG. 38A). Tumor volume was recorded and shown for each individual recipient. Tumor growth inhibition was calculated for all groups at 39 days post tumor inoculation (FIG. 38B). As shown, the optimized CAR-iTs demonstrated robust reduction of tumor volume and near 100% tumor growth inhibition (TGI) in the presence of Herceptin as compared to the CAR-iT without the mAb treatment or to the mAb only treatment (FIGS. 38A and 38B). It is noted that the data demonstrates that optimized effector cells comprising the HER2-CAR are compatible with Herceptin, i.e., having no obvious competition via steric hinderance, possibly by targeting separate HER2 antigens. Herceptin is the current standard of care for metastatic HER2$^+$ cancer treatment. However, Herceptin is known for its related tumor resistance mechanisms, including but not limited to antigen shielding, antigen downregulation, lack of internalization, and insensitivity to dimerization. The compatibility of CasMab250-CAR with anti-HER2 antibody as shown here further provides a treatment option for HER2 related cancers and diseases in addition to dual targeting utilizing ADCC antibodies targeting different kinds liquid or solid tumor antigens, such as EGFR, MICA/B, among many others disclosed in this application.

Example 10—Intelligent Design of the Solid Tumor Targeting Backbone Additionally Provides a Cytokine Signal-Based Selection for Efficient Subsequent CAR/Transgene Insertion and Screening As one example, for iPSC-derived NK cells, CAR-IL15RF was used to co-express with a CAR. Autonomous cytokine signaling delivered by IL15RF has been demonstrated not only to improve persistence in vivo but also enables cells to expand in vitro independently of cytokine support. The ability to expand independently of cytokine support was further utilized as a model of selection that allows modified cells to expand while unmodified cells remain inactive.

The solid tumor targeting backbone of this application, instead of having the cytokine signaling complex co-expressed with hnCD16 by knocking in hnCD16-IL15RF to the CD38 locus, it was consciously designed to co-express CAR with the IL15RF at a selected locus (or IL7RF for iT cells). This arrangement of the elements in the backbone provides a system of cytokine signal based selection of gene editing to improve engineering efficiency in selection for transgene while eliminating off-target engineering.

When a master cell bank (MCB) of iPSCs engineered with CD38_(2 or more of TGFβR redirector, CXCR2 and ADR)-hnCD16 is established, validated, and cryopreserved, the engineered MCB iPSCs can be used repeatedly as a resource and a starting point to subsequently insert any targeting modality, including a CAR, with, for example, IL15RF attached in a bicistronic construct. In screening for CAR insertion, with IL15RF acting as a selector in culture, cytokine independence leads to outgrowth of transgene positive cells. Such outgrowth of modified cells during culture alleviates the need for sorting, which increases the screening throughput and scale for a large number of CAR positive cells having a tumor targeting backbone preassembled, with each CAR and the CAR cell product having a different binding specificity to an antigen associated with one, or a set of, tumor indication(s).

Other receptor fusion designs that allow for selection of modified cells through cytokine-free expansion of differential survival are also conceivable based on the observation and application of transgene-2A-IL15RF, especially fusion receptors of cytokine receptor subunits acting through the common IL2 beta and gamma chains in addition to fusion receptors designed from various alpha chains known to drive proliferation and/or survival.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

SEQUENCE LISTING

```
Sequence total quantity: 191
SEQ ID NO: 1           moltype = AA  length = 360
FEATURE                Location/Qualifiers
source                 1..360
                       mol_type = protein
                       organism = synthetic construct
SEQUENCE: 1
MEDFNMESDS FEDFWKGEDL SNYSYSSTLP PFLLDAAPCE PESLEINKYF VVIIYALVFL  60
LSLLGNSLVM LVILYSRVGR SVTDVYLLNL ALADLLFALT LPIWAASKVN GWIFGTFLCK 120
VVSLLKEVNF YSGILLLACI SVDRYLAIVH ATRTLTQKRY LVKFICLSIW GLSLLLALPV 180
LLFRRTVYSS NVSPACYEDM GNNTANWRML LRILPQSFGF IVPLLIMLFC YGFTLRTLFK 240
AHMGQKHRAM RVIFAVVLIF LLCWLPYNLV LLADTLMRTQ VIQETCERRN HIDRALDATE 300
ILGILHSCLN PLIYAFIGQK FRHGLLKILA IHGLISKDSL PKDSRPSFVG SSSGHTSTTL 360

SEQ ID NO: 2           moltype = AA  length = 15
FEATURE                Location/Qualifiers
source                 1..15
                       mol_type = protein
                       organism = synthetic construct
SEQUENCE: 2
MEDFNMESDS FEDFW                                                   15

SEQ ID NO: 3           moltype = AA  length = 200
FEATURE                Location/Qualifiers
```

```
source                  1..200
                        mol_type = protein
                        organism = synthetic construct
SEQUENCE: 3
MEDFNMESDS FEDFWKGEDL SNYSYSSTLP PFLLDAAPCE PESLEINKYF VVIIYALVFL    60
LSLLGNSLVM LVILYSRVGR SVTDVYLLNL ALADLLFALT LPIWAASKVN GWIFGTFLCK   120
VVSLLKEVNF YSGILLLACI SVDRYLAIVH ATRTLTQKRY LVKFICLSIW GLSLLLALPV   180
LLFRRTVYSS NVSPACYEDM                                              200

SEQ ID NO: 4            moltype = AA  length = 135
FEATURE                 Location/Qualifiers
source                  1..135
                        mol_type = protein
                        organism = synthetic construct
SEQUENCE: 4
MEDFNMESDS FEDFWKGEDL SNYSYSSTLP PFLLDAAPCE PESLEINKYF VVIIYALVFL    60
LSLLGNSLVM LVILYSRVGR SVTDVYLLNL ALADLLFALT LPIWAASKVN GWIFGTFLCK   120
VVSLLKEVNF YSGIL                                                   135

SEQ ID NO: 5            moltype = AA  length = 172
FEATURE                 Location/Qualifiers
source                  1..172
                        mol_type = protein
                        organism = synthetic construct
SEQUENCE: 5
MEDFNMESDS FEDFWKGEDL SNYSYSSTLP PFLLDAAPCE PESLEINKYF VVIIYALVFL    60
LSLLGNSLVM LVILYSRVGR SVTDVYLLNL ALADLLFALT LPIWAASKVN GWIFGTFLCK   120
VVSLLKEVNF YSGILLLACI SVDRYLAIVH ATRTLTQKRY LVKFICLSIW GL           172

SEQ ID NO: 6            moltype = AA  length = 138
FEATURE                 Location/Qualifiers
source                  1..138
                        mol_type = protein
                        organism = synthetic construct
SEQUENCE: 6
MEDFNMESDS FEDFWKGEDL SNYSYSSTLP PFLLDAAPCE PESLEINKYF VVIIYALVFL    60
LSLLGNSLVM LVILYSRVGR SVTDVYLLNL ALADLLFALT LPIWAASKVN GWIFGTFLCK   120
VVSLLKEVNF YSGILLLA                                                138

SEQ ID NO: 7            moltype = AA  length = 368
FEATURE                 Location/Qualifiers
source                  1..368
                        mol_type = protein
                        organism = synthetic construct
SEQUENCE: 7
MVLEVSDHQV LNDAEVAALL ENFSSSYDYG ENESDSCCTS PPCPQDFSLN FDRAFLPALY    60
SLLFLLGLLG NGAVAAVLLS RRTALSSTDT FLLHLAVADT LLVLTLPLWA VDAAVQWVFG   120
SGLCKVAGAL FNINFYAGAL LLACISFDRY LNIVHATQLY RRGPPARVTL TCLAVWGLCL   180
LFALPDFIFL SAHHDERLNA THCQYNFPQV GRTALRVLQL VAGFLLPLLV MAYCYAHILA   240
VLLVSRGQRR LRAMRLVVVV VVAFALCWTP YHLVVLVDIL MDLGALARNC GRESRVDVAK   300
SVTSGLGYMH CCLNPLLYAF VGVKFRERMW MLLLRLGCPN QRGLQRQPSS SRRDSSWSET   360
SEASYSGL                                                           368

SEQ ID NO: 8            moltype = AA  length = 415
FEATURE                 Location/Qualifiers
source                  1..415
                        mol_type = protein
                        organism = synthetic construct
SEQUENCE: 8
MELRKYGPGR LAGTVIGGAA QSKSQTKSDS ITKEFLPGLY TAPSSPFPPS QVSDHQVLND    60
AEVAALLENF SSSYDYGENE SDSCCTSPPC PQDFSLNFDR AFLPALYSLL FLLGLLGNGA   120
VAAVLLSRRT ALSSTDTFLL HLAVADTLLV LTLPLWAVDA AVQWVFGSGL CKVAGALFNI   180
NFYAGALLLA CISFDRYLNI VHATQLYRRG PPARVTLTCL AVWGLCLLFA LPDFIFLSAH   240
HDERLNATHC QYNFPQVGRT ALRVLQLVAG FLLPLLVMAY CYAHILAVLL VSRGQRRLRA   300
MRLVVVVVVA FALCWTPYHL VVLVDILMDL GALARNCGRE SRVDVAKSVT SGLGYMHCCL   360
NPLLYAFVGV KFRERMWMLL LRLGCPNQRG LQRQPSSSRR DSSWSETSEA SYSGL        415

SEQ ID NO: 9            moltype = AA  length = 267
FEATURE                 Location/Qualifiers
source                  1..267
                        mol_type = protein
                        organism = synthetic construct
SEQUENCE: 9
MVLEVSDHQV LNDAEVAALL ENFSSSYDYG ENESDSCCTS PPCPQDFSLN FDRAFLPALY    60
SLLFLLGLLG NGAVAAVLLS RRTALSSTDT FLLHLAVADT LLVLTLPLWA VDAAVQWVFG   120
SGLCKVAGAL FNINFYAGAL LLACISFDRY LNIVHATQLY RRGPPARVTL TCLAVWGLCL   180
LFALPDFIFL SAHHDERLNA THCQYNFPQG SSSGSGCGCC SCAWAAPTRE GSRGSHRLPA   240
GIHPGLRPQR PPTRACEAGI RAPLSPI                                      267
```

```
SEQ ID NO: 10              moltype = AA   length = 144
FEATURE                    Location/Qualifiers
source                     1..144
                           mol_type = protein
                           organism = synthetic construct
SEQUENCE: 10
TIPPHVQKSV NNDMIVTDNN GAVKFPQLCK FCDVRFSTCD NQKSCMSNCS ITSICEKPQE   60
VCVAVWRKND ENITLETVCH DPKLPYHDFI LEDAASPKCI MKEKKKPGET FFMCSCSSDE  120
CNDNIIFSEE YNTSNPDLLL VIFQ                                        144

SEQ ID NO: 11              moltype = AA   length = 286
FEATURE                    Location/Qualifiers
source                     1..286
                           mol_type = protein
                           organism = synthetic construct
SEQUENCE: 11
NCRNTGPWLK KVLKCNTPDP SKFFSQLSSE HGGDVQKWLS SPFPSSSFSP GGLAPEISPL   60
EVLERDKVTQ LLLQQDKVPE PASLSSNHSL TSCFTNQGYF FFHLPDALEI EACQVYFTYD  120
PYSEEDPDEG VAGAPTGSSP QPLQPLSGED DAYCTFPSRD DLLLFSPSLL GGPSPPSTAP  180
GGSGAGEERM PPSLQERVPR DWDPQPLGPP TPGVPDLVDF QPPPELVLRE AGEEVPDAGP  240
REGVSFPWSR PPGQGEFRAL NARLPLNTDA YLSLQELQGQ DPTHLV                286

SEQ ID NO: 12              moltype = AA   length = 219
FEATURE                    Location/Qualifiers
source                     1..219
                           mol_type = protein
                           organism = synthetic construct
SEQUENCE: 12
HYFQQKVFVL LAALRPQWCS REIPDPANST CAKKYPIAEE KTQLPLDRLL IDWPTPEDPE   60
PLVISEVLHQ VTPVFRHPPC SNWPQREKGI QGHQASEKDM MHSASSPPPP RALQAESRQL  120
VDLYKVLESR GSDPKPENPA CPWTVLPAGD LPTHDGYLPS NIDDLPSHEA PLADSLEELE  180
PQHISLSVFP SSSLHPLTFS CGDKLTLDQL KMRCDSLML                        219

SEQ ID NO: 13              moltype = AA   length = 51
FEATURE                    Location/Qualifiers
source                     1..51
                           mol_type = protein
                           organism = synthetic construct
SEQUENCE: 13
SDPKPENPAC PWTVLPAGDL PTHDGYLPSN IDDLPSHEAP LADSLEELEP Q            51

SEQ ID NO: 14              moltype = AA   length = 191
FEATURE                    Location/Qualifiers
source                     1..191
                           mol_type = protein
                           organism = synthetic construct
SEQUENCE: 14
YRVDLVLFYR HLTRRDETLT DGKTYDAFVS YLKECRPENG EEHTFAVEIL PRVLEKHFGY   60
KLCIFERDVV PGGAVVDEIH SLIEKSRRLI IVLSKSYMSN EVRYELESGL HEALVERKIK  120
IILIEFTPVT DFTFLPQSLK LLKSHRVLKW KADKSLSYNS RFWKNLLYLM PAKTVKPGRD  180
EPEVLPVLSE S                                                      191

SEQ ID NO: 15              moltype = AA   length = 285
FEATURE                    Location/Qualifiers
source                     1..285
                           mol_type = protein
                           organism = synthetic construct
SEQUENCE: 15
SLKTHPLWRL WKKIWAVPSP ERFFMPLYKG CSGDFKKWVG APFTGSSLEL GPWSPEVPST   60
LEVYSCHPPR SPAKRLQLTE LQEPAELVES DGVPKPSFWP TAQNSGGSAY SEERDRPYGL  120
VSIDTVTVLD AEGPCTWPCS CEDDGYPALD LDAGLEPSPG LEDPLLDAGT TVLSCGCVSA  180
GSPGLGGPLG SLLDRLKPPL ADGEDWAGGL PWGGRSPGGV SESEAGSPLA GLDMDTFDSG  240
FVGSDCSSPV ECDFTSPGDE GPPRSYLRQW VVIPPPLSSP GPQAS                 285

SEQ ID NO: 16              moltype = AA   length = 221
FEATURE                    Location/Qualifiers
source                     1..221
                           mol_type = protein
                           organism = synthetic construct
SEQUENCE: 16
TIPPHVQKSV NNDMIVTDNN GAVKFPQLCK FCDVRFSTCD NQKSCMSNCS ITSICEKPQE   60
VCVAVWRKND ENITLETVCH DPKLPYHDFI LEDAASPKCI MKEKKKPGET FFMCSCSSDE  120
CNDNIIFSEE YNTSNPDLLL VIFQVTGISL LPPLGVAISV IIIFYCYRVN SDPKPENPAC  180
PWTVLPAGDL PTHDGYLPSN IDDLPSHEAP LADSLEELEP Q                     221

SEQ ID NO: 17              moltype = AA   length = 26
FEATURE                    Location/Qualifiers
```

```
source                  1..26
                        mol_type = protein
                        organism = synthetic construct
SEQUENCE: 17
VTGISLLPPL GVAISVIIIF YCYRVN                                       26

SEQ ID NO: 18           moltype = AA   length = 455
FEATURE                 Location/Qualifiers
source                  1..455
                        mol_type = protein
                        organism = synthetic construct
SEQUENCE: 18
MEFGLSWLFL VAILKGVQCG LLDLRQGMFA QLVAQNVLLI DGPLSWYSDP GLAGVSLTGG   60
LSYKEDTKEL VVAKAGVYYV FFQLELRRVV AGEGSGSVSL ALHLQPLRSA AGAAALALTV  120
DLPPASSEAR NSAFGFQGRL LHLSAGQRLG VHLHTEARAR HAWQLTQGAT VLGLFRVTPE  180
IPAGLPSPRS EESKYGPPCP PCPGQPREPQ VYTLPPSRDE LTKNQVSLTC LVKGFYPSDI  240
AVEWESNGQP ENNYKTTPPV LDSDGSFFLY SKLTVDKSRW QQGNVFSCSV MHEALHNAYT  300
QKSLSLSPGK KDPKFWVLVV VGGVLACYSL LVTVAFIIFW VRSRVKFSRS ADAPAYQQGQ  360
NQLYNELNLG RREEYDVLDK RRGRDPEMGG KPRRKNPQEG LYNELQKDKM AEAYSEIGMK  420
GERRRGKGHD GLYQGLSTAT KDTYDALHMQ ALPPR                            455

SEQ ID NO: 19           moltype = AA   length = 340
FEATURE                 Location/Qualifiers
source                  1..340
                        mol_type = protein
                        organism = synthetic construct
SEQUENCE: 19
MWFLTTLLLW VPVDGQVDTT KAVITLQPPW VSVFQEETVT LHCEVLHLPG SSSTQWFLNG   60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGLQLPTPVW PHYQVSFCLV  300
MVLLFAVDTG LYFSVKTNIR SSTRDWKDHK FKWRKDPQDK                       340

SEQ ID NO: 20           moltype = AA   length = 336
FEATURE                 Location/Qualifiers
source                  1..336
                        mol_type = protein
                        organism = synthetic construct
SEQUENCE: 20
MWFLTTLLLW VPVDGQVDTT KAVITLQPPW VSVFQEETVT LHCEVLHLPG SSSTQWFLNG   60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGLFFPPGYQ VSFCLVMVLL  300
FAVDTGLYFS VKTNIRSSTR DWKDHKFKWR KDPQDK                           336

SEQ ID NO: 21           moltype = AA   length = 335
FEATURE                 Location/Qualifiers
source                  1..335
                        mol_type = protein
                        organism = synthetic construct
SEQUENCE: 21
MWFLTTLLLW VPVDGQVDTT KAVITLQPPW VSVFQEETVT LHCEVLHLPG SSSTQWFLNG   60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGFFPPGYQV SFCLVMVLLF  300
AVDTGLYFSV KTNIRSSTRD WKDHKFKWRK DPQDK                            335

SEQ ID NO: 22           moltype = AA   length = 379
FEATURE                 Location/Qualifiers
source                  1..379
                        mol_type = protein
                        organism = synthetic construct
SEQUENCE: 22
MDWTWILFLV AAATRVHSGI HVFILGCFSA GLPKTEANWV NVISDLKKIE DLIQSMHIDA   60
TLYTESDVHP SCKVTAMKCF LLELQVISLE SGDASIHDTV ENLIILANNS LSSNGNVTES  120
GCKECEELEE KNIKEFLQSF VHIVQMFINT SSGGGSGGGG SGGGGSGGGG SGGGSLQITC  180
PPPMSVEHAD IWVKSYSLYS RERYICNSGF KRKAGTSSLT ECVLNKATNV AHWTTPSLKC  240
IRDPALVHQR PAPPSTVTTA GVTPQPESLS PSGKEPAASS PSSNNTAATT AAIVPGSQLM  300
PSKSPSTGTT EISSHESSHG TPSQTTAKNW ELTASASHQP PGVYPQGHSD TTVAISTSTV  360
LLCGLSAVSL LACYLKSRQ                                              379

SEQ ID NO: 23           moltype = AA   length = 375
FEATURE                 Location/Qualifiers
source                  1..375
                        mol_type = protein
                        organism = synthetic construct
```

```
SEQUENCE: 23
MDWTWILFLV AAATRVHSGI HVFILGCFSA GLPKTEANWV NVISDLKKIE DLIQSMHIDA    60
TLYTESDVHP SCKVTAMKCF LLELQVISLE SGDASIHDTV ENLIILANNS LSSNGNVTES   120
GCKECEELEE KNIKEFLQSF VHIVQMFINT SSGGGSGGGG SGGGGSGGGG SGGGSLQITC   180
PPPMSVEHAD IWVKSYSLYS RERYICNSGF KRKAGTSSLT ECVLNKATNV AHWTTPSLKC   240
IRDPALVHQR PAPPSTVTTA GVTPQPESLS PSGKEPAASS PSSNNTAATT AAIVPGSQLM   300
PSKSPSTGTT EISSHESSHG TPSQTTAKNW ELTASASHQP PGVYPQGHSD TTVAISTSTV   360
LLCGLSAVSL LACYL                                                   375

SEQ ID NO: 24          moltype = AA   length = 242
FEATURE                Location/Qualifiers
source                 1..242
                       mol_type = protein
                       organism = synthetic construct
SEQUENCE: 24
MDWTWILFLV AAATRVHSGI HVFILGCFSA GLPKTEANWV NVISDLKKIE DLIQSMHIDA    60
TLYTESDVHP SCKVTAMKCF LLELQVISLE SGDASIHDTV ENLIILANNS LSSNGNVTES   120
GCKECEELEE KNIKEFLQSF VHIVQMFINT SSGGGSGGGG SGGGGSGGGG SGGGSLQITC   180
PPPMSVEHAD IWVKSYSLYS RERYICNSGF KRKAGTSSLT ECVLNKATNV AHWTTPSLKC   240
IR                                                                 242

SEQ ID NO: 25          moltype = AA   length = 635
FEATURE                Location/Qualifiers
source                 1..635
                       mol_type = protein
                       organism = synthetic construct
SEQUENCE: 25
MDWTWILFLV AAATRVHSDC DIEGKDGKQY ESVLMVSIDQ LLDSMKEIGS NCLNNEFNFF    60
KRHICDANKE GMFLFRAARK LRQFLKMNST GDFDLHLLKV SEGTTILLNC TGQVKGRKPA   120
ALGEAQPTKS LEENKSLKEQ KKLNDLCFLK RLLQEIKTCW NKILMGTKEH SGGGSGGGGS   180
GGGGSGGGGS GGGSLQESGY AQNGDLEDAE LDDYSFSCYS QLEVNGSQHS LTCAFEDPDV   240
NITNLEFEIC GALVEVKCLN FRKLQEIYFI ETKKFLLIGK SNICVKVGEK SLTCKKIDLT   300
TIVKPEAPFD LSVVYREGAN DFVVTFNTSH LQKKYVKVLM HDVAYRQEKD ENKWTHVNLS   360
STKLTLLQRK LQPAAMYEIK VRSIPDHYFK GFWSEWSPSY YFRTPEINNS SGEMDPILLT   420
ISILSFFSVA LLVILACVLW KKRIKPIVWP SLPDHKKTLE HLCKKPRKNL NVSFNPESFL   480
DCQIHRVDDI QARDEVEGFL QDTFPQQLEE SEKQRLGGDV QSPNCPSEDV VITPESFGRD   540
SSLTCLAGNV SACDAPILSS SRSLDCRESG KNGPHVYQDL LLSLGTTNST LPPPFSLQSG   600
ILTLNPVAQG QPILTSLGSN QEEAYVTMSS FYQNQ                              635

SEQ ID NO: 26          moltype = AA   length = 163
FEATURE                Location/Qualifiers
source                 1..163
                       mol_type = protein
                       organism = synthetic construct
SEQUENCE: 26
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP RRKNPQEGLY NELQKDKMAE   120
AYSEIGMKGE RRRGKGHDGL YQGLSTATKD TYDALHMQAL PPR                     163

SEQ ID NO: 27          moltype = AA   length = 153
FEATURE                Location/Qualifiers
source                 1..153
                       mol_type = protein
                       organism = synthetic construct
SEQUENCE: 27
RSKRSRLLHS DYMNMTPRRP GPTRKHYQPY APPRDFAAYR SRVKFSRSAD APAYQQGQNQ    60
LYNELNLGRR EEYDVLDKRR GRDPEMGGKP RRKNPQEGLF NELQKDKMAE AFSEIGMKGE   120
RRRGKGHDGL FQGLSTATKD TFDALHMQAL PPR                                153

SEQ ID NO: 28          moltype = AA   length = 214
FEATURE                Location/Qualifiers
source                 1..214
                       mol_type = protein
                       organism = synthetic construct
SEQUENCE: 28
DGNEEMGGIT QTPYKVSISG TTVILTCPQY PGSEILWQHN DKNIGGDEDD KNIGSDEDHL    60
SLKEFSELEQ SGYYVCYPRG SKPEDANFYL YLRARVCENC MEMDGSADDA KKDAAKKDDA   120
KKDDAKKDGS FKIPIEELED RVFVNCNTSI TWVEGTVGTL LSDITRLDLG KRILDPRGIY   180
RCNGTDIYKD KESTVQVHYR MCQSCVELDP ATVA                               214

SEQ ID NO: 29          moltype = AA   length = 224
FEATURE                Location/Qualifiers
source                 1..224
                       mol_type = protein
                       organism = synthetic construct
SEQUENCE: 29
DGNEEMGGIT QTPYKVSISG TTVILTCPQY PGSEILWQHN DKNIGGDEDD KNIGSDEDHL    60
SLKEFSELEQ SGYYVCYPRG SKPEDANFYL YLRARVCENC MEMDGSADDA KKDAAKKDDA   120
```

```
KKDDAKKDGS QSIKGNHLVK VYDYQEDGSV LLTCDAEAKN ITWFKDGKMI GFLTEDKKKW    180
NLGSNAKDPR GMYQCKGSQN KSKPLQVYYR MCQNCIELNA ATIS                    224

SEQ ID NO: 30           moltype = AA  length = 18
FEATURE                 Location/Qualifiers
source                  1..18
                        mol_type = protein
                        organism = synthetic construct
SEQUENCE: 30
MALPVTALLL PLALLLHA                                                  18

SEQ ID NO: 31           moltype = AA  length = 21
FEATURE                 Location/Qualifiers
source                  1..21
                        mol_type = protein
                        organism = synthetic construct
SEQUENCE: 31
MDFQVQIFSF LLISASVIMS R                                              21

SEQ ID NO: 32           moltype = AA  length = 21
FEATURE                 Location/Qualifiers
source                  1..21
                        mol_type = protein
                        organism = synthetic construct
SEQUENCE: 32
FLVIIVILSA LFLGTLACFC V                                              21

SEQ ID NO: 33           moltype = AA  length = 27
FEATURE                 Location/Qualifiers
source                  1..27
                        mol_type = protein
                        organism = synthetic construct
SEQUENCE: 33
IISFFLALTS TALLFLLFFL TLRFSVV                                        27

SEQ ID NO: 34           moltype = AA  length = 31
FEATURE                 Location/Qualifiers
source                  1..31
                        mol_type = protein
                        organism = synthetic construct
SEQUENCE: 34
VSFCLVMVLL FAVDTGLYFS VKTNIRSSTR D                                   31

SEQ ID NO: 35           moltype = AA  length = 96
FEATURE                 Location/Qualifiers
source                  1..96
                        mol_type = protein
                        organism = synthetic construct
SEQUENCE: 35
IYLIIGICGG GSLLMVFVAL LVFYITKRKK QRSRRNDEEL ETRAHRVATE ERGRKPHQIP    60
ASTPQNPATS QHPPPPPGHR SQAPSHRPPP PGHRVQ                              96

SEQ ID NO: 36           moltype = AA  length = 27
FEATURE                 Location/Qualifiers
source                  1..27
                        mol_type = protein
                        organism = synthetic construct
SEQUENCE: 36
FWVLVVVGGV LACYSLLVTV AFIIFWV                                        27

SEQ ID NO: 37           moltype = AA  length = 21
FEATURE                 Location/Qualifiers
source                  1..21
                        mol_type = protein
                        organism = synthetic construct
SEQUENCE: 37
FLFVLLGVGS MGVAAIVWGA W                                              21

SEQ ID NO: 38           moltype = AA  length = 21
FEATURE                 Location/Qualifiers
source                  1..21
                        mol_type = protein
                        organism = synthetic construct
SEQUENCE: 38
LCYLLDGILF IYGVILTALF L                                              21

SEQ ID NO: 39           moltype = AA  length = 21
FEATURE                 Location/Qualifiers
```

```
source                  1..21
                        mol_type = protein
                        organism = synthetic construct
SEQUENCE: 39
LLAGLVAADA VASLLIVGAV F                                              21

SEQ ID NO: 40           moltype = AA   length = 21
FEATURE                 Location/Qualifiers
source                  1..21
                        mol_type = protein
                        organism = synthetic construct
SEQUENCE: 40
GVLAGIVMGD LVLTVLIALA V                                              21

SEQ ID NO: 41           moltype = AA   length = 21
FEATURE                 Location/Qualifiers
source                  1..21
                        mol_type = protein
                        organism = synthetic construct
SEQUENCE: 41
GVLAGIVMGD LVLTVLIALA V                                              21

SEQ ID NO: 42           moltype = AA   length = 20
FEATURE                 Location/Qualifiers
source                  1..20
                        mol_type = protein
                        organism = synthetic construct
SEQUENCE: 42
CYILDAILFL YGIVLTLLYC                                                20

SEQ ID NO: 43           moltype = AA   length = 21
FEATURE                 Location/Qualifiers
source                  1..21
                        mol_type = protein
                        organism = synthetic construct
SEQUENCE: 43
GWNPHLLLLL LLVIVFIPAF W                                              21

SEQ ID NO: 44           moltype = AA   length = 25
FEATURE                 Location/Qualifiers
source                  1..25
                        mol_type = protein
                        organism = synthetic construct
SEQUENCE: 44
IPWLGHLLVG LSGAFGFIIL VYLLI                                          25

SEQ ID NO: 45           moltype = AA   length = 21
FEATURE                 Location/Qualifiers
source                  1..21
                        mol_type = protein
                        organism = synthetic construct
SEQUENCE: 45
VVISVGSMGL IISLLCVYFW L                                              21

SEQ ID NO: 46           moltype = AA   length = 25
FEATURE                 Location/Qualifiers
source                  1..25
                        mol_type = protein
                        organism = synthetic construct
SEQUENCE: 46
PILLTISILS FFSVALLVIL ACVLW                                          25

SEQ ID NO: 47           moltype = AA   length = 20
FEATURE                 Location/Qualifiers
source                  1..20
                        mol_type = protein
                        organism = synthetic construct
SEQUENCE: 47
VLIGTSVVKI PFTILLFFLL                                                20

SEQ ID NO: 48           moltype = AA   length = 21
FEATURE                 Location/Qualifiers
source                  1..21
                        mol_type = protein
                        organism = synthetic construct
SEQUENCE: 48
PFFFCCFIAV AMGIRFIIMV A                                              21
```

| SEQ ID NO: 49 | moltype = AA   length = 21 |
| --- | --- |
| FEATURE | Location/Qualifiers |
| source | 1..21 |
|  | mol_type = protein |
|  | organism = synthetic construct |

SEQUENCE: 49
AGTVLLLRAG FYAVSFLSVA V                                              21

| SEQ ID NO: 50 | moltype = AA   length = 21 |
| --- | --- |
| FEATURE | Location/Qualifiers |
| source | 1..21 |
|  | mol_type = protein |
|  | organism = synthetic construct |

SEQUENCE: 50
LVPVFCGLLV AKSLVLSALL V                                              21

| SEQ ID NO: 51 | moltype = AA   length = 20 |
| --- | --- |
| FEATURE | Location/Qualifiers |
| source | 1..20 |
|  | mol_type = protein |
|  | organism = synthetic construct |

SEQUENCE: 51
GLAFLVLVAL VWFLVEDWLS                                                20

| SEQ ID NO: 52 | moltype = AA   length = 21 |
| --- | --- |
| FEATURE | Location/Qualifiers |
| source | 1..21 |
|  | mol_type = protein |
|  | organism = synthetic construct |

SEQUENCE: 52
VLLCLLLVPL LLSLFVLGLF L                                              21

| SEQ ID NO: 53 | moltype = AA   length = 11 |
| --- | --- |
| FEATURE | Location/Qualifiers |
| source | 1..11 |
|  | mol_type = protein |
|  | organism = synthetic construct |

SEQUENCE: 53
IYIWAPLAGT C                                                         11

| SEQ ID NO: 54 | moltype = AA   length = 120 |
| --- | --- |
| FEATURE | Location/Qualifiers |
| source | 1..120 |
|  | mol_type = protein |
|  | organism = synthetic construct |

SEQUENCE: 54
WRRKRKEKQS ETSPKEFLTI YEDVKDLKTR RNHEQEQTFP GGGSTIYSMI QSQSSAPTSQ     60
EPAYTLYSLI QPSRKSGSRK RNHSPSFNST IYEVIGKSQP KAQNPARLSR KELENFDVYS    120

| SEQ ID NO: 55 | moltype = AA   length = 42 |
| --- | --- |
| FEATURE | Location/Qualifiers |
| source | 1..42 |
|  | mol_type = protein |
|  | organism = synthetic construct |

SEQUENCE: 55
KRGRKKLLYI FKQPFMRPVQ TTQEEDGCSC RFPEEEEGGC EL                       42

| SEQ ID NO: 56 | moltype = AA   length = 15 |
| --- | --- |
| FEATURE | Location/Qualifiers |
| source | 1..15 |
|  | mol_type = protein |
|  | organism = synthetic construct |

SEQUENCE: 56
WKDHKFKWRK DPQDK                                                     15

| SEQ ID NO: 57 | moltype = AA   length = 46 |
| --- | --- |
| FEATURE | Location/Qualifiers |
| source | 1..46 |
|  | mol_type = protein |
|  | organism = synthetic construct |

SEQUENCE: 57
HQPQKRPPAP SGTQVHQQKG PPLPRPRVQP KPPHGAAENS LSPSSN                    46

| SEQ ID NO: 58 | moltype = AA   length = 41 |
| --- | --- |
| FEATURE | Location/Qualifiers |
| source | 1..41 |
|  | mol_type = protein |
|  | organism = synthetic construct |

```
SEQUENCE: 58
RSKRSRLLHS DYMNMTPRRP GPTRKHYQPY APPRDFAAYR S                          41

SEQ ID NO: 59           moltype = AA   length = 111
FEATURE                 Location/Qualifiers
source                  1..111
                        mol_type = protein
                        organism = synthetic construct
SEQUENCE: 59
FWGRRSCQQR DSGNSPGNAF YSNVLYRPRG APKKSEDCSG EGKDQRGQSI YSTSFPQPAP      60
RQPHLASRPC PSPRPCPSPR PGHPVSMVRV SPRPSPTQQP RPKGFPKVGE E              111

SEQ ID NO: 60           moltype = AA   length = 113
FEATURE                 Location/Qualifiers
source                  1..113
                        mol_type = protein
                        organism = synthetic construct
SEQUENCE: 60
RVKFSRSADA PAYQQGQNQL YNELNLGRRE EYDVLDKRRG RDPEMGGKPQ RRKNPQEGLY      60
NELQKDKMAE AYSEIGMKGE RRRGKGHDGL YQGLSTATKD TYDALHMQAL PPR            113

SEQ ID NO: 61           moltype = AA   length = 112
FEATURE                 Location/Qualifiers
source                  1..112
                        mol_type = protein
                        organism = synthetic construct
SEQUENCE: 61
RVKFSRSADA PAYQQGQNQL YNELNLGRRE EYDVLDKRRG RDPEMGGKPR RKNPQEGLFN      60
ELQKDKMAEA FSEIGMKGER RRGKGHDGLF QGLSTATKDT FDALHMQALP PR             112

SEQ ID NO: 62           moltype = AA   length = 24
FEATURE                 Location/Qualifiers
source                  1..24
                        mol_type = protein
                        organism = synthetic construct
SEQUENCE: 62
LCARPRRSPA QEDGKVYINM PGRG                                             24

SEQ ID NO: 63           moltype = AA   length = 52
FEATURE                 Location/Qualifiers
source                  1..52
                        mol_type = protein
                        organism = synthetic construct
SEQUENCE: 63
YFLGRLVPRG RGAAEAATRK QRITETESPY QELQGQRSDV YSDLNTQRPY YK              52

SEQ ID NO: 64           moltype = AA   length = 61
FEATURE                 Location/Qualifiers
source                  1..61
                        mol_type = protein
                        organism = synthetic construct
SEQUENCE: 64
NRRRRRERRD LFTESWDTQK APNNYRSPIS TSQPTNQSMD DTREDIYVNY PTFSRRPKTR      60
V                                                                      61

SEQ ID NO: 65           moltype = AA   length = 42
FEATURE                 Location/Qualifiers
source                  1..42
                        mol_type = protein
                        organism = synthetic construct
SEQUENCE: 65
RLKIQVRKAA ITSYEKSDGV YTGLSTRNQE TYETLKHEKP PQ                         42

SEQ ID NO: 66           moltype = AA   length = 285
FEATURE                 Location/Qualifiers
source                  1..285
                        mol_type = protein
                        organism = synthetic construct
SEQUENCE: 66
SLKTHPLWRL WKKIWAVPSP ERFFMPLYKG CSGDFKKWVG APFTGSSLEL GPWSPEVPST      60
LEVYSCHPPR SPAKRLQLTE LQEPAELVES DGVPKPSFWP TAQNSGGSAY SEERDRPYGL     120
VSIDTVTVLD AEGPCTWPCS CEDDGYPALD LDAGLEPSPG LEDPLLDAGT TVLSCGCVSA     180
GSPGLGGPLG SLLDRLKPPL ADGEDWAGGL PWGGRSPGGV SESEAGSPLA GLDMDTFDSG     240
FVGSDCSSPV ECDFTSPGDE GPPRSYLRQW VVIPPPLSSP GPQAS                     285

SEQ ID NO: 67           moltype = AA   length = 286
FEATURE                 Location/Qualifiers
```

```
source                   1..286
                         mol_type = protein
                         organism = synthetic construct
SEQUENCE: 67
NCRNTGPWLK KVLKCNTPDP SKFFSQLSSE HGGDVQKWLS SPFPSSSFSP GGLAPEISPL    60
EVLERDKVTQ LLLQQDKVPE PASLSSNHSL TSCFTNQGYF FFHLPDALEI EACQVYFTYD   120
PYSEEDPDEG VAGAPTGSSP QPLQPLSGED DAYCTFPSRD DLLLFSPSLL GGPSPPSTAP   180
GGSGAGEERM PPSLQERVPR DWDPQPLGPP TPGVPDLVDF QPPPELVLRE AGEEVPDAGP   240
REGVSFPWSR PPGQGEFRAL NARLPLNTDA YLSLQELQGQ DPTHLV                  286

SEQ ID NO: 68            moltype = AA  length = 86
FEATURE                  Location/Qualifiers
source                   1..86
                         mol_type = protein
                         organism = Synthetic construct
SEQUENCE: 68
ERTMPRIPTL KNLEDLVTEY HGNFSAWSGV SKGLAESLQP DYSERLCLVS EIPPKGGALG    60
EGPGASPCNQ HSPYWAPPCY TLKPET                                        86

SEQ ID NO: 69            moltype = AA  length = 195
FEATURE                  Location/Qualifiers
source                   1..195
                         mol_type = protein
                         organism = synthetic construct
SEQUENCE: 69
KKRIKPIVWP SLPDHKKTLE HLCKKPRKNL NVSFNPESFL DCQIHRVDDI QARDEVEGFL    60
QDTFPQQLEE SEKQRLGGDV QSPNCPSEDV VITPESFGRD SSLTCLAGNV SACDAPILSS   120
SRSLDCRESG KNGPHVYQDL LLSLGTTNST LPPPFSLQSG ILTLNPVAQG QPILTSLGSN   180
QEEAYVTMSS FYQNQ                                                    195

SEQ ID NO: 70            moltype = AA  length = 39
FEATURE                  Location/Qualifiers
source                   1..39
                         mol_type = protein
                         organism = synthetic construct
SEQUENCE: 70
HRWCSNKKNA AVMDQEPAGN RTVNSEDSDE QDHQEVSYA                           39

SEQ ID NO: 71            moltype = AA  length = 144
FEATURE                  Location/Qualifiers
source                   1..144
                         mol_type = protein
                         organism = synthetic construct
SEQUENCE: 71
IWSAVFLNSL FNQEVQIPLT ESYCGPCPKN WICYKNNCYQ FFDESKNWYE SQASCMSQNA    60
SLLKVYSKED QDLLKLVKSY HWMGLVHIPT NGSWQWEDGS ILSPNLLTII EMQKGDCALY   120
ASSFKGYIEN CSTPNTYICM QRTV                                          144

SEQ ID NO: 72            moltype = AA  length = 45
FEATURE                  Location/Qualifiers
source                   1..45
                         mol_type = protein
                         organism = synthetic construct
SEQUENCE: 72
GSTVYYQGKC LTWKGPRRQL PAVVPAPLPP PCGSSAHLLP PVPGG                    45

SEQ ID NO: 73            moltype = AA  length = 63
FEATURE                  Location/Qualifiers
source                   1..63
                         mol_type = protein
                         organism = synthetic construct
SEQUENCE: 73
WWGDIWWKTM MELRSLDTQK ATCHLQQVTD LPWTSVSSPV EREILYHTVA RTKISDDDDE    60
HTL                                                                  63

SEQ ID NO: 74            moltype = AA  length = 25
FEATURE                  Location/Qualifiers
source                   1..25
                         mol_type = protein
                         organism = synthetic construct
SEQUENCE: 74
RKRTRERASR ASTWEGRRRL NTQTL                                          25

SEQ ID NO: 75            moltype = AA  length = 88
FEATURE                  Location/Qualifiers
source                   1..88
                         mol_type = protein
                         organism = synthetic construct
```

-continued

```
SEQUENCE: 75
WFLKRERQEE YIEEKKRVDI CRETPNICPH SGENTEYDTI PHTNRTILKE DPANTVYSTV    60
EIPKKMENPH SLLTMPDTPR LFAYENVI                                      88

SEQ ID NO: 76           moltype = AA   length = 42
FEATURE                 Location/Qualifiers
source                  1..42
                        mol_type = protein
                        organism = synthetic construct
SEQUENCE: 76
GVLLLSLVIT LYCNHRNRRR VCKCPRPVVK SGDKPSLSAR YV                       42

SEQ ID NO: 77           moltype = AA   length = 549
FEATURE                 Location/Qualifiers
source                  1..549
                        mol_type = protein
                        organism = synthetic construct
SEQUENCE: 77
SNLFVASWIA VMIIFRIGMA VAIFCCFFFP SWRRKRKEKQ SETSPKEFLT IYEDVKDLKT    60
RRNHEQEQTF PGGGSTIYSM IQSQSSAPTS QEPAYTLYSL IQPSRKSGSR KRNHSPSFNS   120
TIYEVIGKSQ PKAQNPARLS RKELENFDVY SNCRNTGPWL KKVLKCNTPD PSKFFSQLSS   180
EHGGDVQKWL SSPFPSSSFS PGGLAPEISP LEVLERDKVT QLLLQQDKVP EPASLSSNHS   240
LTSCFTNQGY FFFHLPDALE IEACQVYFTY DPYSEEDPDE GVAGAPTGSS PQPLQPLSGE   300
DDAYCTFPSR DDLLLFSPSL LGGPSPPSTA PGGSGAGEER MPPSLQERVP RDWDPQPLGP   360
PTPGVPDLVD FQPPPELVLR EAGEEVPDAG PREGVSFPWS RPPGQGEFRA LNARLPLNTD   420
AYLSLQELQG QDPTHLVRVK FSRSADAPAY QQGQNQLYNE LNLGRREEYD VLDKRRGRDP   480
EMGGKPRRKN PQEGLYNELQ KDKMAEAYSE IGMKGERRRG KGHDGLYQGL STATKDTYDA   540
LHMQALPPR                                                          549

SEQ ID NO: 78           moltype = AA   length = 178
FEATURE                 Location/Qualifiers
source                  1..178
                        mol_type = protein
                        organism = synthetic construct
SEQUENCE: 78
IYIWAPLAGT CGVLLLSLVI TLYCKRGRKK LLYIFKQPFM RPVQTTQEED GCSCRFPEEE    60
EGGCELRVKF SRSADAPAYQ QGQNQLYNEL NLGRREEYDV LDKRRGRDPE MGGKPRRKNP   120
QEGLFNELQK DKMAEAFSEI GMKGERRRGK GHDGLFQGLS TATKDTFDAL HMQALPPR     178

SEQ ID NO: 79           moltype = AA   length = 300
FEATURE                 Location/Qualifiers
source                  1..300
                        mol_type = protein
                        organism = synthetic construct
SEQUENCE: 79
FWVLVVVGGV LACYSLLVTV AFIIFWVRSK RSRLLHSDYM NMTPRRPGPT RKHYQPYAPP    60
RDFAAYRSWR RKRKEKQSET SPKEFLTIYE DVKDLKTRRN HEQEQTFPGG GSTIYSMIQS   120
QSSAPTSQEP AYTLYSLIQP SRKSGSRKRN HSPSFNSTIY EVIGKSQPKA QNPARLSRKE   180
LENFDVYSRV KFSRSADAPA YQQGQNQLYN ELNLGRREEY DVLDKRRGRD PEMGGKPRRK   240
NPQEGLYNEL QKDKMAEAYS EIGMKGERRR GKGHDGLYQG LSTATKDTYD ALHMQALPPR   300

SEQ ID NO: 80           moltype = AA   length = 180
FEATURE                 Location/Qualifiers
source                  1..180
                        mol_type = protein
                        organism = synthetic construct
SEQUENCE: 80
FWVLVVVGGV LACYSLLVTV AFIIFWVRSK RSRLLHSDYM NMTPRRPGPT RKHYQPYAPP    60
RDFAAYRSRV KFSRSADAPA YQQGQNQLYN ELNLGRREEY DVLDKRRGRD PEMGGKPRRK   120
NPQEGLFNEL QKDKMAEAFS EIGMKGERRR GKGHDGLFQG LSTATKDTFD ALHMQALPPR   180

SEQ ID NO: 81           moltype = AA   length = 244
FEATURE                 Location/Qualifiers
source                  1..244
                        mol_type = protein
                        organism = synthetic construct
SEQUENCE: 81
FLFVLLGVGS MGVAAIVWGA WFWGRRSCQQ RDSGNSPGNA FYSNVLYRPR GAPKKSEDCS    60
GEGKDQRGQS IYSTSFPQPA PRQPHLASRP CPSPRPCPSP RPGHPVSMVR VSPRPSPTQQ   120
PRPKGFPKVG EERVKFSRSA DAPAYQQGQN QLYNELNLGR REEYDVLDKR RGRDPEMGGK   180
PRRKNPQEGL YNELQKDKMA EAYSEIGMKG ERRRGKGHDG LYQGLSTATK DTYDALHMQA   240
LPPR                                                               244

SEQ ID NO: 82           moltype = AA   length = 194
FEATURE                 Location/Qualifiers
source                  1..194
                        mol_type = protein
                        organism = synthetic construct
```

```
SEQUENCE: 82
GGTVLLLLFV ISITTIIVIF LNRRRRRERR DLFTESWDTQ KAPNNYRSPI STSQPTNQSM    60
DDTREDIYVN YPTFSRRPKT RVRVKFSRSA DAPAYQQGQN QLYNELNLGR REEYDVLDKR   120
RGRDPEMGGK PRRKNPQEGL YNELQKDKMA EAYSEIGMKG ERRRGKGHDG LYQGLSTATK   180
DTYDALHMQA LPPR                                                    194

SEQ ID NO: 83              moltype = AA  length = 186
FEATURE                    Location/Qualifiers
source                     1..186
                           mol_type = protein
                           organism = synthetic construct
SEQUENCE: 83
TTPGERSSLP AFYPGTSGSC SGCGSLSLPL LAGLVAADAV ASLLIVGAVF LCARPRRSPA    60
QEDGKVYINM PGRGRVKFSR SADAPAYQQG QNQLYNELNL GRREEYDVLD KRRGRDPEMG   120
GKPRRKNPQE GLYNELQKDK MAEAYSEIGM KGERRRGKGH DGLYQGLSTA TKDTYDALHM   180
QALPPR                                                             186

SEQ ID NO: 84              moltype = AA  length = 171
FEATURE                    Location/Qualifiers
source                     1..171
                           mol_type = protein
                           organism = synthetic construct
SEQUENCE: 84
VLIGTSVVKI PFTILLFFLL HRWCSNKKNA AVMDQEPAGN RTVNSEDSDE QDHQEVSYAR    60
VKFSRSADAP AYQQGQNQLY NELNLGRREE YDVLDKRRGR DPEMGGKPRR KNPQEGLYNE   120
LQKDKMAEAY SEIGMKGERR RGKGHDGLYQ GLSTATKDTY DALHMQALPP R            171

SEQ ID NO: 85              moltype = AA  length = 83
FEATURE                    Location/Qualifiers
source                     1..83
                           mol_type = protein
                           organism = synthetic construct
SEQUENCE: 85
VLIGTSVVKI PFTILLFFLL HRWCSNKKNA AVMDQEPAGN RTVNSEDSDE QDHQEVSYAL    60
CARPRRSPAQ EDGKVYINMP GRG                                           83

SEQ ID NO: 86              moltype = AA  length = 179
FEATURE                    Location/Qualifiers
source                     1..179
                           mol_type = protein
                           organism = synthetic construct
SEQUENCE: 86
VLIGTSVVKI PFTILLFFLL HRWCSNKKNA AVMDQEPAGN RTVNSEDSDE QDHQEVSYAW    60
RRKRKEKQSE TSPKEFLTIY EDVKDLKTRR NHEQEQTFPG GGSTIYSMIQ SQSSAPTSQE   120
PAYTLYSLIQ PSRKSGSRKR NHSPSFNSTI YEVIGKSQPK AQNPARLSRK ELENFDVYS    179

SEQ ID NO: 87              moltype = AA  length = 190
FEATURE                    Location/Qualifiers
source                     1..190
                           mol_type = protein
                           organism = synthetic construct
SEQUENCE: 87
VSFCLVMVLL FAVDTGLYFS VKTNIRSSTR DWKDHKFKWR KDPQDKWRRK RKEKQSETSP    60
KEFLTIYEDV KDLKTRRNHE QEQTFPGGGS TIYSMIQSQS SAPTSQEPAY TLYSLIQPSR   120
KSGSRKRNHS PSFNSTIYEV IGKSQPKAQN PARLSRKELE NFDVYSLCAR PRRSPAQEDG   180
KVYINMPGRG                                                         190

SEQ ID NO: 88              moltype = AA  length = 107
FEATURE                    Location/Qualifiers
source                     1..107
                           mol_type = protein
                           organism = synthetic construct
SEQUENCE: 88
VSFCLVMVLL FAVDTGLYFS VKTNIRSSTR DWKDHKFKWR KDPQDKNRRR RRERRDLFTE    60
SWDTQKAPNN YRSPISTSQP TNQSMDDTRE DIYVNYPTFS RRPKTRV                 107

SEQ ID NO: 89              moltype = AA  length = 166
FEATURE                    Location/Qualifiers
source                     1..166
                           mol_type = protein
                           organism = synthetic construct
SEQUENCE: 89
MGLAFLVLVA LVWFLVEDWL SRKRTRERAS RASTWEGRRR LNTQTLWRRK RKEKQSETSP    60
KEFLTIYEDV KDLKTRRNHE QEQTFPGGGS TIYSMIQSQS SAPTSQEPAY TLYSLIQPSR   120
KSGSRKRNHS PSFNSTIYEV IGKSQPKAQN PARLSRKELE NFDVYS                 166

SEQ ID NO: 90              moltype = AA  length = 278
FEATURE                    Location/Qualifiers
source                     1..278
```

```
                      mol_type = protein
                      organism = synthetic construct
SEQUENCE: 90
MGLAFLVLVA LVWFLVEDWL SRKRTRERAS RASTWEGRRR LNTQTLWRRK RKEKQSETSP    60
KEFLTIYEDV KDLKTRRNHE QEQTFPGGGS TIYSMIQSQS SAPTSQEPAY TLYSLIQPSR   120
KSGSRKRNHS PSFNSTIYEV IGKSQPKAQN PARLSRKELE NFDVYSRVKF SRSADAPAYQ   180
QGQNQLYNEL NLGRREEYDV LDKRRGRDPE MGGKPRRKNP QEGLYNELQK DKMAEAYSEI   240
GMKGERRRGK GHDGLYQGLS TATKDTYDAL HMQALPPR                          278

SEQ ID NO: 91          moltype = AA   length = 186
FEATURE                Location/Qualifiers
source                 1..186
                       mol_type = protein
                       organism = synthetic construct
SEQUENCE: 91
MGLAFLVLVA LVWFLVEDWL SRKRTRERAS RASTWEGRRR LNTQTLKRKK QRSRRNDEEL    60
ETRAHRVATE ERGRKPHQIP ASTPQNPATS QHPPPPPGHR SQAPSHRPPP PGHRVQHQPQ   120
KRPPAPSGTQ VHQQKGPPLP RPRVQPKPPH GAAENSLSPS SNLCARPRRS PAQEDGKVYI   180
NMPGRG                                                             186

SEQ ID NO: 92          moltype = AA   length = 254
FEATURE                Location/Qualifiers
source                 1..254
                       mol_type = protein
                       organism = synthetic construct
SEQUENCE: 92
IYLIIGICGG GSLLMVFVAL LVFYITKRKK QRSRRNDEEL ETRAHRVATE ERGRKPHQIP    60
ASTPQNPATS QHPPPPPGHR SQAPSHRPPP PGHRVQHQPQ KRPPAPSGTQ VHQQKGPPLP   120
RPRVQPKPPH GAAENSLSPS SNRVKFSRSA DAPAYQQGQN QLYNELNLGR REEYDVLDKR   180
RGRDPEMGGK PRRKNPQEGL YNELQKDKMA EAYSEIGMKG ERRRGKGHDG LYQGLSTATK   240
DTYDALHMQA LPPR                                                    254

SEQ ID NO: 93          moltype = AA   length = 253
FEATURE                Location/Qualifiers
source                 1..253
                       mol_type = protein
                       organism = synthetic construct
SEQUENCE: 93
FLVIIVILSA LFLGTLACFC VWRRKRKEKQ SETSPKEFLT IYEDVKDLKT RRNHEQEQTF    60
PGGGSTIYSM IQSQSSAPTS QEPAYTLYSL IQPSRKSGSR KRNHSPSFNS TIYEVIGKSQ   120
PKAQNPARLS RKELENFDVY SRVKFSRSAD APAYQQGQNQ LYNELNLGRR EEYDVLDKRR   180
GRDPEMGGKP RRKNPQEGLY NELQKDKMAE AYSEIGMKGE RRRGKGHDGL YQGLSTATKD   240
TYDALHMQAL PPR                                                     253

SEQ ID NO: 94          moltype = AA   length = 183
FEATURE                Location/Qualifiers
source                 1..183
                       mol_type = protein
                       organism = synthetic construct
SEQUENCE: 94
FLVIIVILSA LFLGTLACFC VWRRKRKEKQ SETSPKEFLT IYEDVKDLKT RRNHEQEQTF    60
PGGGSTIYSM IQSQSSAPTS QEPAYTLYSL IQPSRKSGSR KRNHSPSFNS TIYEVIGKSQ   120
PKAQNPARLS RKELENFDVY SRLKIQVRKA AITSYEKSDG VYTGLSTRNQ ETYETLKHEK   180
PPQ                                                                183

SEQ ID NO: 95          moltype = AA   length = 221
FEATURE                Location/Qualifiers
source                 1..221
                       mol_type = protein
                       organism = synthetic construct
SEQUENCE: 95
VLLCLLLVPL LLSLFVLGLF LWFLKRERQE EYIEEKKRVD ICRETPNICP HSGENTEYDT    60
IPHTNRTILK EDPANTVYST VEIPKKMENP HSLLTMPDTP RLFAYENVIR VKFSRSADAP   120
AYQQGQNQLY NELNLGRREE YDVLDKRRGR DPEMGGKPRR KNPQEGLYNE LQKDKMAEAY   180
SEIGMKGERR RGKGHDGLYQ GLSTATKDTY DALHMQALPP R                       221

SEQ ID NO: 96          moltype = AA   length = 39
FEATURE                Location/Qualifiers
source                 1..39
                       mol_type = protein
                       organism = synthetic construct
SEQUENCE: 96
IEVMYPPPYL DNEKSNGTII HVKGKHLCPS PLFPGPSKP                           39

SEQ ID NO: 97          moltype = AA   length = 88
FEATURE                Location/Qualifiers
source                 1..88
                       mol_type = protein
                       organism = synthetic construct
```

```
SEQUENCE: 97
ESKYGPPCPP  CPGGGSSGGG  SGGQPREPQV  YTLPPSQEEM  TKNQVSLTCL  VKGFYPSDIA   60
VEWESNGQPE  NNYKTTPPVL  DSDGSFFL                                         88

SEQ ID NO: 98           moltype = AA   length = 89
FEATURE                 Location/Qualifiers
source                  1..89
                        mol_type = protein
                        organism = synthetic construct
SEQUENCE: 98
ESKYGPPCPP  CPAPEFEGGP  SVFLFPPKPK  DTLMISRTPE  VTCVVVDVSQ  EDPEVQFNWY   60
VDGVEVHNAK  TKPREEQFQS  TYRVVSVLT                                        89

SEQ ID NO: 99           moltype = AA   length = 129
FEATURE                 Location/Qualifiers
source                  1..129
                        mol_type = protein
                        organism = synthetic construct
SEQUENCE: 99
ESKYGPPCPP  CPGGGSSGGG  SGGQPREPQV  YTLPPSQEEM  TKNQVSLTCL  VKGFYPSDIA   60
VEWESNGQPE  NNYKTTPPVL  DSDGSFFLYS  RLTVDKSRWQ  EGNVFSCSVM  HEALHNHYTQ  120
KSLSLSLGK                                                               129

SEQ ID NO: 100          moltype = AA   length = 229
FEATURE                 Location/Qualifiers
source                  1..229
                        mol_type = protein
                        organism = synthetic construct
SEQUENCE: 100
ESKYGPPCPP  CPAPEFEGGP  SVFLFPPKPK  DTLMISRTPE  VTCVVVDVSQ  EDPEVQFNWY   60
VDGVEVHNAK  TKPREEQFQS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGK               229

SEQ ID NO: 101          moltype = AA   length = 310
FEATURE                 Location/Qualifiers
source                  1..310
                        mol_type = protein
                        organism = synthetic construct
SEQUENCE: 101
ESKYGPPCPP  CPGGGSSGGG  SGGQPREPQV  YTLPPSQEEM  TKNQVSLTCL  VKGFYPSDIA   60
VEWESNGQPE  NNYKTTPPVL  DSDGSFFLYS  RLTVDKSRWQ  EGNVFSCSVM  HEALHNHYTQ  120
KSLSLSLGKM  FWVLVVVGGV  LACYSLLVTV  AFIIFWVRSK  RSRLLHSDYM  NMTPRRPGPT  180
RKHYQPYAPP  RDFAAYRSRV  KFSRSADAPA  YQQGQNQLYN  ELNLGRREEY  DVLDKRRGRD  240
PEMGGKPRRK  NPQEGLFNEL  QKDKMAEAFS  EIGMKGERRR  GKGHDGLFQG  LSTATKDTFD  300
ALHMQALPPR                                                              310

SEQ ID NO: 102          moltype = AA   length = 263
FEATURE                 Location/Qualifiers
source                  1..263
                        mol_type = protein
                        organism = synthetic construct
SEQUENCE: 102
SNLFVASWIA  VMIIFRIGMA  VAIFCCFFFP  SWRRKRKEKQ  SETSPKEFLT  IYEDVKDLKT   60
RRNHEQEQTF  PGGGSTIYSM  IQSQSSAPTS  QEPAYTLYSL  IQPSRKSGSR  KRNHSPSFNS  120
TIYEVIGKSQ  PKAQNPARLS  RKELENFDVY  SRVKFSRSAD  APAYKQGQNQ  LYNELNLGRR  180
EEYDVLDKRR  GRDPEMGGKP  RRKNPQEGLY  NELQKDKMAE  AYSEIGMKGE  RRRGKGHDGL  240
YQGLSTATKD  TYDALHMQAL  PPR                                             263

SEQ ID NO: 103          moltype = AA   length = 5
FEATURE                 Location/Qualifiers
source                  1..5
                        mol_type = protein
                        organism = synthetic construct
SEQUENCE: 103
NYGMS                                                                     5

SEQ ID NO: 104          moltype = AA   length = 17
FEATURE                 Location/Qualifiers
source                  1..17
                        mol_type = protein
                        organism = synthetic construct
SEQUENCE: 104
TINNNGGGTY  YPDSVKG                                                      17

SEQ ID NO: 105          moltype = AA   length = 7
FEATURE                 Location/Qualifiers
```

-continued

```
source                     1..7
                           mol_type = protein
                           organism = synthetic construct
SEQUENCE: 105
PGLLWDA                                                                    7

SEQ ID NO: 106             moltype = AA   length = 16
FEATURE                    Location/Qualifiers
source                     1..16
                           mol_type = protein
                           organism = synthetic construct
SEQUENCE: 106
KSSQSLLDSD GRTYLN                                                         16

SEQ ID NO: 107             moltype = AA   length = 7
FEATURE                    Location/Qualifiers
source                     1..7
                           mol_type = protein
                           organism = synthetic construct
SEQUENCE: 107
LVSKLDS                                                                    7

SEQ ID NO: 108             moltype = AA   length = 9
FEATURE                    Location/Qualifiers
source                     1..9
                           mol_type = protein
                           organism = synthetic construct
SEQUENCE: 108
WQGTHFPQT                                                                  9

SEQ ID NO: 109             moltype = AA   length = 116
FEATURE                    Location/Qualifiers
source                     1..116
                           mol_type = protein
                           organism = synthetic construct
SEQUENCE: 109
EVQLVESGGG LVQPGGSLKL SCAASGFTFS NYGMSWVRQT PDRRLELVAT INNNGGGTYY         60
PDSVKGRFTI SRDNAKNTLY LQMSSLKSED TAMYYCTSPG LLWDAWGAGT TVTVSS            116

SEQ ID NO: 110             moltype = AA   length = 112
FEATURE                    Location/Qualifiers
source                     1..112
                           mol_type = protein
                           organism = synthetic construct
SEQUENCE: 110
DVVMTQTPLT LSVSIGQPAS ISCKSSQSLL DSDGRTYLNW LLQRPGQSPK RLIYLVSKLD         60
SGAPDRFTGS GSGTDFTLKI SRVEAEDLGV YYCWQGTHFP QTFGGGTKLE IK                112

SEQ ID NO: 111             moltype = AA   length = 18
FEATURE                    Location/Qualifiers
source                     1..18
                           mol_type = protein
                           organism = synthetic construct
SEQUENCE: 111
GSTSGGGSGG GSGGGGSS                                                       18

SEQ ID NO: 112             moltype = AA   length = 18
FEATURE                    Location/Qualifiers
source                     1..18
                           mol_type = protein
                           organism = synthetic construct
SEQUENCE: 112
GSTSGSGKPG SGEGSTKG                                                       18

SEQ ID NO: 113             moltype = AA   length = 17
FEATURE                    Location/Qualifiers
source                     1..17
                           mol_type = protein
                           organism = synthetic construct
SEQUENCE: 113
SSGGGGSGGG GSGGGGS                                                        17

SEQ ID NO: 114             moltype = AA   length = 15
FEATURE                    Location/Qualifiers
source                     1..15
                           mol_type = protein
                           organism = synthetic construct
SEQUENCE: 114
GGGGSGGGGS GGGGS                                                          15
```

```
SEQ ID NO: 115          moltype = AA   length = 246
FEATURE                 Location/Qualifiers
source                  1..246
                        mol_type = protein
                        organism = synthetic construct
SEQUENCE: 115
EVQLVESGGG LVQPGGSLKL SCAASGFTFS NYGMSWVRQT PDRRLELVAT INNNGGGTYY    60
PDSVKGRFTI SRDNAKNTLY LQMSSLKSED TAMYYCTSPG LLWDAWGAGT TVTVSSGSTS   120
GGGSGGGSGG GGSSDVVMTQ TPLTLSVSIG QPASISCKSS QSLLDSDGRT YLNWLLQRPG   180
QSPKRLIYLV SKLDSGAPDR FTGSGSGTDF TLKISRVEAE DLGVYYCWQG THFPQTFGGG   240
TKLEIK                                                              246

SEQ ID NO: 116          moltype = AA   length = 246
FEATURE                 Location/Qualifiers
source                  1..246
                        mol_type = protein
                        organism = synthetic construct
SEQUENCE: 116
DVVMTQTPLT LSVSIGQPAS ISCKSSQSLL DSDGRTYLNW LLQRPGQSPK RLIYLVSKLD    60
SGAPDRFTGS GSGTDFTLKI SRVEAEDLGV YYCWQGTHFP QTFGGGTKLE IKGSTSGGGS   120
GGGSGGGGSS EVQLVESGGG LVQPGGSLKL SCAASGFTFS NYGMSWVRQT PDRRLELVAT   180
INNNGGGTYY PDSVKGRFTI SRDNAKNTLY LQMSSLKSED TAMYYCTSPG LLWDAWGAGT   240
TVTVSS                                                              246

SEQ ID NO: 117          moltype = AA   length = 556
FEATURE                 Location/Qualifiers
source                  1..556
                        mol_type = protein
                        organism = synthetic construct
SEQUENCE: 117
EVQLVESGGG LVQPGGSLKL SCAASGFTFS NYGMSWVRQT PDRRLELVAT INNNGGGTYY    60
PDSVKGRFTI SRDNAKNTLY LQMSSLKSED TAMYYCTSPG LLWDAWGAGT TVTVSSGSTS   120
GGGSGGGSGG GGSSDVVMTQ TPLTLSVSIG QPASISCKSS QSLLDSDGRT YLNWLLQRPG   180
QSPKRLIYLV SKLDSGAPDR FTGSGSGTDF TLKISRVEAE DLGVYYCWQG THFPQTFGGG   240
TKLEIKESKY GPPCPPCPGG GSSGGGSGGQ PREPQVYTLP PSQEEMTKNQ VSLTCLVKGF   300
YPSDIAVEWE SNGQPENNYK TTPPVLDSDG SFFLYSRLTV DKSRWQEGNV FSCSVMHEAL   360
HNHYTQKSLS LSLGKMFWVL VVVGGVLACY SLLVTVAFII FWVRSKRSRL LHSDYMNMTP   420
RRPGPTRKHY QPYAPPRDFA AYRSVKFSR SADAPAYQQG QNQLYNELNL GRREEYDVLD   480
KRRGRDPEMG GKPRRKNPQE GLFNELQKDK MAEAFSEIGM KGERRRGKGH DGLFQGLSTA   540
TKDTFDALHM QALPPR                                                   556

SEQ ID NO: 118          moltype = AA   length = 118
FEATURE                 Location/Qualifiers
source                  1..118
                        mol_type = protein
                        organism = synthetic construct
SEQUENCE: 118
QIQLVQSGPE LKKPGETVKV SCKASGYMFT NYAMNWVKQA PEKGLKWMGW INTHTGDPTY    60
ADDFKGRIAF SLETSASTAY LQINNLKNED TATYFCVRTY GNYAMDYWGQ GTSVTVSS     118

SEQ ID NO: 119          moltype = AA   length = 107
FEATURE                 Location/Qualifiers
source                  1..107
                        mol_type = protein
                        organism = synthetic construct
SEQUENCE: 119
DIQMTQTTSS LSASLGDRVT ISCSASQDIS NYLNWYQQKP DGTVKLLIYD TSILHLGVPS    60
RFSGSGSGTD YSLTISNLEP EDIATYYCQQ YSKFPRTFGG GTTLEIK                 107

SEQ ID NO: 120          moltype = AA   length = 261
FEATURE                 Location/Qualifiers
source                  1..261
                        mol_type = protein
                        organism = synthetic construct
SEQUENCE: 120
MDFQVQIFSF LLISASVIMS RQIQLVQSGP ELKKPGETVK VSCKASGYMF TNYAMNWVKQ    60
APEKGLKWMG WINTHTGDPT YADDFKGRIA FSLETSASTA YLQINNLKNE DTATYFCVRT   120
YGNYAMDYWG QGTSVTVSSG GGGSGGGGSG GGGSDIQMTQ TTSSLSASLG DRVTISCSAS   180
QDISNYLNWY QQKPDGTVKL LIYDTSILHL GVPSRFSGSG SGTDYSLTIS NLEPEDIATY   240
YCQQYSKFPR TFGGGTTLEI K                                             261

SEQ ID NO: 121          moltype = AA   length = 261
FEATURE                 Location/Qualifiers
source                  1..261
                        mol_type = protein
                        organism = synthetic construct
```

```
SEQUENCE: 121
MDFQVQIFSF LLISASVIMS RDIQMTQTTS SLSASLGDRV TISCSASQDI SNYLNWYQQK    60
PDGTVKLLIY DTSILHLGVP SRFSGSGSGT DYSLTISNLE PEDIATYYCQ QYSKFPRTFG   120
GGTTLEIKGG GGSGGGGSGG GGSQIQLVQS GPELKKPGET VKVSCKASGY MFTNYAMNWV   180
KQAPEKGLKW MGWINTHTGD PTYADDFKGR IAFSLETSAS TAYLQINNLK NEDTATYFCV   240
RTYGNYAMDY WGQGTSVTVS S                                            261

SEQ ID NO: 122        moltype = AA  length = 120
FEATURE               Location/Qualifiers
source                1..120
                      mol_type = protein
                      organism = synthetic construct
SEQUENCE: 122
EVQLVESGGG LVQPGGSLRL SCAASGFTFS RYWFSWVRQA PGKGLVWVGE INPSSSTINY    60
APSLKDKFTI SRDNAKNTLY LQMNSLRAED TAVYYCASLY YDYGDAYDYW GQGTLVTVSS   120

SEQ ID NO: 123        moltype = AA  length = 107
FEATURE               Location/Qualifiers
source                1..107
                      mol_type = protein
                      organism = synthetic construct
SEQUENCE: 123
EIVMTQSPAT LSVSPGERAT LSCKASQSVE SNVAWYQQKP GQAPRALIYS ASLRFSGIPA    60
RFSGSGSGTE FTLTISSLQS EDFAVYYCQQ YNNYPLTFGA GTKLELK                 107

SEQ ID NO: 124        moltype = AA  length = 119
FEATURE               Location/Qualifiers
source                1..119
                      mol_type = protein
                      organism = synthetic construct
SEQUENCE: 124
QVQLVQSGAE VKKPGASVKV SCKASGYSFP DYYINWVRQA PGQGLEWMGW IYFASGNSEY    60
NQKFTGRVTM TRDTSINTAY MELSSLTSED TAVYFCASLY DYDWYFDVWG QGTMVTVSS    119

SEQ ID NO: 125        moltype = AA  length = 112
FEATURE               Location/Qualifiers
source                1..112
                      mol_type = protein
                      organism = synthetic construct
SEQUENCE: 125
DIVMTQTPLS LSVTPGQPAS ISCKSSQSLV HSNGNTYLHW YLQKPGQSPQ LLIYKVSNRF    60
SGVPDRFSGS GSGTDFTLKI SRVEAEDVGI YYCSQSSIYP WTFGQGTKLE IK           112

SEQ ID NO: 126        moltype = AA  length = 119
FEATURE               Location/Qualifiers
source                1..119
                      mol_type = protein
                      organism = synthetic construct
SEQUENCE: 126
QVQLVQSGAE VKKPGASVKV SCKASGYSFP DYYINWVRQA PGQGLEWMGW IYFASGNSEY    60
NQKFTGRVTM TRDTSSSTAY MELSSLRSED TAVYFCASLY DYDWYFDVWG QGTMVTVSS    119

SEQ ID NO: 127        moltype = AA  length = 112
FEATURE               Location/Qualifiers
source                1..112
                      mol_type = protein
                      organism = synthetic construct
SEQUENCE: 127
DIVMTQTPLS LSVTPGEPAS ISCKSSQSLV HSNGNTYLHW YLQKPGQSPQ LLIYKVSNRF    60
SGVPDRFSGS GSGADFTLKI SRVEAEDVGV YYCAETSHVP WTFGQGTKLE IK           112

SEQ ID NO: 128        moltype = AA  length = 266
FEATURE               Location/Qualifiers
source                1..266
                      mol_type = protein
                      organism = synthetic construct
SEQUENCE: 128
MDFQVQIFSF LLISASVIMS REVQLVESGG GLVQPGGSLR LSCAASGFTF SRYWFSWVRQ    60
APGKGLVWVG EINPSSSTIN YAPSLKDKFT ISRDNAKNTL YLQMNSLRAE DTAVYYCASL   120
YYDYGDAYDY WGQGTLVTVS SGSTSGSGKP GSGEGSTKGE IVMTQSPATL SVSPGERATL   180
SCKASQSVES NVAWYQQKPG QAPRALIYSA SLRFSGIPAR FSGSGSGTEF TLTISSLQSE   240
DFAVYYCQQY NNYPLTFGAG TKLELK                                       266

SEQ ID NO: 129        moltype = AA  length = 263
FEATURE               Location/Qualifiers
source                1..263
                      mol_type = protein
                      organism = synthetic construct
```

```
SEQUENCE: 129
MDFQVQIFSF LLISASVIMS REIVMTQSPA TLSVSPGERA TLSCKASQSV ESNVAWYQQK    60
PGQAPRALIY SASLRFSGIP ARFSGSGSGT EFTLTISSLQ SEDFAVYYCQ QYNNYPLTFG   120
AGTKLELKGG GGSGGGGSGG GGSEVQLVES GGGLVQPGGS LRLSCAASGF TFSRYWFSWV   180
RQAPGKGLVW VGEINPSSST INYAPSLKDK FTISRDNAKN TLYLQMNSLR AEDTAVYYCA   240
SLYYDYGDAY DYWGQGTLVT VSS                                          263

SEQ ID NO: 130          moltype = AA  length = 270
FEATURE                 Location/Qualifiers
source                  1..270
                        mol_type = protein
                        organism = synthetic construct
SEQUENCE: 130
MDFQVQIFSF LLISASVIMS RQVQLVQSGA EVKKPGASVK VSCKASGYSF PDYYINWVRQ    60
APGQGLEWMG WIYFASGNSE YNQKFTGRVT MTRDTSINTA YMELSSLTSE DTAVYFCASL   120
YDYDWYFDVW GQGTMVTVSS GSTSGSGKPG SGEGSTKGDI VMTQTPLSLS VTPGQPASIS   180
CKSSQSLVHS NGNTYLHWYL QKPGQSPQLL IYKVSNRFSG VPDRFSGSGS GTDFTLKISR   240
VEAEDVGIYY CSQSSIYPWT FGQGTKLEIK                                   270

SEQ ID NO: 131          moltype = AA  length = 270
FEATURE                 Location/Qualifiers
source                  1..270
                        mol_type = protein
                        organism = synthetic construct
SEQUENCE: 131
MDFQVQIFSF LLISASVIMS RDIVMTQTPL SLSVTPGQPA SISCKSSQSL VHSNGNTYLH    60
WYLQKPGQSP QLLIYKVSNR FSGVPDRFSG SGSGTDFTLK ISRVEAEDVG IYYCSQSSIY   120
PWTFGQGTKL EIKGSTSGSG KPGSGEGSTK GQVQLVQSGA EVKKPGASVK VSCKASGYSF   180
PDYYINWVRQ APGQGLEWMG WIYFASGNSE YNQKFTGRVT MTRDTSINTA YMELSSLTSE   240
DTAVYFCASL YDYDWYFDVW GQGTMVTVSS                                   270

SEQ ID NO: 132          moltype = AA  length = 270
FEATURE                 Location/Qualifiers
source                  1..270
                        mol_type = protein
                        organism = synthetic construct
SEQUENCE: 132
MDFQVQIFSF LLISASVIMS RQVQLVQSGA EVKKPGASVK VSCKASGYSF PDYYINWVRQ    60
APGQGLEWMG WIYFASGNSE YNQKFTGRVT MTRDTSSSTA YMELSSLRSE DTAVYFCASL   120
YDYDWYFDVW GQGTMVTVSS GSTSGSGKPG SGEGSTKGDI VMTQTPLSLS VTPGEPASIS   180
CKSSQSLVHS NGNTYLHWYL QKPGQSPQLL IYKVSNRFSG VPDRFSGSGS GADFTLKISR   240
VEAEDVGVYY CAETSHVPWT FGQGTKLEIK                                   270

SEQ ID NO: 133          moltype = AA  length = 270
FEATURE                 Location/Qualifiers
source                  1..270
                        mol_type = protein
                        organism = synthetic construct
SEQUENCE: 133
MDFQVQIFSF LLISASVIMS RDIVMTQTPL SLSVTPGEPA SISCKSSQSL VHSNGNTYLH    60
WYLQKPGQSP QLLIYKVSNR FSGVPDRFSG SGSGADFTLK ISRVEAEDVG VYYCAETSHV   120
PWTFGQGTKL EIKGSTSGSG KPGSGEGSTK GQVQLVQSGA EVKKPGASVK VSCKASGYSF   180
PDYYINWVRQ APGQGLEWMG WIYFASGNSE YNQKFTGRVT MTRDTSSSTA YMELSSLRSE   240
DTAVYFCASL YDYDWYFDVW GQGTMVTVSS                                   270

SEQ ID NO: 134          moltype = AA  length = 122
FEATURE                 Location/Qualifiers
source                  1..122
                        mol_type = protein
                        organism = synthetic construct
SEQUENCE: 134
QVQLVESGGG LVQPGGSLRL SCAASGFTFS SYWMYWVRQT PGKGLEWVST INRDGSATWY    60
ADSVKGRFTI SRDNAKNTGY LQMNSLKPDD TAVYYCVSDP DNYSSDEMVP YWGQGTQVTV   120
SS                                                                 122

SEQ ID NO: 135          moltype = AA  length = 122
FEATURE                 Location/Qualifiers
source                  1..122
                        mol_type = protein
                        organism = synthetic construct
SEQUENCE: 135
EVQLVESGGG LVQPGGSLRL SCAASGFTFS SYWMYWVRQA PGKGLVWVST INRDGSATWY    60
ADSVKGRFTI SRDNAKNTLY LQMNSLRAED TAVYYCARDP DNYSSDEMVP YWGQGTLVTV   120
SS                                                                 122

SEQ ID NO: 136          moltype = AA  length = 122
FEATURE                 Location/Qualifiers
```

```
source                  1..122
                        mol_type = protein
                        organism = synthetic construct
SEQUENCE: 136
EVQLVESGGG LVQPGGSLRL SCAASGFTFS SYWMYWVRQA PGKGLVWVST INRDGSATWY    60
ADSVKGRFTI SRDNAKNTLY LQMNSLRAED TAVYYCVSDP DNYSSDEMVP YWGQGTLVTV   120
SS                                                                 122

SEQ ID NO: 137          moltype = AA   length = 122
FEATURE                 Location/Qualifiers
source                  1..122
                        mol_type = protein
                        organism = synthetic construct
SEQUENCE: 137
EVQLVESGGG LVQPGGSLRL SCAASGFTFS SYWMYWVRQT PGKGLVWVST INRDGSATWY    60
ADSVKGRFTI SRDNAKNTLY LQMNSLRAED TAVYYCVSDP DNYSSDEMVP YWGQGTLVTV   120
SS                                                                 122

SEQ ID NO: 138          moltype = AA   length = 122
FEATURE                 Location/Qualifiers
source                  1..122
                        mol_type = protein
                        organism = synthetic construct
SEQUENCE: 138
EVQLVESGGG LVQPGGSLRL SCAASGFTFS SYWMYWVRQA PGKGLEWVST INRDGSATWY    60
ADSVKGRFTI SRDNAKNTLY LQMNSLRAED TAVYYCVSDP DNYSSDEMVP YWGQGTLVTV   120
SS                                                                 122

SEQ ID NO: 139          moltype = AA   length = 122
FEATURE                 Location/Qualifiers
source                  1..122
                        mol_type = protein
                        organism = synthetic construct
SEQUENCE: 139
EVQLVESGGG LVQPGGSLRL SCAASGFTFS SYWMYWVRQT PGKGLEWVST INRDGSATWY    60
ADSVKGRFTI SRDNAKNTGY LQMNSLRPED TAVYYCVSDP DNYSSDEMVP YWGQGTLVTV   120
SS                                                                 122

SEQ ID NO: 140          moltype = AA   length = 88
FEATURE                 Location/Qualifiers
source                  1..88
                        mol_type = protein
                        organism = synthetic construct
SEQUENCE: 140
ESKYGPPCPP CPGGGSSGGG SGGQPREPQV YTLPPSQEEM TKNQVSLTCL VKGFYPSDIA    60
VEWESNGQPE NNYKTTPPVL DSDGSFFL                                      88

SEQ ID NO: 141          moltype = AA   length = 123
FEATURE                 Location/Qualifiers
source                  1..123
                        mol_type = protein
                        organism = synthetic construct
SEQUENCE: 141
ESKYGPPCPP CPGQPREPQV YTLPPSRDEL TKNQVSLTCL VKGFYPSDIA VEWESNGQPE    60
NNYKTTPPVL DSDGSFFLYS KLTVDKSRWQ QGNVFSCSVM HEALHNAYTQ KSLSLSPGKK   120
DPK                                                                123

SEQ ID NO: 142          moltype = AA   length = 494
FEATURE                 Location/Qualifiers
source                  1..494
                        mol_type = protein
                        organism = synthetic construct
SEQUENCE: 142
MEFGLSWLFL VAILKGVQCG LLDLRQGMFA QLVAQNVLLI DGPLSWYSDP GLAGVSLTGG    60
LSYKEDTKEL VVAKAGVYYV FFQLELRRVV AGEGSGSVSL ALHLQPLRSA AGAAALALTV   120
DLPPASSEAR NSAFGFQGRL LHLSAGQRLG VHLHTEARAR HAWQLTQGAT VLGLFRVTPE   180
IPAGLPSPRS EESKYGPPCP PCPGQPREPQ VYTLPPSRDE LTKNQVSLTC LVKGFYPSDI   240
AVEWESNGQP ENNYKTTPPV LDSDGSFFLY SKLTVDKSRW QQGNVFSCSV MHEALHNAYT   300
QKSLSLSPGK KDPKFWVLVV VGGVLACYSL LVTVAFIIFW VRSKRSRLLH SDYMNMTPRR   360
PGPTRKHYQP YAPPRDFAAY RSRVKFSRSA DAPAYQQGQN QLYNELNLGR REEYDVLDKR   420
RGRDPEMGGK PRRKNPQEGL YNELQKDKMA EAYSEIGMKG ERRRGKGHDG LYQGLSTATK   480
DTYDALHMQA LPPR                                                    494

SEQ ID NO: 143          moltype = AA   length = 455
FEATURE                 Location/Qualifiers
source                  1..455
                        mol_type = protein
                        organism = synthetic construct
```

```
SEQUENCE: 143
MEFGLSWLFL VAILKGVQCG LLDLRQGMFA QLVAQNVLLI DGPLSWYSDP GLAGVSLTGG    60
LSYKEDTKEL VVAKAGVYYV FFQLELRRVV AGEGSGSVSL ALHLQPLRSA AGAAALALTV   120
DLPPASSEAR NSAFGFQGRL LHLSAGQRLG VHLHTEARAR HAWQLTQGAT VLGLFRVTPE   180
IPAGLPSPRS EESKYGPPCP PCPGQPREPQ VYTLPPSRDE LTKNQVSLTC LVKGFYPSDI   240
AVEWESNGQP ENNYKTTPPV LDSDGSFFLY SKLTVDKSRW QQGNVFSCSV MHEALHNAYT   300
QKSLSLSPGK KDPKFWVLVV VGGVLACYSL LVTVAFIIFW VRSRVKFSRS ADAPAYQQGQ   360
NQLYNELNLG RREEYDVLDK RRGRDPEMGG KPRRKNPQEG LFNELQKDKM AEAFSEIGMK   420
GERRRGKGHD GLFQGLSTAT KDTFDALHMQ ALPPR                              455

SEQ ID NO: 144          moltype = AA  length = 494
FEATURE                 Location/Qualifiers
source                  1..494
                        mol_type = protein
                        organism = synthetic construct
SEQUENCE: 144
MEFGLSWLFL VAILKGVQCG LLDLRQGMFA QLVAQNVLLI DGPLSWYSDP GLAGVSLTGG    60
LSYKEDTKEL VVAKAGVYYV FFQLELRRVV AGEGSGSVSL ALHLQPLRSA AGAAALALTV   120
DLPPASSEAR NSAFGFQGRL LHLSAGQRLG VHLHTEARAR HAWQLTQGAT VLGLFRVTPE   180
IPAGLPSPRS EESKYGPPCP PCPGQPREPQ VYTLPPSRDE LTKNQVSLTC LVKGFYPSDI   240
AVEWESNGQP ENNYKTTPPV LDSDGSFFLY SKLTVDKSRW QQGNVFSCSV MHEALHNAYT   300
QKSLSLSPGK KDPKFWVLVV VGGVLACYSL LVTVAFIIFW VRSKRSRLLH SDYMNMTPRR   360
PGPTRKHYQP YAPPRDFAAY RSRVKFSRSA DAPAYQQGQN QLYNELNLGR REEYDVLDKR   420
RGRDPEMGGK PRRKNPQEGL FNELQKDKMA EAFSEIGMKG ERRRGKGHDG LFQGLSTATK   480
DTFDALHMQA LPPR                                                     494

SEQ ID NO: 145          moltype = AA  length = 172
FEATURE                 Location/Qualifiers
source                  1..172
                        mol_type = protein
                        organism = synthetic construct
SEQUENCE: 145
GLLDLRQGMF AQLVAQNVLL IDGPLSWYSD PGLAGVSLTG GLSYKEDTKE LVVAKAGVYY    60
VFFQLELRRV VAGEGSGSVS LALHLQPLRS AAGAAALALT VDLPPASSEA RNSAFGFQGR   120
LLHLSAGQRL GVHLHTEARA RHAWQLTQGA TVLGLFRVTP EIPAGLPSPR SE           172

SEQ ID NO: 146          moltype = AA  length = 119
FEATURE                 Location/Qualifiers
source                  1..119
                        mol_type = protein
                        organism = synthetic construct
SEQUENCE: 146
QVQLKQSGPS LVQPSQRLSI TCTVSGFSLI SYGVHWVRQS PGKGLEWLGV IWRGGSTDYN    60
AAFMSRLSIT KDNSKSQVFF KMNSLQADDT AIYFCAKTLI TTGYAMDYWG QGTSVTVSS    119

SEQ ID NO: 147          moltype = AA  length = 106
FEATURE                 Location/Qualifiers
source                  1..106
                        mol_type = protein
                        organism = synthetic construct
SEQUENCE: 147
DIQLTQSSSS FSVSLGDRVT ITCKASEDIY NRLAWYQQKP GNAPRLLISG ATSLETGVPS    60
RFSGSGSGKD YTLSITSLQT EDVATYYCQQ YWSTPTFGGG TKLEIK                  106

SEQ ID NO: 148          moltype = AA  length = 109
FEATURE                 Location/Qualifiers
source                  1..109
                        mol_type = protein
                        organism = synthetic construct
SEQUENCE: 148
QVELVESGGS LKLSCAASGF DFSRSWMNWV RQAPGKGLEW IGEINPDSST INYTTSLKDK    60
FIISRDNAKN TLYLQMTKVR SEDTALYYCA RYGNWFPYWG QGTLVTVSS               109

SEQ ID NO: 149          moltype = AA  length = 107
FEATURE                 Location/Qualifiers
source                  1..107
                        mol_type = protein
                        organism = synthetic construct
SEQUENCE: 149
DILMTQSQKI MPTSVGDRVS VTCKASQNVD TNVAWYQQKP GQSPKALIYS ASYRYSGVPD    60
RFTGSGSGTD FTLTITNVQS EDLAEYFCQQ YDSYPLTFGA GTKLDLK                 107

SEQ ID NO: 150          moltype = AA  length = 119
FEATURE                 Location/Qualifiers
source                  1..119
                        mol_type = protein
                        organism = synthetic construct
```

```
SEQUENCE: 150
QVQLKQSGPG LVHPSQSLSI TCTVSGFSLT SYGVHWVRQS PGKGLEWLGV MWRGGSTDYN    60
AAFMSRLNIT KDNSKRQVFF KMNSLQADDT AIYYCAKSMI TTGFVMDSWG QGTSVTVSS    119

SEQ ID NO: 151          moltype = AA   length = 107
FEATURE                 Location/Qualifiers
source                  1..107
                        mol_type = protein
                        organism = synthetic construct
SEQUENCE: 151
DIQLTQSPSS FSVSLGDRVT ITCKASEDIY NRLTWYQQKP GNAPRLLISG ATSLETGVPS    60
RFSGSGSGKD YTLSITSLQT EDVATYYCQQ YWSNPYTFGG GTKLEIR                  107

SEQ ID NO: 152          moltype = AA   length = 120
FEATURE                 Location/Qualifiers
source                  1..120
                        mol_type = protein
                        organism = synthetic construct
SEQUENCE: 152
QVQLVESGGG LVQPGGSLRL SCAASGFTFS SYYMNWVRQA PGKGLEWVSG ISGDPSNTYY    60
ADSVKGRFTI SRDNSKNTLY LQMNSLRAED TAVYYCARDL PLVYTGFAYW GQGTLVTVSS   120

SEQ ID NO: 153          moltype = AA   length = 107
FEATURE                 Location/Qualifiers
source                  1..107
                        mol_type = protein
                        organism = synthetic construct
SEQUENCE: 153
DIELTQPPSV SVAPGQTARI SCSGDNLRHY YVYWYQQKPG QAPVLVIYGD SKRPSGIPER    60
FSGSNSGNTA TLTISGTQAE DEADYYCQTY TGGASLVFGG GTKLTVL                  107

SEQ ID NO: 154          moltype = AA   length = 121
FEATURE                 Location/Qualifiers
source                  1..121
                        mol_type = protein
                        organism = synthetic construct
SEQUENCE: 154
QVQLVQSGAE VKKPGASVKV SCKASGYTFT SYSINWVRQA PGQGLEWMGY IDPNRGNTNY    60
AQKFQGRVTM TRDTSISTAY MELSSLRSED TAVYYCAREY IYFIHGMLDF WGQGTLVTVS   120
S                                                                    121

SEQ ID NO: 155          moltype = AA   length = 112
FEATURE                 Location/Qualifiers
source                  1..112
                        mol_type = protein
                        organism = synthetic construct
SEQUENCE: 155
DIVMTQSPLS LPVTPGEPAS ISCRSSQSLL FIDGNNYLNW YLQKPGQSPQ LLIYLGSNRA    60
SGVPDRFSGS GSGTDFTLKI SRVEAEDVGV YYCQQYSSKS ATFGQGTKVE IK           112

SEQ ID NO: 156          moltype = AA   length = 122
FEATURE                 Location/Qualifiers
source                  1..122
                        mol_type = protein
                        organism = synthetic construct
SEQUENCE: 156
QVQLVESGGG LVQPGGSLRL SCAASGFTFS NYGMHWVRQA PGKGLEWVSN IRSDGSWTYY    60
ADSVKGRFTI SRDNSKNTLY LQMNSLRAED TAVYYCARRY WSKSHASVTD YWGQGTLVTV   120
SS                                                                   122

SEQ ID NO: 157          moltype = AA   length = 107
FEATURE                 Location/Qualifiers
source                  1..107
                        mol_type = protein
                        organism = synthetic construct
SEQUENCE: 157
DIQMTQSPSS LSASVGDRVT ITCRASQDIS AFLNWYQQKP GKAPKLLIYK VSNLQSGVPS    60
RFSGSGSGTD FTLTISSLQP EDFATYYCQQ AYSGSITFGQ GTKVEIK                  107

SEQ ID NO: 158          moltype = AA   length = 123
FEATURE                 Location/Qualifiers
source                  1..123
                        mol_type = protein
                        organism = synthetic construct
SEQUENCE: 158
EVQLLESGGG LVQPGGSLRL SCAASGFTFD DYGMSWVRQA PGKGLEWVSD ISWNGGKTHY    60
VDSVKGQFTI SRDNSKNTLY LQMNSLRAED TAVYYCARGS LFHDSSGFYF GHWGQGTLVT   120
VSS                                                                  123
```

| | | |
|---|---|---|
| SEQ ID NO: 159 | moltype = AA length = 110 | |
| FEATURE | Location/Qualifiers | |
| source | 1..110 | |
| | mol_type = protein | |
| | organism = synthetic construct | |

SEQUENCE: 159
QSVLTQPPSA SGTPGQRVTI SCSGSSSNIG DNYVSWYQQL PGTAPKLLIY RDSQRPSGVP 60
DRFSGSKSGT SASLAISGLR SEDEADYYCQ SYDSSLSGSV FGGGTKLTVL 110

| | | |
|---|---|---|
| SEQ ID NO: 160 | moltype = AA length = 122 | |
| FEATURE | Location/Qualifiers | |
| source | 1..122 | |
| | mol_type = protein | |
| | organism = synthetic construct | |

SEQUENCE: 160
EVQLLESGGG LVQPGGSLRL SCAASGFTFN NYDMTWVRQA PGKGLEWVAV ISYDGSDKDY 60
ADSVKGRFTI SRDNSKNTLY LQMNSLRAED TAVYYCARVY YYGFSGPSMD VWGQGTLVTV 120
SS 122

| | | |
|---|---|---|
| SEQ ID NO: 161 | moltype = AA length = 111 | |
| FEATURE | Location/Qualifiers | |
| source | 1..111 | |
| | mol_type = protein | |
| | organism = synthetic construct | |

SEQUENCE: 161
QSVLTQPPSA SGTPGQRVTI SCSGSNSNIG SNTVNWYQQL PGTAPKLLIY SDSNRPSGVP 60
DRFSGSKSGT SASLAISGLR SEDEADYYCQ SYDSSLSGSR VFGGGTKLTV L 111

| | | |
|---|---|---|
| SEQ ID NO: 162 | moltype = AA length = 125 | |
| FEATURE | Location/Qualifiers | |
| source | 1..125 | |
| | mol_type = protein | |
| | organism = synthetic construct | |

SEQUENCE: 162
EVQLLESGGG LVQPGGSLRL SCAASGFTFS SYGMNWVRQA PGKGLEWVSG ISGSGGSTYY 60
ADSVKGRFTI SRDNSKNTLY LQMNSLRAED TAVYYCAKDS NYDFWSGYYY GMDVWGQGTL 120
VTVSS 125

| | | |
|---|---|---|
| SEQ ID NO: 163 | moltype = AA length = 110 | |
| FEATURE | Location/Qualifiers | |
| source | 1..110 | |
| | mol_type = protein | |
| | organism = synthetic construct | |

SEQUENCE: 163
QSVLTQPPSA SGTPGQRVTI SCSGSSSNIG SKTVSWYQQL PGTAPKLLIY DNNKRPSGVP 60
DRFSGSKSGT SASLAISGLR SEDEADYYCS SYAARSTNII FGGGTKLTVL 110

| | | |
|---|---|---|
| SEQ ID NO: 164 | moltype = AA length = 119 | |
| FEATURE | Location/Qualifiers | |
| source | 1..119 | |
| | mol_type = protein | |
| | organism = synthetic construct | |

SEQUENCE: 164
EVQLLESGGG LVQPGGSLRL SCAASGFTFS SYGMHWVRQA PGKGLEWVSR INSDGSSTSY 60
ADSMKGQFTI SRDNSKNTLY LQMNSLRAED TAVYYCARGG YYYYAMDVWG QGTLVTVSS 119

| | | |
|---|---|---|
| SEQ ID NO: 165 | moltype = AA length = 110 | |
| FEATURE | Location/Qualifiers | |
| source | 1..110 | |
| | mol_type = protein | |
| | organism = synthetic construct | |

SEQUENCE: 165
QSVLTQPPSA SGTPGQRVTI SCSGGSSNIG YKTVNWYQQL PGTAPKLLIY DNNKRPSGVP 60
DRFSGSKSGT SASLAISGLR SEDEADYYCA AWDDSLNGLV FGGGTKLTVL 110

| | | |
|---|---|---|
| SEQ ID NO: 166 | moltype = AA length = 114 | |
| FEATURE | Location/Qualifiers | |
| source | 1..114 | |
| | mol_type = protein | |
| | organism = synthetic construct | |

SEQUENCE: 166
QIQLVQSGPE LKKPGETVKI SCKASGYTLT SYGMNWVKQA PGKGLKWMGW INTYTGEPTY 60
ADDFKGRFAF SLETSASTAF LQINNLKNED TATYFCVRRG FAYWGQGTLV TVSA 114

| | | |
|---|---|---|
| SEQ ID NO: 167 | moltype = AA length = 111 | |
| FEATURE | Location/Qualifiers | |
| source | 1..111 | |
| | mol_type = protein | |
| | organism = synthetic construct | |

```
SEQUENCE: 167
NIVLTQSPAS LAVSLGQRAT ISCRASESVE IYGNGFMNWF QQKPGQPPKL LIYRASNLES    60
GIPARFSGSG SRTEFTLTID PVEADDVATY YCQQINEDPF TFGSGTKLEI K            111

SEQ ID NO: 168          moltype = AA  length = 114
FEATURE                 Location/Qualifiers
source                  1..114
                        mol_type = protein
                        organism = synthetic construct
SEQUENCE: 168
QIQLVQSGPE LKKPGETVKI SCKASGYTFT NSGMNWVKQA PGKGLKWMGW INTYTGEPTY    60
ADDFKGRFAF SLETSASSAY LQISNLKNED TATYFCARRG FVYWGQGTLV TVSA         114

SEQ ID NO: 169          moltype = AA  length = 111
FEATURE                 Location/Qualifiers
source                  1..111
                        mol_type = protein
                        organism = synthetic construct
SEQUENCE: 169
DIVLTQSPAS LAVSLGQRAT ISCRASESVA IYGNSFLKWF QQKPGQPPKL LIYRASNLES    60
GIPARFSGSG SGTDFTLTIN PVEADDVATY YCQQINEDPY TFGGGTKLEI K            111

SEQ ID NO: 170          moltype = AA  length = 120
FEATURE                 Location/Qualifiers
source                  1..120
                        mol_type = protein
                        organism = synthetic construct
SEQUENCE: 170
QVQLQQSGAE LARPGTSVKL SCKASGYTFT DYWMQWVKQR PGQGLEWIGT IYPGDGDTGY    60
AQKFKGKATL TADKSSKTVY MHLSSLASED SAVYYCARGD YYGSNSLDYW GQGTSVTVSS   120

SEQ ID NO: 171          moltype = AA  length = 107
FEATURE                 Location/Qualifiers
source                  1..107
                        mol_type = protein
                        organism = synthetic construct
SEQUENCE: 171
DIVMAQSHKF MSTSVGDRVS ITCKASQDVS TVVAWYQQKP GQSPKRLIYS ASYRYIGVPD    60
RFTGSGSGTD FTFTISSVQA EDLAVYYCQQ HYSPPYTFGG GTKLEIK                 107

SEQ ID NO: 172          moltype = AA  length = 120
FEATURE                 Location/Qualifiers
source                  1..120
                        mol_type = protein
                        organism = synthetic construct
SEQUENCE: 172
NVQLVESGGG LVQPGGSRKL SCAASGFTFS NFGMHWVRQA PEKGLEWVAY IRSGSGTIYY    60
SDTVKGRFTI SRDNPKNTLF LQMTSLRSED TAMYYCARSY YDFGAWFAYW GQGTLVTVSA   120

SEQ ID NO: 173          moltype = AA  length = 107
FEATURE                 Location/Qualifiers
source                  1..107
                        mol_type = protein
                        organism = synthetic construct
SEQUENCE: 173
DIVMTQSQKF MSTSVGDRVS VTCKASQNVG TNVAWYQHKP GQSPKIMIYS ASSRYSGVPD    60
RFTGSGSGTL FTLTINNVQS EDLAEYFCQQ YNSYPLTFGS GTKLEIK                 107

SEQ ID NO: 174          moltype = AA  length = 120
FEATURE                 Location/Qualifiers
source                  1..120
                        mol_type = protein
                        organism = synthetic construct
SEQUENCE: 174
QVQLVQSGAE VAKPGTSVKL SCKASGYTFT DYWMQWVKQR PGQGLEWIGT IYPGDGDTGY    60
AQKFQGKATL TADKSSKTVY MHLSSLASED SAVYYCARGD YYGSNSLDYW GQGTSVTVSS   120

SEQ ID NO: 175          moltype = AA  length = 107
FEATURE                 Location/Qualifiers
source                  1..107
                        mol_type = protein
                        organism = synthetic construct
SEQUENCE: 175
DIVMTQSHLS MSTSLGDPVS ITCKASQDVS TVVAWYQQKP GQSPRRLIYS ASYRYIGVPD    60
RFTGSGAGTD FTFTISSVQA EDLAVYYCQQ HYSPPYTFGG GTKLEIK                 107

SEQ ID NO: 176          moltype = AA  length = 122
FEATURE                 Location/Qualifiers
```

```
                                   -continued source                   1..122
                         mol_type = protein
                         organism = synthetic construct
SEQUENCE: 176
EVQLLESGGG LVQPGGSLRL SCAVSGFTFN SFAMSWVRQA PGKGLEWVSA ISGSGGGTYY      60
ADSVKGRFTI SRDNSKNTLY LQMNSLRAED TAVYFCAKDK ILWFGEPVFD YWGQGTLVTV     120
SS                                                                    122

SEQ ID NO: 177           moltype = AA  length = 107
FEATURE                  Location/Qualifiers
source                   1..107
                         mol_type = protein
                         organism = synthetic construct
SEQUENCE: 177
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPPTFGQ GTKVEIK                   107

SEQ ID NO: 178           moltype = AA  length = 121
FEATURE                  Location/Qualifiers
source                   1..121
                         mol_type = protein
                         organism = synthetic construct
SEQUENCE: 178
QVQLVQSGAE VKKPGSSVKV SCKAFGGTFS SYAISWVRQA PGQGLEWMGR IIRFLGIANY      60
AQKFQGRVTL IADKSTNTAY MELSSLRSED TAVYYCAGEP GERDPDAVDI WGQGTMVTVS     120
S                                                                     121

SEQ ID NO: 179           moltype = AA  length = 107
FEATURE                  Location/Qualifiers
source                   1..107
                         mol_type = protein
                         organism = synthetic construct
SEQUENCE: 179
DIQMTQSPSS LSASVGDRVT ITCRASQGIR SWLAWYQQKP EKAPKSLIYA ASSLQSGVPS      60
RFSGSGSGTD FTLTISSLQP EDFATYYCQQ YNSYPLTFGG GTKVEIK                   107

SEQ ID NO: 180           moltype = AA  length = 122
FEATURE                  Location/Qualifiers
source                   1..122
                         mol_type = protein
                         organism = synthetic construct
SEQUENCE: 180
EVQLVQSGAE VKKPGESLKI SCKGSGYSFS NYWIGWVRQM PGKGLEWMGI IYPHDSDARY      60
SPSFQGQVTF SADKSISTAY LQWSSLKASD TAMYYCARHV GWGSRYWYFD LWGRGTLVTV     120
SS                                                                    122

SEQ ID NO: 181           moltype = AA  length = 107
FEATURE                  Location/Qualifiers
source                   1..107
                         mol_type = protein
                         organism = synthetic construct
SEQUENCE: 181
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPPTFGQ GTKVEIK                   107

SEQ ID NO: 182           moltype = AA  length = 122
FEATURE                  Location/Qualifiers
source                   1..122
                         mol_type = protein
                         organism = synthetic construct
SEQUENCE: 182
QVQLVQSGAE VKKPGSSVKV SCKASGGTFS SYAFSWVRQA PGQGLEWMGR VIPFLGIANS      60
AQKFQGRVTI TADKSTSTAY MDLSSLRSED TAVYYCARDD IAALGPFDYW GQGTLVTVSS     120
AS                                                                    122

SEQ ID NO: 183           moltype = AA  length = 107
FEATURE                  Location/Qualifiers
source                   1..107
                         mol_type = protein
                         organism = synthetic construct
SEQUENCE: 183
DIQMTQSPSS LSASVGDRVT ITCRASQGIS SWLAWYQQKP EKAPKSLIYA ASSLQSGVPS      60
RFSGSGSGTD FTLTISSLQP EDFATYYCQQ YNSYPRTFGQ GTKVEIK                   107

SEQ ID NO: 184           moltype = AA  length = 121
FEATURE                  Location/Qualifiers
source                   1..121
                         mol_type = protein
                         organism = synthetic construct
```

```
SEQUENCE: 184
QVQLVQSGAE VKKPGSSVKV SCKAFGGTFS SYAISWVRQA PGQGLEWMGR IIRFLGKTNH    60
AQKFQGRVTL TADKSTNTAY MELSSLRSED TAVYYCAGEP GDRDPDAVDI WGQGTMVTVS   120
S                                                                  121

SEQ ID NO: 185         moltype = AA   length = 107
FEATURE                Location/Qualifiers
source                 1..107
                       mol_type = protein
                       organism = synthetic construct
SEQUENCE: 185
DIQMTQSPSS LSASVGDRVT ITCRASQGIR SWLAWYQQKP EKAPKSLIYA ASSLQSGVPS    60
RFSGSGSGTD FTLTISSLQP EDFATYYCQQ YNSYPLTFGG GTKVEIK                 107

SEQ ID NO: 186         moltype = AA   length = 121
FEATURE                Location/Qualifiers
source                 1..121
                       mol_type = protein
                       organism = synthetic construct
SEQUENCE: 186
QVQLVQSGAE VKKPGSSVKV SCKPSGGTFR SYAISWVRQA PGQGLEWMGR IIVFLGKVNY    60
AQRFQGRVTL TADKSTTTAY MELSSLRSED TAVYYCTGEP GARDPDAFDI WGQGTMVTVS   120
S                                                                  121

SEQ ID NO: 187         moltype = AA   length = 107
FEATURE                Location/Qualifiers
source                 1..107
                       mol_type = protein
                       organism = synthetic construct
SEQUENCE: 187
DIQMTQSPSS LSASVGDRVT ITCRASQGIR SWLAWYQQKP EKAPKSLIYA ASSLQSGVPS    60
RFSGSGSGTD FTLTISSLQP EDFATYYCQQ YNNYPLTFGG GTKVEIK                 107

SEQ ID NO: 188         moltype = AA   length = 121
FEATURE                Location/Qualifiers
source                 1..121
                       mol_type = protein
                       organism = synthetic construct
SEQUENCE: 188
QVQLVQSGAE VKKPGSSVKV SCKAFGGTFS SYAISWVRQA PGQGLEWMGR IIRFLGIANY    60
AQKFQGRVTL IADKSTNTAY MELSSLRSED TAVYYCAGEP GERDPDAVDI WGQGTMVTVS   120
S                                                                  121

SEQ ID NO: 189         moltype = AA   length = 107
FEATURE                Location/Qualifiers
source                 1..107
                       mol_type = protein
                       organism = synthetic construct
SEQUENCE: 189
DIQMTQSPSS LSASVGDRVT ITCRASQGIS NYLAWFQQKP GKAPKSLIYA ASSLQSGVPS    60
RFSGSGSGTD FTLTISSLQP EDFATYYCQQ YNSYPYTFGQ GTKLEIK                 107

SEQ ID NO: 190         moltype = AA   length = 154
FEATURE                Location/Qualifiers
source                 1..154
                       mol_type = protein
                       organism = synthetic construct
SEQUENCE: 190
KRGRKKLLYI FKQPFMRPVQ TTQEEDGCSC RFPEEEEGGC ELRVKFSRSA DAPAYQQGQN    60
QLYNELNLGR REEYDVLDKR RGRDPEMGGK PRRKNPQEGL YNELQKDKMA EAYSEIGMKG   120
ERRRGKGHDG LYQGLSTATK DTYDALHMQA LPPR                              154

SEQ ID NO: 191         moltype = AA   length = 487
FEATURE                Location/Qualifiers
source                 1..487
                       mol_type = protein
                       organism = synthetic construct
SEQUENCE: 191
MDFQVQIFSF LLISASVIMS RDIQMTQSPS SLSASVGDRV TITCRASQGI RSWLAWYQQK    60
PEKAPKSLIY AASSLQSGVP SRFSGSGSGT DFTLTISSLQ PEDFATYYCQ QYNNYPLTFG   120
GGTKVEIKGG GGSGGGGSGG GGSQVQLVQS GAEVKKPGSS VKVSCKPSGG TFRSYAISWV   180
RQAPGQGLEW MGRIIVFLGK VNYAQRFQGR VTLTADKSTT TAYMELSSLR SEDTAVYYCT   240
GEPGARDPDA FDIWGQGTMV TVSSTSTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYQQ GQNLYNELNL GRREEYDVLD KRRGRDPEM    420
GGKPRRKNPQ EGLYNELQKD KMAEAYSEIG MKGERRRGKG HDGLYQGLST ATKDTYDALH   480
MQALPPR                                                            487
```

What is claimed is:

1. A cell or a population thereof, wherein
   (i) the cell is (a) an immune cell; (b) an induced pluripotent cell (iPSC); or (c) a derivative effector cell obtained from differentiating the iPSC; and
   (ii) the cell comprises a polynucleotide encoding a chimeric antigen receptor (CAR) comprising:
   (a) an ectodomain comprising an antigen binding domain recognizing a HER2 (human epidermal growth factor receptor 2) antigen, wherein the antigen binding domain comprises:
      (1) a heavy chain variable (VH) domain comprising a heavy chain complementary determining region 1 (H-CDR1) comprising SEQ ID NO: 103, a heavy chain complementary determining region 2 (H-CDR2) comprising SEQ ID NO: 104, and a heavy chain complementary determining region 3 (H-CDR3) comprising SEQ ID NO: 105; and
      (2) a light chain variable (VL) domain comprising a light chain complementary determining region 1 (L-CDR1) comprising SEQ ID NO: 106, a light chain complementary determining region 2 (L-CDR2) comprising SEQ ID NO: 107, and a light chain complementary determining region 3 (L-CDR3) comprising SEQ ID NO: 108;
   (b) a transmembrane domain; and
   (c) an endodomain comprising at least one signaling domain;
   wherein the at least one signaling domain responds specifically to binding of the CAR to a HER2 antigen expressed on a cancer cell.

2. The cell or population thereof of claim 1, wherein the antigen binding domain:
   (a) comprises a VH domain with at least 80% sequence identity to SEQ ID NO: 109;
   (b) comprises a VL domain with at least 80% sequence identity to SEQ ID NO: 110;
   (c) comprises a single chain variable fragment (scFV) comprising VH-linker-VL or VL-linker-VH, wherein the linker varies in length and sequence, and optionally wherein the linker has at least 80% sequence identity to SEQ ID NOs: 111-114;
   (d) comprises an scFV represented by an amino acid sequence that is of at least about 99%, about 98%, about 96%, about 95%, about 90%, about 85%, or about 80% identity to SEQ ID NO: 115 or SEQ ID NO: 116, wherein each of SEQ ID NOs: 115 and 116 comprises a linker that varies in length and sequence; and/or
   (e) is humanized.

3. The cell or population thereof of claim 1, wherein the at least one signaling domain comprises:
   (a) a signaling domain of any one of: 2B4 (Natural killer Cell Receptor 2B4), 4-1BB (Tumor necrosis factor receptor superfamily member 9), CD16 (IgG Fc region Receptor III-A), CD2 (T-cell surface antigen CD2), CD28 (T-cell-specific surface glycoprotein CD28), CD28H (Transmembrane and immunoglobulin domain-containing protein 2), CD3ζ (T-cell surface glycoprotein CD3 zeta chain), DAP10 (Hematopoietic cell signal transducer), DAP12 (TYRO protein tyrosine kinase-binding protein), DNAM1 (CD226 antigen), FcERIγ (High affinity immunoglobulin epsilon receptor subunit gamma), IL21R (Interleukin-21 receptor), IL-2Rβ/IL15Rβ (Interleukin-2 receptor subunit beta), IL-2Rγ (Cytokine receptor common subunit gamma), IL-7R (Interleukin-7 receptor subunit alpha), KIR2DS2 (Killer cell immunoglobulin-like receptor 2DS2), NKG2D (NKG2-D type II integral membrane protein), NKp30 (Natural cytotoxicity triggering receptor 3), NKp44 (Natural cytotoxicity triggering receptor 2), NKp46 (Natural cytotoxicity triggering receptor 1), CS1 (SLAM family member 7), and CD8 (T-cell surface glycoprotein CD8 alpha chain);
   (b) an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ, IL21R, IL2Rβ (IL15Rβ), IL2Rγ, IL7R, KIR2DS2, NKG2D, NKp30, NKp44, NKp46, CS1, or CD8, represented by SEQ ID NOs: 54-76, respectively; and/or
   (c) an amino acid sequence that has at least about 85%, about 90%, about 95%, about 96%, about 97%, about 98%, or about 99% identity to the cytoplasmic domain, or a portion thereof, of 2B4, CD28, CD3ζ, DAP10, NKG2D, CD3 ζ1XX, DNAM1, CS1, or combinations thereof.

4. The cell or population thereof of claim 3, wherein the endodomain comprises two different signaling domains, and wherein said endodomain domain comprises fused cytoplasmic domains, or portions thereof, in any one of the forms: 2B4-CD3ζ/1XX, 2B4-DNAM1, 2B4-FcERIγ, 2B4-DAP10, CD16-DNAM1, CD16-DAP10, CD16-DAP12, CD2-CD3ζ/1XX, CD2-DNAM1, CD2-FcERIγ, CD2-DAP10, CD28-DNAM1, CD28-FcERIγ, CD28-DAP10, CD28-DAP12, CD28-CD3ζ/1XX, CD28H-CD3ζ/1XX, DAP10-CD3 ζ1XX, DAP10-DAP12, DAP12-CD3ζ/1XX, DAP12-DAP10, DNAM1-CD3ζ/1XX, KIR2DS2-CD3ζ/1XX, KIR2DS2-DAP10, KIR2DS2-2B4, or NKp46-2B4.

5. The cell or population thereof of claim 1, wherein the transmembrane domain comprises an amino acid sequence that has at least about 85%, about 90%, about 95%, about 96%, about 97%, about 98%, or about 99% identity to a transmembrane region, or a portion thereof, of:
   (a) CD2, CD3δ, CD3ε, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide;
   (b) 2B4, CD2, CD16, CD28, CD28H, CD3ζ, DAP10, DAP12, DNAM1, FcERIγ, KIR2DS2, NKG2D, NKp30, NKp44, NKp46, CS1, or CD8; or
   (c) 2B4, CD28, CD28H, DAP10, DNAM1, KIR2DS2, and NKG2D.

6. The cell or population thereof of claim 1, wherein the transmembrane domain and its immediately linked signaling domain are from a same protein or from different proteins.

7. The cell or population thereof of claim 1, wherein the ectodomain comprises one or more of:
   (a) a signal peptide; and/or
   (b) a spacer/hinge.

8. The cell or population thereof of claim 7, wherein the spacer/hinge comprises:
   (a) an IgG4 spacer, a CD28 spacers, a CD8 spacer, a CH3 spacer, a CH2/CH3 spacer, or any combination thereof;
   (b) a short spacer of about 10 to about 80 amino acids; a medium spacer of more than 80 to about 180 amino acids; or a long spacer of more than 180 amino acids; and/or (c) an amino acid sequence of at least about 80%, about 85%, about 90%, about 95%, about 96%, about 97%, about 98%, or about 99% identity to any of SEQ ID NOs: 96-100.

9. The cell or population thereof of claim 8, wherein the spacer/hinge comprises a medium spacer, wherein the spacer comprises an amino acid sequence of at least about 80%, about 85%, about 90%, about 95%, about 96%, about 97%, about 98%, or about 99% identity to SEQ ID NO: 99.

10. The cell or population thereof of claim 1, wherein the CAR comprises an amino acid sequence of at least about 90%, about 95%, about 96%, about 97%, about 98%, or about 99% identity to SEQ ID NO: 117.

11. The cell or population thereof of claim 1, further comprising a solid tumor targeting backbone comprising at least one of:
   (a) a polynucleotide encoding a C—X—C motif chemokine receptor or a variant thereof;
   (b) a polynucleotide encoding a TGFβ signaling redirector receptor (TGFβ-SRR) comprising a partial or full peptide of the extracellular domain (ECD) of transforming growth factor beta receptor (TGFβR); and
   (c) a polynucleotide encoding an allo-immune defense receptor (ADR).

12. The cell or population thereof of claim 11, wherein the solid tumor targeting backbone further comprises:
   (i) CD38 knockout;
   (ii) a polynucleotide encoding an exogenous CD16 or a variant thereof; and
   (iii) a polynucleotide encoding a cytokine signaling complex comprising a partial or full peptide of a cell surface expressed exogenous cytokine and/or a receptor thereof.

13. The cell or population thereof of claim 1, wherein the cell further comprises one or more of:
   (i) HLA-I deficiency and/or HLA-II deficiency;
   (ii) introduction of HLA-G or non-cleavable HLA-G;
   (iii) disruption of least one of B2M, CIITA, TAP1, TAP2, Tapasin, NLRC5, RFXANK, RFX5, RFXAP, TCR, NKG2A, NKG2D, CD25, CD44, CD54, CD56, CD58, CD69, CIS, CBL-B, SOCS2, PD1, CTLA4, LAG3, TIM3, and TIGIT;
   (iv) introduction of at least one of HLA-E, 4-1BBL, CD3, CD4, CD8, CD47, CD113, CD131, CD137, CD80, PDL1, $A_{2A}R$, antigen-specific TCR, chimeric fusion receptor (CFR), Fc receptor, an antibody or functional variant or fragment thereof, a checkpoint inhibitor, an engager, and surface triggering receptor for coupling with an agonist; or
   (v) at least one of the genotypes listed in Table 4.

14. The cell or population thereof of claim 11, wherein the C—X—C motif chemokine receptor comprises CXCR2 or CXCR3.

15. The cell or population thereof of claim 11, wherein the TGFβ-SRR further comprises a partial or full peptide of the intracellular domain (ICD) of a cytokine receptor comprising IL2R, IL12R, IL18R, IL21R, or any combination thereof.

16. The cell or population thereof of claim 15, wherein:
   (a) the cytokine receptor is IL2Rβ, thereby forming a TGFβR2-IL2Rβ redirector receptor, and the intracellular domain (ICD) of IL2Rβ comprises an amino acid sequence represented by SEQ ID NO: 11; or
   (b) the cytokine receptor is IL12Rβ, thereby forming a TGFβR2-IL12Rβ redirector receptor, and the intracellular domain (ICD) of IL12Rβ comprises an amino acid sequence represented by SEQ ID NO: 12 or SEQ ID NO: 13; or
   (c) the cytokine receptor is IL18Rβ, thereby forming a TGFβR2-IL18Rβ redirector receptor, and the intracellular domain (ICD) of IL18Rβ comprises an amino acid sequence represented by SEQ ID NO: 14; or
   (d) the cytokine receptor is IL21R, thereby forming a TGFβR2-IL21R redirector receptor, and the intracellular domain (ICD) of IL21Rβ comprises an amino acid sequence represented by SEQ ID NO: 15; or
   (e) the extracellular domain (ECD) of TGFβR comprises an amino acid sequence represented by SEQ ID NO: 10.

17. The cell or population thereof of claim 15, wherein the cytokine receptor is a fragment of IL2Rβ, forming a TGFβR2-trIL12Rβ redirector receptor which comprises an amino acid sequence having sequence identity of at least 80%, 85%, 90%, 95%, or 97%, 98%, or 99% to a sequence represented by SEQ ID NO: 16, wherein an amino acid sequence represented by SEQ ID NO: 17 comprised in SEQ ID NO: 16 is variable.

18. The cell or population thereof of claim 11, wherein the ADR is specific to 4-1BB or to CD38.

19. The cell or population thereof of claim 11, wherein one or more polynucleotides of the solid tumor targeting backbone are inserted at an endogenous CD38 locus to knock out CD38.

20. The cell or population thereof of claim 12, wherein the polynucleotide encoding the exogenous CD16 or variant thereof and two or more polynucleotides of the solid tumor targeting backbone are co-expressed in a tri-cistronic construct.

21. The cell or population thereof of claim 12, wherein the exogenous CD16 or variant thereof comprises at least one of:
   (a) a high affinity non-cleavable CD16 (hnCD16);
   (b) F176V and S197P in ectodomain domain of CD16;
   (c) a full or partial ectodomain originated from CD64;
   (d) a non-native (or non-CD16) transmembrane domain;
   (e) a non-native (or non-CD16) intracellular domain;
   (f) a non-native (or non-CD16) signaling domain;
   (g) a non-native stimulatory domain; and
   (h) transmembrane, signaling, and stimulatory domains that are not originated from CD16, and are originated from a same or different polypeptide.

22. The cell or population thereof of claim 12, wherein the cell further comprises the cytokine signaling complex comprising:
   (a) a partial or full peptide of a cell surface expressed exogenous cytokine or a receptor thereof comprising at least one of IL2, IL4, IL6, IL7, IL9, IL10, IL11, IL12, IL15, IL18, IL21, or respective receptor thereof; or
   (b) at least one of:
      (i) co-expression of IL15 and IL15Rα with a self-cleaving peptide in-between;
      (ii) a fusion protein of IL15 and IL15Rα;
      (iii) an IL15/IL15Rα fusion protein with intracellular domain of IL15Rα truncated;
      (iv) a fusion protein of IL15 and membrane bound Sushi domain of IL15Rα;
      (v) a fusion protein of IL15 and IL15Rβ;
      (vi) a fusion protein of IL15 and common receptor γC, wherein the common receptor γC is native or modified; and
      (vii) a homodimer of IL15Rβ;

or (c) at least one of:
  (i) a fusion protein of IL7 and IL7Rα;
  (ii) a fusion protein of IL7 and common receptor γC, wherein the common receptor γC is native or modified; and
  (iii) a homodimer of IL7Rβ;
  and optionally, (d) is transiently expressed.

23. The cell or population thereof of claim 1, wherein
  (i) the CAR is co-expressed with a cytokine signaling complex in a bicistronic construct, wherein the cytokine signaling complex comprises a partial or full peptide of a cell surface expressed exogenous cytokine and/or a receptor thereof; and/or
  (ii) wherein the CAR is inserted at a TCR locus, and optionally is operatively linked to an endogenous promoter of the TCR.

24. The cell or population thereof of claim 23, wherein
  (i) the TCR locus is a constant region of TCR alpha and/or TCR beta; and/or
  (ii) the TCR is knocked out by the CAR insertion.

25. The cell or population thereof of claim 1, wherein the cancer cell is a breast cancer cell, an ovary cancer cell, an endometrium cancer cell, a lung cancer cell, an esophageal cancer cell, a salivary gland cancer cell, a bladder cancer cell, a gastric cancer cell, a colorectal cancer cell, or a head and neck cancer cell.

26. The cell or population thereof of claim 1, wherein (i) the iPSC is a clonal iPSC, a single cell dissociated iPSC, an iPSC cell line cell, or an iPSC master cell bank (MCB) cell; or (ii) the derivative cell comprises a derivative $CD34^+$ cell, a derivative hematopoietic stem and progenitor cell, a derivative hematopoietic multipotent progenitor cell, a derivative T cell progenitor, a derivative NK cell progenitor, a derivative T lineage cell, a derivative NKT lineage cell, a derivative NK lineage cell, or a derivative B lineage cell; or (iii) the derivative cell comprises a derivative effector cell having one or more functional features that are not present in a counterpart primary T, NK, NKT, and/or B cell.

27. The cell or population thereof of claim 11, wherein the cell is an NK lineage cell or a T lineage cell, wherein:
  (i) the NK lineage cell or the T lineage cell has improved infiltration and/or retention at tumor sites;
  (ii) the NK lineage cell is capable of recruiting, and/or migrating T cells to tumor sites; or
  (iii) the NK lineage cell or the T lineage cell is capable of reducing tumor immunosuppression in the presence of one or more checkpoint inhibitors.

28. A composition comprising the cell or population thereof of claim 1.

29. The composition of claim 28, further comprising one or more therapeutic agents, wherein the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD).

30. A method of treating a subject using the composition of claim 28, the method comprising introducing the composition to a subject in need of an adoptive cell therapy, wherein the subject has a hematological malignancy, a solid tumor, or cancer.

* * * * *